US010906940B2

(12) United States Patent
Zheng et al.

(10) Patent No.: US 10,906,940 B2
(45) **Date of Patent: *Feb. 2, 2021**

(54) ANTIMICROBIAL PEPTIDES, PHARMACEUTICAL COMPOSITIONS, AND METHODS OF USE THEREOF

(71) Applicant: THE UNITED STATES OF AMERICA, as represented by the Secretary, Department of Health and Human Services, Silver Spring, MD (US)

(72) Inventors: Jie Zheng, Columbia, MD (US); Ann Marie Knolhoff, Silver Spring, MD (US); Eric Wayne Brown, Taneytown, MD (US); Timothy Ray Croley, Severna Park, MD (US)

(73) Assignee: THE UNITED STATES OF AMERICA, as represented by the Secretary, Department of Health and Human Services, Silver Spring, MD (US)

( * ) Notice: Subject to any disclaimer, the term of this patent is extended or adjusted under 35 U.S.C. 154(b) by 59 days.

This patent is subject to a terminal disclaimer.

(21) Appl. No.: 16/145,064

(22) Filed: Sep. 27, 2018

(65) Prior Publication Data

US 2019/0016757 A1 Jan. 17, 2019

Related U.S. Application Data

(63) Continuation of application No. 15/371,683, filed on Dec. 7, 2016, now Pat. No. 10,118,948, which is a continuation-in-part of application No. PCT/US2015/034859, filed on Jun. 9, 2015.

(60) Provisional application No. 62/009,467, filed on Jun. 9, 2014.

(51) Int. Cl.

| | |
|---|---|
| ***C07K 7/56*** | (2006.01) |
| ***C07K 7/08*** | (2006.01) |
| ***C07K 7/64*** | (2006.01) |
| ***A61K 47/54*** | (2017.01) |
| ***A01N 37/46*** | (2006.01) |
| ***A61K 38/10*** | (2006.01) |
| ***C07K 19/00*** | (2006.01) |
| ***A61K 38/00*** | (2006.01) |
| ***A61P 31/04*** | (2006.01) |

(52) U.S. Cl.

CPC ................ *C07K 7/56* (2013.01); *A01N 37/46* (2013.01); *A61K 38/10* (2013.01); *A61K 47/542* (2017.08); *C07K 7/08* (2013.01); *C07K 7/64* (2013.01); *C07K 19/00* (2013.01); *A61K 38/00* (2013.01)

(58) Field of Classification Search

CPC . A01N 37/46; C07K 7/56; C07K 7/64; C07K 7/08; C07K 19/00; A61P 31/04; A61K 38/10; A61K 38/00; A61K 47/542

See application file for complete search history.

(56) References Cited

U.S. PATENT DOCUMENTS

| | | | |
|---|---|---|---|
| 5,762,928 A | 6/1998 | Bolkan | |
| 2012/0041423 A1 | 6/2012 | Yousef et al. | |
| 2013/0164317 A1 | 6/2013 | Yousef et al. | |
| 2017/0145057 A1 | 5/2017 | Zheng et al. | |

FOREIGN PATENT DOCUMENTS

| | | |
|---|---|---|
| UA | 15147 U | 6/2006 |
| WO | WO 2012/166392 A1 | 12/2012 |
| WO | WO 2013/086003 A1 | 6/2013 |
| WO | WO 2015/191551 A1 | 12/2015 |

OTHER PUBLICATIONS

Water, from http://www.biology-online.org/dictionary/Water, accessed Apr. 24, 2014, pp. 1-3.*

DMSO Facts, from http://www.theundergroundcure.com/dmso-facts.html, accessed Nov. 26, 2014, p. 1.*

What Is Sorbic Acid?, from https://www.healthline.com/health/food-nutrition/what-is-sorbic-acid, accessed Sep. 9, 2019, pp. 1-2.*

Falagas et al, Polymyxins, from http://www.antimicrobe.org/d05.asp, accessed Feb. 4, 2018, pp. 1-20.*

Alkotaini et al., "Detection of secreted antimicrobial peptides isolated from cell-free culture supernatant of *Paenibacillus Alvei* AN5," *J Ind Microbiol Biotechnol* 40: 571-579 (2013).

Alkotaini et al., "Isolation and identification of a new intracellular antimicrobial peptide produced by *Paenibacillus Alvei* AN5," *World J Microbiol Biotechnol* 30: 1377-1385 (2014).

Anandaraj et al., "Co-production of two new peptide antibiotics by bacterial isolate *Paenibacillus alvei* NP75," *Biochemical and Biophysical Research Communications* 379: 179-185 (available online Dec. 13, 2008).

Antonopoulos et al., "Effect of *Paenibacillus alvei*, strain K165, on the germination of *Verticillium dahlia* miscrosclerota in planta," *Biological Control* 46: 166-170 (2008).

Cava et al., "Emerging knowledge of regulatory roles of D-amino acids in bacteria," *Cellular and Molecular Life Sciences* 68: 817-831 (e-pub Dec. 14, 2010).

Gardener et al., "Ecology of *Bacillus* and *Paenibacillus* spp. in agricultural systems," *Phytopathology* 94: 1252-1258 (2004).

(Continued)

*Primary Examiner* — Li N Komatsu

(74) *Attorney, Agent, or Firm* — Klarquist Sparkman, LLP

(57) ABSTRACT

Disclosed herein are novel antimicrobial peptides, pharmaceutical compositions containing the peptides, and methods of use of the peptides to inhibit the growth or proliferation of microbes. The antimicrobial peptides are particularly useful to treat infections of dangerous gram positive organisms such as MRSA and VRSA.

25 Claims, 48 Drawing Sheets

Specification includes a Sequence Listing.

(56) References Cited

OTHER PUBLICATIONS

Guo et al., "Isolation of a *Paenibacillus* sp. strain and structural elucidation of its broad-spectrum lipopeptide antibiotic," *Appl. Environ. Microbiol.* 78(9): 3156-3165 (2012).
Hoch and DeMoss "Physiological effects of a constitutive tryptophanase in *Bacillus alvei," Journal of Bacteriology* 90(3): 604-610 (1965).
Huang and Yousef, "Paenibacterin, a novel broad-spectrum lipopeptide antibiotic, neutralises endotoxins and promotes survival in a murine model of Pseudomonas aeruginosa-induced sepsis," *International Journal of Antimicrobial Agents* 44: 74-77 (2014).
Huang and Yousef, "The lipopeptide antibiotic paenibacterin binds to the bacterial outer membrane and exerts bactericidal activity through cytoplasmic membrane damage," *Applied and Environmental Microbiology* 80(9): 2700-2704 (Feb. 21, 2014).
Huang et al., "Biosynthesis of the new broad-spectrum lipopeptide antibiotic paenibacterin in Paenibacillus thiaminolyticus OSY-SE," *Research in Microbiology* 165: 243-251 (e-pub Mar. 5, 2014).
International Preliminary Report on Patentability from PCT Application No. PCT/US2012/038584, 5 pages (dated Nov. 20, 2013).
International Search Report and Written Opinion; International Application No. PCT/US2015/034859; International Filing Date Jun. 9, 2015, 12 pages (dated Aug. 14, 2015).
International Search Report from PCT Application No. PCT/US2012/038584, 4 pages (dated Sep. 27, 2012).
Kim et al., "*Paenibacillus elgii* SD17 as a biocontrol agent against soil-borne turf diseases," *Plant Pathology Journal* 21(4): 328-333 (2005).
Li et al., "Roles of D-amino acids on the bioactivity of host defense peptides," *International Journal of Molecular Sciences* 17(7): 1023, 27 pages, (Jun. 30, 2016).
Liao, "Control of foodborne pathogens and soft-rot bacteria on bell pepper by three strains of bacterial antagonists," *Journal of Food Protection* 72(1): 85-92 (2009).
Written Opinion from PCT Application No. PCT/US2012/038584, 4 pages (dated Sep. 27, 2012).
Allard et al., "In situ evaluation of *Paenibacillus alvei* in reducing carriage of *Salmonella enterica* serovar newport on whole tomato plants," *Applied and Environmental Microbiology* 80(13): 3842-3849 (Epub Apr. 18, 2014).

* cited by examiner

SEQ ID NO. 78

Compound of the present invention SEQ ID NO. 4

Compounds Identified in this Work

MV 1607, F

MW 1623, Y (SEQ ID NO. 77)

FA $C_{13}H_{25}O$

Total Formula $C_{81}H_{138}N_{16}O_{18}$

FIG.16M

```
A6_6i_PbtA   6406 LELPTEFARSEQRSYDGDKLHFAIDGQLNEKLQRLASQSGATLYMVLLAAYTTLLHKYSG
TS_15_PbtA   6407 LELPTEFARGEQRSYDGDKLHFAIDGQLNEKLQRLASQSGATLYMVLLAAYTTLLHKYSG
OSY_SE_pbtA  6355 LELPTDFARPAHQSHEGDTLDFVIDSHMSGGLQRLAEHTCTTLYMVLLAAYTILLHKYSD

A6_6i_PbtA   6466 QNDLVVGTPIAGRTHVDVEPLIGMFVNSLAIRNYPNDDKTFRSYLEEVKESTLSAFEHQD
TS_15_PbtA   6467 QNDLVVGTPIAGRTHVDVEPLIGMFVNSLAIRNYPNDDKTFRSYLEEVKESTLSAFEHQD
OSY_SE_pbtA  6415 QEDIIVGTPIAGRTHADVEPLIGMFVNSLALRSYPCGEKSFLSYLEEVKEMTLAAYENQD

A6_6i_PbtA   6526 YPFDKLVEQLRDAWVPGRNPVFDTMFVLQNAKARTINLGRLAFEPLIPSHTVAKFDLTLE
TS_15_PbtA   6527 YPFDKLVEQLEDAWVPGRNPVFDTMFVLQNAKARTINLRELAFEPLIPSHTVAKFDLTLE
OSY_SE_pbtA  6475 YPFAELVEHVQAVWSPSRNPLFDTMFVLQNTEDRNVRFGELTIEPYTQHHNVAKFDLTLE

A6_6i_PbtA   6586 MAIEDGMLSGQFEYCTKLFSANMIANFAEDFLEILSQACEQPDIRLEDIQLSGSAYQEEE
TS_15_PbtA   6587 MAIEDGMLSGQFEYCTKLFSANMIANFAEDFLEILSQACEQPDLRLEDIQLSGSANQEEE
OSY_SE_pbtA  6535 IALEDGVMSGHFEYCTRLFTTNMVDNFAEDLLSILAQICEQPAIRLGDIHLHGNAEEDEE

A6_6i_PbtA   6646 --LEEEIDFAF
TS_15_PbtA   6647 --LEEEIDFAF
OSY_SE_pbtA  6595 ASLAEEIDFVF
```

A6 6i PtbA is SEQ ID NO. 11
TS-15 PtbA is SEQ ID NO. 14
OSY SE PtbA is SEQ ID NO. 17

FIG.17M

```
A6_6i_PbtB   6227 SAYQILLSKYCCQDDIIVGTPVAGRNHADLEPLIGMFVNTLAIRNRPQGDKTFQSFLAEV
TS_15_PbtB   6227 SAYQILLSKYCCQDDIIVGTPVAGRNHADLEPLIGMFVNTLAIRNRPQGDKTFQSFLAEV
OSY_SE_pbtB  6215 SAYTVLLSKYSCQRDIIVGTPVAGRAHADLEPLIGMFVNTLAIRNHPAGDKTPLSTLFKV

A6_6i_PbtB   6287 KESTLGAFEHQEYPFEELIDLLKLQWETSRNPLFDTVFVLQNTEERRAGIGGLTISPYVT
TS_15_PbtB   6287 KESTLGAFEHQEYPFEELIDLLKLQWETSRNPLFDTVFVLQNTEERRAGIGGLTISPYVT
OSY_SE_pbtB  6275 KETALGAFEHQDYPFEELVERLNVQWDANRNPVFDTMFVMQNTEDHEVRLEALTLSPYVL

A6_6i_PbtB   6347 DDSVSAKFDLTLSVSEEDDGHKGSPLYASKLFKAAGIHRMMRDYLSILSQVCENPRIRIQ
TS_15_PbtB   6347 DDSVSAKFDLTLSVSEEDDGHKGSPLYASKLFKAAGIHRMMRDYLSILSQVCENPRIRIQ
OSY_SE_pbtB  6335 DNPIDAKFDLTLFVSEDNDVIKGGFQYGTKLFKAAMIHKIMRDFLLVLAQIVEDPHIRLR

A6_6i_PbtB   6407 DISISGQQTQEKSKIDTIEFAF
TS_15_PbtB   6407 DISISGQQTQEKSKIDTIEFAF
OSY_SE_pbtB  6395 DIKCNEQSVHNQRSIETIEFAF
```

A6 6i PtbB is SEQ ID NO. 12
TS-15 PtbB is SEQ ID NO. 15
OSY SE PtbB is SEQ ID NO. 18

A6 6i PtbC is SEQ ID NO. 13
TS-15 PtbC is SEQ ID NO. 16
OSY SE PtbC is SEQ ID NO. 19

SEQUENCE LISTING

```
<160> NUMBER OF SEQ ID NOS: 106

<210> SEQ ID NO 1
<211> LENGTH: 13
<212> TYPE: PRT
<213> ORGANISM: Paenibacillus alvei TS-15
<220> FEATURE:
<221> NAME/KEY: MOD_RES
<222> LOCATION: (1)..(1)
<223> OTHER INFORMATION: Lys or Orn
```

<220> FEATURE:
<221> NAME/KEY: MOD_RES
<222> LOCATION: (4)..(4)
<223> OTHER INFORMATION: Lys or Orn
<220> FEATURE:
<221> NAME/KEY: MOD_RES
<222> LOCATION: (6)..(6)
<223> OTHER INFORMATION: Tyr, Phe, or Trp
<220> FEATURE:
<221> NAME/KEY: MOD_RES
<222> LOCATION: (7)..(7)
<223> OTHER INFORMATION: Lys or Orn
<220> FEATURE:
<223> OTHER INFORMATION: See specification as filed for detailed
      description of substitutions and preferred embodiments

<400> SEQUENCE: 1

Xaa Val Thr Xaa Ser Xaa Xaa Ser Ile Pro Ile Pro Ile
1               5                   10

<210> SEQ ID NO 2
<211> LENGTH: 13
<212> TYPE: PRT
<213> ORGANISM: Paenibacillus alvei TS-15
<220> FEATURE:
<221> NAME/KEY: MOD_RES
<222> LOCATION: (1)..(1)
<223> OTHER INFORMATION: Lys or Orn
<220> FEATURE:
<221> NAME/KEY: MOD_RES
<222> LOCATION: (2)..(2)
<223> OTHER INFORMATION: Leu, Ile, Val, or Ala
<220> FEATURE:
<221> NAME/KEY: MOD_RES
<222> LOCATION: (3)..(3)
<223> OTHER INFORMATION: Cys, Tyr, Thr, or Ser
<220> FEATURE:
<221> NAME/KEY: MOD_RES
<222> LOCATION: (4)..(4)
<223> OTHER INFORMATION: Lys or Orn
<220> FEATURE:
<221> NAME/KEY: MOD_RES
<222> LOCATION: (5)..(5)
<223> OTHER INFORMATION: Cys, Tyr, Thr, or Ser
<220> FEATURE:
<221> NAME/KEY: MOD_RES
<222> LOCATION: (6)..(6)
<223> OTHER INFORMATION: Tyr, Phe, or Trp
<220> FEATURE:
<221> NAME/KEY: MOD_RES
<222> LOCATION: (7)..(7)
<223> OTHER INFORMATION: Lys or Orn
<220> FEATURE:
<221> NAME/KEY: MOD_RES
<222> LOCATION: (8)..(8)
<223> OTHER INFORMATION: Cys, Tyr, Thr, or Ser
<220> FEATURE:
<221> NAME/KEY: MOD_RES
<222> LOCATION: (9)..(9)
<223> OTHER INFORMATION: Leu, Ile, Val, or Ala
<220> FEATURE:
<221> NAME/KEY: MOD_RES
<222> LOCATION: (11)..(11)
<223> OTHER INFORMATION: Leu, Ile, Val, or Ala
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Pro Xaa Pro Ile
1               5                   10

<210> SEQ ID NO 3
<211> LENGTH: 13
<212> TYPE: PRT

<213> ORGANISM: Paenibacillus alvei TS-15
<220> FEATURE:
<221> NAME/KEY: MOD_RES
<222> LOCATION: (1)..(1)
<223> OTHER INFORMATION: Lys or Orn
<220> FEATURE:
<221> NAME/KEY: MOD_RES
<222> LOCATION: (4)..(4)
<223> OTHER INFORMATION: Lys or Orn
<220> FEATURE:
<221> NAME/KEY: MOD_RES
<222> LOCATION: (6)..(6)
<223> OTHER INFORMATION: Tyr, Phe, or Trp
<220> FEATURE:
<221> NAME/KEY: MOD_RES
<222> LOCATION: (7)..(7)
<223> OTHER INFORMATION: Lys or Orn
<220> FEATURE:
<221> NAME/KEY: MOD_RES
<222> LOCATION: (11)..(11)
<223> OTHER INFORMATION: Leu, Ile, Val, or Ala
<220> FEATURE:
<223> OTHER INFORMATION: See specification as filed for detailed
      description of substitutions and preferred embodiments

<400> SEQUENCE: 3

```
Xaa Val Thr Xaa Ser Xaa Xaa Ser Ile Pro Xaa Pro Ile
1               5                   10
```

<210> SEQ ID NO 4
<211> LENGTH: 13
<212> TYPE: PRT
<213> ORGANISM: Paenibacillus alvei TS-15
<220> FEATURE:
<221> NAME/KEY: MOD_RES
<222> LOCATION: (1)..(1)
<223> OTHER INFORMATION: D-Orn or Lys
<220> FEATURE:
<221> NAME/KEY: MOD_RES
<222> LOCATION: (4)..(4)
<223> OTHER INFORMATION: D-Orn
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (7)..(7)
<223> OTHER INFORMATION: D-Orn or Lys
<220> FEATURE:
<221> NAME/KEY: MOD_RES
<222> LOCATION: (8)..(8)
<223> OTHER INFORMATION: D-Ser
<220> FEATURE:
<223> OTHER INFORMATION: See specification as filed for detailed
      description of substitutions and preferred embodiments

<400> SEQUENCE: 4

```
Xaa Val Thr Xaa Ser Xaa Xaa Ser Ile Pro Ile Pro Ile
1               5                   10
```

<210> SEQ ID NO 5
<211> LENGTH: 19965
<212> TYPE: DNA
<213> ORGANISM: Paenibacillus alvei A6-6i-x

<400> SEQUENCE: 5

```
gtgaacgcga atcctaacga atggtatcct ttgacgcaag cgcagcgcag aatctggtac      60

acagaaatga tgcatcctaa tacgtcagtt actaccgttg ctggaacaat gtacatacga     120

ggcaaggtag acgttgagat tttgaaaatg gcgatatatc aagtgattat gcagcatgat     180

gccttccgaa tacgaatcgc aatgacagac aatcagccga agcagcaatt tgctcccgta     240
```

```
gagcaaatcg tccctcacgt tgattactta gagtgggata atcagattga agctgagagc    300
tggttacagc gatttaatca tattcctatc catatgttcg acccagcgtt atatcacttt    360
gtcgtattta acgtcaatga tgaggaagca tggttcaatt tgaaaatgaa tcatattgca    420
acggatggcg tctcttctca tcttatcgct tataaaatca tgaagaatta taccgcaatg    480
gtgagtggca acgcggacac ggatgaacaa gagagcactt acctggatta catattcgcg    540
gaacgagagt atgaacaatc tgatcgatac gcgaaagata aggcttattg gctggataag    600
ttcagcacaa tgccagaagt gataggtatc aaatcttacc ctcctcattc aatcggcact    660
gaggccagtc ggacaagcat cacggttagc ggagaaatgt acgagaagct ttaccgattt    720
agccagcagc acaatatcag tctctttact ctatttctag gttctttata cgcatttcta    780
tataagacga cagggaacaa cgatattgct gtcggtgccg cttatgcgaa tcgaacttcc    840
aggcaagaca aggatgcgct gggcatgttc gtaagcacgg tagccgctcg tttgacgatt    900
tccccagacc aagatgtact aaccttccta cataacgttg ccaaagagca aaaagcaatt    960
ttgcggcatc agaagtatcc ttacaaccag cttattcttg atttaagaga gcaaaataat   1020
agtgttgaga ttcaggattt gtaccgtatt tccatcgact atatgccgat acgctggtcc   1080
agtcacggag aactagccgc ccgccaacgc agcagctttt gcggtcatga ggtagacgat   1140
tttgcagttc acgtagaaga tatggtggat gataatcaga tcattttcaa tatcgattat   1200
cgcaaacagt tgttcgaaga gcatgaagtc attcgtatca tcgatcaaat gatgaccatc   1260
gttgatcaga tgttgagtaa tccgagccag agcttgcagc agttgtccat gatcagtgat   1320
aaggaagctc agatcatcct gacacgcttc agcaacggga attggtcaac gccgcagcca   1380
gttggacgaa cgattcacca gttgtttgag gaacaggtcg aacgcacgcc tgatcaggtt   1440
gctgtcgtgt tcggagatcg gcacctaacc tacaaggaac tgaacgaaca agccaattgc   1500
ttcgctcgaa cattgcgagc ccatggtgta gcagcagagc aattcgtagg catcatggca   1560
gaccgctcga ttgagatggt cgtcggtata cttgcaatat tgaaggcggg tggagcctac   1620
gttccgatag atcctgaata tccagaagag cgcattttat atatgctgga agactctaat   1680
gcaagagtac tcgtatcgca aagtcattta cagacacggc tcggttacac aggaacatgg   1740
gtattgcttg atgatgagaa cgactatgaa gcaaaccgcg ataacttgga gtcggtcaac   1800
gaagcacatc atttggctta tgtcatctat acatccggta caactggcaa gccgaagggc   1860
gtcatgattg agcataagca gattacagcc ttgggggatg catggaagca tgcctatcaa   1920
ttagatgaat cgggaattcg gacgctgcaa tgggcaagct tctccttcga cgtatttacg   1980
ggagacatgg tgcgagcgct gctgtacgga ggcgagctta tcatctgccc aagcgaagcg   2040
cgagctaatc ctgaagcgat atgcgagcta atcgcaagac atcgcatcca catattcgaa   2100
tcaaccccag ccctcgttat tccgttgatg gaatatgtgc atgaacaaag gaaggatgta   2160
agcagtctgc gcctgctcgt tgtgggctcg gatcattgcc cggctgcgga atatcgcaag   2220
ctgatggaac gattcggctc gcaaatgaga atcctgaaca gctatggcgt gactgaggct   2280
tgcgtcgatg cgtgctatta cgagaaaaat ggtagtgtgg attccatcac catgcttccg   2340
ataggtaaac cactgccttc ggtatccatg tacattctag acgagaacaa ggcgcttcag   2400
ccaattggaa ttgtaggaga gctctacata ggtggagccg gtgtcggcag aggttatttg   2460
aaccgtgatg acttgacagc agaaaaattc gttgatgacc cctactcaca aggaaagatg   2520
tatcggacag gtgatttggc aagatggctg ccggacggaa acatcgaata ccttggaagg   2580
```

-continued

```
ctcgatcatc aagtcaaaat tcggggtaac cggatagaaa taggagaaat tgaaacgcgc   2640
atgctgcaaa catcactcgt gcgggaagcc gttatcgtag cgcgcgagga tgaaaatgga   2700
ctgaaagctc tgtgcgccta ttatgttgcc gacagcgaga tatccgtaca gcaattgcgt   2760
tcaaccctag cagaacaagt accggattat atgattccgt cttatttcat gaagctggaa   2820
cgattgccgc ttacgccgaa cggcaaaatc gatcggaatg gattgcctgc accgtctggt   2880
caggactatt ccggcaagat ttatgtggag cctcgtaacc aagcggaaca aacgctggct   2940
agcatctgga aaatggtgct tggagtcaag cgagtgggta ttttggatca tttcttcgag   3000
ctaggtggag attcgatcaa gtccattcaa gtatcttctc gcatgcagca agctggatat   3060
aagctggata tccgggatct gttcaagtat ccgaccattg aacaaataag tccacatctg   3120
gtggaggttc agcgaaaagc tgagcaggga gaagagagtg gtgaggttgg gctcactcct   3180
atattgcgct ggtattttga tcgagatgaa gtgagtctgc atcattacaa tcaatccata   3240
atgctgcacc gcaaggctgg attcgatgaa gcggcacttc gcaatgcatt gcacaagata   3300
acggaacatc atgatgcgct gcgcatggta ttccgccgca cggaacaggg agaatacgcg   3360
gcctggaacc ggagaatcga agaaggcgag ctttaccgtc ttgatgtgtt ggatatcaag   3420
gaacgttccg ctggcgtaga aagcgaagaa tctcttcaca acatgctcat agctgaagcc   3480
aatgtgattc aggcggggtt cgatatagag gcagggccac ttgtaggcgc aggattgttc   3540
cgctgcccag atggagatca cctgcttatc gtcattcatc atgctgttat tgatgccgta   3600
tcttggcgaa ttttgctcga ggatctcgcc actggatacg aacaggcact tcaaggcagc   3660
gagattcgtc tccctgacaa gaccgactcc ttccggttat ggtcaagaga gctttcagca   3720
tatgcacagc agtctaacat gaacgaggag ctgaaatatt ggcaccaagt cgcacagacg   3780
acgattactc cactgccgac ggattatgct gggattgctc ttcaacgaga tagcgaatcg   3840
gtcacggttg aatggagtgc tagtgagacc gaactgctgt tgaagcaggc gcatcgggcc   3900
tataacacgc agatggacga tcttctctta acggcactcg gcattgcatt ccggagatgg   3960
tgtgggcatg agcgcatccg aattaatttg gaaggacatg gtcgggagtc gatcctgcca   4020
gatcttgata tcacacgcac ggtaggctgg ttcacgagtg agtatccgca gcttctcgag   4080
gtgggctctg aggaagaact gccgcgaatc atcaagtcgg tcaaagaaga tttgcgcagc   4140
attccgaata aagggattgg ttacggcatt tgtcgatatt tatccaacac gggtatttgt   4200
gaggtttggg gaacagctcc tgaggtcagc ttcaactact tggggcagtt cgaccaagat   4260
ttccagaaca gcgggttttc tccatcgccg tattctaccg gcagcaatat tgggggagat   4320
cagctaagac cttatctgct ggacatgaat ggcatggtct cggacggcaa attgcagctc   4380
gacatcagct atggacggac gcaatatcgt gctgagacga ttgagcgatt ggcaagcttg   4440
attcgggaca gcttacttga aatcatcgag cattgtgtgg ccaaggagcg aacagagctc   4500
acgccaagtg acgtgtcatt gcagcgcatt agcattcaag agttggagca gatcgttgaa   4560
cggacaagcg gtatcggtga agtagaggat atctatgcat taacgccgat gcagaaggga   4620
atgtggttcc atacagctat ggacagccag gcgggggcct atttcgagct tacacgctta   4680
acgcttgagg gaacgctgaa catcgaagcc ttcgctgcaa gctggaatga actggcggct   4740
cggcatgctg tattccgtac caacttcctc gtcgattcga atggcgaacc actgcaagtt   4800
gtatttcgga gcaagcgcat cagcgtgaag cacgaagatt tgcgttccct gaatgcatat   4860
gagcaggctg tggcgattga gaacgaagcg gccaaggaac gcgaacaagg ctttgacctt   4920
gagaatgggg atgtcatgcg cgtgtccgta ctccagacgg cagacgaagt gtatgaagtt   4980
```

-continued

```
ctatggatct cccatcacat cgtcatggat ggatggtgtc tcccgctcgt cgctgctgaa   5040
gtattcaaca cgtactccgc gctggtggaa gacaagaagc cgattcttgc ttcggtacct   5100
tcctataatc attacattca atggctggag cggcaggatg aatccgcagc cgcggcctat   5160
tggaacaatt atttgtctgg atttgaagag acgacagaac ttccgcatag caaggggcgc   5220
agacattctg gtcaatatga agcaggtcag gttcagatcg atctaggcac aagcctgagc   5280
cttgctctca atcaagttgc aacgcagcat caagtgacat tgaatacatt gctgcaggca   5340
tcatggggaa ttttgctcca gaaatacaac agaacttcag atattgtatt cggcagcgtt   5400
gtatccggca gaccggcaga actagtcgga atcgaagaga tgattggttt gttcattaac   5460
acgattcccg tgcgtgtgag cagtcaggcg caggagagat ttgcagaagt aatgacgcgt   5520
atgcaagaag atgcattgtc atctgccaag cacgactact atccgttgta tgaaatccaa   5580
gcacagtgca ccctgaagca gaatctcata actcacatca tggttcttga aaactatccg   5640
atggagcagc agctcgatca atttaacagt tcagacggca gtggactgaa gctgacagac   5700
gttaccgtaa cagaacagac gaattatgat ctgaacctca tcatcatacc tggcgacaat   5760
atcgtcattc gcttcgattt taataaacaa gcactcgaag aagcggatat gaatgtgttg   5820
aagcagcatc tgttgcatgt actggaacaa gttgcatcga atccgcggat atccatagga   5880
gagctgcagc tggcgacgga tgaagagcgt gccgtaatga tgagcgaatt taatgatacg   5940
ttcgtggctt atccgcgcga gaagtcgatc catcgattgt tcgaggagcg agctgaacat   6000
gagccagacg cgctagctgt cgtgtttgga aatgaacaga tgacctacgg agcgttgaat   6060
gccgcagcca atcgaatggc tcggagactc cggcatgccg gggtaacgaa cggtgaactg   6120
gttggcatct gcgcggatcg atcgctggat atggtcgtcg gcttactggc aattatgaag   6180
tccggcgggg cttatgtacc gatcgacccg gcttaccctc aagagcggat tagtgcaatg   6240
ctcgaagata catccattac gacgatggtt acacagaagc atctgtgcag cttatggcct   6300
gaacatttta acgtgatcgt gctggatgtt aacgagacag acgtaagcaa cttaatggaa   6360
gatatagaaa gtacaaacct gtctattgat ggggctggag acgatttggc atacatcatc   6420
tatacgtcag ggtctacggg aacaccgaaa ggggtttgcg taacgcaccg cggggtggtc   6480
aggctcgtat gcggcgcgac gtatgtcgag atcgacagtt cggatgtctt cttgcaaggt   6540
tccacaatct cgttcgatgc agcaaccttt gaaatatggg gaagtctgct gaatggggct   6600
gcgctggcca tcttgccttc tggcaatgtg tcgcttacag attggagcga agcgattcag   6660
cgtcatcggg tgacgacgtt gtggatgaca gctggtttgt tccaggtcat ggttgaacag   6720
caaatcgagg gcttctacgg agtcaagcag ctgcttgtgg gcggagatgt tgtatctcct   6780
acacacgtgc gtaaagtgat ggagaagcat aatggtataa gggtgattaa tggctacggg   6840
ccgacggaaa atacaacctt cacctgctgc cataccatta cggctgctga tttggatcga   6900
ggctgctcga ttccgattgg ccgaccgatt agcaatacgc gagtgtatgt gctggatgaa   6960
gctgggaacg cccttcctgt tggcgtatgt ggagagctgt atgcgggcgg ggatggcttg   7020
gcacgaggat acttgaatcg tccggaattg acagcagaga aattcgtgaa tgatccattt   7080
atcccaggtg aacgcttgta tcggacaggc gatttggcga gatggctgcc agacggttca   7140
atcgaattta tcgggcgctg cgacgaacaa gtgaagattc gcggttaccg gattgaacca   7200
ggtgaggtat tggcctatct tctgcggatc gatgaagtag gcgaggcggc tgtaatcgcg   7260
cgggaggatt cgagtggaca gaaggagcta tgcgcctatt tcacaacgga agctgagcta   7320
```

```
tcagctagtg gactaaggga gacactggct cgtgaactgc cagcttacat gatcccgtcg   7380
cattttattc agattgaaga acttcctttg acacctaacg gcaaggtgga tcgcagagct   7440
ctgcctcaac caggggaagg aatgcatttg aatattcaaa tccagccgcg cacggaactg   7500
gaagctaagc tcgcactcat ctggaaggat gtgcttggtc tcgagaacgt aggcgttaca   7560
gattcattct ttgaactggg cggccattcc ttgcgcgcga cgaccctcgt cagcaaggtg   7620
catcgggagt tgagtgttgt gctgccactg caggatgtat tccgctaccc gacgattgaa   7680
caaatgtctc tcgccataca ggggatgcag aaggaaagct ttgcatccat acctcgggtg   7740
gaagaccgag agtggtaccc ggtatcttcc gcgcagaagc ggctgttcgt tcttcatcag   7800
atggagggcg cagaactgtc ctacaatatg ccgggcgtca tggcgattga aggcaagctc   7860
catcgcgatc gcttggaggc ggcattccgc agcttgatag caagacatga agtgctgcgt   7920
accgggttcg aaatgcacaa cggggaaccc atgcagcgaa tttacagcga tgtagaattt   7980
actgtcgagc attggattgt tggagctgca tcggaagcgg agtcagtcat tcgctcgttc   8040
gtacgggcgt tccaattgaa taagccacca ctgcttcggg tcggactgat cgaagtggac   8100
gcaggtcggc acctgttgct gttcgatatg catcatatta tttcggacgg ggcatccatg   8160
ggcattctgc tagatgaatt cgttgcactg tatagcggcg aacaattgcc tgaattgcgt   8220
cttcagtaca aggattatgc ttcgtggcag cattcggaag catacttgtc caagatggaa   8280
gagcagaagg cgtattggct ggagacattg cgaggcgagc ttccagttct gcagctacca   8340
gtggattaca ctcggcctgc attccgcagc tttgcaggaa gcacgttgga attcattgtt   8400
cctgccgaca agacggacca gcttaagcag cttggagcgg gttcggatgc cacgatgtac   8460
atggtgctgc tggcgttgta tacggccttg cttcacaagt ataccggaca agaagacgtc   8520
atcgtgggga tgccgatagc cggtagaacg catgcagaca tcgagccgct tatcggtatg   8580
ttcgtcaaca cacttccact tcgccattat ccggctggag agaagacgtt ccgctccttc   8640
ctaggggagg ttcggcaatc cacattacaa gcatatgaac accaggaata tccgttcgag   8700
gagcttgttg atcatattca accgacaaga gatgtaagcc gtaatccaat attcgatact   8760
gtgctcgtcc tgcaaaatac agaaaaaggc gcatggtcca tcgatgggct tgccgtgacg   8820
ccgaatccga ttgagcatgc cgttgctaag ttcgacctta cacttcatgt cgaagaagat   8880
gtcgatggcc tggcgtgcag tattgaatat gcaaccgcct tgtacaatcg agaaacgatt   8940
gaacggctgg catgccattt caatcaattg ctggaagcag tcataagcaa tcccgatgct   9000
cggttggagc agcttggcat cataacggag acagagaagc agcaattgtt cgaacagttc   9060
aacgatacgt cagcggatta tccgcgtgat aagacgattc accgactgtt cgaggaacag   9120
gtcgaaagaa cgcctgatgc gattgctgta acgggaacag acggattctt gacttaccag   9180
gagctgaatg aacgggctaa cagcttggcg tgggtactgc gtgcagaagg catcggggca   9240
gacaagctgg taggcatcat ggccgagcgt acgactgata tgcttgtggg gctaatcgcc   9300
atactcaagg ccggaggagc ttacgtacca atcgatcccg aatatccaga cgagcgcatc   9360
agttatatgc tgagcgattc cggggcagat attttgctat tgcctcgaca tctgcggaat   9420
caagtcgcct atgagggcac cgtgttgttc cttgatgacg agcagacata cagcggggac   9480
aagtccaacc cgccatcagt caacaaacct tccgatctgg cttatgtcat ctatacatcg   9540
ggaacgactg gcaagccgaa gggtacattg attgaacata agaacgtcgt gcggctgttg   9600
ttcaacagca gaaatctgtt cgacttccgt tcaaccgata catggacgct gttccactcc   9660
ttctgcttcg acttctcggt atgggaaatg tacggcgctt tactatacgg agggaaattg   9720
```

-continued

```
gtggttgttc cgcagctgac agccaagaac cctgccatgt tcctacagct gctggctgaa   9780
gagcgggtaa cgattttgaa tcagactccg acctatttct atcaattaat aagggaagca   9840
cttacggatg gaagcccaga attgaacatt cgaatggtga tcttcggcgg agaagcgctg   9900
agtccgcagc tgcttaagga ctggagagcg aaatatccgc gcacgcaatt gattaatatg   9960
tacgggatta ctgagacaac ggttcatgtc acgtacaaag agatcacgga agccgagatc  10020
gagcaggcaa gaagcaatat cggattccca atcccgacct tgcgcatcta tattctggat  10080
gcgaatcgac aatgcgtgcc gataggcgtg gctggggaaa tgttcgtcgc aggagaaggg  10140
cttgcacgtg gatatttgaa tcgccctgag ttgaccgcgg acaggttcgt tgacaatcca  10200
ttcgaaccgg gcagcaagat gtacaagaca ggcgacttgg cgaagtggct gcctgacggc  10260
aacattgaat accttggccg gattgatcat caagtaaaaa ttcgcgggta tcgaatcgag  10320
ctaggcgagg tagaagccca agtaacgaag gtagaatcgg ttcgtgaagc cgttgttgtt  10380
gcacgagagg agaatggcga aaagctgttg tgtgcatatt tcgtggcgga tcggcaactg  10440
accgtagggg aaatgagaac cgaattggcg caggagctgc caacttacat gattccatcc  10500
tacttcgtgc agatggagcg gatgccgctt acctccaacg ggaaggttga ccgcaaggcg  10560
ctgcctgcac cggaaggcag catcaacacg ggcaaggaat acgtcgcgcc gcgtacacca  10620
atggaagcta gcttagcccg catgtgggag gaactgcttg gaattgagca ggtcggcgtg  10680
acagacaatt tcttcgagct aggcggacat tccttaagag caactgcgct ggttaacagg  10740
gtgcaccaag agatgaatat ccagttgccg ctgcgcgatg tgttccgctt ctctacgata  10800
gaagaactgg cagctgccat gtccgagatg gcggaggaat cctattcttc gataccagtt  10860
gctgaggttc aggatcatta tccggtatct tccgctcaga agcggctgta catccttcac  10920
cagcttgaag gggcagagca gggctataac atgcctggca tcatgctgct cgaaggcgag  10980
ttggatcgaa gcaggttcga ggctgcattc cgcaaattga ttgcgcatca cgatattttg  11040
cgtaccggct tcgagcttgt gcagggagag gctgtacagc gaatacacga tactgtggat  11100
ttcgcgattg aatatcggaa agtcgaagaa caagaggttc agcagcaagt aaaacagttc  11160
atccgcacat tcgagcttga taagccgccg ctgcttcgtg tcgggttgat cgagattgcg  11220
gggacgaagg aacagcatgt gcttctgttc gatatgcatc atattatttc cgacggggta  11280
tcgatcggta tcgtgctgca ggaaatcatg cggcactatc acggggaaca ggtaccgccg  11340
cttcatattc aatacaagga ttatgcggca tggcagcaat cagaggccca gaaggaacag  11400
ttgaagcatc agaaagctta ttggcttggc caattccaag gtgaattgcc gatattggag  11460
ctgccaacag actatgctcg tccagccatg cagcaatacg gcggtctgac gctgccattt  11520
agaatcgata aggacgtggc agatggtttg aaccgaattg ccgctgacac cggaacgaca  11580
ttgtacatgg ttctcctagc tgcttatacc gtcatgctgc acaagtatac gggccaagaa  11640
gacatcgtgg tcggaacacc gattgccggc agaacacatg aagaacttca accgttaatt  11700
ggcatgttcg tcaatacgct tgccattcgt gcttatccgg aaggtgctaa ggcattccgt  11760
tcctatctgg atgagattag aagcacaatg ctgggggcct acgagcatca acagtatcca  11820
tttgaggaat tggtggaagg tctgcagttg actagggatt taagccgcaa tccgctgttt  11880
gacacgatgt tcgccctaga taatacggac atgaaggctg attccctggg cgagcttcaa  11940
atgaagccat atccactgga atacacaata tcgaagttcg atgtgagctt ggatgtgaag  12000
gcggatgagg cggggctgga ttgcagcttc gagtatgcga cttccttgtt caaatcagag  12060
```

-continued

```
acgatccacc gcatggcaga gcatttcagc catttgttga aggacatcgt caatcacccg  12120
gatgcgcaac tgggcgaact aggaatgctt accgtgcagg agagcgacga gatcttgcag  12180
gtgttcaatc caacccattc attgaaagct cctaacgaaa cgattcatcg attgttcgaa  12240
gaacaggcag aacggacacc agagcaacct gcagtcgtat tcgggaatga gcgcatgact  12300
taccgcgagt tgaacgaacg ggcgaataag cttgcgagaa cattgcgggc agaaggtgtg  12360
gagccagatg acttaattgg cgttatggcc gatcgctcga ttgatatggt cgtggcagtc  12420
atggccgtct tgaagtcagg cggagcctat gtcccgattg atccggaata tccggaggat  12480
cgcattcgct acatgctgga agatgcgaag gcaagaatac ttctgacgca gggtcattta  12540
caagataaag tgaccttcga gggaacgtgg gtgctgctgg aggacgaagc ttcctatcat  12600
gaggacgata cgaacctgga gccgaactgc gagccaggcc atctctgtta tgtcatctat  12660
acatcgggta caaccggcaa tccgaaggga gtcatgatcg agcatcgtca gcttgctgcg  12720
atggcagagg cttggaaggc cgagtatgaa ttgcatgagc cgggcattcg ctggctgcaa  12780
tgggcgagct tctcgttcga cgtattctca ggtgatctcg ctcgcacact gctgcatgga  12840
ggagagcttg tactctgccc gagcgataca agagcgaacc caggtgcact agcagagctt  12900
cttcgcagca gcggcattca gatgttcgaa tcgacacctg cgctcgtcat tccgcttatg  12960
gagcatgtgt atgagcatgg cctggacatc gacagcctga gattattaat tattggctcc  13020
gatctgtgtc ctgcagatga attccgcaag ctacgcgatc gcttcagttc acacatgcgc  13080
attattaaca gctatggcgt cacggaagct tgcgttgatt cgagctacta tgagccgatt  13140
tcatcagatt cagtacgctc tgtgccaatc ggtaagccgc ttccttacgt atcgatgtac  13200
attctcggtg agaacttgtc gcttcagcct gttggtctgg ctggagagct gtatatcgca  13260
ggcgccggag tcggacgcgg atactggaat aggccggaaa tgacagcaga caaattcgtg  13320
cgcgatccgt tcgctgacgg tcaacgcatg tatcgtacag gggatttggc gaaatggctg  13380
ccggacggca acattgaatt aatcgggcgc accgatcatc aggtgaaaat tcgcggctac  13440
cgcatcgaaa tcggagaggt cgaatcgaag ctgcaggaaa cgccgcatat ccgcgaagca  13500
gccgtcgtcg cgaaggaaga tggaagcggg cggaaggtac tgtgtgctta ttacacatcc  13560
gagcgtgagc ttacggcagg tgaatggaga gctgcgttag cgaaggaatt gccggcctac  13620
atgataccat cgcacttcat gaggcttgag cgaatgccgc ttacgccgaa cggcaagctg  13680
gatcgcaagg gacttccagc accggaaggc gctgcgtata cggggacgga atatgaagct  13740
ccacgcacgg atgcagagat tgcgttggct gccgcatggc agagtgtctt gcatgtggag  13800
cgggttggaa cgaatgatca tttcttcgaa ctgggtggag attcgatcaa atcgattcaa  13860
gtgtcatcgc gtctgcatca ggctggatac aagttagaaa tacgcgacct gttcaaatac  13920
ccaacgatag cgcaattgag tccgcagctt cagccgatcg gcaggatagc tgatcaaggc  13980
gaggtgtctg gcgaggttga gctgacgcca atccaatgct ggtatttcgg actggatctg  14040
gatgacatgc atcattataa ccagtcgttc atgctgtatc ggcaggacgg atttaatgag  14100
gaggctctgc gcaagacttt acgatccatc gtggagcatc atgatgcgct gcgaatggta  14160
ttccgtaaat cagacgctgg ggttacggct tggaatcggg caatcgaaga gggtgaactg  14220
ttcgacttcc ttgccttcga tatcgcaaac agtggagatg ctgaacaggt tatcgaagcg  14280
aaagcgaacg acatacaggc tagcatcgat ttgcagggcg ggccgcttgt gaaggctgga  14340
ttgttccgct gcgagcaagg ccatcatctg ctcatcgcga tccaccatgc tgtcatggat  14400
ggagtatcat ggcgcatcct gctggaggat atcgcgacag gctacgagca agcgtgcaag  14460
```

-continued ggtgacgaca ttcgcttgcc ttcgaagacc gattcttatg ctgcgtggtc acggagtttg 14520
gtcgaatatg ctgaacacac ggatttgggt catgagcgca gctattggag acacgtcttg 14580
aacgctggaa cgaatccgct gccgaaggac tttgacacag aatcaagtct gcagcaggac 14640
agtaattccg tcaccgtagc ttggaatcaa caggatacgg agcatttact gaagcgggtg 14700
caccgagcct ataacaccga tatgaatgag atcttgctgg ccgctctcgc gatagccata 14760
cagaaatgga gtgggcacaa tcaaattctc gtcaacctag agggtcatgg acgtgagcca 14820
atcgcaggcg acctagatat ttcacggaca gtcggctggt tcacaagcga atatccggtt 14880
ctgctgaaag cggagcgaga tcgaggtttg gcgtaccaca tcaagagagc gaaggaagaa 14940
ttgcggcaga ttccgaacaa gggaatcggt tacggcatat gccgctactt gtctgagccg 15000
caagatagtt tggaatgggg agctgcccca gagattagct tcaactactt gggacaattc 15060
gatcaagact cgatgggaag cggcatgatg ttgtctccat attcgaaagg ttccgatgga 15120
agcgccttgc atacacgtca atatgtcctc gacatcaatg gcgccataac tgacggcata 15180
ttgaccttgg atatgagcta cagcgagaaa gagtaccgca aggagacgat ggaactgctg 15240
gcaggccatt tccacgagag tctgctcgag atcatcgacc actgtgtctc acgtgagcag 15300
acagaattga cgccgagtga tctgctgctg caaggactga gtatcgaaca gctggagcag 15360
attgctgaag agacgaaaga gcttggcatc atcgaaaata tgtacatgct gaccccgatg 15420
cagaagggga tgtggttcca taacgctctc gatggtcaag aaggcgcatc gggtgcttat 15480
ttcgaacaaa cccgatttac tctgcgaggt gagcttgatc ctgccctgtt tgcccagagc 15540
ctgcacgagc tggctgcccg gcattccgtg ctgcggacga acttctgcag cttggacggg 15600
gaaccggtac agatggtgtt ccgggaagga cgaattacat tcacgtacga ggatctgagc 15660
caattgccag ctgatgagca agcagttgtg atggaacgtg ttgtcgcgag cgacaagctg 15720
caagggttcg atctggaacg cgatccgctt gttcgcgtca cattgatgcg tacggaggca 15780
tctagctgcc atgtactgtg gagttctcat catattctga tggatggctg gtgcttgccg 15840
cagttgacgg acgagttgtt ccgcatatac tcagctgtca cgaatcatgc agccggaact 15900
actgaagcta ctggaacggt cggaattccc ggatctgccg aatccatgcg gaacaaagag 15960
gccaacctgc ctgactatag ccgatatatc gaatggctgg cagagcagga catgagtgcg 16020
gcggcagaat attggaacgg gtacttggcg ggctacgagc agcagacacg attgccaaat 16080
gggaagatca cagtcaagga taagccatat gtgctggaac aagcgtcccg caagctcgga 16140
attgatctta cttcccgtat gattcggatt gccaagcagc atcaagttac gttaaatacg 16200
ctgctgcaag ccgcttgggg gatcgtgctt cagaagtata acgggacgca agatgtcgtg 16260
ttcggcggag tcgtatcggg tcgacctgct gatgttccgg gtgtcgaatc gatgattgga 16320
ctattcatta acacgattcc ggttcgtgta agctgcgaag ccggcgcaag cttctcagac 16380
gtgatggagc agctgcaaaa tgcggcactc gaatctgggc gatatgatta ttatccgctc 16440
tatgagattc aatcgagaac gtcacagaag tcggaactaa tcagccacat catggtgttt 16500
gagaactatc cattggacga gcgaatggag caaaccggag acggtaacga cggagctctc 16560
gctttaaccg atgttcaagc agctgaacag accaattatg atttcaatct aatggtagtg 16620
ccgggtgatg aacttatcat tcgctttgat ttcaactcgg aagtgtatga tcgcggtcat 16680
atggaacggc tgcatcatca tctgatgcat gtactggagc aagtaacagg caatcctgca 16740
atctccattg ctgaagtgca gctctctacc gaagcggaga aggcagaagt ccaatctgca 16800
ttcaatgaca cagttgtcga ctaccctcgc gaacagacga ttcattggat gttcgaagag 16860
caggtgcagc ggacgccgga tgctgcagca gtgctgtatg gggatgacgt cataacctac 16920
cgagagctga acgaacgtgc gaaccggctg gcaaggacgc tgcgtgcggc aggggttgaa 16980
cccgatcaga ttgtcggtat tatggcagag cgttctctgg agctaatggt tggcattatg 17040
gggattctga aggcaggagg cgcctatgtg cctatcgcac cggattatcc agaggaacgc 17100
attcgatata tgctggacga ttccaaggct caggtgctgc ttgttcaagg aagcgcggga 17160
gaagcggttg acttcgtggg ccgcatcatc aatctggatg atgcagaagc atacgatgag 17220
gacagttcga atcctgagcc agtcaacaag ccgaccgata tagcctacat catctatacg 17280
tcgggaacga ccggacgtcc aaaaggggtt atggtcgagc atacttcggt catcaaccgc 17340
ttgctgtgga tgcagaagcg ctatccgata ggatcggaag atacgattat gcagaagacg 17400
gcgatcacgt ttgacgtatc ggtctgggag ctgttctggt gggcatttgt cggctcgaag 17460
gtgcttatgc tttcagtcgg tggggagaag aacccacatg cgattgtgga tgcgattgag 17520
cgtcaccgga taacgacgat gcacttcgtt ccatccatgc tgcacgcgtt ccttgagcat 17580
gtggagcaaa tgacagatgc agagcgtgag cgcggtctcg caccgctgcg gcaggtgttc 17640
acgagtggcg aggcactgct tgcctcacag gtcgagcggt tccaccgtta tattgcacct 17700
gcaagcggag cgcagcttat taatctatac gggccgactg aggcgacggt ggacgtaacg 17760
tacttcgact gcgagccagg ccagacttat gtaagtgtgc cgattggcaa gccaattgac 17820
aatacgagca tttatatcgt gaatgagcat aatcaagtgc agccgatcgg cgttgctggt 17880
gaactgtgca tcgcgggagt ggggttggcg cgcggttact ggaaccgtcc agagctgaca 17940
gcagagaaat tcgttacaat tccttccgtc ggcgaacgga tgtatcgaac cggagacttg 18000
gcacggtggc tgcctgacgg caatatcgaa tacttgggcc gaatcgacca tcaagtgaaa 18060
atccgcggat atcggattga attgggcgag ctggagactg cactgctgaa tgtccaagaa 18120
attcgggaga cggttgtagt tgcgcgagaa gaggaagacg gacagaaatc actctgcgcc 18180
tattatgtcg cagatggcga tccaacggta ggtaacctta gagcggcgct tgctgctgaa 18240
ctgccaagct acatgattcc atcgtacttc attcagctgg agcagatgcc gctggcgccg 18300
aacggcaagc ttgatcgtaa agcgctccct gctccgaagg acgtgattca gacgggaact 18360
gatcacgccg caccacgaac agcattggaa gtgaagctcg ttcgcatatg gcaggaagta 18420
ctcggtctcg atcaaatcgg agtgaaggac gacttcttcg aattgggcgg gcactccttg 18480
cgcgcaactg cgttggcaag caaggtaagc aaggaaatgc acgttgctct tccgctgcgg 18540
gatattttcc actattcgac gctggaagcg atggcgcagg cgatcggcga gttggagaag 18600
caggagcacc gagcgattcc tatcgcgcca atggccgagc attatccatt ggcttcagcc 18660
cagaagcggt tatacattct tcaccaggct gaaggagcgc agcagagcta caacatgccg 18720
gggcgatgt ccgtaagtgg acacatcgat cgaaatcgac tggaagcggc gctgctgcga 18780
ttgattgcac gccatgacac actgcgcaca agcttcgaaa tggttgatgg tgagcctgta 18840
cagcgcgtac accagcacgt tgatttcgcg ttagagtatt cgactgcgag agagaaggat 18900
atggagcagg ttgccaagca gtttgttcgc gattttgatc tggagcagcc tccactactg 18960
agagtcggac ttgtccaact tgagcaagaa gaacaacatc tattgctgtt cgatatgcat 19020
cacatcatat cggacgggat ctctatggac atattggttg acgagcttgc tcgcttgtac 19080
gacggagagg aacttcctcc acttgaaatc cagtacaaag attatgtgct gtggcagcag 19140
gcagaagcaa gcagcgagca gatgaaggaa catgaagaat actggctgcg gacattgggc 19200
aatgaacttc cgttactgga gctgccgacc gaatttgcaa gaagcgagca gcgcagctat 19260
gacggagata agctgcactt tgcgattgat gggcagttga acgagaagct gcagcgcttg 19320
gcatcccaat cgggagcaac cctatatatg gtgctgctgg cggcttatac gaccttgctt 19380
cataaatatt caggacaaaa tgacctggtt gtgggcaccc caattgcggg cagaacccat 19440
gtagatgtag aaccgctaat cgggatgttc gtcaattcgc ttgcgattcg taattaccca 19500
aatgatgaca agacgttccg cagttattta gaggaagtga aggaatcgac gctgagcgcc 19560
ttcgagcatc aggattatcc gttcgataag ctggtggagc agttagagga tgcttgggtt 19620
ccaggccgta atccggtatt cgacacaatg ttcgtcctgc agaacgcaaa agcgcgcacg 19680
atcaacctgg gagaattggc cttcgagcct ctaattccat cacatacggt tgcgaaattc 19740
gatttaacct tggaaatggc tatcgaagac ggcatgctga gcgggcagtt tgaatattgc 19800
acaaagctgt tttccgccaa catgattgcg aatttcgcag aagacttctt ggaaattcta 19860
tctcaagctt gcgagcagcc tgacatccgc ttggaggata ttcaactgag cggcagtgct 19920
tatcaagagg aagaattgga agaagaaatt gactttgcat tctaa 19965

<210> SEQ ID NO 6
<211> LENGTH: 19287
<212> TYPE: DNA
<213> ORGANISM: Paenibacillus alvei A6-6i-x

<400> SEQUENCE: 6
atggcttttg ataaagaaat cgaattttgg aaagcgaaac tcgatactga agatacgcct 60
acgactttgc cctacacgag cactccaagc agtgaagcgg cacgacatta ttccgtttct 120
gttacgatgc ctgctgaaat ttcggaacga attattcgca tgtctaaggg ctcgcatcaa 180
gcagccttca tgattttact aggtggcatc caatgcttgc tgcacaaata cacgagcgag 240
aatcgcatcg tcatcggcat gcctattgtg cgaaaagcag gggagaagag acttcccatc 300
aatcaagtcg tcctattgaa ggagaatgtc aatgaagagc tcacgttcaa atccttgctt 360
acttcactga aacaatcctt tacagaagcg attcgacatc agcatatccc cttccggctc 420
ataactgagc agatgaatgt acaagaaaag aatggcttgc ctgtcatcaa tacgatggca 480
gctctgaaga atatacatac cgttaacttt attccaacgg ttgttgcaga tgtattgttc 540
caatttgagt tcgaagctga gaacctcctt ttgagcgttg tatataacga acgtgtctat 600
gactcggtat ttatatcgca aatcattgag catttgcagc gcgtgctgag catcgtattg 660
cttgagccaa atacgaattt gggggatctt cgcttacttt cggatgagga aacatcgctg 720
ctcctgcacg gatttaatac aacggctgca gagtatccac gtgaccgaac aattcatgaa 780
ctcttcacgg aacaagcacg tcgcacgccg gatgctgttg cggcagttta tgggcagcaa 840
cagttaacat atgccgagct aaatggaagg gcgaacaggc tggcgcgtac gttacagaac 900
gctggcgttc gatccgatca gctcgttggc atcatggccg aacggtcgct cgaaatgatt 960
gtaggcttgc tagccatcat gaaggctggt ggggcctatg ttccaatcga ccctgaatat 1020
ccgcaggagc gcattcgtta tatgctcgag gattcgggag cgcagacgct actgcttcaa 1080
gaccatcttc gcgagcgtgt cacctatgag ggcacgatcg tggatatgaa tagcgaacat 1140
aattatcatg acgacgggac ggaacttgcc tctgtgtccg attcaagcaa cttggcatat 1200
gtcatctata catcgggcac gacaggcaat ccgaaagggg tcatgattga acatagaagc 1260
gcagtcaatg cgctgttgtg gagaattcgg acatacgggc tttcttcctc cgaccggatt 1320

-continued

```
ctgcaattgt tttcattttc ctttgacggc ttcgtcatga gcgcgttctg ctcattattg   1380
tccggcgcag gtttattttt acttaaggaa gaggacgcga aggatccgct cgccttgcat   1440
ggcgctatca gccaatcagg aatcacgcac ttcatttgcg taccaaatct atacggagcg   1500
ctgctcaatg tgatgcaggc cgagtctgtg tctacgctgc gtacagtgac attggctggc   1560
gagagtgtca gcagtgcatt agtagctaga agcaaggagc agcttcctaa tgtgaagctg   1620
tttaatgaat atggtccaac agagaacagc gtcgtggcga cctgcgcaat tggcctcgag   1680
aaggatcaac ccatcaccat tggtacaccg atctctaatg cgagtgtgct cattttgaat   1740
acttctgggg agttgcagcc gttacatgtg ccgggcgaat tatgcatagc cggtgagggg   1800
ctggcgagag gttacttgaa ccgtcccgaa ttaacggaag agaaatttgc cgctcatcca   1860
tttgtgccag gagaacgcat ttaccatact ggtgattccg ccagatggct gccgaacggc   1920
acaattgaat atttgggacg gattgatcac caagtcaaaa tccgtggatt ccgtatcgag   1980
ctgggcgaaa tcgagtcgag cttgaagaag atagcgggtg tgcgagaggt catcgtggat   2040
gctaggccgg acggtaatgg ccaacatatg ctgtgtgcgt acatggtagc tgacgctgag   2100
cttactgtga cggaattaag ggaggcgttg tcttccaatc tgccggatta catgattcct   2160
tctcactttg tgcaaatgga acagctgcca cttacgccaa gcggcaagct ggatcgcaag   2220
tcattgcccg atccccaagc taacatggct attggcacgg agtatattgc gcctcgtact   2280
ccacttgaag cacgacttgc gcaaatctgg caggagtcgc ttggtgtgga aagggtcggc   2340
atcaaggata atttcttcgc ccttggcgga cactcgctgc gggcagctac attggcaagc   2400
aagcttcaca aggagttgaa cgtcaatgtg ccgcttcggg atttgttccg aaatccgacg   2460
atcgaagaat tggctttgct tatggatggg atggagcagc aggagttcag cgcgattgaa   2520
cgggtgaagg aaagcgagta ttattcggta tcttcagcgc aaaagaggct gtatgtcctg   2580
cagcagctcg aaggtgcgga acagagttac aatatgccgg gtgccatgct gctggaggga   2640
ctgctggata gagaacgcct cgaagcctca ttccgcaagc tgattgcacg acatgagaca   2700
ctgcgtaccg gattcgagct gatggacgga gaaccggtgc agaaggtgta tcaggatgta   2760
agctttgcca ttgaatatat gcagacaagc gaggcggaag cggcgcagaa agcccgcgaa   2820
tttatccgag cgttcgactt gatgactccg ccgttgatga gggttggctt aattgaaatg   2880
gcaccggatc gacatgtgct cctctatgac atgcaccata tcatttctga cggtgcatct   2940
atgggagtcg tagtagagga gttcgctcgg ttgtacgggg gtgaggagct gccaccgctg   3000
cgtattcaat ataaagactt tgccgcttgg cagcagtcgg aagcacagca gaagcgttcg   3060
aagcagcagg agacctactg gttgcaaaca tttggcggag aactgcctgt acttgagctt   3120
ccaacggatt acgcgcgtcc agccattcag agctacgaag gggagaccta tgaatttacg   3180
gtcgattcgg atataagtac ggcattgcaa cgcctcgcag cggatagcgg aacgacgtta   3240
tacatggttc tgctcgcagc ttacacggtg ctgctgcata agtacacggg tcaggaagat   3300
attgtcgtcg gcacgacgaa cgcagggaga atgcacgacg atttgcagcc gcttattggt   3360
atgttcgtca atacgctcgc aattcgcaat tatccggctg gagaatcgac gtttcgtgct   3420
tatttggaac aagtgaagga gcaggcgtta gctgcatttg aacatcagga gtacccattc   3480
gaagagcttg ttgagaagct tcatgttaca agagacatga gccgcaaccc gctgttcgat   3540
acgatgttct ccctgcaaaa tatggagaac aaggattttg aacttccagg actccaattg   3600
aagccgtatg gcttcgaaca ccaaatatcc aagttcgatc tcagcttgga cgttgcggaa   3660
ggagcggatg ggctcgcttg cagcttggag tatgcttcgt ccttatacag acaagacaca   3720
```

```
atcgtaagaa tggcggatca ttatcgacag ctgcttcatt caattgcaca gtcgcctgag   3780
gcgcaaatct ccgtgctcgg gatgttgacg ccgggtgagc aagagcaaat tcgattcaag   3840
ttcaatcatg atccgtcaga aatggagcag aagcacacgg ttcatcaact ctttgaggag   3900
caggccgctc ttacaccgga acgaactgcg gtcgtgcatg agaatgaaca actgtcgtat   3960
cgggagttga acgagagggc gaaccgtctg gcacgtacgc ttcgtcaaca cggcgtgcag   4020
ccggagcagc ttgtcggcat cttggcagac cgttcgctgg acatgatcgt gggcattatg   4080
gcgatcttga aggcaggcgg cgcttacgtt ccaattgatc cgaaatatcc ggaagaacgt   4140
atccgttaca tgctggagga ttccaaggca aacgtattgg tgacgcagag ccatttacag   4200
tctctctcat cgtttgacgg tacatgggtt ctgcttgatg aggagtcatc ctatgctgag   4260
gatgctgcca atcttgtgtc catcactgaa ccacaacact tggcttacgt catttataca   4320
tcgggcacga cgggacagcc gaagggtgcc atgatcgagc acagacaact gacagttatg   4380
gcgaaggctt gggagcgtga atatcgtctg cgcgaagaga gtattcgctg gatgcaatgg   4440
gcaagcttct cgttcgacgt attttcaggc gacttgattc gtgcgctgct gcatggcgga   4500
gagctggttc tttgcccaga gcacgcacgt gcgaatccgg ctgaaatcta cgaattgatc   4560
cggaagcatc gtcttcatat gttcgactgc acaccgtcta tcgtcattcc gctcatggaa   4620
tatgtgtatg agaacaagct ggatattagc agcttgaagc ttgtcgccgt tgggtcggac   4680
tattgcccgc cggatgagtt tcagaagatg cttgatcgat ttggttcgca gttccgcatc   4740
attaatagct acggcgtaac ggagacgtgc atcgatgcca gctattatga accaacgact   4800
ccaactgttc caagagcgct gccgattgga aaaccattgc cgggtgtaac gatgtacatt   4860
atggacggac agcgttcctt gctaccggtt ggtgtcatcg gtgagctcta tatcggcggt   4920
ccttgcgttg gccgtgggta ttggaatcgc tcggaaatga cgaacgagaa attcgttgaa   4980
gatccattcc ttcaggatta ccggatgtac cgcacagggg atctggctcg ctggatgccg   5040
gatggcaata tcgaatattt aggccgtatc gaccatcaag cgaaaatacg cggttaccgt   5100
attgagatcg gcgaagtcga gtccaagctt ctcaaggtag agacagttcg tgagagtgtc   5160
atcgtagcgc gtcaggatcc gaacgggaca aaagcattat gcgcttattt cgttgcggat   5220
cgcaatctga cggtgagtga actgagaagc gcattggccg atgaattgcc ggcatatatg   5280
attccatcct attttgttca actggatcgt ctgccgctca caccgaatgg aaaagttgat   5340
cgcaaggcgc tgcctgcccc ggaagcgggt gcgcacacgg ggattgaata cgtggcgcca   5400
cgcacggaag aggagttagc actggcgaat gtatggcaaa ccgtccttgg tattgaacga   5460
gtcggtgtgc aggatcattt cttcgagctt ggaggcgact caattaagtc tatccaagtc   5520
gcttcccgat tgcagcaagc aggctataag cttgaaattc gcgatctgtt caagtaccca   5580
acgattgctc aactgggatc ccacttgcag agggcaagca aggttgcaga tcagggcgaa   5640
gtatcaggtg acgtgccgct tacaccgatt cttggatggt ttttcgaaca gcagtttgcc   5700
gacgcgcatc actataacca atcgatcatg ctgtaccgga gagaaggctt tgacgaggcg   5760
gcaatccgca atgtacttca ggcagtaacg gaacatcacg atgcgctgcg catcgtattc   5820
cgacggaacg atcaaggcga ttatacagct tggaaccgcg caatcgaaga aggagaattg   5880
ttccatctgg aagtgctgaa ccttactggc tcagcatcag gtgatcatga gcagaatgta   5940
cggcagatca ttgaagccaa ggctagtgag attcagcgca gcttcgacct gcacgatggg   6000
ccgttggcaa gagccggatt gttccgtacc gatgaggggg atcatcttct gcttgtcatg   6060
```

```
caccatggcg ttgttgacgg tgtgtcctgg cgcatcctgc tggaggatat cgctgctgga   6120
tatgaacaag cgttgaaggg agagcctgtt cggctgcctg ccaagacgga cagcttccgc   6180
acatgggcga atcatctcgc gtcatatgcg cgaagcgaag ccatgataga ggaacaagtc   6240
ttctgggaac aggcagaagc gaatgcaacg agtattttgc ctttgccgaa ggatttcgaa   6300
gcggagacat ccttgcagca ggatagcgag tcggtcgtag tggaatggag ccgggaggag   6360
acggatatgc tgctgaagca tgttcaccgg gcttataaca cggacatgaa cgacattctg   6420
ctcgcggcgc tcggcatggc tatacagcaa tggtgtggac atgagaaagc cctagttaca   6480
cttgaaggac acggccgcga aaatatcatg ccggagcttg atatttcacg cactgtgggg   6540
tggttcacga gtgaatatcc attcctgctc gagagcgatc cgaacaagag tttgtcctat   6600
cgaatcaaac gaatgaagga aaatttgcga cgtattccga ataaaggcat cggttatggc   6660
attcatcgat atttatcgga ctcaggtatg tctggtacgg aaaatgtatc acgatcagaa   6720
gcatcagctc agccagaaat cagcttcaac tatttgggac aattcgatca ggatttgcag   6780
aacaatgaga tggaagtatc tccatattcg ggcggcgcag agataagcgt tcgtcaggct   6840
cgtaacacca cgcttgattt taacgggatg atatcggctg ggttcttgc attggaagtg    6900
agctacagca gcaagcaata ccgccgcgat acgatcgacc ggctggcagc attgctgaag   6960
ggaagtttgc aggagatcgt tgcccactgc gcatcaaaag ataagccaga attgacacca   7020
agtgacgtat tggttaacgg gcttggtatt gaggatctgg agcgtattgc ggagcagacg   7080
agggatctcg gggacatcga gaacatttat gcactgacgc cgatgcagaa gggaatgtgg   7140
ttccataacg cgatggacgg tcaagcgggg gcttattttg aacagactcg ctttacgatt   7200
caaggagagc ttgacgttca gctattcgca agcagcctag acgtactcgc gacacgacat   7260
gcggtgcttc gcaccaattt cttcagcggc tggaacggag aattgctgca aattgtatac   7320
cggaacaaga atctggaatt tagttacgag gatctaacgg aattgccgga ggatgagaag   7380
caggatcgag ttgaagcgat ggcgcaagct gataagctcc gtggattcga tctggagcac   7440
gatgcgctga tgcgggtgtc cgtgttgcgg acgaacgtga actgcagtca tgtcatttgg   7500
agctctcatc atattctgat ggacggctgg tgcttgccgc agctcacaca agaatggcta   7560
gagacgtatt ccgattccgt aaatggacgg tctagcagcc gatcgggagc atcgccatac   7620
agcctctata ttgaatggct gtacaagcag gattacacag ctgcatccca gtattggagt   7680
gactatctgg cggattacga tcagcaaacg gttcttccgc agaagaaatc gagcgggcgc   7740
agcgatgtat atattgctga taatctcgta tttgaactgg gcgaggcttt aactgcgaag   7800
atgcatcggg tcgcaaagca gcatcagctg acgctgaaca cgctaatgca ggcggcatgg   7860
ggcattattt tgcaaaagta caacggtacc ggcgacgctg tattcggcgg agtcgtatca   7920
ggtagaccgg cggaaatccc aggcattgaa tccatgattg gactattcat taacaccatt   7980
ccgattcgtg ttgcgtgcga agcggatgac agatttgccg acgttatgaa gcggcttcag   8040
gagaaggcgc tggagtcagg gcggtatgat tattatccgc tgtatgacat acaggcgctt   8100
agcacgcaca agcaggattt gatcaatcat attttggtgt tcgaaaatta cccgatggaa   8160
gagcaaatgg aacaggctgg tgatgagcgg ggacaattga acattaccga tgtgcgggtg   8220
gccgaacaga cgagctatga tttcaatctc gtcgtgatgc caggcgagga catgatgatt   8280
cgcctcgagt acaatgccgt catgtatgat cgagcagata tggagagagt gcggcagcat   8340
ctgattcatg tccttgagca ggtaacagct gatccggcca ttgctgtgaa agatgtccgt   8400
ctggcgaccg acgacgagaa ggcagagctt ctgacggcat tcaatgatac ggaaatcgaa   8460
```

-continued

```
tatcctcgcg aacagatgat tcatcggatg ttcgaggagc aggttcagcg gacgccggat   8520
gcgacggcgg tgttgtacgg agcagctgcg atgacctacc gggagatgaa tgaacgtgcc   8580
aatcagttgg cgcggacact gcgagcagca ggcgtcgttc cggatcaaat cgtcggtatt   8640
atggcggaac gatcgctaga gctaatggtt ggcatcatgg ggatattgaa agctggcggc   8700
gcctatgtgc cgatcgctcc ggattatccc gaagagcgca tccgatatat gctggacgat   8760
tccgaggctc aagtattgat tgttcaaggc agcgcgggtg aagcgattga ttttgcaggc   8820
cgcgtaatta atctggatga tgctgactcg tacgatcagg acagctcgaa cctagagatg   8880
gtgaacaaac caaccgatat cgcctatatc atctatacat caggtacgac cggacgtccg   8940
aaaggggtta tggtcgagca tacatcagtc atcaaccgct tgttgtggat gcagaagcgg   9000
tacccgattg gcgcggatga cacaattatg cagaagacgg cgatcacgtt cgacgtatcc   9060
gtttgggagc tgttctggtg ggcatttgtc ggctcgaaag tgcttatgct tccagttggc   9120
ggagagaaga atccggcagc aatcgttgag gcgatcgaac aatacgaaat tacgacaatg   9180
cacttcgtac catctatgct gcatgccttc ctcgagcata ttgagcagct gcctgaagcg   9240
gagcgtgagc gcctgtctcc gctgcagcag gtgttcacga gcggagaggc actgttggca   9300
tcgcaggtag agcgattcca tcagtatgtt gtacctgcca gcggagcacg actcatcaat   9360
ctgtacggtc cgacagaggc gacggtggat gtcacgtact tcgactgcga accaggccaa   9420
acttatgtga gcgtgccgat tggcaagccg attgacaata cacgcatcta tattgtgaac   9480
gagcactttc aagtacagcc gatcggcgta gcgggcgaac tgtgtatcgc gggcgtcgga   9540
ttggcgcgcg gatactggaa ccgtccagaa ctgacagaag agaaattcgt attggtgcct   9600
tctgtgggtg aacggatgta ccgaacgggc gatctcgcgc ggtggctgcc agacggcaac   9660
atcgaatatt taggacggat tgatcatcag gtgaaaattc gcggttaccg aattgagctt   9720
ggcgagctgg agactgcgct gctgaatatt gacgcggttc gggagacggt tgtcgttgcg   9780
agggaagacg agagcggaca gaagtcactt tgcgcctact atgtagcaga cggagaagca   9840
acaataagtg acctgcgagc cgcacttgcc gccgagctgc cgagctacat gattccatca   9900
tacttcgtaa ggctggagca gatgccgctg gcgccgaacg gcaagctgga tcgcaaagct   9960
ttgccggctc cagagagaag ccttcaagtt gaatcggaat atgttgcgcc gcgcacggaa  10020
gcggaacaga tgctgacaac cgtatggcaa gccgtacttg gcatcgaacg tgttgggata  10080
accgatcact tcttcgagct tggcggagat tccatcaagt ccattcaagt ggcagcaaga  10140
atgcagcagg cgggcttcaa gcttgaaatt cgcgacttgt tcaaataccc gacggttaca  10200
cagttggttc catacatgca gccgattaat cgaacggctg atcagggaga agtcgtcggt  10260
gaggtgccga tgacaccgat tctgcattgg ttcgagcatc agcagtttgc gaatccgcat  10320
catttcaatc agtcggtaat gttgtatcgc aaggatggct ttgtcgcaga tgcagtgtgc  10380
aaggcgcttc ataagctggt tgaacatcac gatgcgcttc gtattgtaat tcagagaacg  10440
gaacaaggag aatattcgct ctggaaccga tccctagtag aaggcgaact cttcagtatg  10500
gaagagatcg atttaacgga tcagtcggat ttcgctgcag cgattgaagc ggaagcaaac  10560
cacattcaag gcagtattga tctacaggca gggcctctgg tcaaggcagg cttattccac  10620
ggcagtgacg gtgatcactt gctgcttgtt atccaccacg cagtcatcga tggcgtgtct  10680
tggagaatat tgcttgagga tctcgcatca ggctatgaac aggcgctgaa tcaacgccaa  10740
gtacgtctgc cgatgaagac agacagcttc cgtacatggg cggaacagct agtagagtat  10800
```

-continued

```
gcgaatagtc cagcgatgga taaggaatct gcttattggc tcggcgtcgc gcagacggaa  10860
gtggccgccc tgcctaaaga cagcgagtgc acggtttcct tgcagcgcga cagtgaatcc  10920
gtcgtgctcg agtggaatcg ggaagataca gaacggcttc tgaagcatgt tcaccgtgct  10980
tacaacaccg aaatggatga tattctgctc acagcgcttg gcagggcact catgaagtgg  11040
cgcggcatcg agcgcatact ggttacgctg gaagggcatg gtcgcgagtc cattatacaa  11100
ggcatggata ttacgcggac ggttggctgg tttacgaccg aatatccgtt tgagctcggg  11160
atggaagcga acgacagtct tggatctcag atcaagaagg taaaagagga tttgcgccgc  11220
attccgaaca aaggaatcgg gtacggtctg ttccggtatt tatccaattc gggcaaacag  11280
gcttggaatg atgcgccaac gacacaaatt cgttacaact acctgggaca gttcgatgcg  11340
gacttgagca ataacgaaat gagtgtatct ccatatgcaa gcggttcgga gattagcgat  11400
gagcaggagc gcaagtatcc gctcgatatt aacggcgtga tcgcagaagg ccaattgaca  11460
ctgggattaa gttacagcgt caaggagtat cgcaaagaga cgatggagga attgggcgat  11520
ttccttacag aatcactgaa ggaaattatc gcacactgcg aatcacagga acggacgcaa  11580
ttgacgccaa gtgatgtctt gtttaaggga cttagcttgg agtggctgga tcggatatct  11640
tcgcaaatgc agcatatcgg cgagatcgag aatgtatatg cattgacgcc gatgcagaag  11700
ggaatgtggt tccacagcgc gatggacagt ctgacggggg cgtaccatga gcagacgatg  11760
ttcacattgg aaggttcgct tgatgtggaa ctgttctcca gcagtctgaa cgaattggcg  11820
aagcggcacg ctgtgttgcg aacgaacttc attagcggcc ctcaaggcga accggtacaa  11880
gtcgtattcc ggaacaaacc aatcggattc tcgttccagg atgtgcgcgc tttgaatgaa  11940
gaggagcagc aatccttcat taaggaagcg gtcagcagtg accaactgct tggcttcgat  12000
ctcgcacaag gtgccctgat gcgcgtatcg gctatccgta caggggaatt gagctgccgt  12060
gtactgtgga gctctcacca tatcttgatg gacggctggt gcctgccaca gctgatgcaa  12120
gagctgttcg atacgtatgc cgccttgctg cagaagaagt cgccggatag aacagcggtt  12180
ccagcttaca gccaatacat tgaatggcta gggcagcagg acgaggaggc ggccgggact  12240
tattggtctg catacttgga tgattacgat caggtaacag agatcccgca agaatcatcg  12300
gcgggaatcg atagcgaacc atataaggct gaaaaatgga gtcgtgaatt ggatgctggc  12360
ttgagcgcat ccattagccg gacggcgaga cagcatcagg ttacgcttaa tactttactg  12420
caagcggcat ggggcgttat tttgcaaaaa tacaatggca caaatgatgt tgttttcggc  12480
agcgtcgtat caggcagacc agcagaggtg ccaggcattg agacgatgat cggcttattc  12540
attaatacga ttccgatccg cgtcaagtgc gagggaagca ccagctttgc ggaactgatg  12600
gggctgcttc aagaacaagc gctggagtcc ggcaagtacg attattatcc gctgtatgag  12660
atacaatctc gcagtgcgct gaagcagaat gcgatcagac aaattatggt gttcgagaac  12720
tacccgatgg acgaacagct agagcaggcg ggcggtgacg agcacggtat gccatcctta  12780
actgatgtag cggtggagga acagaccaat tacgacttca acttgatcgt tgtaccggga  12840
gaacaaatct ctattcggtt tgattacaat gctaaccgct tcgtacaagc agacatggaa  12900
cggttgatgg ggcatttgaa caatattttg gagcagatcg tagacaatcc acggattgct  12960
gtagaagatc tggagctcgc gacggaagcc gagaagtcgg aagtagtcca atcattcaac  13020
gatacattta cgaattaccc tcgagacatg atgctgcatc gcttattcga ggaacaagcc  13080
gaacgacatc ctgatgcagt agccatctcc ttccgagatt tccagatgac gtatcgtgat  13140
ttgaacgatc gggtgaaccg attggcacgt acactgcggg cagtcggagt tggaacggat  13200
```

-continued

```
aagctggtag gcctcatgtc tgaacgttcg ccggatatga ttattggtat tctggcaatc  13260
ttgaaggcag gaggcgggta tgtgccaatc gatccggaat atccgggaga acggattcgg  13320
tacatgcttg aagattccgg tgcgcgaatc atgctggcac agcagcattt aacggggaaa  13380
attccagtca tggacgcatc accacttgat gcaattatca atcttgacac cgaaacatcc  13440
tatgacagca acggttcgaa tcttgaggcg aacacagacg caagcagcga gaacttagcc  13500
tgtgtaatct acacatccgg cacgacgggt aagccgaagg ggaacttgac gacgcaccgc  13560
aatattgtac gtgtggtgag agaaaccgag tatatcgaca tcacaaatca tgacaacgtg  13620
ctgcaaatgt ccagctatgc atttgacggg tcgaccttcg acatctatgg tgcactgctg  13680
aacggggcca agcttgttct tgtaccacat gagacgcttc tggaagtacg gcaattggct  13740
gagttgatcg tacaagagaa gatttcggtt atgttcatca cgacggcgta cttcaacgta  13800
ctggttgatg tccaggcttc ctgcttgagc aatattcggg ctatcttatt cggtggcgaa  13860
cgggtatctg tcagccacgt tcgcaaggcg ctcaatcatg tcgcgccagg tgcactcaag  13920
catgtatacg gcccgacgga gagtaccgta ttcgcgactt gccacgatgt gcacgaagtc  13980
acggagaatg cggtgacggt accgattgga cgtccgatca gcaatacgtc aatctatatc  14040
gttgatgcga acaataagct gcagccagta ggcgttgccg gcgagttgtg cgtggcaggt  14100
gatggattgg cacgaggata tttgaatcgt ccagacttga cggcagagaa gttcgtcgat  14160
tccccgtacg tccagggaga gcggatgtac cgcacgggag acttggcgaa atggcttcct  14220
gacggttcca ttgaatatgt tggccgaatc gaccaacagg tgaaaattcg cggatatcgg  14280
attgagctag gagaaatcga ggcgcagctg ctgaatgtag aggatgtgca ggaagcggtc  14340
gtcgtcgcac gagacactga cacaggcgag aagcagctat gcgcctacta tgtagcgatg  14400
cgtccgcttg aggcgaatca tttgcgcgaa gtgatgggtc aagctatgcc aagttatatg  14460
cttccagcgc actttattca gctggaacag cttccactca caccgaacgg caaggtagac  14520
cgcaaggcgc tgccggctcc ggaagaagga cggagcggag agactttcgt tacgccgcgg  14580
acgccgcttg aagcacagct tgttcaaatt tggcaggatg tgctcggtat tagcagtata  14640
agcgtgacgg atcatttctt cgagttgggt ggtcattccc tgaaggcgac gctgctcgta  14700
aacagactgc atcaggagct taatatcgag ttgccgttga aagacgtatt tcaatatccg  14760
acgcttgaag tgatggcgaa gcgactcagc aatgcggagg gaagcaggca tgtgagtatc  14820
ccggtggcgg ctccaagcca gcattatccg gtgtcttcgg ctcaaaaacg cttgtatatt  14880
cttcatcagc ttgaaggggc ggaactgagt tacaacatgc cgaacatgat gctgcttgag  14940
ggagctgtgg atcttgggcg attggaagaa gccttcaaga gactgattga gcgccatgaa  15000
acgctgcgca ctggatttga gattgtgaac ggcgagcctg tgcaacggat ttacccggaa  15060
gtagacttcg caatcgagca tgtgctcgcc agcgaggaag gtgcttcgaa gcttatgcag  15120
cagtttgtgc gttccttcca attggagaaa ccgcctctgc tgcgaatcgg aattatcgaa  15180
ttgtccgaag aacgttccat tctcatgttc gatatgcatc atatcatctc agacggtacg  15240
tcgatgggca ttctcatcaa tgagtttgtc cacttgtaca gtggggcaga gcttacgccg  15300
ctgcggattc aatataagga ttacgccgta tggcagcaat cggatactca gcagaaggca  15360
atgaagctgc aagaaggata ttggctgaag gtgctgggtg gagagcttcc ggtgctggaa  15420
atgccgacgg actccattcg tccgacaacg caaagcttcc gcggagattt gctgcagttc  15480
gatctagatc cagtaagaag tgcggggctg cggagaattg cagcggagaa cggagccaca  15540
```

-continued

```
atgtacatgg tgcttcttgc gctgtacaag acgatgctgc acaagtattc cgctcaagag  15600
gacattatcg taggtacgcc gatcgcaggc cggaaccatg gagacttaca gccgcttctc  15660
ggtatgttcg tcaatacgct ggccattcga agctatccgg ctgccagcaa gactttctta  15720
tcctatttgg atgaaataaa agaaacaacg cttggcgcct tcgagaatca gaattatcca  15780
ttcgaagcat tggtcgaaca ggtgcaagtg atgcgcgata tgagccgcaa tccggtattt  15840
gatacgatgt ttattttgca aaatgcggat caaggtgaaa tgaagatcga tggggtacga  15900
ctccagtcgg tgccgaatga acacaccgta tccaagttcg atttgacctt ccaagcggaa  15960
gaggatgaag cggaaatcgt gtgcagcatt gaatacgcaa cagatttatt caagcgaggc  16020
acgattgagc gaatggcaag acatttcgaa caattagtcg atgcggtgct ggataacccg  16080
caagcaagtc tgtctaactt gagcatggta accaatgagg aaaaggcgct gcttcaggat  16140
aagttcaatg atacggatat ggcgcatcca agcgacaaga cggttcatga actgttcgcg  16200
gaacaggtgg agcggacacc agatgctgtt gctgtcgtct ctggctgcga gcaattaagc  16260
tacggagagc tcaaccggaa ggcgaatcag ctagcgtgga agctgcgtga gtatggggtg  16320
accgcagagc agcctgtcgg gattattgtc gagcgaacgc tggatacagt cgtcgcagtg  16380
atggccgtac tcaaagcatc gggcacattc gtaccgatcg atcccgagta tcctgagacg  16440
cgtattcgct atatgctggc agacagcggg gctaagctgg tgttggcgca atcggagctg  16500
ccggggatca ttcctgatga cgtccgccta attgatgtac gcgatgagtc cctgtaccaa  16560
ggcgacggag ctgacgtacc gaatggcagc aaaccgtcca acctgctcta tatcatctac  16620
acatccggaa cgacgggcaa tccgaaaggg gtcatgctgg agcacggcaa catggtcaac  16680
ctgctgcatt atcagcagaa aggcacgaac attccgatgc cttcgcggat cttgcaatat  16740
gcgtccggca gcttcgatgt atgctatcag gaaatgttct ctgcgctctt gttcggcgga  16800
agcttgtata tggtcgacaa tgagatgcgc aaggatccgg tgcgcttgtt ccaggaaatc  16860
gaaaagcatg aaatcgacgt gttgttcatt ccagtggcgt tcctgaaatt catcttcgcc  16920
gagccagagt gggccgaagc attcccgcgc tgcgttcgcc atatcattac ggcgggcgag  16980
cagttggtcg tgacaccgca agtgcaggcg tgcttaaagc gactcgatat ctgcctgcac  17040
aaccattacg ggccatcaga gactcatgtc gtgacgacct acacgatgac gccggaaatt  17100
atcgaggttg gtctgccgcc aattggcaag ccaattgcga acacgagcat ttacatcgtg  17160
aacgacagct tcgagctgca gccaatcggc gtgaagggcg agctcttcgt atccggggca  17220
tgtgtcggac gcgggtactg gggaagaacg gacttgacgg aggagaagtt cctagataac  17280
ccgttcgtcc ctggtgagcg gctatacaag acaggtgacg tagcgcgctg gcttccagac  17340
ggcagcatcg attatgtggg ccgaagcgac catcaggtga aaatccgggg cttccgcatt  17400
gagctgggcg aggtggaatc gcagctcttg catgtaccgg cggtacagga ggcgaccgtg  17460
gtggcactgg aagatcatgc gggccagaag cagctgtgcg cgtatttcac agcagagcgc  17520
tcgctcacgg cgggcgagct gcgggcagta ttgtcgcagg agctgccagg ctacatgatt  17580
ccgtcctact tcgtacagtt ggagcggctg ccgctgacgc cgaatgggaa gatcgatcgg  17640
agagcgctgc cgaagccaga aggcggcatt gagactggaa cggagtatgt cgcgccgcgt  17700
acagatacgg aagcaagact tgcacgcatt tggcaggatg tattggggtt accgagcgta  17760
ggcgtgaagg acaacttctt cgagctgggc ggccactcgc tgcgggcaac gacgctggtg  17820
agcaggctgt acaaggaaat gaacgtcaac ttcccgttaa gaggtgtgtt ccgtcatccg  17880
actatcgagg agatgtctca agcaatctcg caaatggaga cctcatggta tacagccatt  17940
```

ccgattgccg aggagcaaga atactacccg ttatcttcgg ctcagttgcg actctatatc 18000
atgagccagc tggaaggaag cgagctcagc tacaatatgc ctggcatgct ggtgcttgaa 18060
ggacagctga atcgagatca attccagaca gcatttttga agctcatcgc tcgtcacgag 18120
actttacgta ctggctttga gatggtagac ggcgagccga tgcagcgcat ccatcgcaat 18180
acggaattcg ctattgacta cagacaggta tccgaggacg aagttccgga gatgattgga 18240
caatttatcc gacagttcga cctggagcat ccgccattat tgcgggtcgg gttgttcgaa 18300
gttgggcagg atcggcatat tctcgtcttt gatatgcacc atatcatttc tgacggtgtc 18360
tcaatgagca atttagttga tgaatttact cgattgtatg cgaatgaaga acggcctccg 18420
ctgcgtatcc agtacaaaga ttatgcggta tggcagcagg cgagagagaa tctcgaacgg 18480
aggaagcgcc aagaagacta ttggatgagt gtgctgcaag gcgatcttcc aaacgcagag 18540
ttgccgatgg attatgatag aacggcggtt cgcagcttcg atggggagca gatcgaattc 18600
gaaattaacc cggttgtgac gggacagttg aaccaacttg cttctaatca tgagtgcacg 18660
ctgtacatgg tcttaatgtc cgcctatcag attctgttat ccaaatattg cggtcaggat 18720
gacattattg ttggtactcc tgttgcgggt cgcaatcatg ccgatttgga gccgttgatc 18780
ggtatgttcg tcaataccct cgcgattcgt aaccgtccgc agggcgataa aacgttccaa 18840
tcgttcttgg cagaggtgaa agagtcaaca ttaggggcat tcgaacatca ggagtatcca 18900
ttcgaggaac tgattgacct cttgaagctg cagtgggaga caagccgcaa tccattgttc 18960
gatacggtgt tcgtcctcca gaatacggag gagcgtgaag ccggaatcgg tggattgacg 19020
atatcacctt acgtgacaga tgactcggtc agcgcgaagt tcgatctgac gctatctgta 19080
tcggaagaag acgatgggat gaagggaagc ttcctgtatg cttccaagct gttcaaagca 19140
gctggcatac acagaatgat gagagattac ttgtcaatcc tgtcccaagt atgcgagaac 19200
cctcgcatcc gcattcaaga tatttcgata agtggacagc agacacagga aaagagcaag 19260
atcgacacga ttgagttcgc gttctaa 19287

<210> SEQ ID NO 7
<211> LENGTH: 9450
<212> TYPE: DNA
<213> ORGANISM: Paenibacillus alvei A6-6i-x

<400> SEQUENCE: 7
atgaagtcgg tatatgagaa agaagaagcc tattggaatg gaatgtttga ttcggatgac 60
agcatgagca tattgccata ttgcagtaca cacggaagag aagcgaacgc ggatacgaat 120
gccgccaaag tgtctatgat ccgtgcactc ccaacagatc tgtcagacag aatgaacacc 180
cttgcgaacg gttcggatgt tgccctgtac atgattggat tggcaggggt cacttgcttg 240
ctccaccatt atacgaaccg agaaaatgtg cttgtaggca tgccgacaat agatgaatcg 300
gaagatgact catcacctcg tgacgtactc ataatgaaga cgaatttgac acgcggaagc 360
agcttccgtt ccgtattggg gtcaatcaag acagccgtcg gaggagcatt ggagcatcgt 420
catcttccgt ttcggaagat ggtacacaac ctaaacctgg agatggacac gaacggactt 480
ccggtgatga atacggtagt gtctttttca gctatacata ccgcttctat cgaccttagc 540
gtcagctccg acgtcatatt ccgattcgat gcgaaggacg atggccttca tttggaggtg 600
ctttatgatg aaagccgcta tgatgcctcc tatattgcca ctctattcga acattttttc 660
cgactgcttc attttgtgtt attccagccg gatcagccta tcggcaatac cgagttattg 720

-continued

```
tccgctgagg agaagcatcg cttgcttcat gaatttaacg atgtgtggac ggatttccct    780
cgtcaagcaa cgctatatca gttcattgag gaacatgcgg agcgacagcc agatgcaatc    840
gcggtttctt atgaagatac caagctgacg tatcgtgagc tgaacgcaag ggcgaatcga    900
cttgccagaa cacttagatc tgaaggtgtg cagacagaag cactagttgg gctcatggct    960
gaaagatcga tcgacatgat tgttgggatg cttgccgttt tgaaggcggg aggcggctac   1020
gtcgcgattg atccggagta tccggaggag cgcgttcgct acatgctgga agattcgggt   1080
gctcgtgtca ttctggttca gcagcatttg cagaatcgtg tgccaaatac ggaatcagca   1140
gctagactcc tcacacttga cgatgagcag tcttatcatg aggatgcttc gaatttggaa   1200
tcgaggagta cagctgtaga tttggcttgc gtcatctaca cttcggggac aacgggtaat   1260
cccaaaggta acctgacgac acaccgcaat atcgtacgca tcgtgaagaa taccaactat   1320
atcgaaatta cggagcagga taaggtactg caattatcga gttattcttt cgatggctcc   1380
gcattcgata ttttcggggc attaacgaat ggggcccaac tggttcttgt tcctcatcat   1440
acattgcttg atgcacgcaa gctggcggag ctgatcgaaa cggaacgaat atcggtcatg   1500
ctgattacta ctgcttattt caatgttctt gttgacgtaa acatatcctg tctgcgtcat   1560
atccgcgcga tattgttcgg aggcgagcgc tcctctgtcg cgcatgtgcg tagagcactt   1620
gaacagacag gtccgggaag actgaagcat gcctacggcc cttctgaaag tacggtatat   1680
gcgacatggc atgatgtgac agagatttcg gagcgagccg taagtgtacc gatcggtcgt   1740
ccaatcagta atacagccat ttatatcgtc aatgaacgaa atgatttaca gccgataggg   1800
gtatccggtg agctgtgtgt agcgggagaa gggttagttc gcggatattt gaaccgtcca   1860
gaactgactg agcagaagtt cgttgataat ccgttcgtac cgggagagcg catgtatcgt   1920
actggggact tggcgagatg gctgccggac ggaacgattg aatatgttgg ccgaatggat   1980
gatcaggtga aaatcagagg ccatcgcatc gagattgggg aagtagaggc gcagctgctc   2040
aaagtggcgc cgattcagaa ggcgacgatt gtcgtccgag gccgcgagga cggagagaag   2100
cagctgtgcg catattatgt agcagatcgt ctgcttcctg caggcgagat tagaacaatg   2160
cttgccaaag aactgcctag ttatatgatt ccggcatact tcatccagct tgaacagatg   2220
ccgttgacga ctaacggcaa agtagatcgc aaagccctgc cagaaccgga agagcacgta   2280
caagcagaga cagaatatgt ggcgcctaga agtgaacagg aaattcggct tgcgagagtc   2340
tggcaggaag tgctcggtct aagccgagtc ggtgcaaagg atcatttctt cgagctgggc   2400
ggccattcat tacgagcgac gacactggtc agcaagctgc acaaagaaga gaatatcagc   2460
ctgtctctgc gcgatgtgtt ccgcaatcct actttggaag cgatggccgc gctcatggaa   2520
gatgctcaag gacgcaaatt cgcacccatc ccgacagttg aggagaagga tgtatatccg   2580
gtatcttcgg tgcagaagcg attgttcatt ttgcatcagc tggaaggagc tgagcagagc   2640
tataacatgc caggggcatt actgcttgag ggcgatgttg accggaaccg attggagtat   2700
gcattccgtc agctgatcac acgtcacgaa acgcttcgca ccggctttga aatggtgaat   2760
ggagaacctg tgcagcgcat ttatccgact gttgattttg tagtggaaga gatgtcagcc   2820
ctggaagggt cggaagtcga ggagcaaatc cggcaattca ttcgcgcttt cgatctgtcc   2880
acagcgccac tgttcagggc ggggctgatt aagcttgctc cgcagcgtca cattctcctg   2940
ttcgacatgc accatatcat ttcggacggc acgtcaattg gcattatgat cgaggaattc   3000
acaagcttat acagtggcaa tgagcttgag ccgcttcgca ttcagtacaa ggactttgct   3060
gcgtggcagc gttccgagga gcagatcgag cagttgaagc gccaagaaac ttactggttg   3120
```

```
cagcaaatgg aaggcgtact tcctgtgctt gagctgccta ctgattatgt acgtcccgct   3180
gtacagagtc atgatggtgc gctgttcgag ttctcgcttg atcgcgagca gagccaagac   3240
ttgaggaaat tagccgccga tacgagaacg accttgtaca tggtgctgct agcggcatac   3300
acgatcatcc ttcacaagta ttcaggccag gaagacattg ttgtaggaac accgattgcg   3360
ggtcgaacgc atgacgatgt gcagccgctt atcggtatgt tcgtcaacac gctggcgatt   3420
cgcaattatc cttcaggatc caagtctgtg cttacctact tggaggaaat caaagaaacg   3480
acgctgggag cgttcgagca tcaggactat ccgtttgagg aactcgtgga gaacgtgcaa   3540
atttcgcgag atatgagtcg tcatccggtc ttcgacacga tgttcgccct tgagaataca   3600
gagcatcggg aattcgatct ggatggactt caggtgaagc catacggtgc tgaatacggc   3660
atggctaagt tcgacttgaa tctgaccgta acagaagatg gcgatggact ctactgcacc   3720
atggagtatg ctacagcatt gtacaatcga tcgaccattg aaaggctttg cggccatttc   3780
ctgcaggtcg ttggaagcat gactcataat ccgcaagcag caatctcatc actgcaaatg   3840
gtaaccagcg aggagaaggc tcaactgcaa catgaattca atggtacggt tatggagtac   3900
tcaagtgaca agacggttca tgaactgttt gcggaacagg tggagcggac accggatgct   3960
gttgctgtcg tctctggcag cgagcaatta agctacggag agctgaaccg taaggcgaat   4020
cagctagcgt ggaagctgcg tgagtatggg gtgaccgcag agcagcctgt cggcattatt   4080
gtcgagcgaa cgctggatac agtcgtcgca gtgatagccg tactcaaagc atcgggcaca   4140
ttcgtaccga tcgatcccga atatccagag acgcgtattc gctacatgtt ggcagacagc   4200
ggggctaagc tggttttggc gcaatcggag ctaccaggga tcatttctga tgacgtccgc   4260
ctaattgatg tacgcgataa gtctctgtac caaggcgacg gagctgacgt accgaatggc   4320
agcaaaccgt ccaacctgct ctatatcatc tacacatccg gcacgacggg caatccgaaa   4380
ggggtcatgc tggagcacgg caacatggtt aacctgctgc attatcagca gaatggcacg   4440
aacattccga tgccttcgcg gatattgcaa tatgcgtctg gcagcttcga tgtatgctat   4500
caggaaatgt tctcagcgct cctgttcggt ggaagcttgt atatggtcga caatgagatg   4560
cgcaaggatc cggtacgctt gttccaggaa atcgaaaagc atgaaatcga cgtgatgtac   4620
attccagtgg cgttcctgaa attcatcttc gccgagccgg agtgggcaga agcgttcccg   4680
cgctgcgttc gccatatcat tacggcgggc gagcagttgg tcgtgacacc gcaagtgcag   4740
gcgtgcttga agcgactcga tatctgcctg cataaccatt atgggccatc ggagactcat   4800
gtcgtgacga cctatacgat gacgccggaa gttatcgagg ttggtctgcc gccaatcgga   4860
aagccgatcg cgaacacgag catttacatc gtgaacgaca gcttcgagct gcagccgatc   4920
ggcgtgaagg gtgagctcta cgtatctggg gcatgtgtcg gacgcgggta ctggggaaga   4980
acggacttaa cggaggagaa gttcctagat aacccgttcg cccctggtga gcggctgtac   5040
aagacaggtg acgtagcgcg ctggcttcca gacggcagca ttgagtatgt gggccgaagc   5100
gaccatcagg taaaaattcg gggcttccgc attgagctgg gcgaggtgga atcgcagctc   5160
ttgcatgtac cggcggtaca ggaggcgacc gtggtggcac tggaagatca tgcgggccag   5220
aagcagctgt gcgcgtattt cgcggcagag cgctcgctca cggcaggcga gctgcggcaa   5280
gcattgtcgc aggagctgcc aggctacatg attccgtcct acttcgtaca gttggagcgg   5340
ctgccgctga cgccgaatgg gaagatcgat cggagagcgc tgccgaagcc agaaggcggc   5400
attgagactg gaacggagta tgtcgcgccg cgtacagata cggaagcaag acttgcacgc   5460
```

-continued

```
atttggcagg atgtattggg gttaccaagc gtaggcgtga aggacaactt cttcgagctg   5520
ggtggtcact cgctgcgggc aacgacgctg gtgagcaggc tgtacaagga aatgaacgtc   5580
aacttcccgt taagaggtgt gttccgtcat ccgaccatcg aggagatggc gaaggcgata   5640
accgagatgc atcaagaact ttacacggaa atacctatcg ctgaggaaaa agcctattat   5700
ccgttatctt cagcgcagaa acggctgttc attgtaagcc agctgacagg agccgaggta   5760
agctataaca tgccgggagt gctgattctc gaaggagagc tggatcgtgc gcgattcgaa   5820
cgggctttcc agaagctgat cgaccgacat gaatcgctgc ggacaagctt cgagacggta   5880
cgcggtgagc ctgtgcagcg cattcactcg caggtggagt tcgctatcga atatcacctt   5940
gcagcagaac aagatgcaga ggcgctgatc actcatttcg tacgtccatt ccagcttaaa   6000
caagcaccgc tgctcagagt cggattgatt gaaactggac atgaacgtca tattctgatg   6060
ttcgacatgc accatatcat ttccgatggc gtaacgatgg ggcatgtcgt gaatgaattc   6120
tcccggatat atgcaggcga tcaactgccg gcgctgcgta tccaatataa ggactatgct   6180
gtatggcagc aatccaatga atatgcagag aagcttgcgc atcaggaatc ctattggctg   6240
aagcaattgg acggagaact gccgacgctc gaattgccga ccgattatgt gcgaccggct   6300
gtacagcagt tcgaaggga tgtggccttg ttcaccttaa cgaacagtca ggccgagcag    6360
ttgcaacgat tagcggcaaa ctacggcgca accttataca tggttctgct tgcagcatat   6420
accgtgatcc tgcacaaata tacgggacag gacgatatca ttgtcggtac accgatcgcg   6480
ggccgcaacc atacggaatt ggagccgctc gttgggatgt tcgtcaatac gctcgccatt   6540
cgcaattatc caactggtga gaaatccttc gcagaactgt tggccgaggt gaaggatacg   6600
gccctcgccg cattcgagaa tcaggattat ccgttcgaaa cgttggtaga gaaggttcat   6660
aagtctaggg acatgagccg aaatccagtg ttcgatacga tattcagtgt agagcatgaa   6720
cagcagagtt ccttccatat tgatgggctt cggataagtc catacccgca cagccattct   6780
gtcgcgaagt tcgacttaac cttccatgcc gaacagaatg aagaagggat actatgtggt   6840
ctagggtatg cgactgcttt atatgcgaaa gagaccgcga ggcggatggg agaacatttc   6900
gtgcaattaa tagatgccat catcgcagaa ccgaatgcga agctgatgtc tctgaatatg   6960
atgagcctgc aggaaagaga gcaggtcaag ctggtattta atgatacgat aacgaattat   7020
ccgcgggaga agacgattca acatttgttc gaggagcagg cagagaaatc gccggatgcg   7080
gttgccgtcc aattcggagg agaagggctc acataccgcg agttgaatga acggtcgaat   7140
cgcttggcga gaacactgcg aggtaagggt gtaaaagccg gccgctgcgt aggtctaatg   7200
acggatcgtt cgctagacat gattgtagcg attatggcga ccctgaaggc aggcggggca   7260
tatgtgccaa ttgatccgga ctatccagag gaacgcattc gatacatgat cgacgattcg   7320
ggaacatcgc ttctagtcgt tcaacgtcat ttgcaggcga accatattcc tgcggattgc   7380
atggttgtac ttgtagatga tgagggctcc taccacgcag acggcacgaa tctggagcag   7440
cataatgggg cttctgatct cgcctacgtc atttatacgt caggtacaac gggaatgccg   7500
aaggggaatt taacaactca ccgcaacatc gttagagtag tgcgggatgc gaaatatatc   7560
gagatcgatc agcatgacac ggtgctgcaa ttatccagct acgcttttga cggctcgact   7620
ttcgacatat ttggcgcctt gctgaatgga gcgaagcttg tcctgataac gcgcgaggta   7680
gtactcgacg ctggacgatt ggccgacacc atcgagagcg agaagatttc ggtcatgttt   7740
attaccaccg cctatttcaa tctgctcgtc gacctgagag tggacagcct gcgccatatg   7800
cgtgcgatat tgttcggtgg ggagcgcgca tctgtgagcc atgtgcgcaa ggcgctccgg   7860
```

```
catttgggtc caggcaagct taagcatgta tatgggccaa cggagagcac cgtatttgcg   7920

actagccaca acgttgatga agtagctgac agcgccgtta ccataccgat cggacgccca   7980

attggcaata cggccgtata tattgttggc gagggagacg ttctgcagcc gattggtgta   8040

gctggtgagt tatgcgtagc gggcgatgga gtagccatag gatatttgaa ccgtccagat   8100

ttgtcaggag ccaagttcgt gaataatccg ttcgttccgg gtgatcgcat gtaccgaacg   8160

ggtgacttgg caagatggct atcagatgga acgatagagt atgtgggacg gaaagacgat   8220

caggtgaaaa tccgtggtta tcgaatcgag cttggtgagg tcgaagctca tctgttagac   8280

cttgaggcga ttcaagaagc tgtggtcatc gtcagggagg aaagtgacgg gcagaagcgc   8340

ctatgcgctt actatgtagc agctcgtctg attacggctg gtgagatgcg gatagctttg   8400

gctcagcagc tcccgggata tatgcttcca tcctacttcg tacagctcga taagcttcca   8460

ctgtcaccga acggcaaggt gaaccggaag gcacttccgg cccctgaatt gcatgtgcag   8520

gcagcctcgg aatacgtggc cccgcgcacg ccgcaagaag tactgcttgc tcacatatgg   8580

agggaggtgc tcgggctagg tcaggtaggc gttaaggata atttcttcga gcttggcggt   8640

cattccttaa gcttaatgag gctagtggag cgcgtctata ccgagactga ggttgaaatc   8700

ccaattcaca gcgtattccg ggagccgaca attgaagcga tggcgtacga aatgttgaaa   8760

tctgaacttg ctggcaaggc aggaaatcac ttcatgaaat tgaacgaaaa cggtcatatc   8820

cctgtcttct gcttccctcc gggacttggc tacggtctca gctacttgga actggccaag   8880

cagctggatc atcactgcat cctgcatggc attgacttta tcgatgatgc tgaaactcgg   8940

gaggaactgc ttgaacgata cgtgaatgcg atccttgctg ttcaaccgca gccgccattt   9000

atattgttag gctattctct aggtggcaat ctgacgttcg aggttgcgaa agcgttggag   9060

tgccgagggt atccggtgtc ggatgtcatc atggttgatt ccttgcggaa gctgaaggtg   9120

catgaagtag acgaattcga cggcgacatc gatcaaatga ttgatggtgt ggaggaactg   9180

aaagaaatgc tggttcacca tcctcttctc cgcgatcaag ttaagaacaa gatgagggcg   9240

tactggtcgt acgcgactga actcgttaac tccgacatca ttgatgccaa tattcatgca   9300

ctgatggcgg agccatccga ggtgaaccag gcaggacggg gagcagctcg cgacatggca   9360

ggaggctact cgcggcaggt atgcggagta caacctacgc ggtgtgcacg aagaagtgct   9420

tcaaccgcct ttcttggaag cgaacgctaa                                    9450
```

```
<210> SEQ ID NO 8
<211> LENGTH: 19968
<212> TYPE: DNA
<213> ORGANISM: Paenibacillus alvei TS-15

<400> SEQUENCE: 8

gtgaacgcga atcctaacga atggtatcct ttgacgcaag cgcagcgcag aatctggtac     60

acagaaatga tgcatcctaa tacgtcggtt actaccgttg ctggaacaat gtacatacga    120

ggcaaggtag acgttgagat tttgaaaatg gcgatatatc aagtgatcat gcagcatgat    180

gccttccgaa tacgaatcgc aatgacagac aatcagccga agcagcaatt tgctcccgta    240

gagcaaatcg tccctcacgt tgattactta gagtgggata atcagattga agctgagagt    300

tggttacagc ggtttaatca tattcctatc catatgttcg acccagcgtt ataccacttt    360

gtcatattta acgtcaatga tgaggaaaca tggttcaatt tgaaaatgaa tcatattgca    420

acggatggag tctcttctca tcttatcgct tataaaatca tgaagaatta taccgcaatg    480
```

-continued

```
gtgagtggca acgcggacac ggacgaacaa gagagcactt acctggacta catattcgcg    540
gaacgagagt atgaacaatc cgatcgatac gcgaaagata aggcatattg gctggataag    600
ttcagcacaa tgccagaagt gataggcatc aaatcttacc ctcctcattc aatcggcaca    660
gaggccagtc ggacaagcac cacggttagc ggagaaatgt acgagaagct ttaccgattt    720
agccagcagc acaatatcag tctctttact ctatttctag gttctttata cgcatttcta    780
tataagacga cagggaacaa cgatattgct gtcggtgccg cttatgcgaa tcgaacttcc    840
aggcaagaca aggatgcgct gggcatgttc gtaagcacgg tagccgctcg tttgacgatt    900
accccagacc aagacgtact aaccttccta cataacgttg ccaaagagca aaaagcaatt    960
ttgcggcatc agaagtatcc atacaaccag cttattcttg atttaagaga acaaaataat   1020
agtgtcgaga ttcaggattt gtaccgtata tccattgact atatgccgat acgctggtcc   1080
agttacggag aactagctgt ccgccaacgc agcagctttt gcggtcatga ggtggacgat   1140
tttgcagttc acgtagaaga tatggtggat gataatcaga ttattttcaa tatcgattat   1200
cgcaagcagt tgttcgaaga gcatgaggtc attcgtatga tcgaacaaat gatgaccatc   1260
gttgatcaga tgttgaataa tccgagccag aacttgcagc agttgtccat gatcagtgat   1320
aaggaagctc agatcatcct gacacgcttc agcaacggga attggtcaac gccgcagcca   1380
gttggacgaa cgattcacca gttgtttgag gaacaggtcg aacgcacgcc tgatcaggtc   1440
gctgtcgtgt tcggagatcg gcacctaacc tacaaggaac tgaacgaaca agccaattgc   1500
ttcgctcgaa cattgcgagc ccatggtgta gcagcagagc aattcgtagg catcatggca   1560
gaccgctcga ttgagatggt catcggtatt cttgcaatct tgaaggcggg tggagcctac   1620
gttccgatag atcctgagta cccagaagaa cgcatcctgt atatgctgga agactcaaat   1680
gcaagagtac tcgtatcgca aagtcatttg cagacgcggg tcggttacac aggaacatgg   1740
gtattgcttg ataatgagaa cgactacgaa tcaagccgcg ataacttggt gcctgtcaac   1800
gaagcacatc atttggcgta cgtcatctat acatccggta caactggcaa gccgaagggc   1860
gtcatgattg agcataagca gattactgcc ttgggggatg catggaagca tgcctatcaa   1920
ttagatgaac cgggaattcg gacgctgcaa tgggcaagct tctccttcga cgtatttacg   1980
ggagacatgg tgcgagcgct gctgtacgga ggcgagctta tcatctgccc aagcgaagcg   2040
cgagctaacc ctgaagcgat atgtgagcta atcgcaagac atcgcatcca catattcgaa   2100
tcaaccccag cccttgttat tccgttgatg gaatatgtgc atgaacaagg caaggatgta   2160
agcagtctgc gcctgctcgt tgttggctcg gatcattgcc cggccgcgga atatcgcaag   2220
ctgattgaac gattcggctc gcaaatgaga atcctgaaca gctatggcgt gactgaggct   2280
tgcgtcgatg cttgctatta cgagagaaat tgtagtgtgg attccatcac aatgctcccg   2340
ataggtaaac cactgccttc agtatccatg tacattctag acgagaacaa ggcgctccag   2400
ccaatcggaa ttgtaggaga gctctacata ggtggagccg gtgtcggcag aggttatctg   2460
aaccgtgatg acttgacagc agaaaaattc gttgatgacc cctactctca aggaaagatg   2520
tatcggacag gtgatttggc aagatggctg ccggacggaa acattgaata ccttggaagg   2580
ctcgatcatc aagtcaaaat tcggggtaat cggatagaaa taggggaaat tgaaacacgc   2640
atgctgcaaa catcacttgt gcgggaagcc gttatcgtag cgcgcgagga tgaaaatgga   2700
ctgaaagctc tgtgcgccta ttatgttgcc gatagcgaga tatccgtaca gcaattgcgt   2760
tcaaccctgg cagaacaagt acctgattat atgattccgt cttatttcat gaagctggaa   2820
cgattgccgc ttacgccgaa cggcaaaatc gatcggaatg gattgcctgc accatctggt   2880
```

-continued

```
caggactatt ccggcaagat ttatgtggag cctcgtaacc aagcggaaca aacgctggtt   2940
agcatctggc aaatggtgct tggagtcaag cgagttggca ttttggatca tttcttcgag   3000
ctaggtggag attcgatcaa gtccattcaa gtatcatctc gcatgcagca agctggatat   3060
aagctggata tccgggatct gttcaagtat ccgaccattg aacagataag tccacatctg   3120
gtggaggttc agcgaaaagc tgagcaggga gaagagaacg gtgaggttgg gctcactcct   3180
atattgcgct ggtattttga acgagatgaa gcgagtctgc atcattacaa tcaatccatc   3240
atgctgcacc gcaaggatgg attcgatgag gcggcacttc gcaatgcact gcacaagatt   3300
acggaacatc atgatgcgct gcgcatggta ttccgccgta cggaacaggg agaatacgcg   3360
gcctggaacc ggagaatcga agaaggcgag ctttaccgtc ttgatgtgtt ggatatcaag   3420
gaacgttccg ctggcgatga aagcgaagaa tctcttcata acatgctcat ggcagaagct   3480
gatgcgattc agaatgggtt caatttagag gcagggccac tcgtaggtgc aggattgttc   3540
cgctgcccag atggagatca tctgcttatc gtcattcatc atgctgttat cgatgccgta   3600
tcctggcgga ttttgcttga ggatcttgct accggatacg aacaggcact tctaggcagc   3660
gagattcgtc tccctgccaa gagcgattcc ttccggttat ggtcaagaca gctttcagca   3720
tatgcgcagc agtctaacat gaacgaggag ctgaaatatt ggcagcaagt cgcacagacg   3780
acgattactc cactgccgac ggattacgct gggactgctc ttcaacttga tagtgaatcg   3840
gtaacggtcg aatggagtgc taacgagacc gaactgctgt tgaagcaggc gcatcgggcg   3900
tataacacgc agatggacga tcttctttta acggcactcg gcattgcatt ccggagatgg   3960
tgcggacatg agcgtatccg aattaatttg gaaggacatg gtcgggagtc gatcctgcca   4020
gatctcgata tcacacgtac ggtaggctgg ttcacgagtg agtatccgca gcttctcgag   4080
gtgggctctg aggaagaact gccgcgaatc atcaagtcag tcaaagaaga tttgcgcagc   4140
attccgaata aagggatcgg ttacggcatt tgtcgatatt tatcagacaa gagtatgcag   4200
gatgattggg gaacagcacc tgaggttagc ttcaactact tggggcagtt cgaccaagat   4260
ttccagaaca gcgggttttc tccatcgccg tattctaccg gcagcaatat tgggggagat   4320
cagctaagac cttatctgct agacatgaat ggaatggtct cggatggcaa attgcagctc   4380
gacatcagct atggacggac gcaatatcgt gttgagacga ttgagcgatt ggcaagcttg   4440
attcgggaca gcttacttga aatcatcgat cattgtgtgg ccaaagagca aacagagctc   4500
acgccaagtg acgtgtcatt gcagcgcatt agcattcaag agttggagca gatcgttgaa   4560
cggacaagtg gtatcggtga agtagaggat atctatgcat taacgccgat gcagaaggga   4620
atgtggttcc atacagctat ggacagccag gcgggagcct atttcgaact tacgcgctta   4680
acgcttaagg gagcgttgaa catcgaagcc ttcgccgcaa gctggaatga actggccgct   4740
cggcatgctg tattccgtac caacttcctc gtcgattcga acggtgaacc gctgcaagtt   4800
gtatttcgta gcaagcgcat tagcgtgaag cacgaagatt tgcggtccct gaattcatat   4860
gagcaggctg tggcgattga gaacgaagcg gccaaggaac gcgcacaagg ctttgacctt   4920
gagaatggga atgtcatgcg cgtgtccgta ctccagacgg cagacgaagt gtatgaagtg   4980
ctgtggatct cccatcacat cgtcatggat ggttggtgcc tcccgctcgt cgctgctgaa   5040
gtattcagta cgtactccgc actggtggaa gacaagaagc cgattcttgc ttcggtacct   5100
tcctataatc aatacattca atggctggag cggcaggatg aatccgcagc cgcggcctat   5160
tggaaccatt atttgtctgg atttgaagag acgacagaac ttcctcatag caaggggcgc   5220
```

-continued

```
agacattctg gtcaatatga agcaggtcag gttcagatcg atctaggcac aagcctgagc   5280
ctcgctctca atcaagttgc aacgcagcat caagtgacac tgaatacatt gctgcaggca   5340
tcatggggaa tattgctcca gaaatacaac agaacttcag atattgtatt cggcagtgtt   5400
gtatctggca gaccggcaga actagtcgga atcgaagaga tgattggctt attcattaat   5460
acgattcccg tgcgcgtgag cagtcaggcc catgagagat ttatagaagt aatgacgcga   5520
atgcaagacg atgcattgtc atctgccaag catgactact atccgttgta tgaaattcaa   5580
gcacaatgca cgctgaagca ggatctcatt aatcacatca tggtacttga aaactacccg   5640
atggagcagc agctcgatca gtttaacagt tcggacggca gtggactgaa gctgacagac   5700
gtaaccgtat cagaacaaac gaatttcgat ctgaacctca tcatcattcc tggcgacaat   5760
atcgtcattc gtttcgattt taataaacaa gcactcgcag aaacggatat gaacgtgttg   5820
aaggagcatc tgttgcatgt actggaacaa gttgcatcga atccgcggat atccatagga   5880
gagctgcagc tggcgacgga tgaagagcgt gccgtaatga tgagcgaatt taatgatacg   5940
ttcgtggctt atccgcgcga gaagtcgatc cacagattgt tcgaggagcg agctaaacaa   6000
gagccagacg cgctagccgt cgtgtttgga aatgatcaga tgacctacgg agcgttgaat   6060
gccgcagcca accgaatggc ttggagactc cggtatgctg gagtgacgag cggtgaactg   6120
gttggcatct gcgcggatcg ctcgctggaa atggtcgtcg gcttgctggc aattatgaag   6180
gccggtgggg cttatgtacc gatcgaccca gcttaccctc aagagcggat tagcgcaatg   6240
cttgaagata catccattgc gacgatggtt acgcagaggc atctgtgcag cttatggcct   6300
gaacatctca acgtgattgc gctggatgat aacgagacag acgtaagtaa ttcaatggaa   6360
gatgtagaaa gtaacctgcc tattgatggg gcgggagacg atttggcata catcatctat   6420
acgtcagggt ctacgggaac gccgaaaggg gtctgcgtaa cgcaccgcgg agtcgtcagg   6480
ctcgtatgcg ccgcgacgta tgtcgagatc aacagctcgg atgtcttctt gcaaggttcc   6540
acaatctcgt tcgatgctgc aacctttgaa atatggggca gtctgctgaa tggggctgcg   6600
ctggccatcc tgcctcctgg caatgtgtcg cttacagatt ggagcgaagc gattcagcgt   6660
catcgggtga cgacgttgtg gatgacagct ggtttgttcc aggtcatggt tgaacagcaa   6720
attgagggct tctacggagt caagcagctc ctggtaggtg gagatgttgt atctcctaca   6780
cacgtgcgca aagtgatgga gaagcataac ggtattaggg tgattaatgg ctacgggccg   6840
acggaaaata caaccttcac ctgctgccat accattacgg ctgctgattt ggatcgaggc   6900
tcaattccga ttggccaacc gattggcaat acgcgagtgt atgtgctgga tgaagctggg   6960
aacgttcttc ccgttggcgt atgcggcgag ctgtatgcgg gcggagatgg tttggcacga   7020
ggatacttga atcgtccgga attgacggca gagaaattcg tgaatgatcc atttatccca   7080
ggcgaacgct tgtatcggac aggtgatttg gcgagatggc tgccggacgg ttcgatcgaa   7140
tttatcgggc gctgcgacga acaagtgaag attcgcggtt accggattga accaggtgag   7200
gttttggcct atcttctgag gatcgatgaa gtaggtgagg cggctgtaat cgcgcgggag   7260
gattcgagtg gacagaagga gctatgtgcc tatttcacag cggaagttga gctatcggct   7320
agtggactaa gggagacact ggctcgtgaa ctgccagctt acatgatccc atcgcatttt   7380
attcagatcg aagaacttcc tttgacacct aacggcaagg tggatcgcag agccctgcct   7440
ctaccagagg aagggctgcg tatgaacttg aagatccaac cgcgtacgga actggaagct   7500
aagcttgcac tcatctggca agatgtgctt ggtctcgaga acgtaggcgt tacagattca   7560
ttctttgaac tgggtggaca ctccttgcgc gcgaccaccc tcgttagcaa ggtacatcgg   7620
```

-continued

```
gagttgaata tagcgctgcc gctgcaggat gtattccgct acccgacgat tgaacaaatg   7680
tctctcgcca tacaggggat gcagaaggaa agctttgctt ccatacctcg ggtggaagac   7740
cgagaatggt acccggtatc ttccgcgcag aagcggctgt tcgttcttca tcagatggag   7800
ggcgcagaac tgtcctacaa tatgccgggc gtcatggcga ttgaaggcaa gctccatcgc   7860
gatcgcttgg aagcagcatt ccgcggcttg attgcaagac atgaagtgct gcgtaccggg   7920
ttcgaaatgt acaacgggga acctatgcag cgaatttaca gcgatgtaga atttactgtc   7980
gagcatggga tagttggagc tgcatcggaa gcggagtcag tcattcgctc gtttgtacgg   8040
gcgttccaat tgaataagcc cccgctgctt cgggtcggac tgatcgaagt ggacgcggat   8100
cggcacctgt tgctgttcga tatgcatcat atcatttcgg acggggcatc catgggtata   8160
ttgctagatg aattcgttgc actgtatagc ggcgaagaat tgcctgaact gcgtcttcag   8220
tacaaggatt atgcttcgtg gcagcaatcg gaagattact tgtcaaggat ggaagaacag   8280
aaagcgtatt ggctggagac attgcgaggc gagcttccag ttctgcagct tccagtggat   8340
tacactcggc ctgcattccg cagctttgca ggaagcacgc tggaattcat cgttcctgcc   8400
gacaaggcag accagcttaa gcagcttgga gcaggttcgg atgccacaat gtacatggtg   8460
ctgctggcgt tgtatacggc cttgcttcac aaatataccg gacaagaaga cgtcatcgtg   8520
gggatgccga tagccggtag aacgcatgca gacatcgagc cgcttatcgg tatgttcgtc   8580
aacacacttc cacttcgcca ttatccggct ggagagaaga cgttccgctc cttcctaggg   8640
gaggttcggc aatccacatt acaagcatac gaacaccagg aatatccgtt cgaggagctt   8700
gttgatcata ttcaaccgac aagagatgta agccgtaatc caatattcga tactgtgctc   8760
gtcctgcaaa atacagaaaa aggcgcatgg tccatcgatg gacttgccgt gacgccgaat   8820
ccgattgagc atgccgttgc taagttcgac cttacacttc atgtcgaaga aggtatcgat   8880
ggcctggcgt gcagcattga atatgcaaca gctctgtacc accgagaaac gatcgaacgg   8940
ctggcatgcc atttcaatca attgctggag gcagtcataa gcaatcccga agctcggttg   9000
gatcagcttg gcatcataac ggagactgag aagcagcaat tgtttgaaga gttcaacgat   9060
acgtcagcgg attatccgcg tgataagacg attcaccgac tgttcgagga acaggtcgaa   9120
agaacgcctg atgcgattgc tgtaacggga tcagacggat tcttgactta ccaggagctg   9180
aatgaacggg ctaacagctt ggcatgggta ctgcgtgcag aaggcatcgg ggcagacaag   9240
ctggtaggca tcatggctga gcgtacgacg gatatgcttg tggggctgat cgccatactc   9300
aaggccggag gagcttacgt gccaatcgac ccggaatatc cagaagagcg catcagttac   9360
atgctgagcg attcaggggc agatattttg ctattgcctc gccatctgcg ggagcaagtc   9420
gcctacgaag gcaccgtatt gttccttgat gacgagcaga catacagcgg ggataagtcc   9480
aatccgtcat cggtcaacaa gccttccgat ctggcttatg tcatctatac atcgggaacg   9540
actggcaagc cgaagggtac attgattgaa cataagaacg tcgtgcggct gttgttcaac   9600
agcagaaatc tgttcgactt ccgttcaact gatacatgga cgctgttcca ctccttctgc   9660
ttcgacttct cggtatggga aatgtacggc gccttactat acggaggaag attggtggtt   9720
gtaccacagc ttacagccaa gaaccctgcc atgttcctgc agctgctggc tgaagaacgg   9780
gtaacgattt tgaatcagac accgacctac ttctatcaat taattcggga agcacttgca   9840
gatggaagtc cagaattgaa cattcgaatg gtgatcttcg gcggagaagc gctgagtccg   9900
cagctgctta aggactggag agcgaaatat ccgcgcacgc aattgattaa tatgtacggg   9960
```

-continued

```
attaccgaga ctacggttca tgtcacgtac aaagagatca cggaaaccga gatcgagcag  10020
gcaagaagca atatcggatt cccaatcccg accttgcgta tctatattct ggatgcgaat  10080
cgaaattgcg tgccgatagg cgtggccggg gaaatgttcg tcgcaggaga agggcttgca  10140
cgcgggtatt tgaatcgccc tgagttgact gaagacagat tcgttgacaa tccattcgaa  10200
ccgggcagca agatgtacaa gacaggcgac ttggcgaagt ggctgcctga cggcaacatt  10260
gaatacctag gccggattga tcatcaagta aaaattcgcg ggtatcggat cgagctaggc  10320
gaggtagaag cccaagtaac gaaggtagaa tcggttcgtg aagccattgt tattgcacgg  10380
gaggagaacg gcgaaaagct gttgtgtgct tacttcgtgg cagatcgaca actgaccgta  10440
ggggaaatga gaaccgaatt ggcgcaggag ctgccagctt acatgattcc atcctacttc  10500
gtgcagttgg agcggatgcc gcttacctcc aacgggaagg ttgaccgcaa ggcgctgcct  10560
gcaccggaag gcagcatcaa cacgggcaag gaatacgtag cgccgcgtac atcaatggaa  10620
gctagcttag ctcgcatgtg ggatgaactg ctcgggattg agcaggtcgg cgtaacagac  10680
aatttcttcg agctaggcgg acattccttg cgcgcaactg cgctggttaa cagggtgcac  10740
caagagatga atattcagtt gccgctgcgc gatgtgttcc ggttctcaac gattgaagaa  10800
ctggcagctg ccatgtccga gatggcagag gaatcctatt cttcgattcc ggttgctgaa  10860
gttcaggaac attatccggt atcttccgct cagaagcggc tgtatatcct tcaccagctt  10920
gaaggggcag agcagggcta taacatgcct ggcatcatgc tgattgaagg cgagttggat  10980
cgaagcaggt tcgaggctgc attccgtaaa ttgatcgcgc gtcacgatat attgcgcact  11040
ggcttcgagc tcgtgaaggg agaagctgta cagcggatac acgataccct ggatttcgcg  11100
attgaatatc ggaaagtcga agaacaagag gttcagcagc aagtaaggca gttcattcgt  11160
acattcgagc ttgataagcc gccgctgctt cgtgtcgggt tgatcgagat tgcggaagca  11220
aaggaacagc atgtgcttct gttcgatatg catcatatta tttccgacgg cgtatcgatc  11280
ggtatcgtgc tgcaggaaat catgcggcac tatcacgggg aagaggtacc gccgcttcat  11340
attcaataca aggattatgc ggcatggcag caatcagagg cccagaagga acagttgaag  11400
catcagcaag catattggct tgaccaattc caaggtgaat tgccgatatt ggagttgcca  11460
acagactatg ctcggccggc cattcagcaa tacgatggcc tcacgctgcc atttagaatc  11520
gataaggacg tggcagatgg cttgaaccga attgccgctg acaccggaac gacattgtac  11580
atggtgctcc tagctgctta taccatcatg cttcacaagt atacgggcca agaagacatc  11640
gtggtcggaa caccgattgc cggcagaaca catgaagagc tgcagccgtt aattggtatg  11700
ttcgtcaata cacttgccat tcgtgcttat ccggaaggtg ctaaggcatt ccgttcctat  11760
ctggatgaga ttagaagcac aatgttgggg gcctacgagc atcaacagta tccatttgag  11820
gaattggtgg aaggtctgca gttgactagg gatttaagtc gcaatccgtt gtttgacacc  11880
atgttcgccc tagacaatac ggacatgatg gttgattcac tcggcgagct tcatatgaag  11940
ccatatccgc tggaatacac aatatcgaag ttcgatgtga gcttggatgt gaaggcagat  12000
gagcgcgggc tggattgcag cttcgagtat gcgacttctt tgttcaaatc agagacgatc  12060
caccgcatgg cagagcattt cagccaattg ttgaaggaca tcgtcaatca cccagatgcg  12120
caactgggcg aactagggat gcttaccgtg cacgagagcg acgagatttt gcaggtgttc  12180
aatccaaccc attcattgaa agctcctgat ggaacgattc atcgattgtt cgaagaacag  12240
gcagaacgga caccggagca acctgcagtc gtgttcggga atgagcgcat gacttaccgc  12300
gagttgaacg aacgggcgaa taagcttgcg agaacattgc gggcagaagg tgtggagcca  12360
```

gatgacttaa ttggcgttat ggccgatcgc tcgattgata tggtcgtggc agttatggcc 12420
gtcttgaagt caggcggagc ttatgtcccg attgatccgg aatatccaga ggatcgcatt 12480
cgctacatgc tggaagatgc gaaggcaaga atacttctga cgcagtgtca tttacaagat 12540
aaagtgtcct tcgagggaac gtgggtgctg ttggaagacg aagcttccta tcatgaggac 12600
gatacgaacc tggagccgat ctgcgaacct gaccatctct gttatgtcat ctatacatca 12660
ggtacaaccg gcaatccgaa gggagtcatg atcgagcatc gtcagctcgc tgcgatggca 12720
gaggcttgga aggccgagta tgaattgcat gagccgggaa ttcgctggct gcaatgggcg 12780
agcttctcgt tcgacgtatt ctcaggtgat ctcgctcgca cactgctgca tggaggagag 12840
cttatactct gcccaagcga cacaagagcg aacccgggtg cactagctga gcttcttcgc 12900
agcagcggta ttcagatgtt cgaatcgacg cctgctctcg tcattccgct tatggagcat 12960
gtgtatgagc atcgcgtgga catcgacagc ctgagattat taattattgg ctctgatctg 13020
tgtcctgcag atgaattccg caagctgctc gatcgcttcg gttcacactt gcgcatcatt 13080
aatagctatg gcgtcactga agcttgcgtt gactcgagct attatgagcc ggttttatca 13140
gatccagtgc gctctgtgcc aatcggtaag ccgcttcctt atgtatcgat gtacattctc 13200
ggtgagaact tatcgcttca gcctgttggt ctggctggag agctgtatat cgcaggcgct 13260
ggagtcggac gcggatactg gaataggcca gaaatgacag cagacaaatt cgtgcgcgat 13320
ccgtttgctg acggacaatg catgtatcgt acaggggatt tggcgaaatg gctgctggac 13380
ggcaacattg aattaatcgg gcgcacagat catcaggtga aaattcgcgg ctaccgcatc 13440
gaaatcggag aggtcgaatc gaagctgcag caaacgccgg atatccgcga agcagccgtc 13500
gtcgcgaagg aagatggaag cgggcggaag gtactgtgtg cttattacac atcctatcgt 13560
gaactgacgg caggtgaatg gagatctgca ttggcgaagg aactgccggc ctacatgata 13620
ccgtcgcact ttatgaggct tgagcggatg ccgcttacgc cgaacggcaa gctggatcgc 13680
aagggacttc cagcaccgga aggcgctgcg tataccggga cggaatatga agctccacgc 13740
acggatgcag agattgcgtt ggctgccgca tggcagagtg tcttgcatgt ggagcgggtt 13800
ggaacgaatg atcatttctt cgaactgggt ggagactcga tcaaatcgat tcaagtgtca 13860
tcgcgtctgc atcaggctgg atacaagttg gaaatacgag acctattcaa atacccgacg 13920
atagcgcaat tgagtctaca gcttcagccg attggcagga tagctgatca aggcgaggtg 13980
catggcgagg tcgagcttac tccgatccaa cgctggtatt tcggactgga tctggatgac 14040
atgcatcatt ataaccagtc gttcttgctg taccggcagg gcggatttaa tgaagaggct 14100
ctgcgcaaga ctttacgaac catcgtggag catcatgatg cgctgcgaat ggtattccgt 14160
aaatcagccg ctggcgttac ggcttggaac cgggcaatcg aggagggtga gctgttcgac 14220
ttccttgcct tcgatatcgc aaacagtgga gatgcagaac aggttatcga agcgaaagcg 14280
aacgacatac aggctagcat cgatttgcag ggcgggccgc ttgtgaaggc tggattgttc 14340
cgctgcgagc aaggccatca tctgctcatc gcgatccacc atgctgtcat agacggcgtg 14400
tcatggcgca tcctgctgga ggatatatcg gcaggctacg agcaagcgtg caagggtgac 14460
gacatccgct tgccttcgaa gacggattct tatgctgcgt ggtcacggag tttggtcgaa 14520
tatgcttcac tcacggattt gggtcatgag cgcagctatt ggagacacgt cttgaacgca 14580
ggagcgaatc cgctgccgaa ggactttgac acagaatcaa gtctgcagca ggacagtaat 14640
tccgtcaccg tagcttggaa tcaacaggat acggagcatt tactgaagcg agtgcaccga 14700

-continued

```
gcctataaca ctgatatgaa tgagatcttg ctggccgctc tcgcgatagc catacagaaa  14760
tggagtgggc acaatcaaat tctcatcaac ctcgagggcc atggacgtga gccaatcgct  14820
ggtgacctag atatttcacg gacagtcggc tggttcacga gcgaatatcc ggttctgctg  14880
caagcggagc gagatcgagg attggcgtac cacatcaaga gggcgaagga agaattgcgg  14940
cagattccga acaagggaat cggttacggc atatgccgct acttgtctga gccggatgat  15000
agcttggaat ggggagctgc tccagagatt agcttcaact acttgggaca attcgatcaa  15060
gacacgatgg aaggcggcat tatgttgtct ccatattcga aaggttccga tggaagcgcc  15120
ttgcatacac gtcaatatgt cctcgacatc aattgcgcaa taacgaacgg catgttgacc  15180
ttggatatga gctacagcga gaaagagtac cgcaaggaga cgatggaact gctggcaggc  15240
catttccacg agagtctgct cgagatcatc aaccactgtg tctcacgtga gcagacagaa  15300
ttgacgccga gtgatctgct gctgcatgga ctgagtatcg agcagctgga gcagattgct  15360
gaagagatgc gagagcttgg catcatcgaa aatatgtaca tgttgacccc gatgcagaag  15420
gggatgtggt tccataacgc tctcgatggt caagaaggcg cgacgggtgc atatttcgaa  15480
caaacccgat ttacgctgcg aggtgagctg gatcctgccc tgtttgccca gagcctgcac  15540
gaactggctg cccggcattc cgtgctgagg acgaacttct gcagcttgga cggggaacca  15600
gtacaggtgg ttttccggga aggacggatt acattcacat acgaggatct gagccaattg  15660
ccagctgaag agcaagcagc agtgatagaa cgtattgtcg cgagcgataa gctgcgaggg  15720
ttcgatctgg aacgcgatcc gcttgttcgc gtcacattga tgcgtacgga ggcatccagc  15780
tgccatgtac tatggagttc ccatcatatt ctgatggatg gctggtgctt gccgcagttg  15840
acggacgagt tgttccgcat atactcagcc gtcacgaatc ataatgctgg aactactgaa  15900
gctactggaa ctgtcggaac attaggagcc ttcggagctg ctgaatcttt gcggaacaaa  15960
gaggctggcc tgcctgacta tagccgatat atcgaatggc tggcagagca ggacatgagt  16020
gcggcggcag catattggaa cgggtacttg gcgggatacg agcagcagac acgattgcca  16080
aatgggaaga tcacaggcaa ggataagccg tatgtgctgg aacaagcgtc ccgcaagctc  16140
ggaattgagc ttacttcccg tatgattcgg attgccaagc agcatcaagt tacgttaaat  16200
acgctgctgc aggcggcatg gggatcgtg cttcagaagt ataacggtac gcaagatgtt  16260
gtgttcggcg gagtcgtatc gggtcgacct gctgatgttc cgggtgtcga atcgatgatt  16320
ggactattca ttaacacgat tccggttcgt gtaagcaacg aagccggagc aagcttctca  16380
gacgtgatgg agcagctgca aaatgcggca ctcgaatctg ggcgatatga ttattatccg  16440
ctctatgaga ttcaatcgag aacatcacag aagtcggaac taatcagcca catcatggtg  16500
tttgagaact atccattgga cgagcgaatg gagcaaacca gagacggaaa cgacggagct  16560
ctcgctttaa ccgatgttca ggcagctgaa cagacgaatt atgatttcaa tctaatggtc  16620
gtgccgggtg atgaacttat cattcgcttt gatttcaact cggaagtgta tgagcgcggt  16680
catatggaac ggctgcatca tcatctgatg catgtgttgg agcaagtaac gggcaatcct  16740
gcaatctcca tagctgaagt gcagctcgct accgaagctg agaaggccga actccaatct  16800
gcattcaatg acacagctgt cgactaccct cgcgaacaga cgattcatcg gatgttcgaa  16860
gaacaggtgc agcagacgcc ggatgctgca gcagtgctgt atggggatga cagcataacc  16920
taccgagagc tgaacgaacg cgcgaaccag ctggcaagga cgctgcgtgc ggcaggggtt  16980
gaacccgatc agattgtcgg tattatggcc gagcgttccc tggagctaat ggttggcatt  17040
atggggattc tgaaggcggg aggcgcctac gtgcctatcg caccggatta tccagaggat  17100
```

-continued

```
cgcattcggt atatgctgga cgattccgag gctcaggtgc tgcttgttca aggaagcgcg  17160
ggagaagcag ttgacttcgc gggccgcatc attaatctgg atgatgcaga agcatacgat  17220
ggagacggat cgaatcctga gccagtcaac aagccgaccg atatcgccta catcatctat  17280
acgtctggca cgaccggacg tccgaaaggg gttatggtcg agcatacttc ggtcatcaac  17340
cgcttgctgt ggatgcagaa gcgctatccg attggagcgg aagatacgat tatgcagaag  17400
acagcgatca catttgacgt atcggtctgg gagctgttct ggtgggcgtt tgtcggctcg  17460
aaggtgctta tgctttcagt cggtggggag aagagcccac atgcgattgt ggatgcgatt  17520
gagcgtcacc gaataacgac gatgcacttc gtgccatcca tgctgcacgc gttccttgag  17580
catgtggagc aattgacaga tgcagagcgt gagcgcggtc tcgcaccgct gcggcaggtg  17640
ttcacgagtg gcgaggcact gcttgcctcc caggtcgagc ggttccaccg ttatattgca  17700
cctgcaagcg gagcgcagct cattaatctg tatggaccga ctgaggcgac ggtggacgtg  17760
acgtacttcg attgcgagcc aggccagact tatgtaagtg tgccgattgg caagccaatt  17820
gataatacga gcattcatat cgtgaatgag cataatcaag tgcagccgat cggcgttgct  17880
ggtgaactgt gcatcgcggg cgtagggttg gcgcgcggtt actggaaccg tccagagctg  17940
acagcagaga aattcgtcac gattccttcc gtcggcgaac ggatgtatcg aaccggagac  18000
ttagcacggt ggctgcctga cggcaatatc gaatacttgg gtcgaatcga ccatcaggtg  18060
aaaatccgcg gatatcggat tgaattgggc gagctggaaa gtgcactgct gaatgtccaa  18120
gaaattcggg agacggttgt agtcgcgcga gaagaggaag acggacagaa atcgctctgc  18180
gcctattatg tcgcagatgg cgatccaacg gcaggtgacc ttagagcggc gcttgctgct  18240
gaactgccaa gctacatgat tccatcgtac ttcattcggc tggagcagat gccgctggcg  18300
ccgaacggca agcttgatcg taaagcgctc cctgctccga aggacgtgat ccggactgga  18360
actgatcgca tcgcaccacg aacagcattg gaagtgaagc tcgttcgcat atggcaggaa  18420
gtactcggtc tcgatcaaat cggagtgaag gacgacttct tcgaattggg ggggcactcc  18480
ttacgcgcaa ctgcgttggc aagcaaggta agcaaggaaa tgcacgttgc tcttccgctg  18540
cgggatattt tccactattc gacgctggaa gcgatggcgc aggcgatcgg cgagttggag  18600
aagcaggagc accgagcgat tcctatcgcg ccaatggccg agcattatca attggcttca  18660
gcccagaagc ggttatacat tctgcaccag gctgaaggag cgcagcagag ctacaatatg  18720
ccgggggcga tgtccgtaag tggacacatc gatcgaaatc gactagaagc ggcgcttctg  18780
caattgattg cacgccatga cacactgcgc acaagcttcg aaatggttga tggtgagcct  18840
gtacagcgcg tacaccagca cgttgatttc gcgttagagt attcgactgc gagagagaag  18900
gatatcgatc aggttgccga gcagtttgtc cgcgattttg atctggagca gcctccgcta  18960
ctgagagtcg gactcgtcca actggagcaa gaagaacaac atctattgct gctcgatatg  19020
catcacatca tttcggacgg gatctctatg gacatattgg ttgacgagct tgctcgcttg  19080
tacgacggag aggaacttcc tccgcttgaa atccagtaca aagattatgt gctgtggcag  19140
caggcagaag caagcagcga gcagatgaag gaacatgaag aatactggct gcggacattg  19200
ggcaatgaac ttccgttact ggagctgccg accgaatttg cgagaggcga gcagcgcagc  19260
tatgacggag ataagctgca ctttgcgatt gatgggcagt tgaacgagaa gctgcagcgc  19320
ttggcatccc aatcgggagc aaccctatac atggtgctgc tggcggctta tacgaccttg  19380
cttcataaat attcaggaca aaatgacttg gttgtgggta ccccaattgc gggcagaacc  19440
```

-continued

```
catgtagatg tagaaccgtt aatcgggatg ttcgtcaatt cgcttgcgat tcgcaattac  19500

ccgaatgatg acaagacgtt ccgcagttat ttagaggaag tgaaggaatc gacgctgagc  19560

gccttcgagc atcaggatta tccgttcgat aagctggtgg agcagttaga ggatgcttgg  19620

gttccaggcc gtaatccggt attcgacaca atgttcgtgc tgcagaacgc aaaagcgcgc  19680

acgatcaacc tgagagaatt ggccttcgag cctctaattc catcacatac ggttgcgaaa  19740

ttcgatttaa ccttggaaat ggctattgaa gacggcatgc tgagcgggca gtttgaatat  19800

tgcacgaagc tgttttccgc caacatgatt gcgaatttcg cagaagactt cttggagatt  19860

ctatctcaag cttgcgagca gcctgacctc cgcttggagg atattcaact gagcggcagt  19920

gctaatcaag aggaagaatt ggaagaagaa attgactttg cattctaa              19968
```

<210> SEQ ID NO 9
<211> LENGTH: 19287
<212> TYPE: DNA
<213> ORGANISM: Paenibacillus alvei TS-15

<400> SEQUENCE: 9

```
atggcttttg ataaagaaat cgaattttgg aaagcgaaac tcgatactga agatacgcct     60

actactttgc cctacaccaa catttcaagc agtgaagcgg cacgacatta ttccgtttct    120

gttacgatgc ctgctgaaat tacggaacga ataattcgca tgtctaaagg ctcgcatcaa    180

gcagccttca tgattttatt aggcggcatc caatgcttgc tgcacaaata cacgagcgag    240

aattgcatcg tcatcggcat gcctatcgtg caaaaagcag gggagaagag acttcccatc    300

aatcaagtcg tcctattgaa ggagaatgtg aatgaagagc tcacgttcaa atccttgcta    360

acctcactga aacaatcctt tacagaagcg attcgacatc agaatatccc cttccggctc    420

ataactgagc agatgaatgt gcaagaaaag aatggcttgc ctgtcatcaa tacgatggca    480

gctctgaaga atatacatac cgttaacttt attccaacgg ttgttgcaga tgtattgttc    540

caatttgagt tcgaggctga gaacctcctt ttgagcgttg tatataacga acgtgtctat    600

gattcagtgt ttatatcaca aatcattgag catttgcagc gcgtgctgag catcgtattg    660

cttgagccaa atacgaattt ggggaatctt cgcttgcttt cggatgagga aacatcgctg    720

ctcctgcatg gcttcaatgc gacggctgca gagtatccgc gtgaccgaac gattcatgaa    780

ctcttcacgg aacaagcacg tcgcacgccg gatgctgttg cagcagtttt ggggcagcaa    840

cagttaacat atgccgagct aaatggaagg gcgaacaggc tggcgcgtac gttacagaac    900

gctggcgttc gaaccgatca gctcgtcggc attatggccg aacggtcgct cgaaatgatt    960

gtaggcttgc tagccatcat gaaggctggt ggggcttatg tgccgatcga ccctgaatat   1020

ccgcaggagc gtattcgtta tatgctcgag gattcgggag cgcagatgct actgcttcaa   1080

gaccatcttc gcgagcgtgt cagctatgag ggcacgatcg tggatatgaa tagcgaacat   1140

aattatcatg acgacgagac ggaacttgcc tctgtgtccg attcaagcaa cttggcatat   1200

gtcatctata cttcgggcac gacaggcaat ccgaaagggg tcatgattga acatagaagc   1260

gcagtcaatg cgctgttgtg gagaattcgg acatacgggc tttcttcctc cgaccgggtt   1320

ctgcaattat tttcattttc ctttgacggc ttcgtcatga gcgcgttctg ctcattattg   1380

tccggcgcag gtttattttt acttaaggaa gaggacgcga aggatccgct cgccttgcat   1440

ggcgctatca gccaatctgg aatcacgcac ttcatttgcg taccaaatct atacggagcg   1500

ctgctcaatg tgatgcaggc cgaatctgtg tctacgctgc gtacagtgac attggctggc   1560

gagagtgtca gcagtgcatt agtagctaga agccaggagc agcttcctga tgtgaagctg   1620
```

-continued

```
tttaatgaat atggcccgac agagaacagc gtcgtggcga cctgtgcaat cggcctcgag   1680
aaggatcaac ccatcaccat tggtacaccg atctctaatg cgagtgtgct gattttgaat   1740
acttctggag agttgcagcc gttacatgtg ccgggcgaat tatgcatagc cggtgaggga   1800
ctggcgagag gctacttgaa ccgtcccgaa ttaacggaag agaaatttgc cgctcatcca   1860
tttgtgccag gcgaacgtat ttaccatact ggtgattccg ccagatggct gccgaacggc   1920
acaatcgaat atttgggacg aattgatcat caagtcaaaa tccgtggatt ccgaatcgaa   1980
ctgggcgaaa tcgagtcgag cttgaagaat gtagcgggtg tgcgagaggt catcgtggat   2040
gcaaggccgg acggtaatgg ccaacaaatg ctgtgtgcgt acatggtagc agactctgtg   2100
cttactgtga atgaattgag ggaggcgctg tcttcccatc tgccggatta catgattcct   2160
tctcattttg tgcaaatgga acagctgccc cttacgccaa gcggcaagct ggatcgtaag   2220
tcattgcccg atcctcaggc taacattgcg attgggacgg agtatattgc accgcgtact   2280
ccacttgaag cacgtcttgc gcaaatctgg caagagtcgc ttggtgtgga gaaggtcggt   2340
atcaaggata atttcttcgc ccttggcgga cattcgctgc gggccgctac attggcaagc   2400
aagcttcaca aggagttgaa cgtcaatgtg ccgcttcgtg atttgttccg taatccgacg   2460
atcgaagaac tggctttgct tatggaaggg atggagcagc aggagtttag cgcgattgaa   2520
cgggtgaagg aacgtgagta ttattcggta tcttcagcgc aaaagaggct gtttgtcctg   2580
cagcagctcg aaggtgcgga acagagttac aatatgccag gtgccatgct gctggaggga   2640
ctgctggata gagaacgcct cgaagcctca ttccgcaagc tgattgcacg acatgagaca   2700
ctgcgtaccg gattcgagct aatggacgga gaaccggtgc agaaggtgta tcagaatgta   2760
agctttgcca ttgaatatat gcaggcaagc gaggaggaag cggcgcagaa agcccgcgaa   2820
tttatccgag cgttcgactt gatgactccg ccgttgctga gggttggctt aattgaaatg   2880
gcaccggatc gacatgtgct cctctatgac atgcaccata tcatttctga cggtgcatct   2940
atgggagtcg tagtagagga gttcgctcgg ttgtacgggg gtgaagagct gccatcgctg   3000
cgcattcaat ataaagactt tgccgcttgg cagcagtcgg aagtacagca gaagcgttcg   3060
atgcagcagg aggcctattg gttgcaagca tttggcggcg aactgcctgt acttgaactt   3120
ccaacggata acgcgcgtcc agccattcag agctacgaag ggagacccta tgaatttacg   3180
gttgattcgg atataagtac ggcattgcaa cgcctcgcag cggatagcgg aacgacgtta   3240
tacatggttc tgctcgcagc ttacacggtg ctgctgcata agtacacggg tcaggaagat   3300
attgtcgtcg gcacgacgaa cgcagggaga atgcacgacg atttgcagcc gcttattggt   3360
atgttcgtca atacgctcgc aattcgcaat tatccggctg gagaatcgac gttccgtgct   3420
tatttggaac aagtgaaaga gcaggcgtta gctgcatttg aacaccagga gtacccattc   3480
gaagagcttg ttgagaagct tcgagttgca agagacatga gccgcaatcc gctgttcgat   3540
acgatgttct ccctgcaaaa tatggagaat aaggacttcg agcttccagg actccaattg   3600
aagccgtatg gcttcgaaca tcaaatatcc aagttcgatc tcagcttgga cgttgcggaa   3660
ggagcggatg ggctcgcttg cagcttggag tatgcttcgt ccttatacag acaagacaca   3720
atcgtaagaa tggcgaatca ttatcgacag ctgcttcatt caattgcaca gtcgcctgag   3780
gcgcaaatcg ccgtgctcgg gatgttgacg ccgggtgagc aagagcagat tcgattcaag   3840
ttcaatcatg atccgtcaga tatggagcag aagcacacgg ttcatcaact ctttgaggag   3900
caggccgctc ttacaccgga acgaactgcg gtcgtgcatg agaatgaaca actgtcgtat   3960
```

caggagttga atgagagggc gaaccgtctg gcacgtacgc ttcgtcaaca cggcgtgcag 4020
ccggagcagc tcgtcggcat cttggcagat cgttcgctgg acatgatcgt gggcattatg 4080
gcgatcttga aggcaggcgg cgcttacgtt ccaattgatc cgaaatatcc ggaagaacgt 4140
atccgttaca tgctggagga ttccaaggca aatgtattgg tgacgcagag ccatttacag 4200
tctctctcat cgttcgacgg tacatgggtt ctgcttgatg aggagtcatc ctatgctgag 4260
gatgctgcca atcttgtgtc catcaatgaa ccacaacacc tggcttacgt catttataca 4320
tcgggcacga cgggacagcc gaagggtgcc atgatcgagc acagacaact gacagttatg 4380
gcgaaggctt gggaacgtga atatcgtctg cgggaagaga gcattcgctg gatgcaatgg 4440
gcgagcttct cattcgacgt attttcaggc gatttgattc gtgcgctgct gcatggcgga 4500
gagctggttc tttgcccaga gcacgcacgt gcgaatccgg ctgaaatcta cgaattgatc 4560
cggaagcatc gtcttcatat gttcgactgc acaccgtcta tcgtcattcc gctcatggaa 4620
tatgtgtatg agaacaagct ggatatcagc agcttgaagc ttgtcgccgt tgggtcggac 4680
tattgcccgc cggatgagtt tcagaagatg ctggatcgat tcggttcgca gttccgcatc 4740
attaatagct acggcgtgac ggagacatgc atcgatgcca gctattatga accaacgact 4800
ccaactgttc caagagcgct gccgattgga aaaccattgc cgggtgtaac gatgtacatt 4860
atggacggac agcgttcttt gcttccggtt ggtgtcatcg gtgagctcta catcggcggc 4920
ccttgcgtcg gccgtgggta ttggaatcgt tcggaaatga cgagcgagaa attcgtcgca 4980
gatccattcc tccaggatca ccgaatgtac cgcacagggg atctggctcg ctggatgccg 5040
gatggcaaca tcgaatattt aggccgtatc gaccatcagg tgaaaatacg cggttatcgc 5100
atagaaatcg gcgaagtcga gtccaagctt cttaaagtgg agactgttcg ggagagtgtc 5160
gtcgtggcgc gtcaggatcc gaacgggaca aaagcattat gcgcttattt cgttgcggat 5220
cgcaatctga cggtgagtga actgagaagc gcaatggctg atgaattgcc cgcatatatg 5280
attccatcgt atttcgttca attggaccgc ctaccgctta cgccgaatgg aaaagtcgac 5340
cgcaaggcgc tgcctgcccc ggaagcggga gcgcacacgg gcattgaata catggcgcca 5400
cgcacggaag aggagttagc gctggcgaat gtatggcaaa ctgtccttgg tattgaacga 5460
gtcggtgtgc tggatcattt ctttgagctt ggaggcgact ccatcaagtc tatccaagtt 5520
gcttcccgat tgcagcaagc aggctataag cttgaaattc gcgatctgtt caagtatcca 5580
acgattgccc aattggggtc acacttgcag agggcaagca aggtcgcaga tcagggcgaa 5640
gtatcaggtg acgtgccgct tacgccgatt cttggatggt ttttcgaaca gcagtttgcc 5700
gacgcgcatc actataacca gtcgatcatg ctgtaccgga gagaaggctt taacgaagcg 5760
gcaatccgca atgtacttca ggcagtaacg gaacatcacg atgcgctgcg catcgtattc 5820
cgacggaatg atcaaggtga ttatacagct tggaatcggg caatcgaaga aggagaattg 5880
ttccatctgg aagtgctgaa ccttacagga acaacagcag gtgatcatga gcagaatgta 5940
cggcagatca ttgaagccaa ggccacggag attcagcgta gcttcgacct gcacgatggg 6000
ccgttggcaa gagcgggatt gttccgtacc gatgaggggg atcatcttct tcttgtcatg 6060
caccatggcg ttgttgacgg tgtgtcctgg cgcatcctgc tggaggatat cgctactgga 6120
tatgaacaag cgttgaaggg agagcctgtt cggctgcctg ccaagacgga cagcttccgc 6180
acatgggcga atcagctcgc gtcatatgca cgaagcgaag ccatgataga ggaacaaatc 6240
ttctgggaac aggcagaagc gaatggaacg agtattttgt ctttgccgaa ggatttcgaa 6300
gcggagacat ccttgcagca ggatagcgaa tcggtcgtag tggaatggag ccgggaggag 6360

```
acggatatgc tgctgaagca tgttcaccgg gcttataaca cggacatgaa cgacattctg   6420

ctcgcagcgc tcggcatggc tatacagcaa tggtgtggac atgagaaagc cctagttaca   6480

cttgaaggac acggccgcga gaatatcatg ccggagcttg atatttcgcg cactgtgggg   6540

tggttcacga gtgaatatcc atttctgctc gagagcgatc cgaacaagag tttgtcctat   6600

cgaatcaaac gaatgaagga aaatttgcga cggattccga acaaaggcat cggttatggc   6660

attcatcgat atttatcggg ctcaggtacg tctggtacga aaaatgtatc acgatcagaa   6720

gcatcagctc agccagaaat cagcttcaac tatttgggac aattcgatca ggatttgcag   6780

aacaatgaga tggaagtctc tccatattcg ggcggcgcag agataagcgt tcgtcaggct   6840

cgtaacacca cgcttgattt taacgggatg atatcggctg gggttcttgc attggaagtg   6900

agctacagca gcaagcaata ccgccgcgat acgattgacc ggctggcagg attgctgaag   6960

ggaagtttgc aggagatcgt tgcttactgc gcatcgaaag acaagcctga attgacacct   7020

agtgacgtat tagttaacgg gcttggtatt gaggatctgg agcgtattgc ggagcagacg   7080

agggatctcg gggacatcga gaacatttat gcactgacgc cgatgcagaa gggaatgtgg   7140

ttccataatg cgatggacgg tcaagcgggc gcttattttg aacagactcg ctttacgatt   7200

caaggagagc ttgacgttca gctattcgca agcagcctag atgtactcgc gacgcgccat   7260

gcggtgcttc gcaccaattt cttcagcggc tggaacggag aattgctgca aattgtatac   7320

cggaacaaga atctggaatt tagttacgag gatctatcgg aattgccgga gcatgagaag   7380

caggatcgag ttgaagcgat ggcgcaagct gacaagcagc ggggcttcga tctggagcgc   7440

gatgcgctca tgcgggtgtt cgtgttgcgg acgagcttga actgcagtca tgtcatttgg   7500

agctctcatc atattctgat ggacggctgg tgcttgccgc agctcacgca agaatggctc   7560

gagacgtatt ccgattccgt aaatggacgg tcaagcagcc gatcgggagc atcgccatac   7620

agtctctata ttgaatggct gtacaagcag aattacacag ctgcatccca gtattggagc   7680

gactatctgt cggattacga tcagcaaacg gttcttccgc agaagaaatc gagcgggcgc   7740

agcgatgtat atattgctga caatctcgtt tttgaactgg gcgaggcttt aactgcgaag   7800

atgcatcggg tagcgaagca gcatcagctg acgctgaaca cgctaatgca ggcggcatgg   7860

ggcattattt tgcagaagta taacaatacc ggggacgctg tattcggcgg agtcgtatca   7920

ggcagaccgg cggaaatccc aggtattgaa tccatgattg gactattcat caacaccatt   7980

ccgattcgag ttgtgtgtga agcggatgac agatttgccg acgtgatgaa gcagcttcag   8040

gagaaggcac tggagtcagg gcggtatgat tattatccgc tgtatgacat ccaggcgctc   8100

agcacgcata agcaggattt gattaatcat attctggtgt tcgagaatta cccgatggaa   8160

gagcaaatgg aacaggctgg tgatgagcgg ggacaattga acattactga tgtgcgagtg   8220

gctgagcaga cgagctatga tttcaatctc gtcgtgatgc caggcgagga tatgatgatt   8280

cgcctcgagt acaatgccgt catgtatgat cgagcagaca tggagagaat acggcagcat   8340

ctgattcacg tcctcaagca ggtaacagca gatccggcca tagctgtgaa agacgtccgt   8400

ctggcgaccg acgacgagaa ggcagagctg ctgacggcat tcaatgatac ggaagtcgaa   8460

tatcctcgcg aacagatgat tcatcggatg ttcgaagagc aggttcagcg gacgccggat   8520

gcgacggcgg tgttgtgtgg agcagctaca atgacctacc gggagatgaa tgaacgtgcc   8580

aatcagttgg cgcggacatt gcgggcagca ggcgtcgtac cggatcagat cgtcggtata   8640

atggcggaac gatcgcttga actaatggtc ggcatcatgg ggatattgaa agctggcggc   8700
```

gcctatgtgc cgatcgcgcc ggattatccc gaagagcgca tccgatatat gctggacgat 8760
tccgaggctc aagtactgat tgttcaaggc agcgcgggtg aagcaattga ttttgcgggt 8820
cacgttatta atctggacga tgttgactcg tacgatcagg acagttcgaa ccttgagatg 8880
gtcaacaagc cgaccgatat cgcctacatt atctatactt caggtacgac cggacgtccg 8940
aaaggggtta tggtcgagca tacgtcagtc atcaaccgct tgttgtggat gcagaagcgg 9000
tacccgattg atgcggatga caccattatg cagaagacgg cgatcacgtt cgacgtatct 9060
gtttgggagt tgttctggtg ggcatttgtc ggatcgaagg tgctaatgct tccagttggc 9120
ggagagaaga atccggcagc aatcgttgag gcgatcgaac agtacgatat ttctacaatg 9180
cactttgtac catctatgct gcatgccttc ctcgagcata tcgagcagct gcctgaagcc 9240
gaacgtgagc gtctgtctcc actgaagcag gtgttcacca gcggagaggc tctattggca 9300
tcgcaggtcg agcgattcca tcagtatgtt gcacctgcca gcggagcacg actcatcaat 9360
ctgtacggtc cgacagaggc gacggtggat gtcacgtact tcgactgcga accaggccaa 9420
acgtatgtga gcgtgccgat tggcaagccg attgacaaca cacgcattta tattgtgaac 9480
gggaacaatc aagtacagcc gatcggcgta gcgggcgaac tgtgcatcgc gggcgtcgga 9540
ttggcgcgcg gatactggaa tcgccctgaa ctgacagaag agaaattcgt attggtgcct 9600
tccgtgggtg aacggatgta ccgaacgggg gatctcgcgc ggtggctgcc agacggcaac 9660
atcgaatatt tgggacggat tgatcatcag gtgaaaatcc gcggctatcg aatcgagctt 9720
ggcgagcttg agactgcgct gctgaaaatt gacgcggttc gggagacagt cgtcgttgcg 9780
agggaagacg agagcggaca gaagtcactt tgcgcctact atgtagcaga cggagaagca 9840
acagtaagtg acctgcgagc cgcgcttgcc gccgaactgc cgagctacat gattccatca 9900
tacttcgtaa gactggagca gatgccgctg gcgccgaacg gcaagctgga tcgcaaagct 9960
ttgccggctc cagagagaag ccttcaagtt gaatcggaat atgttgcgcc gcgcacggaa 10020
gcggaacaga tgctggcaac cgtatggcaa gccgtacttg gcatcgaacg tgtcgggata 10080
accgatcact tcttcgagct tggcggagat tccatcaagt ccattcaagt ggcagcaaga 10140
atgcagcagg cgggcttcaa gcttgatatt cgcgacttgt tcaaatactc aacggttaca 10200
cagttggttc catacatgca gccgattaat cgaacggctg atcagggaga agtcgtcggt 10260
gaggtgccga tgacaccgat tctgcattgg ttcgagcatc agcagtttgc gaatccgcat 10320
catttcaatc agtcggtaat gctgtatcgc aaggatggct ttgtcgcaga tgcagtgcgc 10380
aaggcgcttc ataagttggt tgaacaccac gatgcgcttc gtattgtaat tcagagaacg 10440
gaacaaggag aatattcgct ctggaatcga tccctagtag agggtgagct cttcagtatg 10500
ggagagatcg atttaacgga tcagtcggat ttcgccgcag cgattgaagc ggaagcaaac 10560
cacattcaag gcagtattga tctacaagcg ggacctttgg tcaaggcagg cttattccat 10620
ggcagtgacg gtgatcactt gctgctcgtt atccaccacg cagtcatcga tggcgtgtct 10680
tggagaatat tgcttgagga cctcgcagca ggctatgaac aggcgctgaa tcaacgccag 10740
gtgcgtctgc cgatgaagac agacagcttc cgtacatggg cggaacagct agtagagtat 10800
gcgaatagtc cagcgatgga taaggaatct gcttattggc tcagcgtcgc gcagacggaa 10860
gtggcggccc tgcctaaaga cagcgagtgt acagtttcct tgcagcgcga cagtgaatcc 10920
gttgtgctcg agtggaataa ggaagatacg gaacggcttc tgaagcacgt tcaccgcgct 10980
tacaacaccg aaatggacga tattctgctc acagcgcttg gcagagcact catgaagtgg 11040
cgcggcatcg accgcgtact ggttacgctg gaaggacatg gtcgcgagtc cattttacaa 11100

-continued gacatggata ttacgcggac ggttggctgg tttacgaccg aatatccgtt tgagctcggg 11160
atggaagcga acgacagtct tggatctcag atcaagaagg taaaagagga tttgcgccgc 11220
attccgaaca aaggaatcgg gtacggtctg ttccggtatt tatccaattc gggcaaacag 11280
gcttggaatg atgcgccaac gacacaaatt cgttacaact acctgggaca gttcgatgcg 11340
gacttgagca ataacgaact gagcgtatct ccatatgcaa gcggttcgga gattagcgat 11400
gagcaggagc gcaagtatcc gctcgatatt aacggcgtta tcgcagaagg ccaattgacg 11460
ctgggcttaa gttacagtgt caaggagtac cacaaagaga cgatggagga attgggcgat 11520
ctccttacag aatcactgaa ggaaattatc gcacactgcg aatcacagga acggacgcaa 11580
ttgacgccaa gtgatgtctt gtttaaggga cttagcttgg agtggctgga tcggatatct 11640
tcgcaaatgc agcatatcgg agagatcgag aatgtatatg cattgacgcc gatgcagaag 11700
ggaatgtggt tccacagtgc gatggatagt ctgacagggg cgtaccatga gcagacgatg 11760
ttcacattgg aaggtacgct tgatgtggaa ctgttctcca gcagtctgaa cgaattggcg 11820
aagcggcacg ctgtgttgcg aacgaacttc attagcggcc ctcaaggcga accggtacaa 11880
gtcgtattcc ggaacaagcc aatcggattt tcattccagg atgtgcgcgc tctgaatgaa 11940
gaggagcagc aatccttcat taaggaagcg gtcagcagtg accaactgct tggcttcgat 12000
ctcgcacaag gtgccttgat gcgcgtttcg gctatccgta caggggaatt gagctgccgt 12060
gtactgtgga gctctcacca tatcttgatg gacggctggt gcctgcccca gctgatgcaa 12120
gagctgttcg atacgtatgc cgccttgctg cagaagaagt cgccggatag aacagtggtt 12180
ccagcttaca gccaatatat tgaatggcta gggcagcagg acgaggaggc ggccgggact 12240
tattggtctg catacttggc tgattacgat caggtaacag agatcccaca agaatcatcg 12300
gcgggaatcg atagcgaacc atataaggct gaaaaatgga gccgtgaatt ggatgctggc 12360
ttgagcgcat ccatcagccg ggcggcaaga cagcatcagg tcacgctcaa tactttgctg 12420
caagcggcat ggggcgttat tttgcaaaaa tacaatggca caaatgatgt tgtattcggc 12480
agcgtcgtat caggcagacc agcggaggtg ccaggcattg agacgatgat cggcttattc 12540
attaatacga ttccgatccg cgtcaagtgc gagggaagca ccagctttgc ggaactgatg 12600
gggctgcttc aagagcaagc gctggagtcc ggcaagtacg attattatcc actgtatgag 12660
atacaatctc gcagtgcgct gaagcagaat gcgatcagac aaattatggt gttcgagaac 12720
tacccgatgg acgaacagct agagcaggcg ggcggcgacg agcacggtat gccatcctta 12780
actgatgtag cggtggagga acagaccaat tacgacttca acttgatcgt cgtaccggga 12840
gaacagatct ctattcggtt tgattacaat gctaaccgct tcgtacaagc agacatggaa 12900
cggttgatgg ggcatttgaa caatattttg gagcagatcg tagacaatcc acgggttgct 12960
gtagaagatc tggagctcgc gacggaagcc gagaagtcgg aagtgatcca atcattcaac 13020
gatacactta cgaactaccc gagagacatg atgctgcatc gcttattcga ggaacaagcc 13080
gaacgacatc ctgatgcagt agccatctcc ttccgagatg tccagatgac gtatcgtgat 13140
ttgaacgatc gggcgaaccg attggcacgc acactgcggg cagtcggagt tggaacggat 13200
aagctggtag gtctcatgtc tgaacgttcg ccggatatga ttattggtat tctggcaatc 13260
ttgaaggcag gaggcgggta tgtgccaatc gatccggaat atccggaaga acggattcgg 13320
tacatgcttg aagattccgg tgcgcgaatc atgctggcac agcagcactt aacggggaaa 13380
attccagcaa tggacgcttc accacttgat gcaattatca atcttgacac cgaaacatcc 13440

-continued

```
tatgacagca acggttcgaa tcttgaggcg aacacagatg caagcagcga gaacttagcc  13500
tatgtaatct acacatccgg cacgacgggt aagccgaagg ggaacttgac gacgcaccgc  13560
aatattgtac gtgtggtgag agaaaccgag tacatcgaca tcacgaatca tgacaacgtg  13620
ctgcaaatgt ccagctatgc atttgacggg tcgaccttcg acatctatgg cgcactgctg  13680
aatggggcca agcttgttct tgtaccacac gagacgcttc tggaagtgcg gcaattggct  13740
gagttgatcg tacaagagaa gatttcggtt atgttcatca cgacggcgta cttcaacgta  13800
ctggttgatg tccaggcttc ctgcttgagc aatattcggg ctatcttatt cggtggcgaa  13860
cgggtatctg tcagccacgt ccgcaaggcg cttaatcatg tcgcgccagg tacactcaag  13920
catgtatacg gcccgacgga gagcaccgta ttcgcgactt gccacgatgt atacgaagtc  13980
acggagaatg cggtgacggt accgattgga cgtccgatca gcaatacgtc aatctatatc  14040
gttgatgcga acaataagct gcagccagta ggcgttgccg gcgagttgtg cgtggcaggt  14100
gatggattgg cacgaggata tttgaatcgt ccagacttga cggcagagaa gttcgtcgat  14160
tccccgtacg tccagggaga gcggatgtac cgcacgggag acttggcgaa atggcttcct  14220
gacggttcca ttgaatatgt tggccgaatc gaccaacagg tgaaaattcg cggatatcgg  14280
attgagctag gagagatcga ggcgcagctg ctgaatgtag aggatgtgca ggaagcggtc  14340
gtcgtcgcac gagacaatga cacaggcgag aagcagctat gtgcctacta tgtagcgatg  14400
cgtccgcttg aggcgaatca tttgcgcgaa gtgatgggtc aagctatgcc aagttacatg  14460
ctgccagcgc actttgttca gctggaacag cttccactca caccgaacgg caaggtagac  14520
cgcaaggcgc tgccggctcc ggaagaagga cggagcggag agactttcgt tgcaccgcga  14580
acgccgcttg aagcacagct tgttcaaatt tggcaggatg tgctcggtat tagcagtgta  14640
agcgtgacgg ctcatttctt cgagttgggt ggtcattccc tgaaggcgac gctgctcgtg  14700
aacagactgc atcaggagct taatatcgag ttgccgttga aggacgtatt tcaatatccg  14760
acgcttgaag cgatggcgaa gcgacttagc aatgcggaag gaagcaggca tgtgagtatc  14820
ccggtggcgg ctccaagcca gcattatccg gtgtcttcgg ctcaaaaacg cttgtatatt  14880
cttcatcagc ttgaaggggc ggagctgagt tacaacatgc cgaacatgct gctgcttgag  14940
ggagctgtgg atcttgggcg attggaagaa gccttcaaga gactgattga gcgtcatgaa  15000
acgctgcgca ccggatttga gatcgtgaac ggcgagcctg ttcaacgaat ttacccggaa  15060
gtagacttcg caatcgagca tgtgctcgca agcgaggaag gtgcttcgaa gcttatgcag  15120
cagtttgtgc gttccttcca attggagaag ccgcctctgc tgcgaatcgg agttatcgaa  15180
ttgtccgaag aacgctccat tctcatgttc gatatgcatc atatcatctc agacggttcg  15240
tcgatgggca ttctcatcaa tgaatttgtc cacttgtaca gtggagaaga gcttacgccg  15300
ctgcggattc aatataagga ttacgccgta tggcagcaat cggatactca gcaggaggca  15360
atgaagctgc aagaaggata ttggctgaag gtactggggg gagagcttcc ggtgctggaa  15420
atgccgacgg actccattcg tccgacaacg caaagcttcc gcggagattt gctgcagttc  15480
gatctagatc cagtgagaag tgcggggctg cggagaattg cagcggagaa cggagccacg  15540
atgtatatgg tgctgctcgc gctgtacaag acgatgctgc acaagtactc cggtcaagag  15600
gacattatcg taggtacgcc gatcgcaggc cggaaccatg gagacttaca gccgcttctc  15660
ggcatgttcg tcaatacgct ggccattcga agctatccgg cagccagcaa gactttcttg  15720
tcctatttgg gtgaaataaa agaatcaacg cttggcgcct tcgagaatca gaattatcca  15780
ttcgaggcat tggtcgaaca ggtgcaagtg atgcgcgata tgagccgcaa tccggtattt  15840
```

```
gatacgatgt ttattttgca aaatgcggat caaggtgaaa tgaagattga tgggctacga  15900
ctccagtcgg tgccgaatga acacaccgta tccaagttcg atttgacctt ccaagcggaa  15960
gaggatgaag cggaaatcgt gtgcagcatt gaatacgcaa cagatttatt taagcgaggt  16020
acgattgagc gaatggcaag acatttcgaa caattagtcc atacggtgct ggataacccg  16080
caagcaagtc tgtctaactt gagcatggta acaaatgagg aaaaggctct gcttcaggat  16140
aagttcaatg atacggatat ggcgcatcca agcgacaaga cggttcatga actgttcgcg  16200
gaacaggtgg agcggacacc agatgctgtt gctgtcgtct ctggcagcga gcaattaagc  16260
tacggagatc tcaaccggaa agcgaatcag cttgcgtgga agctgcgtga gtatggcgtg  16320
accgcagagc agcctgtcgg cattattgtc gagcgaacgc tggatactgt cgtcgcagtg  16380
ctggctgtac tcaaagcatc gggcactttc gtaccgatcg atcccgaata tccagagacg  16440
cgtattcgct atatgctggc agacagcggg gctaagctgg ttttggcgca atcggagctg  16500
tcagggatca ttcctgatga cgtccgcctg attgatgtac gcgatgagtc cctataccaa  16560
ggcgacggag ctgacgtacc aaatggcagc aaaccgtcca acctgctcta tatcatctac  16620
acatccggaa cgacgggcaa tccgaaaggg gtcatgctgg agcaccgcaa catggtcaac  16680
ctgctgcatt atcagcagaa aggcacgaac attccgatgc cttcgcggat tttgcaatat  16740
gcgtctggca gcttcgatgt atgctatcag gaaatgttct ctgcgctcct gttcggcgga  16800
agcctgtata tggttgacaa tgagatgcgc aaggatccgg tacgcttgtt ccaggaaatc  16860
gaaaagcatg aaatcgacgt gatgtacatt ccagtggcgt tcctaaaatt catcttcgcc  16920
gagccggagt gggcagaagc gttcccgcgc tgcgttcgcc atatcattac ggcgggcgag  16980
cagttggtcg tgacaccgca agtgcaggct tgcttgaagc gactcgatat ctgcctgcac  17040
aaccattacg ggccatcgga gactcatgtt gtgacgacct acacgatgac gccggaagtt  17100
atcgaggttg gtctgccgcc aatcggcaag ccgattgcga acacgagcat ttatatcgtg  17160
aatgacagct ttgagctgca gccgatcggc gtgaagggcg agctctacgt atccggggca  17220
tgtgtcggac gcgggtactg gggaagaacg gacttaactg aggagaagtt ccttgataac  17280
ccgttcgccc ctggcgagcg gctgtacaag acaggtgacg tggcgcgctg gcttccagac  17340
ggcagcattg agtatgtggg ccgaagcgac catcaggtga aaattcgggg cttccgcatt  17400
gagctgggcg aggtggaatc gcagttgctg catgtaccgg cggtacagga ggcgaccgtg  17460
gtggcactgg aagatcatgc gggtcagaag cagttgtgcg cgtatttcac agcagaatgc  17520
tcactcacgg ccggcgagct gcgggcagca ttgtcgcagg agctgccagg ctacatgatt  17580
ccgtcctact tcgtacagtt ggagcgactg ccgctgacgc cgaatgggaa gatcgatcgg  17640
agagcgctgc cgaagccaga aggcggcatt gagactggaa cggagtatgt cgcgccgcgt  17700
acagagacgg aagcaaggct tgcacgcatt tggcaggatg tattgggatt agcaagcgta  17760
ggcgtgaagg acaacttctt cgagcttggc ggtcactcgc tgcgggcaac gacgctggtg  17820
agcaggctgt acaaggaaat gaacgtcaac ttcccgttaa ggggtgtgtt ccgtcatccg  17880
actatcgagg agatgtctca agcaatctcg caaatggaga cctcattgta tacagccatt  17940
ccgatcgccg aggagcaaga atactacccg ttatcttcgg ctcagttgcg actctatatc  18000
atgagccagc tggaaggaag cgagctcagc tacaatatgc ctggcatgct ggtgcttgaa  18060
ggacagctga atcgagatca attccagacg gcatttttga agctcatcgc tcgtcacgag  18120
acattgcgta ctggctttga gatggtagac ggcgagccga tgcagcgcat ccatcgcaat  18180
```

acggaattcg ctattgacta cagacaggta tccgaggacg aagttccgga gataattgga 18240
caattcatcc gaccgttcga cctggagcat ccgccattat tgcgggtcgg gttgttcgaa 18300
gttgggcagg atcggcatat tctcgtcttt gatatgcacc acatcatttc tgacggtgcc 18360
tcaatgagca atctagttga tgaatttact cgattgtatg cgaatgaaga acggccgccg 18420
ctgcgtatcc agtacaagga ttatgcagta tggcagcagg cgagtgagaa tcttgagagg 18480
ctgaagcgcc aagaagacta ttggatgagt atgctgcaag gcgatcttcc gaacacagag 18540
ttgccgttgg attatgatag agcggcggtt cgcagcttcg aaggggagca gatcgaattc 18600
gaaattaacc cggttgtgac gggccagctg aaccaacttg cttctaatca tgagtgcacg 18660
ctgtacatgg tgttattgtc cgcctatcag attctgttat ccaaatattg cggtcaggat 18720
gacattattg tcggtactcc tgttgcgggt cgcaatcatg ccgatttgga gccattgatc 18780
ggtatgttcg tcaataccct cgcgattcgt aaccgtccgc agggcgataa aacgttccaa 18840
tcgttcttgg cagaggtgaa agagtcaaca ttaggggcat tcgaacatca ggagtatcca 18900
ttcgaggaac tgattgacct cttgaagctg cagtgggaga caagccgcaa tccattgttc 18960
gatacggtgt tcgtcctcca gaatacggag gagcgtgaag ccggaatcgg tggactgacg 19020
atatcgcctt acgtgacaga tgactcggtc agcgcgaagt tcgatctgac gctgtctgta 19080
tcggaagaag acgatggtat gaagggaagc ttcctgtatg cttccaagct gttcaaagca 19140
gctggcatac acagaatgat gagagattac ttgtcaatac tgtcccaagt atgcgagaac 19200
cctcgcatcc gcattcaaga tatttcgata agtggacagc agacacagga aaagagcaag 19260
atcgacacga tcgagttcgc gttctaa 19287

<210> SEQ ID NO 10
<211> LENGTH: 9504
<212> TYPE: DNA
<213> ORGANISM: Paenibacillus alvei TS-15

<400> SEQUENCE: 10
atgaagtcgg tatatgagaa agaagaagcc tattggaatg ggatgtttga ttcggatgac 60
agcatgagca tcttgccata ttgcagtaca cacggaagag aagcgaacgc ggatacgaat 120
gccgccaaag tgtctatgat ccgggcactc ccttcagaac tgtcagacag aatgaacacc 180
cttgcgaacg gttcggatat tgccctgtac atgattggat tggcaggggc cacttgcttg 240
ctccaccatt atacgaaccg agaaaatgtg cttgtaggca tgccgacgat agatgaatcg 300
gatgatgact catcacctcg tgacgtactc attatgaaga cgaatttgac acgcggaagc 360
agcttccgtt ccgtattggg gtcaatcaag acagctgtcg gaggagcagt ggagcatcgt 420
catcttccgt ttcggaagat ggtacacaac ctaaacctgg agatggacac gaacggactt 480
ccggtgatga atacggtagt gtcttattca gccatacata ccgcttctat cgaccttagt 540
gtcagctccg acgtcatgtt ccgattcgat gcgaaggacg atggccttca tttggaggtg 600
ctttatgatg aaagccgcta tgacgcctcc tatattgcca ctctattcga acatttttc 660 cgactgcttc attttgtgtt attccagccg gaccagccta tcggcaatgc cgtgttattg 720
tcggaagatg agaagcatcg cctgcttcat gaatttaacg atgtgtggac ggatttccct 780
cgtcaagcaa cgctacatca gttcattgag gaacatgcgg aacgacagcc agaggcaatc 840
gcggtttctt atgaagatac caagctgacg tatcgtgagc tgaatgcccg ggcgaatcgc 900
cttgcccgaa cacttagatc tgaaggtgtg cagccagaag cgctagttgg tctcatggct 960
gaaagatcga tcgacatgat tgttgggatg cttgccgttt tgaaggcggg aggcggctac 1020

-continued

```
gtcgcgattg atccggaata tccggaggag cgcgttcgct acatgctgga agattcgggt   1080
gctcgtgtca ttctggttca gcagcatttg cagaatcgtg tgccaaatac ggaatcagca   1140
gctagactcc ttacacttga cgatgagcag tcttatcatg aggatgcttc gaagttggaa   1200
tcgaagagta cagctgtaga tttggcttgc gtcatctaca cttcggggac aacgggcaat   1260
cccaaaggta acctgacgac acaccgcaat atcgtacgca tcgtgaagaa taccaactat   1320
atcgaaatta cggagcagga taaggtactg caattatcga gttattcttt cgatggctcc   1380
gcattcgata ttttcggggc attaacgaat ggggcccaac tggttcttgt tcctcatcat   1440
acattgcttg atgcaagcaa gctggcggag ctgatcgaaa cggaacaaat atcggttatg   1500
ctgattacta ctgcttattt caacgttctt gtagacgtga acgtatcctg cctgcgccat   1560
atccgcgcga tattgttcgg aggcgagcgc tcttctgtcg cacatgtgcg acaagcactt   1620
gaacagacag ggccaggaag gctgaagcat gcctacggtc cttctgaaag tacggtatat   1680
gcgacatggc atgatgtgac agagatttcg gagcaagccg taagtgtacc gatcggtcgt   1740
cctatcagta atacagccat ctacatcgtc aatgaacgaa atgatttaca gcctataggg   1800
gtatccggtg agctgtgtgt agcgggagaa ggattagttc gtggatattt gaaccgtcca   1860
gaactgactg cacagaagtt cgttgataat ccgttcgtac cgggagagcg catgtatcgt   1920
actggggact tggcgagatg gctgccggac ggaacgattg aatatgttgg ccgaatggat   1980
gatcaggtga aaatcagagg ccatcgcatc gagattgggg aagtagaggc gcagctgctc   2040
aaagtggcgc tgattcagaa ggcgacgatt gtcgtccgag gccgcgagga cggagagaag   2100
cagctgtgcg cgtattatgt agcagatcgt ctgctttctg caggcgagat tagaacaata   2160
cttgccaaag aactgcctag ttatatgatt ccggcatact tcattcagct tgaacagatg   2220
ccattgacga ctaacggcaa ggtagatcgt aaagccctgc cagcaccgga agagcacgta   2280
caagcagaga cggaatatgt ggcgcctaga agtgaacaag aaattcggct tgcgagagtc   2340
tggcaggaag tgctcggtct aagccgagtt ggtgcaaagg atcatttctt cgagctgggc   2400
ggtcactcat tacgagcgac gacactagtc agcaagctgc acaaagaaga gaatatcagc   2460
ctgtccctcc gcgacgtgtt ccgcaatcct actttggaag cgatggccgc gctcatggaa   2520
gctgctcaag gccgcacatt ctcaccaatc ccgacagttg aagagaagga tgtatatccg   2580
gtatcttcgg tgcagaagcg attgttcatt ttgcatcagc tggaaggagc agagcagagc   2640
tataacatgc caggggcatt actgcttgag ggtgatgttg accggaaccg attggagcat   2700
gcattccgtc agctgatcac acgtcacgaa acgcttcgca ccggctttga gatggtgaat   2760
ggagaacctg tgcagcgcat ttatccgact gtagaatttg tagtggaaga gatgtcggcc   2820
gtagaagggg cggaagccga gaagcaaatt cggcaattca ttcgcgcttt cgatctgtcc   2880
acaccgccac tgttcagggc agggctgatt gaacttgctc cgcagcgtca cattctccta   2940
ttcgacatgc accatatcat ttcggacgga acgtcaattg gcattatgat cgaggaattc   3000
acaagcttat acagtgggaa cgagcttgag ccgcttcgca ttcagtacaa ggactttgct   3060
gcgtggcagc gttccgagga gcagatcgag cagttgaaga gccaagaagc ctattggctg   3120
aggcaaatgg aaggcgtact tcctgtgctt gagctgccta ctgattatgt acgtcctgct   3180
gtacagagcc atgatggcgc gttgttcgag ttctcgattg atcgtgagca gagccaagac   3240
ttgaggaatt tagccgccga tacgagaacg accttgtaca tggtgctgct agcggcatac   3300
acgatcatcc tccacaagta ttcaggccag gaagacattg ttgttggaac accgattgcg   3360
```

```
ggtcgaacgc acgacgatgt gcagccactt atcggtatgt tcgtcaacac gttggcgatt   3420
cgcaattatc cttctgggtc taagtctgtg cttacctact tggaggaaat caaagaaacg   3480
acgctgggag cgttcgagca tcaagactat ccgttcgagg aactcgtgga aaacgtgcaa   3540
atttcgcgag atatgagccg tcatccggtg ttcgacacga tgttcgccct tgagaataca   3600
gagcatcggg aattcgatct ggatggtctt caggtaaagc cgtacggtgc tgaacacggg   3660
atggctaagt ttgatttgaa tctgaccata acagaagatg gcgatggact ttactgcacc   3720
atggagtatg ctacagcatt gtacaatcgc tcgacgatcg caaggctttg cggccatttc   3780
ctgcaggtcg ttggaagcat gactcataat ccgcaagcgg caatctcatc actgcaaatg   3840
gtaaccatcg aggagaaggc tgagctgcaa gatgaattca atgatacgga tatggtgtac   3900
ccaagtgaca agacggttca tgaactgttc gcggaacagg tggagcggac accagatgct   3960
gttgctgtcg tctctggcag cgagcaatta agctacggag atctcaaccg taaggcgaat   4020
cagcttgcgt ggaagctgcg tgagtatggc gtgaccgcag agcagcctgt cggcattatt   4080
gttgagcgaa cgctggatac agtcgtcgca gtgctggctg tactcaaagc atcgggcaca   4140
ttcgtaccaa ttgatcccga gtatcctgag acgcgtattc gctatatgct ggcagacagc   4200
ggggctaagc tggtgttggc gcaatcggat ctgccaggga tcattcctga tgacgtccgc   4260
ctgattgatg tacgcgatga gtccctgtac caaggcgacg gagctgacgt accaaatggc   4320
agcaaaccgt ccaacctact ctatatcatc tacacatccg gaacgacggg caatccgaaa   4380
ggggtcatgc tggagcaccg caacatggtt aacctgctgc attatcagca gaaaggcacg   4440
aacattccga tgccttcgcg gattttgcaa tatgcgtctg gcagcttcga tgtatgctat   4500
caggaaatgt tctctgcgct cctgttcggc ggaagcctgt atatggttga caatgagatg   4560
cgcaaggatc cggtacgctt gttccaggaa atcgaaaagc atgaaatcga cgtgatgtac   4620
attccagtgg cgttcctgaa attcatcttc gccgagccgg agtgggcaga agcgttcccg   4680
cgctgcgttc gccatatcat tacggcgggc gagcagttgg tcgtgacacc gcaagtgcag   4740
gcgtgcttga agcgactcga tatcagcctg cacaaccatt acgggccatc ggagactcat   4800
gtcgtgacga cctacacgat gatgccagat gttatcgagg ttggtctgcc gccaatcggc   4860
aagccgatcg cgaacacgag catttttatc gtggatgaca gctttgagtt gcagccgatc   4920
ggcgtgaagg gcgagctcta cgtttccggg gcaagtgtcg gacgcgggta ctggggaaga   4980
acggacttaa ctgaggagaa gttccttgat aacccgttcg cacctggcga gcggctgtac   5040
aagacaggtg acgtagcgcg ctggcttcca gacggcagca ttgagtatgt gggacgaagt   5100
gaccatcagg tgaaaatccg gggcttccgc attgagctgg gcgaggtgga atcgcagttg   5160
ctgcatgtac cggcggtaca ggaggcgacc atggtggcac tggaagatca tgcgggtcag   5220
aagcagttgt gcgcgtattt cacagcagaa tgctcactca cggccggcga gctgcgggca   5280
gcattgtcgc aggagctgcc aggctacatg attccgtcct acttcgtaca gttggagcga   5340
ctgccgctga cgccgaatgg gaagatcgat cggagagcgc tgccgaagcc agaaggcggc   5400
attgagactg gaacggagta tgtcgcgccg cgtacagaga cggaagcaag gcttgcacgc   5460
atttggcagg atgtattggg attagcaagc gtaggcgtga aggacaactt cttcgagctg   5520
ggcggtcact cgctgcgggc aacgacgctg gtgagcaggc tgtacaagga aatgaacgtc   5580
aacttcccgt taagaggtgt gttccgtcat ccgaccatcg aggagatggc gaaggcgata   5640
accgagatgc atcaagaact ttacacggaa atacctatcg ctgaggaaaa agcctattat   5700
ccgttatctt cagcgcagaa aaggctgttc attgtaagcc agctgacagg agccgaggta   5760
```

```
agctataaca tgccgggggt gctgattctc gaaggagagc tggatcgtgc gcgattcgaa   5820
cgggctttcc agaagctgat cgaccgacat gaatcgctgc ggacaagctt cgagacggta   5880
cgcggtgagc ctgtacagcg cattcactcg caggtggagt tcgctatcga atatcacctt   5940
gcagcagaaa aagatgcaga ggcgctgatc actcatttcg tacgtccatt ccagcttaat   6000
caagcaccgc tgctcagagt cggattgatt gaaactggac atgaacgcca tattctgatg   6060
ttcgacatgc accatatcat ttccgatggc gtaacgatgg ggcatgtcgt gaatgaattc   6120
tcccggatat atgcaggcga tcaactgccg gcgctgcgta tccaatataa ggactatgct   6180
gcatggcagc aatccaatga atatgcagag aagcttgcgc atcaggaatc ctattggctg   6240
aagcaattgg acggagaact gccgacgctc gaactgccga ctgattatgt gcgaccggct   6300
gtacagcagt tcgaaggtga tgtggccttg ttcaccttaa cgaacagtca ggccgagcag   6360
ctgcaacgat tagcggcaaa ctacggcgca accttatata tggttctgct tgcagcatat   6420
accgtgctcc tgcacaaata tacgggacag gacgatatca ttgtcggaac accgatcgcg   6480
ggccgcaatc atacggaatt ggagccgctg gttgggatgt tcgtcaatac gctcgccatc   6540
cgcaattatc caacgggtga gaaatccttc gcggaactgt tggcggaggt gaaggatacg   6600
gccctcgccg cattcgagaa tcaggattat ccgttcgaaa cgttggtaga gaaggttcat   6660
aagtctcggg atatgagccg aaatccagtg tttgatacga tattcagtgt tgagcatgaa   6720
cagcagagtt ccttccatat cgatgggctt cggataagtc catacccgca cagccattct   6780
gtcgcgaagt tcgatttgac cttccatgcc gaacagaatg aagaagggat actatgtgga   6840
ctaggctatg cgactgcttt atatgcgaaa gagactgcgg ggcggatggg agaacatttc   6900
gtgcaattaa tagatgccat catcgcagaa ccgaatgcga agctaatgtc actgaatatg   6960
atgagcctgc aggaaagaga gcaagtaaag ctggtattta atgatacgat aacgagttat   7020
ccgcgggaga agacgattca acatttgttc gaagagcagg cagagaaatc gccggatgcg   7080
gttgctatcc aattcggaga agaacggctc acataccgcg agttgaatga acggtcgaat   7140
cgtttggcga gaacactgcg aggtaagggt gtaaaagccg gccgcttcgt aggtctaatg   7200
acagatcgtt cgctagacat gattgtggcg attatggcga ccctgaaggc aggcggggca   7260
tatgtgccaa ttgatccgga ttatccggaa gaacgcattc gatacatgat cgacgattcg   7320
ggagcatcgc ttctagtcgt gcaacgtcat tttcagtcga accatattgc tgcggattgc   7380
atggttgtac ttgtagatga tgaggactcc tatcacgcag atggcacgaa tctggagcag   7440
cataatgggg cttctgatct cgcctacgtc atttacacgt caggtacaac gggaatgccg   7500
aaggggaatt taacaaccca ccgcaacatc gttagagtag tgcgggatgc gaaatatatc   7560
gagatcgatc agcatgacac ggtgctgcaa ttatccagct acgcttttga cggctcaacc   7620
ttcgacatat ttggagcctt gatgaatgga gcgaagcttg tactgattcc gcgcgaggta   7680
gtgctcgacg ctggccgact ggccgacacc atcgagatcg agaagatttc ggtcatgttc   7740
attactactg cctatctcaa tctgctcgtc gacttgagag tggacagtct acgccatatg   7800
cgcgcgatat tgttcggtgg tgaacgcgca tctgtgagcc atgtgcgcaa ggcgctccgg   7860
catttgggcc caggcaagct taagcatgta tacgggccaa cggagagcac cgtatttgcg   7920
actagccaca acgttgatga agtagctgac agcgccgtaa cgataccgat cggacgcccg   7980
attggcaata cggccgtata tatcgttggc gagggagacg ttctgcagcc gattggcgta   8040
gctggtgagt tatgcgtagc gggagatgga gtagccgtag ggtatttgaa ccgcccagaa   8100
```

```
ttgtcgggag ccaagttcgt gaataacccg ttcgttccgg gtgatcgcat gtaccgaacg   8160

ggtgatttgg caagatggct ttcagacgga acgatagagt atgtgggacg gatagacgat   8220

caggtgaaaa tacgtggtta tcgaatcgag cttggtgagg tcgaagctca tctgttagac   8280

cttgaggcaa tccaagaagc tgtggtcatc gtcagggagg aaagtgacgg gcagaagcgc   8340

ctatgcgctt actatgtagc aggtcgtccg attacggctg gtgagatgcg gatagctttg   8400

gctcaggagc tcccgggata catgcttcca tcctacttcg tacagctcga taagcttcca   8460

ttatcaccga acggcaaggt gaaccggaag gcacttccgg ctcctgaatt gcatgtgcag   8520

gcggcttcgg aatacgtggc tccacgcacg ccacaagaag tactgctcgc tcacatatgg   8580

agggaggtgc tcgggcttgg tcaggtaggc gttaaggata atttcttcga gcttggcgga   8640

cattccttaa gcctgatgaa gcttgtagag cgtgtctata ccgagactga ggttgaaatc   8700

ccaattcaca gcgtattccg ggaaccgaca attgaagcga tggcgtacga gatgttgaaa   8760

tccgaacttg caggcaaggc aggaaatcat tttatgaaat tgaacgaaaa cggtcatatc   8820

cctgtcttct gcttccctcc gggacttggc tacggtctca gctacttgga gctggctaag   8880

caactggatc atcactgcat cctgcatggc atcgacttta tcgatgatgc tgatactcgg   8940

gaggaactgc ttgaacgata cgtggatgct atccttgctg ttcaaccgca gccgccattt   9000

gtattgctcg gttattctct aggcggcaac ctgacgttcg aggttgcgaa agcgctggag   9060

tccagagggt atccggtatc ggatgtcatc atgattgatt ccttgcggaa gctgaaggtg   9120

catgaagtag acgaattcga cggcgacatt gatcagatga ttgatggtgt ggaggagctg   9180

aaagaaatgc tggttcacca tccgcttctc cgcgatcagg tgaagaacaa gatgagggcg   9240

tactggtcgt acgcgactga actcgttaac tccgatatca tcgatgccaa tattcatgca   9300

ctgatggcgg agccatccga ggtgaaccag gcagatgggg agcagctcgc aacatggcag   9360

gaggctactc gcggcaggta tgtggaatac aacctccgcg gtgtgcacga agatgtgctt   9420

caaccgcctt tcttagaagc gaacgctaac gtcatgcaag caatcattcg acatattctc   9480

gagcaaacaa tggttaccca ctag                                          9504
```

<210> SEQ ID NO 11
<211> LENGTH: 6654
<212> TYPE: PRT
<213> ORGANISM: Paenibacillus alvei A6-6i-x

<400> SEQUENCE: 11

```
Met Asn Ala Asn Pro Asn Glu Trp Tyr Pro Leu Thr Gln Ala Gln Arg
1               5                   10                  15

Arg Ile Trp Tyr Thr Glu Met Met His Pro Asn Thr Ser Val Thr Thr
            20                  25                  30

Val Ala Gly Thr Met Tyr Ile Arg Gly Lys Val Asp Val Glu Ile Leu
        35                  40                  45

Lys Met Ala Ile Tyr Gln Val Ile Met Gln His Asp Ala Phe Arg Ile
    50                  55                  60

Arg Ile Ala Met Thr Asp Asn Gln Pro Lys Gln Gln Phe Ala Pro Val
65                  70                  75                  80

Glu Gln Ile Val Pro His Val Asp Tyr Leu Glu Trp Asp Asn Gln Ile
                85                  90                  95

Glu Ala Glu Ser Trp Leu Gln Arg Phe Asn His Ile Pro Ile His Met
            100                 105                 110

Phe Asp Pro Ala Leu Tyr His Phe Val Val Phe Asn Val Asn Asp Glu
        115                 120                 125
```

-continued

```
Glu Ala Trp Phe Asn Leu Lys Met Asn His Ile Ala Thr Asp Gly Val
    130                 135                 140

Ser Ser His Leu Ile Ala Tyr Lys Ile Met Lys Asn Tyr Thr Ala Met
145                 150                 155                 160

Val Ser Gly Asn Ala Asp Thr Asp Glu Gln Glu Ser Thr Tyr Leu Asp
                165                 170                 175

Tyr Ile Phe Ala Glu Arg Glu Tyr Glu Gln Ser Asp Arg Tyr Ala Lys
            180                 185                 190

Asp Lys Ala Tyr Trp Leu Asp Lys Phe Ser Thr Met Pro Glu Val Ile
        195                 200                 205

Gly Ile Lys Ser Tyr Pro Pro His Ser Ile Gly Thr Glu Ala Ser Arg
    210                 215                 220

Thr Ser Ile Thr Val Ser Gly Glu Met Tyr Glu Lys Leu Tyr Arg Phe
225                 230                 235                 240

Ser Gln Gln His Asn Ile Ser Leu Phe Thr Leu Phe Leu Gly Ser Leu
                245                 250                 255

Tyr Ala Phe Leu Tyr Lys Thr Thr Gly Asn Asn Asp Ile Ala Val Gly
            260                 265                 270

Ala Ala Tyr Ala Asn Arg Thr Ser Arg Gln Asp Lys Asp Ala Leu Gly
        275                 280                 285

Met Phe Val Ser Thr Val Ala Ala Arg Leu Thr Ile Ser Pro Asp Gln
    290                 295                 300

Asp Val Leu Thr Phe Leu His Asn Val Ala Lys Glu Gln Lys Ala Ile
305                 310                 315                 320

Leu Arg His Gln Lys Tyr Pro Tyr Asn Gln Leu Ile Leu Asp Leu Arg
                325                 330                 335

Glu Gln Asn Asn Ser Val Glu Ile Gln Asp Leu Tyr Arg Ile Ser Ile
            340                 345                 350

Asp Tyr Met Pro Ile Arg Trp Ser Ser His Gly Glu Leu Ala Ala Arg
        355                 360                 365

Gln Arg Ser Ser Phe Cys Gly His Glu Val Asp Asp Phe Ala Val His
    370                 375                 380

Val Glu Asp Met Val Asp Asp Asn Gln Ile Ile Phe Asn Ile Asp Tyr
385                 390                 395                 400

Arg Lys Gln Leu Phe Glu Glu His Glu Val Ile Arg Ile Ile Asp Gln
                405                 410                 415

Met Met Thr Ile Val Asp Gln Met Leu Ser Asn Pro Ser Gln Ser Leu
            420                 425                 430

Gln Gln Leu Ser Met Ile Ser Asp Lys Glu Ala Gln Ile Ile Leu Thr
        435                 440                 445

Arg Phe Ser Asn Gly Asn Trp Ser Thr Pro Gln Pro Val Gly Arg Thr
    450                 455                 460

Ile His Gln Leu Phe Glu Glu Gln Val Glu Arg Thr Pro Asp Gln Val
465                 470                 475                 480

Ala Val Val Phe Gly Asp Arg His Leu Thr Tyr Lys Glu Leu Asn Glu
                485                 490                 495

Gln Ala Asn Cys Phe Ala Arg Thr Leu Arg Ala His Gly Val Ala Ala
            500                 505                 510

Glu Gln Phe Val Gly Ile Met Ala Asp Arg Ser Ile Glu Met Val Val
        515                 520                 525

Gly Ile Leu Ala Ile Leu Lys Ala Gly Gly Ala Tyr Val Pro Ile Asp
    530                 535                 540
```

-continued

```
Pro Glu Tyr Pro Glu Glu Arg Ile Leu Tyr Met Leu Glu Asp Ser Asn
545                 550                 555                 560

Ala Arg Val Leu Val Ser Gln Ser His Leu Gln Thr Arg Leu Gly Tyr
                565                 570                 575

Thr Gly Thr Trp Val Leu Leu Asp Asp Glu Asn Asp Tyr Glu Ala Asn
            580                 585                 590

Arg Asp Asn Leu Glu Ser Val Asn Glu Ala His His Leu Ala Tyr Val
        595                 600                 605

Ile Tyr Thr Ser Gly Thr Thr Gly Lys Pro Lys Gly Val Met Ile Glu
    610                 615                 620

His Lys Gln Ile Thr Ala Leu Gly Asp Ala Trp Lys His Ala Tyr Gln
625                 630                 635                 640

Leu Asp Glu Ser Gly Ile Arg Thr Leu Gln Trp Ala Ser Phe Ser Phe
                645                 650                 655

Asp Val Phe Thr Gly Asp Met Val Arg Ala Leu Leu Tyr Gly Gly Glu
            660                 665                 670

Leu Ile Ile Cys Pro Ser Glu Ala Arg Ala Asn Pro Glu Ala Ile Cys
        675                 680                 685

Glu Leu Ile Ala Arg His Arg Ile His Ile Phe Glu Ser Thr Pro Ala
    690                 695                 700

Leu Val Ile Pro Leu Met Glu Tyr Val His Glu Gln Arg Lys Asp Val
705                 710                 715                 720

Ser Ser Leu Arg Leu Leu Val Val Gly Ser Asp His Cys Pro Ala Ala
                725                 730                 735

Glu Tyr Arg Lys Leu Met Glu Arg Phe Gly Ser Gln Met Arg Ile Leu
            740                 745                 750

Asn Ser Tyr Gly Val Thr Glu Ala Cys Val Asp Ala Cys Tyr Tyr Glu
        755                 760                 765

Lys Asn Gly Ser Val Asp Ser Ile Thr Met Leu Pro Ile Gly Lys Pro
    770                 775                 780

Leu Pro Ser Val Ser Met Tyr Ile Leu Asp Glu Asn Lys Ala Leu Gln
785                 790                 795                 800

Pro Ile Gly Ile Val Gly Glu Leu Tyr Ile Gly Gly Ala Gly Val Gly
                805                 810                 815

Arg Gly Tyr Leu Asn Arg Asp Asp Leu Thr Ala Glu Lys Phe Val Asp
            820                 825                 830

Asp Pro Tyr Ser Gln Gly Lys Met Tyr Arg Thr Gly Asp Leu Ala Arg
        835                 840                 845

Trp Leu Pro Asp Gly Asn Ile Glu Tyr Leu Gly Arg Leu Asp His Gln
    850                 855                 860

Val Lys Ile Arg Gly Asn Arg Ile Glu Ile Gly Glu Ile Glu Thr Arg
865                 870                 875                 880

Met Leu Gln Thr Ser Leu Val Arg Glu Ala Val Ile Val Ala Arg Glu
                885                 890                 895

Asp Glu Asn Gly Leu Lys Ala Leu Cys Ala Tyr Tyr Val Ala Asp Ser
            900                 905                 910

Glu Ile Ser Val Gln Gln Leu Arg Ser Thr Leu Ala Glu Gln Val Pro
        915                 920                 925

Asp Tyr Met Ile Pro Ser Tyr Phe Met Lys Leu Glu Arg Leu Pro Leu
    930                 935                 940

Thr Pro Asn Gly Lys Ile Asp Arg Asn Gly Leu Pro Ala Pro Ser Gly
945                 950                 955                 960

Gln Asp Tyr Ser Gly Lys Ile Tyr Val Glu Pro Arg Asn Gln Ala Glu
```

-continued 965 970 975

Gln Thr Leu Ala Ser Ile Trp Lys Met Val Leu Gly Val Lys Arg Val
980 985 990

Gly Ile Leu Asp His Phe Phe Glu Leu Gly Gly Asp Ser Ile Lys Ser
995 1000 1005

Ile Gln Val Ser Ser Arg Met Gln Gln Ala Gly Tyr Lys Leu Asp
1010 1015 1020

Ile Arg Asp Leu Phe Lys Tyr Pro Thr Ile Glu Gln Ile Ser Pro
1025 1030 1035

His Leu Val Glu Val Gln Arg Lys Ala Glu Gln Gly Glu Glu Ser
1040 1045 1050

Gly Glu Val Gly Leu Thr Pro Ile Leu Arg Trp Tyr Phe Asp Arg
1055 1060 1065

Asp Glu Val Ser Leu His His Tyr Asn Gln Ser Ile Met Leu His
1070 1075 1080

Arg Lys Ala Gly Phe Asp Glu Ala Ala Leu Arg Asn Ala Leu His
1085 1090 1095

Lys Ile Thr Glu His His Asp Ala Leu Arg Met Val Phe Arg Arg
1100 1105 1110

Thr Glu Gln Gly Glu Tyr Ala Ala Trp Asn Arg Arg Ile Glu Glu
1115 1120 1125

Gly Glu Leu Tyr Arg Leu Asp Val Leu Asp Ile Lys Glu Arg Ser
1130 1135 1140

Ala Gly Val Glu Ser Glu Glu Ser Leu His Asn Met Leu Ile Ala
1145 1150 1155

Glu Ala Asn Val Ile Gln Ala Gly Phe Asp Ile Glu Ala Gly Pro
1160 1165 1170

Leu Val Gly Ala Gly Leu Phe Arg Cys Pro Asp Gly Asp His Leu
1175 1180 1185

Leu Ile Val Ile His His Ala Val Ile Asp Ala Val Ser Trp Arg
1190 1195 1200

Ile Leu Leu Glu Asp Leu Ala Thr Gly Tyr Glu Gln Ala Leu Gln
1205 1210 1215

Gly Ser Glu Ile Arg Leu Pro Asp Lys Thr Asp Ser Phe Arg Leu
1220 1225 1230

Trp Ser Arg Glu Leu Ser Ala Tyr Ala Gln Gln Ser Asn Met Asn
1235 1240 1245

Glu Glu Leu Lys Tyr Trp His Gln Val Ala Gln Thr Thr Ile Thr
1250 1255 1260

Pro Leu Pro Thr Asp Tyr Ala Gly Ile Ala Leu Gln Arg Asp Ser
1265 1270 1275

Glu Ser Val Thr Val Glu Trp Ser Ala Ser Glu Thr Glu Leu Leu
1280 1285 1290

Leu Lys Gln Ala His Arg Ala Tyr Asn Thr Gln Met Asp Asp Leu
1295 1300 1305

Leu Leu Thr Ala Leu Gly Ile Ala Phe Arg Arg Trp Cys Gly His
1310 1315 1320

Glu Arg Ile Arg Ile Asn Leu Glu Gly His Gly Arg Glu Ser Ile
1325 1330 1335

Leu Pro Asp Leu Asp Ile Thr Arg Thr Val Gly Trp Phe Thr Ser
1340 1345 1350

Glu Tyr Pro Gln Leu Leu Glu Val Gly Ser Glu Glu Glu Leu Pro
1355 1360 1365

```
Arg Ile  Ile Lys Ser Val Lys  Glu Asp Leu Arg Ser  Ile Pro Asn
    1370                 1375                 1380

Lys Gly  Ile Gly Tyr Gly Ile  Cys Arg Tyr Leu Ser  Asn Thr Gly
    1385                 1390                 1395

Ile Cys  Glu Val Trp Gly Thr  Ala Pro Glu Val Ser  Phe Asn Tyr
    1400                 1405                 1410

Leu Gly  Gln Phe Asp Gln Asp  Phe Gln Asn Ser Gly  Phe Ser Pro
    1415                 1420                 1425

Ser Pro  Tyr Ser Thr Gly Ser  Asn Ile Gly Gly Asp  Gln Leu Arg
    1430                 1435                 1440

Pro Tyr  Leu Leu Asp Met Asn  Gly Met Val Ser Asp  Gly Lys Leu
    1445                 1450                 1455

Gln Leu  Asp Ile Ser Tyr Gly  Arg Thr Gln Tyr Arg  Ala Glu Thr
    1460                 1465                 1470

Ile Glu  Arg Leu Ala Ser Leu  Ile Arg Asp Ser Leu  Leu Glu Ile
    1475                 1480                 1485

Ile Glu  His Cys Val Ala Lys  Glu Arg Thr Glu Leu  Thr Pro Ser
    1490                 1495                 1500

Asp Val  Ser Leu Gln Arg Ile  Ser Ile Gln Glu Leu  Glu Gln Ile
    1505                 1510                 1515

Val Glu  Arg Thr Ser Gly Ile  Gly Glu Val Glu Asp  Ile Tyr Ala
    1520                 1525                 1530

Leu Thr  Pro Met Gln Lys Gly  Met Trp Phe His Thr  Ala Met Asp
    1535                 1540                 1545

Ser Gln  Ala Gly Ala Tyr Phe  Glu Leu Thr Arg Leu  Thr Leu Glu
    1550                 1555                 1560

Gly Thr  Leu Asn Ile Glu Ala  Phe Ala Ala Ser Trp  Asn Glu Leu
    1565                 1570                 1575

Ala Ala  Arg His Ala Val Phe  Arg Thr Asn Phe Leu  Val Asp Ser
    1580                 1585                 1590

Asn Gly  Glu Pro Leu Gln Val  Val Phe Arg Ser Lys  Arg Ile Ser
    1595                 1600                 1605

Val Lys  His Glu Asp Leu Arg  Ser Leu Asn Ala Tyr  Glu Gln Ala
    1610                 1615                 1620

Val Ala  Ile Glu Asn Glu Ala  Ala Lys Glu Arg Glu  Gln Gly Phe
    1625                 1630                 1635

Asp Leu  Glu Asn Gly Asp Val  Met Arg Val Ser Val  Leu Gln Thr
    1640                 1645                 1650

Ala Asp  Glu Val Tyr Glu Val  Leu Trp Ile Ser His  His Ile Val
    1655                 1660                 1665

Met Asp  Gly Trp Cys Leu Pro  Leu Val Ala Ala Glu  Val Phe Asn
    1670                 1675                 1680

Thr Tyr  Ser Ala Leu Val Glu  Asp Lys Lys Pro Ile  Leu Ala Ser
    1685                 1690                 1695

Val Pro  Ser Tyr Asn His Tyr  Ile Gln Trp Leu Glu  Arg Gln Asp
    1700                 1705                 1710

Glu Ser  Ala Ala Ala Ala Tyr  Trp Asn Asn Tyr Leu  Ser Gly Phe
    1715                 1720                 1725

Glu Glu  Thr Thr Glu Leu Pro  His Ser Lys Gly Arg  Arg His Ser
    1730                 1735                 1740

Gly Gln  Tyr Glu Ala Gly Gln  Val Gln Ile Asp Leu  Gly Thr Ser
    1745                 1750                 1755
```

```
Leu Ser Leu Ala Leu Asn Gln Val Ala Thr Gln His Gln Val Thr
    1760                1765                1770

Leu Asn Thr Leu Leu Gln Ala Ser Trp Gly Ile Leu Leu Gln Lys
    1775                1780                1785

Tyr Asn Arg Thr Ser Asp Ile Val Phe Gly Ser Val Val Ser Gly
    1790                1795                1800

Arg Pro Ala Glu Leu Val Gly Ile Glu Glu Met Ile Gly Leu Phe
    1805                1810                1815

Ile Asn Thr Ile Pro Val Arg Val Ser Ser Gln Ala Gln Glu Arg
    1820                1825                1830

Phe Ala Glu Val Met Thr Arg Met Gln Glu Asp Ala Leu Ser Ser
    1835                1840                1845

Ala Lys His Asp Tyr Tyr Pro Leu Tyr Glu Ile Gln Ala Gln Cys
    1850                1855                1860

Thr Leu Lys Gln Asn Leu Ile Thr His Ile Met Val Leu Glu Asn
    1865                1870                1875

Tyr Pro Met Glu Gln Gln Leu Asp Gln Phe Asn Ser Ser Asp Gly
    1880                1885                1890

Ser Gly Leu Lys Leu Thr Asp Val Thr Val Thr Glu Gln Thr Asn
    1895                1900                1905

Tyr Asp Leu Asn Leu Ile Ile Ile Pro Gly Asp Asn Ile Val Ile
    1910                1915                1920

Arg Phe Asp Phe Asn Lys Gln Ala Leu Glu Glu Ala Asp Met Asn
    1925                1930                1935

Val Leu Lys Gln His Leu Leu His Val Leu Glu Gln Val Ala Ser
    1940                1945                1950

Asn Pro Arg Ile Ser Ile Gly Glu Leu Gln Leu Ala Thr Asp Glu
    1955                1960                1965

Glu Arg Ala Val Met Met Ser Glu Phe Asn Asp Thr Phe Val Ala
    1970                1975                1980

Tyr Pro Arg Glu Lys Ser Ile His Arg Leu Phe Glu Glu Arg Ala
    1985                1990                1995

Glu His Glu Pro Asp Ala Leu Ala Val Val Phe Gly Asn Glu Gln
    2000                2005                2010

Met Thr Tyr Gly Ala Leu Asn Ala Ala Ala Asn Arg Met Ala Arg
    2015                2020                2025

Arg Leu Arg His Ala Gly Val Thr Asn Gly Glu Leu Val Gly Ile
    2030                2035                2040

Cys Ala Asp Arg Ser Leu Asp Met Val Val Gly Leu Leu Ala Ile
    2045                2050                2055

Met Lys Ser Gly Gly Ala Tyr Val Pro Ile Asp Pro Ala Tyr Pro
    2060                2065                2070

Gln Glu Arg Ile Ser Ala Met Leu Glu Asp Thr Ser Ile Thr Thr
    2075                2080                2085

Met Val Thr Gln Lys His Leu Cys Ser Leu Trp Pro Glu His Phe
    2090                2095                2100

Asn Val Ile Val Leu Asp Val Asn Glu Thr Asp Val Ser Asn Leu
    2105                2110                2115

Met Glu Asp Ile Glu Ser Thr Asn Leu Ser Ile Asp Gly Ala Gly
    2120                2125                2130

Asp Asp Leu Ala Tyr Ile Ile Tyr Thr Ser Gly Ser Thr Gly Thr
    2135                2140                2145

Pro Lys Gly Val Cys Val Thr His Arg Gly Val Val Arg Leu Val
```

-continued

```
    2150                2155                2160

Cys Gly  Ala Thr Tyr Val Glu  Ile Asp Ser Ser Asp  Val Phe Leu
    2165                2170                2175

Gln Gly  Ser Thr Ile Ser Phe  Asp Ala Ala Thr Phe  Glu Ile Trp
    2180                2185                2190

Gly Ser  Leu Leu Asn Gly Ala  Ala Leu Ala Ile Leu  Pro Ser Gly
    2195                2200                2205

Asn Val  Ser Leu Thr Asp Trp  Ser Glu Ala Ile Gln  Arg His Arg
    2210                2215                2220

Val Thr  Thr Leu Trp Met Thr  Ala Gly Leu Phe Gln  Val Met Val
    2225                2230                2235

Glu Gln  Gln Ile Glu Gly Phe  Tyr Gly Val Lys Gln  Leu Leu Val
    2240                2245                2250

Gly Gly  Asp Val Val Ser Pro  Thr His Val Arg Lys  Val Met Glu
    2255                2260                2265

Lys His  Asn Gly Ile Arg Val  Ile Asn Gly Tyr Gly  Pro Thr Glu
    2270                2275                2280

Asn Thr  Thr Phe Thr Cys Cys  His Thr Ile Thr Ala  Ala Asp Leu
    2285                2290                2295

Asp Arg  Gly Cys Ser Ile Pro  Ile Gly Arg Pro Ile  Ser Asn Thr
    2300                2305                2310

Arg Val  Tyr Val Leu Asp Glu  Ala Gly Asn Ala Leu  Pro Val Gly
    2315                2320                2325

Val Cys  Gly Glu Leu Tyr Ala  Gly Gly Asp Gly Leu  Ala Arg Gly
    2330                2335                2340

Tyr Leu  Asn Arg Pro Glu Leu  Thr Ala Glu Lys Phe  Val Asn Asp
    2345                2350                2355

Pro Phe  Ile Pro Gly Glu Arg  Leu Tyr Arg Thr Gly  Asp Leu Ala
    2360                2365                2370

Arg Trp  Leu Pro Asp Gly Ser  Ile Glu Phe Ile Gly  Arg Cys Asp
    2375                2380                2385

Glu Gln  Val Lys Ile Arg Gly  Tyr Arg Ile Glu Pro  Gly Glu Val
    2390                2395                2400

Leu Ala  Tyr Leu Leu Arg Ile  Asp Glu Val Gly Glu  Ala Ala Val
    2405                2410                2415

Ile Ala  Arg Glu Asp Ser Ser  Gly Gln Lys Glu Leu  Cys Ala Tyr
    2420                2425                2430

Phe Thr  Thr Glu Ala Glu Leu  Ser Ala Ser Gly Leu  Arg Glu Thr
    2435                2440                2445

Leu Ala  Arg Glu Leu Pro Ala  Tyr Met Ile Pro Ser  His Phe Ile
    2450                2455                2460

Gln Ile  Glu Glu Leu Pro Leu  Thr Pro Asn Gly Lys  Val Asp Arg
    2465                2470                2475

Arg Ala  Leu Pro Gln Pro Gly  Glu Gly Met His Leu  Asn Ile Gln
    2480                2485                2490

Ile Gln  Pro Arg Thr Glu Leu  Glu Ala Lys Leu Ala  Leu Ile Trp
    2495                2500                2505

Lys Asp  Val Leu Gly Leu Glu  Asn Val Gly Val Thr  Asp Ser Phe
    2510                2515                2520

Phe Glu  Leu Gly Gly His Ser  Leu Arg Ala Thr Thr  Leu Val Ser
    2525                2530                2535

Lys Val  His Arg Glu Leu Ser  Val Val Leu Pro Leu  Gln Asp Val
    2540                2545                2550
```

-continued

```
Phe Arg  Tyr Pro Thr Ile Glu  Gln Met Ser Leu Ala  Ile Gln Gly
    2555                 2560                 2565

Met Gln  Lys Glu Ser Phe Ala  Ser Ile Pro Arg Val  Glu Asp Arg
    2570                 2575                 2580

Glu Trp  Tyr Pro Val Ser Ser  Ala Gln Lys Arg Leu  Phe Val Leu
    2585                 2590                 2595

His Gln  Met Glu Gly Ala Glu  Leu Ser Tyr Asn Met  Pro Gly Val
    2600                 2605                 2610

Met Ala  Ile Glu Gly Lys Leu  His Arg Asp Arg Leu  Glu Ala Ala
    2615                 2620                 2625

Phe Arg  Ser Leu Ile Ala Arg  His Glu Val Leu Arg  Thr Gly Phe
    2630                 2635                 2640

Glu Met  His Asn Gly Glu Pro  Met Gln Arg Ile Tyr  Ser Asp Val
    2645                 2650                 2655

Glu Phe  Thr Val Glu His Trp  Ile Val Gly Ala Ala  Ser Glu Ala
    2660                 2665                 2670

Glu Ser  Val Ile Arg Ser Phe  Val Arg Ala Phe Gln  Leu Asn Lys
    2675                 2680                 2685

Pro Pro  Leu Leu Arg Val Gly  Leu Ile Glu Val Asp  Ala Gly Arg
    2690                 2695                 2700

His Leu  Leu Leu Phe Asp Met  His His Ile Ile Ser  Asp Gly Ala
    2705                 2710                 2715

Ser Met  Gly Ile Leu Leu Asp  Glu Phe Val Ala Leu  Tyr Ser Gly
    2720                 2725                 2730

Glu Gln  Leu Pro Glu Leu Arg  Leu Gln Tyr Lys Asp  Tyr Ala Ser
    2735                 2740                 2745

Trp Gln  His Ser Glu Ala Tyr  Leu Ser Lys Met Glu  Glu Gln Lys
    2750                 2755                 2760

Ala Tyr  Trp Leu Glu Thr Leu  Arg Gly Glu Leu Pro  Val Leu Gln
    2765                 2770                 2775

Leu Pro  Val Asp Tyr Thr Arg  Pro Ala Phe Arg Ser  Phe Ala Gly
    2780                 2785                 2790

Ser Thr  Leu Glu Phe Ile Val  Pro Ala Asp Lys Thr  Asp Gln Leu
    2795                 2800                 2805

Lys Gln  Leu Gly Ala Gly Ser  Asp Ala Thr Met Tyr  Met Val Leu
    2810                 2815                 2820

Leu Ala  Leu Tyr Thr Ala Leu  Leu His Lys Tyr Thr  Gly Gln Glu
    2825                 2830                 2835

Asp Val  Ile Val Gly Met Pro  Ile Ala Gly Arg Thr  His Ala Asp
    2840                 2845                 2850

Ile Glu  Pro Leu Ile Gly Met  Phe Val Asn Thr Leu  Pro Leu Arg
    2855                 2860                 2865

His Tyr  Pro Ala Gly Glu Lys  Thr Phe Arg Ser Phe  Leu Gly Glu
    2870                 2875                 2880

Val Arg  Gln Ser Thr Leu Gln  Ala Tyr Glu His Gln  Glu Tyr Pro
    2885                 2890                 2895

Phe Glu  Glu Leu Val Asp His  Ile Gln Pro Thr Arg  Asp Val Ser
    2900                 2905                 2910

Arg Asn  Pro Ile Phe Asp Thr  Val Leu Val Leu Gln  Asn Thr Glu
    2915                 2920                 2925

Lys Gly  Ala Trp Ser Ile Asp  Gly Leu Ala Val Thr  Pro Asn Pro
    2930                 2935                 2940
```

-continued

```
Ile Glu  His Ala Val Ala Lys  Phe Asp Leu Thr Leu  His Val Glu
    2945                 2950                 2955

Glu Asp  Val Asp Gly Leu Ala  Cys Ser Ile Glu Tyr  Ala Thr Ala
    2960                 2965                 2970

Leu Tyr  Asn Arg Glu Thr Ile  Glu Arg Leu Ala Cys  His Phe Asn
    2975                 2980                 2985

Gln Leu  Leu Glu Ala Val Ile  Ser Asn Pro Asp Ala  Arg Leu Glu
    2990                 2995                 3000

Gln Leu  Gly Ile Ile Thr Glu  Thr Glu Lys Gln Gln  Leu Phe Glu
    3005                 3010                 3015

Gln Phe  Asn Asp Thr Ser Ala  Asp Tyr Pro Arg Asp  Lys Thr Ile
    3020                 3025                 3030

His Arg  Leu Phe Glu Glu Gln  Val Glu Arg Thr Pro  Asp Ala Ile
    3035                 3040                 3045

Ala Val  Thr Gly Thr Asp Gly  Phe Leu Thr Tyr Gln  Glu Leu Asn
    3050                 3055                 3060

Glu Arg  Ala Asn Ser Leu Ala  Trp Val Leu Arg Ala  Glu Gly Ile
    3065                 3070                 3075

Gly Ala  Asp Lys Leu Val Gly  Ile Met Ala Glu Arg  Thr Thr Asp
    3080                 3085                 3090

Met Leu  Val Gly Leu Ile Ala  Ile Leu Lys Ala Gly  Gly Ala Tyr
    3095                 3100                 3105

Val Pro  Ile Asp Pro Glu Tyr  Pro Asp Glu Arg Ile  Ser Tyr Met
    3110                 3115                 3120

Leu Ser  Asp Ser Gly Ala Asp  Ile Leu Leu Leu Pro  Arg His Leu
    3125                 3130                 3135

Arg Asn  Gln Val Ala Tyr Glu  Gly Thr Val Leu Phe  Leu Asp Asp
    3140                 3145                 3150

Glu Gln  Thr Tyr Ser Gly Asp  Lys Ser Asn Pro Pro  Ser Val Asn
    3155                 3160                 3165

Lys Pro  Ser Asp Leu Ala Tyr  Val Ile Tyr Thr Ser  Gly Thr Thr
    3170                 3175                 3180

Gly Lys  Pro Lys Gly Thr Leu  Ile Glu His Lys Asn  Val Val Arg
    3185                 3190                 3195

Leu Leu  Phe Asn Ser Arg Asn  Leu Phe Asp Phe Arg  Ser Thr Asp
    3200                 3205                 3210

Thr Trp  Thr Leu Phe His Ser  Phe Cys Phe Asp Phe  Ser Val Trp
    3215                 3220                 3225

Glu Met  Tyr Gly Ala Leu Leu  Tyr Gly Gly Lys Leu  Val Val Val
    3230                 3235                 3240

Pro Gln  Leu Thr Ala Lys Asn  Pro Ala Met Phe Leu  Gln Leu Leu
    3245                 3250                 3255

Ala Glu  Glu Arg Val Thr Ile  Leu Asn Gln Thr Pro  Thr Tyr Phe
    3260                 3265                 3270

Tyr Gln  Leu Ile Arg Glu Ala  Leu Thr Asp Gly Ser  Pro Glu Leu
    3275                 3280                 3285

Asn Ile  Arg Met Val Ile Phe  Gly Gly Glu Ala Leu  Ser Pro Gln
    3290                 3295                 3300

Leu Leu  Lys Asp Trp Arg Ala  Lys Tyr Pro Arg Thr  Gln Leu Ile
    3305                 3310                 3315

Asn Met  Tyr Gly Ile Thr Glu  Thr Thr Val His Val  Thr Tyr Lys
    3320                 3325                 3330

Glu Ile  Thr Glu Ala Glu Ile  Glu Gln Ala Arg Ser  Asn Ile Gly
```

```
    3335                3340                3345

Phe Pro  Ile Pro Thr Leu Arg  Ile Tyr Ile Leu Asp  Ala Asn Arg
    3350                3355                3360

Gln Cys  Val Pro Ile Gly Val  Ala Gly Glu Met Phe  Val Ala Gly
    3365                3370                3375

Glu Gly  Leu Ala Arg Gly Tyr  Leu Asn Arg Pro Glu  Leu Thr Ala
    3380                3385                3390

Asp Arg  Phe Val Asp Asn Pro  Phe Glu Pro Gly Ser  Lys Met Tyr
    3395                3400                3405

Lys Thr  Gly Asp Leu Ala Lys  Trp Leu Pro Asp Gly  Asn Ile Glu
    3410                3415                3420

Tyr Leu  Gly Arg Ile Asp His  Gln Val Lys Ile Arg  Gly Tyr Arg
    3425                3430                3435

Ile Glu  Leu Gly Glu Val Glu  Ala Gln Val Thr Lys  Val Glu Ser
    3440                3445                3450

Val Arg  Glu Ala Val Val Val  Ala Arg Glu Glu Asn  Gly Glu Lys
    3455                3460                3465

Leu Leu  Cys Ala Tyr Phe Val  Ala Asp Arg Gln Leu  Thr Val Gly
    3470                3475                3480

Glu Met  Arg Thr Glu Leu Ala  Gln Glu Leu Pro Thr  Tyr Met Ile
    3485                3490                3495

Pro Ser  Tyr Phe Val Gln Met  Glu Arg Met Pro Leu  Thr Ser Asn
    3500                3505                3510

Gly Lys  Val Asp Arg Lys Ala  Leu Pro Ala Pro Glu  Gly Ser Ile
    3515                3520                3525

Asn Thr  Gly Lys Glu Tyr Val  Ala Pro Arg Thr Pro  Met Glu Ala
    3530                3535                3540

Ser Leu  Ala Arg Met Trp Glu  Glu Leu Leu Gly Ile  Glu Gln Val
    3545                3550                3555

Gly Val  Thr Asp Asn Phe Phe  Glu Leu Gly Gly His  Ser Leu Arg
    3560                3565                3570

Ala Thr  Ala Leu Val Asn Arg  Val His Gln Glu Met  Asn Ile Gln
    3575                3580                3585

Leu Pro  Leu Arg Asp Val Phe  Arg Phe Ser Thr Ile  Glu Glu Leu
    3590                3595                3600

Ala Ala  Ala Met Ser Glu Met  Ala Glu Glu Ser Tyr  Ser Ser Ile
    3605                3610                3615

Pro Val  Ala Glu Val Gln Asp  His Tyr Pro Val Ser  Ser Ala Gln
    3620                3625                3630

Lys Arg  Leu Tyr Ile Leu His  Gln Leu Glu Gly Ala  Glu Gln Gly
    3635                3640                3645

Tyr Asn  Met Pro Gly Ile Met  Leu Leu Glu Gly Glu  Leu Asp Arg
    3650                3655                3660

Ser Arg  Phe Glu Ala Ala Phe  Arg Lys Leu Ile Ala  His His Asp
    3665                3670                3675

Ile Leu  Arg Thr Gly Phe Glu  Leu Val Gln Gly Glu  Ala Val Gln
    3680                3685                3690

Arg Ile  His Asp Thr Val Asp  Phe Ala Ile Glu Tyr  Arg Lys Val
    3695                3700                3705

Glu Glu  Gln Glu Val Gln Gln  Gln Val Lys Gln Phe  Ile Arg Thr
    3710                3715                3720

Phe Glu  Leu Asp Lys Pro Pro  Leu Leu Arg Val Gly  Leu Ile Glu
    3725                3730                3735
```

-continued

```
Ile Ala  Gly Thr Lys Glu Gln  His Val Leu Leu Phe  Asp Met His
    3740                 3745                 3750

His Ile  Ile Ser Asp Gly Val  Ser Ile Gly Ile Val  Leu Gln Glu
    3755                 3760                 3765

Ile Met  Arg His Tyr His Gly  Glu Gln Val Pro Pro  Leu His Ile
    3770                 3775                 3780

Gln Tyr  Lys Asp Tyr Ala Ala  Trp Gln Gln Ser Glu  Ala Gln Lys
    3785                 3790                 3795

Glu Gln  Leu Lys His Gln Lys  Ala Tyr Trp Leu Gly  Gln Phe Gln
    3800                 3805                 3810

Gly Glu  Leu Pro Ile Leu Glu  Leu Pro Thr Asp Tyr  Ala Arg Pro
    3815                 3820                 3825

Ala Met  Gln Gln Tyr Gly Gly  Leu Thr Leu Pro Phe  Arg Ile Asp
    3830                 3835                 3840

Lys Asp  Val Ala Asp Gly Leu  Asn Arg Ile Ala Ala  Asp Thr Gly
    3845                 3850                 3855

Thr Thr  Leu Tyr Met Val Leu  Leu Ala Ala Tyr Thr  Val Met Leu
    3860                 3865                 3870

His Lys  Tyr Thr Gly Gln Glu  Asp Ile Val Val Gly  Thr Pro Ile
    3875                 3880                 3885

Ala Gly  Arg Thr His Glu Glu  Leu Gln Pro Leu Ile  Gly Met Phe
    3890                 3895                 3900

Val Asn  Thr Leu Ala Ile Arg  Ala Tyr Pro Glu Gly  Ala Lys Ala
    3905                 3910                 3915

Phe Arg  Ser Tyr Leu Asp Glu  Ile Arg Ser Thr Met  Leu Gly Ala
    3920                 3925                 3930

Tyr Glu  His Gln Gln Tyr Pro  Phe Glu Glu Leu Val  Glu Gly Leu
    3935                 3940                 3945

Gln Leu  Thr Arg Asp Leu Ser  Arg Asn Pro Leu Phe  Asp Thr Met
    3950                 3955                 3960

Phe Ala  Leu Asp Asn Thr Asp  Met Lys Ala Asp Ser  Leu Gly Glu
    3965                 3970                 3975

Leu Gln  Met Lys Pro Tyr Pro  Leu Glu Tyr Thr Ile  Ser Lys Phe
    3980                 3985                 3990

Asp Val  Ser Leu Asp Val Lys  Ala Asp Glu Ala Gly  Leu Asp Cys
    3995                 4000                 4005

Ser Phe  Glu Tyr Ala Thr Ser  Leu Phe Lys Ser Glu  Thr Ile His
    4010                 4015                 4020

Arg Met  Ala Glu His Phe Ser  His Leu Leu Lys Asp  Ile Val Asn
    4025                 4030                 4035

His Pro  Asp Ala Gln Leu Gly  Glu Leu Gly Met Leu  Thr Val Gln
    4040                 4045                 4050

Glu Ser  Asp Glu Ile Leu Gln  Val Phe Asn Pro Thr  His Ser Leu
    4055                 4060                 4065

Lys Ala  Pro Asn Glu Thr Ile  His Arg Leu Phe Glu  Glu Gln Ala
    4070                 4075                 4080

Glu Arg  Thr Pro Glu Gln Pro  Ala Val Val Phe Gly  Asn Glu Arg
    4085                 4090                 4095

Met Thr  Tyr Arg Glu Leu Asn  Glu Arg Ala Asn Lys  Leu Ala Arg
    4100                 4105                 4110

Thr Leu  Arg Ala Glu Gly Val  Glu Pro Asp Asp Leu  Ile Gly Val
    4115                 4120                 4125
```

```
Met Ala  Asp Arg Ser Ile Asp  Met Val Val Ala Val  Met Ala Val
    4130                 4135                 4140

Leu Lys  Ser Gly Gly Ala Tyr  Val Pro Ile Asp Pro  Glu Tyr Pro
    4145                 4150                 4155

Glu Asp  Arg Ile Arg Tyr Met  Leu Glu Asp Ala Lys  Ala Arg Ile
    4160                 4165                 4170

Leu Leu  Thr Gln Gly His Leu  Gln Asp Lys Val Thr  Phe Glu Gly
    4175                 4180                 4185

Thr Trp  Val Leu Leu Glu Asp  Glu Ala Ser Tyr His  Glu Asp Asp
    4190                 4195                 4200

Thr Asn  Leu Glu Pro Asn Cys  Glu Pro Gly His Leu  Cys Tyr Val
    4205                 4210                 4215

Ile Tyr  Thr Ser Gly Thr Thr  Gly Asn Pro Lys Gly  Val Met Ile
    4220                 4225                 4230

Glu His  Arg Gln Leu Ala Ala  Met Ala Glu Ala Trp  Lys Ala Glu
    4235                 4240                 4245

Tyr Glu  Leu His Glu Pro Gly  Ile Arg Trp Leu Gln  Trp Ala Ser
    4250                 4255                 4260

Phe Ser  Phe Asp Val Phe Ser  Gly Asp Leu Ala Arg  Thr Leu Leu
    4265                 4270                 4275

His Gly  Gly Glu Leu Val Leu  Cys Pro Ser Asp Thr  Arg Ala Asn
    4280                 4285                 4290

Pro Gly  Ala Leu Ala Glu Leu  Leu Arg Ser Ser Gly  Ile Gln Met
    4295                 4300                 4305

Phe Glu  Ser Thr Pro Ala Leu  Val Ile Pro Leu Met  Glu His Val
    4310                 4315                 4320

Tyr Glu  His Gly Leu Asp Ile  Asp Ser Leu Arg Leu  Leu Ile Ile
    4325                 4330                 4335

Gly Ser  Asp Leu Cys Pro Ala  Asp Glu Phe Arg Lys  Leu Arg Asp
    4340                 4345                 4350

Arg Phe  Ser Ser His Met Arg  Ile Ile Asn Ser Tyr  Gly Val Thr
    4355                 4360                 4365

Glu Ala  Cys Val Asp Ser Ser  Tyr Tyr Glu Pro Ile  Ser Ser Asp
    4370                 4375                 4380

Ser Val  Arg Ser Val Pro Ile  Gly Lys Pro Leu Pro  Tyr Val Ser
    4385                 4390                 4395

Met Tyr  Ile Leu Gly Glu Asn  Leu Ser Leu Gln Pro  Val Gly Leu
    4400                 4405                 4410

Ala Gly  Glu Leu Tyr Ile Ala  Gly Ala Gly Val Gly  Arg Gly Tyr
    4415                 4420                 4425

Trp Asn  Arg Pro Glu Met Thr  Ala Asp Lys Phe Val  Arg Asp Pro
    4430                 4435                 4440

Phe Ala  Asp Gly Gln Arg Met  Tyr Arg Thr Gly Asp  Leu Ala Lys
    4445                 4450                 4455

Trp Leu  Pro Asp Gly Asn Ile  Glu Leu Ile Gly Arg  Thr Asp His
    4460                 4465                 4470

Gln Val  Lys Ile Arg Gly Tyr  Arg Ile Glu Ile Gly  Glu Val Glu
    4475                 4480                 4485

Ser Lys  Leu Gln Glu Thr Pro  His Ile Arg Glu Ala  Ala Val Val
    4490                 4495                 4500

Ala Lys  Glu Asp Gly Ser Gly  Arg Lys Val Leu Cys  Ala Tyr Tyr
    4505                 4510                 4515

Thr Ser  Glu Arg Glu Leu Thr  Ala Gly Glu Trp Arg  Ala Ala Leu
```

-continued

```
    4520                4525                4530

Ala Lys  Glu Leu Pro Ala Tyr  Met Ile Pro Ser His  Phe Met Arg
    4535                4540                4545

Leu Glu  Arg Met Pro Leu Thr  Pro Asn Gly Lys Leu  Asp Arg Lys
    4550                4555                4560

Gly Leu  Pro Ala Pro Glu Gly  Ala Ala Tyr Thr Gly  Thr Glu Tyr
    4565                4570                4575

Glu Ala  Pro Arg Thr Asp Ala  Glu Ile Ala Leu Ala  Ala Ala Trp
    4580                4585                4590

Gln Ser  Val Leu His Val Glu  Arg Val Gly Thr Asn  Asp His Phe
    4595                4600                4605

Phe Glu  Leu Gly Gly Asp Ser  Ile Lys Ser Ile Gln  Val Ser Ser
    4610                4615                4620

Arg Leu  His Gln Ala Gly Tyr  Lys Leu Glu Ile Arg  Asp Leu Phe
    4625                4630                4635

Lys Tyr  Pro Thr Ile Ala Gln  Leu Ser Pro Gln Leu  Gln Pro Ile
    4640                4645                4650

Gly Arg  Ile Ala Asp Gln Gly  Glu Val Ser Gly Glu  Val Glu Leu
    4655                4660                4665

Thr Pro  Ile Gln Cys Trp Tyr  Phe Gly Leu Asp Leu  Asp Asp Met
    4670                4675                4680

His His  Tyr Asn Gln Ser Phe  Met Leu Tyr Arg Gln  Asp Gly Phe
    4685                4690                4695

Asn Glu  Glu Ala Leu Arg Lys  Thr Leu Arg Ser Ile  Val Glu His
    4700                4705                4710

His Asp  Ala Leu Arg Met Val  Phe Arg Lys Ser Asp  Ala Gly Val
    4715                4720                4725

Thr Ala  Trp Asn Arg Ala Ile  Glu Glu Gly Glu Leu  Phe Asp Phe
    4730                4735                4740

Leu Ala  Phe Asp Ile Ala Asn  Ser Gly Asp Ala Glu  Gln Val Ile
    4745                4750                4755

Glu Ala  Lys Ala Asn Asp Ile  Gln Ala Ser Ile Asp  Leu Gln Gly
    4760                4765                4770

Gly Pro  Leu Val Lys Ala Gly  Leu Phe Arg Cys Glu  Gln Gly His
    4775                4780                4785

His Leu  Leu Ile Ala Ile His  His Ala Val Met Asp  Gly Val Ser
    4790                4795                4800

Trp Arg  Ile Leu Leu Glu Asp  Ile Ala Thr Gly Tyr  Glu Gln Ala
    4805                4810                4815

Cys Lys  Gly Asp Asp Ile Arg  Leu Pro Ser Lys Thr  Asp Ser Tyr
    4820                4825                4830

Ala Ala  Trp Ser Arg Ser Leu  Val Glu Tyr Ala Glu  His Thr Asp
    4835                4840                4845

Leu Gly  His Glu Arg Ser Tyr  Trp Arg His Val Leu  Asn Ala Gly
    4850                4855                4860

Thr Asn  Pro Leu Pro Lys Asp  Phe Asp Thr Glu Ser  Ser Leu Gln
    4865                4870                4875

Gln Asp  Ser Asn Ser Val Thr  Val Ala Trp Asn Gln  Gln Asp Thr
    4880                4885                4890

Glu His  Leu Leu Lys Arg Val  His Arg Ala Tyr Asn  Thr Asp Met
    4895                4900                4905

Asn Glu  Ile Leu Leu Ala Ala  Leu Ala Ile Ala Ile  Gln Lys Trp
    4910                4915                4920
```

Ser Gly His Asn Gln Ile Leu Val Asn Leu Glu Gly His Gly Arg
4925 4930 4935

Glu Pro Ile Ala Gly Asp Leu Asp Ile Ser Arg Thr Val Gly Trp
4940 4945 4950

Phe Thr Ser Glu Tyr Pro Val Leu Leu Lys Ala Glu Arg Asp Arg
4955 4960 4965

Gly Leu Ala Tyr His Ile Lys Arg Ala Lys Glu Glu Leu Arg Gln
4970 4975 4980

Ile Pro Asn Lys Gly Ile Gly Tyr Gly Ile Cys Arg Tyr Leu Ser
4985 4990 4995

Glu Pro Gln Asp Ser Leu Glu Trp Gly Ala Ala Pro Glu Ile Ser
5000 5005 5010

Phe Asn Tyr Leu Gly Gln Phe Asp Gln Asp Ser Met Gly Ser Gly
5015 5020 5025

Met Met Leu Ser Pro Tyr Ser Lys Gly Ser Asp Gly Ser Ala Leu
5030 5035 5040

His Thr Arg Gln Tyr Val Leu Asp Ile Asn Gly Ala Ile Thr Asp
5045 5050 5055

Gly Ile Leu Thr Leu Asp Met Ser Tyr Ser Glu Lys Glu Tyr Arg
5060 5065 5070

Lys Glu Thr Met Glu Leu Leu Ala Gly His Phe His Glu Ser Leu
5075 5080 5085

Leu Glu Ile Ile Asp His Cys Val Ser Arg Glu Gln Thr Glu Leu
5090 5095 5100

Thr Pro Ser Asp Leu Leu Leu Gln Gly Leu Ser Ile Glu Gln Leu
5105 5110 5115

Glu Gln Ile Ala Glu Glu Thr Lys Glu Leu Gly Ile Ile Glu Asn
5120 5125 5130

Met Tyr Met Leu Thr Pro Met Gln Lys Gly Met Trp Phe His Asn
5135 5140 5145

Ala Leu Asp Gly Gln Glu Gly Ala Ser Gly Ala Tyr Phe Glu Gln
5150 5155 5160

Thr Arg Phe Thr Leu Arg Gly Glu Leu Asp Pro Ala Leu Phe Ala
5165 5170 5175

Gln Ser Leu His Glu Leu Ala Ala Arg His Ser Val Leu Arg Thr
5180 5185 5190

Asn Phe Cys Ser Leu Asp Gly Glu Pro Val Gln Met Val Phe Arg
5195 5200 5205

Glu Gly Arg Ile Thr Phe Thr Tyr Glu Asp Leu Ser Gln Leu Pro
5210 5215 5220

Ala Asp Glu Gln Ala Val Val Met Glu Arg Val Val Ala Ser Asp
5225 5230 5235

Lys Leu Gln Gly Phe Asp Leu Glu Arg Asp Pro Leu Val Arg Val
5240 5245 5250

Thr Leu Met Arg Thr Glu Ala Ser Ser Cys His Val Leu Trp Ser
5255 5260 5265

Ser His His Ile Leu Met Asp Gly Trp Cys Leu Pro Gln Leu Thr
5270 5275 5280

Asp Glu Leu Phe Arg Ile Tyr Ser Ala Val Thr Asn His Ala Ala
5285 5290 5295

Gly Thr Thr Glu Ala Thr Gly Thr Val Gly Ile Pro Gly Ser Ala
5300 5305 5310

-continued

```
Glu Ser  Met Arg Asn Lys Glu  Ala Asn Leu Pro Asp  Tyr Ser Arg
    5315                 5320                 5325

Tyr Ile  Glu Trp Leu Ala Glu  Gln Asp Met Ser Ala  Ala Ala Glu
    5330                 5335                 5340

Tyr Trp  Asn Gly Tyr Leu Ala  Gly Tyr Glu Gln Gln  Thr Arg Leu
    5345                 5350                 5355

Pro Asn  Gly Lys Ile Thr Val  Lys Asp Lys Pro Tyr  Val Leu Glu
    5360                 5365                 5370

Gln Ala  Ser Arg Lys Leu Gly  Ile Asp Leu Thr Ser  Arg Met Ile
    5375                 5380                 5385

Arg Ile  Ala Lys Gln His Gln  Val Thr Leu Asn Thr  Leu Leu Gln
    5390                 5395                 5400

Ala Ala  Trp Gly Ile Val Leu  Gln Lys Tyr Asn Gly  Thr Gln Asp
    5405                 5410                 5415

Val Val  Phe Gly Gly Val Val  Ser Gly Arg Pro Ala  Asp Val Pro
    5420                 5425                 5430

Gly Val  Glu Ser Met Ile Gly  Leu Phe Ile Asn Thr  Ile Pro Val
    5435                 5440                 5445

Arg Val  Ser Cys Glu Ala Gly  Ala Ser Phe Ser Asp  Val Met Glu
    5450                 5455                 5460

Gln Leu  Gln Asn Ala Ala Leu  Glu Ser Gly Arg Tyr  Asp Tyr Tyr
    5465                 5470                 5475

Pro Leu  Tyr Glu Ile Gln Ser  Arg Thr Ser Gln Lys  Ser Glu Leu
    5480                 5485                 5490

Ile Ser  His Ile Met Val Phe  Glu Asn Tyr Pro Leu  Asp Glu Arg
    5495                 5500                 5505

Met Glu  Gln Thr Gly Asp Gly  Asn Asp Gly Ala Leu  Ala Leu Thr
    5510                 5515                 5520

Asp Val  Gln Ala Ala Glu Gln  Thr Asn Tyr Asp Phe  Asn Leu Met
    5525                 5530                 5535

Val Val  Pro Gly Asp Glu Leu  Ile Ile Arg Phe Asp  Phe Asn Ser
    5540                 5545                 5550

Glu Val  Tyr Asp Arg Gly His  Met Glu Arg Leu His  His His Leu
    5555                 5560                 5565

Met His  Val Leu Glu Gln Val  Thr Gly Asn Pro Ala  Ile Ser Ile
    5570                 5575                 5580

Ala Glu  Val Gln Leu Ser Thr  Glu Ala Glu Lys Ala  Glu Val Gln
    5585                 5590                 5595

Ser Ala  Phe Asn Asp Thr Val  Val Asp Tyr Pro Arg  Glu Gln Thr
    5600                 5605                 5610

Ile His  Trp Met Phe Glu Glu  Gln Val Gln Arg Thr  Pro Asp Ala
    5615                 5620                 5625

Ala Ala  Val Leu Tyr Gly Asp  Asp Val Ile Thr Tyr  Arg Glu Leu
    5630                 5635                 5640

Asn Glu  Arg Ala Asn Arg Leu  Ala Arg Thr Leu Arg  Ala Ala Gly
    5645                 5650                 5655

Val Glu  Pro Asp Gln Ile Val  Gly Ile Met Ala Glu  Arg Ser Leu
    5660                 5665                 5670

Glu Leu  Met Val Gly Ile Met  Gly Ile Leu Lys Ala  Gly Gly Ala
    5675                 5680                 5685

Tyr Val  Pro Ile Ala Pro Asp  Tyr Pro Glu Glu Arg  Ile Arg Tyr
    5690                 5695                 5700

Met Leu  Asp Asp Ser Lys Ala  Gln Val Leu Leu Val  Gln Gly Ser
```

```
    5705                5710                5715

Ala Gly  Glu Ala Val Asp Phe  Val Gly Arg Ile Ile  Asn Leu Asp
    5720                5725                5730

Asp Ala  Glu Ala Tyr Asp Glu  Asp Ser Ser Asn Pro  Glu Pro Val
    5735                5740                5745

Asn Lys  Pro Thr Asp Ile Ala  Tyr Ile Ile Tyr Thr  Ser Gly Thr
    5750                5755                5760

Thr Gly  Arg Pro Lys Gly Val  Met Val Glu His Thr  Ser Val Ile
    5765                5770                5775

Asn Arg  Leu Leu Trp Met Gln  Lys Arg Tyr Pro Ile  Gly Ser Glu
    5780                5785                5790

Asp Thr  Ile Met Gln Lys Thr  Ala Ile Thr Phe Asp  Val Ser Val
    5795                5800                5805

Trp Glu  Leu Phe Trp Trp Ala  Phe Val Gly Ser Lys  Val Leu Met
    5810                5815                5820

Leu Ser  Val Gly Gly Glu Lys  Asn Pro His Ala Ile  Val Asp Ala
    5825                5830                5835

Ile Glu  Arg His Arg Ile Thr  Thr Met His Phe Val  Pro Ser Met
    5840                5845                5850

Leu His  Ala Phe Leu Glu His  Val Glu Gln Met Thr  Asp Ala Glu
    5855                5860                5865

Arg Glu  Arg Gly Leu Ala Pro  Leu Arg Gln Val Phe  Thr Ser Gly
    5870                5875                5880

Glu Ala  Leu Leu Ala Ser Gln  Val Glu Arg Phe His  Arg Tyr Ile
    5885                5890                5895

Ala Pro  Ala Ser Gly Ala Gln  Leu Ile Asn Leu Tyr  Gly Pro Thr
    5900                5905                5910

Glu Ala  Thr Val Asp Val Thr  Tyr Phe Asp Cys Glu  Pro Gly Gln
    5915                5920                5925

Thr Tyr  Val Ser Val Pro Ile  Gly Lys Pro Ile Asp  Asn Thr Ser
    5930                5935                5940

Ile Tyr  Ile Val Asn Glu His  Asn Gln Val Gln Pro  Ile Gly Val
    5945                5950                5955

Ala Gly  Glu Leu Cys Ile Ala  Gly Val Gly Leu Ala  Arg Gly Tyr
    5960                5965                5970

Trp Asn  Arg Pro Glu Leu Thr  Ala Glu Lys Phe Val  Thr Ile Pro
    5975                5980                5985

Ser Val  Gly Glu Arg Met Tyr  Arg Thr Gly Asp Leu  Ala Arg Trp
    5990                5995                6000

Leu Pro  Asp Gly Asn Ile Glu  Tyr Leu Gly Arg Ile  Asp His Gln
    6005                6010                6015

Val Lys  Ile Arg Gly Tyr Arg  Ile Glu Leu Gly Glu  Leu Glu Thr
    6020                6025                6030

Ala Leu  Leu Asn Val Gln Glu  Ile Arg Glu Thr Val  Val Val Ala
    6035                6040                6045

Arg Glu  Glu Glu Asp Gly Gln  Lys Ser Leu Cys Ala  Tyr Tyr Val
    6050                6055                6060

Ala Asp  Gly Asp Pro Thr Val  Gly Asn Leu Arg Ala  Ala Leu Ala
    6065                6070                6075

Ala Glu  Leu Pro Ser Tyr Met  Ile Pro Ser Tyr Phe  Ile Gln Leu
    6080                6085                6090

Glu Gln  Met Pro Leu Ala Pro  Asn Gly Lys Leu Asp  Arg Lys Ala
    6095                6100                6105
```

```
Leu Pro Ala Pro Lys Asp Val Ile Gln Thr Gly Thr Asp His Ala
    6110                6115                6120

Ala Pro Arg Thr Ala Leu Glu Val Lys Leu Val Arg Ile Trp Gln
    6125                6130                6135

Glu Val Leu Gly Leu Asp Gln Ile Gly Val Lys Asp Asp Phe Phe
    6140                6145                6150

Glu Leu Gly Gly His Ser Leu Arg Ala Thr Ala Leu Ala Ser Lys
    6155                6160                6165

Val Ser Lys Glu Met His Val Ala Leu Pro Leu Arg Asp Ile Phe
    6170                6175                6180

His Tyr Ser Thr Leu Glu Ala Met Ala Gln Ala Ile Gly Glu Leu
    6185                6190                6195

Glu Lys Gln Glu His Arg Ala Ile Pro Ile Ala Pro Met Ala Glu
    6200                6205                6210

His Tyr Pro Leu Ala Ser Ala Gln Lys Arg Leu Tyr Ile Leu His
    6215                6220                6225

Gln Ala Glu Gly Ala Gln Gln Ser Tyr Asn Met Pro Gly Ala Met
    6230                6235                6240

Ser Val Ser Gly His Ile Asp Arg Asn Arg Leu Glu Ala Ala Leu
    6245                6250                6255

Leu Arg Leu Ile Ala Arg His Asp Thr Leu Arg Thr Ser Phe Glu
    6260                6265                6270

Met Val Asp Gly Glu Pro Val Gln Arg Val His Gln His Val Asp
    6275                6280                6285

Phe Ala Leu Glu Tyr Ser Thr Ala Arg Glu Lys Asp Met Glu Gln
    6290                6295                6300

Val Ala Lys Gln Phe Val Arg Asp Phe Asp Leu Glu Gln Pro Pro
    6305                6310                6315

Leu Leu Arg Val Gly Leu Val Gln Leu Glu Gln Glu Glu Gln His
    6320                6325                6330

Leu Leu Leu Phe Asp Met His His Ile Ile Ser Asp Gly Ile Ser
    6335                6340                6345

Met Asp Ile Leu Val Asp Glu Leu Ala Arg Leu Tyr Asp Gly Glu
    6350                6355                6360

Glu Leu Pro Pro Leu Glu Ile Gln Tyr Lys Asp Tyr Val Leu Trp
    6365                6370                6375

Gln Gln Ala Glu Ala Ser Ser Glu Gln Met Lys Glu His Glu Glu
    6380                6385                6390

Tyr Trp Leu Arg Thr Leu Gly Asn Glu Leu Pro Leu Leu Glu Leu
    6395                6400                6405

Pro Thr Glu Phe Ala Arg Ser Glu Gln Arg Ser Tyr Asp Gly Asp
    6410                6415                6420

Lys Leu His Phe Ala Ile Asp Gly Gln Leu Asn Glu Lys Leu Gln
    6425                6430                6435

Arg Leu Ala Ser Gln Ser Gly Ala Thr Leu Tyr Met Val Leu Leu
    6440                6445                6450

Ala Ala Tyr Thr Thr Leu Leu His Lys Tyr Ser Gly Gln Asn Asp
    6455                6460                6465

Leu Val Val Gly Thr Pro Ile Ala Gly Arg Thr His Val Asp Val
    6470                6475                6480

Glu Pro Leu Ile Gly Met Phe Val Asn Ser Leu Ala Ile Arg Asn
    6485                6490                6495
```

```
Tyr Pro  Asn Asp Asp Lys Thr  Phe Arg Ser Tyr Leu  Glu Glu Val
    6500                 6505                 6510

Lys Glu  Ser Thr Leu Ser Ala  Phe Glu His Gln Asp  Tyr Pro Phe
    6515                 6520                 6525

Asp Lys  Leu Val Glu Gln Leu  Glu Asp Ala Trp Val  Pro Gly Arg
    6530                 6535                 6540

Asn Pro  Val Phe Asp Thr Met  Phe Val Leu Gln Asn  Ala Lys Ala
    6545                 6550                 6555

Arg Thr  Ile Asn Leu Gly Glu  Leu Ala Phe Glu Pro  Leu Ile Pro
    6560                 6565                 6570

Ser His  Thr Val Ala Lys Phe  Asp Leu Thr Leu Glu  Met Ala Ile
    6575                 6580                 6585

Glu Asp  Gly Met Leu Ser Gly  Gln Phe Glu Tyr Cys  Thr Lys Leu
    6590                 6595                 6600

Phe Ser  Ala Asn Met Ile Ala  Asn Phe Ala Glu Asp  Phe Leu Glu
    6605                 6610                 6615

Ile Leu  Ser Gln Ala Cys Glu  Gln Pro Asp Ile Arg  Leu Glu Asp
    6620                 6625                 6630

Ile Gln  Leu Ser Gly Ser Ala  Tyr Gln Glu Glu Glu  Leu Glu Glu
    6635                 6640                 6645

Glu Ile  Asp Phe Ala Phe
    6650
```

<210> SEQ ID NO 12
<211> LENGTH: 6428
<212> TYPE: PRT
<213> ORGANISM: Paenibacillus alvei A6-6i-x

<400> SEQUENCE: 12

```
Met Ala Phe Asp Lys Glu Ile Glu Phe Trp Lys Ala Lys Leu Asp Thr
1               5                   10                  15

Glu Asp Thr Pro Thr Thr Leu Pro Tyr Thr Ser Thr Pro Ser Ser Glu
            20                  25                  30

Ala Ala Arg His Tyr Ser Val Ser Val Thr Met Pro Ala Glu Ile Ser
        35                  40                  45

Glu Arg Ile Ile Arg Met Ser Lys Gly Ser His Gln Ala Ala Phe Met
    50                  55                  60

Ile Leu Leu Gly Gly Ile Gln Cys Leu Leu His Lys Tyr Thr Ser Glu
65                  70                  75                  80

Asn Arg Ile Val Ile Gly Met Pro Ile Val Arg Lys Ala Gly Glu Lys
                85                  90                  95

Arg Leu Pro Ile Asn Gln Val Val Leu Leu Lys Glu Asn Val Asn Glu
            100                 105                 110

Glu Leu Thr Phe Lys Ser Leu Leu Thr Ser Leu Lys Gln Ser Phe Thr
        115                 120                 125

Glu Ala Ile Arg His Gln His Ile Pro Phe Arg Leu Ile Thr Glu Gln
    130                 135                 140

Met Asn Val Gln Glu Lys Asn Gly Leu Pro Val Ile Asn Thr Met Ala
145                 150                 155                 160

Ala Leu Lys Asn Ile His Thr Val Asn Phe Ile Pro Thr Val Val Ala
                165                 170                 175

Asp Val Leu Phe Gln Phe Glu Phe Glu Ala Glu Asn Leu Leu Leu Ser
            180                 185                 190

Val Val Tyr Asn Glu Arg Val Tyr Asp Ser Val Phe Ile Ser Gln Ile
        195                 200                 205
```

```
Ile Glu His Leu Gln Arg Val Leu Ser Ile Val Leu Leu Glu Pro Asn
    210                 215                 220

Thr Asn Leu Gly Asp Leu Arg Leu Leu Ser Asp Glu Glu Thr Ser Leu
225                 230                 235                 240

Leu Leu His Gly Phe Asn Thr Thr Ala Ala Glu Tyr Pro Arg Asp Arg
                245                 250                 255

Thr Ile His Glu Leu Phe Thr Glu Gln Ala Arg Arg Thr Pro Asp Ala
            260                 265                 270

Val Ala Ala Val Tyr Gly Gln Gln Gln Leu Thr Tyr Ala Glu Leu Asn
        275                 280                 285

Gly Arg Ala Asn Arg Leu Ala Arg Thr Leu Gln Asn Ala Gly Val Arg
    290                 295                 300

Ser Asp Gln Leu Val Gly Ile Met Ala Glu Arg Ser Leu Glu Met Ile
305                 310                 315                 320

Val Gly Leu Leu Ala Ile Met Lys Ala Gly Gly Ala Tyr Val Pro Ile
                325                 330                 335

Asp Pro Glu Tyr Pro Gln Glu Arg Ile Arg Tyr Met Leu Glu Asp Ser
            340                 345                 350

Gly Ala Gln Thr Leu Leu Leu Gln Asp His Leu Arg Glu Arg Val Thr
        355                 360                 365

Tyr Glu Gly Thr Ile Val Asp Met Asn Ser Glu His Asn Tyr His Asp
    370                 375                 380

Asp Gly Thr Glu Leu Ala Ser Val Ser Asp Ser Ser Asn Leu Ala Tyr
385                 390                 395                 400

Val Ile Tyr Thr Ser Gly Thr Thr Gly Asn Pro Lys Gly Val Met Ile
                405                 410                 415

Glu His Arg Ser Ala Val Asn Ala Leu Leu Trp Arg Ile Arg Thr Tyr
            420                 425                 430

Gly Leu Ser Ser Ser Asp Arg Ile Leu Gln Leu Phe Ser Phe Ser Phe
        435                 440                 445

Asp Gly Phe Val Met Ser Ala Phe Cys Ser Leu Leu Ser Gly Ala Gly
    450                 455                 460

Leu Phe Leu Leu Lys Glu Glu Asp Ala Lys Asp Pro Leu Ala Leu His
465                 470                 475                 480

Gly Ala Ile Ser Gln Ser Gly Ile Thr His Phe Ile Cys Val Pro Asn
                485                 490                 495

Leu Tyr Gly Ala Leu Leu Asn Val Met Gln Ala Glu Ser Val Ser Thr
            500                 505                 510

Leu Arg Thr Val Thr Leu Ala Gly Glu Ser Val Ser Ser Ala Leu Val
        515                 520                 525

Ala Arg Ser Lys Glu Gln Leu Pro Asn Val Lys Leu Phe Asn Glu Tyr
    530                 535                 540

Gly Pro Thr Glu Asn Ser Val Val Ala Thr Cys Ala Ile Gly Leu Glu
545                 550                 555                 560

Lys Asp Gln Pro Ile Thr Ile Gly Thr Pro Ile Ser Asn Ala Ser Val
                565                 570                 575

Leu Ile Leu Asn Thr Ser Gly Glu Leu Gln Pro Leu His Val Pro Gly
            580                 585                 590

Glu Leu Cys Ile Ala Gly Glu Gly Leu Ala Arg Gly Tyr Leu Asn Arg
        595                 600                 605

Pro Glu Leu Thr Glu Glu Lys Phe Ala Ala His Pro Phe Val Pro Gly
    610                 615                 620
```

-continued

Glu Arg Ile Tyr His Thr Gly Asp Ser Ala Arg Trp Leu Pro Asn Gly
625 630 635 640

Thr Ile Glu Tyr Leu Gly Arg Ile Asp His Gln Val Lys Ile Arg Gly
645 650 655

Phe Arg Ile Glu Leu Gly Glu Ile Glu Ser Ser Leu Lys Lys Ile Ala
660 665 670

Gly Val Arg Glu Val Ile Val Asp Ala Arg Pro Asp Gly Asn Gly Gln
675 680 685

His Met Leu Cys Ala Tyr Met Val Ala Asp Ala Glu Leu Thr Val Thr
690 695 700

Glu Leu Arg Glu Ala Leu Ser Ser Asn Leu Pro Asp Tyr Met Ile Pro
705 710 715 720

Ser His Phe Val Gln Met Glu Gln Leu Pro Leu Thr Pro Ser Gly Lys
725 730 735

Leu Asp Arg Lys Ser Leu Pro Asp Pro Gln Ala Asn Met Ala Ile Gly
740 745 750

Thr Glu Tyr Ile Ala Pro Arg Thr Pro Leu Glu Ala Arg Leu Ala Gln
755 760 765

Ile Trp Gln Glu Ser Leu Gly Val Glu Arg Val Gly Ile Lys Asp Asn
770 775 780

Phe Phe Ala Leu Gly Gly His Ser Leu Arg Ala Ala Thr Leu Ala Ser
785 790 795 800

Lys Leu His Lys Glu Leu Asn Val Asn Val Pro Leu Arg Asp Leu Phe
805 810 815

Arg Asn Pro Thr Ile Glu Glu Leu Ala Leu Leu Met Asp Gly Met Glu
820 825 830

Gln Gln Glu Phe Ser Ala Ile Glu Arg Val Lys Glu Ser Glu Tyr Tyr
835 840 845

Ser Val Ser Ser Ala Gln Lys Arg Leu Tyr Val Leu Gln Gln Leu Glu
850 855 860

Gly Ala Glu Gln Ser Tyr Asn Met Pro Gly Ala Met Leu Leu Glu Gly
865 870 875 880

Leu Leu Asp Arg Glu Arg Leu Glu Ala Ser Phe Arg Lys Leu Ile Ala
885 890 895

Arg His Glu Thr Leu Arg Thr Gly Phe Glu Leu Met Asp Gly Glu Pro
900 905 910

Val Gln Lys Val Tyr Gln Asp Val Ser Phe Ala Ile Glu Tyr Met Gln
915 920 925

Thr Ser Glu Ala Glu Ala Ala Gln Lys Ala Arg Glu Phe Ile Arg Ala
930 935 940

Phe Asp Leu Met Thr Pro Pro Leu Met Arg Val Gly Leu Ile Glu Met
945 950 955 960

Ala Pro Asp Arg His Val Leu Leu Tyr Asp Met His His Ile Ile Ser
965 970 975

Asp Gly Ala Ser Met Gly Val Val Val Glu Glu Phe Ala Arg Leu Tyr
980 985 990

Gly Gly Glu Glu Leu Pro Pro Leu Arg Ile Gln Tyr Lys Asp Phe Ala
995 1000 1005

Ala Trp Gln Gln Ser Glu Ala Gln Gln Lys Arg Ser Lys Gln Gln
1010 1015 1020

Glu Thr Tyr Trp Leu Gln Thr Phe Gly Gly Glu Leu Pro Val Leu
1025 1030 1035

Glu Leu Pro Thr Asp Tyr Ala Arg Pro Ala Ile Gln Ser Tyr Glu

```
    1040                1045                1050

Gly Glu  Thr Tyr Glu Phe Thr  Val Asp Ser Asp Ile  Ser Thr Ala
    1055                1060                1065

Leu Gln  Arg Leu Ala Ala Asp  Ser Gly Thr Thr Leu  Tyr Met Val
    1070                1075                1080

Leu Leu  Ala Ala Tyr Thr Val  Leu Leu His Lys Tyr  Thr Gly Gln
    1085                1090                1095

Glu Asp  Ile Val Val Gly Thr  Thr Asn Ala Gly Arg  Met His Asp
    1100                1105                1110

Asp Leu  Gln Pro Leu Ile Gly  Met Phe Val Asn Thr  Leu Ala Ile
    1115                1120                1125

Arg Asn  Tyr Pro Ala Gly Glu  Ser Thr Phe Arg Ala  Tyr Leu Glu
    1130                1135                1140

Gln Val  Lys Glu Gln Ala Leu  Ala Ala Phe Glu His  Gln Glu Tyr
    1145                1150                1155

Pro Phe  Glu Glu Leu Val Glu  Lys Leu His Val Thr  Arg Asp Met
    1160                1165                1170

Ser Arg  Asn Pro Leu Phe Asp  Thr Met Phe Ser Leu  Gln Asn Met
    1175                1180                1185

Glu Asn  Lys Asp Phe Glu Leu  Pro Gly Leu Gln Leu  Lys Pro Tyr
    1190                1195                1200

Gly Phe  Glu His Gln Ile Ser  Lys Phe Asp Leu Ser  Leu Asp Val
    1205                1210                1215

Ala Glu  Gly Ala Asp Gly Leu  Ala Cys Ser Leu Glu  Tyr Ala Ser
    1220                1225                1230

Ser Leu  Tyr Arg Gln Asp Thr  Ile Val Arg Met Ala  Asp His Tyr
    1235                1240                1245

Arg Gln  Leu Leu His Ser Ile  Ala Gln Ser Pro Glu  Ala Gln Ile
    1250                1255                1260

Ser Val  Leu Gly Met Leu Thr  Pro Gly Glu Gln Glu  Gln Ile Arg
    1265                1270                1275

Phe Lys  Phe Asn His Asp Pro  Ser Glu Met Glu Gln  Lys His Thr
    1280                1285                1290

Val His  Gln Leu Phe Glu Glu  Gln Ala Ala Leu Thr  Pro Glu Arg
    1295                1300                1305

Thr Ala  Val Val His Glu Asn  Glu Gln Leu Ser Tyr  Arg Glu Leu
    1310                1315                1320

Asn Glu  Arg Ala Asn Arg Leu  Ala Arg Thr Leu Arg  Gln His Gly
    1325                1330                1335

Val Gln  Pro Glu Gln Leu Val  Gly Ile Leu Ala Asp  Arg Ser Leu
    1340                1345                1350

Asp Met  Ile Val Gly Ile Met  Ala Ile Leu Lys Ala  Gly Gly Ala
    1355                1360                1365

Tyr Val  Pro Ile Asp Pro Lys  Tyr Pro Glu Glu Arg  Ile Arg Tyr
    1370                1375                1380

Met Leu  Glu Asp Ser Lys Ala  Asn Val Leu Val Thr  Gln Ser His
    1385                1390                1395

Leu Gln  Ser Leu Ser Ser Phe  Asp Gly Thr Trp Val  Leu Leu Asp
    1400                1405                1410

Glu Glu  Ser Ser Tyr Ala Glu  Asp Ala Ala Asn Leu  Val Ser Ile
    1415                1420                1425

Thr Glu  Pro Gln His Leu Ala  Tyr Val Ile Tyr Thr  Ser Gly Thr
    1430                1435                1440
```

-continued

```
Thr Gly  Gln Pro Lys Gly Ala  Met Ile Glu His Arg  Gln Leu Thr
    1445                 1450                 1455

Val Met  Ala Lys Ala Trp Glu  Arg Glu Tyr Arg Leu  Arg Glu Glu
    1460                 1465                 1470

Ser Ile  Arg Trp Met Gln Trp  Ala Ser Phe Ser Phe  Asp Val Phe
    1475                 1480                 1485

Ser Gly  Asp Leu Ile Arg Ala  Leu Leu His Gly Gly  Glu Leu Val
    1490                 1495                 1500

Leu Cys  Pro Glu His Ala Arg  Ala Asn Pro Ala Glu  Ile Tyr Glu
    1505                 1510                 1515

Leu Ile  Arg Lys His Arg Leu  His Met Phe Asp Cys  Thr Pro Ser
    1520                 1525                 1530

Ile Val  Ile Pro Leu Met Glu  Tyr Val Tyr Glu Asn  Lys Leu Asp
    1535                 1540                 1545

Ile Ser  Ser Leu Lys Leu Val  Ala Val Gly Ser Asp  Tyr Cys Pro
    1550                 1555                 1560

Pro Asp  Glu Phe Gln Lys Met  Leu Asp Arg Phe Gly  Ser Gln Phe
    1565                 1570                 1575

Arg Ile  Ile Asn Ser Tyr Gly  Val Thr Glu Thr Cys  Ile Asp Ala
    1580                 1585                 1590

Ser Tyr  Tyr Glu Pro Thr Thr  Pro Thr Val Pro Arg  Ala Leu Pro
    1595                 1600                 1605

Ile Gly  Lys Pro Leu Pro Gly  Val Thr Met Tyr Ile  Met Asp Gly
    1610                 1615                 1620

Gln Arg  Ser Leu Leu Pro Val  Gly Val Ile Gly Glu  Leu Tyr Ile
    1625                 1630                 1635

Gly Gly  Pro Cys Val Gly Arg  Gly Tyr Trp Asn Arg  Ser Glu Met
    1640                 1645                 1650

Thr Asn  Glu Lys Phe Val Glu  Asp Pro Phe Leu Gln  Asp Tyr Arg
    1655                 1660                 1665

Met Tyr  Arg Thr Gly Asp Leu  Ala Arg Trp Met Pro  Asp Gly Asn
    1670                 1675                 1680

Ile Glu  Tyr Leu Gly Arg Ile  Asp His Gln Ala Lys  Ile Arg Gly
    1685                 1690                 1695

Tyr Arg  Ile Glu Ile Gly Glu  Val Glu Ser Lys Leu  Leu Lys Val
    1700                 1705                 1710

Glu Thr  Val Arg Glu Ser Val  Ile Val Ala Arg Gln  Asp Pro Asn
    1715                 1720                 1725

Gly Thr  Lys Ala Leu Cys Ala  Tyr Phe Val Ala Asp  Arg Asn Leu
    1730                 1735                 1740

Thr Val  Ser Glu Leu Arg Ser  Ala Leu Ala Asp Glu  Leu Pro Ala
    1745                 1750                 1755

Tyr Met  Ile Pro Ser Tyr Phe  Val Gln Leu Asp Arg  Leu Pro Leu
    1760                 1765                 1770

Thr Pro  Asn Gly Lys Val Asp  Arg Lys Ala Leu Pro  Ala Pro Glu
    1775                 1780                 1785

Ala Gly  Ala His Thr Gly Ile  Glu Tyr Val Ala Pro  Arg Thr Glu
    1790                 1795                 1800

Glu Glu  Leu Ala Leu Ala Asn  Val Trp Gln Thr Val  Leu Gly Ile
    1805                 1810                 1815

Glu Arg  Val Gly Val Gln Asp  His Phe Phe Glu Leu  Gly Gly Asp
    1820                 1825                 1830
```

-continued

```
Ser Ile  Lys Ser Ile Gln Val  Ala Ser Arg Leu Gln  Gln Ala Gly
    1835                 1840                 1845

Tyr Lys  Leu Glu Ile Arg Asp  Leu Phe Lys Tyr Pro  Thr Ile Ala
    1850                 1855                 1860

Gln Leu  Gly Ser His Leu Gln  Arg Ala Ser Lys Val  Ala Asp Gln
    1865                 1870                 1875

Gly Glu  Val Ser Gly Asp Val  Pro Leu Thr Pro Ile  Leu Gly Trp
    1880                 1885                 1890

Phe Phe  Glu Gln Gln Phe Ala  Asp Ala His His Tyr  Asn Gln Ser
    1895                 1900                 1905

Ile Met  Leu Tyr Arg Arg Glu  Gly Phe Asp Glu Ala  Ala Ile Arg
    1910                 1915                 1920

Asn Val  Leu Gln Ala Val Thr  Glu His His Asp Ala  Leu Arg Ile
    1925                 1930                 1935

Val Phe  Arg Arg Asn Asp Gln  Gly Asp Tyr Thr Ala  Trp Asn Arg
    1940                 1945                 1950

Ala Ile  Glu Glu Gly Glu Leu  Phe His Leu Glu Val  Leu Asn Leu
    1955                 1960                 1965

Thr Gly  Ser Ala Ser Gly Asp  His Glu Gln Asn Val  Arg Gln Ile
    1970                 1975                 1980

Ile Glu  Ala Lys Ala Ser Glu  Ile Gln Arg Ser Phe  Asp Leu His
    1985                 1990                 1995

Asp Gly  Pro Leu Ala Arg Ala  Gly Leu Phe Arg Thr  Asp Glu Gly
    2000                 2005                 2010

Asp His  Leu Leu Leu Val Met  His His Gly Val Val  Asp Gly Val
    2015                 2020                 2025

Ser Trp  Arg Ile Leu Leu Glu  Asp Ile Ala Ala Gly  Tyr Glu Gln
    2030                 2035                 2040

Ala Leu  Lys Gly Glu Pro Val  Arg Leu Pro Ala Lys  Thr Asp Ser
    2045                 2050                 2055

Phe Arg  Thr Trp Ala Asn His  Leu Ala Ser Tyr Ala  Arg Ser Glu
    2060                 2065                 2070

Ala Met  Ile Glu Glu Gln Val  Phe Trp Glu Gln Ala  Glu Ala Asn
    2075                 2080                 2085

Ala Thr  Ser Ile Leu Pro Leu  Pro Lys Asp Phe Glu  Ala Glu Thr
    2090                 2095                 2100

Ser Leu  Gln Gln Asp Ser Glu  Ser Val Val Val Glu  Trp Ser Arg
    2105                 2110                 2115

Glu Glu  Thr Asp Met Leu Leu  Lys His Val His Arg  Ala Tyr Asn
    2120                 2125                 2130

Thr Asp  Met Asn Asp Ile Leu  Leu Ala Ala Leu Gly  Met Ala Ile
    2135                 2140                 2145

Gln Gln  Trp Cys Gly His Glu  Lys Ala Leu Val Thr  Leu Glu Gly
    2150                 2155                 2160

His Gly  Arg Glu Asn Ile Met  Pro Glu Leu Asp Ile  Ser Arg Thr
    2165                 2170                 2175

Val Gly  Trp Phe Thr Ser Glu  Tyr Pro Phe Leu Leu  Glu Ser Asp
    2180                 2185                 2190

Pro Asn  Lys Ser Leu Ser Tyr  Arg Ile Lys Arg Met  Lys Glu Asn
    2195                 2200                 2205

Leu Arg  Arg Ile Pro Asn Lys  Gly Ile Gly Tyr Gly  Ile His Arg
    2210                 2215                 2220

Tyr Leu  Ser Asp Ser Gly Met  Ser Gly Thr Glu Asn  Val Ser Arg
```

```
    2225                2230                2235

Ser Glu  Ala Ser Ala Gln Pro  Glu Ile Ser Phe Asn  Tyr Leu Gly
    2240                2245                2250

Gln Phe  Asp Gln Asp Leu Gln  Asn Asn Glu Met Glu  Val Ser Pro
    2255                2260                2265

Tyr Ser  Gly Gly Ala Glu Ile  Ser Val Arg Gln Ala  Arg Asn Thr
    2270                2275                2280

Thr Leu  Asp Phe Asn Gly Met  Ile Ser Ala Gly Val  Leu Ala Leu
    2285                2290                2295

Glu Val  Ser Tyr Ser Ser Lys  Gln Tyr Arg Arg Asp  Thr Ile Asp
    2300                2305                2310

Arg Leu  Ala Ala Leu Leu Lys  Gly Ser Leu Gln Glu  Ile Val Ala
    2315                2320                2325

His Cys  Ala Ser Lys Asp Lys  Pro Glu Leu Thr Pro  Ser Asp Val
    2330                2335                2340

Leu Val  Asn Gly Leu Gly Ile  Glu Asp Leu Glu Arg  Ile Ala Glu
    2345                2350                2355

Gln Thr  Arg Asp Leu Gly Asp  Ile Glu Asn Ile Tyr  Ala Leu Thr
    2360                2365                2370

Pro Met  Gln Lys Gly Met Trp  Phe His Asn Ala Met  Asp Gly Gln
    2375                2380                2385

Ala Gly  Ala Tyr Phe Glu Gln  Thr Arg Phe Thr Ile  Gln Gly Glu
    2390                2395                2400

Leu Asp  Val Gln Leu Phe Ala  Ser Ser Leu Asp Val  Leu Ala Thr
    2405                2410                2415

Arg His  Ala Val Leu Arg Thr  Asn Phe Phe Ser Gly  Trp Asn Gly
    2420                2425                2430

Glu Leu  Leu Gln Ile Val Tyr  Arg Asn Lys Asn Leu  Glu Phe Ser
    2435                2440                2445

Tyr Glu  Asp Leu Thr Glu Leu  Pro Glu Asp Glu Lys  Gln Asp Arg
    2450                2455                2460

Val Glu  Ala Met Ala Gln Ala  Asp Lys Leu Arg Gly  Phe Asp Leu
    2465                2470                2475

Glu His  Asp Ala Leu Met Arg  Val Ser Val Leu Arg  Thr Asn Val
    2480                2485                2490

Asn Cys  Ser His Val Ile Trp  Ser Ser His His Ile  Leu Met Asp
    2495                2500                2505

Gly Trp  Cys Leu Pro Gln Leu  Thr Gln Glu Trp Leu  Glu Thr Tyr
    2510                2515                2520

Ser Asp  Ser Val Asn Gly Arg  Ser Ser Ser Arg Ser  Gly Ala Ser
    2525                2530                2535

Pro Tyr  Ser Leu Tyr Ile Glu  Trp Leu Tyr Lys Gln  Asp Tyr Thr
    2540                2545                2550

Ala Ala  Ser Gln Tyr Trp Ser  Asp Tyr Leu Ala Asp  Tyr Asp Gln
    2555                2560                2565

Gln Thr  Val Leu Pro Gln Lys  Lys Ser Ser Gly Arg  Ser Asp Val
    2570                2575                2580

Tyr Ile  Ala Asp Asn Leu Val  Phe Glu Leu Gly Glu  Ala Leu Thr
    2585                2590                2595

Ala Lys  Met His Arg Val Ala  Lys Gln His Gln Leu  Thr Leu Asn
    2600                2605                2610

Thr Leu  Met Gln Ala Ala Trp  Gly Ile Ile Leu Gln  Lys Tyr Asn
    2615                2620                2625
```

```
Gly Thr  Gly Asp Ala Val Phe  Gly Gly Val Val Ser  Gly Arg Pro
    2630                 2635                 2640

Ala Glu  Ile Pro Gly Ile Glu  Ser Met Ile Gly Leu  Phe Ile Asn
    2645                 2650                 2655

Thr Ile  Pro Ile Arg Val Ala  Cys Glu Ala Asp Asp  Arg Phe Ala
    2660                 2665                 2670

Asp Val  Met Lys Arg Leu Gln  Glu Lys Ala Leu Glu  Ser Gly Arg
    2675                 2680                 2685

Tyr Asp  Tyr Tyr Pro Leu Tyr  Asp Ile Gln Ala Leu  Ser Thr His
    2690                 2695                 2700

Lys Gln  Asp Leu Ile Asn His  Ile Leu Val Phe Glu  Asn Tyr Pro
    2705                 2710                 2715

Met Glu  Glu Gln Met Glu Gln  Ala Gly Asp Glu Arg  Gly Gln Leu
    2720                 2725                 2730

Asn Ile  Thr Asp Val Arg Val  Ala Glu Gln Thr Ser  Tyr Asp Phe
    2735                 2740                 2745

Asn Leu  Val Val Met Pro Gly  Glu Asp Met Met Ile  Arg Leu Glu
    2750                 2755                 2760

Tyr Asn  Ala Val Met Tyr Asp  Arg Ala Asp Met Glu  Arg Val Arg
    2765                 2770                 2775

Gln His  Leu Ile His Val Leu  Glu Gln Val Thr Ala  Asp Pro Ala
    2780                 2785                 2790

Ile Ala  Val Lys Asp Val Arg  Leu Ala Thr Asp Asp  Glu Lys Ala
    2795                 2800                 2805

Glu Leu  Leu Thr Ala Phe Asn  Asp Thr Glu Ile Glu  Tyr Pro Arg
    2810                 2815                 2820

Glu Gln  Met Ile His Arg Met  Phe Glu Glu Gln Val  Gln Arg Thr
    2825                 2830                 2835

Pro Asp  Ala Thr Ala Val Leu  Tyr Gly Ala Ala Ala  Met Thr Tyr
    2840                 2845                 2850

Arg Glu  Met Asn Glu Arg Ala  Asn Gln Leu Ala Arg  Thr Leu Arg
    2855                 2860                 2865

Ala Ala  Gly Val Val Pro Asp  Gln Ile Val Gly Ile  Met Ala Glu
    2870                 2875                 2880

Arg Ser  Leu Glu Leu Met Val  Gly Ile Met Gly Ile  Leu Lys Ala
    2885                 2890                 2895

Gly Gly  Ala Tyr Val Pro Ile  Ala Pro Asp Tyr Pro  Glu Glu Arg
    2900                 2905                 2910

Ile Arg  Tyr Met Leu Asp Asp  Ser Glu Ala Gln Val  Leu Ile Val
    2915                 2920                 2925

Gln Gly  Ser Ala Gly Glu Ala  Ile Asp Phe Ala Gly  Arg Val Ile
    2930                 2935                 2940

Asn Leu  Asp Asp Ala Asp Ser  Tyr Asp Gln Asp Ser  Ser Asn Leu
    2945                 2950                 2955

Glu Met  Val Asn Lys Pro Thr  Asp Ile Ala Tyr Ile  Ile Tyr Thr
    2960                 2965                 2970

Ser Gly  Thr Thr Gly Arg Pro  Lys Gly Val Met Val  Glu His Thr
    2975                 2980                 2985

Ser Val  Ile Asn Arg Leu Leu  Trp Met Gln Lys Arg  Tyr Pro Ile
    2990                 2995                 3000

Gly Ala  Asp Asp Thr Ile Met  Gln Lys Thr Ala Ile  Thr Phe Asp
    3005                 3010                 3015
```

-continued

```
Val Ser  Val Trp Glu Leu Phe  Trp Trp Ala Phe Val  Gly Ser Lys
    3020                 3025                 3030

Val Leu  Met Leu Pro Val Gly  Gly Glu Lys Asn Pro  Ala Ala Ile
    3035                 3040                 3045

Val Glu  Ala Ile Glu Gln Tyr  Glu Ile Thr Thr Met  His Phe Val
    3050                 3055                 3060

Pro Ser  Met Leu His Ala Phe  Leu Glu His Ile Glu  Gln Leu Pro
    3065                 3070                 3075

Glu Ala  Glu Arg Glu Arg Leu  Ser Pro Leu Gln Gln  Val Phe Thr
    3080                 3085                 3090

Ser Gly  Glu Ala Leu Leu Ala  Ser Gln Val Glu Arg  Phe His Gln
    3095                 3100                 3105

Tyr Val  Val Pro Ala Ser Gly  Ala Arg Leu Ile Asn  Leu Tyr Gly
    3110                 3115                 3120

Pro Thr  Glu Ala Thr Val Asp  Val Thr Tyr Phe Asp  Cys Glu Pro
    3125                 3130                 3135

Gly Gln  Thr Tyr Val Ser Val  Pro Ile Gly Lys Pro  Ile Asp Asn
    3140                 3145                 3150

Thr Arg  Ile Tyr Ile Val Asn  Glu His Phe Gln Val  Gln Pro Ile
    3155                 3160                 3165

Gly Val  Ala Gly Glu Leu Cys  Ile Ala Gly Val Gly  Leu Ala Arg
    3170                 3175                 3180

Gly Tyr  Trp Asn Arg Pro Glu  Leu Thr Glu Glu Lys  Phe Val Leu
    3185                 3190                 3195

Val Pro  Ser Val Gly Glu Arg  Met Tyr Arg Thr Gly  Asp Leu Ala
    3200                 3205                 3210

Arg Trp  Leu Pro Asp Gly Asn  Ile Glu Tyr Leu Gly  Arg Ile Asp
    3215                 3220                 3225

His Gln  Val Lys Ile Arg Gly  Tyr Arg Ile Glu Leu  Gly Glu Leu
    3230                 3235                 3240

Glu Thr  Ala Leu Leu Asn Ile  Asp Ala Val Arg Glu  Thr Val Val
    3245                 3250                 3255

Val Ala  Arg Glu Asp Glu Ser  Gly Gln Lys Ser Leu  Cys Ala Tyr
    3260                 3265                 3270

Tyr Val  Ala Asp Gly Glu Ala  Thr Ile Ser Asp Leu  Arg Ala Ala
    3275                 3280                 3285

Leu Ala  Ala Glu Leu Pro Ser  Tyr Met Ile Pro Ser  Tyr Phe Val
    3290                 3295                 3300

Arg Leu  Glu Gln Met Pro Leu  Ala Pro Asn Gly Lys  Leu Asp Arg
    3305                 3310                 3315

Lys Ala  Leu Pro Ala Pro Glu  Arg Ser Leu Gln Val  Glu Ser Glu
    3320                 3325                 3330

Tyr Val  Ala Pro Arg Thr Glu  Ala Glu Gln Met Leu  Thr Thr Val
    3335                 3340                 3345

Trp Gln  Ala Val Leu Gly Ile  Glu Arg Val Gly Ile  Thr Asp His
    3350                 3355                 3360

Phe Phe  Glu Leu Gly Gly Asp  Ser Ile Lys Ser Ile  Gln Val Ala
    3365                 3370                 3375

Ala Arg  Met Gln Gln Ala Gly  Phe Lys Leu Glu Ile  Arg Asp Leu
    3380                 3385                 3390

Phe Lys  Tyr Pro Thr Val Thr  Gln Leu Val Pro Tyr  Met Gln Pro
    3395                 3400                 3405

Ile Asn  Arg Thr Ala Asp Gln  Gly Glu Val Val Gly  Glu Val Pro
```

```
    3410                3415                3420

Met Thr  Pro Ile Leu His Trp  Phe Glu His Gln Gln  Phe Ala Asn
    3425                3430                3435

Pro His  His Phe Asn Gln Ser  Val Met Leu Tyr Arg  Lys Asp Gly
    3440                3445                3450

Phe Val  Ala Asp Ala Val Cys  Lys Ala Leu His Lys  Leu Val Glu
    3455                3460                3465

His His  Asp Ala Leu Arg Ile  Val Ile Gln Arg Thr  Glu Gln Gly
    3470                3475                3480

Glu Tyr  Ser Leu Trp Asn Arg  Ser Leu Val Glu Gly  Glu Leu Phe
    3485                3490                3495

Ser Met  Glu Glu Ile Asp Leu  Thr Asp Gln Ser Asp  Phe Ala Ala
    3500                3505                3510

Ala Ile  Glu Ala Glu Ala Asn  His Ile Gln Gly Ser  Ile Asp Leu
    3515                3520                3525

Gln Ala  Gly Pro Leu Val Lys  Ala Gly Leu Phe His  Gly Ser Asp
    3530                3535                3540

Gly Asp  His Leu Leu Leu Val  Ile His His Ala Val  Ile Asp Gly
    3545                3550                3555

Val Ser  Trp Arg Ile Leu Leu  Glu Asp Leu Ala Ser  Gly Tyr Glu
    3560                3565                3570

Gln Ala  Leu Asn Gln Arg Gln  Val Arg Leu Pro Met  Lys Thr Asp
    3575                3580                3585

Ser Phe  Arg Thr Trp Ala Glu  Gln Leu Val Glu Tyr  Ala Asn Ser
    3590                3595                3600

Pro Ala  Met Asp Lys Glu Ser  Ala Tyr Trp Leu Gly  Val Ala Gln
    3605                3610                3615

Thr Glu  Val Ala Ala Leu Pro  Lys Asp Ser Glu Cys  Thr Val Ser
    3620                3625                3630

Leu Gln  Arg Asp Ser Glu Ser  Val Val Leu Glu Trp  Asn Arg Glu
    3635                3640                3645

Asp Thr  Glu Arg Leu Leu Lys  His Val His Arg Ala  Tyr Asn Thr
    3650                3655                3660

Glu Met  Asp Asp Ile Leu Leu  Thr Ala Leu Gly Arg  Ala Leu Met
    3665                3670                3675

Lys Trp  Arg Gly Ile Glu Arg  Ile Leu Val Thr Leu  Glu Gly His
    3680                3685                3690

Gly Arg  Glu Ser Ile Ile Gln  Gly Met Asp Ile Thr  Arg Thr Val
    3695                3700                3705

Gly Trp  Phe Thr Thr Glu Tyr  Pro Phe Glu Leu Gly  Met Glu Ala
    3710                3715                3720

Asn Asp  Ser Leu Gly Ser Gln  Ile Lys Lys Val Lys  Glu Asp Leu
    3725                3730                3735

Arg Arg  Ile Pro Asn Lys Gly  Ile Gly Tyr Gly Leu  Phe Arg Tyr
    3740                3745                3750

Leu Ser  Asn Ser Gly Lys Gln  Ala Trp Asn Asp Ala  Pro Thr Thr
    3755                3760                3765

Gln Ile  Arg Tyr Asn Tyr Leu  Gly Gln Phe Asp Ala  Asp Leu Ser
    3770                3775                3780

Asn Asn  Glu Met Ser Val Ser  Pro Tyr Ala Ser Gly  Ser Glu Ile
    3785                3790                3795

Ser Asp  Glu Gln Glu Arg Lys  Tyr Pro Leu Asp Ile  Asn Gly Val
    3800                3805                3810
```

```
Ile Ala Glu Gly Gln Leu Thr Leu Gly Leu Ser Tyr Ser Val Lys
    3815                3820                3825

Glu Tyr Arg Lys Glu Thr Met Glu Glu Leu Gly Asp Phe Leu Thr
    3830                3835                3840

Glu Ser Leu Lys Glu Ile Ile Ala His Cys Glu Ser Gln Glu Arg
    3845                3850                3855

Thr Gln Leu Thr Pro Ser Asp Val Leu Phe Lys Gly Leu Ser Leu
    3860                3865                3870

Glu Trp Leu Asp Arg Ile Ser Ser Gln Met Gln His Ile Gly Glu
    3875                3880                3885

Ile Glu Asn Val Tyr Ala Leu Thr Pro Met Gln Lys Gly Met Trp
    3890                3895                3900

Phe His Ser Ala Met Asp Ser Leu Thr Gly Ala Tyr His Glu Gln
    3905                3910                3915

Thr Met Phe Thr Leu Glu Gly Ser Leu Asp Val Glu Leu Phe Ser
    3920                3925                3930

Ser Ser Leu Asn Glu Leu Ala Lys Arg His Ala Val Leu Arg Thr
    3935                3940                3945

Asn Phe Ile Ser Gly Pro Gln Gly Glu Pro Val Gln Val Val Phe
    3950                3955                3960

Arg Asn Lys Pro Ile Gly Phe Ser Phe Gln Asp Val Arg Ala Leu
    3965                3970                3975

Asn Glu Glu Glu Gln Gln Ser Phe Ile Lys Glu Ala Val Ser Ser
    3980                3985                3990

Asp Gln Leu Leu Gly Phe Asp Leu Ala Gln Gly Ala Leu Met Arg
    3995                4000                4005

Val Ser Ala Ile Arg Thr Gly Glu Leu Ser Cys Arg Val Leu Trp
    4010                4015                4020

Ser Ser His His Ile Leu Met Asp Gly Trp Cys Leu Pro Gln Leu
    4025                4030                4035

Met Gln Glu Leu Phe Asp Thr Tyr Ala Ala Leu Leu Gln Lys Lys
    4040                4045                4050

Ser Pro Asp Arg Thr Ala Val Pro Ala Tyr Ser Gln Tyr Ile Glu
    4055                4060                4065

Trp Leu Gly Gln Gln Asp Glu Glu Ala Ala Gly Thr Tyr Trp Ser
    4070                4075                4080

Ala Tyr Leu Asp Asp Tyr Asp Gln Val Thr Glu Ile Pro Gln Glu
    4085                4090                4095

Ser Ser Ala Gly Ile Asp Ser Glu Pro Tyr Lys Ala Glu Lys Trp
    4100                4105                4110

Ser Arg Glu Leu Asp Ala Gly Leu Ser Ala Ser Ile Ser Arg Thr
    4115                4120                4125

Ala Arg Gln His Gln Val Thr Leu Asn Thr Leu Leu Gln Ala Ala
    4130                4135                4140

Trp Gly Val Ile Leu Gln Lys Tyr Asn Gly Thr Asn Asp Val Val
    4145                4150                4155

Phe Gly Ser Val Val Ser Gly Arg Pro Ala Glu Val Pro Gly Ile
    4160                4165                4170

Glu Thr Met Ile Gly Leu Phe Ile Asn Thr Ile Pro Ile Arg Val
    4175                4180                4185

Lys Cys Glu Gly Ser Thr Ser Phe Ala Glu Leu Met Gly Leu Leu
    4190                4195                4200
```

```
Gln Glu  Gln Ala Leu Glu Ser  Gly Lys Tyr Asp Tyr  Tyr Pro Leu
    4205                 4210                 4215

Tyr Glu  Ile Gln Ser Arg Ser  Ala Leu Lys Gln Asn  Ala Ile Arg
    4220                 4225                 4230

Gln Ile  Met Val Phe Glu Asn  Tyr Pro Met Asp Glu  Gln Leu Glu
    4235                 4240                 4245

Gln Ala  Gly Gly Asp Glu His  Gly Met Pro Ser Leu  Thr Asp Val
    4250                 4255                 4260

Ala Val  Glu Glu Gln Thr Asn  Tyr Asp Phe Asn Leu  Ile Val Val
    4265                 4270                 4275

Pro Gly  Glu Gln Ile Ser Ile  Arg Phe Asp Tyr Asn  Ala Asn Arg
    4280                 4285                 4290

Phe Val  Gln Ala Asp Met Glu  Arg Leu Met Gly His  Leu Asn Asn
    4295                 4300                 4305

Ile Leu  Glu Gln Ile Val Asp  Asn Pro Arg Ile Ala  Val Glu Asp
    4310                 4315                 4320

Leu Glu  Leu Ala Thr Glu Ala  Glu Lys Ser Glu Val  Val Gln Ser
    4325                 4330                 4335

Phe Asn  Asp Thr Phe Thr Asn  Tyr Pro Arg Asp Met  Met Leu His
    4340                 4345                 4350

Arg Leu  Phe Glu Glu Gln Ala  Glu Arg His Pro Asp  Ala Val Ala
    4355                 4360                 4365

Ile Ser  Phe Arg Asp Phe Gln  Met Thr Tyr Arg Asp  Leu Asn Asp
    4370                 4375                 4380

Arg Val  Asn Arg Leu Ala Arg  Thr Leu Arg Ala Val  Gly Val Gly
    4385                 4390                 4395

Thr Asp  Lys Leu Val Gly Leu  Met Ser Glu Arg Ser  Pro Asp Met
    4400                 4405                 4410

Ile Ile  Gly Ile Leu Ala Ile  Leu Lys Ala Gly Gly  Gly Tyr Val
    4415                 4420                 4425

Pro Ile  Asp Pro Glu Tyr Pro  Gly Glu Arg Ile Arg  Tyr Met Leu
    4430                 4435                 4440

Glu Asp  Ser Gly Ala Arg Ile  Met Leu Ala Gln Gln  His Leu Thr
    4445                 4450                 4455

Gly Lys  Ile Pro Val Met Asp  Ala Ser Pro Leu Asp  Ala Ile Ile
    4460                 4465                 4470

Asn Leu  Asp Thr Glu Thr Ser  Tyr Asp Ser Asn Gly  Ser Asn Leu
    4475                 4480                 4485

Glu Ala  Asn Thr Asp Ala Ser  Ser Glu Asn Leu Ala  Cys Val Ile
    4490                 4495                 4500

Tyr Thr  Ser Gly Thr Thr Gly  Lys Pro Lys Gly Asn  Leu Thr Thr
    4505                 4510                 4515

His Arg  Asn Ile Val Arg Val  Val Arg Glu Thr Glu  Tyr Ile Asp
    4520                 4525                 4530

Ile Thr  Asn His Asp Asn Val  Leu Gln Met Ser Ser  Tyr Ala Phe
    4535                 4540                 4545

Asp Gly  Ser Thr Phe Asp Ile  Tyr Gly Ala Leu Leu  Asn Gly Ala
    4550                 4555                 4560

Lys Leu  Val Leu Val Pro His  Glu Thr Leu Leu Glu  Val Arg Gln
    4565                 4570                 4575

Leu Ala  Glu Leu Ile Val Gln  Glu Lys Ile Ser Val  Met Phe Ile
    4580                 4585                 4590

Thr Thr  Ala Tyr Phe Asn Val  Leu Val Asp Val Gln  Ala Ser Cys
```

4595 4600 4605

Leu Ser Asn Ile Arg Ala Ile Leu Phe Gly Gly Glu Arg Val Ser
4610 4615 4620

Val Ser His Val Arg Lys Ala Leu Asn His Val Ala Pro Gly Ala
4625 4630 4635

Leu Lys His Val Tyr Gly Pro Thr Glu Ser Thr Val Phe Ala Thr
4640 4645 4650

Cys His Asp Val His Glu Val Thr Glu Asn Ala Val Thr Val Pro
4655 4660 4665

Ile Gly Arg Pro Ile Ser Asn Thr Ser Ile Tyr Ile Val Asp Ala
4670 4675 4680

Asn Asn Lys Leu Gln Pro Val Gly Val Ala Gly Glu Leu Cys Val
4685 4690 4695

Ala Gly Asp Gly Leu Ala Arg Gly Tyr Leu Asn Arg Pro Asp Leu
4700 4705 4710

Thr Ala Glu Lys Phe Val Asp Ser Pro Tyr Val Gln Gly Glu Arg
4715 4720 4725

Met Tyr Arg Thr Gly Asp Leu Ala Lys Trp Leu Pro Asp Gly Ser
4730 4735 4740

Ile Glu Tyr Val Gly Arg Ile Asp Gln Gln Val Lys Ile Arg Gly
4745 4750 4755

Tyr Arg Ile Glu Leu Gly Glu Ile Glu Ala Gln Leu Leu Asn Val
4760 4765 4770

Glu Asp Val Gln Glu Ala Val Val Val Ala Arg Asp Thr Asp Thr
4775 4780 4785

Gly Glu Lys Gln Leu Cys Ala Tyr Tyr Val Ala Met Arg Pro Leu
4790 4795 4800

Glu Ala Asn His Leu Arg Glu Val Met Gly Gln Ala Met Pro Ser
4805 4810 4815

Tyr Met Leu Pro Ala His Phe Ile Gln Leu Glu Gln Leu Pro Leu
4820 4825 4830

Thr Pro Asn Gly Lys Val Asp Arg Lys Ala Leu Pro Ala Pro Glu
4835 4840 4845

Glu Gly Arg Ser Gly Glu Thr Phe Val Thr Pro Arg Thr Pro Leu
4850 4855 4860

Glu Ala Gln Leu Val Gln Ile Trp Gln Asp Val Leu Gly Ile Ser
4865 4870 4875

Ser Ile Ser Val Thr Asp His Phe Phe Glu Leu Gly Gly His Ser
4880 4885 4890

Leu Lys Ala Thr Leu Leu Val Asn Arg Leu His Gln Glu Leu Asn
4895 4900 4905

Ile Glu Leu Pro Leu Lys Asp Val Phe Gln Tyr Pro Thr Leu Glu
4910 4915 4920

Val Met Ala Lys Arg Leu Ser Asn Ala Glu Gly Ser Arg His Val
4925 4930 4935

Ser Ile Pro Val Ala Ala Pro Ser Gln His Tyr Pro Val Ser Ser
4940 4945 4950

Ala Gln Lys Arg Leu Tyr Ile Leu His Gln Leu Glu Gly Ala Glu
4955 4960 4965

Leu Ser Tyr Asn Met Pro Asn Met Met Leu Leu Glu Gly Ala Val
4970 4975 4980

Asp Leu Gly Arg Leu Glu Glu Ala Phe Lys Arg Leu Ile Glu Arg
4985 4990 4995

```
His Glu  Thr Leu Arg Thr Gly  Phe Glu Ile Val Asn  Gly Glu Pro
    5000                 5005                 5010

Val Gln  Arg Ile Tyr Pro Glu  Val Asp Phe Ala Ile  Glu His Val
    5015                 5020                 5025

Leu Ala  Ser Glu Glu Gly Ala  Ser Lys Leu Met Gln  Gln Phe Val
    5030                 5035                 5040

Arg Ser  Phe Gln Leu Glu Lys  Pro Pro Leu Leu Arg  Ile Gly Ile
    5045                 5050                 5055

Ile Glu  Leu Ser Glu Glu Arg  Ser Ile Leu Met Phe  Asp Met His
    5060                 5065                 5070

His Ile  Ile Ser Asp Gly Thr  Ser Met Gly Ile Leu  Ile Asn Glu
    5075                 5080                 5085

Phe Val  His Leu Tyr Ser Gly  Ala Glu Leu Thr Pro  Leu Arg Ile
    5090                 5095                 5100

Gln Tyr  Lys Asp Tyr Ala Val  Trp Gln Gln Ser Asp  Thr Gln Gln
    5105                 5110                 5115

Lys Ala  Met Lys Leu Gln Glu  Gly Tyr Trp Leu Lys  Val Leu Gly
    5120                 5125                 5130

Gly Glu  Leu Pro Val Leu Glu  Met Pro Thr Asp Ser  Ile Arg Pro
    5135                 5140                 5145

Thr Thr  Gln Ser Phe Arg Gly  Asp Leu Leu Gln Phe  Asp Leu Asp
    5150                 5155                 5160

Pro Val  Arg Ser Ala Gly Leu  Arg Arg Ile Ala Ala  Glu Asn Gly
    5165                 5170                 5175

Ala Thr  Met Tyr Met Val Leu  Leu Ala Leu Tyr Lys  Thr Met Leu
    5180                 5185                 5190

His Lys  Tyr Ser Ala Gln Glu  Asp Ile Ile Val Gly  Thr Pro Ile
    5195                 5200                 5205

Ala Gly  Arg Asn His Gly Asp  Leu Gln Pro Leu Leu  Gly Met Phe
    5210                 5215                 5220

Val Asn  Thr Leu Ala Ile Arg  Ser Tyr Pro Ala Ala  Ser Lys Thr
    5225                 5230                 5235

Phe Leu  Ser Tyr Leu Asp Glu  Ile Lys Glu Thr Thr  Leu Gly Ala
    5240                 5245                 5250

Phe Glu  Asn Gln Asn Tyr Pro  Phe Glu Ala Leu Val  Glu Gln Val
    5255                 5260                 5265

Gln Val  Met Arg Asp Met Ser  Arg Asn Pro Val Phe  Asp Thr Met
    5270                 5275                 5280

Phe Ile  Leu Gln Asn Ala Asp  Gln Gly Glu Met Lys  Ile Asp Gly
    5285                 5290                 5295

Val Arg  Leu Gln Ser Val Pro  Asn Glu His Thr Val  Ser Lys Phe
    5300                 5305                 5310

Asp Leu  Thr Phe Gln Ala Glu  Glu Asp Glu Ala Glu  Ile Val Cys
    5315                 5320                 5325

Ser Ile  Glu Tyr Ala Thr Asp  Leu Phe Lys Arg Gly  Thr Ile Glu
    5330                 5335                 5340

Arg Met  Ala Arg His Phe Glu  Gln Leu Val Asp Ala  Val Leu Asp
    5345                 5350                 5355

Asn Pro  Gln Ala Ser Leu Ser  Asn Leu Ser Met Val  Thr Asn Glu
    5360                 5365                 5370

Glu Lys  Ala Leu Leu Gln Asp  Lys Phe Asn Asp Thr  Asp Met Ala
    5375                 5380                 5385
```

His Pro Ser Asp Lys Thr Val His Glu Leu Phe Ala Glu Gln Val
5390 5395 5400

Glu Arg Thr Pro Asp Ala Val Ala Val Val Ser Gly Cys Glu Gln
5405 5410 5415

Leu Ser Tyr Gly Glu Leu Asn Arg Lys Ala Asn Gln Leu Ala Trp
5420 5425 5430

Lys Leu Arg Glu Tyr Gly Val Thr Ala Glu Gln Pro Val Gly Ile
5435 5440 5445

Ile Val Glu Arg Thr Leu Asp Thr Val Val Ala Val Met Ala Val
5450 5455 5460

Leu Lys Ala Ser Gly Thr Phe Val Pro Ile Asp Pro Glu Tyr Pro
5465 5470 5475

Glu Thr Arg Ile Arg Tyr Met Leu Ala Asp Ser Gly Ala Lys Leu
5480 5485 5490

Val Leu Ala Gln Ser Glu Leu Pro Gly Ile Ile Pro Asp Asp Val
5495 5500 5505

Arg Leu Ile Asp Val Arg Asp Glu Ser Leu Tyr Gln Gly Asp Gly
5510 5515 5520

Ala Asp Val Pro Asn Gly Ser Lys Pro Ser Asn Leu Leu Tyr Ile
5525 5530 5535

Ile Tyr Thr Ser Gly Thr Thr Gly Asn Pro Lys Gly Val Met Leu
5540 5545 5550

Glu His Gly Asn Met Val Asn Leu Leu His Tyr Gln Gln Lys Gly
5555 5560 5565

Thr Asn Ile Pro Met Pro Ser Arg Ile Leu Gln Tyr Ala Ser Gly
5570 5575 5580

Ser Phe Asp Val Cys Tyr Gln Glu Met Phe Ser Ala Leu Leu Phe
5585 5590 5595

Gly Gly Ser Leu Tyr Met Val Asp Asn Glu Met Arg Lys Asp Pro
5600 5605 5610

Val Arg Leu Phe Gln Glu Ile Glu Lys His Glu Ile Asp Val Leu
5615 5620 5625

Phe Ile Pro Val Ala Phe Leu Lys Phe Ile Phe Ala Glu Pro Glu
5630 5635 5640

Trp Ala Glu Ala Phe Pro Arg Cys Val Arg His Ile Ile Thr Ala
5645 5650 5655

Gly Glu Gln Leu Val Val Thr Pro Gln Val Gln Ala Cys Leu Lys
5660 5665 5670

Arg Leu Asp Ile Cys Leu His Asn His Tyr Gly Pro Ser Glu Thr
5675 5680 5685

His Val Val Thr Thr Tyr Thr Met Thr Pro Glu Ile Ile Glu Val
5690 5695 5700

Gly Leu Pro Pro Ile Gly Lys Pro Ile Ala Asn Thr Ser Ile Tyr
5705 5710 5715

Ile Val Asn Asp Ser Phe Glu Leu Gln Pro Ile Gly Val Lys Gly
5720 5725 5730

Glu Leu Phe Val Ser Gly Ala Cys Val Gly Arg Gly Tyr Trp Gly
5735 5740 5745

Arg Thr Asp Leu Thr Glu Glu Lys Phe Leu Asp Asn Pro Phe Val
5750 5755 5760

Pro Gly Glu Arg Leu Tyr Lys Thr Gly Asp Val Ala Arg Trp Leu
5765 5770 5775

Pro Asp Gly Ser Ile Asp Tyr Val Gly Arg Ser Asp His Gln Val

```
    5780                5785                5790

Lys Ile  Arg Gly Phe Arg Ile  Glu Leu Gly Glu Val  Glu Ser Gln
    5795                5800                5805

Leu Leu  His Val Pro Ala Val  Gln Glu Ala Thr Val  Val Ala Leu
    5810                5815                5820

Glu Asp  His Ala Gly Gln Lys  Gln Leu Cys Ala Tyr  Phe Thr Ala
    5825                5830                5835

Glu Arg  Ser Leu Thr Ala Gly  Glu Leu Arg Ala Val  Leu Ser Gln
    5840                5845                5850

Glu Leu  Pro Gly Tyr Met Ile  Pro Ser Tyr Phe Val  Gln Leu Glu
    5855                5860                5865

Arg Leu  Pro Leu Thr Pro Asn  Gly Lys Ile Asp Arg  Arg Ala Leu
    5870                5875                5880

Pro Lys  Pro Glu Gly Gly Ile  Glu Thr Gly Thr Glu  Tyr Val Ala
    5885                5890                5895

Pro Arg  Thr Asp Thr Glu Ala  Arg Leu Ala Arg Ile  Trp Gln Asp
    5900                5905                5910

Val Leu  Gly Leu Pro Ser Val  Gly Val Lys Asp Asn  Phe Phe Glu
    5915                5920                5925

Leu Gly  Gly His Ser Leu Arg  Ala Thr Thr Leu Val  Ser Arg Leu
    5930                5935                5940

Tyr Lys  Glu Met Asn Val Asn  Phe Pro Leu Arg Gly  Val Phe Arg
    5945                5950                5955

His Pro  Thr Ile Glu Glu Met  Ser Gln Ala Ile Ser  Gln Met Glu
    5960                5965                5970

Thr Ser  Trp Tyr Thr Ala Ile  Pro Ile Ala Glu Glu  Gln Glu Tyr
    5975                5980                5985

Tyr Pro  Leu Ser Ser Ala Gln  Leu Arg Leu Tyr Ile  Met Ser Gln
    5990                5995                6000

Leu Glu  Gly Ser Glu Leu Ser  Tyr Asn Met Pro Gly  Met Leu Val
    6005                6010                6015

Leu Glu  Gly Gln Leu Asn Arg  Asp Gln Phe Gln Thr  Ala Phe Leu
    6020                6025                6030

Lys Leu  Ile Ala Arg His Glu  Thr Leu Arg Thr Gly  Phe Glu Met
    6035                6040                6045

Val Asp  Gly Glu Pro Met Gln  Arg Ile His Arg Asn  Thr Glu Phe
    6050                6055                6060

Ala Ile  Asp Tyr Arg Gln Val  Ser Glu Asp Glu Val  Pro Glu Met
    6065                6070                6075

Ile Gly  Gln Phe Ile Arg Gln  Phe Asp Leu Glu His  Pro Pro Leu
    6080                6085                6090

Leu Arg  Val Gly Leu Phe Glu  Val Gly Gln Asp Arg  His Ile Leu
    6095                6100                6105

Val Phe  Asp Met His His Ile  Ile Ser Asp Gly Val  Ser Met Ser
    6110                6115                6120

Asn Leu  Val Asp Glu Phe Thr  Arg Leu Tyr Ala Asn  Glu Glu Arg
    6125                6130                6135

Pro Pro  Leu Arg Ile Gln Tyr  Lys Asp Tyr Ala Val  Trp Gln Gln
    6140                6145                6150

Ala Arg  Glu Asn Leu Glu Arg  Arg Lys Arg Gln Glu  Asp Tyr Trp
    6155                6160                6165

Met Ser  Val Leu Gln Gly Asp  Leu Pro Asn Ala Glu  Leu Pro Met
    6170                6175                6180
```

Asp Tyr Asp Arg Thr Ala Val Arg Ser Phe Asp Gly Glu Gln Ile
6185 6190 6195

Glu Phe Glu Ile Asn Pro Val Val Thr Gly Gln Leu Asn Gln Leu
6200 6205 6210

Ala Ser Asn His Glu Cys Thr Leu Tyr Met Val Leu Met Ser Ala
6215 6220 6225

Tyr Gln Ile Leu Leu Ser Lys Tyr Cys Gly Gln Asp Asp Ile Ile
6230 6235 6240

Val Gly Thr Pro Val Ala Gly Arg Asn His Ala Asp Leu Glu Pro
6245 6250 6255

Leu Ile Gly Met Phe Val Asn Thr Leu Ala Ile Arg Asn Arg Pro
6260 6265 6270

Gln Gly Asp Lys Thr Phe Gln Ser Phe Leu Ala Glu Val Lys Glu
6275 6280 6285

Ser Thr Leu Gly Ala Phe Glu His Gln Glu Tyr Pro Phe Glu Glu
6290 6295 6300

Leu Ile Asp Leu Leu Lys Leu Gln Trp Glu Thr Ser Arg Asn Pro
6305 6310 6315

Leu Phe Asp Thr Val Phe Val Leu Gln Asn Thr Glu Glu Arg Glu
6320 6325 6330

Ala Gly Ile Gly Gly Leu Thr Ile Ser Pro Tyr Val Thr Asp Asp
6335 6340 6345

Ser Val Ser Ala Lys Phe Asp Leu Thr Leu Ser Val Ser Glu Glu
6350 6355 6360

Asp Asp Gly Met Lys Gly Ser Phe Leu Tyr Ala Ser Lys Leu Phe
6365 6370 6375

Lys Ala Ala Gly Ile His Arg Met Met Arg Asp Tyr Leu Ser Ile
6380 6385 6390

Leu Ser Gln Val Cys Glu Asn Pro Arg Ile Arg Ile Gln Asp Ile
6395 6400 6405

Ser Ile Ser Gly Gln Gln Thr Gln Glu Lys Ser Lys Ile Asp Thr
6410 6415 6420

Ile Glu Phe Ala Phe
6425

<210> SEQ ID NO 13
<211> LENGTH: 3149
<212> TYPE: PRT
<213> ORGANISM: Paenibacillus alvei A6-6i-x

<400> SEQUENCE: 13

Met Lys Ser Val Tyr Glu Lys Glu Glu Ala Tyr Trp Asn Gly Met Phe
1 5 10 15

Asp Ser Asp Asp Ser Met Ser Ile Leu Pro Tyr Cys Ser Thr His Gly
20 25 30

Arg Glu Ala Asn Ala Asp Thr Asn Ala Ala Lys Val Ser Met Ile Arg
35 40 45

Ala Leu Pro Thr Asp Leu Ser Asp Arg Met Asn Thr Leu Ala Asn Gly
50 55 60

Ser Asp Val Ala Leu Tyr Met Ile Gly Leu Ala Gly Val Thr Cys Leu
65 70 75 80

Leu His His Tyr Thr Asn Arg Glu Asn Val Leu Val Gly Met Pro Thr
85 90 95

Ile Asp Glu Ser Glu Asp Asp Ser Ser Pro Arg Asp Val Leu Ile Met

-continued

```
            100                 105                 110

Lys Thr Asn Leu Thr Arg Gly Ser Ser Phe Arg Ser Val Leu Gly Ser
        115                 120                 125

Ile Lys Thr Ala Val Gly Gly Ala Leu Glu His Arg His Leu Pro Phe
    130                 135                 140

Arg Lys Met Val His Asn Leu Asn Leu Glu Met Asp Thr Asn Gly Leu
145                 150                 155                 160

Pro Val Met Asn Thr Val Val Ser Phe Ser Ala Ile His Thr Ala Ser
                165                 170                 175

Ile Asp Leu Ser Val Ser Ser Asp Val Ile Phe Arg Phe Asp Ala Lys
            180                 185                 190

Asp Asp Gly Leu His Leu Glu Val Leu Tyr Asp Glu Ser Arg Tyr Asp
        195                 200                 205

Ala Ser Tyr Ile Ala Thr Leu Phe Glu His Phe Phe Arg Leu Leu His
    210                 215                 220

Phe Val Leu Phe Gln Pro Asp Gln Pro Ile Gly Asn Thr Glu Leu Leu
225                 230                 235                 240

Ser Ala Glu Glu Lys His Arg Leu Leu His Glu Phe Asn Asp Val Trp
                245                 250                 255

Thr Asp Phe Pro Arg Gln Ala Thr Leu Tyr Gln Phe Ile Glu Glu His
            260                 265                 270

Ala Glu Arg Gln Pro Asp Ala Ile Ala Val Ser Tyr Glu Asp Thr Lys
        275                 280                 285

Leu Thr Tyr Arg Glu Leu Asn Ala Arg Ala Asn Arg Leu Ala Arg Thr
    290                 295                 300

Leu Arg Ser Glu Gly Val Gln Thr Glu Ala Leu Val Gly Leu Met Ala
305                 310                 315                 320

Glu Arg Ser Ile Asp Met Ile Val Gly Met Leu Ala Val Leu Lys Ala
                325                 330                 335

Gly Gly Gly Tyr Val Ala Ile Asp Pro Glu Tyr Pro Glu Glu Arg Val
            340                 345                 350

Arg Tyr Met Leu Glu Asp Ser Gly Ala Arg Val Ile Leu Val Gln Gln
        355                 360                 365

His Leu Gln Asn Arg Val Pro Asn Thr Glu Ser Ala Ala Arg Leu Leu
    370                 375                 380

Thr Leu Asp Asp Glu Gln Ser Tyr His Glu Asp Ala Ser Asn Leu Glu
385                 390                 395                 400

Ser Arg Ser Thr Ala Val Asp Leu Ala Cys Val Ile Tyr Thr Ser Gly
                405                 410                 415

Thr Thr Gly Asn Pro Lys Gly Asn Leu Thr Thr His Arg Asn Ile Val
            420                 425                 430

Arg Ile Val Lys Asn Thr Asn Tyr Ile Glu Ile Thr Glu Gln Asp Lys
        435                 440                 445

Val Leu Gln Leu Ser Ser Tyr Ser Phe Asp Gly Ser Ala Phe Asp Ile
    450                 455                 460

Phe Gly Ala Leu Thr Asn Gly Ala Gln Leu Val Leu Val Pro His His
465                 470                 475                 480

Thr Leu Leu Asp Ala Arg Lys Leu Ala Glu Leu Ile Glu Thr Glu Arg
                485                 490                 495

Ile Ser Val Met Leu Ile Thr Thr Ala Tyr Phe Asn Val Leu Val Asp
            500                 505                 510

Val Asn Ile Ser Cys Leu Arg His Ile Arg Ala Ile Leu Phe Gly Gly
        515                 520                 525
```

```
Glu Arg Ser Ser Val Ala His Val Arg Arg Ala Leu Glu Gln Thr Gly
    530                 535                 540

Pro Gly Arg Leu Lys His Ala Tyr Gly Pro Ser Glu Ser Thr Val Tyr
545                 550                 555                 560

Ala Thr Trp His Asp Val Thr Glu Ile Ser Glu Arg Ala Val Ser Val
                565                 570                 575

Pro Ile Gly Arg Pro Ile Ser Asn Thr Ala Ile Tyr Ile Val Asn Glu
            580                 585                 590

Arg Asn Asp Leu Gln Pro Ile Gly Val Ser Gly Glu Leu Cys Val Ala
        595                 600                 605

Gly Glu Gly Leu Val Arg Gly Tyr Leu Asn Arg Pro Glu Leu Thr Glu
    610                 615                 620

Gln Lys Phe Val Asp Asn Pro Phe Val Pro Gly Glu Arg Met Tyr Arg
625                 630                 635                 640

Thr Gly Asp Leu Ala Arg Trp Leu Pro Asp Gly Thr Ile Glu Tyr Val
                645                 650                 655

Gly Arg Met Asp Asp Gln Val Lys Ile Arg Gly His Arg Ile Glu Ile
            660                 665                 670

Gly Glu Val Glu Ala Gln Leu Leu Lys Val Ala Pro Ile Gln Lys Ala
        675                 680                 685

Thr Ile Val Val Arg Gly Arg Glu Asp Gly Glu Lys Gln Leu Cys Ala
    690                 695                 700

Tyr Tyr Val Ala Asp Arg Leu Leu Pro Ala Gly Glu Ile Arg Thr Met
705                 710                 715                 720

Leu Ala Lys Glu Leu Pro Ser Tyr Met Ile Pro Ala Tyr Phe Ile Gln
                725                 730                 735

Leu Glu Gln Met Pro Leu Thr Thr Asn Gly Lys Val Asp Arg Lys Ala
            740                 745                 750

Leu Pro Glu Pro Glu Glu His Val Gln Ala Glu Thr Glu Tyr Val Ala
        755                 760                 765

Pro Arg Ser Glu Gln Glu Ile Arg Leu Ala Arg Val Trp Gln Glu Val
    770                 775                 780

Leu Gly Leu Ser Arg Val Gly Ala Lys Asp His Phe Phe Glu Leu Gly
785                 790                 795                 800

Gly His Ser Leu Arg Ala Thr Thr Leu Val Ser Lys Leu His Lys Glu
                805                 810                 815

Glu Asn Ile Ser Leu Ser Leu Arg Asp Val Phe Arg Asn Pro Thr Leu
            820                 825                 830

Glu Ala Met Ala Ala Leu Met Glu Asp Ala Gln Gly Arg Lys Phe Ala
        835                 840                 845

Pro Ile Pro Thr Val Glu Glu Lys Asp Val Tyr Pro Val Ser Ser Val
    850                 855                 860

Gln Lys Arg Leu Phe Ile Leu His Gln Leu Glu Gly Ala Glu Gln Ser
865                 870                 875                 880

Tyr Asn Met Pro Gly Ala Leu Leu Leu Glu Gly Asp Val Asp Arg Asn
                885                 890                 895

Arg Leu Glu Tyr Ala Phe Arg Gln Leu Ile Thr Arg His Glu Thr Leu
            900                 905                 910

Arg Thr Gly Phe Glu Met Val Asn Gly Glu Pro Val Gln Arg Ile Tyr
        915                 920                 925

Pro Thr Val Asp Phe Val Val Glu Glu Met Ser Ala Leu Glu Gly Ser
    930                 935                 940
```

-continued

Glu Val Glu Glu Gln Ile Arg Gln Phe Ile Arg Ala Phe Asp Leu Ser
945 950 955 960

Thr Ala Pro Leu Phe Arg Ala Gly Leu Ile Lys Leu Ala Pro Gln Arg
965 970 975

His Ile Leu Leu Phe Asp Met His His Ile Ile Ser Asp Gly Thr Ser
980 985 990

Ile Gly Ile Met Ile Glu Glu Phe Thr Ser Leu Tyr Ser Gly Asn Glu
995 1000 1005

Leu Glu Pro Leu Arg Ile Gln Tyr Lys Asp Phe Ala Ala Trp Gln
1010 1015 1020

Arg Ser Glu Glu Gln Ile Glu Gln Leu Lys Arg Gln Glu Thr Tyr
1025 1030 1035

Trp Leu Gln Gln Met Glu Gly Val Leu Pro Val Leu Glu Leu Pro
1040 1045 1050

Thr Asp Tyr Val Arg Pro Ala Val Gln Ser His Asp Gly Ala Leu
1055 1060 1065

Phe Glu Phe Ser Leu Asp Arg Glu Gln Ser Gln Asp Leu Arg Lys
1070 1075 1080

Leu Ala Ala Asp Thr Arg Thr Thr Leu Tyr Met Val Leu Leu Ala
1085 1090 1095

Ala Tyr Thr Ile Ile Leu His Lys Tyr Ser Gly Gln Glu Asp Ile
1100 1105 1110

Val Val Gly Thr Pro Ile Ala Gly Arg Thr His Asp Asp Val Gln
1115 1120 1125

Pro Leu Ile Gly Met Phe Val Asn Thr Leu Ala Ile Arg Asn Tyr
1130 1135 1140

Pro Ser Gly Ser Lys Ser Val Leu Thr Tyr Leu Glu Glu Ile Lys
1145 1150 1155

Glu Thr Thr Leu Gly Ala Phe Glu His Gln Asp Tyr Pro Phe Glu
1160 1165 1170

Glu Leu Val Glu Asn Val Gln Ile Ser Arg Asp Met Ser Arg His
1175 1180 1185

Pro Val Phe Asp Thr Met Phe Ala Leu Glu Asn Thr Glu His Arg
1190 1195 1200

Glu Phe Asp Leu Asp Gly Leu Gln Val Lys Pro Tyr Gly Ala Glu
1205 1210 1215

Tyr Gly Met Ala Lys Phe Asp Leu Asn Leu Thr Val Thr Glu Asp
1220 1225 1230

Gly Asp Gly Leu Tyr Cys Thr Met Glu Tyr Ala Thr Ala Leu Tyr
1235 1240 1245

Asn Arg Ser Thr Ile Glu Arg Leu Cys Gly His Phe Leu Gln Val
1250 1255 1260

Val Gly Ser Met Thr His Asn Pro Gln Ala Ala Ile Ser Ser Leu
1265 1270 1275

Gln Met Val Thr Ser Glu Glu Lys Ala Gln Leu Gln His Glu Phe
1280 1285 1290

Asn Gly Thr Val Met Glu Tyr Ser Ser Asp Lys Thr Val His Glu
1295 1300 1305

Leu Phe Ala Glu Gln Val Glu Arg Thr Pro Asp Ala Val Ala Val
1310 1315 1320

Val Ser Gly Ser Glu Gln Leu Ser Tyr Gly Glu Leu Asn Arg Lys
1325 1330 1335

Ala Asn Gln Leu Ala Trp Lys Leu Arg Glu Tyr Gly Val Thr Ala 1340 1345 1350

Glu Gln Pro Val Gly Ile Ile Val Glu Arg Thr Leu Asp Thr Val
1355 1360 1365

Val Ala Val Ile Ala Val Leu Lys Ala Ser Gly Thr Phe Val Pro
1370 1375 1380

Ile Asp Pro Glu Tyr Pro Glu Thr Arg Ile Arg Tyr Met Leu Ala
1385 1390 1395

Asp Ser Gly Ala Lys Leu Val Leu Ala Gln Ser Glu Leu Pro Gly
1400 1405 1410

Ile Ile Ser Asp Asp Val Arg Leu Ile Asp Val Arg Asp Lys Ser
1415 1420 1425

Leu Tyr Gln Gly Asp Gly Ala Asp Val Pro Asn Gly Ser Lys Pro
1430 1435 1440

Ser Asn Leu Leu Tyr Ile Ile Tyr Thr Ser Gly Thr Thr Gly Asn
1445 1450 1455

Pro Lys Gly Val Met Leu Glu His Gly Asn Met Val Asn Leu Leu
1460 1465 1470

His Tyr Gln Gln Asn Gly Thr Asn Ile Pro Met Pro Ser Arg Ile
1475 1480 1485

Leu Gln Tyr Ala Ser Gly Ser Phe Asp Val Cys Tyr Gln Glu Met
1490 1495 1500

Phe Ser Ala Leu Leu Phe Gly Gly Ser Leu Tyr Met Val Asp Asn
1505 1510 1515

Glu Met Arg Lys Asp Pro Val Arg Leu Phe Gln Glu Ile Glu Lys
1520 1525 1530

His Glu Ile Asp Val Met Tyr Ile Pro Val Ala Phe Leu Lys Phe
1535 1540 1545

Ile Phe Ala Glu Pro Glu Trp Ala Glu Ala Phe Pro Arg Cys Val
1550 1555 1560

Arg His Ile Ile Thr Ala Gly Glu Gln Leu Val Val Thr Pro Gln
1565 1570 1575

Val Gln Ala Cys Leu Lys Arg Leu Asp Ile Cys Leu His Asn His
1580 1585 1590

Tyr Gly Pro Ser Glu Thr His Val Val Thr Thr Tyr Thr Met Thr
1595 1600 1605

Pro Glu Val Ile Glu Val Gly Leu Pro Pro Ile Gly Lys Pro Ile
1610 1615 1620

Ala Asn Thr Ser Ile Tyr Ile Val Asn Asp Ser Phe Glu Leu Gln
1625 1630 1635

Pro Ile Gly Val Lys Gly Glu Leu Tyr Val Ser Gly Ala Cys Val
1640 1645 1650

Gly Arg Gly Tyr Trp Gly Arg Thr Asp Leu Thr Glu Glu Lys Phe
1655 1660 1665

Leu Asp Asn Pro Phe Ala Pro Gly Glu Arg Leu Tyr Lys Thr Gly
1670 1675 1680

Asp Val Ala Arg Trp Leu Pro Asp Gly Ser Ile Glu Tyr Val Gly
1685 1690 1695

Arg Ser Asp His Gln Val Lys Ile Arg Gly Phe Arg Ile Glu Leu
1700 1705 1710

Gly Glu Val Glu Ser Gln Leu Leu His Val Pro Ala Val Gln Glu
1715 1720 1725

Ala Thr Val Val Ala Leu Glu Asp His Ala Gly Gln Lys Gln Leu
1730 1735 1740

```
Cys Ala  Tyr Phe Ala Ala Glu  Arg Ser Leu Thr Ala  Gly Glu Leu
    1745                 1750                 1755

Arg Gln  Ala Leu Ser Gln Glu  Leu Pro Gly Tyr Met  Ile Pro Ser
    1760                 1765                 1770

Tyr Phe  Val Gln Leu Glu Arg  Leu Pro Leu Thr Pro  Asn Gly Lys
    1775                 1780                 1785

Ile Asp  Arg Arg Ala Leu Pro  Lys Pro Glu Gly Gly  Ile Glu Thr
    1790                 1795                 1800

Gly Thr  Glu Tyr Val Ala Pro  Arg Thr Asp Thr Glu  Ala Arg Leu
    1805                 1810                 1815

Ala Arg  Ile Trp Gln Asp Val  Leu Gly Leu Pro Ser  Val Gly Val
    1820                 1825                 1830

Lys Asp  Asn Phe Phe Glu Leu  Gly Gly His Ser Leu  Arg Ala Thr
    1835                 1840                 1845

Thr Leu  Val Ser Arg Leu Tyr  Lys Glu Met Asn Val  Asn Phe Pro
    1850                 1855                 1860

Leu Arg  Gly Val Phe Arg His  Pro Thr Ile Glu Glu  Met Ala Lys
    1865                 1870                 1875

Ala Ile  Thr Glu Met His Gln  Glu Leu Tyr Thr Glu  Ile Pro Ile
    1880                 1885                 1890

Ala Glu  Glu Lys Ala Tyr Tyr  Pro Leu Ser Ser Ala  Gln Lys Arg
    1895                 1900                 1905

Leu Phe  Ile Val Ser Gln Leu  Thr Gly Ala Glu Val  Ser Tyr Asn
    1910                 1915                 1920

Met Pro  Gly Val Leu Ile Leu  Glu Gly Glu Leu Asp  Arg Ala Arg
    1925                 1930                 1935

Phe Glu  Arg Ala Phe Gln Lys  Leu Ile Asp Arg His  Glu Ser Leu
    1940                 1945                 1950

Arg Thr  Ser Phe Glu Thr Val  Arg Gly Glu Pro Val  Gln Arg Ile
    1955                 1960                 1965

His Ser  Gln Val Glu Phe Ala  Ile Glu Tyr His Leu  Ala Ala Glu
    1970                 1975                 1980

Gln Asp  Ala Glu Ala Leu Ile  Thr His Phe Val Arg  Pro Phe Gln
    1985                 1990                 1995

Leu Lys  Gln Ala Pro Leu Leu  Arg Val Gly Leu Ile  Glu Thr Gly
    2000                 2005                 2010

His Glu  Arg His Ile Leu Met  Phe Asp Met His His  Ile Ile Ser
    2015                 2020                 2025

Asp Gly  Val Thr Met Gly His  Val Val Asn Glu Phe  Ser Arg Ile
    2030                 2035                 2040

Tyr Ala  Gly Asp Gln Leu Pro  Ala Leu Arg Ile Gln  Tyr Lys Asp
    2045                 2050                 2055

Tyr Ala  Val Trp Gln Gln Ser  Asn Glu Tyr Ala Glu  Lys Leu Ala
    2060                 2065                 2070

His Gln  Glu Ser Tyr Trp Leu  Lys Gln Leu Asp Gly  Glu Leu Pro
    2075                 2080                 2085

Thr Leu  Glu Leu Pro Thr Asp  Tyr Val Arg Pro Ala  Val Gln Gln
    2090                 2095                 2100

Phe Glu  Gly Asp Val Ala Leu  Phe Thr Leu Thr Asn  Ser Gln Ala
    2105                 2110                 2115

Glu Gln  Leu Gln Arg Leu Ala  Ala Asn Tyr Gly Ala  Thr Leu Tyr
    2120                 2125                 2130
```

-continued

Met Val Leu Leu Ala Ala Tyr Thr Val Ile Leu His Lys Tyr Thr
2135 2140 2145

Gly Gln Asp Asp Ile Ile Val Gly Thr Pro Ile Ala Gly Arg Asn
2150 2155 2160

His Thr Glu Leu Glu Pro Leu Val Gly Met Phe Val Asn Thr Leu
2165 2170 2175

Ala Ile Arg Asn Tyr Pro Thr Gly Glu Lys Ser Phe Ala Glu Leu
2180 2185 2190

Leu Ala Glu Val Lys Asp Thr Ala Leu Ala Ala Phe Glu Asn Gln
2195 2200 2205

Asp Tyr Pro Phe Glu Thr Leu Val Glu Lys Val His Lys Ser Arg
2210 2215 2220

Asp Met Ser Arg Asn Pro Val Phe Asp Thr Ile Phe Ser Val Glu
2225 2230 2235

His Glu Gln Gln Ser Ser Phe His Ile Asp Gly Leu Arg Ile Ser
2240 2245 2250

Pro Tyr Pro His Ser His Ser Val Ala Lys Phe Asp Leu Thr Phe
2255 2260 2265

His Ala Glu Gln Asn Glu Glu Gly Ile Leu Cys Gly Leu Gly Tyr
2270 2275 2280

Ala Thr Ala Leu Tyr Ala Lys Glu Thr Ala Arg Arg Met Gly Glu
2285 2290 2295

His Phe Val Gln Leu Ile Asp Ala Ile Ile Ala Glu Pro Asn Ala
2300 2305 2310

Lys Leu Met Ser Leu Asn Met Met Ser Leu Gln Glu Arg Glu Gln
2315 2320 2325

Val Lys Leu Val Phe Asn Asp Thr Ile Thr Asn Tyr Pro Arg Glu
2330 2335 2340

Lys Thr Ile Gln His Leu Phe Glu Glu Gln Ala Glu Lys Ser Pro
2345 2350 2355

Asp Ala Val Ala Val Gln Phe Gly Gly Glu Gly Leu Thr Tyr Arg
2360 2365 2370

Glu Leu Asn Glu Arg Ser Asn Arg Leu Ala Arg Thr Leu Arg Gly
2375 2380 2385

Lys Gly Val Lys Ala Gly Arg Cys Val Gly Leu Met Thr Asp Arg
2390 2395 2400

Ser Leu Asp Met Ile Val Ala Ile Met Ala Thr Leu Lys Ala Gly
2405 2410 2415

Gly Ala Tyr Val Pro Ile Asp Pro Asp Tyr Pro Glu Glu Arg Ile
2420 2425 2430

Arg Tyr Met Ile Asp Asp Ser Gly Thr Ser Leu Leu Val Val Gln
2435 2440 2445

Arg His Leu Gln Ala Asn His Ile Pro Ala Asp Cys Met Val Val
2450 2455 2460

Leu Val Asp Asp Glu Gly Ser Tyr His Ala Asp Gly Thr Asn Leu
2465 2470 2475

Glu Gln His Asn Gly Ala Ser Asp Leu Ala Tyr Val Ile Tyr Thr
2480 2485 2490

Ser Gly Thr Thr Gly Met Pro Lys Gly Asn Leu Thr Thr His Arg
2495 2500 2505

Asn Ile Val Arg Val Val Arg Asp Ala Lys Tyr Ile Glu Ile Asp
2510 2515 2520

Gln His Asp Thr Val Leu Gln Leu Ser Ser Tyr Ala Phe Asp Gly

```
    2525                2530                2535

Ser Thr  Phe Asp Ile Phe Gly  Ala Leu Leu Asn Gly  Ala Lys Leu
    2540                2545                2550

Val Leu  Ile Thr Arg Glu Val  Val Leu Asp Ala Gly  Arg Leu Ala
    2555                2560                2565

Asp Thr  Ile Glu Ser Glu Lys  Ile Ser Val Met Phe  Ile Thr Thr
    2570                2575                2580

Ala Tyr  Phe Asn Leu Leu Val  Asp Leu Arg Val Asp  Ser Leu Arg
    2585                2590                2595

His Met  Arg Ala Ile Leu Phe  Gly Gly Glu Arg Ala  Ser Val Ser
    2600                2605                2610

His Val  Arg Lys Ala Leu Arg  His Leu Gly Pro Gly  Lys Leu Lys
    2615                2620                2625

His Val  Tyr Gly Pro Thr Glu  Ser Thr Val Phe Ala  Thr Ser His
    2630                2635                2640

Asn Val  Asp Glu Val Ala Asp  Ser Ala Val Thr Ile  Pro Ile Gly
    2645                2650                2655

Arg Pro  Ile Gly Asn Thr Ala  Val Tyr Ile Val Gly  Glu Gly Asp
    2660                2665                2670

Val Leu  Gln Pro Ile Gly Val  Ala Gly Glu Leu Cys  Val Ala Gly
    2675                2680                2685

Asp Gly  Val Ala Ile Gly Tyr  Leu Asn Arg Pro Asp  Leu Ser Gly
    2690                2695                2700

Ala Lys  Phe Val Asn Asn Pro  Phe Val Pro Gly Asp  Arg Met Tyr
    2705                2710                2715

Arg Thr  Gly Asp Leu Ala Arg  Trp Leu Ser Asp Gly  Thr Ile Glu
    2720                2725                2730

Tyr Val  Gly Arg Lys Asp Asp  Gln Val Lys Ile Arg  Gly Tyr Arg
    2735                2740                2745

Ile Glu  Leu Gly Glu Val Glu  Ala His Leu Leu Asp  Leu Glu Ala
    2750                2755                2760

Ile Gln  Glu Ala Val Val Ile  Val Arg Glu Glu Ser  Asp Gly Gln
    2765                2770                2775

Lys Arg  Leu Cys Ala Tyr Tyr  Val Ala Ala Arg Leu  Ile Thr Ala
    2780                2785                2790

Gly Glu  Met Arg Ile Ala Leu  Ala Gln Gln Leu Pro  Gly Tyr Met
    2795                2800                2805

Leu Pro  Ser Tyr Phe Val Gln  Leu Asp Lys Leu Pro  Leu Ser Pro
    2810                2815                2820

Asn Gly  Lys Val Asn Arg Lys  Ala Leu Pro Ala Pro  Glu Leu His
    2825                2830                2835

Val Gln  Ala Ala Ser Glu Tyr  Val Ala Pro Arg Thr  Pro Gln Glu
    2840                2845                2850

Val Leu  Leu Ala His Ile Trp  Arg Glu Val Leu Gly  Leu Gly Gln
    2855                2860                2865

Val Gly  Val Lys Asp Asn Phe  Phe Glu Leu Gly Gly  His Ser Leu
    2870                2875                2880

Ser Leu  Met Arg Leu Val Glu  Arg Val Tyr Thr Glu  Thr Glu Val
    2885                2890                2895

Glu Ile  Pro Ile His Ser Val  Phe Arg Glu Pro Thr  Ile Glu Ala
    2900                2905                2910

Met Ala  Tyr Glu Met Leu Lys  Ser Glu Leu Ala Gly  Lys Ala Gly
    2915                2920                2925
```

Asn His Phe Met Lys Leu Asn Glu Asn Gly His Ile Pro Val Phe
    2930                2935                2940

Cys Phe Pro Pro Gly Leu Gly Tyr Gly Leu Ser Tyr Leu Glu Leu
    2945                2950                2955

Ala Lys Gln Leu Asp His His Cys Ile Leu His Gly Ile Asp Phe
    2960                2965                2970

Ile Asp Asp Ala Glu Thr Arg Glu Glu Leu Leu Glu Arg Tyr Val
    2975                2980                2985

Asn Ala Ile Leu Ala Val Gln Pro Gln Pro Pro Phe Ile Leu Leu
    2990                2995                3000

Gly Tyr Ser Leu Gly Gly Asn Leu Thr Phe Glu Val Ala Lys Ala
    3005                3010                3015

Leu Glu Cys Arg Gly Tyr Pro Val Ser Asp Val Ile Met Val Asp
    3020                3025                3030

Ser Leu Arg Lys Leu Lys Val His Glu Val Asp Glu Phe Asp Gly
    3035                3040                3045

Asp Ile Asp Gln Met Ile Asp Gly Val Glu Glu Leu Lys Glu Met
    3050                3055                3060

Leu Val His His Pro Leu Leu Arg Asp Gln Val Lys Asn Lys Met
    3065                3070                3075

Arg Ala Tyr Trp Ser Tyr Ala Thr Glu Leu Val Asn Ser Asp Ile
    3080                3085                3090

Ile Asp Ala Asn Ile His Ala Leu Met Ala Glu Pro Ser Glu Val
    3095                3100                3105

Asn Gln Ala Gly Arg Gly Ala Ala Arg Asp Met Ala Gly Gly Tyr
    3110                3115                3120

Ser Arg Gln Val Cys Gly Val Gln Pro Thr Arg Cys Ala Arg Arg
    3125                3130                3135

Ser Ala Ser Thr Ala Phe Leu Gly Ser Glu Arg
    3140                3145

<210> SEQ ID NO 14
<211> LENGTH: 6655
<212> TYPE: PRT
<213> ORGANISM: Paenibacillus alvei TS-15

<400> SEQUENCE: 14

Met Asn Ala Asn Pro Asn Glu Trp Tyr Pro Leu Thr Gln Ala Gln Arg
1               5                   10                  15

Arg Ile Trp Tyr Thr Glu Met Met His Pro Asn Thr Ser Val Thr Thr
            20                  25                  30

Val Ala Gly Thr Met Tyr Ile Arg Gly Lys Val Asp Val Glu Ile Leu
        35                  40                  45

Lys Met Ala Ile Tyr Gln Val Ile Met Gln His Asp Ala Phe Arg Ile
    50                  55                  60

Arg Ile Ala Met Thr Asp Asn Gln Pro Lys Gln Gln Phe Ala Pro Val
65                  70                  75                  80

Glu Gln Ile Val Pro His Val Asp Tyr Leu Glu Trp Asp Asn Gln Ile
                85                  90                  95

Glu Ala Glu Ser Trp Leu Gln Arg Phe Asn His Ile Pro Ile His Met
            100                 105                 110

Phe Asp Pro Ala Leu Tyr His Phe Val Ile Phe Asn Val Asn Asp Glu
        115                 120                 125

Glu Thr Trp Phe Asn Leu Lys Met Asn His Ile Ala Thr Asp Gly Val

```
    130                 135                 140

Ser Ser His Leu Ile Ala Tyr Lys Ile Met Lys Asn Tyr Thr Ala Met
145                 150                 155                 160

Val Ser Gly Asn Ala Asp Thr Asp Glu Gln Glu Ser Thr Tyr Leu Asp
                165                 170                 175

Tyr Ile Phe Ala Glu Arg Glu Tyr Glu Gln Ser Asp Arg Tyr Ala Lys
            180                 185                 190

Asp Lys Ala Tyr Trp Leu Asp Lys Phe Ser Thr Met Pro Glu Val Ile
        195                 200                 205

Gly Ile Lys Ser Tyr Pro Pro His Ser Ile Gly Thr Glu Ala Ser Arg
    210                 215                 220

Thr Ser Thr Thr Val Ser Gly Glu Met Tyr Glu Lys Leu Tyr Arg Phe
225                 230                 235                 240

Ser Gln Gln His Asn Ile Ser Leu Phe Thr Leu Phe Leu Gly Ser Leu
                245                 250                 255

Tyr Ala Phe Leu Tyr Lys Thr Thr Gly Asn Asn Asp Ile Ala Val Gly
            260                 265                 270

Ala Ala Tyr Ala Asn Arg Thr Ser Arg Gln Asp Lys Asp Ala Leu Gly
        275                 280                 285

Met Phe Val Ser Thr Val Ala Ala Arg Leu Thr Ile Thr Pro Asp Gln
    290                 295                 300

Asp Val Leu Thr Phe Leu His Asn Val Ala Lys Glu Gln Lys Ala Ile
305                 310                 315                 320

Leu Arg His Gln Lys Tyr Pro Tyr Asn Gln Leu Ile Leu Asp Leu Arg
                325                 330                 335

Glu Gln Asn Asn Ser Val Glu Ile Gln Asp Leu Tyr Arg Ile Ser Ile
            340                 345                 350

Asp Tyr Met Pro Ile Arg Trp Ser Ser Tyr Gly Glu Leu Ala Val Arg
        355                 360                 365

Gln Arg Ser Ser Phe Cys Gly His Glu Val Asp Asp Phe Ala Val His
    370                 375                 380

Val Glu Asp Met Val Asp Asp Asn Gln Ile Ile Phe Asn Ile Asp Tyr
385                 390                 395                 400

Arg Lys Gln Leu Phe Glu Glu His Glu Val Ile Arg Met Ile Glu Gln
                405                 410                 415

Met Met Thr Ile Val Asp Gln Met Leu Asn Asn Pro Ser Gln Asn Leu
            420                 425                 430

Gln Gln Leu Ser Met Ile Ser Asp Lys Glu Ala Gln Ile Ile Leu Thr
        435                 440                 445

Arg Phe Ser Asn Gly Asn Trp Ser Thr Pro Gln Pro Val Gly Arg Thr
    450                 455                 460

Ile His Gln Leu Phe Glu Glu Gln Val Glu Arg Thr Pro Asp Gln Val
465                 470                 475                 480

Ala Val Val Phe Gly Asp Arg His Leu Thr Tyr Lys Glu Leu Asn Glu
                485                 490                 495

Gln Ala Asn Cys Phe Ala Arg Thr Leu Arg Ala His Gly Val Ala Ala
            500                 505                 510

Glu Gln Phe Val Gly Ile Met Ala Asp Arg Ser Ile Glu Met Val Ile
        515                 520                 525

Gly Ile Leu Ala Ile Leu Lys Ala Gly Gly Ala Tyr Val Pro Ile Asp
    530                 535                 540

Pro Glu Tyr Pro Glu Glu Arg Ile Leu Tyr Met Leu Glu Asp Ser Asn
545                 550                 555                 560
```

-continued

```
Ala Arg Val Leu Val Ser Gln Ser His Leu Gln Thr Arg Val Gly Tyr
                565                 570                 575

Thr Gly Thr Trp Val Leu Leu Asp Asn Glu Asn Asp Tyr Glu Ser Ser
            580                 585                 590

Arg Asp Asn Leu Val Pro Val Asn Glu Ala His His Leu Ala Tyr Val
        595                 600                 605

Ile Tyr Thr Ser Gly Thr Thr Gly Lys Pro Lys Gly Val Met Ile Glu
    610                 615                 620

His Lys Gln Ile Thr Ala Leu Gly Asp Ala Trp Lys His Ala Tyr Gln
625                 630                 635                 640

Leu Asp Glu Pro Gly Ile Arg Thr Leu Gln Trp Ala Ser Phe Ser Phe
                645                 650                 655

Asp Val Phe Thr Gly Asp Met Val Arg Ala Leu Leu Tyr Gly Gly Glu
            660                 665                 670

Leu Ile Ile Cys Pro Ser Glu Ala Arg Ala Asn Pro Glu Ala Ile Cys
        675                 680                 685

Glu Leu Ile Ala Arg His Arg Ile His Ile Phe Glu Ser Thr Pro Ala
    690                 695                 700

Leu Val Ile Pro Leu Met Glu Tyr Val His Glu Gln Gly Lys Asp Val
705                 710                 715                 720

Ser Ser Leu Arg Leu Leu Val Val Gly Ser Asp His Cys Pro Ala Ala
                725                 730                 735

Glu Tyr Arg Lys Leu Ile Glu Arg Phe Gly Ser Gln Met Arg Ile Leu
            740                 745                 750

Asn Ser Tyr Gly Val Thr Glu Ala Cys Val Asp Ala Cys Tyr Tyr Glu
        755                 760                 765

Arg Asn Cys Ser Val Asp Ser Ile Thr Met Leu Pro Ile Gly Lys Pro
    770                 775                 780

Leu Pro Ser Val Ser Met Tyr Ile Leu Asp Glu Asn Lys Ala Leu Gln
785                 790                 795                 800

Pro Ile Gly Ile Val Gly Glu Leu Tyr Ile Gly Gly Ala Gly Val Gly
                805                 810                 815

Arg Gly Tyr Leu Asn Arg Asp Asp Leu Thr Ala Glu Lys Phe Val Asp
            820                 825                 830

Asp Pro Tyr Ser Gln Gly Lys Met Tyr Arg Thr Gly Asp Leu Ala Arg
        835                 840                 845

Trp Leu Pro Asp Gly Asn Ile Glu Tyr Leu Gly Arg Leu Asp His Gln
    850                 855                 860

Val Lys Ile Arg Gly Asn Arg Ile Glu Ile Gly Glu Ile Glu Thr Arg
865                 870                 875                 880

Met Leu Gln Thr Ser Leu Val Arg Glu Ala Val Ile Val Ala Arg Glu
                885                 890                 895

Asp Glu Asn Gly Leu Lys Ala Leu Cys Ala Tyr Tyr Val Ala Asp Ser
            900                 905                 910

Glu Ile Ser Val Gln Gln Leu Arg Ser Thr Leu Ala Glu Gln Val Pro
        915                 920                 925

Asp Tyr Met Ile Pro Ser Tyr Phe Met Lys Leu Glu Arg Leu Pro Leu
    930                 935                 940

Thr Pro Asn Gly Lys Ile Asp Arg Asn Gly Leu Pro Ala Pro Ser Gly
945                 950                 955                 960

Gln Asp Tyr Ser Gly Lys Ile Tyr Val Glu Pro Arg Asn Gln Ala Glu
                965                 970                 975
```

```
Gln Thr Leu Val Ser Ile Trp Gln Met Val Leu Gly Val Lys Arg Val
            980                 985                 990

Gly Ile Leu Asp His Phe Phe Glu  Leu Gly Gly Asp Ser  Ile Lys Ser
        995                 1000                 1005

Ile Gln  Val Ser Ser Arg Met  Gln Gln Ala Gly Tyr  Lys Leu Asp
    1010                 1015                 1020

Ile Arg  Asp Leu Phe Lys Tyr  Pro Thr Ile Glu Gln  Ile Ser Pro
    1025                 1030                 1035

His Leu  Val Glu Val Gln Arg  Lys Ala Glu Gln Gly  Glu Glu Asn
    1040                 1045                 1050

Gly Glu  Val Gly Leu Thr Pro  Ile Leu Arg Trp Tyr  Phe Glu Arg
    1055                 1060                 1065

Asp Glu  Ala Ser Leu His His  Tyr Asn Gln Ser Ile  Met Leu His
    1070                 1075                 1080

Arg Lys  Asp Gly Phe Asp Glu  Ala Ala Leu Arg Asn  Ala Leu His
    1085                 1090                 1095

Lys Ile  Thr Glu His His Asp  Ala Leu Arg Met Val  Phe Arg Arg
    1100                 1105                 1110

Thr Glu  Gln Gly Glu Tyr Ala  Ala Trp Asn Arg Arg  Ile Glu Glu
    1115                 1120                 1125

Gly Glu  Leu Tyr Arg Leu Asp  Val Leu Asp Ile Lys  Glu Arg Ser
    1130                 1135                 1140

Ala Gly  Asp Glu Ser Glu Glu  Ser Leu His Asn Met  Leu Met Ala
    1145                 1150                 1155

Glu Ala  Asp Ala Ile Gln Asn  Gly Phe Asn Leu Glu  Ala Gly Pro
    1160                 1165                 1170

Leu Val  Gly Ala Gly Leu Phe  Arg Cys Pro Asp Gly  Asp His Leu
    1175                 1180                 1185

Leu Ile  Val Ile His His Ala  Val Ile Asp Ala Val  Ser Trp Arg
    1190                 1195                 1200

Ile Leu  Leu Glu Asp Leu Ala  Thr Gly Tyr Glu Gln  Ala Leu Leu
    1205                 1210                 1215

Gly Ser  Glu Ile Arg Leu Pro  Ala Lys Ser Asp Ser  Phe Arg Leu
    1220                 1225                 1230

Trp Ser  Arg Gln Leu Ser Ala  Tyr Ala Gln Gln Ser  Asn Met Asn
    1235                 1240                 1245

Glu Glu  Leu Lys Tyr Trp Gln  Gln Val Ala Gln Thr  Thr Ile Thr
    1250                 1255                 1260

Pro Leu  Pro Thr Asp Tyr Ala  Gly Thr Ala Leu Gln  Leu Asp Ser
    1265                 1270                 1275

Glu Ser  Val Thr Val Glu Trp  Ser Ala Asn Glu Thr  Glu Leu Leu
    1280                 1285                 1290

Leu Lys  Gln Ala His Arg Ala  Tyr Asn Thr Gln Met  Asp Asp Leu
    1295                 1300                 1305

Leu Leu  Thr Ala Leu Gly Ile  Ala Phe Arg Arg Trp  Cys Gly His
    1310                 1315                 1320

Glu Arg  Ile Arg Ile Asn Leu  Glu Gly His Gly Arg  Glu Ser Ile
    1325                 1330                 1335

Leu Pro  Asp Leu Asp Ile Thr  Arg Thr Val Gly Trp  Phe Thr Ser
    1340                 1345                 1350

Glu Tyr  Pro Gln Leu Leu Glu  Val Gly Ser Glu Glu  Glu Leu Pro
    1355                 1360                 1365

Arg Ile  Ile Lys Ser Val Lys  Glu Asp Leu Arg Ser  Ile Pro Asn
```

```
    1370                1375                1380

Lys Gly  Ile Gly Tyr Gly Ile  Cys Arg Tyr Leu Ser  Asp Lys Ser
    1385                1390                1395

Met Gln  Asp Asp Trp Gly Thr  Ala Pro Glu Val Ser  Phe Asn Tyr
    1400                1405                1410

Leu Gly  Gln Phe Asp Gln Asp  Phe Gln Asn Ser Gly  Phe Ser Pro
    1415                1420                1425

Ser Pro  Tyr Ser Thr Gly Ser  Asn Ile Gly Gly Asp  Gln Leu Arg
    1430                1435                1440

Pro Tyr  Leu Leu Asp Met Asn  Gly Met Val Ser Asp  Gly Lys Leu
    1445                1450                1455

Gln Leu  Asp Ile Ser Tyr Gly  Arg Thr Gln Tyr Arg  Val Glu Thr
    1460                1465                1470

Ile Glu  Arg Leu Ala Ser Leu  Ile Arg Asp Ser Leu  Leu Glu Ile
    1475                1480                1485

Ile Asp  His Cys Val Ala Lys  Glu Gln Thr Glu Leu  Thr Pro Ser
    1490                1495                1500

Asp Val  Ser Leu Gln Arg Ile  Ser Ile Gln Glu Leu  Glu Gln Ile
    1505                1510                1515

Val Glu  Arg Thr Ser Gly Ile  Gly Glu Val Glu Asp  Ile Tyr Ala
    1520                1525                1530

Leu Thr  Pro Met Gln Lys Gly  Met Trp Phe His Thr  Ala Met Asp
    1535                1540                1545

Ser Gln  Ala Gly Ala Tyr Phe  Glu Leu Thr Arg Leu  Thr Leu Lys
    1550                1555                1560

Gly Ala  Leu Asn Ile Glu Ala  Phe Ala Ala Ser Trp  Asn Glu Leu
    1565                1570                1575

Ala Ala  Arg His Ala Val Phe  Arg Thr Asn Phe Leu  Val Asp Ser
    1580                1585                1590

Asn Gly  Glu Pro Leu Gln Val  Val Phe Arg Ser Lys  Arg Ile Ser
    1595                1600                1605

Val Lys  His Glu Asp Leu Arg  Ser Leu Asn Ser Tyr  Glu Gln Ala
    1610                1615                1620

Val Ala  Ile Glu Asn Glu Ala  Ala Lys Glu Arg Ala  Gln Gly Phe
    1625                1630                1635

Asp Leu  Glu Asn Gly Asn Val  Met Arg Val Ser Val  Leu Gln Thr
    1640                1645                1650

Ala Asp  Glu Val Tyr Glu Val  Leu Trp Ile Ser His  His Ile Val
    1655                1660                1665

Met Asp  Gly Trp Cys Leu Pro  Leu Val Ala Ala Glu  Val Phe Ser
    1670                1675                1680

Thr Tyr  Ser Ala Leu Val Glu  Asp Lys Lys Pro Ile  Leu Ala Ser
    1685                1690                1695

Val Pro  Ser Tyr Asn Gln Tyr  Ile Gln Trp Leu Glu  Arg Gln Asp
    1700                1705                1710

Glu Ser  Ala Ala Ala Ala Tyr  Trp Asn His Tyr Leu  Ser Gly Phe
    1715                1720                1725

Glu Glu  Thr Thr Glu Leu Pro  His Ser Lys Gly Arg  Arg His Ser
    1730                1735                1740

Gly Gln  Tyr Glu Ala Gly Gln  Val Gln Ile Asp Leu  Gly Thr Ser
    1745                1750                1755

Leu Ser  Leu Ala Leu Asn Gln  Val Ala Thr Gln His  Gln Val Thr
    1760                1765                1770
```

```
Leu Asn  Thr Leu Leu Gln Ala  Ser Trp Gly Ile Leu  Leu Gln Lys
    1775                 1780                 1785

Tyr Asn  Arg Thr Ser Asp Ile  Val Phe Gly Ser Val  Val Ser Gly
    1790                 1795                 1800

Arg Pro  Ala Glu Leu Val Gly  Ile Glu Glu Met Ile  Gly Leu Phe
    1805                 1810                 1815

Ile Asn  Thr Ile Pro Val Arg  Val Ser Ser Gln Ala  His Glu Arg
    1820                 1825                 1830

Phe Ile  Glu Val Met Thr Arg  Met Gln Asp Asp Ala  Leu Ser Ser
    1835                 1840                 1845

Ala Lys  His Asp Tyr Tyr Pro  Leu Tyr Glu Ile Gln  Ala Gln Cys
    1850                 1855                 1860

Thr Leu  Lys Gln Asp Leu Ile  Asn His Ile Met Val  Leu Glu Asn
    1865                 1870                 1875

Tyr Pro  Met Glu Gln Gln Leu  Asp Gln Phe Asn Ser  Ser Asp Gly
    1880                 1885                 1890

Ser Gly  Leu Lys Leu Thr Asp  Val Thr Val Ser Glu  Gln Thr Asn
    1895                 1900                 1905

Phe Asp  Leu Asn Leu Ile Ile  Ile Pro Gly Asp Asn  Ile Val Ile
    1910                 1915                 1920

Arg Phe  Asp Phe Asn Lys Gln  Ala Leu Ala Glu Thr  Asp Met Asn
    1925                 1930                 1935

Val Leu  Lys Glu His Leu Leu  His Val Leu Glu Gln  Val Ala Ser
    1940                 1945                 1950

Asn Pro  Arg Ile Ser Ile Gly  Glu Leu Gln Leu Ala  Thr Asp Glu
    1955                 1960                 1965

Glu Arg  Ala Val Met Met Ser  Glu Phe Asn Asp Thr  Phe Val Ala
    1970                 1975                 1980

Tyr Pro  Arg Glu Lys Ser Ile  His Arg Leu Phe Glu  Glu Arg Ala
    1985                 1990                 1995

Lys Gln  Glu Pro Asp Ala Leu  Ala Val Val Phe Gly  Asn Asp Gln
    2000                 2005                 2010

Met Thr  Tyr Gly Ala Leu Asn  Ala Ala Ala Asn Arg  Met Ala Trp
    2015                 2020                 2025

Arg Leu  Arg Tyr Ala Gly Val  Thr Ser Gly Glu Leu  Val Gly Ile
    2030                 2035                 2040

Cys Ala  Asp Arg Ser Leu Glu  Met Val Val Gly Leu  Leu Ala Ile
    2045                 2050                 2055

Met Lys  Ala Gly Gly Ala Tyr  Val Pro Ile Asp Pro  Ala Tyr Pro
    2060                 2065                 2070

Gln Glu  Arg Ile Ser Ala Met  Leu Glu Asp Thr Ser  Ile Ala Thr
    2075                 2080                 2085

Met Val  Thr Gln Arg His Leu  Cys Ser Leu Trp Pro  Glu His Leu
    2090                 2095                 2100

Asn Val  Ile Ala Leu Asp Asp  Asn Glu Thr Asp Val  Ser Asn Ser
    2105                 2110                 2115

Met Glu  Asp Val Glu Ser Asn  Leu Pro Ile Asp Gly  Ala Gly Asp
    2120                 2125                 2130

Asp Leu  Ala Tyr Ile Ile Tyr  Thr Ser Gly Ser Thr  Gly Thr Pro
    2135                 2140                 2145

Lys Gly  Val Cys Val Thr His  Arg Gly Val Val Arg  Leu Val Cys
    2150                 2155                 2160
```

-continued

```
Ala Ala  Thr Tyr Val Glu Ile  Asn Ser Ser Asp Val  Phe Leu Gln
    2165                 2170                 2175

Gly Ser  Thr Ile Ser Phe Asp  Ala Ala Thr Phe Glu  Ile Trp Gly
    2180                 2185                 2190

Ser Leu  Leu Asn Gly Ala Ala  Leu Ala Ile Leu Pro  Pro Gly Asn
    2195                 2200                 2205

Val Ser  Leu Thr Asp Trp Ser  Glu Ala Ile Gln Arg  His Arg Val
    2210                 2215                 2220

Thr Thr  Leu Trp Met Thr Ala  Gly Leu Phe Gln Val  Met Val Glu
    2225                 2230                 2235

Gln Gln  Ile Glu Gly Phe Tyr  Gly Val Lys Gln Leu  Leu Val Gly
    2240                 2245                 2250

Gly Asp  Val Val Ser Pro Thr  His Val Arg Lys Val  Met Glu Lys
    2255                 2260                 2265

His Asn  Gly Ile Arg Val Ile  Asn Gly Tyr Gly Pro  Thr Glu Asn
    2270                 2275                 2280

Thr Thr  Phe Thr Cys Cys His  Thr Ile Thr Ala Ala  Asp Leu Asp
    2285                 2290                 2295

Arg Gly  Ser Ile Pro Ile Gly  Gln Pro Ile Gly Asn  Thr Arg Val
    2300                 2305                 2310

Tyr Val  Leu Asp Glu Ala Gly  Asn Val Leu Pro Val  Gly Val Cys
    2315                 2320                 2325

Gly Glu  Leu Tyr Ala Gly Gly  Asp Gly Leu Ala Arg  Gly Tyr Leu
    2330                 2335                 2340

Asn Arg  Pro Glu Leu Thr Ala  Glu Lys Phe Val Asn  Asp Pro Phe
    2345                 2350                 2355

Ile Pro  Gly Glu Arg Leu Tyr  Arg Thr Gly Asp Leu  Ala Arg Trp
    2360                 2365                 2370

Leu Pro  Asp Gly Ser Ile Glu  Phe Ile Gly Arg Cys  Asp Glu Gln
    2375                 2380                 2385

Val Lys  Ile Arg Gly Tyr Arg  Ile Glu Pro Gly Glu  Val Leu Ala
    2390                 2395                 2400

Tyr Leu  Leu Arg Ile Asp Glu  Val Gly Glu Ala Ala  Val Ile Ala
    2405                 2410                 2415

Arg Glu  Asp Ser Ser Gly Gln  Lys Glu Leu Cys Ala  Tyr Phe Thr
    2420                 2425                 2430

Ala Glu  Val Glu Leu Ser Ala  Ser Gly Leu Arg Glu  Thr Leu Ala
    2435                 2440                 2445

Arg Glu  Leu Pro Ala Tyr Met  Ile Pro Ser His Phe  Ile Gln Ile
    2450                 2455                 2460

Glu Glu  Leu Pro Leu Thr Pro  Asn Gly Lys Val Asp  Arg Arg Ala
    2465                 2470                 2475

Leu Pro  Leu Pro Glu Glu Gly  Leu Arg Met Asn Leu  Lys Ile Gln
    2480                 2485                 2490

Pro Arg  Thr Glu Leu Glu Ala  Lys Leu Ala Leu Ile  Trp Gln Asp
    2495                 2500                 2505

Val Leu  Gly Leu Glu Asn Val  Gly Val Thr Asp Ser  Phe Phe Glu
    2510                 2515                 2520

Leu Gly  Gly His Ser Leu Arg  Ala Thr Thr Leu Val  Ser Lys Val
    2525                 2530                 2535

His Arg  Glu Leu Asn Ile Ala  Leu Pro Leu Gln Asp  Val Phe Arg
    2540                 2545                 2550

Tyr Pro  Thr Ile Glu Gln Met  Ser Leu Ala Ile Gln  Gly Met Gln
```

-continued

```
    2555                2560                2565

Lys Glu  Ser Phe Ala Ser Ile  Pro Arg Val Glu Asp  Arg Glu Trp
    2570                2575                2580

Tyr Pro  Val Ser Ser Ala Gln  Lys Arg Leu Phe Val  Leu His Gln
    2585                2590                2595

Met Glu  Gly Ala Glu Leu Ser  Tyr Asn Met Pro Gly  Val Met Ala
    2600                2605                2610

Ile Glu  Gly Lys Leu His Arg  Asp Arg Leu Glu Ala  Ala Phe Arg
    2615                2620                2625

Gly Leu  Ile Ala Arg His Glu  Val Leu Arg Thr Gly  Phe Glu Met
    2630                2635                2640

Tyr Asn  Gly Glu Pro Met Gln  Arg Ile Tyr Ser Asp  Val Glu Phe
    2645                2650                2655

Thr Val  Glu His Gly Ile Val  Gly Ala Ala Ser Glu  Ala Glu Ser
    2660                2665                2670

Val Ile  Arg Ser Phe Val Arg  Ala Phe Gln Leu Asn  Lys Pro Pro
    2675                2680                2685

Leu Leu  Arg Val Gly Leu Ile  Glu Val Asp Ala Asp  Arg His Leu
    2690                2695                2700

Leu Leu  Phe Asp Met His His  Ile Ile Ser Asp Gly  Ala Ser Met
    2705                2710                2715

Gly Ile  Leu Leu Asp Glu Phe  Val Ala Leu Tyr Ser  Gly Glu Glu
    2720                2725                2730

Leu Pro  Glu Leu Arg Leu Gln  Tyr Lys Asp Tyr Ala  Ser Trp Gln
    2735                2740                2745

Gln Ser  Glu Asp Tyr Leu Ser  Arg Met Glu Glu Gln  Lys Ala Tyr
    2750                2755                2760

Trp Leu  Glu Thr Leu Arg Gly  Glu Leu Pro Val Leu  Gln Leu Pro
    2765                2770                2775

Val Asp  Tyr Thr Arg Pro Ala  Phe Arg Ser Phe Ala  Gly Ser Thr
    2780                2785                2790

Leu Glu  Phe Ile Val Pro Ala  Asp Lys Ala Asp Gln  Leu Lys Gln
    2795                2800                2805

Leu Gly  Ala Gly Ser Asp Ala  Thr Met Tyr Met Val  Leu Leu Ala
    2810                2815                2820

Leu Tyr  Thr Ala Leu Leu His  Lys Tyr Thr Gly Gln  Glu Asp Val
    2825                2830                2835

Ile Val  Gly Met Pro Ile Ala  Gly Arg Thr His Ala  Asp Ile Glu
    2840                2845                2850

Pro Leu  Ile Gly Met Phe Val  Asn Thr Leu Pro Leu  Arg His Tyr
    2855                2860                2865

Pro Ala  Gly Glu Lys Thr Phe  Arg Ser Phe Leu Gly  Glu Val Arg
    2870                2875                2880

Gln Ser  Thr Leu Gln Ala Tyr  Glu His Gln Glu Tyr  Pro Phe Glu
    2885                2890                2895

Glu Leu  Val Asp His Ile Gln  Pro Thr Arg Asp Val  Ser Arg Asn
    2900                2905                2910

Pro Ile  Phe Asp Thr Val Leu  Val Leu Gln Asn Thr  Glu Lys Gly
    2915                2920                2925

Ala Trp  Ser Ile Asp Gly Leu  Ala Val Thr Pro Asn  Pro Ile Glu
    2930                2935                2940

His Ala  Val Ala Lys Phe Asp  Leu Thr Leu His Val  Glu Glu Gly
    2945                2950                2955
```

```
Ile Asp  Gly Leu Ala Cys Ser  Ile Glu Tyr Ala Thr  Ala Leu Tyr
    2960                 2965                 2970

His Arg  Glu Thr Ile Glu Arg  Leu Ala Cys His Phe  Asn Gln Leu
    2975                 2980                 2985

Leu Glu  Ala Val Ile Ser Asn  Pro Glu Ala Arg Leu  Asp Gln Leu
    2990                 2995                 3000

Gly Ile  Ile Thr Glu Thr Glu  Lys Gln Gln Leu Phe  Glu Glu Phe
    3005                 3010                 3015

Asn Asp  Thr Ser Ala Asp Tyr  Pro Arg Asp Lys Thr  Ile His Arg
    3020                 3025                 3030

Leu Phe  Glu Glu Gln Val Glu  Arg Thr Pro Asp Ala  Ile Ala Val
    3035                 3040                 3045

Thr Gly  Ser Asp Gly Phe Leu  Thr Tyr Gln Glu Leu  Asn Glu Arg
    3050                 3055                 3060

Ala Asn  Ser Leu Ala Trp Val  Leu Arg Ala Glu Gly  Ile Gly Ala
    3065                 3070                 3075

Asp Lys  Leu Val Gly Ile Met  Ala Glu Arg Thr Thr  Asp Met Leu
    3080                 3085                 3090

Val Gly  Leu Ile Ala Ile Leu  Lys Ala Gly Gly Ala  Tyr Val Pro
    3095                 3100                 3105

Ile Asp  Pro Glu Tyr Pro Glu  Glu Arg Ile Ser Tyr  Met Leu Ser
    3110                 3115                 3120

Asp Ser  Gly Ala Asp Ile Leu  Leu Leu Pro Arg His  Leu Arg Glu
    3125                 3130                 3135

Gln Val  Ala Tyr Glu Gly Thr  Val Leu Phe Leu Asp  Asp Glu Gln
    3140                 3145                 3150

Thr Tyr  Ser Gly Asp Lys Ser  Asn Pro Ser Ser Val  Asn Lys Pro
    3155                 3160                 3165

Ser Asp  Leu Ala Tyr Val Ile  Tyr Thr Ser Gly Thr  Thr Gly Lys
    3170                 3175                 3180

Pro Lys  Gly Thr Leu Ile Glu  His Lys Asn Val Val  Arg Leu Leu
    3185                 3190                 3195

Phe Asn  Ser Arg Asn Leu Phe  Asp Phe Arg Ser Thr  Asp Thr Trp
    3200                 3205                 3210

Thr Leu  Phe His Ser Phe Cys  Phe Asp Phe Ser Val  Trp Glu Met
    3215                 3220                 3225

Tyr Gly  Ala Leu Leu Tyr Gly  Gly Arg Leu Val Val  Val Pro Gln
    3230                 3235                 3240

Leu Thr  Ala Lys Asn Pro Ala  Met Phe Leu Gln Leu  Leu Ala Glu
    3245                 3250                 3255

Glu Arg  Val Thr Ile Leu Asn  Gln Thr Pro Thr Tyr  Phe Tyr Gln
    3260                 3265                 3270

Leu Ile  Arg Glu Ala Leu Ala  Asp Gly Ser Pro Glu  Leu Asn Ile
    3275                 3280                 3285

Arg Met  Val Ile Phe Gly Gly  Glu Ala Leu Ser Pro  Gln Leu Leu
    3290                 3295                 3300

Lys Asp  Trp Arg Ala Lys Tyr  Pro Arg Thr Gln Leu  Ile Asn Met
    3305                 3310                 3315

Tyr Gly  Ile Thr Glu Thr Thr  Val His Val Thr Tyr  Lys Glu Ile
    3320                 3325                 3330

Thr Glu  Thr Glu Ile Glu Gln  Ala Arg Ser Asn Ile  Gly Phe Pro
    3335                 3340                 3345
```

```
Ile Pro  Thr Leu Arg Ile Tyr  Ile Leu Asp Ala Asn  Arg Asn Cys
    3350                 3355                 3360

Val Pro  Ile Gly Val Ala Gly  Glu Met Phe Val Ala  Gly Glu Gly
    3365                 3370                 3375

Leu Ala  Arg Gly Tyr Leu Asn  Arg Pro Glu Leu Thr  Glu Asp Arg
    3380                 3385                 3390

Phe Val  Asp Asn Pro Phe Glu  Pro Gly Ser Lys Met  Tyr Lys Thr
    3395                 3400                 3405

Gly Asp  Leu Ala Lys Trp Leu  Pro Asp Gly Asn Ile  Glu Tyr Leu
    3410                 3415                 3420

Gly Arg  Ile Asp His Gln Val  Lys Ile Arg Gly Tyr  Arg Ile Glu
    3425                 3430                 3435

Leu Gly  Glu Val Glu Ala Gln  Val Thr Lys Val Glu  Ser Val Arg
    3440                 3445                 3450

Glu Ala  Ile Val Ile Ala Arg  Glu Glu Asn Gly Glu  Lys Leu Leu
    3455                 3460                 3465

Cys Ala  Tyr Phe Val Ala Asp  Arg Gln Leu Thr Val  Gly Glu Met
    3470                 3475                 3480

Arg Thr  Glu Leu Ala Gln Glu  Leu Pro Ala Tyr Met  Ile Pro Ser
    3485                 3490                 3495

Tyr Phe  Val Gln Leu Glu Arg  Met Pro Leu Thr Ser  Asn Gly Lys
    3500                 3505                 3510

Val Asp  Arg Lys Ala Leu Pro  Ala Pro Glu Gly Ser  Ile Asn Thr
    3515                 3520                 3525

Gly Lys  Glu Tyr Val Ala Pro  Arg Thr Ser Met Glu  Ala Ser Leu
    3530                 3535                 3540

Ala Arg  Met Trp Asp Glu Leu  Leu Gly Ile Glu Gln  Val Gly Val
    3545                 3550                 3555

Thr Asp  Asn Phe Phe Glu Leu  Gly Gly His Ser Leu  Arg Ala Thr
    3560                 3565                 3570

Ala Leu  Val Asn Arg Val His  Gln Glu Met Asn Ile  Gln Leu Pro
    3575                 3580                 3585

Leu Arg  Asp Val Phe Arg Phe  Ser Thr Ile Glu Glu  Leu Ala Ala
    3590                 3595                 3600

Ala Met  Ser Glu Met Ala Glu  Glu Ser Tyr Ser Ser  Ile Pro Val
    3605                 3610                 3615

Ala Glu  Val Gln Glu His Tyr  Pro Val Ser Ser Ala  Gln Lys Arg
    3620                 3625                 3630

Leu Tyr  Ile Leu His Gln Leu  Glu Gly Ala Glu Gln  Gly Tyr Asn
    3635                 3640                 3645

Met Pro  Gly Ile Met Leu Ile  Glu Gly Glu Leu Asp  Arg Ser Arg
    3650                 3655                 3660

Phe Glu  Ala Ala Phe Arg Lys  Leu Ile Ala Arg His  Asp Ile Leu
    3665                 3670                 3675

Arg Thr  Gly Phe Glu Leu Val  Lys Gly Glu Ala Val  Gln Arg Ile
    3680                 3685                 3690

His Asp  Thr Leu Asp Phe Ala  Ile Glu Tyr Arg Lys  Val Glu Glu
    3695                 3700                 3705

Gln Glu  Val Gln Gln Gln Val  Arg Gln Phe Ile Arg  Thr Phe Glu
    3710                 3715                 3720

Leu Asp  Lys Pro Pro Leu Leu  Arg Val Gly Leu Ile  Glu Ile Ala
    3725                 3730                 3735

Glu Ala  Lys Glu Gln His Val  Leu Leu Phe Asp Met  His His Ile
```

```
3740                3745                3750

Ile Ser Asp Gly Val Ser Ile Gly Ile Val Leu Gln Glu Ile Met
    3755                3760                3765

Arg His Tyr His Gly Glu Glu Val Pro Pro Leu His Ile Gln Tyr
    3770                3775                3780

Lys Asp Tyr Ala Ala Trp Gln Gln Ser Glu Ala Gln Lys Glu Gln
    3785                3790                3795

Leu Lys His Gln Gln Ala Tyr Trp Leu Asp Gln Phe Gln Gly Glu
    3800                3805                3810

Leu Pro Ile Leu Glu Leu Pro Thr Asp Tyr Ala Arg Pro Ala Ile
    3815                3820                3825

Gln Gln Tyr Asp Gly Leu Thr Leu Pro Phe Arg Ile Asp Lys Asp
    3830                3835                3840

Val Ala Asp Gly Leu Asn Arg Ile Ala Ala Asp Thr Gly Thr Thr
    3845                3850                3855

Leu Tyr Met Val Leu Leu Ala Ala Tyr Thr Ile Met Leu His Lys
    3860                3865                3870

Tyr Thr Gly Gln Glu Asp Ile Val Val Gly Thr Pro Ile Ala Gly
    3875                3880                3885

Arg Thr His Glu Glu Leu Gln Pro Leu Ile Gly Met Phe Val Asn
    3890                3895                3900

Thr Leu Ala Ile Arg Ala Tyr Pro Glu Gly Ala Lys Ala Phe Arg
    3905                3910                3915

Ser Tyr Leu Asp Glu Ile Arg Ser Thr Met Leu Gly Ala Tyr Glu
    3920                3925                3930

His Gln Gln Tyr Pro Phe Glu Glu Leu Val Glu Gly Leu Gln Leu
    3935                3940                3945

Thr Arg Asp Leu Ser Arg Asn Pro Leu Phe Asp Thr Met Phe Ala
    3950                3955                3960

Leu Asp Asn Thr Asp Met Met Val Asp Ser Leu Gly Glu Leu His
    3965                3970                3975

Met Lys Pro Tyr Pro Leu Glu Tyr Thr Ile Ser Lys Phe Asp Val
    3980                3985                3990

Ser Leu Asp Val Lys Ala Asp Glu Arg Gly Leu Asp Cys Ser Phe
    3995                4000                4005

Glu Tyr Ala Thr Ser Leu Phe Lys Ser Glu Thr Ile His Arg Met
    4010                4015                4020

Ala Glu His Phe Ser Gln Leu Leu Lys Asp Ile Val Asn His Pro
    4025                4030                4035

Asp Ala Gln Leu Gly Glu Leu Gly Met Leu Thr Val His Glu Ser
    4040                4045                4050

Asp Glu Ile Leu Gln Val Phe Asn Pro Thr His Ser Leu Lys Ala
    4055                4060                4065

Pro Asp Gly Thr Ile His Arg Leu Phe Glu Glu Gln Ala Glu Arg
    4070                4075                4080

Thr Pro Glu Gln Pro Ala Val Val Phe Gly Asn Glu Arg Met Thr
    4085                4090                4095

Tyr Arg Glu Leu Asn Glu Arg Ala Asn Lys Leu Ala Arg Thr Leu
    4100                4105                4110

Arg Ala Glu Gly Val Glu Pro Asp Asp Leu Ile Gly Val Met Ala
    4115                4120                4125

Asp Arg Ser Ile Asp Met Val Val Ala Val Met Ala Val Leu Lys
    4130                4135                4140
```

-continued

```
Ser Gly  Gly Ala Tyr Val Pro  Ile Asp Pro Glu Tyr  Pro Glu Asp
    4145                 4150                 4155

Arg Ile  Arg Tyr Met Leu Glu  Asp Ala Lys Ala Arg  Ile Leu Leu
    4160                 4165                 4170

Thr Gln  Cys His Leu Gln Asp  Lys Val Ser Phe Glu  Gly Thr Trp
    4175                 4180                 4185

Val Leu  Leu Glu Asp Glu Ala  Ser Tyr His Glu Asp  Asp Thr Asn
    4190                 4195                 4200

Leu Glu  Pro Ile Cys Glu Pro  Asp His Leu Cys Tyr  Val Ile Tyr
    4205                 4210                 4215

Thr Ser  Gly Thr Thr Gly Asn  Pro Lys Gly Val Met  Ile Glu His
    4220                 4225                 4230

Arg Gln  Leu Ala Ala Met Ala  Glu Ala Trp Lys Ala  Glu Tyr Glu
    4235                 4240                 4245

Leu His  Glu Pro Gly Ile Arg  Trp Leu Gln Trp Ala  Ser Phe Ser
    4250                 4255                 4260

Phe Asp  Val Phe Ser Gly Asp  Leu Ala Arg Thr Leu  Leu His Gly
    4265                 4270                 4275

Gly Glu  Leu Ile Leu Cys Pro  Ser Asp Thr Arg Ala  Asn Pro Gly
    4280                 4285                 4290

Ala Leu  Ala Glu Leu Leu Arg  Ser Ser Gly Ile Gln  Met Phe Glu
    4295                 4300                 4305

Ser Thr  Pro Ala Leu Val Ile  Pro Leu Met Glu His  Val Tyr Glu
    4310                 4315                 4320

His Arg  Val Asp Ile Asp Ser  Leu Arg Leu Leu Ile  Ile Gly Ser
    4325                 4330                 4335

Asp Leu  Cys Pro Ala Asp Glu  Phe Arg Lys Leu Leu  Asp Arg Phe
    4340                 4345                 4350

Gly Ser  His Leu Arg Ile Ile  Asn Ser Tyr Gly Val  Thr Glu Ala
    4355                 4360                 4365

Cys Val  Asp Ser Ser Tyr Tyr  Glu Pro Val Leu Ser  Asp Pro Val
    4370                 4375                 4380

Arg Ser  Val Pro Ile Gly Lys  Pro Leu Pro Tyr Val  Ser Met Tyr
    4385                 4390                 4395

Ile Leu  Gly Glu Asn Leu Ser  Leu Gln Pro Val Gly  Leu Ala Gly
    4400                 4405                 4410

Glu Leu  Tyr Ile Ala Gly Ala  Gly Val Gly Arg Gly  Tyr Trp Asn
    4415                 4420                 4425

Arg Pro  Glu Met Thr Ala Asp  Lys Phe Val Arg Asp  Pro Phe Ala
    4430                 4435                 4440

Asp Gly  Gln Cys Met Tyr Arg  Thr Gly Asp Leu Ala  Lys Trp Leu
    4445                 4450                 4455

Leu Asp  Gly Asn Ile Glu Leu  Ile Gly Arg Thr Asp  His Gln Val
    4460                 4465                 4470

Lys Ile  Arg Gly Tyr Arg Ile  Glu Ile Gly Glu Val  Glu Ser Lys
    4475                 4480                 4485

Leu Gln  Gln Thr Pro Asp Ile  Arg Glu Ala Ala Val  Val Ala Lys
    4490                 4495                 4500

Glu Asp  Gly Ser Gly Arg Lys  Val Leu Cys Ala Tyr  Tyr Thr Ser
    4505                 4510                 4515

Tyr Arg  Glu Leu Thr Ala Gly  Glu Trp Arg Ser Ala  Leu Ala Lys
    4520                 4525                 4530
```

```
Glu Leu  Pro Ala Tyr Met Ile  Pro Ser His Phe Met  Arg Leu Glu
    4535                 4540                 4545

Arg Met  Pro Leu Thr Pro Asn  Gly Lys Leu Asp Arg  Lys Gly Leu
    4550                 4555                 4560

Pro Ala  Pro Glu Gly Ala Ala  Tyr Thr Gly Thr Glu  Tyr Glu Ala
    4565                 4570                 4575

Pro Arg  Thr Asp Ala Glu Ile  Ala Leu Ala Ala Ala  Trp Gln Ser
    4580                 4585                 4590

Val Leu  His Val Glu Arg Val  Gly Thr Asn Asp His  Phe Phe Glu
    4595                 4600                 4605

Leu Gly  Gly Asp Ser Ile Lys  Ser Ile Gln Val Ser  Ser Arg Leu
    4610                 4615                 4620

His Gln  Ala Gly Tyr Lys Leu  Glu Ile Arg Asp Leu  Phe Lys Tyr
    4625                 4630                 4635

Pro Thr  Ile Ala Gln Leu Ser  Leu Gln Leu Gln Pro  Ile Gly Arg
    4640                 4645                 4650

Ile Ala  Asp Gln Gly Glu Val  His Gly Glu Val Glu  Leu Thr Pro
    4655                 4660                 4665

Ile Gln  Arg Trp Tyr Phe Gly  Leu Asp Leu Asp Asp  Met His His
    4670                 4675                 4680

Tyr Asn  Gln Ser Phe Leu Leu  Tyr Arg Gln Gly Gly  Phe Asn Glu
    4685                 4690                 4695

Glu Ala  Leu Arg Lys Thr Leu  Arg Thr Ile Val Glu  His His Asp
    4700                 4705                 4710

Ala Leu  Arg Met Val Phe Arg  Lys Ser Ala Ala Gly  Val Thr Ala
    4715                 4720                 4725

Trp Asn  Arg Ala Ile Glu Glu  Gly Glu Leu Phe Asp  Phe Leu Ala
    4730                 4735                 4740

Phe Asp  Ile Ala Asn Ser Gly  Asp Ala Glu Gln Val  Ile Glu Ala
    4745                 4750                 4755

Lys Ala  Asn Asp Ile Gln Ala  Ser Ile Asp Leu Gln  Gly Gly Pro
    4760                 4765                 4770

Leu Val  Lys Ala Gly Leu Phe  Arg Cys Glu Gln Gly  His His Leu
    4775                 4780                 4785

Leu Ile  Ala Ile His His Ala  Val Ile Asp Gly Val  Ser Trp Arg
    4790                 4795                 4800

Ile Leu  Leu Glu Asp Ile Ser  Ala Gly Tyr Glu Gln  Ala Cys Lys
    4805                 4810                 4815

Gly Asp  Asp Ile Arg Leu Pro  Ser Lys Thr Asp Ser  Tyr Ala Ala
    4820                 4825                 4830

Trp Ser  Arg Ser Leu Val Glu  Tyr Ala Ser Leu Thr  Asp Leu Gly
    4835                 4840                 4845

His Glu  Arg Ser Tyr Trp Arg  His Val Leu Asn Ala  Gly Ala Asn
    4850                 4855                 4860

Pro Leu  Pro Lys Asp Phe Asp  Thr Glu Ser Ser Leu  Gln Gln Asp
    4865                 4870                 4875

Ser Asn  Ser Val Thr Val Ala  Trp Asn Gln Gln Asp  Thr Glu His
    4880                 4885                 4890

Leu Leu  Lys Arg Val His Arg  Ala Tyr Asn Thr Asp  Met Asn Glu
    4895                 4900                 4905

Ile Leu  Leu Ala Ala Leu Ala  Ile Ala Ile Gln Lys  Trp Ser Gly
    4910                 4915                 4920

His Asn  Gln Ile Leu Ile Asn  Leu Glu Gly His Gly  Arg Glu Pro
```

4925 4930 4935

Ile Ala Gly Asp Leu Asp Ile Ser Arg Thr Val Gly Trp Phe Thr
4940 4945 4950

Ser Glu Tyr Pro Val Leu Leu Gln Ala Glu Arg Asp Arg Gly Leu
4955 4960 4965

Ala Tyr His Ile Lys Arg Ala Lys Glu Glu Leu Arg Gln Ile Pro
4970 4975 4980

Asn Lys Gly Ile Gly Tyr Gly Ile Cys Arg Tyr Leu Ser Glu Pro
4985 4990 4995

Asp Asp Ser Leu Glu Trp Gly Ala Ala Pro Glu Ile Ser Phe Asn
5000 5005 5010

Tyr Leu Gly Gln Phe Asp Gln Asp Thr Met Glu Gly Gly Ile Met
5015 5020 5025

Leu Ser Pro Tyr Ser Lys Gly Ser Asp Gly Ser Ala Leu His Thr
5030 5035 5040

Arg Gln Tyr Val Leu Asp Ile Asn Cys Ala Ile Thr Asn Gly Met
5045 5050 5055

Leu Thr Leu Asp Met Ser Tyr Ser Glu Lys Glu Tyr Arg Lys Glu
5060 5065 5070

Thr Met Glu Leu Leu Ala Gly His Phe His Glu Ser Leu Leu Glu
5075 5080 5085

Ile Ile Asn His Cys Val Ser Arg Glu Gln Thr Glu Leu Thr Pro
5090 5095 5100

Ser Asp Leu Leu Leu His Gly Leu Ser Ile Glu Gln Leu Glu Gln
5105 5110 5115

Ile Ala Glu Glu Met Arg Glu Leu Gly Ile Ile Glu Asn Met Tyr
5120 5125 5130

Met Leu Thr Pro Met Gln Lys Gly Met Trp Phe His Asn Ala Leu
5135 5140 5145

Asp Gly Gln Glu Gly Ala Thr Gly Ala Tyr Phe Glu Gln Thr Arg
5150 5155 5160

Phe Thr Leu Arg Gly Glu Leu Asp Pro Ala Leu Phe Ala Gln Ser
5165 5170 5175

Leu His Glu Leu Ala Ala Arg His Ser Val Leu Arg Thr Asn Phe
5180 5185 5190

Cys Ser Leu Asp Gly Glu Pro Val Gln Val Val Phe Arg Glu Gly
5195 5200 5205

Arg Ile Thr Phe Thr Tyr Glu Asp Leu Ser Gln Leu Pro Ala Glu
5210 5215 5220

Glu Gln Ala Ala Val Ile Glu Arg Ile Val Ala Ser Asp Lys Leu
5225 5230 5235

Arg Gly Phe Asp Leu Glu Arg Asp Pro Leu Val Arg Val Thr Leu
5240 5245 5250

Met Arg Thr Glu Ala Ser Ser Cys His Val Leu Trp Ser Ser His
5255 5260 5265

His Ile Leu Met Asp Gly Trp Cys Leu Pro Gln Leu Thr Asp Glu
5270 5275 5280

Leu Phe Arg Ile Tyr Ser Ala Val Thr Asn His Asn Ala Gly Thr
5285 5290 5295

Thr Glu Ala Thr Gly Thr Val Gly Thr Leu Gly Ala Phe Gly Ala
5300 5305 5310

Ala Glu Ser Leu Arg Asn Lys Glu Ala Gly Leu Pro Asp Tyr Ser
5315 5320 5325

```
Arg Tyr  Ile Glu Trp Leu Ala  Glu Gln Asp Met Ser  Ala Ala Ala
    5330                 5335                 5340

Ala Tyr  Trp Asn Gly Tyr Leu  Ala Gly Tyr Glu Gln  Gln Thr Arg
    5345                 5350                 5355

Leu Pro  Asn Gly Lys Ile Thr  Gly Lys Asp Lys Pro  Tyr Val Leu
    5360                 5365                 5370

Glu Gln  Ala Ser Arg Lys Leu  Gly Ile Glu Leu Thr  Ser Arg Met
    5375                 5380                 5385

Ile Arg  Ile Ala Lys Gln His  Gln Val Thr Leu Asn  Thr Leu Leu
    5390                 5395                 5400

Gln Ala  Ala Trp Gly Ile Val  Leu Gln Lys Tyr Asn  Gly Thr Gln
    5405                 5410                 5415

Asp Val  Val Phe Gly Gly Val  Val Ser Gly Arg Pro  Ala Asp Val
    5420                 5425                 5430

Pro Gly  Val Glu Ser Met Ile  Gly Leu Phe Ile Asn  Thr Ile Pro
    5435                 5440                 5445

Val Arg  Val Ser Asn Glu Ala  Gly Ala Ser Phe Ser  Asp Val Met
    5450                 5455                 5460

Glu Gln  Leu Gln Asn Ala Ala  Leu Glu Ser Gly Arg  Tyr Asp Tyr
    5465                 5470                 5475

Tyr Pro  Leu Tyr Glu Ile Gln  Ser Arg Thr Ser Gln  Lys Ser Glu
    5480                 5485                 5490

Leu Ile  Ser His Ile Met Val  Phe Glu Asn Tyr Pro  Leu Asp Glu
    5495                 5500                 5505

Arg Met  Glu Gln Thr Arg Asp  Gly Asn Asp Gly Ala  Leu Ala Leu
    5510                 5515                 5520

Thr Asp  Val Gln Ala Ala Glu  Gln Thr Asn Tyr Asp  Phe Asn Leu
    5525                 5530                 5535

Met Val  Val Pro Gly Asp Glu  Leu Ile Ile Arg Phe  Asp Phe Asn
    5540                 5545                 5550

Ser Glu  Val Tyr Glu Arg Gly  His Met Glu Arg Leu  His His His
    5555                 5560                 5565

Leu Met  His Val Leu Glu Gln  Val Thr Gly Asn Pro  Ala Ile Ser
    5570                 5575                 5580

Ile Ala  Glu Val Gln Leu Ala  Thr Glu Ala Glu Lys  Ala Glu Leu
    5585                 5590                 5595

Gln Ser  Ala Phe Asn Asp Thr  Ala Val Asp Tyr Pro  Arg Glu Gln
    5600                 5605                 5610

Thr Ile  His Arg Met Phe Glu  Glu Gln Val Gln Gln  Thr Pro Asp
    5615                 5620                 5625

Ala Ala  Ala Val Leu Tyr Gly  Asp Asp Ser Ile Thr  Tyr Arg Glu
    5630                 5635                 5640

Leu Asn  Glu Arg Ala Asn Gln  Leu Ala Arg Thr Leu  Arg Ala Ala
    5645                 5650                 5655

Gly Val  Glu Pro Asp Gln Ile  Val Gly Ile Met Ala  Glu Arg Ser
    5660                 5665                 5670

Leu Glu  Leu Met Val Gly Ile  Met Gly Ile Leu Lys  Ala Gly Gly
    5675                 5680                 5685

Ala Tyr  Val Pro Ile Ala Pro  Asp Tyr Pro Glu Asp  Arg Ile Arg
    5690                 5695                 5700

Tyr Met  Leu Asp Asp Ser Glu  Ala Gln Val Leu Leu  Val Gln Gly
    5705                 5710                 5715
```

```
Ser Ala  Gly Glu Ala Val Asp  Phe Ala Gly Arg Ile  Ile Asn Leu
    5720                 5725                 5730

Asp Asp  Ala Glu Ala Tyr Asp  Gly Asp Gly Ser Asn  Pro Glu Pro
    5735                 5740                 5745

Val Asn  Lys Pro Thr Asp Ile  Ala Tyr Ile Ile Tyr  Thr Ser Gly
    5750                 5755                 5760

Thr Thr  Gly Arg Pro Lys Gly  Val Met Val Glu His  Thr Ser Val
    5765                 5770                 5775

Ile Asn  Arg Leu Leu Trp Met  Gln Lys Arg Tyr Pro  Ile Gly Ala
    5780                 5785                 5790

Glu Asp  Thr Ile Met Gln Lys  Thr Ala Ile Thr Phe  Asp Val Ser
    5795                 5800                 5805

Val Trp  Glu Leu Phe Trp Trp  Ala Phe Val Gly Ser  Lys Val Leu
    5810                 5815                 5820

Met Leu  Ser Val Gly Gly Glu  Lys Ser Pro His Ala  Ile Val Asp
    5825                 5830                 5835

Ala Ile  Glu Arg His Arg Ile  Thr Thr Met His Phe  Val Pro Ser
    5840                 5845                 5850

Met Leu  His Ala Phe Leu Glu  His Val Glu Gln Leu  Thr Asp Ala
    5855                 5860                 5865

Glu Arg  Glu Arg Gly Leu Ala  Pro Leu Arg Gln Val  Phe Thr Ser
    5870                 5875                 5880

Gly Glu  Ala Leu Leu Ala Ser  Gln Val Glu Arg Phe  His Arg Tyr
    5885                 5890                 5895

Ile Ala  Pro Ala Ser Gly Ala  Gln Leu Ile Asn Leu  Tyr Gly Pro
    5900                 5905                 5910

Thr Glu  Ala Thr Val Asp Val  Thr Tyr Phe Asp Cys  Glu Pro Gly
    5915                 5920                 5925

Gln Thr  Tyr Val Ser Val Pro  Ile Gly Lys Pro Ile  Asp Asn Thr
    5930                 5935                 5940

Ser Ile  His Ile Val Asn Glu  His Asn Gln Val Gln  Pro Ile Gly
    5945                 5950                 5955

Val Ala  Gly Glu Leu Cys Ile  Ala Gly Val Gly Leu  Ala Arg Gly
    5960                 5965                 5970

Tyr Trp  Asn Arg Pro Glu Leu  Thr Ala Glu Lys Phe  Val Thr Ile
    5975                 5980                 5985

Pro Ser  Val Gly Glu Arg Met  Tyr Arg Thr Gly Asp  Leu Ala Arg
    5990                 5995                 6000

Trp Leu  Pro Asp Gly Asn Ile  Glu Tyr Leu Gly Arg  Ile Asp His
    6005                 6010                 6015

Gln Val  Lys Ile Arg Gly Tyr  Arg Ile Glu Leu Gly  Glu Leu Glu
    6020                 6025                 6030

Ser Ala  Leu Leu Asn Val Gln  Glu Ile Arg Glu Thr  Val Val Val
    6035                 6040                 6045

Ala Arg  Glu Glu Glu Asp Gly  Gln Lys Ser Leu Cys  Ala Tyr Tyr
    6050                 6055                 6060

Val Ala  Asp Gly Asp Pro Thr  Ala Gly Asp Leu Arg  Ala Ala Leu
    6065                 6070                 6075

Ala Ala  Glu Leu Pro Ser Tyr  Met Ile Pro Ser Tyr  Phe Ile Arg
    6080                 6085                 6090

Leu Glu  Gln Met Pro Leu Ala  Pro Asn Gly Lys Leu  Asp Arg Lys
    6095                 6100                 6105

Ala Leu  Pro Ala Pro Lys Asp  Val Ile Arg Thr Gly  Thr Asp Arg
```

```
    6110                6115                6120

Ile Ala  Pro Arg Thr Ala Leu  Glu Val Lys Leu Val  Arg Ile Trp
    6125                6130                6135

Gln Glu  Val Leu Gly Leu Asp  Gln Ile Gly Val Lys  Asp Asp Phe
    6140                6145                6150

Phe Glu  Leu Gly Gly His Ser  Leu Arg Ala Thr Ala  Leu Ala Ser
    6155                6160                6165

Lys Val  Ser Lys Glu Met His  Val Ala Leu Pro Leu  Arg Asp Ile
    6170                6175                6180

Phe His  Tyr Ser Thr Leu Glu  Ala Met Ala Gln Ala  Ile Gly Glu
    6185                6190                6195

Leu Glu  Lys Gln Glu His Arg  Ala Ile Pro Ile Ala  Pro Met Ala
    6200                6205                6210

Glu His  Tyr Gln Leu Ala Ser  Ala Gln Lys Arg Leu  Tyr Ile Leu
    6215                6220                6225

His Gln  Ala Glu Gly Ala Gln  Gln Ser Tyr Asn Met  Pro Gly Ala
    6230                6235                6240

Met Ser  Val Ser Gly His Ile  Asp Arg Asn Arg Leu  Glu Ala Ala
    6245                6250                6255

Leu Leu  Gln Leu Ile Ala Arg  His Asp Thr Leu Arg  Thr Ser Phe
    6260                6265                6270

Glu Met  Val Asp Gly Glu Pro  Val Gln Arg Val His  Gln His Val
    6275                6280                6285

Asp Phe  Ala Leu Glu Tyr Ser  Thr Ala Arg Glu Lys  Asp Ile Asp
    6290                6295                6300

Gln Val  Ala Glu Gln Phe Val  Arg Asp Phe Asp Leu  Glu Gln Pro
    6305                6310                6315

Pro Leu  Leu Arg Val Gly Leu  Val Gln Leu Glu Gln  Glu Glu Gln
    6320                6325                6330

His Leu  Leu Leu Leu Asp Met  His His Ile Ile Ser  Asp Gly Ile
    6335                6340                6345

Ser Met  Asp Ile Leu Val Asp  Glu Leu Ala Arg Leu  Tyr Asp Gly
    6350                6355                6360

Glu Glu  Leu Pro Pro Leu Glu  Ile Gln Tyr Lys Asp  Tyr Val Leu
    6365                6370                6375

Trp Gln  Gln Ala Glu Ala Ser  Ser Glu Gln Met Lys  Glu His Glu
    6380                6385                6390

Glu Tyr  Trp Leu Arg Thr Leu  Gly Asn Glu Leu Pro  Leu Leu Glu
    6395                6400                6405

Leu Pro  Thr Glu Phe Ala Arg  Gly Glu Gln Arg Ser  Tyr Asp Gly
    6410                6415                6420

Asp Lys  Leu His Phe Ala Ile  Asp Gly Gln Leu Asn  Glu Lys Leu
    6425                6430                6435

Gln Arg  Leu Ala Ser Gln Ser  Gly Ala Thr Leu Tyr  Met Val Leu
    6440                6445                6450

Leu Ala  Ala Tyr Thr Thr Leu  Leu His Lys Tyr Ser  Gly Gln Asn
    6455                6460                6465

Asp Leu  Val Val Gly Thr Pro  Ile Ala Gly Arg Thr  His Val Asp
    6470                6475                6480

Val Glu  Pro Leu Ile Gly Met  Phe Val Asn Ser Leu  Ala Ile Arg
    6485                6490                6495

Asn Tyr  Pro Asn Asp Asp Lys  Thr Phe Arg Ser Tyr  Leu Glu Glu
    6500                6505                6510
```

Val Lys Glu Ser Thr Leu Ser Ala Phe Glu His Gln Asp Tyr Pro
    6515                6520                6525

Phe Asp Lys Leu Val Glu Gln Leu Glu Asp Ala Trp Val Pro Gly
    6530                6535                6540

Arg Asn Pro Val Phe Asp Thr Met Phe Val Leu Gln Asn Ala Lys
    6545                6550                6555

Ala Arg Thr Ile Asn Leu Arg Glu Leu Ala Phe Glu Pro Leu Ile
    6560                6565                6570

Pro Ser His Thr Val Ala Lys Phe Asp Leu Thr Leu Glu Met Ala
    6575                6580                6585

Ile Glu Asp Gly Met Leu Ser Gly Gln Phe Glu Tyr Cys Thr Lys
    6590                6595                6600

Leu Phe Ser Ala Asn Met Ile Ala Asn Phe Ala Glu Asp Phe Leu
    6605                6610                6615

Glu Ile Leu Ser Gln Ala Cys Glu Gln Pro Asp Leu Arg Leu Glu
    6620                6625                6630

Asp Ile Gln Leu Ser Gly Ser Ala Asn Gln Glu Glu Glu Leu Glu
    6635                6640                6645

Glu Glu Ile Asp Phe Ala Phe
    6650                6655

<210> SEQ ID NO 15
<211> LENGTH: 6428
<212> TYPE: PRT
<213> ORGANISM: Paenibacillus alvei TS-15

<400> SEQUENCE: 15

Met Ala Phe Asp Lys Glu Ile Glu Phe Trp Lys Ala Lys Leu Asp Thr
1               5                   10                  15

Glu Asp Thr Pro Thr Thr Leu Pro Tyr Thr Asn Ile Ser Ser Ser Glu
            20                  25                  30

Ala Ala Arg His Tyr Ser Val Ser Val Thr Met Pro Ala Glu Ile Thr
        35                  40                  45

Glu Arg Ile Ile Arg Met Ser Lys Gly Ser His Gln Ala Ala Phe Met
    50                  55                  60

Ile Leu Leu Gly Gly Ile Gln Cys Leu Leu His Lys Tyr Thr Ser Glu
65                  70                  75                  80

Asn Cys Ile Val Ile Gly Met Pro Ile Val Gln Lys Ala Gly Glu Lys
                85                  90                  95

Arg Leu Pro Ile Asn Gln Val Val Leu Leu Lys Glu Asn Val Asn Glu
            100                 105                 110

Glu Leu Thr Phe Lys Ser Leu Leu Thr Ser Leu Lys Gln Ser Phe Thr
        115                 120                 125

Glu Ala Ile Arg His Gln Asn Ile Pro Phe Arg Leu Ile Thr Glu Gln
    130                 135                 140

Met Asn Val Gln Glu Lys Asn Gly Leu Pro Val Ile Asn Thr Met Ala
145                 150                 155                 160

Ala Leu Lys Asn Ile His Thr Val Asn Phe Ile Pro Thr Val Val Ala
                165                 170                 175

Asp Val Leu Phe Gln Phe Glu Phe Glu Ala Glu Asn Leu Leu Leu Ser
            180                 185                 190

Val Val Tyr Asn Glu Arg Val Tyr Asp Ser Val Phe Ile Ser Gln Ile
        195                 200                 205

Ile Glu His Leu Gln Arg Val Leu Ser Ile Val Leu Leu Glu Pro Asn

-continued

```
    210                 215                 220

Thr Asn Leu Gly Asn Leu Arg Leu Leu Ser Asp Glu Glu Thr Ser Leu
225                 230                 235                 240

Leu Leu His Gly Phe Asn Ala Thr Ala Ala Glu Tyr Pro Arg Asp Arg
                245                 250                 255

Thr Ile His Glu Leu Phe Thr Glu Gln Ala Arg Arg Thr Pro Asp Ala
            260                 265                 270

Val Ala Ala Val Leu Gly Gln Gln Gln Leu Thr Tyr Ala Glu Leu Asn
        275                 280                 285

Gly Arg Ala Asn Arg Leu Ala Arg Thr Leu Gln Asn Ala Gly Val Arg
    290                 295                 300

Thr Asp Gln Leu Val Gly Ile Met Ala Glu Arg Ser Leu Glu Met Ile
305                 310                 315                 320

Val Gly Leu Leu Ala Ile Met Lys Ala Gly Gly Ala Tyr Val Pro Ile
                325                 330                 335

Asp Pro Glu Tyr Pro Gln Glu Arg Ile Arg Tyr Met Leu Glu Asp Ser
            340                 345                 350

Gly Ala Gln Met Leu Leu Leu Gln Asp His Leu Arg Glu Arg Val Ser
        355                 360                 365

Tyr Glu Gly Thr Ile Val Asp Met Asn Ser Glu His Asn Tyr His Asp
    370                 375                 380

Asp Glu Thr Glu Leu Ala Ser Val Ser Asp Ser Ser Asn Leu Ala Tyr
385                 390                 395                 400

Val Ile Tyr Thr Ser Gly Thr Thr Gly Asn Pro Lys Gly Val Met Ile
                405                 410                 415

Glu His Arg Ser Ala Val Asn Ala Leu Leu Trp Arg Ile Arg Thr Tyr
            420                 425                 430

Gly Leu Ser Ser Ser Asp Arg Val Leu Gln Leu Phe Ser Phe Ser Phe
        435                 440                 445

Asp Gly Phe Val Met Ser Ala Phe Cys Ser Leu Leu Ser Gly Ala Gly
    450                 455                 460

Leu Phe Leu Leu Lys Glu Glu Asp Ala Lys Asp Pro Leu Ala Leu His
465                 470                 475                 480

Gly Ala Ile Ser Gln Ser Gly Ile Thr His Phe Ile Cys Val Pro Asn
                485                 490                 495

Leu Tyr Gly Ala Leu Leu Asn Val Met Gln Ala Glu Ser Val Ser Thr
            500                 505                 510

Leu Arg Thr Val Thr Leu Ala Gly Glu Ser Val Ser Ser Ala Leu Val
        515                 520                 525

Ala Arg Ser Gln Glu Gln Leu Pro Asp Val Lys Leu Phe Asn Glu Tyr
    530                 535                 540

Gly Pro Thr Glu Asn Ser Val Val Ala Thr Cys Ala Ile Gly Leu Glu
545                 550                 555                 560

Lys Asp Gln Pro Ile Thr Ile Gly Thr Pro Ile Ser Asn Ala Ser Val
                565                 570                 575

Leu Ile Leu Asn Thr Ser Gly Glu Leu Gln Pro Leu His Val Pro Gly
            580                 585                 590

Glu Leu Cys Ile Ala Gly Glu Gly Leu Ala Arg Gly Tyr Leu Asn Arg
        595                 600                 605

Pro Glu Leu Thr Glu Glu Lys Phe Ala Ala His Pro Phe Val Pro Gly
    610                 615                 620

Glu Arg Ile Tyr His Thr Gly Asp Ser Ala Arg Trp Leu Pro Asn Gly
625                 630                 635                 640
```

```
Thr Ile Glu Tyr Leu Gly Arg Ile Asp His Gln Val Lys Ile Arg Gly
                645                 650                 655

Phe Arg Ile Glu Leu Gly Glu Ile Glu Ser Ser Leu Lys Asn Val Ala
            660                 665                 670

Gly Val Arg Glu Val Ile Val Asp Ala Arg Pro Asp Gly Asn Gly Gln
        675                 680                 685

Gln Met Leu Cys Ala Tyr Met Val Ala Asp Ser Val Leu Thr Val Asn
    690                 695                 700

Glu Leu Arg Glu Ala Leu Ser Ser His Leu Pro Asp Tyr Met Ile Pro
705                 710                 715                 720

Ser His Phe Val Gln Met Glu Gln Leu Pro Leu Thr Pro Ser Gly Lys
                725                 730                 735

Leu Asp Arg Lys Ser Leu Pro Asp Pro Gln Ala Asn Ile Ala Ile Gly
            740                 745                 750

Thr Glu Tyr Ile Ala Pro Arg Thr Pro Leu Glu Ala Arg Leu Ala Gln
        755                 760                 765

Ile Trp Gln Glu Ser Leu Gly Val Glu Lys Val Gly Ile Lys Asp Asn
    770                 775                 780

Phe Phe Ala Leu Gly Gly His Ser Leu Arg Ala Ala Thr Leu Ala Ser
785                 790                 795                 800

Lys Leu His Lys Glu Leu Asn Val Asn Val Pro Leu Arg Asp Leu Phe
                805                 810                 815

Arg Asn Pro Thr Ile Glu Glu Leu Ala Leu Leu Met Glu Gly Met Glu
            820                 825                 830

Gln Gln Glu Phe Ser Ala Ile Glu Arg Val Lys Glu Arg Glu Tyr Tyr
        835                 840                 845

Ser Val Ser Ser Ala Gln Lys Arg Leu Phe Val Leu Gln Gln Leu Glu
    850                 855                 860

Gly Ala Glu Gln Ser Tyr Asn Met Pro Gly Ala Met Leu Leu Glu Gly
865                 870                 875                 880

Leu Leu Asp Arg Glu Arg Leu Glu Ala Ser Phe Arg Lys Leu Ile Ala
                885                 890                 895

Arg His Glu Thr Leu Arg Thr Gly Phe Glu Leu Met Asp Gly Glu Pro
            900                 905                 910

Val Gln Lys Val Tyr Gln Asn Val Ser Phe Ala Ile Glu Tyr Met Gln
        915                 920                 925

Ala Ser Glu Glu Glu Ala Ala Gln Lys Ala Arg Glu Phe Ile Arg Ala
    930                 935                 940

Phe Asp Leu Met Thr Pro Pro Leu Leu Arg Val Gly Leu Ile Glu Met
945                 950                 955                 960

Ala Pro Asp Arg His Val Leu Leu Tyr Asp Met His His Ile Ile Ser
                965                 970                 975

Asp Gly Ala Ser Met Gly Val Val Val Glu Glu Phe Ala Arg Leu Tyr
            980                 985                 990

Gly Gly Glu Glu Leu Pro Ser Leu  Arg Ile Gln Tyr Lys  Asp Phe Ala
        995                 1000                 1005

Ala Trp  Gln Gln Ser Glu Val  Gln Gln Lys Arg Ser  Met Gln Gln
    1010                 1015                 1020

Glu Ala  Tyr Trp Leu Gln Ala  Phe Gly Gly Glu Leu  Pro Val Leu
    1025                 1030                 1035

Glu Leu  Pro Thr Asp Asn Ala  Arg Pro Ala Ile Gln  Ser Tyr Glu
    1040                 1045                 1050
```

```
Gly Glu  Thr Tyr Glu Phe Thr  Val Asp Ser Asp Ile  Ser Thr Ala
    1055                 1060                 1065

Leu Gln  Arg Leu Ala Ala Asp  Ser Gly Thr Thr Leu  Tyr Met Val
    1070                 1075                 1080

Leu Leu  Ala Ala Tyr Thr Val  Leu Leu His Lys Tyr  Thr Gly Gln
    1085                 1090                 1095

Glu Asp  Ile Val Val Gly Thr  Thr Asn Ala Gly Arg  Met His Asp
    1100                 1105                 1110

Asp Leu  Gln Pro Leu Ile Gly  Met Phe Val Asn Thr  Leu Ala Ile
    1115                 1120                 1125

Arg Asn  Tyr Pro Ala Gly Glu  Ser Thr Phe Arg Ala  Tyr Leu Glu
    1130                 1135                 1140

Gln Val  Lys Glu Gln Ala Leu  Ala Ala Phe Glu His  Gln Glu Tyr
    1145                 1150                 1155

Pro Phe  Glu Glu Leu Val Glu  Lys Leu Arg Val Ala  Arg Asp Met
    1160                 1165                 1170

Ser Arg  Asn Pro Leu Phe Asp  Thr Met Phe Ser Leu  Gln Asn Met
    1175                 1180                 1185

Glu Asn  Lys Asp Phe Glu Leu  Pro Gly Leu Gln Leu  Lys Pro Tyr
    1190                 1195                 1200

Gly Phe  Glu His Gln Ile Ser  Lys Phe Asp Leu Ser  Leu Asp Val
    1205                 1210                 1215

Ala Glu  Gly Ala Asp Gly Leu  Ala Cys Ser Leu Glu  Tyr Ala Ser
    1220                 1225                 1230

Ser Leu  Tyr Arg Gln Asp Thr  Ile Val Arg Met Ala  Asn His Tyr
    1235                 1240                 1245

Arg Gln  Leu Leu His Ser Ile  Ala Gln Ser Pro Glu  Ala Gln Ile
    1250                 1255                 1260

Ala Val  Leu Gly Met Leu Thr  Pro Gly Glu Gln Glu  Gln Ile Arg
    1265                 1270                 1275

Phe Lys  Phe Asn His Asp Pro  Ser Asp Met Glu Gln  Lys His Thr
    1280                 1285                 1290

Val His  Gln Leu Phe Glu Glu  Gln Ala Ala Leu Thr  Pro Glu Arg
    1295                 1300                 1305

Thr Ala  Val Val His Glu Asn  Glu Gln Leu Ser Tyr  Gln Glu Leu
    1310                 1315                 1320

Asn Glu  Arg Ala Asn Arg Leu  Ala Arg Thr Leu Arg  Gln His Gly
    1325                 1330                 1335

Val Gln  Pro Glu Gln Leu Val  Gly Ile Leu Ala Asp  Arg Ser Leu
    1340                 1345                 1350

Asp Met  Ile Val Gly Ile Met  Ala Ile Leu Lys Ala  Gly Gly Ala
    1355                 1360                 1365

Tyr Val  Pro Ile Asp Pro Lys  Tyr Pro Glu Glu Arg  Ile Arg Tyr
    1370                 1375                 1380

Met Leu  Glu Asp Ser Lys Ala  Asn Val Leu Val Thr  Gln Ser His
    1385                 1390                 1395

Leu Gln  Ser Leu Ser Ser Phe  Asp Gly Thr Trp Val  Leu Leu Asp
    1400                 1405                 1410

Glu Glu  Ser Ser Tyr Ala Glu  Asp Ala Ala Asn Leu  Val Ser Ile
    1415                 1420                 1425

Asn Glu  Pro Gln His Leu Ala  Tyr Val Ile Tyr Thr  Ser Gly Thr
    1430                 1435                 1440

Thr Gly  Gln Pro Lys Gly Ala  Met Ile Glu His Arg  Gln Leu Thr
```

```
    1445                1450                1455

Val Met  Ala Lys Ala Trp Glu  Arg Glu Tyr Arg Leu  Arg Glu Glu
    1460                1465                1470

Ser Ile  Arg Trp Met Gln Trp  Ala Ser Phe Ser Phe  Asp Val Phe
    1475                1480                1485

Ser Gly  Asp Leu Ile Arg Ala  Leu Leu His Gly Gly  Glu Leu Val
    1490                1495                1500

Leu Cys  Pro Glu His Ala Arg  Ala Asn Pro Ala Glu  Ile Tyr Glu
    1505                1510                1515

Leu Ile  Arg Lys His Arg Leu  His Met Phe Asp Cys  Thr Pro Ser
    1520                1525                1530

Ile Val  Ile Pro Leu Met Glu  Tyr Val Tyr Glu Asn  Lys Leu Asp
    1535                1540                1545

Ile Ser  Ser Leu Lys Leu Val  Ala Val Gly Ser Asp  Tyr Cys Pro
    1550                1555                1560

Pro Asp  Glu Phe Gln Lys Met  Leu Asp Arg Phe Gly  Ser Gln Phe
    1565                1570                1575

Arg Ile  Ile Asn Ser Tyr Gly  Val Thr Glu Thr Cys  Ile Asp Ala
    1580                1585                1590

Ser Tyr  Tyr Glu Pro Thr Thr  Pro Thr Val Pro Arg  Ala Leu Pro
    1595                1600                1605

Ile Gly  Lys Pro Leu Pro Gly  Val Thr Met Tyr Ile  Met Asp Gly
    1610                1615                1620

Gln Arg  Ser Leu Leu Pro Val  Gly Val Ile Gly Glu  Leu Tyr Ile
    1625                1630                1635

Gly Gly  Pro Cys Val Gly Arg  Gly Tyr Trp Asn Arg  Ser Glu Met
    1640                1645                1650

Thr Ser  Glu Lys Phe Val Ala  Asp Pro Phe Leu Gln  Asp His Arg
    1655                1660                1665

Met Tyr  Arg Thr Gly Asp Leu  Ala Arg Trp Met Pro  Asp Gly Asn
    1670                1675                1680

Ile Glu  Tyr Leu Gly Arg Ile  Asp His Gln Val Lys  Ile Arg Gly
    1685                1690                1695

Tyr Arg  Ile Glu Ile Gly Glu  Val Glu Ser Lys Leu  Leu Lys Val
    1700                1705                1710

Glu Thr  Val Arg Glu Ser Val  Val Val Ala Arg Gln  Asp Pro Asn
    1715                1720                1725

Gly Thr  Lys Ala Leu Cys Ala  Tyr Phe Val Ala Asp  Arg Asn Leu
    1730                1735                1740

Thr Val  Ser Glu Leu Arg Ser  Ala Met Ala Asp Glu  Leu Pro Ala
    1745                1750                1755

Tyr Met  Ile Pro Ser Tyr Phe  Val Gln Leu Asp Arg  Leu Pro Leu
    1760                1765                1770

Thr Pro  Asn Gly Lys Val Asp  Arg Lys Ala Leu Pro  Ala Pro Glu
    1775                1780                1785

Ala Gly  Ala His Thr Gly Ile  Glu Tyr Met Ala Pro  Arg Thr Glu
    1790                1795                1800

Glu Glu  Leu Ala Leu Ala Asn  Val Trp Gln Thr Val  Leu Gly Ile
    1805                1810                1815

Glu Arg  Val Gly Val Leu Asp  His Phe Phe Glu Leu  Gly Gly Asp
    1820                1825                1830

Ser Ile  Lys Ser Ile Gln Val  Ala Ser Arg Leu Gln  Gln Ala Gly
    1835                1840                1845
```

```
Tyr Lys  Leu Glu Ile Arg Asp  Leu Phe Lys Tyr Pro  Thr Ile Ala
    1850                 1855                 1860

Gln Leu  Gly Ser His Leu Gln  Arg Ala Ser Lys Val  Ala Asp Gln
    1865                 1870                 1875

Gly Glu  Val Ser Gly Asp Val  Pro Leu Thr Pro Ile  Leu Gly Trp
    1880                 1885                 1890

Phe Phe  Glu Gln Gln Phe Ala  Asp Ala His His Tyr  Asn Gln Ser
    1895                 1900                 1905

Ile Met  Leu Tyr Arg Arg Glu  Gly Phe Asn Glu Ala  Ala Ile Arg
    1910                 1915                 1920

Asn Val  Leu Gln Ala Val Thr  Glu His His Asp Ala  Leu Arg Ile
    1925                 1930                 1935

Val Phe  Arg Arg Asn Asp Gln  Gly Asp Tyr Thr Ala  Trp Asn Arg
    1940                 1945                 1950

Ala Ile  Glu Glu Gly Glu Leu  Phe His Leu Glu Val  Leu Asn Leu
    1955                 1960                 1965

Thr Gly  Thr Thr Ala Gly Asp  His Glu Gln Asn Val  Arg Gln Ile
    1970                 1975                 1980

Ile Glu  Ala Lys Ala Thr Glu  Ile Gln Arg Ser Phe  Asp Leu His
    1985                 1990                 1995

Asp Gly  Pro Leu Ala Arg Ala  Gly Leu Phe Arg Thr  Asp Glu Gly
    2000                 2005                 2010

Asp His  Leu Leu Leu Val Met  His His Gly Val Val  Asp Gly Val
    2015                 2020                 2025

Ser Trp  Arg Ile Leu Leu Glu  Asp Ile Ala Thr Gly  Tyr Glu Gln
    2030                 2035                 2040

Ala Leu  Lys Gly Glu Pro Val  Arg Leu Pro Ala Lys  Thr Asp Ser
    2045                 2050                 2055

Phe Arg  Thr Trp Ala Asn Gln  Leu Ala Ser Tyr Ala  Arg Ser Glu
    2060                 2065                 2070

Ala Met  Ile Glu Glu Gln Ile  Phe Trp Glu Gln Ala  Glu Ala Asn
    2075                 2080                 2085

Gly Thr  Ser Ile Leu Ser Leu  Pro Lys Asp Phe Glu  Ala Glu Thr
    2090                 2095                 2100

Ser Leu  Gln Gln Asp Ser Glu  Ser Val Val Val Glu  Trp Ser Arg
    2105                 2110                 2115

Glu Glu  Thr Asp Met Leu Leu  Lys His Val His Arg  Ala Tyr Asn
    2120                 2125                 2130

Thr Asp  Met Asn Asp Ile Leu  Leu Ala Ala Leu Gly  Met Ala Ile
    2135                 2140                 2145

Gln Gln  Trp Cys Gly His Glu  Lys Ala Leu Val Thr  Leu Glu Gly
    2150                 2155                 2160

His Gly  Arg Glu Asn Ile Met  Pro Glu Leu Asp Ile  Ser Arg Thr
    2165                 2170                 2175

Val Gly  Trp Phe Thr Ser Glu  Tyr Pro Phe Leu Leu  Glu Ser Asp
    2180                 2185                 2190

Pro Asn  Lys Ser Leu Ser Tyr  Arg Ile Lys Arg Met  Lys Glu Asn
    2195                 2200                 2205

Leu Arg  Arg Ile Pro Asn Lys  Gly Ile Gly Tyr Gly  Ile His Arg
    2210                 2215                 2220

Tyr Leu  Ser Gly Ser Gly Thr  Ser Gly Thr Lys Asn  Val Ser Arg
    2225                 2230                 2235
```

-continued

Ser Glu Ala Ser Ala Gln Pro Glu Ile Ser Phe Asn Tyr Leu Gly
2240 2245 2250

Gln Phe Asp Gln Asp Leu Gln Asn Asn Glu Met Glu Val Ser Pro
2255 2260 2265

Tyr Ser Gly Gly Ala Glu Ile Ser Val Arg Gln Ala Arg Asn Thr
2270 2275 2280

Thr Leu Asp Phe Asn Gly Met Ile Ser Ala Gly Val Leu Ala Leu
2285 2290 2295

Glu Val Ser Tyr Ser Ser Lys Gln Tyr Arg Arg Asp Thr Ile Asp
2300 2305 2310

Arg Leu Ala Gly Leu Leu Lys Gly Ser Leu Gln Glu Ile Val Ala
2315 2320 2325

Tyr Cys Ala Ser Lys Asp Lys Pro Glu Leu Thr Pro Ser Asp Val
2330 2335 2340

Leu Val Asn Gly Leu Gly Ile Glu Asp Leu Glu Arg Ile Ala Glu
2345 2350 2355

Gln Thr Arg Asp Leu Gly Asp Ile Glu Asn Ile Tyr Ala Leu Thr
2360 2365 2370

Pro Met Gln Lys Gly Met Trp Phe His Asn Ala Met Asp Gly Gln
2375 2380 2385

Ala Gly Ala Tyr Phe Glu Gln Thr Arg Phe Thr Ile Gln Gly Glu
2390 2395 2400

Leu Asp Val Gln Leu Phe Ala Ser Ser Leu Asp Val Leu Ala Thr
2405 2410 2415

Arg His Ala Val Leu Arg Thr Asn Phe Phe Ser Gly Trp Asn Gly
2420 2425 2430

Glu Leu Leu Gln Ile Val Tyr Arg Asn Lys Asn Leu Glu Phe Ser
2435 2440 2445

Tyr Glu Asp Leu Ser Glu Leu Pro Glu His Glu Lys Gln Asp Arg
2450 2455 2460

Val Glu Ala Met Ala Gln Ala Asp Lys Gln Arg Gly Phe Asp Leu
2465 2470 2475

Glu Arg Asp Ala Leu Met Arg Val Phe Val Leu Arg Thr Ser Leu
2480 2485 2490

Asn Cys Ser His Val Ile Trp Ser Ser His His Ile Leu Met Asp
2495 2500 2505

Gly Trp Cys Leu Pro Gln Leu Thr Gln Glu Trp Leu Glu Thr Tyr
2510 2515 2520

Ser Asp Ser Val Asn Gly Arg Ser Ser Ser Arg Ser Gly Ala Ser
2525 2530 2535

Pro Tyr Ser Leu Tyr Ile Glu Trp Leu Tyr Lys Gln Asn Tyr Thr
2540 2545 2550

Ala Ala Ser Gln Tyr Trp Ser Asp Tyr Leu Ser Asp Tyr Asp Gln
2555 2560 2565

Gln Thr Val Leu Pro Gln Lys Lys Ser Ser Gly Arg Ser Asp Val
2570 2575 2580

Tyr Ile Ala Asp Asn Leu Val Phe Glu Leu Gly Glu Ala Leu Thr
2585 2590 2595

Ala Lys Met His Arg Val Ala Lys Gln His Gln Leu Thr Leu Asn
2600 2605 2610

Thr Leu Met Gln Ala Ala Trp Gly Ile Ile Leu Gln Lys Tyr Asn
2615 2620 2625

Asn Thr Gly Asp Ala Val Phe Gly Gly Val Val Ser Gly Arg Pro

```
    2630                2635                2640

Ala Glu  Ile Pro Gly Ile Glu  Ser Met Ile Gly Leu  Phe Ile Asn
    2645                2650                2655

Thr Ile  Pro Ile Arg Val Val  Cys Glu Ala Asp Asp  Arg Phe Ala
    2660                2665                2670

Asp Val  Met Lys Gln Leu Gln  Glu Lys Ala Leu Glu  Ser Gly Arg
    2675                2680                2685

Tyr Asp  Tyr Tyr Pro Leu Tyr  Asp Ile Gln Ala Leu  Ser Thr His
    2690                2695                2700

Lys Gln  Asp Leu Ile Asn His  Ile Leu Val Phe Glu  Asn Tyr Pro
    2705                2710                2715

Met Glu  Glu Gln Met Glu Gln  Ala Gly Asp Glu Arg  Gly Gln Leu
    2720                2725                2730

Asn Ile  Thr Asp Val Arg Val  Ala Glu Gln Thr Ser  Tyr Asp Phe
    2735                2740                2745

Asn Leu  Val Val Met Pro Gly  Glu Asp Met Met Ile  Arg Leu Glu
    2750                2755                2760

Tyr Asn  Ala Val Met Tyr Asp  Arg Ala Asp Met Glu  Arg Ile Arg
    2765                2770                2775

Gln His  Leu Ile His Val Leu  Lys Gln Val Thr Ala  Asp Pro Ala
    2780                2785                2790

Ile Ala  Val Lys Asp Val Arg  Leu Ala Thr Asp Asp  Glu Lys Ala
    2795                2800                2805

Glu Leu  Leu Thr Ala Phe Asn  Asp Thr Glu Val Glu  Tyr Pro Arg
    2810                2815                2820

Glu Gln  Met Ile His Arg Met  Phe Glu Glu Gln Val  Gln Arg Thr
    2825                2830                2835

Pro Asp  Ala Thr Ala Val Leu  Cys Gly Ala Ala Thr  Met Thr Tyr
    2840                2845                2850

Arg Glu  Met Asn Glu Arg Ala  Asn Gln Leu Ala Arg  Thr Leu Arg
    2855                2860                2865

Ala Ala  Gly Val Val Pro Asp  Gln Ile Val Gly Ile  Met Ala Glu
    2870                2875                2880

Arg Ser  Leu Glu Leu Met Val  Gly Ile Met Gly Ile  Leu Lys Ala
    2885                2890                2895

Gly Gly  Ala Tyr Val Pro Ile  Ala Pro Asp Tyr Pro  Glu Glu Arg
    2900                2905                2910

Ile Arg  Tyr Met Leu Asp Asp  Ser Glu Ala Gln Val  Leu Ile Val
    2915                2920                2925

Gln Gly  Ser Ala Gly Glu Ala  Ile Asp Phe Ala Gly  His Val Ile
    2930                2935                2940

Asn Leu  Asp Asp Val Asp Ser  Tyr Asp Gln Asp Ser  Ser Asn Leu
    2945                2950                2955

Glu Met  Val Asn Lys Pro Thr  Asp Ile Ala Tyr Ile  Ile Tyr Thr
    2960                2965                2970

Ser Gly  Thr Thr Gly Arg Pro  Lys Gly Val Met Val  Glu His Thr
    2975                2980                2985

Ser Val  Ile Asn Arg Leu Leu  Trp Met Gln Lys Arg  Tyr Pro Ile
    2990                2995                3000

Asp Ala  Asp Asp Thr Ile Met  Gln Lys Thr Ala Ile  Thr Phe Asp
    3005                3010                3015

Val Ser  Val Trp Glu Leu Phe  Trp Trp Ala Phe Val  Gly Ser Lys
    3020                3025                3030
```

```
Val Leu Met Leu Pro Val Gly Gly Glu Lys Asn Pro Ala Ala Ile
    3035                3040                3045

Val Glu Ala Ile Glu Gln Tyr Asp Ile Ser Thr Met His Phe Val
    3050                3055                3060

Pro Ser Met Leu His Ala Phe Leu Glu His Ile Glu Gln Leu Pro
    3065                3070                3075

Glu Ala Glu Arg Glu Arg Leu Ser Pro Leu Lys Gln Val Phe Thr
    3080                3085                3090

Ser Gly Glu Ala Leu Leu Ala Ser Gln Val Glu Arg Phe His Gln
    3095                3100                3105

Tyr Val Ala Pro Ala Ser Gly Ala Arg Leu Ile Asn Leu Tyr Gly
    3110                3115                3120

Pro Thr Glu Ala Thr Val Asp Val Thr Tyr Phe Asp Cys Glu Pro
    3125                3130                3135

Gly Gln Thr Tyr Val Ser Val Pro Ile Gly Lys Pro Ile Asp Asn
    3140                3145                3150

Thr Arg Ile Tyr Ile Val Asn Gly Asn Asn Gln Val Gln Pro Ile
    3155                3160                3165

Gly Val Ala Gly Glu Leu Cys Ile Ala Gly Val Gly Leu Ala Arg
    3170                3175                3180

Gly Tyr Trp Asn Arg Pro Glu Leu Thr Glu Glu Lys Phe Val Leu
    3185                3190                3195

Val Pro Ser Val Gly Glu Arg Met Tyr Arg Thr Gly Asp Leu Ala
    3200                3205                3210

Arg Trp Leu Pro Asp Gly Asn Ile Glu Tyr Leu Gly Arg Ile Asp
    3215                3220                3225

His Gln Val Lys Ile Arg Gly Tyr Arg Ile Glu Leu Gly Glu Leu
    3230                3235                3240

Glu Thr Ala Leu Leu Lys Ile Asp Ala Val Arg Glu Thr Val Val
    3245                3250                3255

Val Ala Arg Glu Asp Glu Ser Gly Gln Lys Ser Leu Cys Ala Tyr
    3260                3265                3270

Tyr Val Ala Asp Gly Glu Ala Thr Val Ser Asp Leu Arg Ala Ala
    3275                3280                3285

Leu Ala Ala Glu Leu Pro Ser Tyr Met Ile Pro Ser Tyr Phe Val
    3290                3295                3300

Arg Leu Glu Gln Met Pro Leu Ala Pro Asn Gly Lys Leu Asp Arg
    3305                3310                3315

Lys Ala Leu Pro Ala Pro Glu Arg Ser Leu Gln Val Glu Ser Glu
    3320                3325                3330

Tyr Val Ala Pro Arg Thr Glu Ala Glu Gln Met Leu Ala Thr Val
    3335                3340                3345

Trp Gln Ala Val Leu Gly Ile Glu Arg Val Gly Ile Thr Asp His
    3350                3355                3360

Phe Phe Glu Leu Gly Gly Asp Ser Ile Lys Ser Ile Gln Val Ala
    3365                3370                3375

Ala Arg Met Gln Gln Ala Gly Phe Lys Leu Asp Ile Arg Asp Leu
    3380                3385                3390

Phe Lys Tyr Ser Thr Val Thr Gln Leu Val Pro Tyr Met Gln Pro
    3395                3400                3405

Ile Asn Arg Thr Ala Asp Gln Gly Glu Val Val Gly Glu Val Pro
    3410                3415                3420
```

```
Met Thr  Pro Ile Leu His Trp  Phe Glu His Gln Gln  Phe Ala Asn
    3425                 3430                 3435

Pro His  His Phe Asn Gln Ser  Val Met Leu Tyr Arg  Lys Asp Gly
    3440                 3445                 3450

Phe Val  Ala Asp Ala Val Arg  Lys Ala Leu His Lys  Leu Val Glu
    3455                 3460                 3465

His His  Asp Ala Leu Arg Ile  Val Ile Gln Arg Thr  Glu Gln Gly
    3470                 3475                 3480

Glu Tyr  Ser Leu Trp Asn Arg  Ser Leu Val Glu Gly  Glu Leu Phe
    3485                 3490                 3495

Ser Met  Gly Glu Ile Asp Leu  Thr Asp Gln Ser Asp  Phe Ala Ala
    3500                 3505                 3510

Ala Ile  Glu Ala Glu Ala Asn  His Ile Gln Gly Ser  Ile Asp Leu
    3515                 3520                 3525

Gln Ala  Gly Pro Leu Val Lys  Ala Gly Leu Phe His  Gly Ser Asp
    3530                 3535                 3540

Gly Asp  His Leu Leu Leu Val  Ile His His Ala Val  Ile Asp Gly
    3545                 3550                 3555

Val Ser  Trp Arg Ile Leu Leu  Glu Asp Leu Ala Ala  Gly Tyr Glu
    3560                 3565                 3570

Gln Ala  Leu Asn Gln Arg Gln  Val Arg Leu Pro Met  Lys Thr Asp
    3575                 3580                 3585

Ser Phe  Arg Thr Trp Ala Glu  Gln Leu Val Glu Tyr  Ala Asn Ser
    3590                 3595                 3600

Pro Ala  Met Asp Lys Glu Ser  Ala Tyr Trp Leu Ser  Val Ala Gln
    3605                 3610                 3615

Thr Glu  Val Ala Ala Leu Pro  Lys Asp Ser Glu Cys  Thr Val Ser
    3620                 3625                 3630

Leu Gln  Arg Asp Ser Glu Ser  Val Val Leu Glu Trp  Asn Lys Glu
    3635                 3640                 3645

Asp Thr  Glu Arg Leu Leu Lys  His Val His Arg Ala  Tyr Asn Thr
    3650                 3655                 3660

Glu Met  Asp Asp Ile Leu Leu  Thr Ala Leu Gly Arg  Ala Leu Met
    3665                 3670                 3675

Lys Trp  Arg Gly Ile Asp Arg  Val Leu Val Thr Leu  Glu Gly His
    3680                 3685                 3690

Gly Arg  Glu Ser Ile Leu Gln  Asp Met Asp Ile Thr  Arg Thr Val
    3695                 3700                 3705

Gly Trp  Phe Thr Thr Glu Tyr  Pro Phe Glu Leu Gly  Met Glu Ala
    3710                 3715                 3720

Asn Asp  Ser Leu Gly Ser Gln  Ile Lys Lys Val Lys  Glu Asp Leu
    3725                 3730                 3735

Arg Arg  Ile Pro Asn Lys Gly  Ile Gly Tyr Gly Leu  Phe Arg Tyr
    3740                 3745                 3750

Leu Ser  Asn Ser Gly Lys Gln  Ala Trp Asn Asp Ala  Pro Thr Thr
    3755                 3760                 3765

Gln Ile  Arg Tyr Asn Tyr Leu  Gly Gln Phe Asp Ala  Asp Leu Ser
    3770                 3775                 3780

Asn Asn  Glu Leu Ser Val Ser  Pro Tyr Ala Ser Gly  Ser Glu Ile
    3785                 3790                 3795

Ser Asp  Glu Gln Glu Arg Lys  Tyr Pro Leu Asp Ile  Asn Gly Val
    3800                 3805                 3810

Ile Ala  Glu Gly Gln Leu Thr  Leu Gly Leu Ser Tyr  Ser Val Lys
```

```
    3815                3820                3825

Glu Tyr  His Lys Glu Thr Met  Glu Glu Leu Gly Asp  Leu Leu Thr
    3830                3835                3840

Glu Ser  Leu Lys Glu Ile Ile  Ala His Cys Glu Ser  Gln Glu Arg
    3845                3850                3855

Thr Gln  Leu Thr Pro Ser Asp  Val Leu Phe Lys Gly  Leu Ser Leu
    3860                3865                3870

Glu Trp  Leu Asp Arg Ile Ser  Ser Gln Met Gln His  Ile Gly Glu
    3875                3880                3885

Ile Glu  Asn Val Tyr Ala Leu  Thr Pro Met Gln Lys  Gly Met Trp
    3890                3895                3900

Phe His  Ser Ala Met Asp Ser  Leu Thr Gly Ala Tyr  His Glu Gln
    3905                3910                3915

Thr Met  Phe Thr Leu Glu Gly  Thr Leu Asp Val Glu  Leu Phe Ser
    3920                3925                3930

Ser Ser  Leu Asn Glu Leu Ala  Lys Arg His Ala Val  Leu Arg Thr
    3935                3940                3945

Asn Phe  Ile Ser Gly Pro Gln  Gly Glu Pro Val Gln  Val Val Phe
    3950                3955                3960

Arg Asn  Lys Pro Ile Gly Phe  Ser Phe Gln Asp Val  Arg Ala Leu
    3965                3970                3975

Asn Glu  Glu Glu Gln Gln Ser  Phe Ile Lys Glu Ala  Val Ser Ser
    3980                3985                3990

Asp Gln  Leu Leu Gly Phe Asp  Leu Ala Gln Gly Ala  Leu Met Arg
    3995                4000                4005

Val Ser  Ala Ile Arg Thr Gly  Glu Leu Ser Cys Arg  Val Leu Trp
    4010                4015                4020

Ser Ser  His His Ile Leu Met  Asp Gly Trp Cys Leu  Pro Gln Leu
    4025                4030                4035

Met Gln  Glu Leu Phe Asp Thr  Tyr Ala Ala Leu Leu  Gln Lys Lys
    4040                4045                4050

Ser Pro  Asp Arg Thr Val Val  Pro Ala Tyr Ser Gln  Tyr Ile Glu
    4055                4060                4065

Trp Leu  Gly Gln Gln Asp Glu  Glu Ala Ala Gly Thr  Tyr Trp Ser
    4070                4075                4080

Ala Tyr  Leu Ala Asp Tyr Asp  Gln Val Thr Glu Ile  Pro Gln Glu
    4085                4090                4095

Ser Ser  Ala Gly Ile Asp Ser  Glu Pro Tyr Lys Ala  Glu Lys Trp
    4100                4105                4110

Ser Arg  Glu Leu Asp Ala Gly  Leu Ser Ala Ser Ile  Ser Arg Ala
    4115                4120                4125

Ala Arg  Gln His Gln Val Thr  Leu Asn Thr Leu Leu  Gln Ala Ala
    4130                4135                4140

Trp Gly  Val Ile Leu Gln Lys  Tyr Asn Gly Thr Asn  Asp Val Val
    4145                4150                4155

Phe Gly  Ser Val Val Ser Gly  Arg Pro Ala Glu Val  Pro Gly Ile
    4160                4165                4170

Glu Thr  Met Ile Gly Leu Phe  Ile Asn Thr Ile Pro  Ile Arg Val
    4175                4180                4185

Lys Cys  Glu Gly Ser Thr Ser  Phe Ala Glu Leu Met  Gly Leu Leu
    4190                4195                4200

Gln Glu  Gln Ala Leu Glu Ser  Gly Lys Tyr Asp Tyr  Tyr Pro Leu
    4205                4210                4215
```

```
Tyr Glu  Ile Gln Ser Arg Ser  Ala Leu Lys Gln Asn  Ala Ile Arg
    4220                 4225                 4230

Gln Ile  Met Val Phe Glu Asn  Tyr Pro Met Asp Glu  Gln Leu Glu
    4235                 4240                 4245

Gln Ala  Gly Gly Asp Glu His  Gly Met Pro Ser Leu  Thr Asp Val
    4250                 4255                 4260

Ala Val  Glu Glu Gln Thr Asn  Tyr Asp Phe Asn Leu  Ile Val Val
    4265                 4270                 4275

Pro Gly  Glu Gln Ile Ser Ile  Arg Phe Asp Tyr Asn  Ala Asn Arg
    4280                 4285                 4290

Phe Val  Gln Ala Asp Met Glu  Arg Leu Met Gly His  Leu Asn Asn
    4295                 4300                 4305

Ile Leu  Glu Gln Ile Val Asp  Asn Pro Arg Val Ala  Val Glu Asp
    4310                 4315                 4320

Leu Glu  Leu Ala Thr Glu Ala  Glu Lys Ser Glu Val  Ile Gln Ser
    4325                 4330                 4335

Phe Asn  Asp Thr Leu Thr Asn  Tyr Pro Arg Asp Met  Met Leu His
    4340                 4345                 4350

Arg Leu  Phe Glu Glu Gln Ala  Glu Arg His Pro Asp  Ala Val Ala
    4355                 4360                 4365

Ile Ser  Phe Arg Asp Val Gln  Met Thr Tyr Arg Asp  Leu Asn Asp
    4370                 4375                 4380

Arg Ala  Asn Arg Leu Ala Arg  Thr Leu Arg Ala Val  Gly Val Gly
    4385                 4390                 4395

Thr Asp  Lys Leu Val Gly Leu  Met Ser Glu Arg Ser  Pro Asp Met
    4400                 4405                 4410

Ile Ile  Gly Ile Leu Ala Ile  Leu Lys Ala Gly Gly  Gly Tyr Val
    4415                 4420                 4425

Pro Ile  Asp Pro Glu Tyr Pro  Glu Glu Arg Ile Arg  Tyr Met Leu
    4430                 4435                 4440

Glu Asp  Ser Gly Ala Arg Ile  Met Leu Ala Gln Gln  His Leu Thr
    4445                 4450                 4455

Gly Lys  Ile Pro Ala Met Asp  Ala Ser Pro Leu Asp  Ala Ile Ile
    4460                 4465                 4470

Asn Leu  Asp Thr Glu Thr Ser  Tyr Asp Ser Asn Gly  Ser Asn Leu
    4475                 4480                 4485

Glu Ala  Asn Thr Asp Ala Ser  Ser Glu Asn Leu Ala  Tyr Val Ile
    4490                 4495                 4500

Tyr Thr  Ser Gly Thr Thr Gly  Lys Pro Lys Gly Asn  Leu Thr Thr
    4505                 4510                 4515

His Arg  Asn Ile Val Arg Val  Val Arg Glu Thr Glu  Tyr Ile Asp
    4520                 4525                 4530

Ile Thr  Asn His Asp Asn Val  Leu Gln Met Ser Ser  Tyr Ala Phe
    4535                 4540                 4545

Asp Gly  Ser Thr Phe Asp Ile  Tyr Gly Ala Leu Leu  Asn Gly Ala
    4550                 4555                 4560

Lys Leu  Val Leu Val Pro His  Glu Thr Leu Leu Glu  Val Arg Gln
    4565                 4570                 4575

Leu Ala  Glu Leu Ile Val Gln  Glu Lys Ile Ser Val  Met Phe Ile
    4580                 4585                 4590

Thr Thr  Ala Tyr Phe Asn Val  Leu Val Asp Val Gln  Ala Ser Cys
    4595                 4600                 4605
```

-continued

```
Leu Ser  Asn Ile Arg Ala Ile  Leu Phe Gly Gly Glu  Arg Val Ser
    4610                 4615                 4620

Val Ser  His Val Arg Lys Ala  Leu Asn His Val Ala  Pro Gly Thr
    4625                 4630                 4635

Leu Lys  His Val Tyr Gly Pro  Thr Glu Ser Thr Val  Phe Ala Thr
    4640                 4645                 4650

Cys His  Asp Val Tyr Glu Val  Thr Glu Asn Ala Val  Thr Val Pro
    4655                 4660                 4665

Ile Gly  Arg Pro Ile Ser Asn  Thr Ser Ile Tyr Ile  Val Asp Ala
    4670                 4675                 4680

Asn Asn  Lys Leu Gln Pro Val  Gly Val Ala Gly Glu  Leu Cys Val
    4685                 4690                 4695

Ala Gly  Asp Gly Leu Ala Arg  Gly Tyr Leu Asn Arg  Pro Asp Leu
    4700                 4705                 4710

Thr Ala  Glu Lys Phe Val Asp  Ser Pro Tyr Val Gln  Gly Glu Arg
    4715                 4720                 4725

Met Tyr  Arg Thr Gly Asp Leu  Ala Lys Trp Leu Pro  Asp Gly Ser
    4730                 4735                 4740

Ile Glu  Tyr Val Gly Arg Ile  Asp Gln Gln Val Lys  Ile Arg Gly
    4745                 4750                 4755

Tyr Arg  Ile Glu Leu Gly Glu  Ile Glu Ala Gln Leu  Leu Asn Val
    4760                 4765                 4770

Glu Asp  Val Gln Glu Ala Val  Val Val Ala Arg Asp  Asn Asp Thr
    4775                 4780                 4785

Gly Glu  Lys Gln Leu Cys Ala  Tyr Tyr Val Ala Met  Arg Pro Leu
    4790                 4795                 4800

Glu Ala  Asn His Leu Arg Glu  Val Met Gly Gln Ala  Met Pro Ser
    4805                 4810                 4815

Tyr Met  Leu Pro Ala His Phe  Val Gln Leu Glu Gln  Leu Pro Leu
    4820                 4825                 4830

Thr Pro  Asn Gly Lys Val Asp  Arg Lys Ala Leu Pro  Ala Pro Glu
    4835                 4840                 4845

Glu Gly  Arg Ser Gly Glu Thr  Phe Val Ala Pro Arg  Thr Pro Leu
    4850                 4855                 4860

Glu Ala  Gln Leu Val Gln Ile  Trp Gln Asp Val Leu  Gly Ile Ser
    4865                 4870                 4875

Ser Val  Ser Val Thr Ala His  Phe Phe Glu Leu Gly  Gly His Ser
    4880                 4885                 4890

Leu Lys  Ala Thr Leu Leu Val  Asn Arg Leu His Gln  Glu Leu Asn
    4895                 4900                 4905

Ile Glu  Leu Pro Leu Lys Asp  Val Phe Gln Tyr Pro  Thr Leu Glu
    4910                 4915                 4920

Ala Met  Ala Lys Arg Leu Ser  Asn Ala Glu Gly Ser  Arg His Val
    4925                 4930                 4935

Ser Ile  Pro Val Ala Ala Pro  Ser Gln His Tyr Pro  Val Ser Ser
    4940                 4945                 4950

Ala Gln  Lys Arg Leu Tyr Ile  Leu His Gln Leu Glu  Gly Ala Glu
    4955                 4960                 4965

Leu Ser  Tyr Asn Met Pro Asn  Met Leu Leu Leu Glu  Gly Ala Val
    4970                 4975                 4980

Asp Leu  Gly Arg Leu Glu Glu  Ala Phe Lys Arg Leu  Ile Glu Arg
    4985                 4990                 4995

His Glu  Thr Leu Arg Thr Gly  Phe Glu Ile Val Asn  Gly Glu Pro
```

```
    5000                5005                5010

Val Gln  Arg Ile Tyr Pro Glu  Val Asp Phe Ala Ile  Glu His Val
    5015                5020                5025

Leu Ala  Ser Glu Glu Gly Ala  Ser Lys Leu Met Gln  Gln Phe Val
    5030                5035                5040

Arg Ser  Phe Gln Leu Glu Lys  Pro Pro Leu Leu Arg  Ile Gly Val
    5045                5050                5055

Ile Glu  Leu Ser Glu Glu Arg  Ser Ile Leu Met Phe  Asp Met His
    5060                5065                5070

His Ile  Ile Ser Asp Gly Ser  Ser Met Gly Ile Leu  Ile Asn Glu
    5075                5080                5085

Phe Val  His Leu Tyr Ser Gly  Glu Glu Leu Thr Pro  Leu Arg Ile
    5090                5095                5100

Gln Tyr  Lys Asp Tyr Ala Val  Trp Gln Gln Ser Asp  Thr Gln Gln
    5105                5110                5115

Glu Ala  Met Lys Leu Gln Glu  Gly Tyr Trp Leu Lys  Val Leu Gly
    5120                5125                5130

Gly Glu  Leu Pro Val Leu Glu  Met Pro Thr Asp Ser  Ile Arg Pro
    5135                5140                5145

Thr Thr  Gln Ser Phe Arg Gly  Asp Leu Leu Gln Phe  Asp Leu Asp
    5150                5155                5160

Pro Val  Arg Ser Ala Gly Leu  Arg Arg Ile Ala Ala  Glu Asn Gly
    5165                5170                5175

Ala Thr  Met Tyr Met Val Leu  Leu Ala Leu Tyr Lys  Thr Met Leu
    5180                5185                5190

His Lys  Tyr Ser Gly Gln Glu  Asp Ile Ile Val Gly  Thr Pro Ile
    5195                5200                5205

Ala Gly  Arg Asn His Gly Asp  Leu Gln Pro Leu Leu  Gly Met Phe
    5210                5215                5220

Val Asn  Thr Leu Ala Ile Arg  Ser Tyr Pro Ala Ala  Ser Lys Thr
    5225                5230                5235

Phe Leu  Ser Tyr Leu Gly Glu  Ile Lys Glu Ser Thr  Leu Gly Ala
    5240                5245                5250

Phe Glu  Asn Gln Asn Tyr Pro  Phe Glu Ala Leu Val  Glu Gln Val
    5255                5260                5265

Gln Val  Met Arg Asp Met Ser  Arg Asn Pro Val Phe  Asp Thr Met
    5270                5275                5280

Phe Ile  Leu Gln Asn Ala Asp  Gln Gly Glu Met Lys  Ile Asp Gly
    5285                5290                5295

Leu Arg  Leu Gln Ser Val Pro  Asn Glu His Thr Val  Ser Lys Phe
    5300                5305                5310

Asp Leu  Thr Phe Gln Ala Glu  Glu Asp Glu Ala Glu  Ile Val Cys
    5315                5320                5325

Ser Ile  Glu Tyr Ala Thr Asp  Leu Phe Lys Arg Gly  Thr Ile Glu
    5330                5335                5340

Arg Met  Ala Arg His Phe Glu  Gln Leu Val His Thr  Val Leu Asp
    5345                5350                5355

Asn Pro  Gln Ala Ser Leu Ser  Asn Leu Ser Met Val  Thr Asn Glu
    5360                5365                5370

Glu Lys  Ala Leu Leu Gln Asp  Lys Phe Asn Asp Thr  Asp Met Ala
    5375                5380                5385

His Pro  Ser Asp Lys Thr Val  His Glu Leu Phe Ala  Glu Gln Val
    5390                5395                5400
```

```
Glu Arg  Thr Pro Asp Ala Val  Ala Val Val Ser Gly  Ser Glu Gln
    5405                 5410                 5415

Leu Ser  Tyr Gly Asp Leu Asn  Arg Lys Ala Asn Gln  Leu Ala Trp
    5420                 5425                 5430

Lys Leu  Arg Glu Tyr Gly Val  Thr Ala Glu Gln Pro  Val Gly Ile
    5435                 5440                 5445

Ile Val  Glu Arg Thr Leu Asp  Thr Val Val Ala Val  Leu Ala Val
    5450                 5455                 5460

Leu Lys  Ala Ser Gly Thr Phe  Val Pro Ile Asp Pro  Glu Tyr Pro
    5465                 5470                 5475

Glu Thr  Arg Ile Arg Tyr Met  Leu Ala Asp Ser Gly  Ala Lys Leu
    5480                 5485                 5490

Val Leu  Ala Gln Ser Glu Leu  Ser Gly Ile Ile Pro  Asp Asp Val
    5495                 5500                 5505

Arg Leu  Ile Asp Val Arg Asp  Glu Ser Leu Tyr Gln  Gly Asp Gly
    5510                 5515                 5520

Ala Asp  Val Pro Asn Gly Ser  Lys Pro Ser Asn Leu  Leu Tyr Ile
    5525                 5530                 5535

Ile Tyr  Thr Ser Gly Thr Thr  Gly Asn Pro Lys Gly  Val Met Leu
    5540                 5545                 5550

Glu His  Arg Asn Met Val Asn  Leu Leu His Tyr Gln  Gln Lys Gly
    5555                 5560                 5565

Thr Asn  Ile Pro Met Pro Ser  Arg Ile Leu Gln Tyr  Ala Ser Gly
    5570                 5575                 5580

Ser Phe  Asp Val Cys Tyr Gln  Glu Met Phe Ser Ala  Leu Leu Phe
    5585                 5590                 5595

Gly Gly  Ser Leu Tyr Met Val  Asp Asn Glu Met Arg  Lys Asp Pro
    5600                 5605                 5610

Val Arg  Leu Phe Gln Glu Ile  Glu Lys His Glu Ile  Asp Val Met
    5615                 5620                 5625

Tyr Ile  Pro Val Ala Phe Leu  Lys Phe Ile Phe Ala  Glu Pro Glu
    5630                 5635                 5640

Trp Ala  Glu Ala Phe Pro Arg  Cys Val Arg His Ile  Ile Thr Ala
    5645                 5650                 5655

Gly Glu  Gln Leu Val Val Thr  Pro Gln Val Gln Ala  Cys Leu Lys
    5660                 5665                 5670

Arg Leu  Asp Ile Cys Leu His  Asn His Tyr Gly Pro  Ser Glu Thr
    5675                 5680                 5685

His Val  Val Thr Thr Tyr Thr  Met Thr Pro Glu Val  Ile Glu Val
    5690                 5695                 5700

Gly Leu  Pro Pro Ile Gly Lys  Pro Ile Ala Asn Thr  Ser Ile Tyr
    5705                 5710                 5715

Ile Val  Asn Asp Ser Phe Glu  Leu Gln Pro Ile Gly  Val Lys Gly
    5720                 5725                 5730

Glu Leu  Tyr Val Ser Gly Ala  Cys Val Gly Arg Gly  Tyr Trp Gly
    5735                 5740                 5745

Arg Thr  Asp Leu Thr Glu Glu  Lys Phe Leu Asp Asn  Pro Phe Ala
    5750                 5755                 5760

Pro Gly  Glu Arg Leu Tyr Lys  Thr Gly Asp Val Ala  Arg Trp Leu
    5765                 5770                 5775

Pro Asp  Gly Ser Ile Glu Tyr  Val Gly Arg Ser Asp  His Gln Val
    5780                 5785                 5790
```

-continued

```
Lys Ile  Arg Gly Phe Arg Ile  Glu Leu Gly Glu Val  Glu Ser Gln
    5795                 5800                 5805

Leu Leu  His Val Pro Ala Val  Gln Glu Ala Thr Val  Val Ala Leu
    5810                 5815                 5820

Glu Asp  His Ala Gly Gln Lys  Gln Leu Cys Ala Tyr  Phe Thr Ala
    5825                 5830                 5835

Glu Cys  Ser Leu Thr Ala Gly  Glu Leu Arg Ala Ala  Leu Ser Gln
    5840                 5845                 5850

Glu Leu  Pro Gly Tyr Met Ile  Pro Ser Tyr Phe Val  Gln Leu Glu
    5855                 5860                 5865

Arg Leu  Pro Leu Thr Pro Asn  Gly Lys Ile Asp Arg  Arg Ala Leu
    5870                 5875                 5880

Pro Lys  Pro Glu Gly Gly Ile  Glu Thr Gly Thr Glu  Tyr Val Ala
    5885                 5890                 5895

Pro Arg  Thr Glu Thr Glu Ala  Arg Leu Ala Arg Ile  Trp Gln Asp
    5900                 5905                 5910

Val Leu  Gly Leu Ala Ser Val  Gly Val Lys Asp Asn  Phe Phe Glu
    5915                 5920                 5925

Leu Gly  Gly His Ser Leu Arg  Ala Thr Thr Leu Val  Ser Arg Leu
    5930                 5935                 5940

Tyr Lys  Glu Met Asn Val Asn  Phe Pro Leu Arg Gly  Val Phe Arg
    5945                 5950                 5955

His Pro  Thr Ile Glu Glu Met  Ser Gln Ala Ile Ser  Gln Met Glu
    5960                 5965                 5970

Thr Ser  Leu Tyr Thr Ala Ile  Pro Ile Ala Glu Glu  Gln Glu Tyr
    5975                 5980                 5985

Tyr Pro  Leu Ser Ser Ala Gln  Leu Arg Leu Tyr Ile  Met Ser Gln
    5990                 5995                 6000

Leu Glu  Gly Ser Glu Leu Ser  Tyr Asn Met Pro Gly  Met Leu Val
    6005                 6010                 6015

Leu Glu  Gly Gln Leu Asn Arg  Asp Gln Phe Gln Thr  Ala Phe Leu
    6020                 6025                 6030

Lys Leu  Ile Ala Arg His Glu  Thr Leu Arg Thr Gly  Phe Glu Met
    6035                 6040                 6045

Val Asp  Gly Glu Pro Met Gln  Arg Ile His Arg Asn  Thr Glu Phe
    6050                 6055                 6060

Ala Ile  Asp Tyr Arg Gln Val  Ser Glu Asp Glu Val  Pro Glu Ile
    6065                 6070                 6075

Ile Gly  Gln Phe Ile Arg Pro  Phe Asp Leu Glu His  Pro Pro Leu
    6080                 6085                 6090

Leu Arg  Val Gly Leu Phe Glu  Val Gly Gln Asp Arg  His Ile Leu
    6095                 6100                 6105

Val Phe  Asp Met His His Ile  Ile Ser Asp Gly Ala  Ser Met Ser
    6110                 6115                 6120

Asn Leu  Val Asp Glu Phe Thr  Arg Leu Tyr Ala Asn  Glu Glu Arg
    6125                 6130                 6135

Pro Pro  Leu Arg Ile Gln Tyr  Lys Asp Tyr Ala Val  Trp Gln Gln
    6140                 6145                 6150

Ala Ser  Glu Asn Leu Glu Arg  Leu Lys Arg Gln Glu  Asp Tyr Trp
    6155                 6160                 6165

Met Ser  Met Leu Gln Gly Asp  Leu Pro Asn Thr Glu  Leu Pro Leu
    6170                 6175                 6180

Asp Tyr  Asp Arg Ala Ala Val  Arg Ser Phe Glu Gly  Glu Gln Ile
```

```
    6185                6190                6195

Glu Phe  Glu Ile Asn Pro Val  Val Thr Gly Gln Leu  Asn Gln Leu
    6200                6205                6210

Ala Ser  Asn His Glu Cys Thr  Leu Tyr Met Val Leu  Leu Ser Ala
    6215                6220                6225

Tyr Gln  Ile Leu Leu Ser Lys  Tyr Cys Gly Gln Asp  Asp Ile Ile
    6230                6235                6240

Val Gly  Thr Pro Val Ala Gly  Arg Asn His Ala Asp  Leu Glu Pro
    6245                6250                6255

Leu Ile  Gly Met Phe Val Asn  Thr Leu Ala Ile Arg  Asn Arg Pro
    6260                6265                6270

Gln Gly  Asp Lys Thr Phe Gln  Ser Phe Leu Ala Glu  Val Lys Glu
    6275                6280                6285

Ser Thr  Leu Gly Ala Phe Glu  His Gln Glu Tyr Pro  Phe Glu Glu
    6290                6295                6300

Leu Ile  Asp Leu Leu Lys Leu  Gln Trp Glu Thr Ser  Arg Asn Pro
    6305                6310                6315

Leu Phe  Asp Thr Val Phe Val  Leu Gln Asn Thr Glu  Glu Arg Glu
    6320                6325                6330

Ala Gly  Ile Gly Gly Leu Thr  Ile Ser Pro Tyr Val  Thr Asp Asp
    6335                6340                6345

Ser Val  Ser Ala Lys Phe Asp  Leu Thr Leu Ser Val  Ser Glu Glu
    6350                6355                6360

Asp Asp  Gly Met Lys Gly Ser  Phe Leu Tyr Ala Ser  Lys Leu Phe
    6365                6370                6375

Lys Ala  Ala Gly Ile His Arg  Met Met Arg Asp Tyr  Leu Ser Ile
    6380                6385                6390

Leu Ser  Gln Val Cys Glu Asn  Pro Arg Ile Arg Ile  Gln Asp Ile
    6395                6400                6405

Ser Ile  Ser Gly Gln Gln Thr  Gln Glu Lys Ser Lys  Ile Asp Thr
    6410                6415                6420

Ile Glu  Phe Ala Phe
    6425


<210> SEQ ID NO 16
<211> LENGTH: 3167
<212> TYPE: PRT
<213> ORGANISM: Paenibacillus alvei TS-15

<400> SEQUENCE: 16

Met Lys Ser Val Tyr Glu Lys Glu Glu Ala Tyr Trp Asn Gly Met Phe
1               5                   10                  15

Asp Ser Asp Asp Ser Met Ser Ile Leu Pro Tyr Cys Ser Thr His Gly
            20                  25                  30

Arg Glu Ala Asn Ala Asp Thr Asn Ala Ala Lys Val Ser Met Ile Arg
        35                  40                  45

Ala Leu Pro Ser Glu Leu Ser Asp Arg Met Asn Thr Leu Ala Asn Gly
    50                  55                  60

Ser Asp Ile Ala Leu Tyr Met Ile Gly Leu Ala Gly Ala Thr Cys Leu
65                  70                  75                  80

Leu His His Tyr Thr Asn Arg Glu Asn Val Leu Val Gly Met Pro Thr
                85                  90                  95

Ile Asp Glu Ser Asp Asp Asp Ser Ser Pro Arg Asp Val Leu Ile Met
            100                 105                 110
```

-continued

```
Lys Thr Asn Leu Thr Arg Gly Ser Ser Phe Arg Ser Val Leu Gly Ser
        115                 120                 125

Ile Lys Thr Ala Val Gly Gly Ala Val Glu His Arg His Leu Pro Phe
    130                 135                 140

Arg Lys Met Val His Asn Leu Asn Leu Glu Met Asp Thr Asn Gly Leu
145                 150                 155                 160

Pro Val Met Asn Thr Val Val Ser Tyr Ser Ala Ile His Thr Ala Ser
                165                 170                 175

Ile Asp Leu Ser Val Ser Ser Asp Val Met Phe Arg Phe Asp Ala Lys
            180                 185                 190

Asp Asp Gly Leu His Leu Glu Val Leu Tyr Asp Glu Ser Arg Tyr Asp
        195                 200                 205

Ala Ser Tyr Ile Ala Thr Leu Phe Glu His Phe Phe Arg Leu Leu His
    210                 215                 220

Phe Val Leu Phe Gln Pro Asp Gln Pro Ile Gly Asn Ala Val Leu Leu
225                 230                 235                 240

Ser Glu Asp Glu Lys His Arg Leu Leu His Glu Phe Asn Asp Val Trp
                245                 250                 255

Thr Asp Phe Pro Arg Gln Ala Thr Leu His Gln Phe Ile Glu Glu His
            260                 265                 270

Ala Glu Arg Gln Pro Glu Ala Ile Ala Val Ser Tyr Glu Asp Thr Lys
        275                 280                 285

Leu Thr Tyr Arg Glu Leu Asn Ala Arg Ala Asn Arg Leu Ala Arg Thr
    290                 295                 300

Leu Arg Ser Glu Gly Val Gln Pro Glu Ala Leu Val Gly Leu Met Ala
305                 310                 315                 320

Glu Arg Ser Ile Asp Met Ile Val Gly Met Leu Ala Val Leu Lys Ala
                325                 330                 335

Gly Gly Gly Tyr Val Ala Ile Asp Pro Glu Tyr Pro Glu Glu Arg Val
            340                 345                 350

Arg Tyr Met Leu Glu Asp Ser Gly Ala Arg Val Ile Leu Val Gln Gln
        355                 360                 365

His Leu Gln Asn Arg Val Pro Asn Thr Glu Ser Ala Ala Arg Leu Leu
    370                 375                 380

Thr Leu Asp Asp Glu Gln Ser Tyr His Glu Asp Ala Ser Lys Leu Glu
385                 390                 395                 400

Ser Lys Ser Thr Ala Val Asp Leu Ala Cys Val Ile Tyr Thr Ser Gly
                405                 410                 415

Thr Thr Gly Asn Pro Lys Gly Asn Leu Thr Thr His Arg Asn Ile Val
            420                 425                 430

Arg Ile Val Lys Asn Thr Asn Tyr Ile Glu Ile Thr Glu Gln Asp Lys
        435                 440                 445

Val Leu Gln Leu Ser Ser Tyr Ser Phe Asp Gly Ser Ala Phe Asp Ile
    450                 455                 460

Phe Gly Ala Leu Thr Asn Gly Ala Gln Leu Val Leu Val Pro His His
465                 470                 475                 480

Thr Leu Leu Asp Ala Ser Lys Leu Ala Glu Leu Ile Glu Thr Glu Gln
                485                 490                 495

Ile Ser Val Met Leu Ile Thr Thr Ala Tyr Phe Asn Val Leu Val Asp
            500                 505                 510

Val Asn Val Ser Cys Leu Arg His Ile Arg Ala Ile Leu Phe Gly Gly
        515                 520                 525

Glu Arg Ser Ser Val Ala His Val Arg Gln Ala Leu Glu Gln Thr Gly
```

-continued

```
    530                 535                 540

Pro Gly Arg Leu Lys His Ala Tyr Gly Pro Ser Glu Ser Thr Val Tyr
545                 550                 555                 560

Ala Thr Trp His Asp Val Thr Glu Ile Ser Glu Gln Ala Val Ser Val
                565                 570                 575

Pro Ile Gly Arg Pro Ile Ser Asn Thr Ala Ile Tyr Ile Val Asn Glu
            580                 585                 590

Arg Asn Asp Leu Gln Pro Ile Gly Val Ser Gly Glu Leu Cys Val Ala
        595                 600                 605

Gly Glu Gly Leu Val Arg Gly Tyr Leu Asn Arg Pro Glu Leu Thr Ala
    610                 615                 620

Gln Lys Phe Val Asp Asn Pro Phe Val Pro Gly Glu Arg Met Tyr Arg
625                 630                 635                 640

Thr Gly Asp Leu Ala Arg Trp Leu Pro Asp Gly Thr Ile Glu Tyr Val
                645                 650                 655

Gly Arg Met Asp Asp Gln Val Lys Ile Arg Gly His Arg Ile Glu Ile
            660                 665                 670

Gly Glu Val Glu Ala Gln Leu Leu Lys Val Ala Leu Ile Gln Lys Ala
        675                 680                 685

Thr Ile Val Val Arg Gly Arg Glu Asp Gly Glu Lys Gln Leu Cys Ala
    690                 695                 700

Tyr Tyr Val Ala Asp Arg Leu Leu Ser Ala Gly Glu Ile Arg Thr Ile
705                 710                 715                 720

Leu Ala Lys Glu Leu Pro Ser Tyr Met Ile Pro Ala Tyr Phe Ile Gln
                725                 730                 735

Leu Glu Gln Met Pro Leu Thr Thr Asn Gly Lys Val Asp Arg Lys Ala
            740                 745                 750

Leu Pro Ala Pro Glu Glu His Val Gln Ala Glu Thr Glu Tyr Val Ala
        755                 760                 765

Pro Arg Ser Glu Gln Glu Ile Arg Leu Ala Arg Val Trp Gln Glu Val
    770                 775                 780

Leu Gly Leu Ser Arg Val Gly Ala Lys Asp His Phe Phe Glu Leu Gly
785                 790                 795                 800

Gly His Ser Leu Arg Ala Thr Thr Leu Val Ser Lys Leu His Lys Glu
                805                 810                 815

Glu Asn Ile Ser Leu Ser Leu Arg Asp Val Phe Arg Asn Pro Thr Leu
            820                 825                 830

Glu Ala Met Ala Ala Leu Met Glu Ala Ala Gln Gly Arg Thr Phe Ser
        835                 840                 845

Pro Ile Pro Thr Val Glu Glu Lys Asp Val Tyr Pro Val Ser Ser Val
    850                 855                 860

Gln Lys Arg Leu Phe Ile Leu His Gln Leu Glu Gly Ala Glu Gln Ser
865                 870                 875                 880

Tyr Asn Met Pro Gly Ala Leu Leu Leu Glu Gly Asp Val Asp Arg Asn
                885                 890                 895

Arg Leu Glu His Ala Phe Arg Gln Leu Ile Thr Arg His Glu Thr Leu
            900                 905                 910

Arg Thr Gly Phe Glu Met Val Asn Gly Glu Pro Val Gln Arg Ile Tyr
        915                 920                 925

Pro Thr Val Glu Phe Val Val Glu Glu Met Ser Ala Val Glu Gly Ala
    930                 935                 940

Glu Ala Glu Lys Gln Ile Arg Gln Phe Ile Arg Ala Phe Asp Leu Ser
945                 950                 955                 960
```

-continued

```
Thr Pro Pro Leu Phe Arg Ala Gly Leu Ile Glu Leu Ala Pro Gln Arg
                965                 970                 975

His Ile Leu Leu Phe Asp Met His His Ile Ile Ser Asp Gly Thr Ser
            980                 985                 990

Ile Gly Ile Met Ile Glu Glu Phe  Thr Ser Leu Tyr Ser  Gly Asn Glu
        995                 1000                 1005

Leu Glu  Pro Leu Arg Ile Gln  Tyr Lys Asp Phe Ala  Ala Trp Gln
    1010                 1015                 1020

Arg Ser  Glu Glu Gln Ile Glu  Gln Leu Lys Ser Gln  Glu Ala Tyr
    1025                 1030                 1035

Trp Leu  Arg Gln Met Glu Gly  Val Leu Pro Val Leu  Glu Leu Pro
    1040                 1045                 1050

Thr Asp  Tyr Val Arg Pro Ala  Val Gln Ser His Asp  Gly Ala Leu
    1055                 1060                 1065

Phe Glu  Phe Ser Ile Asp Arg  Glu Gln Ser Gln Asp  Leu Arg Asn
    1070                 1075                 1080

Leu Ala  Ala Asp Thr Arg Thr  Thr Leu Tyr Met Val  Leu Leu Ala
    1085                 1090                 1095

Ala Tyr  Thr Ile Ile Leu His  Lys Tyr Ser Gly Gln  Glu Asp Ile
    1100                 1105                 1110

Val Val  Gly Thr Pro Ile Ala  Gly Arg Thr His Asp  Asp Val Gln
    1115                 1120                 1125

Pro Leu  Ile Gly Met Phe Val  Asn Thr Leu Ala Ile  Arg Asn Tyr
    1130                 1135                 1140

Pro Ser  Gly Ser Lys Ser Val  Leu Thr Tyr Leu Glu  Glu Ile Lys
    1145                 1150                 1155

Glu Thr  Thr Leu Gly Ala Phe  Glu His Gln Asp Tyr  Pro Phe Glu
    1160                 1165                 1170

Glu Leu  Val Glu Asn Val Gln  Ile Ser Arg Asp Met  Ser Arg His
    1175                 1180                 1185

Pro Val  Phe Asp Thr Met Phe  Ala Leu Glu Asn Thr  Glu His Arg
    1190                 1195                 1200

Glu Phe  Asp Leu Asp Gly Leu  Gln Val Lys Pro Tyr  Gly Ala Glu
    1205                 1210                 1215

His Gly  Met Ala Lys Phe Asp  Leu Asn Leu Thr Ile  Thr Glu Asp
    1220                 1225                 1230

Gly Asp  Gly Leu Tyr Cys Thr  Met Glu Tyr Ala Thr  Ala Leu Tyr
    1235                 1240                 1245

Asn Arg  Ser Thr Ile Ala Arg  Leu Cys Gly His Phe  Leu Gln Val
    1250                 1255                 1260

Val Gly  Ser Met Thr His Asn  Pro Gln Ala Ala Ile  Ser Ser Leu
    1265                 1270                 1275

Gln Met  Val Thr Ile Glu Glu  Lys Ala Glu Leu Gln  Asp Glu Phe
    1280                 1285                 1290

Asn Asp  Thr Asp Met Val Tyr  Pro Ser Asp Lys Thr  Val His Glu
    1295                 1300                 1305

Leu Phe  Ala Glu Gln Val Glu  Arg Thr Pro Asp Ala  Val Ala Val
    1310                 1315                 1320

Val Ser  Gly Ser Glu Gln Leu  Ser Tyr Gly Asp Leu  Asn Arg Lys
    1325                 1330                 1335

Ala Asn  Gln Leu Ala Trp Lys  Leu Arg Glu Tyr Gly  Val Thr Ala
    1340                 1345                 1350
```

Glu Gln Pro Val Gly Ile Ile Val Glu Arg Thr Leu Asp Thr Val
1355 1360 1365

Val Ala Val Leu Ala Val Leu Lys Ala Ser Gly Thr Phe Val Pro
1370 1375 1380

Ile Asp Pro Glu Tyr Pro Glu Thr Arg Ile Arg Tyr Met Leu Ala
1385 1390 1395

Asp Ser Gly Ala Lys Leu Val Leu Ala Gln Ser Asp Leu Pro Gly
1400 1405 1410

Ile Ile Pro Asp Asp Val Arg Leu Ile Asp Val Arg Asp Glu Ser
1415 1420 1425

Leu Tyr Gln Gly Asp Gly Ala Asp Val Pro Asn Gly Ser Lys Pro
1430 1435 1440

Ser Asn Leu Leu Tyr Ile Ile Tyr Thr Ser Gly Thr Thr Gly Asn
1445 1450 1455

Pro Lys Gly Val Met Leu Glu His Arg Asn Met Val Asn Leu Leu
1460 1465 1470

His Tyr Gln Gln Lys Gly Thr Asn Ile Pro Met Pro Ser Arg Ile
1475 1480 1485

Leu Gln Tyr Ala Ser Gly Ser Phe Asp Val Cys Tyr Gln Glu Met
1490 1495 1500

Phe Ser Ala Leu Leu Phe Gly Gly Ser Leu Tyr Met Val Asp Asn
1505 1510 1515

Glu Met Arg Lys Asp Pro Val Arg Leu Phe Gln Glu Ile Glu Lys
1520 1525 1530

His Glu Ile Asp Val Met Tyr Ile Pro Val Ala Phe Leu Lys Phe
1535 1540 1545

Ile Phe Ala Glu Pro Glu Trp Ala Glu Ala Phe Pro Arg Cys Val
1550 1555 1560

Arg His Ile Ile Thr Ala Gly Glu Gln Leu Val Val Thr Pro Gln
1565 1570 1575

Val Gln Ala Cys Leu Lys Arg Leu Asp Ile Ser Leu His Asn His
1580 1585 1590

Tyr Gly Pro Ser Glu Thr His Val Val Thr Thr Tyr Thr Met Met
1595 1600 1605

Pro Asp Val Ile Glu Val Gly Leu Pro Pro Ile Gly Lys Pro Ile
1610 1615 1620

Ala Asn Thr Ser Ile Phe Ile Val Asp Asp Ser Phe Glu Leu Gln
1625 1630 1635

Pro Ile Gly Val Lys Gly Glu Leu Tyr Val Ser Gly Ala Ser Val
1640 1645 1650

Gly Arg Gly Tyr Trp Gly Arg Thr Asp Leu Thr Glu Glu Lys Phe
1655 1660 1665

Leu Asp Asn Pro Phe Ala Pro Gly Glu Arg Leu Tyr Lys Thr Gly
1670 1675 1680

Asp Val Ala Arg Trp Leu Pro Asp Gly Ser Ile Glu Tyr Val Gly
1685 1690 1695

Arg Ser Asp His Gln Val Lys Ile Arg Gly Phe Arg Ile Glu Leu
1700 1705 1710

Gly Glu Val Glu Ser Gln Leu Leu His Val Pro Ala Val Gln Glu
1715 1720 1725

Ala Thr Met Val Ala Leu Glu Asp His Ala Gly Gln Lys Gln Leu
1730 1735 1740

Cys Ala Tyr Phe Thr Ala Glu Cys Ser Leu Thr Ala Gly Glu Leu

```
    1745                1750                1755

Arg Ala  Ala Leu Ser Gln Glu  Leu Pro Gly Tyr Met  Ile Pro Ser
    1760                1765                1770

Tyr Phe  Val Gln Leu Glu Arg  Leu Pro Leu Thr Pro  Asn Gly Lys
    1775                1780                1785

Ile Asp  Arg Arg Ala Leu Pro  Lys Pro Glu Gly Gly  Ile Glu Thr
    1790                1795                1800

Gly Thr  Glu Tyr Val Ala Pro  Arg Thr Glu Thr Glu  Ala Arg Leu
    1805                1810                1815

Ala Arg  Ile Trp Gln Asp Val  Leu Gly Leu Ala Ser  Val Gly Val
    1820                1825                1830

Lys Asp  Asn Phe Phe Glu Leu  Gly Gly His Ser Leu  Arg Ala Thr
    1835                1840                1845

Thr Leu  Val Ser Arg Leu Tyr  Lys Glu Met Asn Val  Asn Phe Pro
    1850                1855                1860

Leu Arg  Gly Val Phe Arg His  Pro Thr Ile Glu Glu  Met Ala Lys
    1865                1870                1875

Ala Ile  Thr Glu Met His Gln  Glu Leu Tyr Thr Glu  Ile Pro Ile
    1880                1885                1890

Ala Glu  Glu Lys Ala Tyr Tyr  Pro Leu Ser Ser Ala  Gln Lys Arg
    1895                1900                1905

Leu Phe  Ile Val Ser Gln Leu  Thr Gly Ala Glu Val  Ser Tyr Asn
    1910                1915                1920

Met Pro  Gly Val Leu Ile Leu  Glu Gly Glu Leu Asp  Arg Ala Arg
    1925                1930                1935

Phe Glu  Arg Ala Phe Gln Lys  Leu Ile Asp Arg His  Glu Ser Leu
    1940                1945                1950

Arg Thr  Ser Phe Glu Thr Val  Arg Gly Glu Pro Val  Gln Arg Ile
    1955                1960                1965

His Ser  Gln Val Glu Phe Ala  Ile Glu Tyr His Leu  Ala Ala Glu
    1970                1975                1980

Lys Asp  Ala Glu Ala Leu Ile  Thr His Phe Val Arg  Pro Phe Gln
    1985                1990                1995

Leu Asn  Gln Ala Pro Leu Leu  Arg Val Gly Leu Ile  Glu Thr Gly
    2000                2005                2010

His Glu  Arg His Ile Leu Met  Phe Asp Met His His  Ile Ile Ser
    2015                2020                2025

Asp Gly  Val Thr Met Gly His  Val Val Asn Glu Phe  Ser Arg Ile
    2030                2035                2040

Tyr Ala  Gly Asp Gln Leu Pro  Ala Leu Arg Ile Gln  Tyr Lys Asp
    2045                2050                2055

Tyr Ala  Ala Trp Gln Gln Ser  Asn Glu Tyr Ala Glu  Lys Leu Ala
    2060                2065                2070

His Gln  Glu Ser Tyr Trp Leu  Lys Gln Leu Asp Gly  Glu Leu Pro
    2075                2080                2085

Thr Leu  Glu Leu Pro Thr Asp  Tyr Val Arg Pro Ala  Val Gln Gln
    2090                2095                2100

Phe Glu  Gly Asp Val Ala Leu  Phe Thr Leu Thr Asn  Ser Gln Ala
    2105                2110                2115

Glu Gln  Leu Gln Arg Leu Ala  Ala Asn Tyr Gly Ala  Thr Leu Tyr
    2120                2125                2130

Met Val  Leu Leu Ala Ala Tyr  Thr Val Leu Leu His  Lys Tyr Thr
    2135                2140                2145
```

Gly Gln Asp Asp Ile Ile Val Gly Thr Pro Ile Ala Gly Arg Asn
2150 2155 2160

His Thr Glu Leu Glu Pro Leu Val Gly Met Phe Val Asn Thr Leu
2165 2170 2175

Ala Ile Arg Asn Tyr Pro Thr Gly Glu Lys Ser Phe Ala Glu Leu
2180 2185 2190

Leu Ala Glu Val Lys Asp Thr Ala Leu Ala Ala Phe Glu Asn Gln
2195 2200 2205

Asp Tyr Pro Phe Glu Thr Leu Val Glu Lys Val His Lys Ser Arg
2210 2215 2220

Asp Met Ser Arg Asn Pro Val Phe Asp Thr Ile Phe Ser Val Glu
2225 2230 2235

His Glu Gln Gln Ser Ser Phe His Ile Asp Gly Leu Arg Ile Ser
2240 2245 2250

Pro Tyr Pro His Ser His Ser Val Ala Lys Phe Asp Leu Thr Phe
2255 2260 2265

His Ala Glu Gln Asn Glu Glu Gly Ile Leu Cys Gly Leu Gly Tyr
2270 2275 2280

Ala Thr Ala Leu Tyr Ala Lys Glu Thr Ala Gly Arg Met Gly Glu
2285 2290 2295

His Phe Val Gln Leu Ile Asp Ala Ile Ile Ala Glu Pro Asn Ala
2300 2305 2310

Lys Leu Met Ser Leu Asn Met Met Ser Leu Gln Glu Arg Glu Gln
2315 2320 2325

Val Lys Leu Val Phe Asn Asp Thr Ile Thr Ser Tyr Pro Arg Glu
2330 2335 2340

Lys Thr Ile Gln His Leu Phe Glu Glu Gln Ala Glu Lys Ser Pro
2345 2350 2355

Asp Ala Val Ala Ile Gln Phe Gly Glu Glu Arg Leu Thr Tyr Arg
2360 2365 2370

Glu Leu Asn Glu Arg Ser Asn Arg Leu Ala Arg Thr Leu Arg Gly
2375 2380 2385

Lys Gly Val Lys Ala Gly Arg Phe Val Gly Leu Met Thr Asp Arg
2390 2395 2400

Ser Leu Asp Met Ile Val Ala Ile Met Ala Thr Leu Lys Ala Gly
2405 2410 2415

Gly Ala Tyr Val Pro Ile Asp Pro Asp Tyr Pro Glu Glu Arg Ile
2420 2425 2430

Arg Tyr Met Ile Asp Asp Ser Gly Ala Ser Leu Leu Val Val Gln
2435 2440 2445

Arg His Phe Gln Ser Asn His Ile Ala Ala Asp Cys Met Val Val
2450 2455 2460

Leu Val Asp Asp Glu Asp Ser Tyr His Ala Asp Gly Thr Asn Leu
2465 2470 2475

Glu Gln His Asn Gly Ala Ser Asp Leu Ala Tyr Val Ile Tyr Thr
2480 2485 2490

Ser Gly Thr Thr Gly Met Pro Lys Gly Asn Leu Thr Thr His Arg
2495 2500 2505

Asn Ile Val Arg Val Val Arg Asp Ala Lys Tyr Ile Glu Ile Asp
2510 2515 2520

Gln His Asp Thr Val Leu Gln Leu Ser Ser Tyr Ala Phe Asp Gly
2525 2530 2535

-continued

```
Ser Thr Phe Asp Ile Phe Gly Ala Leu Met Asn Gly Ala Lys Leu
    2540                2545                2550

Val Leu Ile Pro Arg Glu Val Val Leu Asp Ala Gly Arg Leu Ala
    2555                2560                2565

Asp Thr Ile Glu Ile Glu Lys Ile Ser Val Met Phe Ile Thr Thr
    2570                2575                2580

Ala Tyr Leu Asn Leu Leu Val Asp Leu Arg Val Asp Ser Leu Arg
    2585                2590                2595

His Met Arg Ala Ile Leu Phe Gly Gly Glu Arg Ala Ser Val Ser
    2600                2605                2610

His Val Arg Lys Ala Leu Arg His Leu Gly Pro Gly Lys Leu Lys
    2615                2620                2625

His Val Tyr Gly Pro Thr Glu Ser Thr Val Phe Ala Thr Ser His
    2630                2635                2640

Asn Val Asp Glu Val Ala Asp Ser Ala Val Thr Ile Pro Ile Gly
    2645                2650                2655

Arg Pro Ile Gly Asn Thr Ala Val Tyr Ile Val Gly Glu Gly Asp
    2660                2665                2670

Val Leu Gln Pro Ile Gly Val Ala Gly Glu Leu Cys Val Ala Gly
    2675                2680                2685

Asp Gly Val Ala Val Gly Tyr Leu Asn Arg Pro Glu Leu Ser Gly
    2690                2695                2700

Ala Lys Phe Val Asn Asn Pro Phe Val Pro Gly Asp Arg Met Tyr
    2705                2710                2715

Arg Thr Gly Asp Leu Ala Arg Trp Leu Ser Asp Gly Thr Ile Glu
    2720                2725                2730

Tyr Val Gly Arg Ile Asp Asp Gln Val Lys Ile Arg Gly Tyr Arg
    2735                2740                2745

Ile Glu Leu Gly Glu Val Glu Ala His Leu Leu Asp Leu Glu Ala
    2750                2755                2760

Ile Gln Glu Ala Val Val Ile Val Arg Glu Glu Ser Asp Gly Gln
    2765                2770                2775

Lys Arg Leu Cys Ala Tyr Tyr Val Ala Gly Arg Pro Ile Thr Ala
    2780                2785                2790

Gly Glu Met Arg Ile Ala Leu Ala Gln Glu Leu Pro Gly Tyr Met
    2795                2800                2805

Leu Pro Ser Tyr Phe Val Gln Leu Asp Lys Leu Pro Leu Ser Pro
    2810                2815                2820

Asn Gly Lys Val Asn Arg Lys Ala Leu Pro Ala Pro Glu Leu His
    2825                2830                2835

Val Gln Ala Ala Ser Glu Tyr Val Ala Pro Arg Thr Pro Gln Glu
    2840                2845                2850

Val Leu Leu Ala His Ile Trp Arg Glu Val Leu Gly Leu Gly Gln
    2855                2860                2865

Val Gly Val Lys Asp Asn Phe Phe Glu Leu Gly Gly His Ser Leu
    2870                2875                2880

Ser Leu Met Lys Leu Val Glu Arg Val Tyr Thr Glu Thr Glu Val
    2885                2890                2895

Glu Ile Pro Ile His Ser Val Phe Arg Glu Pro Thr Ile Glu Ala
    2900                2905                2910

Met Ala Tyr Glu Met Leu Lys Ser Glu Leu Ala Gly Lys Ala Gly
    2915                2920                2925

Asn His Phe Met Lys Leu Asn Glu Asn Gly His Ile Pro Val Phe
```

```
    2930                2935                2940

Cys Phe  Pro Pro Gly Leu Gly  Tyr Gly Leu Ser Tyr  Leu Glu Leu
    2945                2950                2955

Ala Lys  Gln Leu Asp His His  Cys Ile Leu His Gly  Ile Asp Phe
    2960                2965                2970

Ile Asp  Asp Ala Asp Thr Arg  Glu Glu Leu Leu Glu  Arg Tyr Val
    2975                2980                2985

Asp Ala  Ile Leu Ala Val Gln  Pro Gln Pro Pro Phe  Val Leu Leu
    2990                2995                3000

Gly Tyr  Ser Leu Gly Gly Asn  Leu Thr Phe Glu Val  Ala Lys Ala
    3005                3010                3015

Leu Glu  Ser Arg Gly Tyr Pro  Val Ser Asp Val Ile  Met Ile Asp
    3020                3025                3030

Ser Leu  Arg Lys Leu Lys Val  His Glu Val Asp Glu  Phe Asp Gly
    3035                3040                3045

Asp Ile  Asp Gln Met Ile Asp  Gly Val Glu Glu Leu  Lys Glu Met
    3050                3055                3060

Leu Val  His His Pro Leu Leu  Arg Asp Gln Val Lys  Asn Lys Met
    3065                3070                3075

Arg Ala  Tyr Trp Ser Tyr Ala  Thr Glu Leu Val Asn  Ser Asp Ile
    3080                3085                3090

Ile Asp  Ala Asn Ile His Ala  Leu Met Ala Glu Pro  Ser Glu Val
    3095                3100                3105

Asn Gln  Ala Asp Gly Glu Gln  Leu Ala Thr Trp Gln  Glu Ala Thr
    3110                3115                3120

Arg Gly  Arg Tyr Val Glu Tyr  Asn Leu Arg Gly Val  His Glu Asp
    3125                3130                3135

Val Leu  Gln Pro Pro Phe Leu  Glu Ala Asn Ala Asn  Val Met Gln
    3140                3145                3150

Ala Ile  Ile Arg His Ile Leu  Glu Gln Thr Met Val  Thr His
    3155                3160                3165


<210> SEQ ID NO 17
<211> LENGTH: 6605
<212> TYPE: PRT
<213> ORGANISM: Paenibacillus sp. OSY-SE

<400> SEQUENCE: 17

Met Glu Met Met His Pro Asn Thr Thr Val Ser Thr Val Ala Gly Thr
1               5                   10                  15

Leu Val Ile Arg Gly Glu Val Asp Ala Ala Val Leu Lys Glu Ser Ile
            20                  25                  30

Cys Gln Val Ile Thr Gln His Asp Ala Phe Arg Ile Arg Ile Met Thr
        35                  40                  45

Gln Asp Asn Gln Pro Ile Gln Arg Leu Glu Pro Glu Ser Ala Ile Thr
    50                  55                  60

Pro Glu Val Asp Tyr Met Glu Trp Asp Asp His Leu Glu Ala Lys Asp
65                  70                  75                  80

Trp Leu Asn Arg Phe Asn Arg Ile Pro Ile Ser Ile Phe Asp Asp Lys
                85                  90                  95

Leu Tyr Asn Phe Thr Val Phe Asn Val Asn Asn Gln Glu Tyr Trp Ile
            100                 105                 110

His Leu Lys Ile Asn His Ile Ile Ala Asp Gly Val Thr Ser His Leu
        115                 120                 125
```

-continued

```
Ile Gly Asn Lys Ile Met Gln Thr Tyr Met Glu Leu Thr Ser Gly Thr
    130                 135                 140

Phe Ser Ala Asn Asp Lys Lys Asn Ser Tyr Leu Asp Tyr Thr Tyr Ala
145                 150                 155                 160

Glu Gln Glu Tyr Glu Lys Ser Asp Arg Tyr Gln Lys Asp Lys Ala Tyr
                165                 170                 175

Trp Leu Glu Lys Phe Gln Thr Met Pro Glu Thr Thr Gly Ile Lys Pro
            180                 185                 190

Tyr Pro Pro Tyr Ser Ile Ser Thr Glu Ala Lys Arg Ala Tyr Val Ala
        195                 200                 205

Leu Thr Gly Glu Arg Tyr Glu Gln Leu Lys Val Phe Ser Glu Gln Asn
    210                 215                 220

Asn Ile Ser Leu Phe Thr Leu Phe Leu Ala Thr Val Tyr Met Phe Leu
225                 230                 235                 240

Tyr Lys Thr Thr Gly Asn Leu Asp Ile Ala Val Gly Thr Ala Tyr Ala
                245                 250                 255

Asn Arg Thr Ser Arg Lys Glu Lys Glu Met Leu Gly Met Phe Val Ser
            260                 265                 270

Thr Val Ala Thr Arg Leu Ser Leu Asp Pro Asn Gln Asp Leu Ile Ser
        275                 280                 285

Ile Leu His Asn Val Ser Lys Glu Gln Lys Thr Asn Leu Arg His Gln
    290                 295                 300

Lys Tyr Pro Tyr Asn Gln Leu Ile Leu Asp Leu Arg Lys Glu His Lys
305                 310                 315                 320

His Ser Asp Ile Gln Asp Leu Tyr Gly Val Ser Val Asp Tyr Met Pro
                325                 330                 335

Ile Asn Trp Ser Ser Tyr Gly Gln Leu Ser Ile Gln Gln Arg Ser Ser
            340                 345                 350

Phe Cys Gly His Glu Val Asp Asp Leu Ala Val His Val Glu Asp Met
        355                 360                 365

Leu Asp Asp Gln Gln Leu Val Ile Asn Val Asp Tyr Arg Ile Gln Leu
    370                 375                 380

Phe Glu Glu Arg Glu Ile Thr Arg Ile Ile Glu Gln Met Leu Thr Ile
385                 390                 395                 400

Val Asp Gly Ile Leu His Asn Pro Gln Gln Thr Leu His Glu Leu Thr
                405                 410                 415

Met Leu Asn Asn Glu Glu Ala Arg Lys Ile Leu Thr Gln Phe Asn Asp
            420                 425                 430

Thr Ala Ala Glu Phe Pro Arg Asp Lys Thr Val His Gln Leu Phe Glu
        435                 440                 445

Glu Gln Ala Ala Arg Thr Pro Asn His Val Ala Ala Val Tyr Glu Asp
    450                 455                 460

Glu Gln Leu Thr Tyr Arg Glu Leu Asn Glu Arg Ala Asn Arg Leu Ala
465                 470                 475                 480

Arg Thr Leu Arg Ala Glu Gly Val Gln Pro Glu Gln Leu Val Gly Ile
                485                 490                 495

Met Ala Asp Arg Ser Leu Glu Met Ile Val Gly Ile Leu Ala Ile Leu
            500                 505                 510

Lys Ala Gly Gly Ala Tyr Val Pro Ile Asp Pro Glu Tyr Pro Glu Glu
        515                 520                 525

Arg Ile Arg Tyr Met Leu Asp Asp Ser Asn Ala Arg Val Leu Leu Ala
    530                 535                 540

Gln Arg His Leu Gln Ala Arg Ile Ala Phe Thr Gly Thr Trp Val Ile
```

```
545                 550                 555                 560

Leu Asp Glu Asn Ala Phe Tyr Asp Glu Asp Gly Thr Asn Leu Glu Ser
                565                 570                 575

Asn Asn Asp Pro Ser Asn Leu Ser Tyr Val Ile Tyr Thr Ser Gly Thr
            580                 585                 590

Thr Gly Lys Pro Lys Gly Val Met Ile Glu His Arg Gln Leu Val Ala
        595                 600                 605

Met Ala His Ala Trp Lys Ser Arg Tyr His Leu His Glu Ala Gly Ile
    610                 615                 620

Arg Trp Leu Gln Trp Ala Ser Phe Ser Phe Asp Val Phe Ser Gly Asp
625                 630                 635                 640

Met Val Arg Thr Leu Leu Asn Gly Gly Glu Leu Ile Leu Cys Pro Gly
                645                 650                 655

His Ala Arg Ala Asn Pro Glu Ala Ile Cys Glu Leu Ile Arg Lys His
            660                 665                 670

Arg Ile Gln Met Phe Glu Ser Thr Pro Ala Leu Val Val Pro Leu Met
        675                 680                 685

Glu Tyr Ile Tyr Asp Asn Lys Met Asp Ile His Ser Leu Gln Leu Leu
    690                 695                 700

Ile Ile Gly Ser Asp Tyr Cys Pro Ala Glu Glu Phe Gln Lys Leu Met
705                 710                 715                 720

Glu Arg Phe Gly Ser Gln Met Arg Ile Leu Asn Ser Tyr Gly Val Thr
                725                 730                 735

Glu Ala Cys Val Asp Ala Ser Tyr Phe Glu Gln Thr Asp Ser Asp Ala
            740                 745                 750

Leu Arg Thr Leu Pro Ile Gly Lys Pro Leu Pro Ala Val Ser Met Met
        755                 760                 765

Val Leu Asp Asp Asn Arg Ser Leu Gln Pro Ile Gly Ile Thr Gly Glu
    770                 775                 780

Leu Tyr Ile Gly Gly Ala Cys Val Gly Arg Gly Tyr Leu Asn Arg Pro
785                 790                 795                 800

Asp Leu Thr Ala Glu Lys Phe Val Asp Asn Pro Tyr Ala Pro Ser Glu
                805                 810                 815

Met Met Tyr Arg Thr Gly Asp Leu Ala Arg Trp Leu Pro Asp Gly Asn
            820                 825                 830

Ile Glu Tyr Leu Gly Arg Ile Asp His Gln Val Lys Ile Arg Gly Tyr
        835                 840                 845

Arg Ile Glu Ile Gly Glu Ile Glu Ser Gln Leu Leu Lys Ala Glu Ser
    850                 855                 860

Val Arg Glu Ser Val Val Val Ala Arg Glu Asp Gly Ser Gly Gln Lys
865                 870                 875                 880

Val Leu Cys Ala Tyr Tyr Val Ala Asp Arg Glu Leu Thr Val Asn Glu
                885                 890                 895

Leu Arg Gly Lys Met Ala Glu Glu Leu Pro Gly Tyr Met Ile Pro Ser
            900                 905                 910

Tyr Phe Met Gln Leu Glu Gln Met Pro Leu Thr Pro Asn Gly Lys Val
        915                 920                 925

Asp Arg Lys Gly Leu Pro Ala Pro Glu Gly Ser Ala His Thr Gly Thr
    930                 935                 940

Glu Tyr Val Glu Pro Ser Ser Ala Ala Glu Lys Met Leu Ala Ala Val
945                 950                 955                 960

Trp Gln Ala Val Leu Gly Ile Glu Arg Val Gly Ala Ser Glu His Phe
                965                 970                 975
```

-continued

```
Phe Glu Leu Gly Gly Asp Ser Ile Lys Ser Ile Gln Val Ser Ser Arg
            980                 985                 990

Leu Arg Gln Ala Gly Tyr Lys Met  Glu Ile Arg Asp Leu  Phe Lys Tyr
        995                 1000                 1005

Pro Thr  Ile Ala Glu Leu Ser  Leu His Ile Gln Pro  Ala Gly Arg
    1010                 1015                 1020

Met Ala  Asp Gln Ser Glu Val  Val Gly Lys Ala Glu  Leu Thr Pro
    1025                 1030                 1035

Ile Gln  Arg Trp Phe Phe Ala  Gln Arg Phe Ala Asp  Pro His His
    1040                 1045                 1050

Tyr Asn  Gln Ser Ile Met Leu  Tyr Arg Lys Glu Gly  Phe Asp Glu
    1055                 1060                 1065

Ala Ala  Ile Arg Lys Thr Leu  Glu Lys Ile Ala Glu  His His Asp
    1070                 1075                 1080

Ala Leu  Arg Met Val Phe Arg  Lys Thr Glu Ser Gly  Tyr Ala Ala
    1085                 1090                 1095

Trp Asn  Arg Gly Ile Gly Glu  Gly Glu Leu Tyr Arg  Leu Asn Val
    1100                 1105                 1110

Ala Asp  Phe Arg Asn Glu Ser  Ala Cys Gly Pro Leu  Ile Ala Ala
    1115                 1120                 1125

Gln Ala  Asn Glu Ile Gln Gly  Gly Ile Asp Ile Glu  Thr Gly Pro
    1130                 1135                 1140

Leu Val  Arg Ala Gly Leu Phe  Gln Cys Ala Asp Gly  Asp His Leu
    1145                 1150                 1155

Leu Leu  Val Ile His His Thr  Val Ile Asp Gly Val  Ser Trp Arg
    1160                 1165                 1170

Ile Leu  Leu Glu Asp Ile Ala  Val Gly Tyr Glu Gln  Ala Leu Lys
    1175                 1180                 1185

Gly Glu  Glu Val Arg Leu Pro  Ser Lys Thr Asp Ala  Tyr Arg Thr
    1190                 1195                 1200

Trp Ser  Glu Arg Leu Ala Ser  Tyr Ala Asp Ser Gln  Thr Val Ile
    1205                 1210                 1215

Asn Glu  Arg Ala Tyr Trp Gln  Arg Ile Thr Gln Thr  Glu Met Asn
    1220                 1225                 1230

Pro Leu  Pro Lys Asp Tyr Glu  Ala Asp Cys Ser Leu  Gln Lys Asp
    1235                 1240                 1245

Ser Glu  Ser Val Ile Val Gln  Trp Ser Pro Glu Asp  Thr Glu Gln
    1250                 1255                 1260

Leu Leu  Lys His Val His Lys  Ala Tyr Asn Thr Glu  Met Asn Asp
    1265                 1270                 1275

Ile Leu  Leu Thr Ala Leu Gly  Thr Ala Val Gln Arg  Trp Ser Gly
    1280                 1285                 1290

Arg Asp  Arg Val Leu Val Asn  Leu Glu Gly His Gly  Arg Glu Ala
    1295                 1300                 1305

Ile Ile  Ala Asp Ile Asp Ile  Ser Arg Thr Val Gly  Trp Phe Thr
    1310                 1315                 1320

Ser Glu  Tyr Pro Val Leu Leu  Glu Met Glu Gln Ala  Lys Gly Leu
    1325                 1330                 1335

Ser Tyr  Arg Ile Lys Lys Val  Lys Glu Asp Leu Arg  Gln Ile Pro
    1340                 1345                 1350

Asn Lys  Gly Ile Gly Tyr Gly  Ile Cys Arg Tyr Met  Ser Asp Leu
    1355                 1360                 1365
```

```
Pro Tyr Glu Ala Ser Trp Gly Ala Asn Pro Glu Ile Ser Phe Asn
    1370                1375                1380

Tyr Leu Gly Gln Phe Asp Gln Asp Leu Gln Ser Asn Gly Met Leu
    1385                1390                1395

Met Ser Pro Leu Ser Ser Gly Ser Asn Thr Ser Gly Asn Gln Ala
    1400                1405                1410

Arg Gln Tyr Ala Leu Asp Ile Asn Gly Met Ile Met Asp Gly Ser
    1415                1420                1425

Leu Val Phe Asp Leu Ser Tyr Gly Ser Lys Glu Tyr Arg Arg Glu
    1430                1435                1440

Thr Ile Glu Asp Leu Ala Gly Met Leu Gln Glu Ile Leu Arg Glu
    1445                1450                1455

Ile Ile Ala His Cys Thr Ala Lys Glu Arg Pro Glu Leu Thr Pro
    1460                1465                1470

Ser Asp Val Leu Leu Gln Gly Leu Ser Val Glu Glu Leu Glu Gln
    1475                1480                1485

Ile Val Glu Gln Thr Gln His Ile Gly Asp Ile Glu Asn Met Tyr
    1490                1495                1500

Lys Leu Thr Pro Met Gln Lys Gly Met Trp Phe His Ser Ala Met
    1505                1510                1515

Asp Arg Gln Ala Gly Ala Tyr Phe Glu Gln Thr Arg Phe Thr Leu
    1520                1525                1530

Gln Gly Asp Leu Asp Val Asp Ala Phe Ala Lys Ser Trp Thr Ala
    1535                1540                1545

Leu Ala Ala Arg His Thr Val Leu Arg Thr Asn Phe His Asn Gly
    1550                1555                1560

Trp Lys Gly Glu Pro Leu Gln Ile Val Tyr Arg Asp Lys Arg Ile
    1565                1570                1575

Gly Phe Ala Tyr Glu Asp Val Ser Ala Leu Lys Pro Ala Lys Gln
    1580                1585                1590

Arg Ala His Ile Glu Asn Ala Val Asn Glu Asp Lys Leu Arg Gly
    1595                1600                1605

Phe Asp Leu Glu Gln Asp Glu Leu Met Arg Val Leu Val Met Arg
    1610                1615                1620

Thr Ala Gln Glu Ser Tyr His Val Leu Trp Ser Ser His His Ile
    1625                1630                1635

Leu Met Asp Gly Trp Cys Leu Pro Leu Val Ala Lys Glu Val Phe
    1640                1645                1650

Asp Thr Tyr Ser Ala Tyr Val Arg His Arg His Leu Glu Lys Thr
    1655                1660                1665

Thr Val Pro Ala Tyr Ser Gln Tyr Ile Glu Trp Leu Glu Gln Gln
    1670                1675                1680

Asp Glu Glu Ala Ala Ser Ala Tyr Trp Ser Glu Tyr Leu Ala Gly
    1685                1690                1695

Tyr Asp Gln His Thr Ala Leu Pro Gln Gly Lys Asp Gln Gly Arg
    1700                1705                1710

Ser Glu Ala Tyr Ala Ala Glu His Ile Asp Cys Glu Leu Gly Lys
    1715                1720                1725

Asp Leu Ser Val Arg Leu Asn Glu Ala Ala Lys Arg Asn Leu Val
    1730                1735                1740

Thr Leu Ser Thr Leu Leu Gln Thr Thr Trp Gly Ile Met Leu Gln
    1745                1750                1755

Lys Tyr Asn Gly Thr Gly Asp Val Val Phe Gly Gly Val Val Ser
```

```
    1760                1765                1770

Gly Arg  Pro Ala Asp Met Pro  Gly Ile Glu Glu Met  Ile Gly Leu
    1775                1780                1785

Phe Ile  Asn Thr Ile Pro Val  Arg Val Thr Ala Asp  Ala Gly Glu
    1790                1795                1800

Ser Phe  Ala Asp Ile Met Cys  Arg Leu Gln Glu Gln  Ala Leu Ala
    1805                1810                1815

Ser Ala  Lys His Asp His Tyr  Pro Leu Tyr Glu Ile  Gln Ala Gln
    1820                1825                1830

Ser Ala  Gln Lys Gln Glu Leu  Ile Asn His Ile Met  Val Phe Glu
    1835                1840                1845

Asn Tyr  Pro Met Glu Glu Gln  Ile Glu Gln Leu Glu  Ser Leu Asp
    1850                1855                1860

Gly Lys  Gly Leu Lys Leu Lys  Asp Val Met Val Thr  Glu Gln Thr
    1865                1870                1875

Asn Tyr  Asp Phe Asn Leu Val  Ile Met Pro Gly Asp  Glu Ile Val
    1880                1885                1890

Ile Arg  Leu Asp Tyr Asn Gly  Ile Val Phe Asp Arg  Thr Ser Met
    1895                1900                1905

Glu Gln  Leu Lys Gly His Leu  Val Asn Met Leu Glu  Gln Ile Ala
    1910                1915                1920

Ala Asn  Pro Gln Ile Pro Val  Gly Glu Leu Glu Leu  Ala Thr Ala
    1925                1930                1935

Ala Glu  Lys Ala Gln Ile Val  Asp Val Phe Asn Asn  Thr Val Val
    1940                1945                1950

Glu Tyr  Pro Arg Glu Lys Thr  Ile His Gln Leu Phe  Glu Glu Arg
    1955                1960                1965

Glu Glu  Arg Ile Pro Asp Ala  Val Ala Val Ile Phe  Glu Asp Lys
    1970                1975                1980

Arg Leu  Thr Tyr Ala Glu Leu  Asn Ala Ala Ala Asn  Arg Ile Ala
    1985                1990                1995

His Leu  Leu Arg Asp Arg Gly  Val Ala Arg Gly Thr  Leu Val Gly
    2000                2005                2010

Ile Cys  Ala Glu Arg Ser Leu  Glu Met Val Val Gly  Leu Leu Gly
    2015                2020                2025

Ile Leu  Lys Ala Gly Gly Ala  Tyr Val Pro Ile Asp  Pro Ser Tyr
    2030                2035                2040

Pro Gln  Glu Arg Ile Asn Ala  Met Leu Glu Asp Thr  Ala Ile Ser
    2045                2050                2055

Val Met  Leu Thr Gln Ala His  Leu Gln Thr Ser Val  Pro Asn Ser
    2060                2065                2070

Ile Asp  Ser Val Leu Leu Asp  Ala Ala Ala Glu Thr  Ile Leu Glu
    2075                2080                2085

Gly Ser  Trp Pro Asn Leu Thr  Asp Thr Ala Ala Thr  Ala Asp Asp
    2090                2095                2100

Val Ala  Tyr Ile Ile Tyr Thr  Ser Gly Ser Thr Gly  Ile Pro Lys
    2105                2110                2115

Gly Val  Cys Val Thr His Arg  Gly Val Val Arg Leu  Val Ala Asp
    2120                2125                2130

Ala Asn  Tyr Val Asp Ile Ser  Ser Lys Asp Val Phe  Leu Gln Gly
    2135                2140                2145

Ser Thr  Ile Ser Phe Asp Ala  Ala Thr Phe Glu Ile  Trp Gly Ser
    2150                2155                2160
```

```
Leu Leu  Asn Gly Ala Ala Leu  Ala Val Leu Pro Pro  Gly Asn Val
    2165                 2170                 2175

Ser Leu  Thr Glu Trp Thr Arg  Ala Ile Gln Gln His  Gln Val Thr
    2180                 2185                 2190

Ile Leu  Trp Leu Thr Ala Gly  Leu Phe His Val Met  Val Asp Asn
    2195                 2200                 2205

Gln Leu  Gln Ala Leu Gln Gly  Val Gln Gln Leu Leu  Val Gly Gly
    2210                 2215                 2220

Asp Val  Val Ser Lys Thr His  Ala Thr Lys Val Leu  Glu Arg Tyr
    2225                 2230                 2235

Asn Gly  Ile Arg Leu Ile Asn  Gly Tyr Gly Pro Thr  Glu Asn Thr
    2240                 2245                 2250

Thr Phe  Thr Cys Cys His Glu  Ile Ser Ala Ala Asp  Met Glu Arg
    2255                 2260                 2265

Pro Ser  Ile Pro Ile Gly Arg  Pro Ile Gly Asn Thr  Gln Ala Tyr
    2270                 2275                 2280

Val Leu  Asp Gly Ala Gly Lys  Leu Leu Pro Ala Gly  Val Ile Gly
    2285                 2290                 2295

Glu Leu  Tyr Thr Gly Gly Asp  Gly Leu Ala Gln Gly  Tyr Leu Asn
    2300                 2305                 2310

Arg Pro  Glu Leu Thr Ala Glu  Lys Phe Val Asp Ser  Pro Ile Val
    2315                 2320                 2325

Pro Ala  Thr Arg Leu Tyr Arg  Thr Gly Asp Leu Ala  Arg Trp Leu
    2330                 2335                 2340

Pro Asp  Gly Thr Ile Glu Tyr  Val Gly Arg Ile Asp  Asp Gln Val
    2345                 2350                 2355

Lys Ile  Arg Gly Tyr Arg Ile  Glu Leu Gly Glu Val  Glu Ala His
    2360                 2365                 2370

Leu Leu  Lys Val Glu Pro Val  Gln Ser Ala Ala Val  Ile Ala Arg
    2375                 2380                 2385

Lys Asp  Glu Ser Gly Gln Asn  Met Leu Cys Ala Tyr  Tyr Ala Ala
    2390                 2395                 2400

Asp Lys  Glu Leu Thr Ala Ser  Glu Leu Arg Ser Ala  Leu Ser Gln
    2405                 2410                 2415

Glu Leu  Pro Gly Tyr Met Ile  Pro Thr His Phe Val  Gln Val Glu
    2420                 2425                 2430

Arg Met  Pro Leu Thr Pro Asn  Gly Lys Val Asp Arg  Lys Ala Leu
    2435                 2440                 2445

Pro Glu  Pro Glu Gly Arg Ile  Met Thr Gly Ile Glu  His Val Ala
    2450                 2455                 2460

Pro Arg  Thr Pro Leu Glu Ser  Lys Leu Ala His Ile  Trp Gln Glu
    2465                 2470                 2475

Val Leu  Gly Leu Glu Lys Val  Ser Val Lys Asp Ser  Phe Phe Glu
    2480                 2485                 2490

Leu Gly  Gly His Ser Leu Arg  Ala Thr Thr Leu Val  Ser Lys Leu
    2495                 2500                 2505

Gln Gln  Glu Leu His Val Ser  Met Pro Leu Arg Glu  Val Phe Arg
    2510                 2515                 2520

Phe Pro  Thr Ile Glu Glu Gln  Ala Gln Val Ile Gly  Gly Met Glu
    2525                 2530                 2535

Gln Glu  Glu Tyr Arg Ala Ile  Pro Gln Val Gly Glu  Arg Glu Cys
    2540                 2545                 2550
```

```
Tyr Pro  Val Ser Ser Ala Gln  Lys Arg Leu Tyr Ile  Leu His Gln
    2555                 2560                 2565

Leu Glu  Gly Ala Glu Gln Thr  Tyr Asn Met Pro Gly  Val Met Thr
    2570                 2575                 2580

Leu Ala  Gly Pro Leu Asp Arg  Glu Arg Leu Glu Thr  Ala Phe Arg
    2585                 2590                 2595

Lys Leu  Ile Ser Arg His Glu  Thr Leu Arg Thr Gly  Phe Glu Met
    2600                 2605                 2610

Val Asp  Gly Val Pro Val Gln  Arg Val Tyr Glu Glu  Val Asp Phe
    2615                 2620                 2625

Ala Val  Glu Tyr Ala Gln Ala  Ser Glu Glu Ala Ala  Gly Glu Ala
    2630                 2635                 2640

Val His  Ala Phe Ile Arg Ala  Phe Asp Leu Gln Lys  Pro Pro Leu
    2645                 2650                 2655

Leu Arg  Ile Gly Leu Ile Glu  Leu Ala Lys Glu Arg  His Leu Leu
    2660                 2665                 2670

Met Phe  Asp Met His His Ile  Ile Ser Asp Gly Ala  Ser Ile Gly
    2675                 2680                 2685

Ile Leu  Ile Glu Glu Phe Val  Arg Leu Tyr Arg Gly  Glu Glu Ile
    2690                 2695                 2700

Ser Pro  Leu Arg Ile Gln Tyr  Lys Asp Tyr Ala Ala  Trp Leu Gln
    2705                 2710                 2715

Ser Glu  Ala Gln Gln Asp Trp  Ser Lys Gln Gln Glu  Ala Tyr Trp
    2720                 2725                 2730

Leu Asp  Ala Leu Arg Gly Glu  Leu Pro Val Leu Glu  Leu Pro Thr
    2735                 2740                 2745

Asp Tyr  Ala Arg Pro Leu Phe  Arg Ser Tyr Glu Gly  Ser Thr Phe
    2750                 2755                 2760

Glu Phe  Thr Ile Gln Arg Arg  Glu Ala Glu Arg Leu  Arg Gln Leu
    2765                 2770                 2775

Ala Ala  Glu Ser Gly Ala Thr  Leu Tyr Met Val Leu  Leu Ala Leu
    2780                 2785                 2790

Tyr Thr  Thr Met Leu His Lys  Tyr Thr Gly Gln Glu  Asp Ile Ile
    2795                 2800                 2805

Val Gly  Met Pro Ile Ala Gly  Arg Thr His Gly Asp  Leu Gln Pro
    2810                 2815                 2820

Leu Ile  Gly Met Phe Val Asn  Thr Leu Ala Ile Arg  Ser Tyr Pro
    2825                 2830                 2835

Ala Gly  Glu Lys Thr Phe Leu  Ser Phe Leu Glu Glu  Val Lys Asp
    2840                 2845                 2850

Thr Thr  Met Arg Ala Tyr Glu  His Gln Asp Tyr Pro  Phe Glu Glu
    2855                 2860                 2865

Leu Val  Glu Asn Val Arg Val  Pro Arg Asp Ala Ser  Arg Asn Pro
    2870                 2875                 2880

Leu Phe  Asp Thr Val Phe Val  Leu Gln Asn Thr Glu  Gln Gly Thr
    2885                 2890                 2895

Phe Asp  Ile Asp Gly Leu Gln  Leu Leu Pro His Pro  Ala Glu His
    2900                 2905                 2910

Pro Val  Ala Lys Phe Asp Leu  Thr Phe His Ile Glu  Glu Glu Glu
    2915                 2920                 2925

Glu Gly  Leu Ala Cys Ser Ile  Glu Tyr Ala Thr Ala  Leu Phe Gln
    2930                 2935                 2940

Arg Glu  Thr Val Ala Arg Met  Ala Gln His Phe Arg  Gln Leu Val
```

```
    2945                2950                2955

Glu Ala  Val Thr Gly Glu Pro  Val Asp Arg Leu Asp  Arg Leu Glu
    2960                2965                2970

Met Leu  Thr Ala Glu Glu Lys  Val Gln Leu Val Asp  Arg Phe Asn
    2975                2980                2985

Asp Thr  Gly Ala Asp Tyr Pro  Arg Glu Lys Thr Ile  His Leu Leu
    2990                2995                3000

Phe Glu  Glu Gln Ala Glu Arg  Thr Pro Ala Ala Val  Ala Val Ile
    3005                3010                3015

Phe Glu  Asn Ala Gln Leu Thr  Tyr Arg Glu Leu Asn  Glu Arg Ala
    3020                3025                3030

Asn Arg  Leu Ala His Thr Leu  Arg Ala Lys Asp Val  Gln Thr Asp
    3035                3040                3045

Ser Leu  Val Gly Ile Met Ala  Glu Arg Ser Pro Glu  Met Ile Val
    3050                3055                3060

Gly Ile  Leu Ala Ile Leu Lys  Ala Gly Gly Ala Tyr  Val Pro Ile
    3065                3070                3075

Asp Pro  Glu Tyr Pro Glu Glu  Arg Ile Arg Tyr Met  Leu Asp Asp
    3080                3085                3090

Ser Gly  Ala Gln Val Leu Leu  Leu Pro His Asp Leu  Arg Asp Lys
    3095                3100                3105

Val Gly  Phe Asp Gly Thr Val  Val Met Leu Asp Asp  Glu Gln Ser
    3110                3115                3120

Tyr Val  Glu Asp Ser Ser Asn  Pro Ala Thr Ala Ser  Lys Pro Ser
    3125                3130                3135

Asp Leu  Ala Tyr Val Ile Tyr  Thr Ser Gly Thr Thr  Gly Lys Pro
    3140                3145                3150

Lys Gly  Thr Leu Ile Glu His  Lys Asn Val Val Arg  Leu Leu Phe
    3155                3160                3165

Asn Ser  Lys Asn Leu Phe Asp  Phe Asn Ser Ala Asp  Thr Trp Thr
    3170                3175                3180

Leu Phe  His Ser Phe Cys Phe  Asp Phe Ser Val Trp  Glu Met Tyr
    3185                3190                3195

Gly Ala  Leu Leu Tyr Gly Gly  Arg Leu Val Val Val  Pro Gln Leu
    3200                3205                3210

Thr Ala  Lys Asn Pro Ala Gln  Phe Leu Glu Leu Leu  His Glu Gln
    3215                3220                3225

Gln Val  Thr Ile Leu Asn Gln  Thr Pro Thr Tyr Phe  Tyr Gln Leu
    3230                3235                3240

Leu Arg  Glu Ala Leu Ala Glu  Pro Gly Gln Glu Leu  Lys Val Arg
    3245                3250                3255

Lys Val  Ile Phe Gly Gly Glu  Ala Leu Asn Pro Gln  Leu Leu Lys
    3260                3265                3270

Asp Trp  Lys Thr Lys Tyr Pro  His Thr Gln Leu Ile  Asn Met Tyr
    3275                3280                3285

Gly Ile  Thr Glu Thr Thr Val  His Val Thr Tyr Lys  Glu Ile Thr
    3290                3295                3300

Gln Val  Glu Ile Glu Gln Ala  Lys Ser Asn Ile Gly  Arg Pro Ile
    3305                3310                3315

Pro Thr  Leu Lys Val Tyr Val  Leu Asp Ala Asn Arg  Gln Cys Val
    3320                3325                3330

Pro Val  Gly Val Ala Gly Glu  Met Tyr Val Ala Gly  Asp Gly Leu
    3335                3340                3345
```

-continued

```
Ala Arg Gly Tyr Leu His Arg Pro Glu Leu Thr Ala Asp Lys Phe
    3350                3355                3360

Val Asp Ser Pro Phe Glu Ser Gly Gly Arg Met Tyr Arg Thr Gly
    3365                3370                3375

Asp Leu Ala Arg Trp Leu Pro Asp Gly Asn Ile Glu Tyr Leu Gly
    3380                3385                3390

Arg Ile Asp His Gln Val Lys Ile Arg Gly Tyr Arg Ile Glu Leu
    3395                3400                3405

Gly Glu Val Glu Ala Gln Leu Thr Lys Val Asp Pro Val Arg Glu
    3410                3415                3420

Ala Ile Val Ile Ala Arg Glu Asp Gly His Gly Glu Lys Gln Leu
    3425                3430                3435

Cys Ala Tyr Phe Val Ala Ala Arg Glu Leu Thr Val Gly Glu Leu
    3440                3445                3450

Arg Gln Glu Leu Ser His Ala Leu Pro Ala Tyr Met Ile Pro Ala
    3455                3460                3465

Tyr Phe Val Gln Leu Glu Arg Met Pro Leu Thr Pro Asn Gly Lys
    3470                3475                3480

Ile Asp Arg Lys Ala Leu Pro Ala Pro Glu Asp Ser Val Asn Thr
    3485                3490                3495

Gly Thr Glu Tyr Ile Ala Pro Arg Thr Leu Leu Glu Ser Asp Leu
    3500                3505                3510

Thr Arg Ile Trp Gln Asp Val Leu Gly Leu Glu Ser Ile Gly Val
    3515                3520                3525

Lys Asp Asn Phe Phe Glu Leu Gly Gly His Ser Leu Arg Ala Thr
    3530                3535                3540

Thr Leu Val Asn Lys Val His Gln Glu Met Asn Val Asn Leu Pro
    3545                3550                3555

Leu Arg Asp Val Phe Arg Phe Ser Thr Ile Glu Glu Met Ala Cys
    3560                3565                3570

Ala Ile Ala Glu Met Glu Gln Arg Thr Tyr Met Ser Ile Pro Ala
    3575                3580                3585

Ile Glu Thr Arg Asp Tyr Tyr Pro Val Ser Ser Ala Gln Lys Arg
    3590                3595                3600

Leu Tyr Ile Leu His Gln Ile Glu Gly Ala Glu Gln Gly Tyr Asn
    3605                3610                3615

Met Pro Gly Val Leu Leu Leu Glu Gly Met Leu Asp Gln Glu Lys
    3620                3625                3630

Phe Glu Glu Ala Phe His Gly Ile Val Ala Arg His Glu Thr Leu
    3635                3640                3645

Arg Thr Gly Phe Glu Met Val Asn Gly Glu Pro Val Gln Arg Val
    3650                3655                3660

Tyr Glu Lys Val Asp Phe Ala Val Glu Tyr Arg Gln Ala Asp Glu
    3665                3670                3675

Glu Glu Val Glu Ala Val Val Arg Asp Phe Val Arg Thr Phe Asp
    3680                3685                3690

Leu Glu Lys Pro Pro Leu Leu Arg Ile Gly Leu Leu Glu Leu Ala
    3695                3700                3705

Lys Glu Arg His Val Leu Leu Tyr Asp Met His His Ile Ile Ser
    3710                3715                3720

Asp Gly Val Ser Met Gly Ile Val Val Glu Glu Phe Val Arg Leu
    3725                3730                3735
```

```
Tyr Ala  Gly Ala Ala Leu Glu  Pro Leu Arg Ile Gln  Tyr Lys Asp
    3740                 3745                 3750

Tyr Ala  Ala Trp Gln Leu Ser  Glu Ala Gln Gln Asp  Trp Met Lys
    3755                 3760                 3765

Arg Gln  Glu Gly Tyr Trp Arg  Asp Val Phe Arg Gly  Glu Leu Pro
    3770                 3775                 3780

Val Leu  Glu Met Pro Thr Asp  Tyr Val Arg Pro Ala  Val Gln Gln
    3785                 3790                 3795

Tyr Ala  Gly Ser Thr Leu Ser  Phe Asp Ile Asp Pro  Gln Met Ser
    3800                 3805                 3810

Glu Gly  Leu Arg Arg Ile Ala  Ala Glu Thr Gly Thr  Thr Leu Tyr
    3815                 3820                 3825

Met Val  Leu Leu Ala Ala Tyr  Thr Ile Leu Leu His  Lys Tyr Thr
    3830                 3835                 3840

Gly Gln  Glu Asp Val Ile Val  Gly Thr Pro Ile Ala  Gly Arg Thr
    3845                 3850                 3855

His Gly  Asp Leu Gln Pro Leu  Ile Gly Met Phe Val  Asn Thr Leu
    3860                 3865                 3870

Ala Ile  Arg Asn Tyr Pro Ala  Gly Glu Lys Thr Phe  Arg Ser Tyr
    3875                 3880                 3885

Leu Ala  Glu Val Lys Glu Thr  Thr Leu Gly Ala Tyr  Glu His Gln
    3890                 3895                 3900

Asn Tyr  Pro Phe Glu Glu Leu  Val Asp Lys Leu Gln  Val Ala Arg
    3905                 3910                 3915

Asp Leu  Ser Arg Asn Pro Leu  Phe Asp Thr Met Phe  Ala Leu Asn
    3920                 3925                 3930

Asn Thr  Glu Pro Glu Thr Phe  Pro Leu Glu Gly Leu  Arg Leu Thr
    3935                 3940                 3945

Pro Tyr  Pro Ser Glu Tyr Thr  Ile Ser Lys Phe Asp  Leu Ser Leu
    3950                 3955                 3960

Asp Val  Ser Glu Lys Asn Asp  Arg Leu Glu Cys Ser  Leu Glu Tyr
    3965                 3970                 3975

Ala Thr  Ala Leu Tyr Lys Pro  Asp Thr Ala Glu Arg  Met Ala Gln
    3980                 3985                 3990

His Phe  Gln Gln Leu Ile Asp  Ser Ile Val Asp Gln  Pro Glu Ala
    3995                 4000                 4005

Lys Leu  Val Ser Leu Gly Met  Leu Thr Glu Glu Glu  Lys Ala Gln
    4010                 4015                 4020

Ile Gln  His Val Phe Asn Arg  Ala Glu Ala Gly His  Ser Gln Glu
    4025                 4030                 4035

Lys Thr  Val Pro Glu Leu Phe  Glu Glu Gln Val Glu  Arg Thr Pro
    4040                 4045                 4050

Asp Arg  Ile Ala Val Val His  Glu Asp Lys Gln Leu  Thr Tyr Arg
    4055                 4060                 4065

Glu Leu  Asn Glu Arg Ala Asn  Arg Leu Ala Arg Thr  Leu Arg Ala
    4070                 4075                 4080

Glu Gly  Val Glu Pro Glu Gln  Leu Val Gly Ile Met  Ala Asp Arg
    4085                 4090                 4095

Ser Leu  Asp Met Ile Val Gly  Ile Met Ala Ile Leu  Lys Ser Gly
    4100                 4105                 4110

Gly Ala  Tyr Val Pro Ile Asp  Pro Lys Tyr Pro Glu  Asp Arg Ile
    4115                 4120                 4125

Arg Tyr  Met Leu Asp Asp Ser  His Ala Gln Val Leu  Leu Ala Gln
```

-continued

```
    4130                4135                4140

Arg His  Met Gln Ala Ser Val  Ala Phe Ala Gly Thr  Trp Val Ile
    4145                4150                4155

Leu Asp  Glu Glu Ala Phe Tyr  His Glu Asp Gly Thr  Asn Leu Glu
    4160                4165                4170

Pro Leu  Asn Glu Pro Met His  Leu Ser Tyr Val Ile  Tyr Thr Ser
    4175                4180                4185

Gly Thr  Thr Gly Asn Pro Lys  Gly Val Met Ile Glu  His Arg Gln
    4190                4195                4200

Leu Val  Ala Ile Ala Asp Ala  Trp Lys Arg Glu Tyr  Arg Leu Glu
    4205                4210                4215

Glu Glu  Gly Ile Arg Trp Leu  Gln Trp Ala Ser Phe  Ser Phe Asp
    4220                4225                4230

Val Phe  Ser Gly Asp Met Val  Arg Thr Leu Leu Tyr  Gly Gly Glu
    4235                4240                4245

Leu Ile  Leu Cys Pro Glu Gln  Ala Arg Ala Asn Pro  Ala Ala Ile
    4250                4255                4260

Ser Glu  Leu Ile Arg Lys His  Gln Ile Gln Met Phe  Glu Ser Thr
    4265                4270                4275

Pro Ala  Leu Val Ile Pro Phe  Met Asp Tyr Val Tyr  Asp Asn Asn
    4280                4285                4290

Leu Asp  Ile Ser Ser Leu Lys  Met Leu Ile Val Gly  Ser Asp His
    4295                4300                4305

Cys Pro  Thr Ala Glu Phe Asp  Lys Leu Thr Glu Arg  Cys Gly Ser
    4310                4315                4320

His Met  Arg Ile Leu Asn Ser  Tyr Gly Val Thr Glu  Ala Cys Val
    4325                4330                4335

Asp Ala  Cys Tyr Tyr Glu Arg  Thr Thr Pro Asp Ala  Leu Arg Thr
    4340                4345                4350

Leu Pro  Ile Gly Lys Pro Leu  Pro Ala Val Thr Met  Tyr Ile Leu
    4355                4360                4365

Asp Asp  Asn Arg Ser Leu Gln  Pro Ile Gly His Thr  Gly Glu Leu
    4370                4375                4380

Tyr Ile  Gly Gly Ala Gly Val  Gly Arg Gly Tyr Leu  Asn Arg Pro
    4385                4390                4395

Asp Leu  Thr Val Glu Lys Phe  Val Asp Asn Pro Phe  Met Pro Gly
    4400                4405                4410

Ala Arg  Met Tyr Arg Thr Gly  Asp Leu Ala Arg Trp  Leu Pro Asp
    4415                4420                4425

Gly Asn  Ile Glu Tyr Ala Gly  Arg Ile Asp His Gln  Val Lys Ile
    4430                4435                4440

Arg Gly  Tyr Arg Ile Glu Ile  Gly Glu Val Glu Ser  Gln Leu Leu
    4445                4450                4455

Ala Ala  Ala Gly Val Arg Glu  Ala Ala Val Val Ala  Arg Glu Asp
    4460                4465                4470

Gly Ser  Gly Gln Lys Val Leu  Cys Ala Tyr Phe Val  Ala Asp Ser
    4475                4480                4485

Ala Leu  Thr Val Gly Glu Leu  Arg Ala Ser Met Ala  Gln Gln Leu
    4490                4495                4500

Pro Gly  Tyr Met Ile Pro Ala  His Phe Val Gln Leu  Glu Arg Met
    4505                4510                4515

Pro Leu  Thr Pro Asn Gly Lys  Val Asp Arg Lys Gly  Leu Pro Ala
    4520                4525                4530
```

```
Pro Glu Gly Asn Ala Tyr Thr Gly Ala Glu His Val Ala Pro Arg
    4535                4540                4545

Thr Glu Ala Glu Lys Thr Leu Ala Ala Val Trp Gln Val Val Leu
    4550                4555                4560

Gly Ala Glu Gln Val Gly Leu Met Asp His Phe Phe Glu Leu Gly
    4565                4570                4575

Gly Asp Ser Ile Lys Ser Ile Gln Val Ser Ser Arg Leu His Gln
    4580                4585                4590

Ala Gly Tyr Lys Leu Glu Ile Arg Asp Leu Phe Lys Tyr Pro Thr
    4595                4600                4605

Ile Ala Glu Leu Ser Pro His Ile Gln Pro Ile Gly Arg Lys Ala
    4610                4615                4620

Asp Gln Gly Ala Val Thr Gly Glu Ala Ala Leu Thr Pro Ile Gln
    4625                4630                4635

His Trp Phe Phe Gly Gln Arg Phe Ala Asp Pro His His Tyr Asn
    4640                4645                4650

Gln Ser Ile Met Leu Tyr Arg Lys Glu Gly Phe Asp Glu Ala Ala
    4655                4660                4665

Ile Arg Lys Thr Leu Glu Lys Ile Ala Glu His His Asp Ala Leu
    4670                4675                4680

Arg Met Val Phe Arg Lys Thr Glu His Gly Tyr Ala Ala Trp Asn
    4685                4690                4695

Arg Gly Ile Gly Glu Gly Glu Leu Tyr Ser Leu Asn Val Ala Asp
    4700                4705                4710

Phe Thr Asp Asp Pro Ala Cys Tyr Arg Ala Ile Glu Ala Lys Ala
    4715                4720                4725

Asn Glu Ile Gln Ser Gly Ile Asn Leu Gln Ala Gly Pro Leu Leu
    4730                4735                4740

Arg Ala Gly Leu Phe Thr Cys Ala His Gly His His Leu Leu Ile
    4745                4750                4755

Val Ile His His Ala Val Thr Asp Gly Val Ser Trp Arg Ile Leu
    4760                4765                4770

Leu Glu Asp Ile Ala Ala Gly Tyr Glu Gln Ala Leu Lys Gly Glu
    4775                4780                4785

Ala Ile Arg Leu Pro Ala Lys Thr Asp Ser Tyr Leu Thr Trp Ser
    4790                4795                4800

Lys Gln Leu Ser Gly Tyr Ala Gln Ser Pro Ala Ile Glu Gln Glu
    4805                4810                4815

Arg Ser Tyr Trp Gln Arg Ile Ala Gln Ser Asn Thr Lys Pro Leu
    4820                4825                4830

Pro Lys Asp Arg Thr Val Asn Val Ser Leu Gln Arg Asp Ser Glu
    4835                4840                4845

Ser Val Ser Val Gln Trp Ser Arg Glu Asp Thr Glu Gln Leu Leu
    4850                4855                4860

Lys His Val His Arg Ala Tyr Asn Thr Asp Met Asn Asp Ile Leu
    4865                4870                4875

Leu Thr Ala Leu Gly Met Ala Ile Gln Gln Trp Ser Gly Arg Asp
    4880                4885                4890

Arg Met Leu Val Asn Leu Glu Gly His Gly Arg Glu Ser Ile Met
    4895                4900                4905

Ala Asp Val Asp Ile Ser Arg Thr Val Gly Trp Phe Thr Ser Glu
    4910                4915                4920
```

```
Tyr Pro  Val Leu Leu Glu Met  Glu Pro Asp Lys Ser  Leu Ser His
    4925                 4930                 4935

Cys Ile  Lys Lys Val Lys Glu  Asp Leu Arg Gln Ile  Pro His Lys
    4940                 4945                 4950

Gly Ile  Gly Tyr Gly Ile Cys  Arg Tyr Leu Ser Gly  Thr Met Glu
    4955                 4960                 4965

Asp Ala  Ala Trp Gly Thr Ala  Pro Glu Ile Ser Phe  Asn Tyr Leu
    4970                 4975                 4980

Gly Gln  Phe Asp Gln Asp Leu  Asn Ser Asn Gly Met  Glu Met Ser
    4985                 4990                 4995

Pro Tyr  Ser Ser Gly Thr Asp  Ala Ser Gly Lys Gln  Val Arg Gln
    5000                 5005                 5010

Tyr Ala  Leu Asp Ile Asn Gly  Gly Ile Thr Asp Gly  Ser Leu Ser
    5015                 5020                 5025

Phe Asp  Leu Ser Tyr Ser Arg  Lys Glu Tyr Arg Arg  Glu Thr Met
    5030                 5035                 5040

Glu Asp  Leu Ala Gly Arg Leu  Arg Glu Ser Leu Gln  Glu Ile Ile
    5045                 5050                 5055

Ala His  Cys Ala Ala Lys Glu  Arg Thr Glu Leu Thr  Pro Ser Asp
    5060                 5065                 5070

Val Leu  Leu Gln Gly Leu Ser  Val Glu Glu Leu Glu  Leu Ile Val
    5075                 5080                 5085

Glu Gln  Thr Arg His Val Gly  Glu Ile Glu Asn Ile  Tyr Ala Leu
    5090                 5095                 5100

Thr Pro  Met Gln Lys Gly Met  Trp Phe His Asn Ala  Ile Asp Gln
    5105                 5110                 5115

Gln Ala  Gly Ala Tyr Phe Glu  Gln Thr Arg Phe Thr  Ile Gln Gly
    5120                 5125                 5130

Val Leu  Asp Val Asp Val Phe  Ala Met Ser Leu Asn  Val Leu Ala
    5135                 5140                 5145

Lys Arg  His Ala Val Leu Arg  Thr Asn Phe Tyr Ser  Gly Trp Asn
    5150                 5155                 5160

Gly Glu  Pro Leu Gln Ile Val  Tyr Arg Asp Lys Arg  Ile Ala Phe
    5165                 5170                 5175

Val Tyr  Glu Asp Leu Arg His  Leu Pro Ala Ala Glu  Gln Thr Ala
    5180                 5185                 5190

His Ile  Glu His Ala Ala Arg  Glu Asp Lys Leu Lys  Gly Phe Asp
    5195                 5200                 5205

Leu Glu  Gln Asp Ala Leu Val  Arg Val Ala Leu Met  Arg Thr Gly
    5210                 5215                 5220

Ala Ala  Ser Cys Arg Val Leu  Trp Ser Ser His His  Ile Leu Met
    5225                 5230                 5235

Asp Gly  Trp Cys Leu Pro Gln  Leu Thr Gln Glu Leu  Phe Asp Thr
    5240                 5245                 5250

Tyr Ser  Ser Tyr Met Lys Gln  His His Asp Glu Gln  Ala Leu Pro
    5255                 5260                 5265

Ala Tyr  Ser Gln Ser Ser Tyr  Ser Gln Tyr Ile Glu  Trp Leu Glu
    5270                 5275                 5280

Gln Gln  Asp Glu Glu Ala Ala  Ala Gly Tyr Trp Ser  Glu Tyr Leu
    5285                 5290                 5295

Ala Gly  Tyr Asp Gln Gln Thr  Leu Leu Pro Gln Gly  Lys Thr Gln
    5300                 5305                 5310

Gly Arg  Asp Glu Ala Tyr Val  Leu Glu His Val Val  Cys Glu Leu
```

```
    5315                5320                5325

Gly Lys  Thr Leu Thr Gly Arg  Met Ser Gln Leu Ala  Lys Gln His
    5330                5335                5340

Ser Val  Thr Leu Asn Thr Leu  Leu Gln Ala Ala Trp  Gly Ile Ile
    5345                5350                5355

Leu Gln  Lys Tyr Asn Gly Thr  Asp Asp Val Val Phe  Gly Gly Val
    5360                5365                5370

Val Ser  Gly Arg Pro Ala Ala  Ile Pro Gly Ile Glu  Thr Met Ile
    5375                5380                5385

Gly Leu  Phe Ile Asn Thr Ile  Pro Val Arg Val Ala  Cys Ala Ala
    5390                5395                5400

Glu Thr  Ser Phe Thr Gln Val  Met Arg Arg Leu Gln  Glu Gln Ala
    5405                5410                5415

Leu Asp  Ser Gly Arg Tyr Asp  Tyr Tyr Pro Leu Tyr  Glu Ile Gln
    5420                5425                5430

Ala Gln  Cys Ala Gln Lys Gln  Glu Leu Ile Ser His  Ile Met Val
    5435                5440                5445

Phe Glu  Asn Tyr Pro Val Asp  Glu Gln Met Glu Gln  Thr Gly Ser
    5450                5455                5460

Lys Asp  Ser Gly Thr Leu Ser  Ile Thr Asp Val Glu  Val Ala Glu
    5465                5470                5475

Gln Thr  Asn Tyr Asp Phe Asn  Leu Met Val Val Pro  Gly Glu Glu
    5480                5485                5490

Leu Val  Val Arg Phe Asp Phe  Asn Gly Ser Val Phe  Asp Arg Thr
    5495                5500                5505

Ser Ile  Glu Arg Leu Thr Gly  His Leu Val His Val  Leu Glu Gln
    5510                5515                5520

Ile Thr  Ala Asn Pro Gln Ile  Ser Val Gly Asp Leu  Glu Leu Ala
    5525                5530                5535

Thr Ala  Ala Glu Lys Val Glu  Ile Val Asp Val Phe  Asn Asp Thr
    5540                5545                5550

Ala Ala  Asp Tyr Pro Arg Glu  Lys Thr Ile His Gln  Met Phe Glu
    5555                5560                5565

Glu Gln  Val Glu Arg Thr Pro  Asp Ala Val Ala Val  Met Phe Glu
    5570                5575                5580

Gln Glu  Arg Leu Thr Tyr Arg  Glu Leu Asn Glu Cys  Val Asn Arg
    5585                5590                5595

Leu Ala  Arg Thr Leu Arg Thr  Gln Gly Val Gln Pro  Asp Gln Arg
    5600                5605                5610

Val Gly  Ile Met Val Glu Arg  Ser Leu Glu Met Met  Val Gly Ile
    5615                5620                5625

Met Ala  Ile Leu Lys Ala Gly  Gly Ala Tyr Val Pro  Ile Ala Pro
    5630                5635                5640

Asp Tyr  Pro Glu Glu Arg Ile  His Tyr Met Leu Glu  Asp Ser Gly
    5645                5650                5655

Ala Gln  Val Leu Leu Leu Gln  Gly Arg Ser Gly Glu  Ser Val Ser
    5660                5665                5670

Phe Ala  Gly Arg Ile Val Asn  Leu Asp Asp Glu Ser  Ser Tyr Ala
    5675                5680                5685

Glu Asp  Gly Ser Asn Leu Glu  Trp Val Asn Gln Ala  Ser Asp Ala
    5690                5695                5700

Ala Tyr  Val Ile Tyr Thr Ser  Gly Thr Thr Gly Lys  Pro Lys Gly
    5705                5710                5715
```

```
Val Leu Val Glu His Gly Ser Val Ile Asn Arg Leu Leu Trp Met
    5720                5725                5730

Gln Lys Gln Tyr Pro Ile Asn Ala Asn Asp Thr Ile Met Gln Lys
    5735                5740                5745

Thr Ala Ile Thr Phe Asp Val Ser Val Trp Glu Leu Phe Trp Trp
    5750                5755                5760

Ala Phe Val Gly Ser Lys Val Cys Leu Leu Pro Val Gly Gly Glu
    5765                5770                5775

Lys Asn Pro Ala Val Ile Leu Asp Thr Ile Ala Gln Gln His Ile
    5780                5785                5790

Ser Thr Met His Phe Val Pro Ser Met Leu His Ala Phe Leu Glu
    5795                5800                5805

Tyr Val Glu Glu Gln Pro Ile Ala Glu Arg Glu Arg Ser Leu Ala
    5810                5815                5820

Ala Leu Ser Arg Val Phe Ala Ser Gly Glu Ala Leu Thr Leu Ser
    5825                5830                5835

Gln Val Glu Arg Phe Glu Arg Cys Ile Ala Pro Ala Ser Gly Ala
    5840                5845                5850

Arg Leu Ile Asn Leu Tyr Gly Pro Thr Glu Ala Thr Val Asp Val
    5855                5860                5865

Thr Tyr Tyr Asp Cys Glu Ala Gly Gln Pro Tyr Thr Ser Val Pro
    5870                5875                5880

Ile Gly Lys Pro Ile Asp Asn Thr Gln Ile Tyr Ile Val Asn Arg
    5885                5890                5895

Gln Asp Gln Leu Gln Pro Ile Gly Val Ala Gly Glu Leu Cys Ile
    5900                5905                5910

Ala Gly Val Gly Leu Ala Arg Gly Tyr Leu Lys Arg Pro Glu Leu
    5915                5920                5925

Thr Ala Glu Lys Phe Val Thr Ile Pro Phe Met Pro Gly Ala Arg
    5930                5935                5940

Met Tyr Arg Thr Gly Asp Leu Ala Arg Trp Leu Pro Asp Gly Ser
    5945                5950                5955

Ile Glu Tyr Leu Gly Arg Ile Asp His Gln Val Lys Ile Arg Gly
    5960                5965                5970

Tyr Arg Ile Glu Leu Gly Glu Ile Glu Ala Gln Leu Leu Gln Val
    5975                5980                5985

Glu Phe Ile Arg Glu Ala Val Val Val Ala Arg Glu Asp Glu Ser
    5990                5995                6000

Gly Gln Lys Ala Leu Cys Ala Tyr Phe Ala Ala Asp Ser Glu Leu
    6005                6010                6015

Pro Val Ser Glu Leu Arg Ser Ala Leu Ala Val Glu Leu Pro Gly
    6020                6025                6030

Tyr Met Ile Pro Ser Tyr Phe Val Gln Leu Glu Arg Leu Pro Leu
    6035                6040                6045

Ser Ala Asn Gly Lys Leu Asp Arg Lys Ala Leu Pro Ala Pro Gly
    6050                6055                6060

Gly Ser Met Arg Ser Gly Lys Glu His Val Ala Pro Arg Ser Leu
    6065                6070                6075

Leu Glu Val Lys Leu Val Arg Ile Trp Gln Glu Val Leu Gly Leu
    6080                6085                6090

Ala His Val Ser Val Lys Asp Asp Phe Phe Glu Leu Gly Gly His
    6095                6100                6105
```

```
Ser Leu  Arg Ala Thr Thr Leu  Val Ser Lys Leu His  Lys Glu Leu
    6110                 6115                 6120

Asn Ile  Asn Leu Pro Leu Arg  Asp Val Phe Arg Tyr  Ser Ile Leu
    6125                 6130                 6135

Glu Asp  Met Ala Leu Ala Ile  Gly Arg Thr Glu Gln  Arg Glu Phe
    6140                 6145                 6150

Gln Thr  Ile Pro Gln Val Glu  Ala Ser Asp Tyr Tyr  Pro Leu Ser
    6155                 6160                 6165

Ser Ala  Gln Lys Arg Leu Tyr  Ile Val Gln Gln Val  Glu Gly Ala
    6170                 6175                 6180

Glu Gln  Ser Tyr Asn Met Pro  Gly Ala Met Ser Ile  Arg Gly Gln
    6185                 6190                 6195

Leu Asp  Arg Asn Gln Phe Glu  Ala Ala Phe Arg Gly  Leu Ile Ala
    6200                 6205                 6210

Arg His  Glu Val Phe Arg Thr  Ser Phe Glu Met Val  Gly Gly Glu
    6215                 6220                 6225

Pro Met  Gln Arg Val His Gln  Asp Thr Ala Phe Ala  Val Glu Tyr
    6230                 6235                 6240

Met Gln  Ala Asn Glu Glu Glu  Ala Glu Ala Ile Ala  His Gln Phe
    6245                 6250                 6255

Val Arg  Thr Phe Asp Leu Glu  Gln Pro Ser Leu Leu  Arg Val Gly
    6260                 6265                 6270

Leu Ile  Glu Leu Asp Arg Glu  His His Ile Met Leu  Phe Asp Met
    6275                 6280                 6285

His His  Ile Ile Ser Asp Gly  Val Ser Met Gly Ile  Leu Val Glu
    6290                 6295                 6300

Glu Phe  Ala Arg Leu Tyr Ser  Gly Glu Glu Leu Pro  Pro Leu Arg
    6305                 6310                 6315

Ile Gln  Tyr Lys Asp Tyr Ala  Ala Trp Gln Gln Ser  Glu Ala Gln
    6320                 6325                 6330

Ser Glu  Arg Ile Lys Gln Gln  Glu Ala Tyr Trp Leu  Asp Ala Leu
    6335                 6340                 6345

Asp Gly  Glu Leu Pro Gln Leu  Glu Leu Pro Thr Asp  Phe Ala Arg
    6350                 6355                 6360

Pro Ala  His Gln Ser His Glu  Gly Asp Thr Leu Asp  Phe Val Ile
    6365                 6370                 6375

Asp Ser  His Met Ser Gly Gly  Leu Gln Arg Leu Ala  Glu His Thr
    6380                 6385                 6390

Gly Thr  Thr Leu Tyr Met Val  Leu Leu Ala Ala Tyr  Thr Ile Leu
    6395                 6400                 6405

Leu His  Lys Tyr Ser Asp Gln  Glu Asp Ile Ile Val  Gly Thr Pro
    6410                 6415                 6420

Ile Ala  Gly Arg Thr His Ala  Asp Val Glu Pro Leu  Ile Gly Met
    6425                 6430                 6435

Phe Val  Asn Ser Leu Ala Leu  Arg Ser Tyr Pro Cys  Gly Glu Lys
    6440                 6445                 6450

Ser Phe  Leu Ser Tyr Leu Glu  Glu Val Lys Glu Met  Thr Leu Ala
    6455                 6460                 6465

Ala Tyr  Glu Asn Gln Asp Tyr  Pro Phe Ala Glu Leu  Val Glu His
    6470                 6475                 6480

Val Gln  Ala Val Trp Ser Pro  Ser Arg Asn Pro Leu  Phe Asp Thr
    6485                 6490                 6495

Met Phe  Val Leu Gln Asn Thr  Glu Asp Arg Asn Val  Arg Phe Gly
```

6500 6505 6510

Glu Leu Thr Ile Glu Pro Tyr Thr Gln His His Asn Val Ala Lys
6515 6520 6525

Phe Asp Leu Thr Leu Glu Ile Ala Leu Glu Asp Gly Val Met Ser
6530 6535 6540

Gly His Phe Glu Tyr Cys Thr Arg Leu Phe Thr Thr Asn Met Val
6545 6550 6555

Asp Asn Phe Ala Glu Asp Leu Leu Ser Ile Leu Ala Gln Ile Cys
6560 6565 6570

Glu Gln Pro Ala Ile Arg Leu Gly Asp Ile His Leu His Gly Asn
6575 6580 6585

Ala Glu Glu Asp Glu Glu Ala Ser Leu Ala Glu Glu Ile Asp Phe
6590 6595 6600

Val Phe
6605

<210> SEQ ID NO 18
<211> LENGTH: 6416
<212> TYPE: PRT
<213> ORGANISM: Paenibacillus sp. OSY-SE

<400> SEQUENCE: 18

Met Asn Leu Ala Phe Glu Lys Glu Thr Asp Phe Trp Asn Ala Gln Phe
1 5 10 15

Asp Ala Glu Asp Ser Pro Ala Ile Leu Pro Tyr Ser Thr Ala Ser Ile
20 25 30

Ser Val Thr Ala Arg Asp His Ser Asn Ser Ile Ser Leu Ser Ala Asp
35 40 45

Val Ser Gln Arg Ile Ser His Met Ser Arg Gly Ser His Leu Ala Glu
50 55 60

Tyr Met Ile Leu Leu Ala Gly Ile Gln Cys Leu Leu Tyr Lys Tyr Thr
65 70 75 80

Gly Glu Glu Ser Val Ile Val Gly Met Pro Ile Val Arg Lys Ser Lys
85 90 95

Asp Thr Arg Arg Pro Ile Asn Asn Val Val Ile Leu Lys Asn Lys Leu
100 105 110

Gly Ala Asn Arg Thr Phe Lys Ser Leu Leu Thr Glu Leu Lys Thr Thr
115 120 125

Leu Thr Ala Ala Ile Asn His Gln Asn Ile Pro Phe Arg Lys Met Thr
130 135 140

Glu His Leu His Leu Glu Ala Val Asn Gly Val Pro Val Val Asn Thr
145 150 155 160

Met Val Ser Met Lys Glu Ile His Thr Ile Glu Phe Ser Gln Ser Val
165 170 175

Val Ser Asp Ile Leu Phe Gln Phe Glu Trp Glu Gln Asp Val Ile Ser
180 185 190

Leu His Val Thr Tyr Asn Glu Asn Arg Tyr Asp Lys Pro Phe Ile Thr
195 200 205

Gln Ile Met Asn His Val Asn Ser Leu Phe Ala Asp Val Leu Tyr Thr
210 215 220

Pro Glu Arg Val Leu Gln Asp Val Asn Leu Leu Ser Glu Gln Glu Thr
225 230 235 240

Ala Gln Leu Leu Tyr Glu Phe Asn Asp Thr Ala Ala Asp Tyr Pro Arg
245 250 255

-continued

```
Asp Lys Thr Ile His Gln Leu Phe Glu Glu Gln Glu Glu Gln Thr Pro
            260                 265                 270

Asp Ala Val Ala Val Leu Phe Glu Asp Lys Gln Leu Thr Tyr Ala Glu
        275                 280                 285

Leu Asn Ala Ala Ala Asn Arg Ile Ala His Leu Leu Arg Glu Arg Gly
    290                 295                 300

Val Ala Arg Gly Thr Leu Val Gly Ile Cys Val Glu Arg Ser Leu Glu
305                 310                 315                 320

Met Val Ile Gly Leu Leu Gly Ile Leu Lys Ala Gly Gly Ala Tyr Val
                325                 330                 335

Pro Ile Asp Pro Asp Tyr Pro Glu Glu Arg Thr Asn Ala Met Leu Glu
            340                 345                 350

Asp Thr Ala Ile Ser Val Leu Leu Thr Gln Ala His Leu Gln Thr Ser
        355                 360                 365

Met Pro Asn Ser Ile Asp Ser Val Leu Leu Asp Ala Ala Ala Glu Thr
    370                 375                 380

Ala Leu Glu Gly Ser Trp Pro Asn Leu Thr Asp Ala Ala Gly Thr Ala
385                 390                 395                 400

Asp Asp Val Ala Tyr Ile Ile Tyr Thr Ser Gly Ser Thr Gly Ile Pro
                405                 410                 415

Lys Gly Val Cys Val Thr His Arg Gly Val Val Arg Leu Ile Ala Ala
            420                 425                 430

Ala Asn Tyr Val Asp Ile Ser Ser Lys Asp Val Phe Leu Gln Gly Ser
        435                 440                 445

Thr Ile Ser Phe Asp Ala Ala Thr Phe Glu Ile Trp Gly Ser Leu Leu
    450                 455                 460

Asn Gly Ala Ala Leu Ala Ile Leu Pro Pro Gly Asn Val Ser Leu Thr
465                 470                 475                 480

Glu Trp Thr Glu Ala Ile Gln Gln His Gln Val Thr Ile Leu Trp Leu
                485                 490                 495

Thr Ala Gly Leu Phe His Val Met Val Glu Asn Gln Leu Gln Ala Leu
            500                 505                 510

Gln Gly Val Gln Gln Leu Leu Val Gly Gly Asp Val Val Ser Lys Thr
        515                 520                 525

His Ala Lys Lys Val Leu Glu Arg Tyr Gln Asp Ile Arg Leu Val Asn
    530                 535                 540

Gly Tyr Gly Pro Thr Glu Asn Thr Thr Phe Thr Cys Cys His Glu Ile
545                 550                 555                 560

Ser Ala Ala Asp Thr Glu Arg Leu Ser Ile Pro Ile Gly Arg Pro Ile
                565                 570                 575

Ala Asn Thr Gln Val Tyr Val Leu Asp Glu Ala Gly Lys Leu Leu Pro
            580                 585                 590

Val Gly Val Val Gly Glu Leu Tyr Thr Gly Gly Asp Gly Leu Ala Arg
        595                 600                 605

Gly Tyr Trp Asn Arg Pro Glu Leu Thr Ala Glu Lys Phe Val Asp Ser
    610                 615                 620

Pro Phe Val Pro Gly Thr Arg Leu Tyr Arg Thr Gly Asp Leu Ala Arg
625                 630                 635                 640

Trp Leu Pro Asp Gly Thr Ile Glu Tyr Val Gly Arg Ile Asp Asp Gln
                645                 650                 655

Val Lys Ile Ser Gly Tyr Arg Ile Glu Leu Gly Glu Val Glu Ala His
            660                 665                 670

Leu Leu Lys Val Glu Ser Val Leu Asp Ala Ile Val Ile Ala Arg Gln
```

```
        675                 680                 685

Asp Glu Ser Gly Gln Lys Thr Leu Cys Ala Tyr Phe Thr Ala Asn Ala
    690                 695                 700

Glu Leu Met Ala Gly Asp Leu Arg Ala Val Leu Ser Gln Glu Leu Pro
705                 710                 715                 720

Ala Tyr Met Ile Pro Thr His Phe Val Gln Val Asp Arg Met Pro Leu
                725                 730                 735

Thr Pro Asn Gly Lys Val Asp Arg Arg Ala Leu Pro Glu Pro Glu Gly
            740                 745                 750

Leu Ile Met Thr Gly Lys Glu His Val Ala Pro Arg Thr Pro Leu Glu
        755                 760                 765

Ser Asn Leu Ala His Leu Trp Gln Glu Val Leu Gly Leu Glu Lys Val
    770                 775                 780

Ser Val Lys Asp Ser Phe Phe Glu Ile Gly Gly His Ser Leu Arg Ala
785                 790                 795                 800

Thr Thr Leu Ala Ser Lys Leu His Lys Glu Leu His Val Ser Leu Pro
                805                 810                 815

Leu Arg Asp Ile Phe Arg His Pro Thr Ile Glu Glu Leu Ala Cys Leu
            820                 825                 830

Ile Asp Gly Met Glu Arg Gln Glu Tyr Arg Gln Ile Pro Leu Leu Asp
        835                 840                 845

Glu Arg Asp Trp Tyr Pro Val Ser Ser Ala Gln Lys Arg Leu Tyr Ile
    850                 855                 860

Leu His Gln Leu Glu Gly Ala Glu Gln Ser Tyr Asn Met Pro Gly Val
865                 870                 875                 880

Met Leu Leu Glu Gly Gln Leu Asp Arg Asn Arg Phe Glu Glu Ala Phe
                885                 890                 895

Arg Ser Leu Ile Gly Arg His Glu Thr Leu Arg Thr Gly Phe Glu Met
            900                 905                 910

Val Asn Gly Glu Pro Val Gln Arg Ile Cys Arg Glu Val Asn Phe Ser
        915                 920                 925

Val Glu Met Met Gln Ala Ser Glu Gly Glu Ala Asp Ala Ala Ile Arg
    930                 935                 940

Ser Phe Ile Arg Pro Phe Asp Leu Glu Lys Pro Pro Leu Leu Arg Val
945                 950                 955                 960

Gly Leu Ile Glu Leu Ser Gln Asp Arg His Ile Leu Met Tyr Asp Met
                965                 970                 975

His His Ile Ile Ser Asp Gly Val Ser Met Glu Ile Val Val Glu Glu
            980                 985                 990

Phe Val Arg Leu Tyr Gly Gly Glu  Lys Leu Pro Pro Leu  Arg Ile Gln
        995                 1000                1005

Tyr Lys  Asp Tyr Ala Ala Trp  Gln Gln Ser Glu Pro  Gln Gln Glu
    1010                 1015                 1020

Leu Met  Lys Gln Gln Glu Ser  Tyr Trp Leu Gln Ala  Phe Gly Gly
    1025                 1030                 1035

Glu Leu  Pro Val Leu Glu Met  Pro Ala Asp Tyr Ala  Arg Pro Ser
    1040                 1045                 1050

Val Gln  Ser Tyr Glu Gly Asp  Thr Phe Glu Phe Ala  Ile Asp Pro
    1055                 1060                 1065

Gly Leu  Ser Glu Ala Leu Arg  Arg Ile Ala Ala Glu  Ser Gly Thr
    1070                 1075                 1080

Thr Leu  Tyr Met Val Leu Leu  Ala Ala Tyr Thr Ile  Leu Leu Gln
    1085                 1090                 1095
```

Lys Tyr Thr Gly Gln Glu Asp Ile Ile Val Gly Thr Pro Asn Ala
1100 1105 1110

Gly Arg Thr His Gly Asp Leu Gln Pro Leu Ile Gly Met Phe Val
1115 1120 1125

Asn Thr Leu Ala Ile Arg Asn Tyr Pro Ala Gly Ser Lys Thr Phe
1130 1135 1140

Leu Glu Tyr Leu Glu Gln Val Lys Glu Thr Ser Leu Gly Ala Phe
1145 1150 1155

Glu Asn Gln Asp Tyr Pro Phe Glu Glu Leu Val Glu Lys Leu Gln
1160 1165 1170

Val Ala Arg Asp Leu Ser Arg Asn Pro Leu Phe Asp Thr Met Phe
1175 1180 1185

Ser Leu His Asn Met Asp Ser Lys Asp Leu Glu Leu Ala Glu Leu
1190 1195 1200

Arg Leu Lys Pro Tyr Pro Ala Glu Tyr Lys Val Ala Lys Phe Asp
1205 1210 1215

Leu Ser Leu Asp Val Ala Glu Gly Ala Glu Gly Met Ala Cys Ser
1220 1225 1230

Leu Glu Tyr Ala Thr Ala Leu Tyr Arg Arg Glu Ser Ile Glu Arg
1235 1240 1245

Met Ala Lys His Phe Gly Gln Leu Leu Glu Ala Ile Thr Gln Glu
1250 1255 1260

Pro Glu Ala Arg Leu Ser Ser Leu Gly Met Leu Thr Glu Glu Glu
1265 1270 1275

Lys Ala Gln Ile Gln His Val Phe Asn Asp Ala Glu Ala Gly Arg
1280 1285 1290

Ser Gln Gln Lys Thr Val Pro Glu Leu Phe Glu Glu Gln Val Glu
1295 1300 1305

Arg Thr Pro Asp Arg Ile Ala Val Val His Glu Asp Lys Gln Leu
1310 1315 1320

Thr Tyr Arg Glu Leu Asn Glu Arg Ala Asn Arg Leu Ala Arg Thr
1325 1330 1335

Leu Arg Ala Glu Asp Val Lys Pro Glu Gln Leu Val Gly Ile Met
1340 1345 1350

Ala Asp Arg Ser Leu Asp Met Ile Val Gly Ile Met Ala Ile Leu
1355 1360 1365

Lys Ser Gly Gly Ala Tyr Val Pro Ile Asp Pro Lys Tyr Pro Glu
1370 1375 1380

Asp Arg Ile His Tyr Met Leu Asp Asp Ser Asn Ala Gln Val Leu
1385 1390 1395

Leu Ala Gln Arg His Leu Gln Ala Arg Ala Ala Phe Ser Gly Arg
1400 1405 1410

Arg Ile Thr Leu Asp Glu Glu Ala Phe Tyr Asp Glu Asp Gly Ser
1415 1420 1425

Asn Leu Glu Arg Val Asn Gln Pro Glu His Leu Ser Tyr Val Ile
1430 1435 1440

Tyr Thr Ser Gly Thr Thr Gly Lys Pro Lys Gly Val Met Ile Glu
1445 1450 1455

His Arg Gln Met Ala Val Leu Ser Ala Ala Trp Glu Ser Glu Tyr
1460 1465 1470

Gly Leu Arg Glu Glu Ser Met Arg Trp Met Gln Trp Ala Ser Phe
1475 1480 1485

```
Ser Phe  Asp Val Phe Ser Gly  Asp Leu Ile Arg Ala  Leu Leu His
    1490                 1495                 1500

Gly Gly  Glu Leu Ile Leu Cys  Pro Glu Glu Ser Arg  Ala Asn Pro
    1505                 1510                 1515

Ala Glu  Ile Tyr Glu Leu Ile  Arg Lys His Arg Ile  Gln Met Phe
    1520                 1525                 1530

Asp Val  Thr Pro Ser Leu Ala  Ile Pro Leu Met Glu  Tyr Val Tyr
    1535                 1540                 1545

Glu Asn  Lys Leu Asp Ile Ser  Ser Met Lys Leu Ala  Val Val Gly
    1550                 1555                 1560

Ala Asp  His Cys Pro Lys Glu  Glu Phe Gln Lys Leu  Leu Glu Arg
    1565                 1570                 1575

Phe Gly  Ser Gln Met Arg Ile  Val Asn Ser Tyr Gly  Val Thr Glu
    1580                 1585                 1590

Thr Thr  Ile Asp Ser Cys Tyr  Phe Glu Gln Ala Ser  Thr Glu Gly
    1595                 1600                 1605

Leu Arg  Thr Val Pro Ile Gly  Lys Pro Leu Pro Gly  Val Thr Met
    1610                 1615                 1620

Tyr Ile  Leu Asp Asp His His  Ser Leu Leu Pro Val  Gly Ile Thr
    1625                 1630                 1635

Gly Glu  Leu Tyr Ile Gly Gly  Pro Cys Val Gly Arg  Gly Tyr Trp
    1640                 1645                 1650

Lys Arg  Pro Asp Leu Thr Ala  Glu Lys Phe Val Asp  Asn Pro Phe
    1655                 1660                 1665

Ala Pro  Gly Glu Arg Met Tyr  Arg Thr Gly Asp Leu  Ala Arg Trp
    1670                 1675                 1680

Leu Pro  Asp Gly Asn Val Glu  Tyr Leu Gly Arg Ile  Asp His Gln
    1685                 1690                 1695

Val Lys  Ile Arg Gly Tyr Arg  Ile Glu Ile Gly Glu  Val Glu Ser
    1700                 1705                 1710

Gln Leu  Leu Lys Thr Pro Phe  Ile Arg Glu Ala Val  Val Val Ala
    1715                 1720                 1725

Arg Glu  Asp Ala Gly Gly Gln  Lys Ser Leu Cys Ala  Tyr Phe Val
    1730                 1735                 1740

Ala Glu  Arg Glu Leu Thr Val  Ser Glu Leu Arg Gly  Ala Leu Ala
    1745                 1750                 1755

Ala Glu  Leu Pro Gly Tyr Met  Ile Pro Ser Tyr Phe  Val Gln Leu
    1760                 1765                 1770

Lys Gln  Leu Pro Leu Thr Pro  Asn Gly Lys Ile Asp  Arg Lys Ala
    1775                 1780                 1785

Leu Pro  Ala Pro Glu Gly Ser  Ala His Thr Gly Thr  Asp Tyr Val
    1790                 1795                 1800

Ala Pro  Arg Thr Glu Ala Glu  Lys Thr Leu Ala Ala  Val Trp Gln
    1805                 1810                 1815

Ala Val  Leu Gly Ala Glu Arg  Val Gly Leu Met Asp  His Phe Phe
    1820                 1825                 1830

Glu Leu  Gly Gly Asp Ser Ile  Lys Ser Ile Gln Val  Ser Ser Arg
    1835                 1840                 1845

Leu His  Gln Ala Gly Tyr Lys  Leu Glu Ile Arg Asp  Leu Phe Lys
    1850                 1855                 1860

Tyr Pro  Thr Ile Ala Glu Leu  Ser Pro His Ile Gln  Pro Val Gly
    1865                 1870                 1875

Arg Met  Ala Asp Gln Gly Glu  Val Ser Gly Thr Val  Pro Leu Thr
```

```
    1880                1885                1890

Pro Ile  Gln Arg Trp Tyr Phe  Gly Gln Gln Phe Ala  Asp Pro His
    1895                1900                1905

His Tyr  Asn Gln Ser Val Met  Leu His Arg Lys Glu  Gly Phe Asp
    1910                1915                1920

Thr Ala  Ala Ile Arg Lys Ala  Leu Gln Lys Leu Val  Glu His His
    1925                1930                1935

Asp Gly  Leu Arg Met Val Phe  Arg Lys Thr Glu Glu  Gly Tyr Thr
    1940                1945                1950

Ala Trp  Asn Arg Gly Ile Gly  Glu Gly Glu Leu Tyr  Arg Leu Tyr
    1955                1960                1965

Val Ala  Asp Phe Thr Gly Val  Ala Ala Cys Glu Arg  Met Ile Glu
    1970                1975                1980

Ala Ala  Ala Asn Glu Ile Gln  Ser Gly Ile Asp Leu  Gln Ala Gly
    1985                1990                1995

Pro Leu  Val Arg Ala Gly Leu  Phe His Gly Ala Asp  Gly Asp His
    2000                2005                2010

Leu Leu  Ile Val Ile His His  Ala Val Val Asp Gly  Val Ser Trp
    2015                2020                2025

Arg Ile  Leu Leu Glu Asp Phe  Ala Ala Ser Tyr Glu  Gln Ala Leu
    2030                2035                2040

Lys Gly  Gln Ala Leu Arg Leu  Pro Phe Lys Thr Asp  Ser Tyr Arg
    2045                2050                2055

Thr Trp  Ser Asp Gln Leu Val  Glu Tyr Ala Arg Ser  Pro Val Met
    2060                2065                2070

Gln Arg  Glu Arg Ala Tyr Trp  Gln Arg Ile Ala Gln  Thr Ala Ala
    2075                2080                2085

Lys Pro  Leu Pro Arg Asp Tyr  Glu Ala Glu Cys Ser  Leu Gln Gln
    2090                2095                2100

Asp Ser  Glu Ser Val Thr Val  Gln Trp Ser Gln Glu  Ala Thr Glu
    2105                2110                2115

Gln Leu  Leu Lys His Val His  Arg Ala Tyr Asn Thr  Glu Met Asn
    2120                2125                2130

Asp Ile  Leu Leu Thr Ala Leu  Gly Met Ala Val Gln  Lys Trp Cys
    2135                2140                2145

Gly Arg  Asp Arg Val Leu Val  Thr Leu Glu Gly His  Gly Arg Glu
    2150                2155                2160

Ser Ile  Met Thr Asp Ile Asp  Ile Thr Arg Thr Val  Gly Trp Phe
    2165                2170                2175

Thr Ser  Glu Tyr Pro Val Leu  Leu Glu Met Glu Pro  Asp Lys Ser
    2180                2185                2190

Leu Ser  Ser Arg Ile Lys Lys  Met Lys Glu Asp Leu  Arg Gln Ile
    2195                2200                2205

Pro Asn  Lys Gly Ile Gly Tyr  Gly Ile Gly Arg Tyr  Met Ser Glu
    2210                2215                2220

Leu His  Asp Glu Ala Val Trp  Gly Gly Ala Glu Pro  Asp Ile Ser
    2225                2230                2235

Phe Asn  Tyr Leu Gly Gln Phe  Asp Gln Asp Met Lys  Asn Asn Glu
    2240                2245                2250

Met Glu  Val Ser Pro Tyr Ser  Ser Gly Met Glu Val  Ser Arg Gln
    2255                2260                2265

Gln Ala  Arg Thr His Ala Leu  Asp Ile Asn Gly Met  Val Ala Asp
    2270                2275                2280
```

```
Gly Ser  Leu Ala Leu Glu Leu  Ser Tyr Ser Arg Lys  Glu Tyr Arg
    2285                 2290                 2295

Lys Glu  Thr Ile Glu Ala Leu  Ser Ile Tyr Leu Gln  Glu Ser Leu
    2300                 2305                 2310

Gln Glu  Ile Ile Leu His Cys  Thr Ala Lys Glu Arg  Pro Glu Val
    2315                 2320                 2325

Thr Pro  Ser Asp Ile Leu Leu  Gln Gly Leu Ser Val  Glu Glu Leu
    2330                 2335                 2340

Glu Gln  Ile Ala Lys Gln Thr  Gln Arg Ile Gly Asp  Ile Glu Asn
    2345                 2350                 2355

Met Tyr  Thr Leu Thr Pro Met  Gln Lys Gly Met Trp  Phe His Ser
    2360                 2365                 2370

Ala Met  Asp Gln His Ala Gly  Ala Tyr Phe Glu Gln  Thr Arg Phe
    2375                 2380                 2385

Thr Leu  Gln Gly Ala Leu Asp  Val Glu Val Phe Ala  Lys Ser Leu
    2390                 2395                 2400

Asp Ala  Leu Ala Lys Gln His  Ala Val Leu Arg Thr  Asn Phe Tyr
    2405                 2410                 2415

Asn Gly  Trp Asn Gly Glu Leu  Leu Gln Ile Val Phe  Arg Asp Lys
    2420                 2425                 2430

Arg Leu  Gly Phe Ala Tyr Glu  Asp Leu Cys Ala Leu  Pro Glu Ala
    2435                 2440                 2445

Glu Arg  Glu Thr His Val Glu  Thr Leu Thr Gln Glu  Asp Arg Met
    2450                 2455                 2460

Arg Gly  Phe Asp Leu Glu Gln  Asp Ala Leu Met Arg  Val Ser Val
    2465                 2470                 2475

Val Arg  Met Ala Glu Glu Ser  Tyr Gln Val Leu Trp  Ser Ser His
    2480                 2485                 2490

His Ile  Leu Met Asp Gly Trp  Cys Leu Pro Gln Leu  Thr Gln Glu
    2495                 2500                 2505

Trp Phe  Asp Thr Tyr Ser Ala  Tyr Val Gln His Gln  His Leu Glu
    2510                 2515                 2520

Arg Thr  Thr Ala Pro Ala Tyr  Ser Gln Tyr Ile Glu  Trp Leu Glu
    2525                 2530                 2535

Gln Gln  Asp Asp Gln Ala Ala  Ser Ala Tyr Trp Ala  Asn Tyr Leu
    2540                 2545                 2550

Ala Gly  Tyr Asp Gln Gln Thr  Val Leu Pro Gln Ala  Lys Gly Gln
    2555                 2560                 2565

Gly Arg  Ser Asp Glu Tyr Ala  Ala Glu Arg Ile Leu  Cys Glu Leu
    2570                 2575                 2580

Gly Lys  Ala Leu Thr Gly Arg  Met Ser His Val Ala  Lys Gln His
    2585                 2590                 2595

Gln Val  Thr Leu Asn Thr Leu  Met Gln Ala Ala Trp  Ala Ile Leu
    2600                 2605                 2610

Leu Gln  Lys Tyr Asn Gly Thr  Asp Asp Val Val Phe  Gly Gly Val
    2615                 2620                 2625

Val Ser  Gly Arg Pro Ala Glu  Ile Pro Gly Ile Glu  Ala Met Ile
    2630                 2635                 2640

Gly Leu  Phe Ile Asn Thr Ile  Pro Val Arg Val Thr  Cys Glu Ala
    2645                 2650                 2655

Glu Thr  Ser Phe Ala Glu Leu  Met Gly Arg Leu Gln  Glu Gln Ala
    2660                 2665                 2670
```

```
Leu Glu  Ser Gly Arg Tyr Asp  Tyr Tyr Pro Leu Tyr  Glu Ile Gln
    2675                 2680                 2685

Ala Gln  Cys Glu Gln Lys Gln  Asp Leu Ile Ser His  Leu Met Val
    2690                 2695                 2700

Phe Glu  Asn Tyr Pro Met Glu  Glu Gln Met Glu Gln  Ala Gly Ser
    2705                 2710                 2715

Asp Asp  Arg Gly Lys Leu Thr  Ile Thr Asp Val Glu  Val Ala Glu
    2720                 2725                 2730

Gln Thr  Asn Tyr Asp Phe Asn  Leu Val Val Val Pro  Gly Asp Glu
    2735                 2740                 2745

Ile Val  Ile Arg Leu Glu Tyr  Asn Ala Asn Val Phe  Asp Arg Glu
    2750                 2755                 2760

Ser Ile  Glu Gln Leu Gln Gly  His Leu Val His Val  Leu Glu Gln
    2765                 2770                 2775

Ile Thr  Ala Asn Pro His Met  Ala Val Gly Glu Leu  Glu Leu Ala
    2780                 2785                 2790

Thr Ala  Gly Glu Lys Thr Gln  Leu Met Leu Ala Phe  Asn Asp Thr
    2795                 2800                 2805

Ala Ala  Glu Tyr Pro Arg Glu  Lys Thr Ile His Gln  Met Phe Glu
    2810                 2815                 2820

Glu Gln  Ala Glu Arg Thr Pro  Asp Ala Ala Ala Val  Leu Phe Glu
    2825                 2830                 2835

Gln Glu  Gln Leu Thr Tyr Arg  Glu Leu Asn Glu Arg  Ala Asn Arg
    2840                 2845                 2850

Leu Ala  Arg Thr Leu Arg Ala  Leu Gly Val Gln Pro  Asp Gln Leu
    2855                 2860                 2865

Val Gly  Ile Met Ala Glu Arg  Ser Leu Glu Met Met  Val Gly Ile
    2870                 2875                 2880

Met Ala  Ile Leu Lys Ala Gly  Gly Ala Tyr Val Pro  Ile Ala Ala
    2885                 2890                 2895

Asp Ser  Pro Glu Glu Arg Ile  Arg Tyr Leu Leu Glu  Asp Ser Gly
    2900                 2905                 2910

Ala Gln  Val Leu Leu Leu Gln  Gly Arg Ala Gly Glu  Glu Val Ser
    2915                 2920                 2925

Phe Ala  Gly Arg Ile Val Asn  Leu Asp Asp Ala Asn  Ser Tyr Ala
    2930                 2935                 2940

Gly Asp  Gly Ser Asn Pro Glu  Arg Val Asn Gln Ala  Ser Asp Ala
    2945                 2950                 2955

Ala Tyr  Val Ile Tyr Thr Ser  Gly Thr Thr Gly Arg  Pro Lys Gly
    2960                 2965                 2970

Val Leu  Val Glu His Gly Ser  Val Ile Asn Arg Leu  Leu Trp Met
    2975                 2980                 2985

Gln Lys  Arg Tyr Pro Ile Gly  Pro Ser Asp Thr Ile  Met Gln Lys
    2990                 2995                 3000

Thr Ala  Ile Thr Phe Asp Val  Ser Val Trp Glu Leu  Phe Trp Trp
    3005                 3010                 3015

Ala Phe  Val Gly Ser Lys Val  Cys Leu Leu Pro Val  Gly Gly Glu
    3020                 3025                 3030

Lys Asn  Pro Ala Val Ile Leu  Asp Thr Ile Glu Arg  Gln His Ile
    3035                 3040                 3045

Ser Thr  Met His Phe Val Pro  Ser Met Leu His Ala  Phe Leu Glu
    3050                 3055                 3060

Tyr Val  Glu Glu Gln Pro Val  Ala Glu Arg Glu Arg  Ser Leu Ala
```

-continued

```
    3065                3070                3075

Ser Leu  Arg Arg Val Phe Ala  Ser Gly Glu Ala Leu  Thr Ala Ser
    3080                3085                3090

Gln Ala  Glu Arg Phe Glu Arg  Cys Ile Ala Pro Val  Asn Gly Ala
    3095                3100                3105

Arg Leu  Ile Asn Leu Tyr Gly  Pro Thr Glu Ala Thr  Val Asp Val
    3110                3115                3120

Thr Tyr  Phe Asp Cys Gln Ala  Gly Gln Pro Tyr Thr  Ser Val Pro
    3125                3130                3135

Ile Gly  Arg Pro Ile Asp Asn  Thr Gln Ile Tyr Ile  Val Asn Arg
    3140                3145                3150

Gln Asn  Gln Leu Gln Pro Ile  Gly Val Ala Gly Glu  Leu Cys Ile
    3155                3160                3165

Ala Gly  Ala Gly Leu Ala Arg  Gly Tyr Trp Glu Arg  Pro Glu Leu
    3170                3175                3180

Thr Ala  Glu Lys Phe Val Glu  Ile Pro Phe Lys Pro  Ser Glu Arg
    3185                3190                3195

Met Tyr  Arg Thr Gly Asp Leu  Ala Arg Trp Leu Pro  Asp Gly Asn
    3200                3205                3210

Ile Glu  Tyr Leu Gly Arg Leu  Asp His Gln Val Lys  Ile Arg Gly
    3215                3220                3225

Tyr Arg  Ile Glu Leu Gly Glu  Ile Glu Ala Gln Leu  Leu Gln Ala
    3230                3235                3240

Ala Ala  Ile Arg Glu Thr Val  Val Val Ala Arg Glu  Asp Glu Ser
    3245                3250                3255

Gly Gln  Lys Ala Leu Cys Ala  Tyr Phe Ala Ala Asp  Ser Glu Leu
    3260                3265                3270

Thr Val  Ser Glu Leu Arg Ser  Ala Leu Ala Ala Gln  Leu Pro Asp
    3275                3280                3285

Tyr Met  Ile Pro Ser Tyr Phe  Val Gln Leu Glu Arg  Leu Pro Leu
    3290                3295                3300

Ser Ala  Asn Gly Lys Ile Asp  Arg Lys Ala Leu Pro  Ser Pro Glu
    3305                3310                3315

Gly Ser  Leu Tyr Thr Gly Thr  Glu Tyr Val Ala Pro  Arg Thr Glu
    3320                3325                3330

Ala Glu  Lys Thr Ile Ala Val  Val Trp Gln Ala Val  Leu Gly Ile
    3335                3340                3345

Glu Arg  Val Gly Val Thr Asp  His Phe Phe Glu Leu  Gly Gly Asp
    3350                3355                3360

Ser Ile  Lys Ser Ile Gln Val  Ala Ser Arg Leu Gln  Gln Ala Gly
    3365                3370                3375

Tyr Lys  Leu Glu Ile Arg Glu  Leu Phe Lys Tyr Pro  Thr Ile Ala
    3380                3385                3390

Gln Leu  Ser Leu Gln Val Arg  Pro Val Ala Arg Met  Ala Asp Gln
    3395                3400                3405

Gly Glu  Val Ala Gly Glu Met  Pro Leu Thr Pro Ile  Leu Ser Trp
    3410                3415                3420

Phe Met  Glu Gln Glu Phe Ala  Asn Pro His His Phe  Asn Gln Ser
    3425                3430                3435

Ile Met  Leu His Arg Gln Glu  Gly Phe Asp Glu Val  Ala Ile Arg
    3440                3445                3450

Lys Thr  Leu His Asn Ile Val  Glu His His Asp Ala  Leu Arg Met
    3455                3460                3465
```

```
Val Phe Arg Lys Thr Glu His Gly Gly Tyr Lys Ala Trp Asn Arg
    3470                3475                3480

Gly Ile Ser Glu Gly Asp Leu Tyr Ser Leu Asp Val Ala Asp Phe
    3485                3490                3495

Lys Glu Asp Pro Glu Cys Gly Arg Ser Ile Glu Ala Lys Ala Asn
    3500                3505                3510

Glu Ile Gln Ser Gly Ile Asp Leu Gln Thr Gly Pro Leu Val Lys
    3515                3520                3525

Ala Gly Leu Phe His Cys Ala Asp Gly Asp His Leu Leu Ile Val
    3530                3535                3540

Ile His His Thr Val Ile Asp Gly Ile Ser Trp Arg Ile Leu Leu
    3545                3550                3555

Glu Asp Ile Ala Asp Gly Tyr Glu Gln Ala Leu Lys Gly Gln Glu
    3560                3565                3570

Ile Arg Leu Pro Val Lys Thr Asp Ser Tyr Arg Ile Trp Ser Glu
    3575                3580                3585

Gln Leu Ala Thr Tyr Ala His Ser Ser Asp Leu Glu Asn Glu Arg
    3590                3595                3600

Ala Tyr Trp Gln Arg Ile Ala Gln Thr Asp Thr Glu Pro Leu Pro
    3605                3610                3615

Lys Asp Trp Glu Ala Ala Cys Ser Leu Gln Arg Glu Ser Glu Ser
    3620                3625                3630

Val Asn Val Gln Trp Ser Arg Glu Asp Thr Glu Arg Leu Leu Lys
    3635                3640                3645

His Val His Arg Ala Tyr Asn Thr Glu Met Asn Asp Ile Leu Leu
    3650                3655                3660

Ala Ala Leu Gly Met Ala Val His Lys Trp Cys Gly Arg Asp Arg
    3665                3670                3675

Val Leu Val Thr Leu Glu Gly His Gly Arg Glu Ser Ile Leu Thr
    3680                3685                3690

Asp Ile Asp Ile Thr Arg Thr Val Gly Trp Phe Thr Ser Glu Tyr
    3695                3700                3705

Pro Val Leu Ile Glu Ala Glu Pro Asp Lys Thr Leu Ser Tyr Arg
    3710                3715                3720

Ile Lys Gln Val Lys Glu Asn Leu Arg Arg Ile Pro Asn Lys Gly
    3725                3730                3735

Ile Gly Tyr Gly Ile Cys Arg Tyr Leu Ser Ser Ala Gln Glu Pro
    3740                3745                3750

Ala Trp Thr Glu Ala Phe Thr Pro Glu Leu Arg Phe Asn Tyr Leu
    3755                3760                3765

Gly Gln Phe Asp Gln Asp Leu Gln Gly Asn Glu Leu Glu Leu Ser
    3770                3775                3780

Ser Tyr Ser Ser Gly Ser Asp Met Ser Asp Glu Gln Val Arg Asn
    3785                3790                3795

Tyr Ser Leu Asp Ile Ser Gly Met Ile Val Asp Gly Leu Leu Ser
    3800                3805                3810

Leu Asp Val Ser Tyr Ser Gly Lys Glu Tyr Arg Lys Glu Thr Ile
    3815                3820                3825

Glu Glu Leu Ala Gly Cys Leu Leu Val Ser Leu Gln Glu Ile Ile
    3830                3835                3840

Asp His Cys Ala Ala Lys Glu Arg Pro Glu Leu Thr Pro Ser Asp
    3845                3850                3855
```

```
Val Leu  Leu Gln Gly Leu Ser  Val Glu Glu Leu Asp  Gln Ile Ala
    3860                 3865                 3870

Glu Gln  Thr Arg Arg Asn Gly  Glu Ile Glu Asn Ile  Tyr Thr Leu
    3875                 3880                 3885

Thr Pro  Met Gln Lys Gly Met  Trp Phe His Ser Ala  Met Asp Arg
    3890                 3895                 3900

Gln Ser  Gly Ala Tyr His Glu  Gln Thr Arg Phe Thr  Ile Glu Gly
    3905                 3910                 3915

Glu Leu  Asp Thr Asp Val Phe  Val Lys Ser Leu Asp  Ala Leu Ala
    3920                 3925                 3930

Asn Asn  His Ala Val Leu Arg  Thr Asn Phe Leu Ser  Gly Trp Asn
    3935                 3940                 3945

Gly Glu  Pro Leu Gln Val Val  Phe Arg Asp Lys Arg  Ile Gly Phe
    3950                 3955                 3960

Ala Tyr  Ala Asp Leu Arg Glu  Leu Gln Glu Ala Asp  Arg Asn Arg
    3965                 3970                 3975

Cys Ile  Glu Lys Ser Ala Ala  Glu Asp His Ala Arg  Gly Phe Asp
    3980                 3985                 3990

Leu Glu  Gln Asp Ala Leu Met  Arg Val Met Val Met  Arg Thr Gly
    3995                 4000                 4005

Glu Ser  Ser Tyr Gln Val Ile  Trp Ser Ser His His  Ile Leu Met
    4010                 4015                 4020

Asp Gly  Trp Cys Leu Pro Gln  Leu Ala Lys Glu Leu  Phe Asp Thr
    4025                 4030                 4035

Tyr Ser  Val Tyr Leu Gln Gln  His His Pro Glu Gln  Ala Thr Ser
    4040                 4045                 4050

Val Pro  Ala Tyr Ser Gln Tyr  Ile Glu Trp Leu Glu  Gln Gln Asp
    4055                 4060                 4065

Glu Ala  Ala Ala Ser Ala Tyr  Trp Ser Glu Tyr Leu  Ala Gly Tyr
    4070                 4075                 4080

Asp Gln  Gln Ala Ala Leu Pro  Gln Gln Thr Ala Gln  Gly Arg Gly
    4085                 4090                 4095

Glu Glu  Tyr Val Ala Glu Lys  Leu Thr Cys Glu Leu  Gly Lys Thr
    4100                 4105                 4110

Leu Ser  Gly Arg Met Ser Arg  Val Ala Arg Gln His  Gln Val Thr
    4115                 4120                 4125

Leu Asn  Thr Leu Leu Gln Ala  Ala Trp Gly Ile Ile  Leu Gln Lys
    4130                 4135                 4140

Tyr Asn  Gly Thr Arg Asp Thr  Val Phe Gly Ser Val  Val Ser Gly
    4145                 4150                 4155

Arg Pro  Ala Glu Ile Pro Gly  Ile Glu Ala Met Ile  Gly Leu Phe
    4160                 4165                 4170

Ile Asn  Thr Ile Pro Val Arg  Val Ser Cys Glu Ala  Lys Thr Ser
    4175                 4180                 4185

Phe Ala  Glu Val Met Gly Arg  Leu Gln Glu Gln Ala  Leu Glu Ser
    4190                 4195                 4200

Gly Lys  Tyr Asp Tyr Tyr Pro  Leu Tyr Glu Ile Gln  Ala Arg Cys
    4205                 4210                 4215

Ser Gln  Lys Gln Asp Leu Ile  Ser Gln Ile Met Val  Phe Glu Asn
    4220                 4225                 4230

Tyr Pro  Met Asp Glu Gln Met  Glu Gln Ala Gly Asn  Asp Asp Gln
    4235                 4240                 4245

Gly Met  Leu Ala Ile Thr Asn  Val Glu Val Ala Glu  Gln Thr Asn
```

4250 4255 4260

Tyr Asp Phe Asn Phe Ile Val Val Pro Gly Glu Glu Ile Val Ile
4265 4270 4275

Asn Phe Asp Tyr Asn Ala Arg Val Phe Asp Arg Thr Ser Met Glu
4280 4285 4290

Arg Leu Gln Gly His Leu Val Asn Val Leu Glu Gln Ile Ala Ala
4295 4300 4305

Asn Pro Gln Val Thr Val Gly Glu Leu Lys Leu Ala Thr Glu Ala
4310 4315 4320

Glu Gln Ala Glu Ile Thr Ser Ile Phe Asn Asn Ala Arg Thr Glu
4325 4330 4335

Tyr Pro Arg Asp Lys Thr Ile His Arg Leu Phe Glu Glu Gln Ala
4340 4345 4350

Glu Arg Thr Pro Asp Ala Ile Ala Val Met Tyr Glu Asn Ser Gln
4355 4360 4365

Leu Thr Tyr Arg Glu Leu Asn Glu Arg Ala Asn Arg Leu Ala Arg
4370 4375 4380

Thr Leu Arg Ala Asp Gly Ala Gly Ala Asp Arg Leu Val Gly Leu
4385 4390 4395

Met Val Glu Arg Ser Leu Asp Met Met Val Gly Ile Ile Ala Ile
4400 4405 4410

Leu Lys Ser Gly Gly Ala Tyr Val Pro Ile Asp Pro Glu Tyr Pro
4415 4420 4425

Glu Glu Arg Ile Arg Tyr Met Leu Glu Asp Ser Gly Thr Gln Ile
4430 4435 4440

Ile Val Thr Gln Arg His Leu Gln Glu Arg Ile Pro Gly Ala Gly
4445 4450 4455

Thr Arg Val Ile Leu Asp Asp Glu His Ser Tyr Ser Ser Asp Ser
4460 4465 4470

Thr Asn Leu Asp Leu Asn Asn Gly Pro Ala Asp Leu Ala Tyr Val
4475 4480 4485

Ile Tyr Thr Ser Gly Thr Thr Gly Lys Pro Lys Gly Asn Leu Thr
4490 4495 4500

Met His Arg Asn Ile Val Arg Val Val Gln Gly Ala Asp Tyr Ile
4505 4510 4515

Asp Ile Gly Glu Gln Asp Asn Val Leu Gln Leu Ser Ser Tyr Ala
4520 4525 4530

Phe Asp Gly Ser Thr Phe Asp Met Tyr Gly Ala Leu Leu Asn Gly
4535 4540 4545

Ala Arg Leu Val Leu Ile Pro Gln Glu Thr Leu Leu Asp Val Glu
4550 4555 4560

Arg Leu Ala Glu Leu Ile Glu Arg Glu Arg Ile Ser Val Met Phe
4565 4570 4575

Ile Thr Thr Ala Phe Phe Asn Val Leu Val Asp Val Lys Ala Asp
4580 4585 4590

Cys Leu Arg His Ile Arg Ala Ile Leu Phe Gly Gly Glu Arg Val
4595 4600 4605

Ser Val Ser His Val Arg Lys Ala Leu Arg His Leu Gly Pro Gly
4610 4615 4620

Lys Ile Lys His Val Tyr Gly Pro Thr Glu Ser Thr Val Phe Ala
4625 4630 4635

Thr Cys His Asp Val Asn Glu Val Ala Ala Asp Ala Leu Asn Val
4640 4645 4650

```
Pro Ile Gly Arg Pro Ile Ser Asn Thr Thr Ile Tyr Ile Val Asn
    4655                 4660                 4665

Glu Glu Asn Gly Leu Gln Pro Ile Gly Val Ala Gly Glu Leu Cys
    4670                 4675                 4680

Val Ala Gly Asp Gly Leu Ala Arg Gly Tyr Leu Asn Arg Pro Glu
    4685                 4690                 4695

Leu Thr Ala Glu Lys Phe Val Asp Asn Pro Phe Val Pro Gly Glu
    4700                 4705                 4710

Arg Met Tyr Arg Thr Gly Asp Leu Ala Arg Trp Leu Pro Asp Gly
    4715                 4720                 4725

Ser Ile Glu Tyr Val Gly Arg Ile Asp His Gln Val Lys Ile Arg
    4730                 4735                 4740

Gly Tyr Arg Ile Glu Leu Gly Glu Val Glu Ala His Leu Leu Lys
    4745                 4750                 4755

Val Gln Pro Val Gln Glu Gly Thr Val Val Ala Arg Glu Thr Gly
    4760                 4765                 4770

Ser Gly Glu Lys Gln Leu Cys Ala Tyr Phe Val Ala Glu Ser Thr
    4775                 4780                 4785

Leu Ser Ala Ser Glu Leu Arg Gly Ala Met Ala Gln Gln Leu Pro
    4790                 4795                 4800

Gly Tyr Met Ile Pro Ser Tyr Phe Val Gln Leu Glu Arg Met Pro
    4805                 4810                 4815

Leu Thr Pro Asn Gly Lys Val Asp Gln Lys Ala Leu Pro Ala Pro
    4820                 4825                 4830

Glu Glu His Val Gln Thr Gly Thr Glu Tyr Ile Ala Pro Arg Thr
    4835                 4840                 4845

Pro Gln Glu Glu Gln Leu Ala Arg Ile Trp Gln Glu Val Leu Gly
    4850                 4855                 4860

Leu Glu Lys Val Gly Val Asn Asp Asn Phe Phe Glu Leu Gly Gly
    4865                 4870                 4875

His Ser Leu Arg Ala Thr Thr Met Ala Ser Lys Leu His Lys Glu
    4880                 4885                 4890

Leu Ser Ile Glu Leu Pro Leu Arg Asp Val Phe Lys His Pro Thr
    4895                 4900                 4905

Leu Glu Ala Met Ala Glu Arg Ile Ala Gly Leu Gly Gln Gln Met
    4910                 4915                 4920

Tyr Thr Ser Ile Pro Leu Val Glu Glu Gln Ala His Tyr Pro Leu
    4925                 4930                 4935

Ser Ser Ala Gln Lys Arg Leu Tyr Ile Leu His Gln Leu Glu Gly
    4940                 4945                 4950

Ala Glu Leu Ser Tyr Asn Met Pro Asn Met Leu Leu Leu Glu Gly
    4955                 4960                 4965

Ala Leu Asp Arg Glu Arg Phe Glu Ala Ala Phe Arg Lys Leu Ile
    4970                 4975                 4980

Ala Arg His Glu Ser Phe Arg Thr Gly Phe Glu Met Ile Asn Gly
    4985                 4990                 4995

Glu Pro Met Gln Arg Ile Tyr Glu Asn Val Asp Phe Ala Val Glu
    5000                 5005                 5010

Tyr Met Gln Ala Ser Asp Lys Glu Ala Glu Ala Arg Leu Arg Gln
    5015                 5020                 5025

Phe Val Arg Ala Phe Lys Leu Glu Glu Pro Pro Leu Leu Arg Val
    5030                 5035                 5040
```

```
Gly Leu  Ile Glu Leu Ala Gln  Glu Arg His Ile Leu  Met Phe Asp
    5045                 5050                 5055

Met His  His Ile Val Ser Asp  Gly Thr Ser Met Gly  Ile Leu Ile
    5060                 5065                 5070

Asn Glu  Phe Val Arg Leu Tyr  Gly Gly Glu Glu Leu  Gln Pro Leu
    5075                 5080                 5085

Arg Ile  Gln Tyr Lys Asp Phe  Ala Ala Trp Gln Gln  Ser Asp Ala
    5090                 5095                 5100

Arg Gln  Glu Gln Met Lys Gln  Gln Glu Ala Tyr Trp  Leu Gln Ala
    5105                 5110                 5115

Leu Gly  Gly Glu Leu Pro Val  Leu Glu Met Pro Thr  Asp His Val
    5120                 5125                 5130

Arg Pro  Ala Val Gln Ser Phe  Arg Gly Asp Ile Leu  Gln Phe Val
    5135                 5140                 5145

Ile Gly  Arg Asp Gln Cys Ala  Ala Leu Arg His Ile  Gly Ser Glu
    5150                 5155                 5160

Asn Gly  Ala Thr Leu Tyr Met  Val Leu Leu Ala Ala  Tyr Thr Ala
    5165                 5170                 5175

Leu Leu  His Lys Tyr Thr Gly  Gln Glu Asp Ile Ile  Val Gly Thr
    5180                 5185                 5190

Pro Ile  Ala Gly Arg Asn His  Gly Asp Val Gln Pro  Leu Ile Gly
    5195                 5200                 5205

Met Phe  Val Asn Thr Leu Ala  Ile Arg Asn Tyr Pro  Met Gly Glu
    5210                 5215                 5220

Lys Thr  Phe His Ser Tyr Leu  Glu Glu Val Lys Asp  Thr Thr Leu
    5225                 5230                 5235

Gly Ala  Tyr Glu Asn Gln Asn  Tyr Pro Phe Glu Asp  Leu Val Glu
    5240                 5245                 5250

Asn Val  Gln Val Ala Arg Asp  Met Ser Arg Asn Pro  Ile Phe Asp
    5255                 5260                 5265

Thr Met  Phe Ile Leu Gln Asn  Ala Glu Gln Gly Glu  Met Asn Ile
    5270                 5275                 5280

Asn Gly  Leu His Ile Ala Asn  Tyr Gln Ser Glu His  Thr Val Ser
    5285                 5290                 5295

Lys Phe  Asp Leu Thr Phe Gln  Ala Glu Glu Ala Glu  Glu Glu Ile
    5300                 5305                 5310

Val Cys  Ser Ile Glu Tyr Ala  Thr Glu Leu Tyr Glu  Leu Glu Thr
    5315                 5320                 5325

Val Glu  Arg Met Ala Gly His  Phe Thr Gln Leu Ile  Asp Ala Val
    5330                 5335                 5340

Val Gly  Asn Pro His Ala Arg  Leu Ala Ser Leu Gln  Met Val Thr
    5345                 5350                 5355

Ala Glu  Glu Gln Asp Gln Ile  Gln Asn Ile Phe Asn  Ala Thr Asp
    5360                 5365                 5370

Met Gly  Tyr Pro Arg Glu Lys  Thr Ile His Gln Met  Phe Glu Glu
    5375                 5380                 5385

Gln Ala  Glu Arg Thr Pro Asp  Ala Pro Ala Val Ser  Phe Gly Asp
    5390                 5395                 5400

Glu Met  Leu Thr Tyr Arg Glu  Leu Asn Arg Lys Ala  Asn Gln Leu
    5405                 5410                 5415

Ala Trp  Val Leu Arg Asp Arg  Gly Val Ala Ser Glu  Arg Pro Val
    5420                 5425                 5430

Gly Ile  Met Val Glu Arg Ser  Ile Ala Met Val Val  Gly Val Leu
```

```
    5435                5440                5445

Ala Val  Leu Lys Ala Gly Gly  Thr Phe Val Pro Ile  Asp Pro Glu
    5450                5455                5460

Tyr Pro  Glu Thr Arg Ile Arg  Tyr Met Leu Glu Asp  Ser Gly Ala
    5465                5470                5475

Lys Leu  Ala Leu Thr Glu Leu  Ala Trp Phe Glu Val  Ile Pro Pro
    5480                5485                5490

Glu Val  Glu Lys Val Asp Ile  His Asp Ala Ser Leu  Tyr Gln Gly
    5495                5500                5505

His Asp  Glu Asn Val Pro Asn  Glu Ser Glu Pro Ser  Asn Leu Leu
    5510                5515                5520

Tyr Ile  Ile Tyr Thr Ser Gly  Thr Thr Gly Asn Pro  Lys Gly Val
    5525                5530                5535

Met Leu  Glu Gln Arg Asn Leu  Ile Asn Leu Leu His  Tyr Glu Gln
    5540                5545                5550

Val Gly  Thr Ser Ile Pro Leu  Pro Ser Arg Ile Leu  Gln Tyr Ala
    5555                5560                5565

Ser Asn  Ser Phe Asp Val Cys  Tyr Gln Glu Met Phe  Ser Ala Leu
    5570                5575                5580

Leu Phe  Gly Gly Cys Leu Phe  Leu Ile Pro Asn Glu  Ala Arg Lys
    5585                5590                5595

Asp Pro  Ala Gln Leu Phe Thr  Trp Ile Gln Asp Asn  Gly Ile Glu
    5600                5605                5610

Val Leu  Tyr Leu Pro Val Ala  Phe Leu Lys Phe Ile  Phe Ala Glu
    5615                5620                5625

Pro Glu  Trp Ala Glu Arg Phe  Pro Asp Cys Val Thr  His Ile Ile
    5630                5635                5640

Thr Ala  Gly Glu Gln Leu Val  Val Thr Pro Gln Ile  Gln Ala Cys
    5645                5650                5655

Leu Gln  Arg Leu Arg Ile Ser  Leu His Asn His Tyr  Gly Pro Ser
    5660                5665                5670

Glu Thr  His Val Val Thr Ala  Tyr Thr Met Glu Pro  Asp Asp Ile
    5675                5680                5685

Ala Val  Gly Leu Pro Pro Ile  Gly Ala Pro Ile Ala  Asn Thr Ala
    5690                5695                5700

Ile Tyr  Ile Leu Asn Asp Arg  Leu Glu Leu Gln Pro  Ile Gly Ile
    5705                5710                5715

Ala Gly  Glu Leu Tyr Val Ser  Gly Asp Cys Val Gly  Arg Gly Tyr
    5720                5725                5730

Trp Gly  Arg Gln Glu Leu Thr  Asp Glu Lys Phe Ile  Ala Asn Pro
    5735                5740                5745

Phe Ala  Pro Gly Asp Leu Met  Tyr Lys Thr Gly Asp  Val Ala Arg
    5750                5755                5760

Trp Leu  Pro Asp Gly Thr Ile  Glu Tyr Val Gly Arg  Ser Asp His
    5765                5770                5775

Gln Val  Lys Ile Arg Gly Phe  Arg Ile Glu Leu Gly  Glu Val Glu
    5780                5785                5790

Ser Gln  Leu Leu Ser Val Glu  Phe Val Gln Glu Ala  Thr Val Met
    5795                5800                5805

Ala Arg  Glu Asp Asp Gly Gly  Gln Lys Gln Leu Cys  Ala Tyr Phe
    5810                5815                5820

Val Ala  Glu Arg Pro Leu Ser  Ala Ala Glu Leu Arg  Gly Gly Leu
    5825                5830                5835
```

```
Ser Gln Asp Leu Pro Gly Tyr Met Ile Pro Ser Tyr Phe Val Gln
    5840                5845                5850

Leu Asp Arg Leu Pro Leu Thr Pro Asn Gly Lys Ile Asp Arg Arg
    5855                5860                5865

Ala Leu Pro Glu Pro Glu Gly Ser Leu His Thr Gly Ala Glu Phe
    5870                5875                5880

Val Ala Pro Arg Thr Pro Leu Glu Ala Gln Leu Ala Arg Ile Trp
    5885                5890                5895

Gln Asp Val Leu Gly Leu Pro Asp Val Ser Val Lys Asp Asn Phe
    5900                5905                5910

Phe Asp Leu Gly Gly His Ser Leu Arg Ala Thr Thr Leu Ala Ser
    5915                5920                5925

Lys Val Phe Lys Glu Met His Val Asn Leu Pro Leu Arg Asp Val
    5930                5935                5940

Phe Arg Cys Pro Thr Ile Glu Glu Met Ala Gly Met Ile Ala Gly
    5945                5950                5955

Met Glu Lys Gln Glu Tyr Ala Ala Ile Pro Leu Ala Glu Glu Ser
    5960                5965                5970

Asp Val Tyr Pro Leu Ser Ser Ala Gln Lys Arg Leu Tyr Ile Val
    5975                5980                5985

Ser Gln Leu Glu Gly Ala Asp Leu Ser Tyr Asn Met Pro Gly Val
    5990                5995                6000

Val Ser Leu Glu Gly Thr Leu Asp Arg Glu Arg Phe Glu Leu Ala
    6005                6010                6015

Phe Leu Lys Leu Ile Ser Arg His Glu Thr Leu Arg Thr Gly Phe
    6020                6025                6030

Asp Met Val Asp Gly Glu Pro Ile Gln Arg Val His Arg Ser Val
    6035                6040                6045

Lys Phe Val Val Glu His Arg Lys Ala Ala Thr Val Gln Asp Ala
    6050                6055                6060

Glu Gln Leu Ile Arg Arg Phe Ile Arg Thr Phe Asp Leu Arg Lys
    6065                6070                6075

Pro Pro Leu Leu Arg Val Gly Leu Val Glu Leu Glu Arg Glu Arg
    6080                6085                6090

His Ile Leu Met Phe Asp Met His His Ile Ile Ser Asp Gly Ala
    6095                6100                6105

Ser Leu Gly Asn Leu Val Ser Glu Phe Ala Gln Leu Tyr Ala Gly
    6110                6115                6120

Glu Glu Arg Ala Pro Leu Arg Ile Gln Tyr Lys Asp Tyr Ala Val
    6125                6130                6135

Trp Gln Gln Ser Gly Val His Ser Glu His Met Lys Arg Gln Glu
    6140                6145                6150

Ala Tyr Trp Leu Glu Lys Leu Ala Gly Glu Leu Pro Val Val Glu
    6155                6160                6165

Leu Pro Thr Asp Tyr Asp Arg Pro Ala Val Arg Ser Phe Glu Gly
    6170                6175                6180

Ala Gln Ile Glu Phe Glu Val Asp Ala Ala Leu Thr Gln Arg Leu
    6185                6190                6195

Ser Gln Leu Ala Ser Asn Arg Glu Ser Thr Leu Tyr Met Val Leu
    6200                6205                6210

Leu Ser Ala Tyr Thr Val Leu Leu Ser Lys Tyr Ser Gly Gln Glu
    6215                6220                6225
```

Asp Ile Ile Val Gly Thr Pro Val Ala Gly Arg Ala His Ala Asp
    6230                6235                6240

Leu Glu Pro Leu Ile Gly Met Phe Val Asn Thr Leu Ala Ile Arg
    6245                6250                6255

Asn His Pro Ala Gly Asp Lys Thr Phe Leu Ser Leu Leu Glu Glu
    6260                6265                6270

Val Lys Glu Thr Ala Leu Gly Ala Phe Glu His Gln Asp Tyr Pro
    6275                6280                6285

Phe Glu Glu Leu Val Glu Arg Leu Asn Val Gln Trp Asp Ala Asn
    6290                6295                6300

Arg Asn Pro Val Phe Asp Thr Met Phe Val Met Gln Asn Thr Glu
    6305                6310                6315

Asp His Glu Val Arg Leu Glu Ala Leu Thr Leu Ser Pro Tyr Val
    6320                6325                6330

Leu Asp Asn Pro Ile Asp Ala Lys Phe Asp Leu Thr Leu Phe Val
    6335                6340                6345

Ser Glu Asp Asn Asp Val Ile Lys Gly Gly Phe Gln Tyr Gly Thr
    6350                6355                6360

Lys Leu Phe Lys Ala Ala Met Ile His Lys Ile Met Arg Asp Phe
    6365                6370                6375

Leu Leu Val Leu Ala Gln Ile Val Glu Asp Pro His Ile Arg Leu
    6380                6385                6390

Arg Asp Ile Lys Cys Asn Glu Gln Ser Val Asn Asn Gln Arg Ser
    6395                6400                6405

Ile Glu Thr Ile Glu Phe Ala Phe
    6410                6415

<210> SEQ ID NO 19
<211> LENGTH: 3170
<212> TYPE: PRT
<213> ORGANISM: Paenibacillus sp. OSY-SE

<400> SEQUENCE: 19

Met Lys Ser Val Phe Asp Lys Glu Glu Ala Tyr Trp Asn Glu Lys Phe
1               5                   10                  15

Asp Ser Glu Asp Ser Ile Ser Val Leu Pro Tyr Ser Asn Ser Ser Asn
            20                  25                  30

Asn Asn Met Gly Arg Val Asn Thr Met Gly Val Ile Asn Arg Thr Leu
        35                  40                  45

Pro Pro Glu Leu Ser Gln Arg Ile Ile Thr Leu Ala Asn Gly Ser Asp
    50                  55                  60

Met Ala Val Tyr Met Ile Val Leu Ala Gly Val Thr Ser Leu Leu Tyr
65                  70                  75                  80

Lys Tyr Thr Asn Arg Glu Asn Val Leu Val Gly Met Pro Ala Tyr Thr
                85                  90                  95

Ala Leu His Gly Glu His Pro Pro Ile His Asp Phe Leu Val Ile Lys
            100                 105                 110

Asn Asn Val Asn Ser Lys Ser Thr Phe Lys Ser Leu Leu Gly Gln Ile
        115                 120                 125

Lys Ala Ser Val Ser Glu Ala Leu Glu His Gln His Leu Pro Phe Arg
    130                 135                 140

Lys Met Phe Arg Gln Leu Asn Leu Gln Val Asp Pro Gln Gly Leu Pro
145                 150                 155                 160

Ile Val Asn Thr Leu Val Ser Tyr Thr Asn Ile His Thr Ala Ser Leu
                165                 170                 175

```
Glu Gln Ser Ala Ala Ala Glu Ala Ala Phe Gln Phe Glu Phe Val Asn
            180                 185                 190

Asp Arg Ile Gln Leu Arg Met Ser Phe Asp Asp Asn Arg Tyr Arg Ser
        195                 200                 205

Asp Tyr Val Glu Ser Met Leu Ala His Phe Phe Arg Leu Leu Ser Val
    210                 215                 220

Val Leu Phe Gln Pro Glu Leu Glu Ile Gly Lys Val Glu Leu Leu Ser
225                 230                 235                 240

Glu His Glu Gln His His Leu Leu Ala Ile Leu Asn Asp Thr Arg Thr
                245                 250                 255

Glu Tyr Pro Arg Gln Lys Thr Leu His Gln Leu Phe Glu Glu Gln Ala
            260                 265                 270

Glu Arg Met Pro Asp Ala Leu Ala Ala Leu Phe Glu Asp Lys Arg Leu
        275                 280                 285

Thr Tyr Ala Glu Leu Asn Ala Ala Ala Asn Arg Ile Ala Arg Leu Leu
    290                 295                 300

Arg Asp Arg Gly Val Val Arg Gly Thr Leu Val Gly Ile Cys Ala Glu
305                 310                 315                 320

Arg Ser Leu Glu Met Val Ile Gly Leu Leu Gly Ile Leu Lys Ala Gly
                325                 330                 335

Gly Ala Tyr Val Pro Ile Asp Pro Ser Tyr Pro Gln Glu Arg Ile Asn
            340                 345                 350

Ala Met Leu Glu Asp Thr Ala Ile Ser Val Met Leu Thr Gln Ala His
        355                 360                 365

Leu Gln Thr Ser Val Pro Asn Ser Leu Asp Ser Val Leu Leu Asp Thr
    370                 375                 380

Ala Ala Glu Met Thr Leu Glu Gly Ser Trp Pro Asn Leu Thr Asp Thr
385                 390                 395                 400

Ala Ala Thr Ala Asp Asp Val Ala Tyr Ile Ile Tyr Thr Ser Gly Ser
                405                 410                 415

Thr Gly Ile Pro Lys Gly Val Cys Val Thr His Arg Gly Val Val Arg
            420                 425                 430

Leu Val Val Ala Ala Asn Tyr Val Asp Ile Ser Ser Lys Asp Val Phe
        435                 440                 445

Leu Gln Gly Ser Thr Ile Ser Phe Asp Ala Ala Thr Phe Glu Ile Trp
    450                 455                 460

Gly Ser Leu Leu Asn Gly Ala Ala Leu Ala Ile Leu Pro Pro Gly Asn
465                 470                 475                 480

Leu Ser Leu Thr Glu Trp Thr Gln Ala Ile Gln Gln His Gln Val Thr
                485                 490                 495

Ile Leu Trp Leu Thr Ala Gly Leu Phe His Val Met Val Glu Asn Gln
            500                 505                 510

Leu Gln Ala Leu Gln Gly Val Gln Gln Leu Leu Val Gly Gly Asp Val
        515                 520                 525

Val Ser Gln Thr His Ala Lys Lys Val Leu Glu Arg Tyr Lys Asp Ile
    530                 535                 540

Arg Leu Val Asn Gly Tyr Gly Pro Thr Glu Asn Thr Thr Phe Thr Cys
545                 550                 555                 560

Cys His Glu Ile Ser Ala Ala Asp Met Glu Arg Leu Ser Ile Pro Ile
                565                 570                 575

Gly Arg Pro Ile Ala Asn Thr Gln Val Tyr Val Leu Asp Glu Ala Gly
            580                 585                 590
```

```
Lys Leu Leu Pro Val Gly Val Val Gly Glu Leu Tyr Thr Gly Gly Asp
        595                 600                 605

Gly Leu Ala Gln Gly Tyr Trp Asn Arg Pro Glu Leu Thr Ala Glu Lys
    610                 615                 620

Phe Val Asp Asn Pro Phe Val Pro Gly Thr Arg Leu Tyr Arg Thr Gly
625                 630                 635                 640

Asp Leu Ala Arg Trp Leu Pro Asp Gly Thr Leu Glu Tyr Val Gly Arg
                645                 650                 655

Ile Asp Asp Gln Val Lys Ile Arg Gly Tyr Arg Ile Glu Leu Gly Glu
            660                 665                 670

Val Glu Ala His Leu Leu Lys Val Glu Ser Val Leu Asp Ala Ile Val
        675                 680                 685

Ile Ala Arg Gln Asp Glu Ser Gly Gln Lys Thr Leu Cys Ala Tyr Phe
    690                 695                 700

Thr Ala His Ala Glu Leu Met Ala Gly Asp Leu Arg Ala Ala Leu Ser
705                 710                 715                 720

Gln Glu Leu Pro Val Tyr Met Ile Pro Thr His Leu Val Gln Val Asp
                725                 730                 735

Gln Met Pro Leu Thr Pro Asn Gly Lys Val Asp Arg Arg Ala Leu Pro
            740                 745                 750

Glu Pro Glu Gly Leu Ile Met Thr Gly Ile Glu His Val Ala Pro Arg
        755                 760                 765

Ser Pro Leu Glu Ser Lys Leu Ala His Ile Trp Gln Glu Val Leu Gly
    770                 775                 780

Leu Glu Lys Val Ser Val Lys Asp Ser Phe Phe Glu Ile Gly Gly His
785                 790                 795                 800

Ser Leu Arg Ala Thr Thr Leu Ala Ser Lys Leu His Lys Glu Leu His
                805                 810                 815

Val Ser Leu Leu Leu Arg Asp Ile Phe Arg His Pro Thr Ile Glu Glu
            820                 825                 830

Leu Ala Arg Leu Ile Asp Gly Met Glu Arg Gln Ala Tyr Arg Gln Ile
        835                 840                 845

Pro Leu Leu Asp Glu Arg Asp Trp Tyr Pro Val Ser Ser Ala Gln Lys
    850                 855                 860

Arg Leu Tyr Ile Leu His Gln Leu Glu Gly Ala Glu Gln Ser Tyr Asn
865                 870                 875                 880

Met Pro Gly Val Met Leu Leu Glu Gly Gln Leu Asp Arg Asn Arg Phe
                885                 890                 895

Glu Glu Ala Phe Gly Ser Leu Ile Gly Arg His Glu Thr Leu Arg Thr
            900                 905                 910

Gly Phe Glu Met Val Asn Gly Glu Pro Val Gln Arg Val Cys Arg Glu
        915                 920                 925

Val Asn Phe Ser Val Glu Met Met Gln Ala Ser Glu Glu Glu Ala Glu
    930                 935                 940

Ala Val Val Arg Ser Phe Ile Arg Pro Phe Asp Leu Glu Lys Pro Pro
945                 950                 955                 960

Leu Leu Arg Val Gly Leu Ile Glu Leu Asp Gln Asp Arg His Ile Leu
                965                 970                 975

Met Tyr Asp Met His His Ile Ile Ser Asp Gly Val Ser Met Gly Ile
            980                 985                 990

Val Val Glu Glu Phe Val Arg Leu  Tyr Gly Gly Glu Glu  Leu Pro Pro
        995                 1000                 1005

Pro Arg  Ile Gln Tyr Lys Asp  Tyr Ala Ala Trp Gln  Gln Ser Glu
```

```
    1010                1015                1020

Pro Gln  Gln Glu Leu Met Lys  Gln Gln Glu Ser Tyr  Trp Leu Gln
    1025                1030                1035

Ser Leu  Gly Gly Glu Leu Pro  Val Leu Glu Leu Pro  Ala Asp Tyr
    1040                1045                1050

Ala Arg  Pro Ser Val Gln Ser  Tyr Glu Gly Asp Thr  Phe Glu Phe
    1055                1060                1065

Ala Ile  Asp Pro Arg Leu Ser  Glu Ala Leu His Gly  Val Ala Ala
    1070                1075                1080

Glu Ser  Gly Thr Thr Leu Tyr  Met Val Leu Leu Ala  Ala Tyr Thr
    1085                1090                1095

Ile Leu  Leu His Lys Tyr Thr  Gly Gln Glu Asp Ile  Ile Val Gly
    1100                1105                1110

Thr Pro  Asn Ala Gly Arg Thr  His Gly Asp Leu Gln  Pro Leu Ile
    1115                1120                1125

Gly Met  Phe Val Asn Thr Leu  Ala Ile Arg Asn Tyr  Pro Ala Gly
    1130                1135                1140

Ser Lys  Thr Phe Leu Glu Tyr  Leu Glu Glu Val Lys  Glu Thr Ser
    1145                1150                1155

Leu Gly  Ala Phe Glu Asn Gln  Asp Tyr Pro Phe Glu  Glu Leu Val
    1160                1165                1170

Glu Lys  Leu Gln Val Ala Arg  Asp Leu Ser Arg Asn  Pro Leu Phe
    1175                1180                1185

Asp Thr  Met Phe Ala Leu Gln  Asn Met Asp Asp Lys  Asp Leu Glu
    1190                1195                1200

Leu Ala  Gly Leu Arg Leu Lys  Pro Tyr Pro Ala Glu  Tyr Lys Val
    1205                1210                1215

Ala Lys  Phe Asp Leu Ser Leu  Asp Val Ala Glu Gly  Val Glu Gly
    1220                1225                1230

Met Ala  Cys Ser Leu Glu Tyr  Ala Thr Ala Leu Tyr  Arg Pro Glu
    1235                1240                1245

Ser Ile  Glu Arg Met Ala Lys  His Phe Gly Arg Leu  Leu Glu Ala
    1250                1255                1260

Val Ala  His Glu Pro Glu Ala  Arg Leu Ala Ser Leu  Gly Met Leu
    1265                1270                1275

Thr Glu  Glu Glu Glu Glu Gln  Ile Arg His Val Phe  Asn Asp Thr
    1280                1285                1290

Glu Ala  Gly Arg Ser Gln Gln  Asn Thr Val Pro Glu  Leu Phe Glu
    1295                1300                1305

Glu Gln  Val Glu Arg Thr Pro  Asp Arg Ile Ala Val  Val His Glu
    1310                1315                1320

Asp Lys  Gln Leu Thr Tyr Arg  Glu Leu Asn Glu Arg  Ala Asn Arg
    1325                1330                1335

Leu Ala  Arg Thr Leu Arg Ala  Glu Gly Val Lys Pro  Glu Gln Leu
    1340                1345                1350

Val Gly  Ile Met Ala Asp Arg  Ser Leu Glu Met Ile  Val Gly Ile
    1355                1360                1365

Met Ala  Ile Leu Lys Ser Gly  Gly Ala Tyr Val Pro  Ile Asp Pro
    1370                1375                1380

Gln Tyr  Pro Glu Asp Arg Ile  His Tyr Met Leu Asp  Asn Ser Asn
    1385                1390                1395

Ala Gln  Val Leu Leu Ala Gln  Arg His Leu Gln Ala  Arg Ala Ala
    1400                1405                1410
```

```
Phe Ser  Gly Arg Arg Ile Met  Leu Asp Glu Glu Ala  Phe Tyr Gly
    1415                 1420                 1425

Ala Asp  Gly Ser Asn Leu Glu  Arg Val Asn Gln Pro  Glu His Leu
    1430                 1435                 1440

Ser Tyr  Val Ile Tyr Thr Ser  Gly Thr Thr Gly Lys  Pro Lys Gly
    1445                 1450                 1455

Val Met  Ile Glu His Arg Gln  Met Ala Val Leu Ser  Ala Ala Trp
    1460                 1465                 1470

Glu Arg  Glu Tyr Gly Leu Gln  Glu Glu Ser Met Arg  Trp Met Gln
    1475                 1480                 1485

Trp Ala  Ser Phe Ser Phe Asp  Val Phe Ser Gly Asp  Leu Ile Arg
    1490                 1495                 1500

Ala Leu  Leu His Gly Gly Glu  Leu Ile Leu Cys Pro  Glu Asp Ala
    1505                 1510                 1515

Arg Ala  Asn Pro Ala Glu Ile  Tyr Glu Leu Ile Arg  Lys His Arg
    1520                 1525                 1530

Ile Gln  Met Phe Asp Val Thr  Pro Ser Leu Val Ile  Pro Leu Met
    1535                 1540                 1545

Glu Tyr  Val Tyr Glu Asn Lys  Leu Asp Ile Ser Ser  Met Lys Leu
    1550                 1555                 1560

Ala Val  Val Gly Ala Asp His  Cys Pro Lys Glu Glu  Phe Gln Lys
    1565                 1570                 1575

Leu Leu  Glu Arg Phe Gly Ser  Gln Met Arg Ile Val  Asn Ser Tyr
    1580                 1585                 1590

Gly Val  Thr Glu Thr Thr Ile  Asp Ser Cys Tyr Phe  Glu Gln Ala
    1595                 1600                 1605

Ser Thr  Glu Gly Leu Arg Thr  Val Pro Ile Gly Lys  Pro Leu Pro
    1610                 1615                 1620

Gly Val  Thr Met Tyr Ile Leu  Asp Asp Gln His Ser  Leu Leu Pro
    1625                 1630                 1635

Val Gly  Ile Thr Gly Glu Leu  Tyr Ile Gly Gly Pro  Cys Val Gly
    1640                 1645                 1650

Arg Gly  Tyr Trp Lys Arg Pro  Asp Leu Thr Ala Glu  Lys Phe Val
    1655                 1660                 1665

Asp Asn  Pro Phe Ala Pro Gly  Glu Arg Met Tyr Arg  Thr Gly Asp
    1670                 1675                 1680

Leu Ala  Arg Trp Leu Pro Asp  Gly Asn Val Glu Tyr  Leu Gly Arg
    1685                 1690                 1695

Ile Asp  His Gln Val Lys Ile  Arg Gly Tyr Arg Ile  Glu Ile Gly
    1700                 1705                 1710

Glu Val  Glu Thr Gln Leu Leu  Arg Thr Pro Phe Ile  Arg Glu Ala
    1715                 1720                 1725

Val Val  Val Ala Arg Glu Asp  Val Ser Gly Gln Lys  Ser Leu Cys
    1730                 1735                 1740

Ala Tyr  Phe Val Ala Glu Arg  Glu Leu Thr Val Ser  Glu Leu Arg
    1745                 1750                 1755

Arg Ala  Leu Ala Ala Glu Leu  Pro Gly Tyr Met Ile  Pro Ser Tyr
    1760                 1765                 1770

Phe Val  Gln Met Glu Arg Leu  Pro Leu Thr Pro Asn  Gly Lys Ile
    1775                 1780                 1785

Asp Arg  Lys Ala Leu Pro Ala  Pro Glu Gly Ser Ala  His Thr Gly
    1790                 1795                 1800
```

```
Ala Glu  Phe Val Ala Pro Arg  Thr Ser Leu Glu Ala  Gln Leu Ala
    1805                 1810                 1815

Arg Ile  Trp Gln Glu Val Leu  Gly Leu Pro Asp Val  Ser Val Lys
    1820                 1825                 1830

Asp Asn  Phe Phe Asp Leu Gly  Gly His Ser Leu Arg  Ala Thr Thr
    1835                 1840                 1845

Leu Ala  Ser Lys Val Phe Lys  Glu Met His Ile Asn  Leu Pro Leu
    1850                 1855                 1860

Arg Asp  Val Phe Arg Tyr Pro  Thr Ile Glu Glu Leu  Ala Glu Leu
    1865                 1870                 1875

Ile Ala  Gly Met Lys Lys Gln  Glu Tyr Ala Val Ile  Pro Leu Ala
    1880                 1885                 1890

Glu Glu  Arg Asp Val Tyr Pro  Leu Ser Ser Ala Gln  Lys Arg Leu
    1895                 1900                 1905

Tyr Ile  Val Ser Gln Leu Glu  Gly Ala Glu Leu Ser  Tyr Asn Met
    1910                 1915                 1920

Pro Gly  Val Ile Thr Leu Glu  Gly Pro Leu Asp Arg  Thr Arg Phe
    1925                 1930                 1935

Asp Gly  Ala Phe Gln Gln Leu  Ile Ala Arg His Glu  Ala Leu Arg
    1940                 1945                 1950

Thr Gly  Phe Glu Met Val Asn  Gly Glu Pro Val Gln  Arg Ile His
    1955                 1960                 1965

Arg Asp  Val Arg Leu Thr Val  Glu Tyr Val Gln Ala  Asp Glu Glu
    1970                 1975                 1980

Glu Ala  Glu Lys Leu Val Gln  Arg Phe Val Arg Ser  Phe Asp Leu
    1985                 1990                 1995

Lys Leu  Arg Pro Leu Leu Arg  Val Gly Leu Ile Ala  Ile Glu Arg
    2000                 2005                 2010

Glu Arg  His Ile Leu Met Phe  Asp Met His His Ile  Ile Ser Asp
    2015                 2020                 2025

Gly Val  Thr Met Gly Ile Leu  Val Asp Glu Phe Ala  Arg Leu Tyr
    2030                 2035                 2040

Ala Gly  Glu Asp Leu Pro Pro  Leu Arg Ile Gln Tyr  Lys Asp Tyr
    2045                 2050                 2055

Ala Val  Trp Gln Gln Ser Glu  Asp Arg Ser Val Glu  Leu Arg Arg
    2060                 2065                 2070

Gln Glu  Ala Tyr Trp Leu Glu  Arg Leu Gln Gly Glu  Leu Pro Val
    2075                 2080                 2085

Leu Glu  Leu Pro Thr Asp Tyr  Val Arg Pro Ala Val  Gln Lys Phe
    2090                 2095                 2100

Asp Gly  Asp Val Ala Leu Phe  Thr Ile Asp Pro His  Leu Ser Glu
    2105                 2110                 2115

Gln Leu  Arg Arg Leu Ala Ser  Asp Thr Gly Ser Thr  Leu Tyr Met
    2120                 2125                 2130

Val Leu  Leu Ala Ala Tyr Thr  Thr Leu Leu His Lys  Tyr Thr Gly
    2135                 2140                 2145

Gln Glu  Asp Ile Ile Val Gly  Thr Pro Ile Ala Gly  Arg Ser His
    2150                 2155                 2160

Ser Asp  Leu Glu Pro Leu Ile  Gly Met Phe Val Asn  Thr Leu Ala
    2165                 2170                 2175

Val Arg  Asn Tyr Pro Ala Ser  Glu Lys Ala Phe Leu  Ser Tyr Leu
    2180                 2185                 2190

Ala Glu  Val Lys Glu Thr Thr  Leu Gly Ala Phe Glu  His Gln Asp
```

```
    2195                2200                2205

Tyr Pro  Phe Glu Asp Leu Val  Glu Lys Val Arg Val  Ser Arg Asp
    2210                2215                2220

Leu Ser  Arg Asn Pro Leu Phe  Asp Thr Met Phe Ser  Leu Glu Asn
    2225                2230                2235

Ala Glu  Gln Gly Gly Ile Glu  Ile Glu Gly Leu Gln  Leu Lys Ser
    2240                2245                2250

Tyr Pro  Asn Glu His Met Thr  Ala Lys Phe Asp Leu  Thr Phe His
    2255                2260                2265

Ala Glu  Glu Gly Glu Glu Gly  Ile Leu Cys Gly Leu  Val Tyr Ala
    2270                2275                2280

Thr Ala  Leu Tyr Lys Arg Asp  Thr Val Glu Arg Met  Met Leu His
    2285                2290                2295

Phe Lys  Gln Leu Leu Ala Ala  Ile Ala His Asp Pro  Arg Ala Gln
    2300                2305                2310

Leu Ser  Thr Leu Asn Met Met  Thr Ala Gln Glu Arg  Glu Glu Ile
    2315                2320                2325

Ile Gly  Val Phe Asn Asp Thr  Gly Thr Lys Tyr Pro  Arg Glu Lys
    2330                2335                2340

Thr Ile  Gln His Leu Phe Glu  Glu Gln Val Glu Arg  Thr Pro Asp
    2345                2350                2355

Ala Ala  Ala Ile Val Tyr Gly  Asp Glu Arg Met Thr  Tyr Arg Glu
    2360                2365                2370

Leu Asn  Gly Arg Ala Asn Arg  Leu Ala Arg Thr Leu  Arg Thr Lys
    2375                2380                2385

Gly Val  Gln Ala Asp Arg Leu  Val Gly Leu Met Ala  Glu Arg Ser
    2390                2395                2400

Leu Glu  Met Ile Val Gly Ile  Leu Ala Ile Leu Lys  Ala Gly Gly
    2405                2410                2415

Ala Tyr  Val Pro Ile Asp Pro  Glu Tyr Pro Glu Glu  Arg Val Arg
    2420                2425                2430

Tyr Met  Leu Glu Asp Ser Gly  Thr Gln Ile Ile Leu  Thr Gln His
    2435                2440                2445

Glu Leu  Gln Ser Arg Ile Pro  Val Gln Ala Ser Phe  Val Leu Leu
    2450                2455                2460

Asp Asp  Glu His Ser Tyr Ser  Ala Asp Asp Ser Asn  Leu Glu Gln
    2465                2470                2475

Asn Asn  Gly Pro Ala Asp Leu  Ala Tyr Val Ile Tyr  Thr Ser Gly
    2480                2485                2490

Thr Thr  Gly Lys Pro Lys Gly  Asn Leu Ala Thr His  Arg Asn Ile
    2495                2500                2505

Val Arg  Val Val Gln Gly Thr  Ser Tyr Ile Asp Phe  Ser Glu Arg
    2510                2515                2520

Asp Asn  Val Leu Gln Leu Ser  Asn Tyr Ala Phe Asp  Gly Ser Thr
    2525                2530                2535

Phe Asp  Met Tyr Gly Ala Leu  Leu Asn Gly Ala Lys  Leu Val Leu
    2540                2545                2550

Ile Pro  Gln Glu Thr Leu Leu  Glu Val Gly Lys Leu  Ala Gly Leu
    2555                2560                2565

Ile Glu  Arg Glu Arg Ile Ser  Val Met Phe Ile Thr  Thr Ala Tyr
    2570                2575                2580

Phe Asn  Ile Leu Ile Asp Met  Lys Ala Asp Cys Leu  Arg His Ile
    2585                2590                2595
```

Arg Thr Ile Leu Phe Gly Gly Glu Arg Val Ser Ile Ser His Val
2600 2605 2610

Arg Lys Ala Leu Tyr Gln Leu Gly Pro Gly Lys Ile Lys His Val
2615 2620 2625

Tyr Gly Pro Thr Glu Ser Thr Val Phe Ala Thr Cys His Asp Val
2630 2635 2640

Asn Glu Val Ala Glu Asp Ala Val Thr Val Pro Ile Gly Arg Pro
2645 2650 2655

Ile Ser Asn Thr Thr Ile Tyr Ile Val Asn Ala Gln Asn Asp Leu
2660 2665 2670

Gln Pro Ile Gly Val Ala Gly Glu Leu Cys Ile Ala Gly Asp Gly
2675 2680 2685

Leu Ala Arg Gly Tyr Leu Asn Arg Pro Glu Leu Thr Ala Ala Lys
2690 2695 2700

Phe Val Asp Asn Pro Phe Ala Pro Arg Glu Arg Met Tyr Arg Thr
2705 2710 2715

Gly Asp Leu Ala Arg Trp Leu Pro Asp Gly Thr Ile Glu Tyr Val
2720 2725 2730

Gly Arg Ile Asp Asp Gln Val Lys Ile Arg Gly Tyr Arg Ile Glu
2735 2740 2745

Leu Gly Glu Val Glu Thr His Leu Leu Arg Val Glu Pro Ile Gln
2750 2755 2760

Glu Ala Thr Val Ile Ala Arg Glu Ser Asp Ser Gly Glu Lys Arg
2765 2770 2775

Leu Cys Ala Tyr Tyr Val Ala Asp Arg Pro Leu Pro Ala Asn Glu
2780 2785 2790

Leu Arg Gly Ile Leu Ala Gln Asp Leu Pro Gly Tyr Met Ile Pro
2795 2800 2805

Leu His Phe Val Gln Leu Asp Arg Met Pro Leu Thr Pro Asn Gly
2810 2815 2820

Lys Val Asp Arg Lys Ala Leu Pro Ala Pro Glu Asp His Leu Met
2825 2830 2835

Thr Gly Thr Glu Tyr Val Ala Pro Arg Thr Thr Gln Glu Ala Gln
2840 2845 2850

Leu Ala Gln Ile Trp Gln Glu Val Leu Gly Ile Glu Lys Ile Gly
2855 2860 2865

Val Gln Asp Asn Phe Phe Glu Leu Gly Gly His Ser Ile Ser Leu
2870 2875 2880

Met Gln Leu Ile His Arg Ile Tyr Ile Glu Leu Gly Ala Glu Ile
2885 2890 2895

Ala Leu His Ser Val Phe Gln Arg Pro Thr Val Glu Ala Met Ala
2900 2905 2910

Tyr Glu Ile Val Lys Val Glu Tyr Glu Glu Lys Ser Ser Ser Gln
2915 2920 2925

Phe Thr Lys Leu Asn Glu Asn Gly Leu Val Asn Val Phe Cys Leu
2930 2935 2940

Pro Pro Gly Phe Gly Tyr Gly Leu Ser Tyr Leu Glu Leu Ala Lys
2945 2950 2955

Gln Met Glu Asn Ser Cys Ile Leu Tyr Gly Ile Asp Phe Ile Asp
2960 2965 2970

Asp Ala Glu Ser Tyr Glu Asp Met Leu Asp Arg Tyr Val Asp Ala
2975 2980 2985

-continued

```
Val Val  Ala Ile Gln Ser Gln  Ser Pro Tyr Val Leu  Leu Gly Tyr
    2990                 2995                 3000

Ser Leu  Gly Gly Asn Leu Thr  Phe Glu Ile Ala Lys  Ala Met Glu
    3005                 3010                 3015

Lys Arg  Gly Tyr Arg Val Ser  Asp Ile Ile Met Leu  Asp Ser Thr
    3020                 3025                 3030

Arg Lys  Leu Ala Ala Gln Thr  Val Asp Glu Phe Glu  Ser Asp Ile
    3035                 3040                 3045

Asp Gln  Met Leu Glu Ala Val  Gly Glu Gln Glu Met  Gln Leu Leu
    3050                 3055                 3060

Ser Asn  Pro Leu Ile Arg Glu  Arg Val Lys His Lys  Met Arg Ala
    3065                 3070                 3075

Tyr Trp  Thr Tyr Gly Ser Gln  Leu Val Asn Thr Gly  Ala Val Glu
    3080                 3085                 3090

Ala Asn  Ile Tyr Ala Leu Ile  Ala Glu Asp Ser Asp  Ala Val Arg
    3095                 3100                 3105

Pro Asp  Asn Val Thr Ser Ala  Leu Trp Asp Gly Ala  Thr Arg Gln
    3110                 3115                 3120

Ala Tyr  Cys Glu His Arg Leu  Ile Gly Val His Glu  Asp Val Leu
    3125                 3130                 3135

Leu Pro  Gly Phe Ile Glu His  Asn Val Lys Val Ile  His Ala Val
    3140                 3145                 3150

Val His  Gln Ile Ile Glu Gln  Thr Arg Gly Val His  Glu Val Leu
    3155                 3160                 3165

Ser Arg
    3170
```

<210> SEQ ID NO 20
<211> LENGTH: 34
<212> TYPE: PRT
<213> ORGANISM: Paenibacillus alvei A6-6i-x

<400> SEQUENCE: 20

```
Leu Ala Trp Ala Phe Asp Val Phe Thr Gly Asp Arg Glu Ser Val Val
1               5                   10                  15

Gly Ser Asp Leu Asn Ser Tyr Gly Val Thr Glu Ala Cys Val Asp Ala
            20                  25                  30

Cys Tyr
```

<210> SEQ ID NO 21
<211> LENGTH: 10
<212> TYPE: PRT
<213> ORGANISM: Paenibacillus alvei A6-6i-x

<400> SEQUENCE: 21

```
Asp Val Gly Glu Val Gly Ser Val Asp Lys
1               5                   10
```

<210> SEQ ID NO 22
<211> LENGTH: 34
<212> TYPE: PRT
<213> ORGANISM: Paenibacillus alvei A6-6i-x

<400> SEQUENCE: 22

```
Leu Gly Ala Ser Phe Asp Ala Ala Thr Phe Glu Gly Trp Met Leu Val
1               5                   10                  15

Gly Gly Asp Ile Asn Gly Tyr Gly Pro Thr Glu Asn Thr Thr Phe Thr
            20                  25                  30
```

Cys Cys

<210> SEQ ID NO 23
<211> LENGTH: 10
<212> TYPE: PRT
<213> ORGANISM: Paenibacillus alvei A6-6i-x

<400> SEQUENCE: 23

Asp Ala Phe Trp Leu Gly Gly Thr Phe Lys
1               5                   10

<210> SEQ ID NO 24
<211> LENGTH: 34
<212> TYPE: PRT
<213> ORGANISM: Paenibacillus alvei A6-6i-x

<400> SEQUENCE: 24

Leu Asn Ser His Phe Asp Phe Ser Val Trp Glu Gly Asn Gln Ile Phe
1               5                   10                  15

Gly Gly Glu Ile Asn Met Tyr Gly Ile Thr Glu Thr Thr Val His Val
            20                  25                  30

Thr Tyr

<210> SEQ ID NO 25
<211> LENGTH: 10
<212> TYPE: PRT
<213> ORGANISM: Paenibacillus alvei A6-6i-x

<400> SEQUENCE: 25

Asp Phe Trp Asn Ile Gly Met Val His Lys
1               5                   10

<210> SEQ ID NO 26
<211> LENGTH: 34
<212> TYPE: PRT
<213> ORGANISM: Paenibacillus alvei A6-6i-x

<400> SEQUENCE: 26

Met Ala Trp Ala Phe Asp Val Phe Ser Gly Asp Arg Glu Ser Ile Ile
1               5                   10                  15

Gly Ser Asp Ile Asn Ser Tyr Gly Val Thr Glu Ala Cys Val Asp Ser
            20                  25                  30

Ser Tyr

<210> SEQ ID NO 27
<211> LENGTH: 10
<212> TYPE: PRT
<213> ORGANISM: Paenibacillus alvei A6-6i-x

<400> SEQUENCE: 27

Asp Val Gly Glu Ile Gly Ser Val Asp Lys
1               5                   10

<210> SEQ ID NO 28
<211> LENGTH: 34
<212> TYPE: PRT
<213> ORGANISM: Paenibacillus alvei A6-6i-x

<400> SEQUENCE: 28

Arg Trp Met Thr Phe Asp Val Ser Val Trp Glu Trp His Phe Phe Thr
1               5                   10                  15

-continued

Ser Gly Glu Ile Asn Leu Tyr Gly Pro Thr Glu Ala Thr Val Asp Val
20 25 30

Thr Tyr

<210> SEQ ID NO 29
<211> LENGTH: 10
<212> TYPE: PRT
<213> ORGANISM: Paenibacillus alvei A6-6i-x

<400> SEQUENCE: 29

Asp Val Trp His Phe Ser Leu Val Asp Lys
1 5 10

<210> SEQ ID NO 30
<211> LENGTH: 34
<212> TYPE: PRT
<213> ORGANISM: Paenibacillus alvei A6-6i-x

<400> SEQUENCE: 30

Ala Trp Arg Phe Phe Asp Gly Phe Val Met Ser Cys Ile Cys Thr Leu
1 5 10 15

Ala Gly Glu Phe Asn Glu Tyr Gly Pro Thr Glu Asn Ser Val Val Ala
20 25 30

Thr Cys

<210> SEQ ID NO 31
<211> LENGTH: 10
<212> TYPE: PRT
<213> ORGANISM: Paenibacillus alvei A6-6i-x

<400> SEQUENCE: 31

Asp Gly Met Ile Thr Ala Glu Val Val Lys
1 5 10

<210> SEQ ID NO 32
<211> LENGTH: 34
<212> TYPE: PRT
<213> ORGANISM: Paenibacillus alvei A6-6i-x

<400> SEQUENCE: 32

Met Ala Trp Ala Phe Asp Val Phe Ser Gly Asp Arg Asp Cys Ala Val
1 5 10 15

Gly Ser Asp Ile Asn Ser Tyr Gly Val Thr Glu Thr Cys Ile Asp Ala
20 25 30

Ser Tyr

<210> SEQ ID NO 33
<211> LENGTH: 10
<212> TYPE: PRT
<213> ORGANISM: Paenibacillus alvei A6-6i-x

<400> SEQUENCE: 33

Asp Val Gly Asp Ala Gly Ser Ile Asp Lys
1 5 10

<210> SEQ ID NO 34
<211> LENGTH: 34
<212> TYPE: PRT
<213> ORGANISM: Paenibacillus alvei A6-6i-x

<400> SEQUENCE: 34

Arg Trp Met Thr Phe Asp Val Ser Val Trp Glu Trp His Phe Phe Thr

```
1               5                   10                  15

Ser Gly Glu Ile Asn Leu Tyr Gly Pro Thr Glu Ala Thr Val Asp Val
            20                  25                  30

Thr Tyr


<210> SEQ ID NO 35
<211> LENGTH: 10
<212> TYPE: PRT
<213> ORGANISM: Paenibacillus alvei A6-6i-x

<400> SEQUENCE: 35

Asp Val Trp His Phe Ser Leu Val Asp Lys
1               5                   10


<210> SEQ ID NO 36
<211> LENGTH: 34
<212> TYPE: PRT
<213> ORGANISM: Paenibacillus alvei A6-6i-x

<400> SEQUENCE: 36

Val Glu Thr Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Cys


<210> SEQ ID NO 37
<211> LENGTH: 10
<212> TYPE: PRT
<213> ORGANISM: Paenibacillus alvei A6-6i-x

<400> SEQUENCE: 37

Asp Gly Phe Phe Leu Gly Val Val Phe Lys
1               5                   10


<210> SEQ ID NO 38
<211> LENGTH: 34
<212> TYPE: PRT
<213> ORGANISM: Paenibacillus alvei A6-6i-x

<400> SEQUENCE: 38

Leu Tyr Gln Ala Phe Asp Val Cys Tyr Gln Glu Ser Phe Ile Ile Thr
1               5                   10                  15

Ala Gly Glu His Asn His Tyr Gly Pro Ser Glu Thr His Val Val Thr
            20                  25                  30

Thr Tyr


<210> SEQ ID NO 39
<211> LENGTH: 10
<212> TYPE: PRT
<213> ORGANISM: Paenibacillus alvei A6-6i-x

<400> SEQUENCE: 39

Asp Val Gln Phe Ile Ala His Val Val Lys
1               5                   10


<210> SEQ ID NO 40
<211> LENGTH: 34
<212> TYPE: PRT
<213> ORGANISM: Paenibacillus alvei A6-6i-x

<400> SEQUENCE: 40
```

```
Ile Asn Thr Ser Phe Asp Gly Ser Ala Phe Asp Gly Leu Ile Leu Phe
1               5                   10                  15

Gly Gly Glu Lys His Ala Tyr Gly Pro Ser Glu Ser Thr Val Tyr Ala
            20                  25                  30

Thr Trp


<210> SEQ ID NO 41
<211> LENGTH: 10
<212> TYPE: PRT
<213> ORGANISM: Paenibacillus alvei A6-6i-x

<400> SEQUENCE: 41

Asp Gly Phe Leu Leu Gly Ala Val Tyr Lys
1               5                   10


<210> SEQ ID NO 42
<211> LENGTH: 34
<212> TYPE: PRT
<213> ORGANISM: Paenibacillus alvei A6-6i-x

<400> SEQUENCE: 42

Leu Tyr Gln Ala Phe Asp Val Cys Tyr Gln Glu Ser Tyr Ile Ile Thr
1               5                   10                  15

Ala Gly Glu His Asn His Tyr Gly Pro Ser Glu Thr His Val Val Thr
            20                  25                  30

Thr Tyr


<210> SEQ ID NO 43
<211> LENGTH: 10
<212> TYPE: PRT
<213> ORGANISM: Paenibacillus alvei A6-6i-x

<400> SEQUENCE: 43

Asp Val Gln Tyr Ile Ala His Val Val Lys
1               5                   10


<210> SEQ ID NO 44
<211> LENGTH: 34
<212> TYPE: PRT
<213> ORGANISM: Paenibacillus alvei A6-6i-x

<400> SEQUENCE: 44

Val Asp Ala Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Ser


<210> SEQ ID NO 45
<211> LENGTH: 10
<212> TYPE: PRT
<213> ORGANISM: Paenibacillus alvei A6-6i-x

<400> SEQUENCE: 45

Asp Gly Phe Phe Leu Gly Val Val Phe Lys
1               5                   10


<210> SEQ ID NO 46
<211> LENGTH: 34
<212> TYPE: PRT
<213> ORGANISM: Paenibacillus alvei TS-15
```

<400> SEQUENCE: 46

Leu Ala Trp Ala Phe Asp Val Phe Thr Gly Asp Arg Glu Ser Val Val
1 5 10 15

Gly Ser Asp Leu Asn Ser Tyr Gly Val Thr Glu Ala Cys Val Asp Ala
20 25 30

Cys Tyr

<210> SEQ ID NO 47
<211> LENGTH: 10
<212> TYPE: PRT
<213> ORGANISM: Paenibacillus alvei TS-15

<400> SEQUENCE: 47

Asp Val Gly Glu Val Gly Ser Val Asp Lys
1 5 10

<210> SEQ ID NO 48
<211> LENGTH: 34
<212> TYPE: PRT
<213> ORGANISM: Paenibacillus alvei TS-15

<400> SEQUENCE: 48

Leu Ala Ala Ser Phe Asp Ala Ala Thr Phe Glu Gly Trp Met Leu Val
1 5 10 15

Gly Gly Asp Ile Asn Gly Tyr Gly Pro Thr Glu Asn Thr Thr Phe Thr
20 25 30

Cys Cys

<210> SEQ ID NO 49
<211> LENGTH: 10
<212> TYPE: PRT
<213> ORGANISM: Paenibacillus alvei TS-15

<400> SEQUENCE: 49

Asp Ala Phe Trp Leu Gly Gly Thr Phe Lys
1 5 10

<210> SEQ ID NO 50
<211> LENGTH: 34
<212> TYPE: PRT
<213> ORGANISM: Paenibacillus alvei TS-15

<400> SEQUENCE: 50

Leu Asn Ser His Phe Asp Phe Ser Val Trp Glu Gly Asn Gln Ile Phe
1 5 10 15

Gly Gly Glu Ile Asn Met Tyr Gly Ile Thr Glu Thr Thr Val His Val
20 25 30

Thr Tyr

<210> SEQ ID NO 51
<211> LENGTH: 10
<212> TYPE: PRT
<213> ORGANISM: Paenibacillus alvei TS-15

<400> SEQUENCE: 51

Asp Phe Trp Asn Ile Gly Met Val His Lys
1 5 10

<210> SEQ ID NO 52
<211> LENGTH: 34

<212> TYPE: PRT
<213> ORGANISM: Paenibacillus alvei TS-15

<400> SEQUENCE: 52

Met Ala Trp Ala Phe Asp Val Phe Ser Gly Asp Arg Glu Ser Ile Ile
1 5 10 15

Gly Ser Asp Ile Asn Ser Tyr Gly Val Thr Glu Ala Cys Val Asp Ser
20 25 30

Ser Tyr

<210> SEQ ID NO 53
<211> LENGTH: 10
<212> TYPE: PRT
<213> ORGANISM: Paenibacillus alvei TS-15

<400> SEQUENCE: 53

Asp Val Gly Glu Ile Gly Ser Val Asp Lys
1 5 10

<210> SEQ ID NO 54
<211> LENGTH: 34
<212> TYPE: PRT
<213> ORGANISM: Paenibacillus alvei TS-15

<400> SEQUENCE: 54

Arg Trp Met Thr Phe Asp Val Ser Val Trp Glu Trp His Phe Phe Thr
1 5 10 15

Ser Gly Glu Ile Asn Leu Tyr Gly Pro Thr Glu Ala Thr Val Asp Val
20 25 30

Thr Tyr

<210> SEQ ID NO 55
<211> LENGTH: 10
<212> TYPE: PRT
<213> ORGANISM: Paenibacillus alvei TS-15

<400> SEQUENCE: 55

Asp Val Trp His Phe Ser Leu Val Asp Lys
1 5 10

<210> SEQ ID NO 56
<211> LENGTH: 34
<212> TYPE: PRT
<213> ORGANISM: Paenibacillus alvei TS-15

<400> SEQUENCE: 56

Ala Trp Arg Phe Phe Asp Gly Phe Val Met Ser Cys Ile Cys Thr Leu
1 5 10 15

Ala Gly Glu Phe Asn Glu Tyr Gly Pro Thr Glu Asn Ser Val Val Ala
20 25 30

Thr Cys

<210> SEQ ID NO 57
<211> LENGTH: 10
<212> TYPE: PRT
<213> ORGANISM: Paenibacillus alvei TS-15

<400> SEQUENCE: 57

Asp Gly Met Ile Thr Ala Glu Val Val Lys
1 5 10

<210> SEQ ID NO 58
<211> LENGTH: 34
<212> TYPE: PRT
<213> ORGANISM: Paenibacillus alvei TS-15

<400> SEQUENCE: 58

```
Met Ala Trp Ala Phe Asp Val Phe Ser Gly Asp Arg Asp Cys Ala Val
1               5                   10                  15

Gly Ser Asp Ile Asn Ser Tyr Gly Val Thr Glu Thr Cys Ile Asp Ala
            20                  25                  30

Ser Tyr
```

<210> SEQ ID NO 59
<211> LENGTH: 10
<212> TYPE: PRT
<213> ORGANISM: Paenibacillus alvei TS-15

<400> SEQUENCE: 59

```
Asp Val Gly Asp Ala Gly Ser Ile Asp Lys
1               5                   10
```

<210> SEQ ID NO 60
<211> LENGTH: 34
<212> TYPE: PRT
<213> ORGANISM: Paenibacillus alvei TS-15

<400> SEQUENCE: 60

```
Arg Trp Met Thr Phe Asp Val Ser Val Trp Glu Trp His Phe Phe Thr
1               5                   10                  15

Ser Gly Glu Ile Asn Leu Tyr Gly Pro Thr Glu Ala Thr Val Asp Val
            20                  25                  30

Thr Tyr
```

<210> SEQ ID NO 61
<211> LENGTH: 10
<212> TYPE: PRT
<213> ORGANISM: Paenibacillus alvei TS-15

<400> SEQUENCE: 61

```
Asp Val Trp His Phe Ser Leu Val Asp Lys
1               5                   10
```

<210> SEQ ID NO 62
<211> LENGTH: 34
<212> TYPE: PRT
<213> ORGANISM: Paenibacillus alvei TS-15

<400> SEQUENCE: 62

```
Val Glu Thr Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Cys
```

<210> SEQ ID NO 63
<211> LENGTH: 10
<212> TYPE: PRT
<213> ORGANISM: Paenibacillus alvei TS-15

<400> SEQUENCE: 63

```
Asp Gly Phe Phe Leu Gly Val Val Phe Lys
1               5                   10
```

<210> SEQ ID NO 64
<211> LENGTH: 34
<212> TYPE: PRT
<213> ORGANISM: Paenibacillus alvei TS-15

<400> SEQUENCE: 64

```
Leu Tyr Gln Ala Phe Asp Val Cys Tyr Gln Glu Ser Phe Ile Ile Thr
1               5                   10                  15

Ala Gly Glu His Asn His Tyr Gly Pro Ser Glu Thr His Val Val Thr
            20                  25                  30

Thr Tyr
```

<210> SEQ ID NO 65
<211> LENGTH: 10
<212> TYPE: PRT
<213> ORGANISM: Paenibacillus alvei TS-15

<400> SEQUENCE: 65

```
Asp Val Gln Phe Ile Ala His Val Val Lys
1               5                   10
```

<210> SEQ ID NO 66
<211> LENGTH: 34
<212> TYPE: PRT
<213> ORGANISM: Paenibacillus alvei TS-15

<400> SEQUENCE: 66

```
Ile Asn Thr Ser Phe Asp Gly Ser Ala Phe Asp Gly Leu Ile Leu Phe
1               5                   10                  15

Gly Gly Glu Lys His Ala Tyr Gly Pro Ser Glu Ser Thr Val Tyr Ala
            20                  25                  30

Thr Trp
```

<210> SEQ ID NO 67
<211> LENGTH: 10
<212> TYPE: PRT
<213> ORGANISM: Paenibacillus alvei TS-15

<400> SEQUENCE: 67

```
Asp Gly Phe Leu Leu Gly Ala Val Tyr Lys
1               5                   10
```

<210> SEQ ID NO 68
<211> LENGTH: 34
<212> TYPE: PRT
<213> ORGANISM: Paenibacillus alvei TS-15

<400> SEQUENCE: 68

```
Leu Tyr Gln Ala Phe Asp Val Cys Tyr Gln Glu Ser Tyr Ile Ile Thr
1               5                   10                  15

Ala Gly Glu His Asn His Tyr Gly Pro Ser Glu Thr His Val Val Thr
            20                  25                  30

Thr Tyr
```

<210> SEQ ID NO 69
<211> LENGTH: 10
<212> TYPE: PRT
<213> ORGANISM: Paenibacillus alvei TS-15

<400> SEQUENCE: 69

```
Asp Val Gln Tyr Ile Ala His Val Val Lys
1               5                   10


<210> SEQ ID NO 70
<211> LENGTH: 34
<212> TYPE: PRT
<213> ORGANISM: Paenibacillus alvei TS-15

<400> SEQUENCE: 70

Val Asp Ala Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
            20                  25                  30

Thr Ser


<210> SEQ ID NO 71
<211> LENGTH: 10
<212> TYPE: PRT
<213> ORGANISM: Paenibacillus alvei TS-15

<400> SEQUENCE: 71

Asp Gly Phe Phe Leu Gly Val Val Phe Lys
1               5                   10


<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

agagtttgat cctggctcag                                              20


<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

ggttaccttg ttacgactt                                               19


<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

ctcctacggg aggcagca                                                18


<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
```

cgtattaccg cggctgctgg 20

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
agggttgcgc tcgttg 16

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D-Orn
<220> FEATURE:
<221> NAME/KEY: MOD_RES
<222> LOCATION: (4)..(4)
<223> OTHER INFORMATION: D-Orn
<220> FEATURE:
<221> NAME/KEY: MOD_RES
<222> LOCATION: (8)..(8)
<223> OTHER INFORMATION: D-Ser
<220> FEATURE:
<223> OTHER INFORMATION: See specification as filed for detailed
description of substitutions and preferred embodiments

<400> SEQUENCE: 77

Xaa Val Thr Xaa Ser Tyr Lys Ser Ile Pro Ile Pro Ile
1 5 10

<210> SEQ ID NO 78
<211> LENGTH: 13
<212> TYPE: PRT
<213> ORGANISM: Paenibacillus sp. OSY-SE
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 78

Xaa Val Thr Xaa Ser Val Lys Ser Ile Pro Val Lys Ile
1 5 10

<210> SEQ ID NO 79
<211> LENGTH: 13
<212> TYPE: PRT
<213> ORGANISM: Paenibacillus alvei TS-15
<220> FEATURE:
<221> NAME/KEY: MOD_RES
<222> LOCATION: (1)..(1)
<223> OTHER INFORMATION: D-Orn
<220> FEATURE:
<221> NAME/KEY: MOD_RES
<222> LOCATION: (4)..(4)
<223> OTHER INFORMATION: D-Orn
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (7)..(7)
<223> OTHER INFORMATION: Lys or D-Orn
<220> FEATURE:
<221> NAME/KEY: MOD_RES
<222> LOCATION: (8)..(8)
<223> OTHER INFORMATION: D-Ser

<400> SEQUENCE: 79

Xaa Val Thr Xaa Ser Xaa Xaa Ser Ile Pro Ile Pro Ile
1 5 10

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Orn

<400> SEQUENCE: 80

Xaa Ser Tyr Lys Ser Ile
1 5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (6)..(6)
<223> OTHER INFORMATION: Orn

<400> SEQUENCE: 81

Ile Ser Lys Tyr Ser Xaa
1 5

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 82

Xaa Val Thr Xaa Ser Phe Xaa Ser Ile Pro Ile Pro Ile
1 5 10

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ser Phe Lys Ser
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Phe Lys Ser Ile
1

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Ser Phe Lys Ser Ile
1 5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Ser Phe Lys Ser Ile Pro
1 5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Orn

<400> SEQUENCE: 87

Xaa Ser Ile Pro Ile Pro Ile
1 5

<210> SEQ ID NO 88
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 88

Ser Phe Lys Ser Ile Pro Ile
1               5


<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 89

Xaa Ser Phe Lys Ser Ile Pro Ile
1               5


<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 90

Xaa Ser Phe Lys Ser Ile Pro Ile Pro Ile
1               5                   10


<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Orn

<400> SEQUENCE: 91

Thr Xaa Ser Phe Ser Ile Pro Ile Pro Ile
1               5                   10


<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Orn

<400> SEQUENCE: 92

Val Thr Xaa Ser Phe Lys Ile Pro Ile Pro Ile
1               5                   10
```

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 93

Xaa Val Thr Xaa Ser Phe Lys Ser Ile Pro Ile Pro Ile
1               5                   10

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Tyr Lys Ser
1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Tyr Lys Ser Ile
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Tyr Lys Ser Ile Pro
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Tyr Lys Ser Ile Pro Ile
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Orn

<400> SEQUENCE: 98

Xaa Ser Tyr Lys Ser Ile Pro Ile
1 5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Orn

<400> SEQUENCE: 99

Xaa Ser Tyr Lys Ser Ile Pro Ile Pro Ile
1 5 10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Orn

<400> SEQUENCE: 100

Thr Xaa Ser Tyr Ser Ile Pro Ile Pro Ile
1 5 10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Orn

<400> SEQUENCE: 101

Val Thr Xaa Ser Tyr Lys Ser Ile Pro Ile Pro Ile
1 5 10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 102

Xaa Val Thr Xaa Ser Tyr Lys Ser Ile Pro Ile Pro Ile
1 5 10

<210> SEQ ID NO 103
<211> LENGTH: 5
<212> TYPE: PRT
<213> ORGANISM: Unknown
<220> FEATURE:
<223> OTHER INFORMATION: Description of Unknown:
pbtA sequence
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 103

Xaa Val Thr Xaa Ser
1 5

<210> SEQ ID NO 104
<211> LENGTH: 5
<212> TYPE: PRT
<213> ORGANISM: Unknown
<220> FEATURE:
<223> OTHER INFORMATION: Description of Unknown:
pbtB sequence
<220> FEATURE:
<221> NAME/KEY: MOD_RES
<222> LOCATION: (2)..(2)
<223> OTHER INFORMATION: Orn

<400> SEQUENCE: 104

Tyr Xaa Ser Ile Pro
1 5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Orn

<400> SEQUENCE: 105

Ser Phe Xaa Ser Ile
1 5

<210> SEQ ID NO 106
<211> LENGTH: 5
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Orn

<400> SEQUENCE: 106

Phe Ser Xaa Thr Val
1               5
```

ANTIMICROBIAL PEPTIDES, PHARMACEUTICAL COMPOSITIONS, AND METHODS OF USE THEREOF

CROSS-REFERENCE TO RELATED APPLICATIONS

This is a continuation of U.S. patent application Ser. No. 15/371,683, filed on Dec. 7, 2016, which issued as U.S. Pat. No. 10,118,948, which is a continuation in part of PCT/US2015/034859, filed on Jun. 9, 2015, which claims the benefit of U.S. Provisional Application 62/009,467 filed on Jun. 9, 2014, which are all incorporated herein by reference in their entirety.

FIELD OF THE DISCLOSURE

The present disclosure is related to antimicrobial peptides, pharmaceutical compositions containing the antimicrobial peptides, and methods of treating microbial infections with the antimicrobial peptides.

BACKGROUND

Antibiotic-resistant pathogenic bacteria such as methicillin resistant *Staphylococcus aureus* (MRSA), fluoroquinolone resistant *Pseudomonas aeruginosa* and *Clostridium difficile*, and multi-drug resistant *Salmonella* spp. are an emerging problem in modern medicine. The loss of efficacy of current antibiotics makes the identification and development of new antibiotics more critical. The environment, for example, is an important source of microbial strains capable of producing potent antimicrobials which can be isolated and purified from their natural sources.

*Paenibacillus*, spore-forming species widely distributed in the environment, are a potential source of new antimicrobials. Strains of *Paenibacillus* can produce diverse antimicrobial agents including lantibiotics, lipopeptides, and macrolides. Lipopeptides, for example, are compounds that are generally not synthesized by ribosomes, and that are active against a wide range of bacteria, fungi, and oomycetes. Lipopeptides can act as antiviral and antitumor agents, immunomodulators or specific toxins and enzyme inhibitors.

There is thus a need to identify and develop antimicrobial agents that are effective against a broad spectrum of microbial pathogens such as Gram-positive and Gram-negative bacteria.

BRIEF SUMMARY

In an aspect, included herein is a peptide of the sequence (SEQ ID NO: 2)
$Xaa_1$-$Xaa_2$-$Xaa_3$-$Xaa_4$-$Xaa_5$-$Xaa_6$-$Xaa_7$-$Xaa_8$-$Xaa_9$-$Pro_{10}$-$Xaa_{11}$-$Pro_{12}$-$Ile_{13}$,, wherein $Xaa_6$ is Tyr, Phe, or Trp; $Xaa_1$, $Xaa_4$ and $Xaa_7$ are each independently Lys or Orn; $Xaa_2$, $Xaa_9$ and $Xaa_{11}$ are each independently Leu, Ile, Val, or Ala; $Xaa_3$, $Xaa_5$, and $Xaa_8$ are each independently Cys, Tyr, Thr, or Ser; wherein the peptide optionally includes a saturated or unsaturated, substituted or unsubstituted, linear or branched $C_4$-$C_{20}$ fatty acid group, or a saturated or unsaturated, linear or branched $C_4$-$C_{20}$ ester covalently linked to $Xaa_1$.

In another aspect, included herein is a peptide of the sequence (SEQ ID NO: 3)
$Xaa_1$-$Val_2$-$Thr_3$-$Xaa_4$-$Ser_5$-$Xaa_6$-$Xaa_7$-$Ser_8$-$Ile_9$-$Pro_{10}$-$Xaa_{11}$-$Pro_{12}$-$Ile_{13}$,, wherein $Xaa_6$ is Tyr, Phe, or Trp; $Xaa_{11}$ is Leu, Ile, Val, or Ala; and $Xaa_1$, $Xaa_4$ and $Xaa_7$ are independently Lys or Orn, wherein the peptide optionally includes a saturated or unsaturated, substituted or unsubstituted, linear or branched $C_4$-$C_{20}$ fatty acid group, or a saturated or unsaturated, linear or branched $C_4$-$C_{20}$ ester covalently linked to $Xaa_1$.

In certain aspects, the peptides are cyclized through a bond between $Thr_3$ and $Ile_{13}$.

Further included herein is a composition comprising the peptides described above and a carrier, vehicle, excipient, or diluent.

In yet another aspect, a process for preparing the peptides described above comprises (a) cultivating a host cell under conditions that allow for production of the peptide; and (b) purifying and isolating the peptide.

In a further aspect, a process for preparing a composition comprising the peptides described above comprises (a) cultivating a host cell under conditions that allow for production of the peptide; (b) purifying and isolating the peptide, and (c) producing a composition comprising the isolated peptide and a carrier, vehicle, excipient, or diluent.

In a still further aspect, a method of inhibiting growth or proliferation of a microbe comprises contacting the microbe or a surface or product which may contain a microbe with the peptide described above.

In a still further aspect, a method of inhibiting growth or proliferation of a microbe in a subject comprises administering to the subject a composition comprising one or more of the peptides described above, wherein the peptide is administered in an amount effective to inhibit growth or proliferation of the microbe.

BRIEF DESCRIPTION OF THE DRAWINGS

FIGS. 10A and 10B disclose SEQ ID NOS 83-96, 87, and 97-102, respectively, in order of appearance.

FIG. 16A-16M is a ptbA alignment for strains A6-6i, TS-15 and OSY SE. The protein sequences for A6-6i is SEQ ID NO: 11. The protein sequences for TS-15 ptbA is SEQ ID NO: 14, respectively. The protein sequences for OSY-SE ptbA is SEQ ID NO: 17.

FIG. 17A-17M is a ptbB alignment for strains A6-6i, TS-15 and OSY SE. The protein sequences for A6-6i ptbB, is SEQ ID NO: 12. The protein sequences for TS-15 ptbB is SEQ ID NO:15. The protein sequences for OSY-SE ptbB, and ptbC are SEQ ID NO: 18.

Figure 1A:
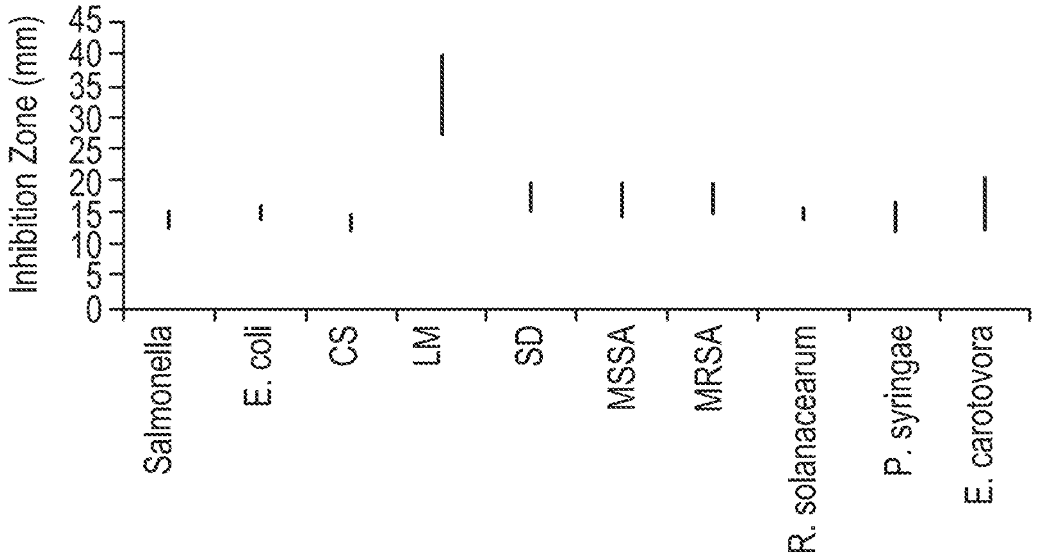
FIGS. 1A and 1B show in vitro inhibition of foodborne pathogens and tomato bacterial phytopathogens by *Paenibacillus alvei* TS-15 (FIG. 1A; ATCC PTA-121756) and A6-6i (FIG. 1B; ATCC PTA-121885) on tryptic soy agar (TSA). The inhibition zones (mm) were measured against strains from *Salmonella* spp., *Escherichia coli* (*E. coli*), Cronobacter sakazakii (CS), *Listeria monocytogenes* (LM), *Shigella dysenteriae* (SD), Methicillin sensitive *Staphylococcus aureus* (MSSA), Methicillin resistant *Staphylococcus aureus* (MRSA), *Ralstonia solanacearum* race 5 (*R. solanacearum*), *Pseudomonas syringae* pv. tomato strain dc3000 (*P. syringae*), and *Erwinia carotovora* subsp. *carotovora* (*E. carotovora*). The plots represents the lowest, highest, and average measurements in each of the species listed above. The experiment was repeated twice.

The above-described and other features will be appreciated and understood by those skilled in the art from the following detailed description, drawings, and appended claims.

SEQUENCE LISTING

The Sequence Listing is submitted as an ASCII text file [9531-98583-13 SL.txt, Sep. 23, 2019, 585,667 bytes], which is incorporated by reference herein.

DETAILED DESCRIPTION

Described herein are novel peptides, specifically cyclic peptides, that have antimicrobial and broad-spectrum antibacterial activity. Specifically, the peptides are active against dangerous Gram-positive organisms such as MRSA and VRSA.

Recently, tomatoes have been implicated as a primary vehicle in foodborne outbreaks of *Salmonella* Newport and other *Salmonella* serovars. Long-term intervention measures to reduce *Salmonella* prevalence on tomatoes remain elusive for growing and post-harvest environments. A naturally-occurring bacterium identified by 16S rDNA sequencing as *Paenibacillus alvei* was isolated epiphytically from plants native to the Virginia Eastern Shore tomato growing region. After initial antimicrobial activity screening against *Salmonella* and 10 other bacterial pathogens associated with the human food supply, strain TS-15 was further used to challenge an attenuated strain of S. Newport on inoculated tomatoes, leaves, and blossoms of tomato plants in an insect-screened high tunnel with a split-plot design. Survival of *Salmonella* after inoculation was measured for groups with and without the antagonist at days 0, 1, 2, 3, and 5 for blossoms and day 6 for tomatoes and leaves, respectively. TS-15 exhibited broad range antimicrobial activity against both major foodborne pathogens and major tomato plant-associated bacterial pathogens. After *P. alvei* strain TS-15 was applied onto the tomatoes, leaves, and blossoms of tomato plants, the concentration of S. Newport was significantly lower ($p \leq 0.05$) compared with controls. Surprisingly, more than 90% of the plants had no detectable levels of *Salmonella* by day 5 for blossoms. The naturally occurring antagonist strain TS-15 is highly effective in reducing carriage of *Salmonella* Newport on whole tomato plants. The application of *P. alvei* strain TS-15 is a promising approach for reducing the risk of *Salmonella* contamination during tomato production. In addition, *Paenibacillus* strain A6-6i was found to retain comparable properties. Given to the fact that this activity can be attributed to the bactericidal compounds within, the present inventors have chemically isolated, purified, and identified certain compounds responsible for anti-*Salmonella* and other antibiotic effects including effects on dangerous gram positive organisms such as MRSA and VRSA.

More specifically, antimicrobial compounds were isolated from these *Paenibacillus* strains and a combination of low and high resolution mass spectrometry with multiple-stage tandem mass spectrometry was used for identification. A group of closely related cyclic lipopeptides was identified, differing primarily by fatty acid chain length and one of two possible amino acid substitutions. Variation in the fatty acid length resulted in mass differences of 14 Da and yields groups of related $MS^n$ spectra. Despite the inherent complexity of MS/MS spectra of cyclic compounds, straightforward analysis of these spectra was accomplished by determining differences in complementary product ion series between compounds that differ in molecular weight by 14 Da.

An “antimicrobial compound” is a compound that exhibits antimicrobial activity or a compound that affects microbial activity, meaning a compound that slows or stops growth and/or proliferation, slows or stops the rate of growth and/or proliferation, or stuns, inactivates, or kills a microbe. Antimicrobial compounds include antibiotics, antibacterials (e.g., bactericidal or bacteriostatic agents), antivirals (e.g., virucidal agents), antifungals (e.g., fungicidal or fungistatic agents), mold-inhibiting agents, anthelminthics (e.g., vermifuge or vermicidal agents), antiparasitics, and the like. Antimicrobial activity can be determined using methods described herein as well as methods known in the art.

As used herein, amino acids include alpha-amino acids of the general formula $H_2NCHRCOOH$ when free and HNCHRCO when in a polypeptide, wherein R is an amino acid side chain comprising an organic substituent, as well as uniquely structured amino acids such as, for example, proline Amino acids include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, aminobutryic acid (alpha, beta, and gamma) diaminobutyric acid, and the like. The term “amino acid side chain” refers to the various organic substituent groups (e.g., “R” in $H_2NCHRCOOH$) that differentiate one amino acid from another Amino acids include both L-form and D-form amino acids.

In one aspect, an antimicrobial peptide has the sequence:

(SEQ ID NO: 1)
$Xaa_1$-$Val_2$-$Thr_3$-$Xaa_4$-$Ser_5$-$Xaa_6$-$Xaa_7$-$Ser_8$-$Ile_9$-$Pro_{10}$-$Ile_{11}$-$Pro_{12}$-$Ile_{13}$,, wherein $Xaa_6$ is Tyr, Phe, or Trp, specifically Tyr or Phe; $Xaa_1$, $Xaa_4$, and $Xaa_7$ are each independently Lys or Orn; or, (SEQ ID NO: 2)
$Xaa_1$-$Xaa_2$-$Xaa_3$-$Xaa_4$-$Xaa_5$-$Xaa_6$-$Xaa_7$-$Xaa_8$-$Xaa_9$-$Pro_{10}$-$Xaa_{11}$-$Pro_{12}$-$Ile_{13}$, wherein $Xaa_6$ is Tyr, Phe, or Trp, specifically Tyr or Phe; $Xaa_1$, $Xaa_4$, and $Xaa_7$ are each independently Lys or Orn; $Xaa_2$, $Xaa_9$ and $Xaa_{11}$ are each independently a hydrophobic amino acid selected from Leu, Ile, Val, and Ala; $Xaa_3$, $Xaa_5$, and $Xaa_8$ are each independently an amino acid selected from amino acids that can form a hydrogen bond, a disulfide bond, a thioether bond, or an ester bond, such as Cys, Tyr, Thr, and Ser.

In a more specific aspect, an antimicrobial peptide has the sequence:

(SEQ ID NO: 3)
Xaa1-Val2-Thr3-Xaa4-Ser5-Xaa6-Xaa7-Ser8-Ile9-Pro10-Xaa11-Pro12-Ile13,, wherein $Xaa_6$ is Tyr, Phe, or Trp, specifically Tyr or Phe; Xaa1, Xaa4, and Xaa7 are each independently Lys or Orn; Xaa11 is a hydrophobic amino acid selected from Leu, Be, Val, and Ala. In a specific embodiment, Xaa1 and Xaa4 are Orn and Xaa11 is Ile; more specifically, (SEQ ID NO: 79)
D-Orn1-Val2-Thr3-D-Orn4-Ser5-Xaa6-Xaa7-D-Ser8-Ile9-Pro10-Ile11-Pro12-Ile13,, wherein Xaa6 is Tyr or Phe; and Xaa7 is Lys or D-Orn.

In a specific embodiment, the peptide is (SEQ ID NO: 77)
D-Orn1-Val2-Thr3-D-Orn4-Ser5-Tyr6-Lys7-D-Ser8-Ile9-Pro10-Ile11-Pro12-Ile13,.

In an aspect, the peptide comprises D-Lys at position 7. In another aspect, the peptide comprises L-Lys at position 7

In certain embodiments, the peptides of SEQ ID NOs: 1-4 include a fatty acid group, particularly a saturated or unsaturated, substituted or unsubstituted, linear or branched $C_4$-$C_{20}$ fatty acid group, or a saturated or unsaturated, linear or branched $C_4$-$C_{20}$ ester covalently linked to the amino acid at the 1 position, e.g., $Xaa_1$. The fatty acid chain is diverse in the number of —$CH_2$. For example, the molecular formula of the acyl chain can be $C_{10}H_{19}O$, $C_{11}H_{21}O$, $C_{12}H_{23}O$, $C_{13}H_{25}O$, $C_{14}H_{27}O$, or $C_{15}H_{29}O$. The ester group differs similarly ($C_{10}H_{19}O_2$, $C_{11}H_{21}O_2$, $C_{12}H_{23}O_2$, $C_{13}H_{25}O_2$, $C_{14}H_{27}O_2$, or $C_{15}H_{29}O_2$).

Depending on the functional groups, peptides can be cyclized C-terminus to N-terminus, C-terminus to side-chain, side-chain to N-terminus, or side-chain to side-chain. In one aspect, the peptide is cyclized through a bond between $Thr_3$ and $Ile_{13}$.

In a specific embodiment, when $Xaa_6$ is Tyr, the amino acid at the 1 position is covalently linked to a fatty acid group or an ester group, and when $Xaa_6$ is Phe, the amino acid at the 1 position is covalently linked to a fatty acid group.

It is noted that the presently disclosed compounds are distinct from the cyclic peptides disclosed in US2013/0164317, which requires that $X_{12}$ is an amino acid with a charged side chain. In the present compounds, $X_{12}$ is a Proline, which is expected to impart a unique structure and also antimicrobial properties to the disclosed peptides.

Also included herein are methods of producing an antimicrobial compound, specifically an antimicrobial peptide, by (a) cultivating a host cell under conditions that allow for production of the antimicrobial peptide; and optionally (b) purifying/isolating the antimicrobial peptide.

Host cells are cultivated in a nutrient medium suitable for production of the antimicrobial peptide using techniques known in the art. For example, the cell is cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. A suitable nutrient medium (e.g., a medium comprising carbon and nitrogen sources, inorganic salts, etc.) is used to cultivate the cells. In embodiments wherein the antimicrobial peptide is secreted from the cell into the nutrient medium, the antimicrobial peptide can be recovered directly from the medium. If the antimicrobial peptide is not secreted, it can be recovered from cell lysates or as inclusion bodies. The antimicrobial peptide may be recovered from the nutrient medium or cell lysates by procedures including, but not limited to, centrifugation, filtration, extraction, spray-drying, evaporation, and precipitation.

The antimicrobial peptides disclosed herein may be purified by a variety of procedures including, but not limited to, chromatography (e.g., ion exchange, affinity, hydrophobic, chromatofocusing, and size exclusion), electrophoretic procedures (e.g., preparative isoelectric focusing), differential solubility (e g, ammonium sulfate precipitation), SDS-PAGE, and extraction.

Bacterial cultures for the production of the antimicrobial peptides can be grown using suitable methods and media useful for bacterial cell growth, maintenance, and/or protein production.

In some embodiments of this process, the antimicrobial peptide is isolated and/or purified using a suitable technique known in the art, including liquid chromatography, phase separation, using organic solvents and/or aqueous solvent or buffer systems. In some embodiments the antimicrobial peptide is purified to about 75%, 80%, 85%, 90%, 91%, 92%, 93%, 94%, 95%, 96%, 97%, 98%, or 99% or more. Analysis of purity can be made using an analytical method or technique such as, for example, mass spectrometry, gel electrophoresis, fluorescence, colorimetric assays, NMR, UV-Vis, total amino acid hydrolysis, chromatographic separation methods that utilize, for example, liquid chromatographic methods such as HPLC, FPLC, size exclusion, affinity binding, hydrophobic interaction, ionic charge, where purity can be assessed based on peak area.

In other embodiments, the antimicrobial peptides can be generated by standard chemical and/or protein and peptide synthetic techniques as are known in the art. Some embodiments relate to a synthetic strategy that incorporates a combination of chemical, peptide, and enzymatic (e.g., cyclase) synthetic steps. Chemical techniques for cyclizing peptides are well-known in the art.

Aspects of the disclosure relate to compositions and formulations, including pharmaceutical compositions and formulations that comprise an effective amount of at least one antimicrobial peptide. Such compositions and formulations comprise an effective amount of an antimicrobial peptide in combination with a carrier, vehicle, excipient, or diluent, including pharmaceutically and/or agriculturally acceptable carriers, vehicles, excipients, and diluents. An "effective amount" relates to a quantity of an antimicrobial peptide that is high enough to provide a significant positive result (e.g., slow or stop microbial activity) or positive modification of the subject's condition to be treated, and is suitably low enough to avoid serious side effects (at a reasonable benefit/risk ratio). Carriers, vehicles, excipients, and diluents are one or more compatible substances that are suitable for administration to a mammal such as, for example, solid or liquid fillers, diluents, hydrotopes, surface-active agents, and encapsulating substances. "Compatible" means that the components of the composition are capable of being mixed with the active agent, and with each other, in a manner such that there is no interaction which would substantially reduce the efficacy of the composition under ordinary use situations. Carriers, vehicles, excipients, and diluents are suitably of sufficiently high purity and sufficiently low toxicity to render them suitable for administration to the subject being treated, such as a human subject. The carrier, vehicle, excipient, or diluent can be inert, or it can possess pharmaceutical benefits and/or aesthetic benefits, or both. Suitable carriers, vehicles, excipients, and diluents are known in the art.

The antimicrobial compositions are applicable in a variety of products and applications, ranging from, for example, products of low and high pH-values, highly concentrated and diluted products, products usable in the technical field (e.g., in detergents for industrial or house-hold use), in the pharmaceutical field (e.g., for cleaning/disinfection of equipment or in the preparation of pharmaceutical compositions or their packaging, and in surgical supplies and sterilization of tools/hospital operating rooms), in personal care (e.g., in manufacture of cosmetics, shampoos, creams and lotions), in the feed industry (e.g., for cleaning of equipment, in the manufacture, storage, handling and preparation of animal feed and drink products) and in the food and drink industry (post-harvest foods, food processing surfaces and packaging). The antimicrobial peptides are also useful in post-surgical bandage and would dressing prep, external wound healing and cleansing. In addition, the antimicrobial peptides are useful in post-harvest and food preservation applications against spoilage organisms. In embodiments relating to use of the compositions in a product, the antimicrobial composition can be provided as an ingredient in the final product (e.g., cosmetic, detergent, pharmaceutical, food, or drink product). Accordingly, in some embodiments, the compositions are effective against certain yeasts, fungi, and bacteria commonly associated with food-spoilage. Standard methods can be used in the manufacture of such products that comprise one or more of the antimicrobial peptide described herein.

In some embodiments, the antimicrobial composition is present on the surface of the products or inside the products. In some embodiments, the disclosure includes a method for reducing or preventing the presence, growth or activity of a microbe (e.g., gram-positive or gram-negative bacteria) in a product, such as a food or drink product, wherein the method comprises contacting the food or drink product during one or more of the various stages in the food processing process including the stages of the manufacture, the handling, the storage and/or the preparation of the food or drink product with the antibacterial compositions that are disclosed herein. The antimicrobial composition may be applied or introduced by a suitable route or method such as, for example, as a spray, a rinse or a wash solution or as solution wherein the various food products are dipped. Further, the antimicrobial composition may be used to treat containers or packaging film prior to, simultaneously with, or subsequently after packaging the products.

In one aspect, a method of inhibiting growth or proliferation of a microbe comprises contact of the microbe with an antimicrobial peptide as described herein. “Contacting,” as used herein as in “contacting a cell,” refers to contacting a cell directly or indirectly in vitro, ex vivo, or in vivo (i.e., within a subject, such as a mammal, including humans, mice, rats, rabbits, cats, and dogs). Contacting a cell, which also includes “reacting” a cell, can occur as a result of administration to a subject. Contacting encompasses administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as defined herein.

The antimicrobial compositions described herein may be provided in solid or liquid form. When in liquid form, the composition is typically an aqueous composition, which may be a solution, emulsion, or dispersion.

Accordingly, the methods described herein include administration of one or more pharmaceutical compositions, in which an antimicrobial peptide is admixed together with one or more pharmaceutically acceptable carriers, excipients, buffers, adjuvants, stabilizers, or other materials, as described herein.

“Pharmaceutically acceptable,” as used herein, pertains to compounds, materials, compositions, and/or dosage forms which are, within the scope of sound medical judgment, suitable for use in contact with the tissues of a subject (e.g., a human) without excessive toxicity, irritation, allergic response, or other problem or complication, commensurate with a reasonable benefit/risk ratio. Each carrier, excipient, etc. must also be “acceptable” in the sense of being compatible with the other ingredients of the formulation.

The formulations may conveniently be presented in unit dosage form and may be prepared by methods known in the art of pharmacy. Such methods include the step of bringing into association the active compound(s) with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) are typically presented as discrete units such as capsules, cachets or tablets, each containing a predetermined amount of the active compound; as a powder or granules; as a solution or suspension in an aqueous or nonaqueous liquid; or as an oil-in-water liquid emulsion or a water-in-oil liquid emulsion; as a bolus; as an electuary; or as a paste.

A tablet may be made by compression or molding, optionally with one or more accessory ingredients. Compressed tablets are prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets are made by molding in a suitable machine a mixture of the powdered compound moistened with an inert liquid diluent. The tablets are optionally coated or scored and may be formulated so as to provide slow or controlled release of the active compound therein using, for example, hydroxypropylmethyl cellulose in varying proportions to provide the desired release profile. Tablets are optionally provided with an enteric coating, to provide release in parts of the gut other than the stomach.

Formulations suitable for parenteral administration (e.g., by injection, including cutaneous, subcutaneous, intramuscular, intravenous and intradermal injection), include aqueous and nonaqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of isotonic vehicles for use in such formulations include Sodium Chloride Injection, Ringer’s Solution, or Lactated Ringer’s Injection. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. Formulations suitable for topical administration to the eye also include eye drops wherein the active compound is dissolved or suspended in a suitable carrier, especially an aqueous solvent for the active compound.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. The topical formulations may desirably include a compound which enhances absorption or penetration of the active compound through the skin or other affected areas. Examples of such dermal penetration enhancers include dimethylsulfoxide.

It will be appreciated that appropriate dosages of the active compounds, and compositions comprising the active compounds, can vary from subject to subject. Determining the optimal dosage will generally involve the balancing of the level of therapeutic benefit against any risk or deleterious side effects of the treatments described herein. The selected dosage level will depend on a variety of factors including, but not limited to, the species of the particular subject, the activity of the particular compound, the route of administration, the time of administration, the rate of excretion of the compound, the duration of the treatment, whether other drugs, compounds, and/or materials are used in combination, and the age, sex, weight, condition, general health, and prior medical history of the subject. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day, administered in a single or multiple doses per day.

A method of inhibiting growth or proliferation of a microbe in a subject comprises administering to the subject a composition comprising an antimicrobial peptide, wherein the antimicrobial peptide is administered in an amount effective to inhibit growth or proliferation of the microbe.

In an embodiment, a method of treating a condition or disease associated with the presence of a microbe comprises administering to a subject in need thereof a composition comprising an antimicrobial peptide, wherein the antimicrobial peptide is administered in an amount effective to treat the condition or disease.

In an embodiment, a method of treating a microbial infection comprises administering to a subject in need thereof a composition comprising an antimicrobial peptide, wherein the antimicrobial peptide is administered in an amount effective to treat the microbial infection. Exemplary infections include MRSA, VRSA, and CRE infections.

"Administration" or "administering," as used herein, refers to providing, contacting, and/or delivery of a compound or compounds by an appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional, or intracranial injection), transdermal, topical, buccal, rectal, vaginal, nasal, ophthalmic, via inhalation, and implants.

As used herein, the terms "treatment," "treating," or "treat" refer to both therapeutic treatment and prophylactic or preventative measures. Those subjects in need of treatment include those already showing clinical signs of the particular disease, disorder, or condition as well as those prone to having or developing the disease, disorder, or condition, or those in which the disease, disorder, or condition is to be prevented. Many diseases, disorders, and conditions relate to the presence of microbes and are known to those of skill in the art, including secondary conditions resulting from opportunistic infections arising from other primary diseases and disorders (e.g., immune-suppressing conditions). Thus, a variety of patient classes can benefit from the methods of treatment described herein.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as fowl (e.g., ducks, chickens, etc.), amphibians, reptiles) and mammals, such as non-human primates, domesticated and/or agriculturally useful animals (such as horses, goats, sheep, dogs, cats, cows, pigs, etc.), and rodents (such as mice, rats, hamsters, guinea pigs, etc.).

In some embodiments the "effective amount" is an amount sufficient to stop or slow the progression of the disease, disorder, or condition. In some embodiments the effective amount is an amount sufficient to reverse disease, disorder, or condition, or repair the clinical signs of a disease, disorder, or condition. In embodiments the amount is sufficient to stop or slow the progression of an infection that is directly or indirectly related to a microbe. In some embodiments the effective amount is sufficient to stop or slow the proliferation and/or growth of a microbe. In further embodiments, the effective amount is sufficient to kill a microbe.

"Co-administered," as used herein, refers to simultaneous or sequential administration of multiple compounds or agents. A first compound or agent may be administered before, concurrently with, or after administration of a second compound or agent. The first compound or agent and the second compound or agent may be simultaneously or sequentially administered on the same day, or may be sequentially administered within 1 day, 2 days, 3 days, 4 days, 5 days, 6 days, 1 week, 2 weeks, 3 weeks or one month of each other. Suitably, compounds or agents are co-administered during the period in which each of the compounds or agents are exerting at least some physiological effect and/or has remaining efficacy. In some embodiments, the methods described herein can comprise co-administering two or more active agents disclosed herein. In some embodiments, the methods comprising co-administering two or more active agents include at least one antimicrobial agent disclosed herein in combination with a known active agent against a particular indication. In some further embodiments, the known active agent also exhibits antimicrobial activity.

Additional antimicrobial agents can be selected based on the particular method and indication, such that it can provide an additive or a synergistic antimicrobial effect when compared to administration of the antimicrobial agent alone. For example, other antibiotics such as polymyxin B can be concurrently applied to increase its effect against gram-negative bacteria. Furthermore, fungicides can be co-administered for broader protection.

The invention is further illustrated by the following non-limiting examples.

EXAMPLES

Methods

Bacterial Cell Culture: *Paenibacillus alvei* strains A6-6i and TS-15, naturally-occurring bacterium previously isolated from plant and soil native to the Virginia Eastern Shore tomato growing region, were propagated on tryptic soy agar (TSA) at 35° C. The indicator strains (Table 1) included were also propagated on TSA at 35° C. Stock cultures grown overnight at 35° C. on TSA were resuspended in brain heart infusion broth (BHI) with 25% glycerol and stored at −80° C. Three tomato plant-associated bacterial pathogens including *Erwinia carotovora* subsp. *carotovora, Pseudomonas*

*syringae* pv. tomato strain dc3000, and *Ralstonia solanacearum* race 5 were grown on TSA at 25° C. (Table 1).

TABLE 1

| Strain | Reference or source |
|---|---|
| *Salmonella enterica* subsp. *enterica* serovar Newport #17 | CFSAN laboratory collection |
| *Salmonella enterica* subsp. *enterica* Saintpaul | CFSAN laboratory collection |
| *Salmonella enterica* subsp. *enterica* Montevideo 42N | CFSAN laboratory collection |
| *Salmonella enterica* subsp. *enterica Javiana* | CFSAN laboratory collection |
| *Salmonella enterica* subsp. *enterica Typhimurium* 368477 | CFSAN laboratory collection |
| *Salmonella enterica* subsp. *enterica Typhimurium* SAR C #1 | SGSC[a] |
| *Salmonella enterica* subsp. *enterica Typhi* SAR C #3 | SGSC |
| *Salmonella enterica* subsp. *arizonae* SAR C #5 | SGSC |
| *Salmonella enterica* subsp. *arizonae* SAR C #7 | SGSC |
| *Salmonella enterica* subsp. *arizonae* SAR C #9 | SGSC |
| *Salmonella bongori* SAR C #11 | SGSC |
| *Salmonella bongori* SAR C #13 | SGSC |
| *Salmonella bongori* SAR C #15 | SGSC |
| *Escherichia coli* O157: H7 IS O57 | CFSAN laboratory collection |
| *Escherichia coli* O157: H7 EDL933 | CFSAN laboratory collection |
| *Escherichia coli* ATCC 51434 | ATCC[b] |
| *Escherichia coli* ATCC BAA-179 | ATCC |
| *Shigella dysenteriae* 2457T | CFSAN laboratory collection |
| *Shigella dysenteriae* BS103 | CFSAN laboratory collection |
| *Cronobacter sakazakii* E932 | CFSAN laboratory collection |
| *Cronobacter sakazakii* E784 | CFSAN laboratory collection |
| *Listeria monocytogenes* N1-225 | CFSAN laboratory collection |
| *Listeria monocytogenes* R2-583 | CFSAN laboratory collection |
| Methicillin-resistant *Staphylococcus aureus* #9 | CFSAN laboratory collection |
| Methicillin-resistant *Staphylococcus aureus* #12 | CFSAN laboratory collection |
| Methicillin-resistant *Staphylococcus aureus* #28 | CFSAN laboratory collection |
| Methicillin-resistant *Staphylococcus aureus* #29 | CFSAN laboratory collection |
| Methicillin-resistant *Staphylococcus aureus* #30 | CFSAN laboratory collection |
| *Staphylococcu aureus* NRS70 | NARSA[c] |
| *Staphylococcu aureus* NRS106 | NARSA |
| *Staphylococcu aureus* NRS107 | NARSA |
| *Staphylococcu aureus* NRS271 | NARSA |
| *Salmonella enterica* Newport #17 ΔtolC::aph | CFSAN laboratory collection |
| *Erwinia carotovora* subsp. *carotovora* | Dr. Dilip Lakshman, ARS[d] |
| *Pseudomonas syringae* pv. tomato strain dc3000 | Dr. Dilip Lakshman, ARS |
| *Ralstonia solanacearum* race 5 | Dr. Dilip Lakshman, ARS |

[a]SGSC, *Salmonella* Genetic Stock Centre, University of Calgary, Canada
[b]ATCC, American Type Culture Collection, Manassas, VA, USA
[c]NARSA, Network on Antimicrobial Resistance in *Staphylococcus aureus*, Chantilly, VA, USA
[d]ARS, Agricultural Research Service, Department of Agriculture, Beltsville, MD, USA Determination of Mode of Action and Spectrum of Antimicrobial Activities To determine mode of action and antimicrobial spectrum of the bacterial antagonists, both agar plug assay (using bacterial culture) and bioscreen assay (using culture supernatant) were performed against a broad spectrum of major foodborne pathogens and bacterial phytopathogens (Table 1). In the agar plug assay, bactericidal effects against pathogenic bacterial strains in the zone of inhibition were confirmed when no viable cells were recovered on TSA plates. In the bioscreen assay, the antagonist supernatant from overnight culture was filter sterilized with a 0.22 μm pore-size cellulose acetate (CA) membrane filter. Each 3 ml TS-15 cell-free culture supernatant (CFCS) was inoculated with 3 μl of $10^8$ cfu/mL bacterial culture (Table 1). Aliquots (200 μl) were then dispensed into sterile Bioscreen C microwell plates (Growth Curves USA, Piscataway, N.J.) and incubated as described for the respective bacterial strains. Bacterial growth was determined in five replicates by measuring $O.D._{600}$ at 20-min intervals for 24 hours.

Fraction Collection: The modified method was based on methods known in the art. Cells were removed from Petri dishes using cell scrapers and were deposited into Eppendorf tubes. A final volume of 100 μL of acetonitrile was added for every dish of scraped cells. The samples were shaken for 30 minutes and centrifuged at 7710 g for 15 minutes. The supernatant was removed and evaporated. The sample was reconstituted in water and was filtered with a 0.22 μm Nylon filter. Fraction collection by liquid chromatography (LC) was achieved using a Shimadzu Nexera with a Kinetex C18 column (1.7μ, 100 Å, 150×2.10 mm). The separation was performed with a column temperature of 60° C. and a flow rate of 400 μL/min using water with 0.1% formic acid (v/v) and acetonitrile with 0.1% formic acid (v/v) with the following gradient: 5 min hold at 95% water, 50 min linear gradient from 95% to 5% water, 5 min equilibration at 95% water. Fractions were concentrated and biological activity was tested against MRSA and *E. coli*. Fractions with activity were further examined by multiple mass spectrometry (MS) platforms.

Bioactivity Assay: Ten microliters of the 1-minute fractions from *Paenibacillus alvei* strain A6-6i or TS-15 were spotted directly on plates containing a lawn of $10^6$ cells of *Escherichia coli* O157:H7 strain EDL933 and Methicillin-resistant *Staphylococcus aureus* strain #12, respectively. After incubation at 35±2° C. for 24 hours, the antimicrobial activity exhibited by 1-minute fractions was observed as a clear zone of inhibition (ZI). The fraction that exhibited the ZI was focused henceforth. As a control experiment, 10 μL of serial two-fold polymyxin B (Sigma-Aldrich, St. Louis, Mo.) dilutions starting from 1 mg/mL stock were spotted on a lawn of $10^6$ cells of *Salmonella enterica* serovar Montevideo strain 29N.

Matrix-Assisted Laser Desorption/Ionization Time-of-Flight Mass Spectrometry (MALDI-TOF/MS) Analysis:

Fractions that were found to be active were diluted 1:30 in water and 1 μL was placed onto the MALDI target with 1 μL of prepared CHCA matrix (20 mg/mL in 70% acetonitrile with 0.1% formic acid). The MALDI instrument used to analyze the samples was an Applied Biosystems/MDS Sciex 4800 MALDI TOF/TOF Analyzer. The laser power was optimized for each analysis to use the minimum level required for sufficient ionization. Tandem mass spectrometry (MS/MS) was also performed on ions of interest using post-source decay (PSD).

LC/MS Analysis with High-Resolution Mass Spectrometry: The sample extract (prior to fraction collection) and resulting fractions were analyzed using the same LC conditions listed previously coupled to a high-resolution mass spectrometer (Q-EXACTIVE™, Thermo Scientific). The Q-EXACTIVE™ settings used were: 140,000 resolution, le6 AGC target, Maximum IT 60 ms, and a mass range of 300-4000 Da was monitored; the settings for the heated electrospray ionization probe (HESI-II) were: 4 kV spray voltage, 50 psi sheath gas, 15 (arbitrary units) auxiliary gas, 380° C. capillary temperature, and 300° C. heater temperature. Active fractions were further analyzed with LC-MS/MS with the following modified conditions: 1 μL injection of the 1:30 diluted fraction, 35,000 resolution for full scan mode, and Maximum IT of 120 ms.

$MS^n$ Analysis: Multiple-stage mass spectrometry experiments ($MS^n$) were performed using an Orbitrap ELITE™ (Thermo Scientific). Fractions were diluted 1:30 in 70% methanol with 0.1% formic acid. Infusion for nanospray was accomplished using the Triversa Nanomate (Advion) with 1.5 kV voltage and 0.3 psi gas pressure. A mass range of 225 to 2000 was monitored in full MS mode with 120,000 resolution. Both collision-induced dissociation (CID) and electron-transfer dissociation (ETD) were used for MS/MS and $MS^n$ experiments.

16S rRNA Gene Amplification and Sequencing: Genomic DNA of potential bacterial antagonists was extracted using the WIZARD® genomic DNA purification kit (Promega, Madison, Wis.). A pair of universal primers specific for bacterial 16S rRNA, Eubac27 and R1492, were used to amplify the corresponding gene. PCR amplification of the 16S rRNA was performed with a HOTSTART TAQ® plus DNA polymerase kit (QIAGEN, Valencia, Calif.) under the following conditions: after an initial 5-minute incubation at 95° C., the mixture was subjected to 30 cycles, each including 1 minute at 95° C., 1 minute at 58° C., and 1 minute at 72° C. A final extension was performed at 72° C. for 10 minutes. Both strands of purified PCR products were directly Sanger sequenced using the following primers:27F (5'-AGAGTTTGATCCTGGCTCAG-3'; SEQ ID NO: 72), 1492R (5'-GGTTACCTTGTTACGACTT-3'; SEQ ID NO: 73), 357F (5'-CTCCTACGGGAGGCAGCA-3'; SEQ ID NO: 74), 518R (5'-CGTATTACCGCGGCTGCTGG-3'; SEQ ID NO: 75), and 1100R (5'-AGGGTTGCGCTCGTTG-3'; SEQ ID NO: 76) Sequence fragments were edited and assembled into contigs using Molecular Evolutionary Genetics Analysis software v.5.0(MEGA 5.0). The BLAST algorithm was used for a homology search againstGENBANK®. Only results from the highest-score queries were considered for phylotype identification, with 99% minimum similarity.

Whole Genome Sequencing: Genomic DNA was isolated from an overnight culture of each strain using a QIAGEN DNEASY® blood and tissue kit (QIAGEN Inc., Valencia, Calif.). Genome sequencing was performed using 454 Titanium sequencing technology (Roche, Branford, Conn.), achieving >25× average genome coverage. De novo assembly was created for each genome using the 454 Life Sciences Newbler software package, v.2.5.3 (Roche). The genomic DNA of *P. alvei* strains TS-15 and A6-6i was also sequenced using the Pacific Biosciences (PacBio) RS sequencing platform. A single 10-kb library was sequenced using C2 chemistry on 8 single-molecule real-time (SMRT) cells with a 90-min collection protocol on the PacBio RS. The 10-kb continuous-long-read (CLR) data were de novo assembled using the PacBio hierarchical genome assembly process (HGAP)/Quiver software package, followed by Minimus 2, and they were polished with Quiver. The assembled contigs from both approaches were annotated with the NCBI Prokaryotic Genomes Automatic Annotation Pipeline.

Identification and Characterization of the pbt Gene Cluster: Genomic comparison of pbt gene cluster (NRPS genes involved in the biosynthesis of a non-ribosomal lipopeptide antibiotic) between these two strains and *P. thiaminolyticus* strain OSY-SE (accession #ALKF00000000) as described in U.S. Publication No. US2013/0164317 was performed. The nonribosomal peptide synthetase (NRPS) machinery is composed of modular multi-domain enzymes which act as an assembly line to incorporate each amino acid monomer by one module. A typical module (C-A-T) in an NRPS contains a carrier Thiolation (T) domain and two catalytic domains, an adenylation (A) domain for amino acid activation and selectivity and a condensation (C) domain catalyzing peptide bond formation. In the termination module (C-A-T-Te), the Te-domain is responsible for releasing the assembled peptide. Additionally, optional epimerase (E) domain may also be present for L- to D-epimerization of amino acids. The NRPS in *P. alvei* strains A6-6i and TS-15 genomes was analyzed by NRPSpredictor2, a webserver for predicting NRPS adenylation domain. The A domain possesses a conserved binding pocket for amino acid recognition and activation. The substrate specificity of A-domain for amino acid was identified using NRPSpredictor2, based on the fingerprint residues at the substrate-binding site. In addition, epimerization (E) domains and the Te domain were identified (PKS/NRPS analysis webserver).

Example 1: Broad Antimicrobial Spectrum of *P. alvei* Strains A6-6i and TS-15

Figure 1B:
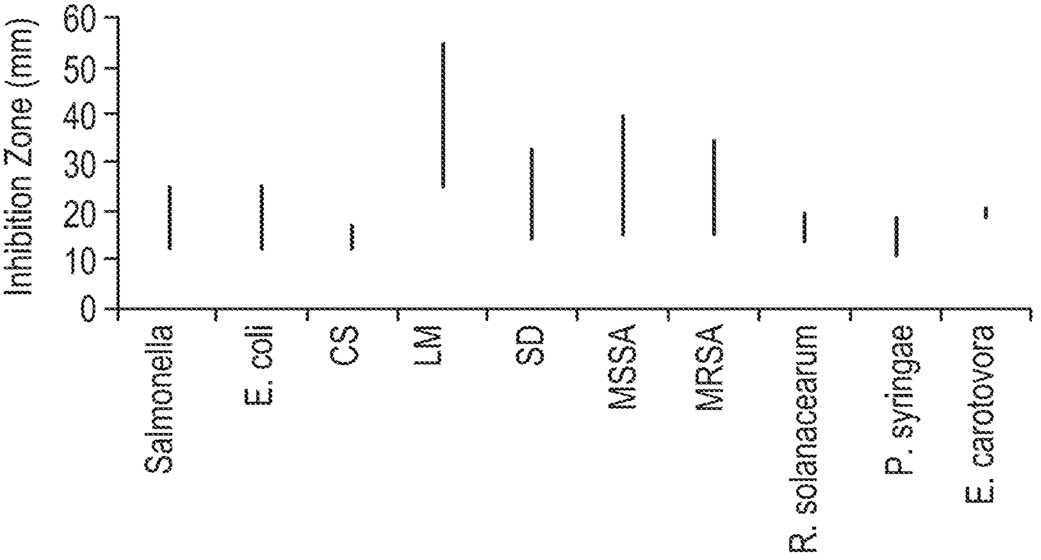

In vitro agar plug assays showed inhibition zones against all the indicator strains including six major foodborne pathogens and three major tomato bacterial phytopathogens when challenged with both *P. alvei* isolates (FIGS. 1A and 1B). Notably, the antagonist migrated outward from the plug after forming the inhibition zone with SD (*S. dysenteriae*) or LM (*L. monocytogenes*), and the antagonistic growth ring expanded with time, especially in the case of *Listeria*. Both A6-6i and TS-15 had a wide range of inhibition against MRSA strains with zone diameters from 15 to 35 mm, and 15 to 20 mm, respectively. It is also interesting to note that strain A6-6i showed strong inhibitory effects on various MRSA strains tested despite the fact that some strains were resistant to up to 14 different antimicrobial drugs.

Figure 2A:
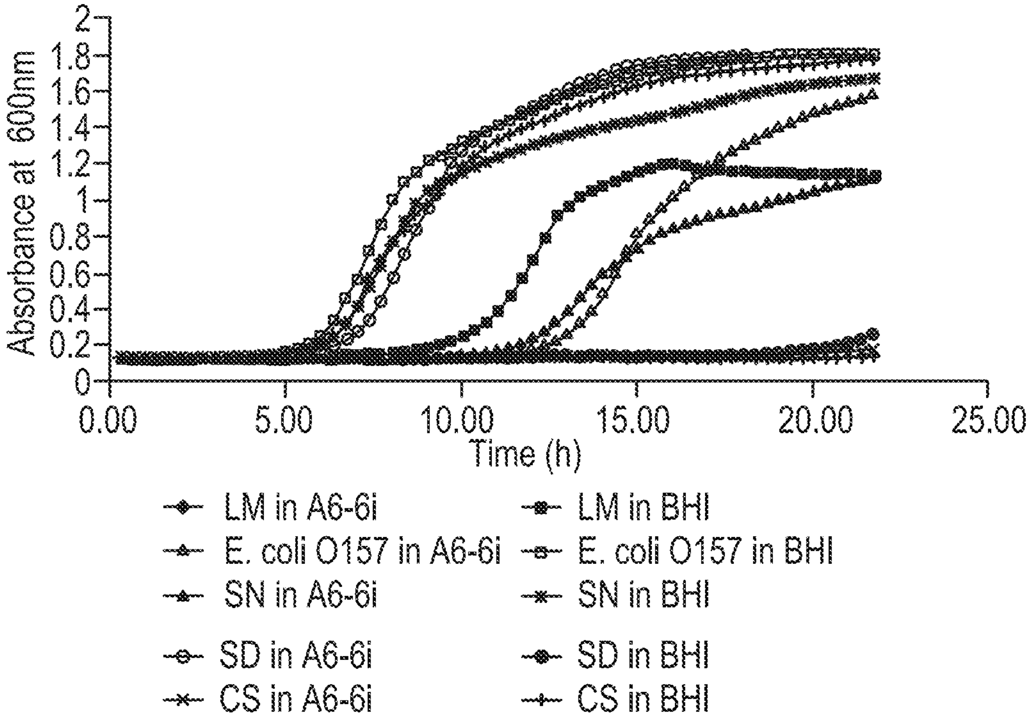
FIGS. 2A and 2B show growth inhibition of major foodborne pathogens in *P. alvei* A6-6i cell free culture supernatant (CFCS). Brain Heart Infusion (BHI) broth was used as a control. Bacterial growth of A) *L. monocytogenes* (LM), *S. dysenteriae* (SD), *E. coli* 0157, C. sakazakii (CS), and S. Newport strains; and B) Methicillin resistant *S. aureus* (MRSA) strains in *P. alvei* A6-6i CFCS and BHI was determined in five replicates by measuring $O.D._{600}$ at 20-minute intervals for 24 hours. The experiment was repeated twice.
Figure 2B:
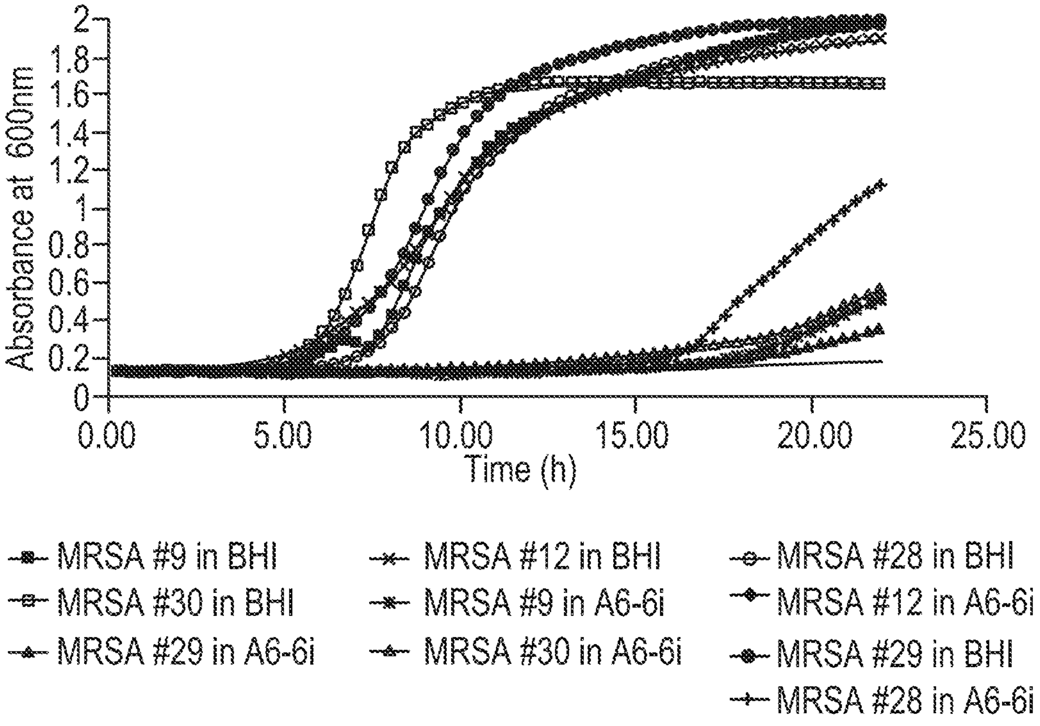

When supernatants were tested against the panel of gram-negative and gram-positive bacteria using the Bioscreen assay, both A6-6i (FIG. 2) and TS-15 (not shown) CFCS exhibited a broad spectrum of antimicrobial activity, in which the lag phase was significantly extended in all the pathogens tested and the cell density was largely reduced at the end of incubation. Furthermore, the lag phase in CS (C. sakazakii), SD (*S. dysenteriae*), LM (*L. monocytogenes*), and some MRSA strains were extended to almost 24 hours in both A6-6i and TS-15 CFCS. Compared to A6-6i, CFCS from TS-15 had a much stronger inhibitory effect when tested against SN (S. Newport) (not shown).

Example 2: Bioactivity Results

Figure 3:
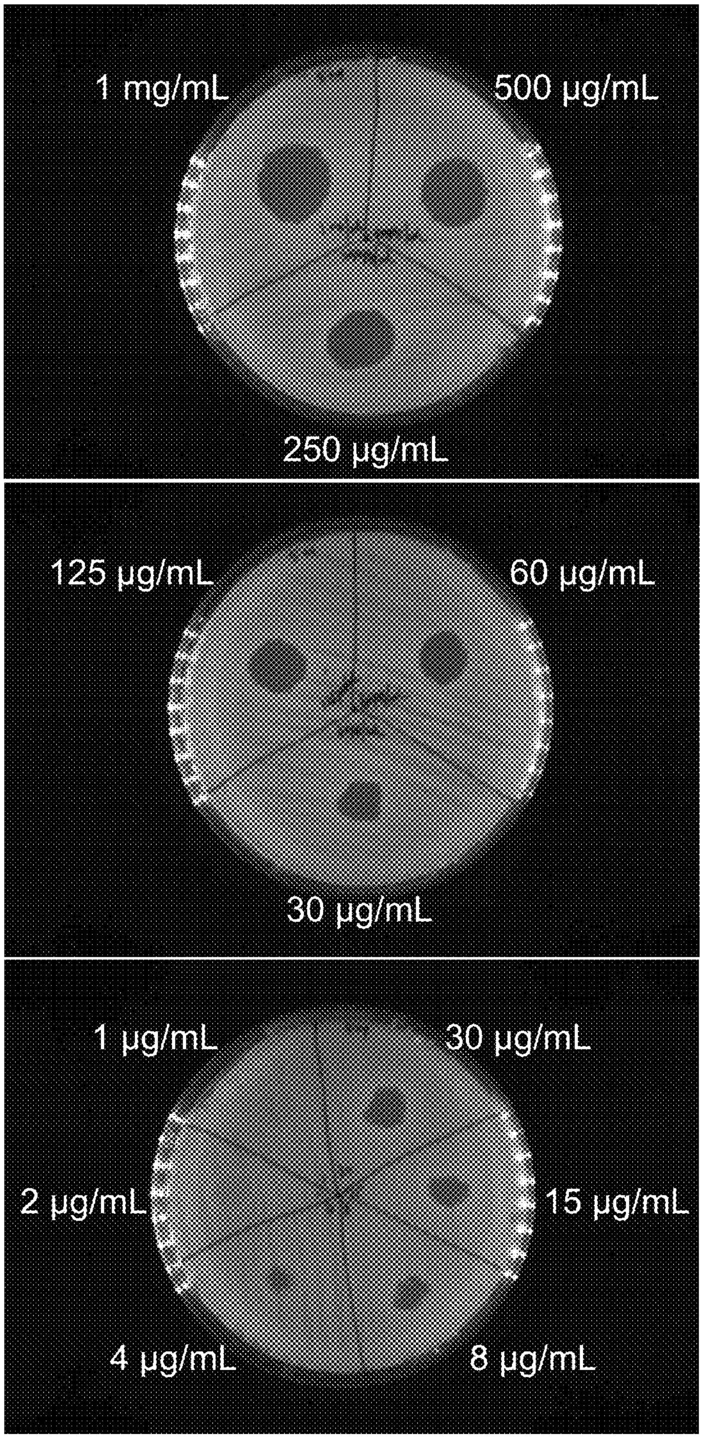
FIG. 3 shows a polymyxin B standard on a *Salmonella* lawn. A 10 μL volume of 2-fold serial polymyxin B dilutions starting from 1 mg/mL to 1 μg/mL was spotted on a lawn of $10^6$ cells of *Salmonella enterica* serovar Montevideo strain 29N. The zone of inhibition (ZI) was observed after 24 hour incubation at 35±2° C.
Figure 4:
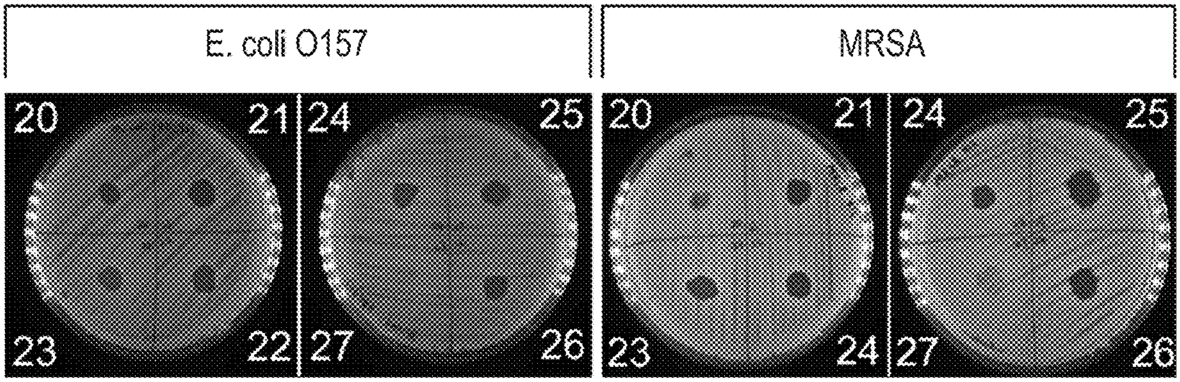
FIG. 4 shows TS-15 1-minute active fractions against pathogens. A 10 μL volume from the 1-minute fractions of *P. alvei* strains TS-15 was spotted on a lawn of $10^6$ cells of A) *Escherichia coli* O157:H7 strain EDL933; B) Methicillin-resistant *Staphylococcus aureus* strain #12. After incubation at 35±2° C. for 24 hours, the antimicrobial activity exhibited by the 1-minute fractions was observed as a clear zone of inhibition (ZI). These experiments were also done for *P. alvei* strain A6-6i (data not shown).

Polymyxin B showed clear antimicrobial dose response against S. Montevideo (control experiment). The minimum inhibitory concentration for polymyxin B to show clear ZI was 4 μg/mL on the lawn of S. Montevideo strain 29N (FIG. 3). Seven of the 1-minute fractions showed antimicrobial activity against both *E. coli* O157:H7 strain EDL933 and Methicillin-resistant *S. aureus* strain #12 (FIG. 4). Similarly, multiple 1-minute fractions from *P. alvei* strain A6-6i exhibited antimicrobial activities against both strains as well (results not shown).

Example 3: Identification of the Primary Peptide Sequence

Figure 5:
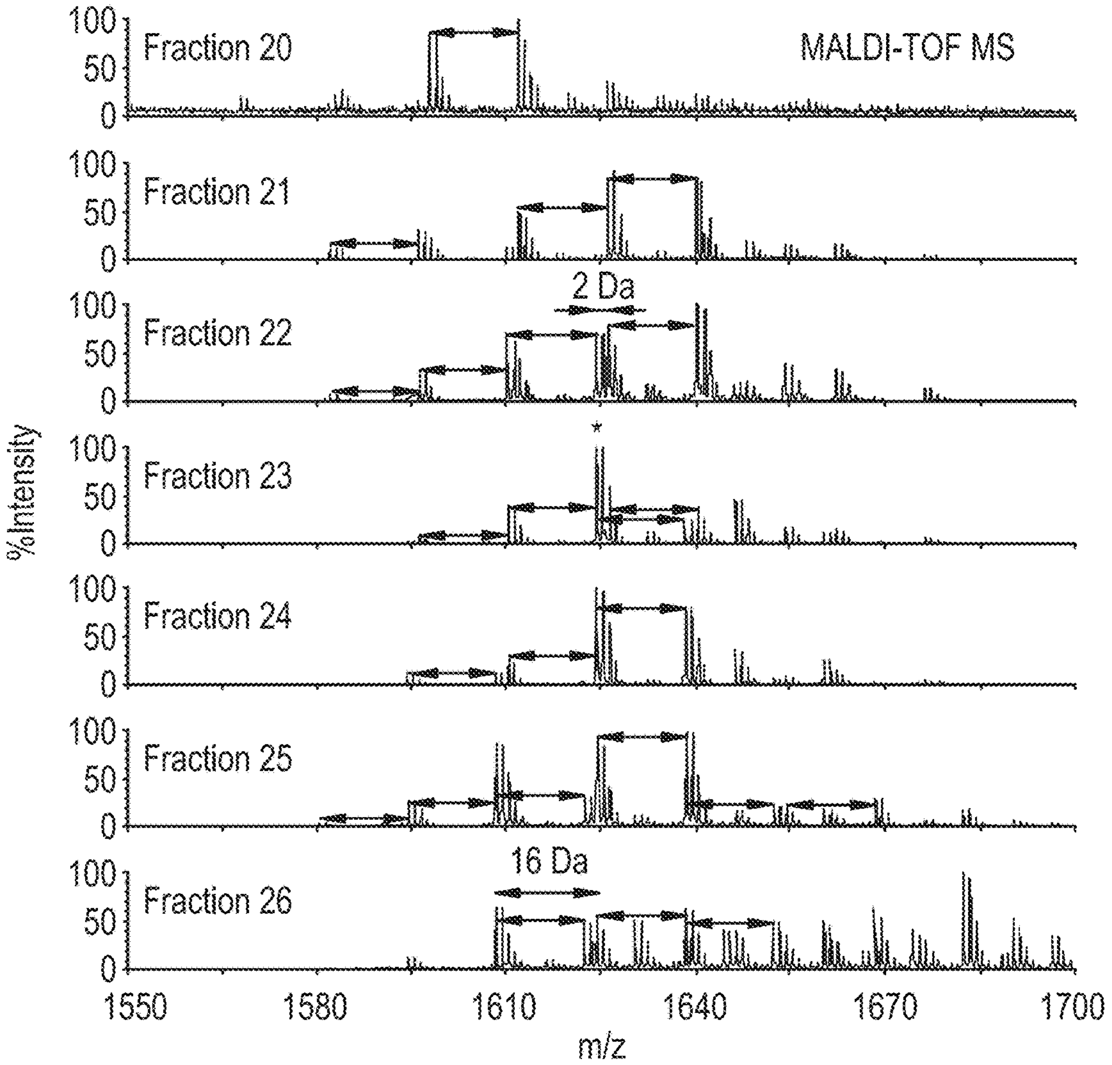
FIG. 5 shows MALDI-TOF MS results for fractions 20-26 from TS-15. The unlabeled arrows indicate a mass difference of 14 Da, which indicates a difference in $CH_2$; an asterisk indicates MW 1623, which is designated as the primary sequence; two examples of a mass difference of 2 and 16 Da are labeled, which correspond to the other molecular variants.

MALDI-TOF MS analysis revealed a number of compounds that were present in each of the seven bioactive fractions, as shown in FIG. 5. The MALDI spectra provided a view of the full complement of compounds from each bioactive fraction within a single spectrum where clusters of these compounds differed by 14 Da, indicated by unlabeled arrows. The compound with a molecular weight of 1623 will be referred to as the primary compound (ion indicated with an asterisk in FIG. 5), although multiple variants of similar abundances are present (FIG. 5).

Figure 6:
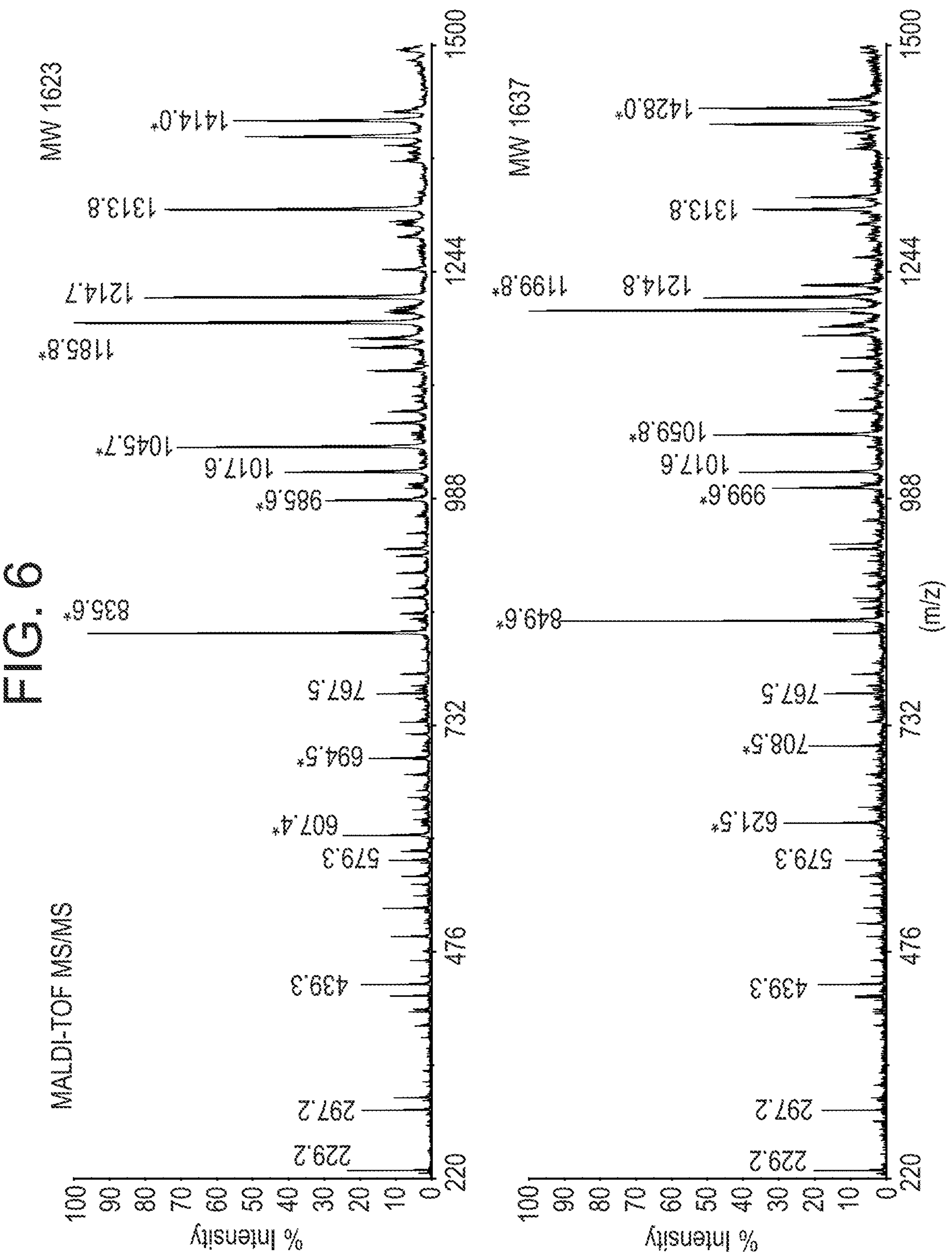
FIG. 6 shows MS/MS similarity. MALDI-TOF MS/MS comparison of two compounds that differ by 14 Da in molecular weight. Mass-to-charge ratios with an asterisk indicate an observed mass difference of 14 Da in the comparison between the two spectra.
Figure 7:
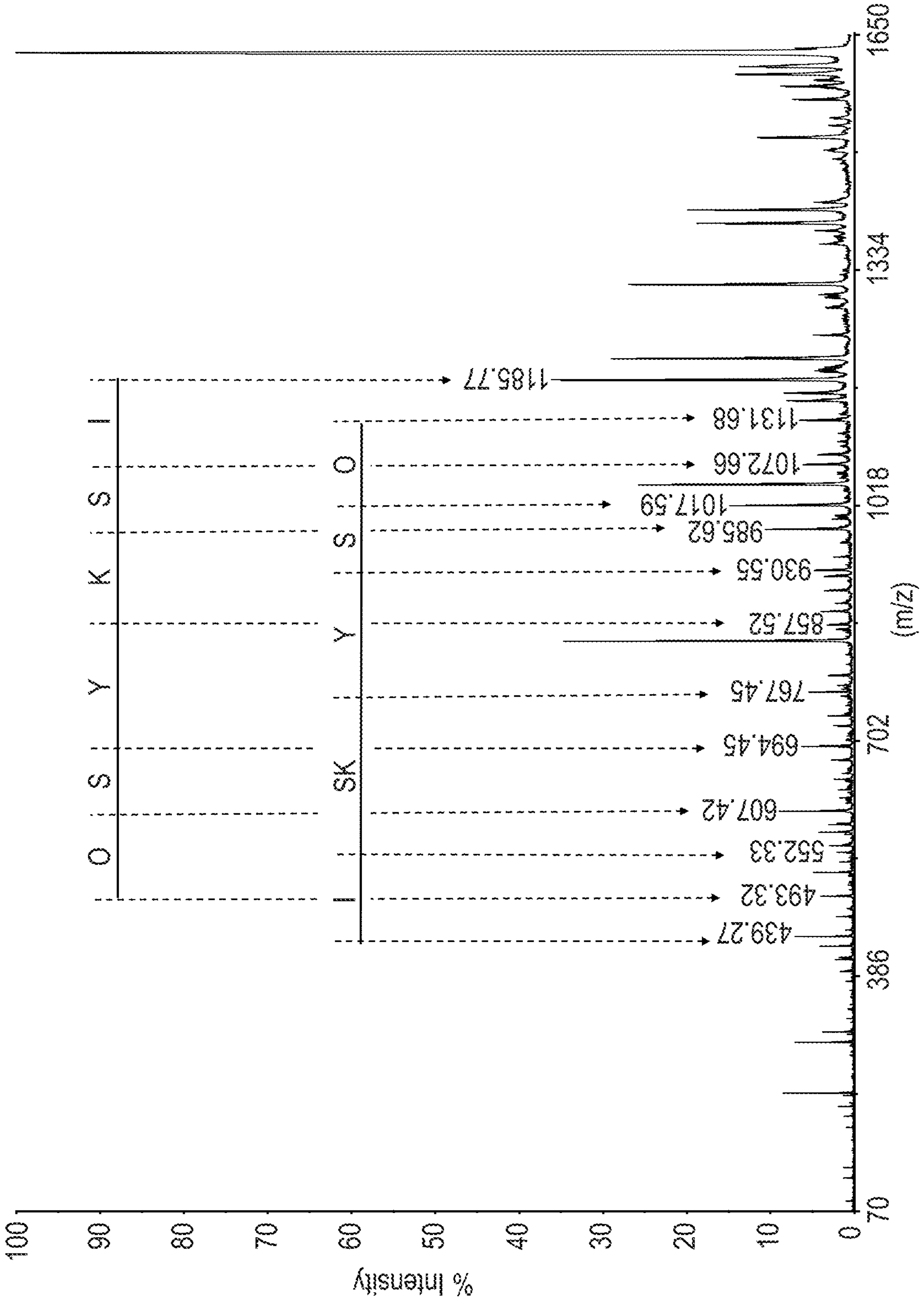
FIG. 7 shows partial sequence information from MALDI-TOF MS/MS spectrum of MW 1623 elucidated by manual de novo sequencing (SEQ ID NOS 80-81, respectively, in order of appearance).

The MALDI-TOF MS/MS analyses of these molecular species revealed similar fragmentation patterns, which confirmed that the compounds that differ by 14 Da were related. As illustrated in FIG. 6, comparison of MS/MS spectra of the primary compound, MW 1623, and the compound of MW 1637, which differ in molecular weight by 14 Da, revealed a series of product ions that shared the same mass and a second product ion series that differed by 14 Da, suggesting that the mass discrepancy between compounds was localized to one region of the molecule. This enabled identification of complementary product ion pairs, with one direction corresponding to the product ion series retaining the region of the molecule that contained the 14 Da mass-shift and the other direction corresponding to product ions that were identical between the two peptides (FIG. 7). Manual de novo sequencing resulted in a partial amino acid sequence, yielding a putative sequence assignment.

Figure 8A:
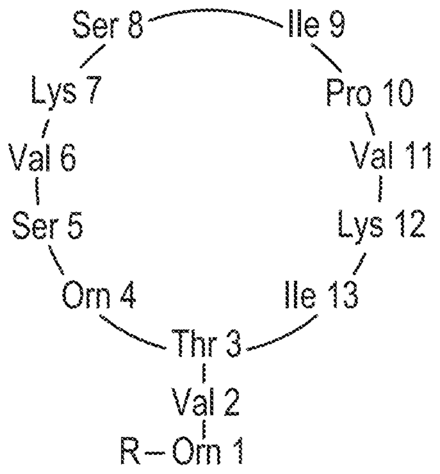
FIGS. 8A and 8B show schematics of a previously published identified lipopeptide and the peptides discovered in current work. A. Molecule described in U.S. Publication No. US2013/0164317 and referred to as paenibacterin. B. Molecule(s) discovered in current work. The “R” group corresponds to an attached acyl chain in structure A and B; however, the “R” group for the structure in B can also be an ester, for example, when Tyr is at position 6.

A compound of the present invention is shown in FIG. 8 B.

Figure 8B:
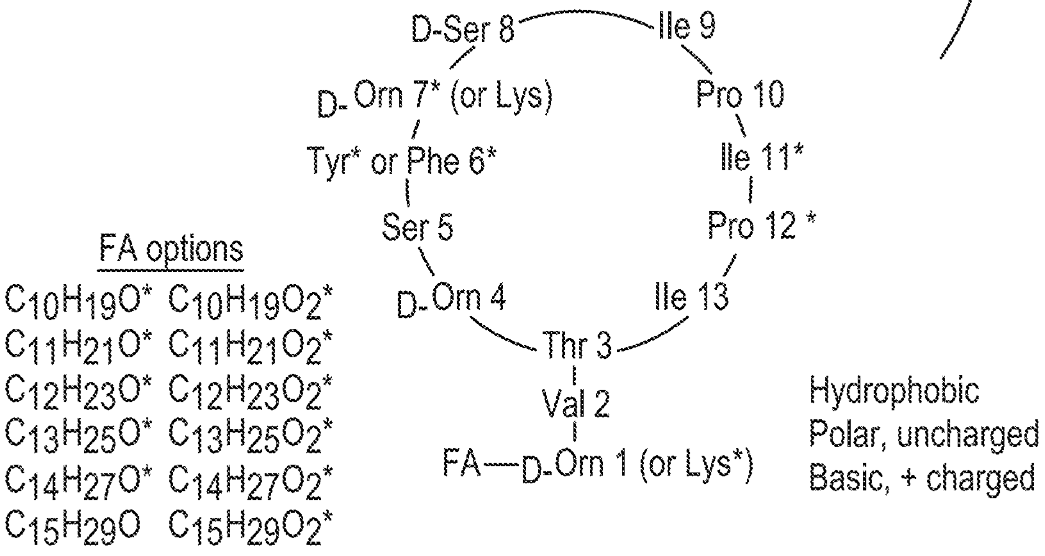

Analysis of MALDI-TOF MS/MS spectra only revealed partial sequence tags. To improve sequence coverage, individual fractions were infused and analyzed with the Orbitrap Elite, allowing for the collection of $MS^n$ data. Again, pairs of $MS^n$ spectra were analyzed and complementary ion pairs were identified based on the presence of 14 Da mass differences. The combined $MS^n$ data allowed a complete amino acid sequence to be determined (FIG. 8B). This amino acid sequence was similar to a previously identified cyclic compound isolated from a different *Paenibacillus* strain which also showed broad-spectrum activity against MRSA and *E. coli*; the structure of that compound, designated as paenibacterin, is shown in FIG. 8 A.

Figure 9:
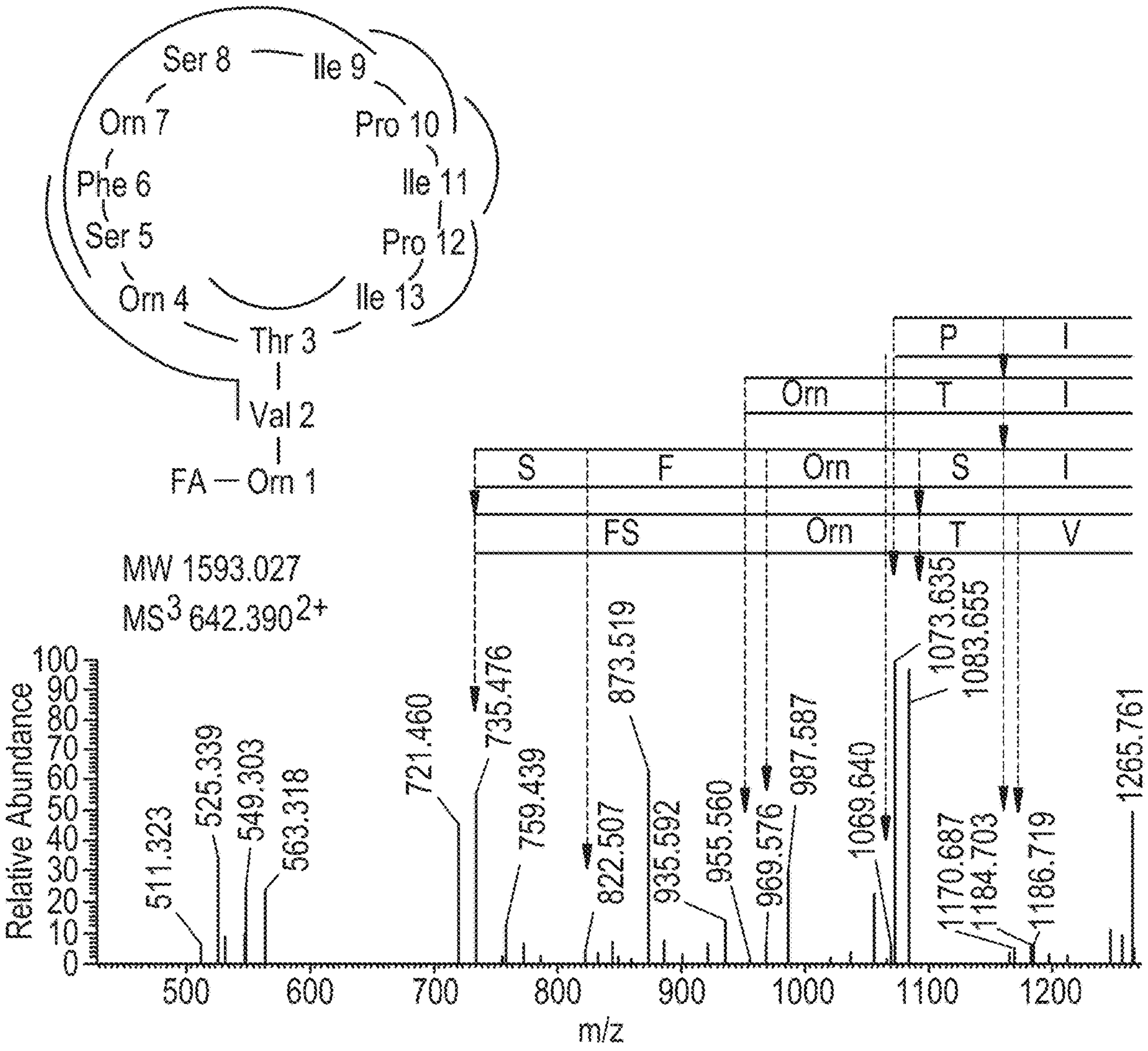
FIG. 9 shows a representative example of different product ion series in an MSn spectrum (MS3 6422+). The corresponding sequences are coded to the amino acids in the inset schematic of the cyclic peptide structure (SEQ ID NOS 82 and 105-106, respectively, in order of appearance).

By determining which series of product ions did or did not contain the molecular component that results in the 14 Da difference, de novo sequencing by $MS^n$ analysis was more straightforward. This was particularly critical because the compounds were cyclic and resulting $MS^n$ spectra can be difficult to interpret due to multiple ring opening events occurring at a distribution of sites. An example is shown in the $MS^3$ spectrum in FIG. 9 where the ring opens at different amino acid positions, yielding a number of different sequence series within the same spectrum; thus, de novo sequencing of the primary sequence of cyclic peptides can be challenging. However, by using the described approach, the assignment of product ions and the identification of the primary sequence and sequence variants were accomplished without linearizing the molecule. The cumulative ion assignments for the primary amino acid sequence can be found in in FIG. 10A, B.

Subsequent analysis with UPLC coupled to high resolution MS provided accurate mass data which confirmed that there were actually three predominant compound series, with each series containing groups of compounds that differ by 14.02 Da. The most pronounced differences between the three observed series were either a decrease of 15.99 Da or an increase of 1.98 Da in mass compared to the primary compound series; examples are designated with arrows in FIG. 5. A comprehensive list of these compounds and their accurate mass molecular weights can be found in Table 2. These are designated as F, Y, and Y, $—CH_2$+O in the table and throughout the figures; F and Y correspond to phenylalanine or tyrosine at position 6 in FIG. 8 B and $—CH_2$+O corresponds to a molecular difference in the fatty acid chain.

TABLE 2

| F $649.390^{2+}$ | | Y $657.394^{2+}$ | | Y $—CH_{2+}O$ $657.394^{2+}$ | |
|---|---|---|---|---|---|
| Nominal Molecular Weight | Complementary Ion Pair | Nominal Molecular Weight | Complementary Ion Pair | Nominal Molecular Weight | Complementary Ion Pair |
| | | 1581 | $269.222^{1+}$ | | |
| 1579 | $283.238^{1+}$ | 1595 | $283.238^{1+}$ | | |
| 1593 | $297.255^{1+}$ | 1609 | $297.253^{1+}$ | | |
| 1607 | $311.269^{1+}$ | 1623 | $311.269^{1+}$ | 1625 | $313.248^{1+}$ |
| | | 1637 | $325.285^{1+}$ | 1639 | $327.264^{1+}$ |
| | | 1651 | $339.301^{1+}$ | 1653 | $341.279^{1+}$ |

Figure 10A:
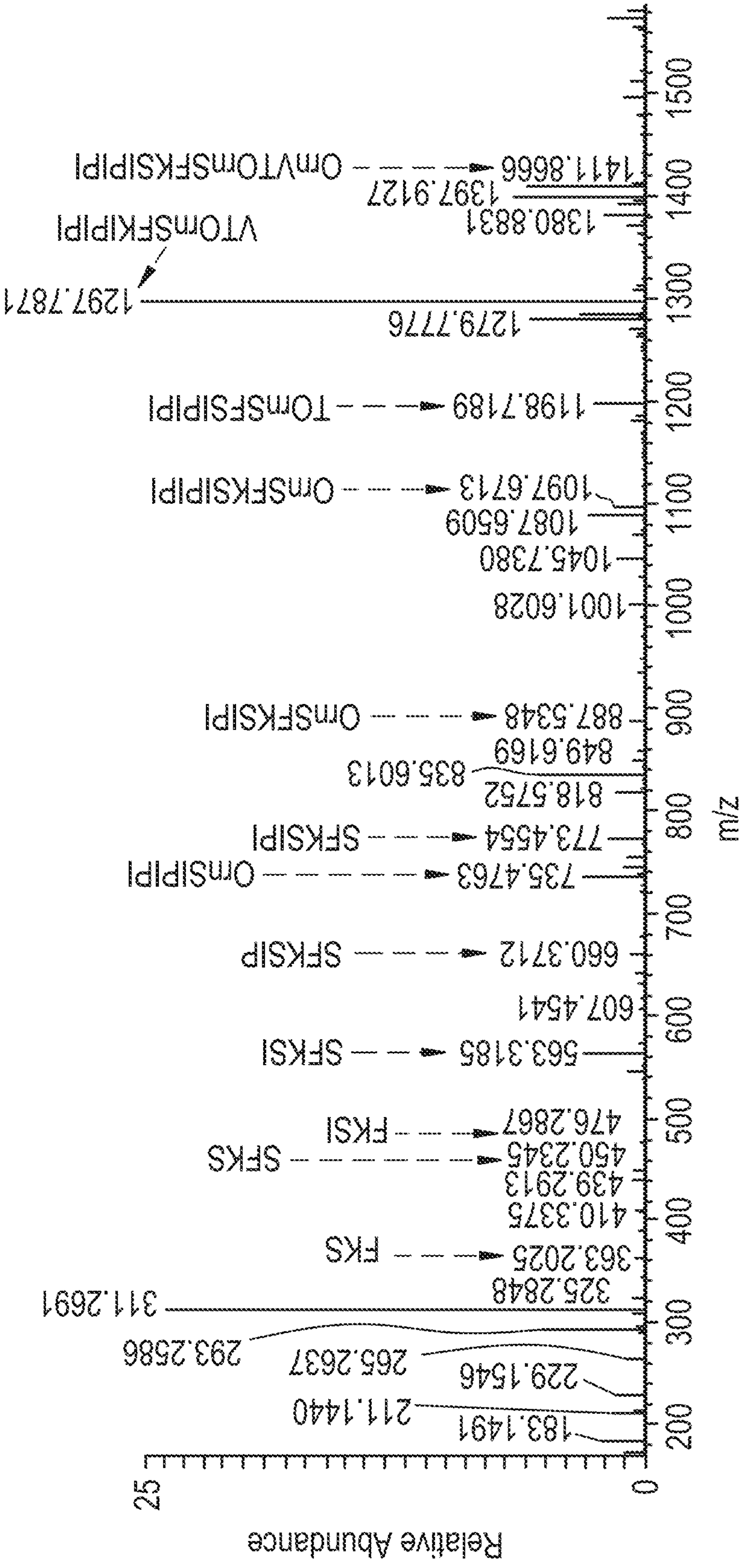
FIGS. 10A and 10B show product ion assignments as a result of combined interpretation of multiple MSn analyses. Representative examples of MS2 spectra are shown for two of the most abundant compounds, containing a Phe (MW 1607) or Tyr (MW 1623) at position 6, respectively. These product ion assignments led to the chemical structure shown in FIG. 8.
Figure 10B:
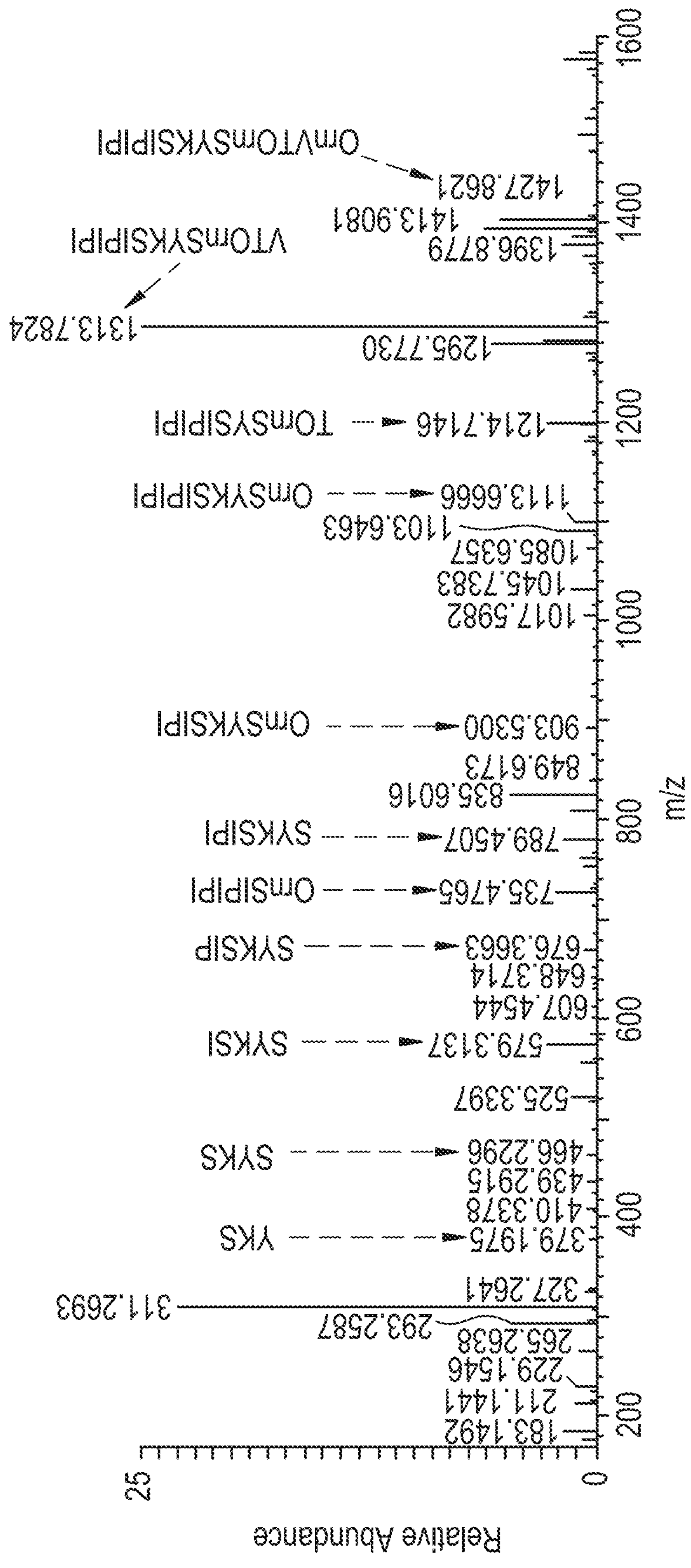
Figure 11:
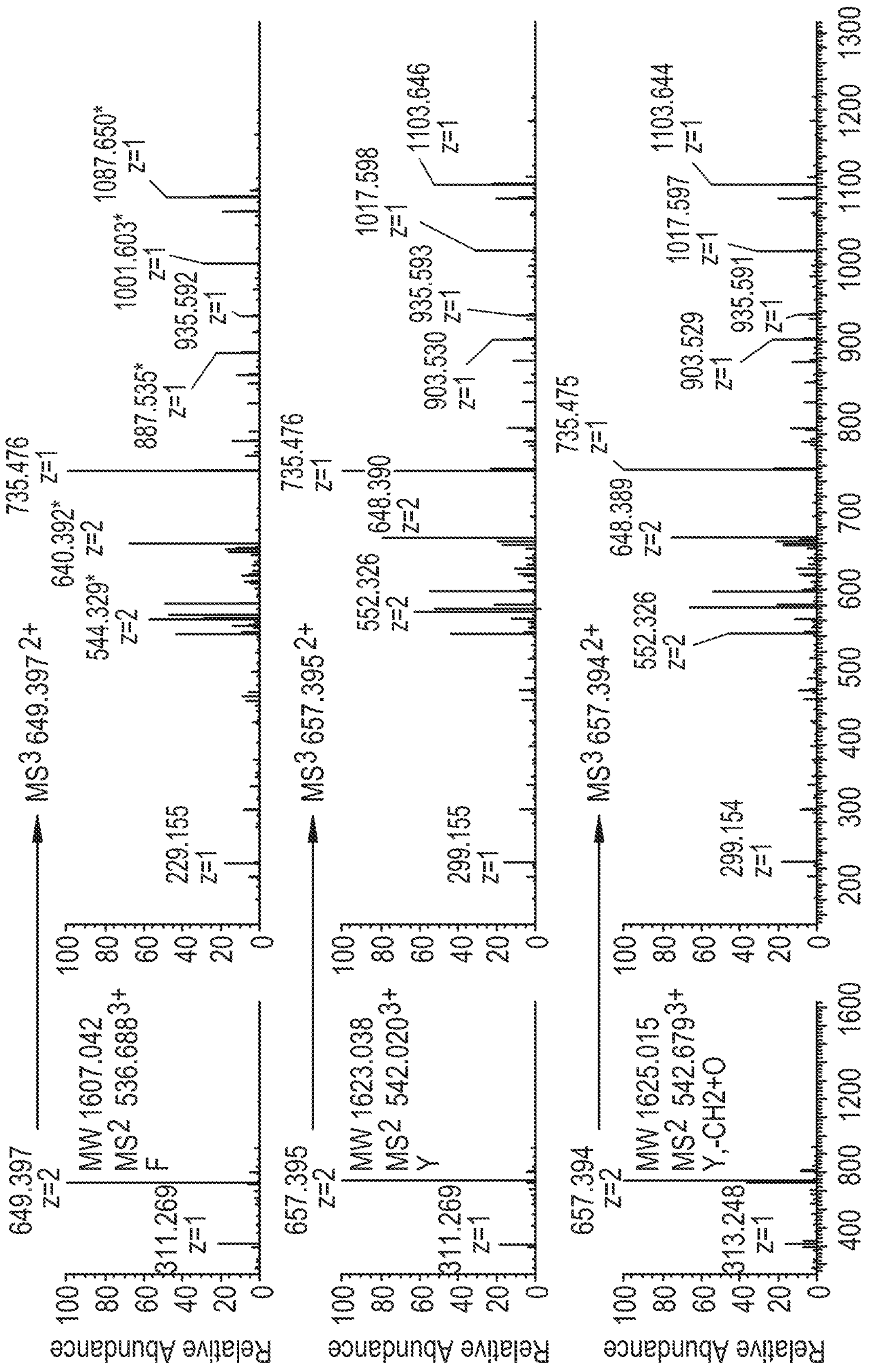
FIG. 11 shows $MS^2$ spectra. Three series of compounds within the class of antibiotics differ by an amino acid or a difference in their attached fatty acid. Compounds that contain a Tyr at position 6 have m/z $657^{2+}$ as a consistent product ion in their resulting MS/MS spectra, while Phe at position 6 results in m/z $649^{2+}$. The m/z values with an asterisk indicate a mass difference of 16 Da between the $MS^3$ spectra, which is the mass difference between Phe and Tyr. The mass difference between MW 1623 and MW 1625 corresponds to one less $CH_2$ group and an additional oxygen in the attached fatty acid ($—CH_2$+O).
Figure 12:
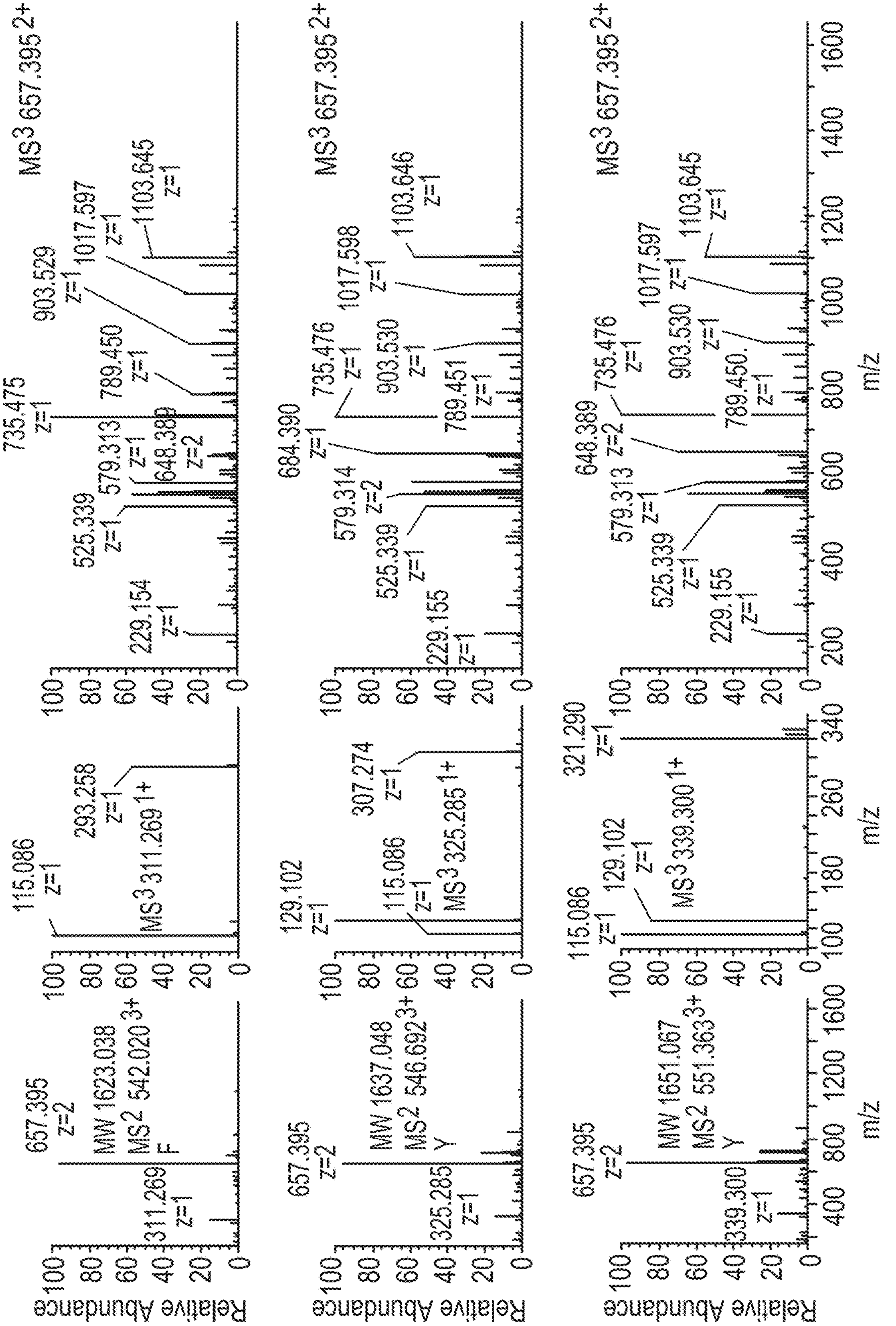
FIG. 12 shows three representative $MS^3$ spectra that demonstrate sequence similarity between compounds of molecular weights that differ by 14 Da and their corresponding complementary ion pair $MS^3$ spectra. $MS^2$ spectra are outlined and $MS^3$ spectra are outlined, with product ions selected for $MS^3$ highlighted.

Two compound series in the bioactive fractions differed from each other by 15.99 Da and exhibited $MS^2$ spectra with all the compounds in one series yielding a product ion at m/z $657^{2+}$ while the other series generates a product at m/z $649^{2+}$ (FIG. 11). FIG. 12 illustrates the $MS^n$ spectra of three precursor ions that differed by 14 Da, all of which generated an $MS^2$ product ion at m/z $657^{2+}$. Because these were conserved product ions within a precursor series that included compounds that differed in molecular weight by 14 Da, we were able to conclude that the region of the compound that yields product ions $657^{2+}$ or $649^{2+}$ does not contain the fatty acid. The $MS^3$ spectra of $657^{2+}$ were consistent with one another confirming that the region of the peptide that generated this sequence was conserved between these compounds (FIG. 12). The $MS^3$ spectra from the ion series that generated an $MS^2$ product ion at $649^{2+}$ were similar to the $657^{2+}$ $MS^3$ spectra, except for a series of product ions that differed by 16 Da (masses with asterisks in FIG. 12). This enabled the distinction between tyrosine and phenylalanine at position 6 (FIG. 8), designated as Y and F in the tables and figures, respectively; these amino acids differ in molecular weight by 16 Da. Assignments for the MS/MS spectrum for a peptide containing Phe are illustrated in FIG. 10A-B, where a direct comparison can be observed between the peptides containing Phe and Tyr at position 6.

Example 4: Identification of the Attached Fatty Acid

The $MS^2$ spectra of the series of compounds that contain a Tyr at position 6 were dominated by product ion $657^{2+}$ and its complementary ion pair (FIG. 11). While $657^{2+}$ was conserved within the Tyr compound series, its complementary ion contained the same 14 Da mass shift as its precursor (i.e., m/z 311, 325, and 339 in FIG. 12). The same trend was also present for the Phe ion series. A list of the multiple complementary ions for $657^{2+}$ and $649^{2+}$ are listed in Table 3. When these complementary ions were dissociated (examples shown in FIG. 12), a loss of ornithine was observed. Subtracting the cyclized peptide sequence mass from the mass of the entire compound yields the mass attributed to an attached fatty acid; molecular formula generation of these masses yield the molecular formulae of the different fatty acid variants (Table 4 and FIG. 8). These fatty acids are similar to what was observed in Guo, et al., although the lengths of the carbon chains differ and both the TS-15 and A6-6i strains presented in the current work exhibit a greater variability in chain length and composition.

Figure 13:
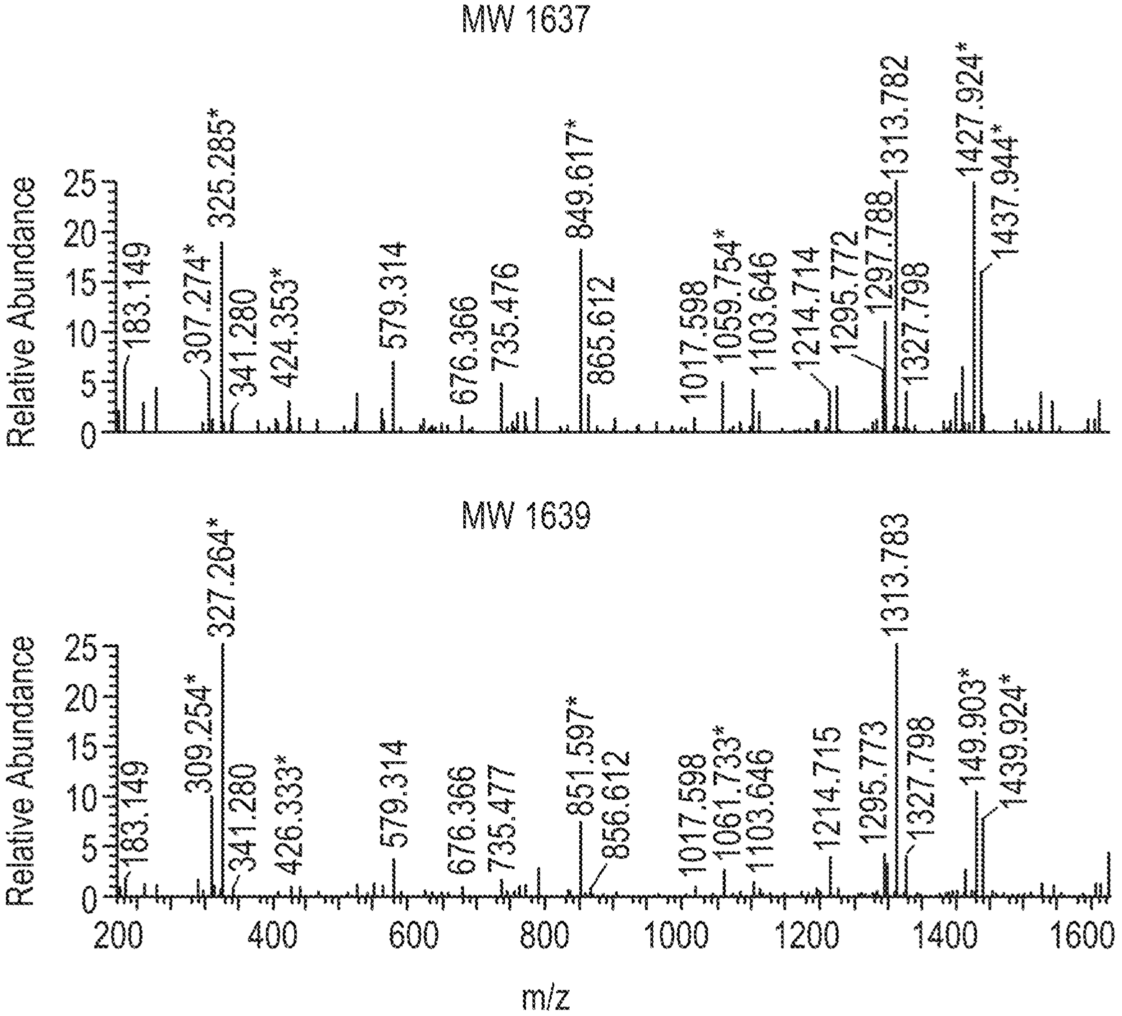
FIG. 13 shows MS/MS comparison of MW 1637 (top) and MW 1639 (bottom). The m/z values with an asterisk indicate a 1.979 Da mass difference between product ions in the two spectra, corresponding to one less $CH_2$ and an additional oxygen in the attached fatty acid compared to the dominant molecular species.

As mentioned previously, three major series of compounds were determined: two series containing a tyrosine at position 6 and one containing phenylalanine. The two compound series containing Tyr differed by a molecular weight of 1.979 Da. Similar to the MS spectral analysis methodology shown in FIG. 2, these compound series also had similar $MS^2$ fragmentation patterns, where some product ion masses are conserved and others differ by 1.979 Da (FIG. 13). This mass difference corresponded to one less $CH_2$ and an additional oxygen (labeled as —$CH_2$+O) in the attached fatty acid compared to the tyrosine molecular series.

TABLE 3

| F $649.390^{2+}$ | | Y $657.394^{2+}$ | | Y —$CH_2$+O $657.394^{2+}$ | |
|---|---|---|---|---|---|
| Nominal Molecular Weight | Complementary Ion Pair | Nominal Molecular Weight | Complementary Ion Pair | Nominal Molecular Weight | Complementary Ion Pair |
| | | 1581 | $269.222^{1+}$ | | |
| 1579 | $283.238^{1+}$ | 1595 | $283.238^{1+}$ | | |
| 1593 | $297.255^{1+}$ | 1609 | $297.253^{1+}$ | | |
| 1607 | $311.269^{1+}$ | 1623 | $311.269^{1+}$ | 1625 | $313.248^{1+}$ |
| | | 1637 | $325.285^{1+}$ | 1639 | $327.264^{1+}$ |
| | | 1651 | $339.301^{1+}$ | 1653 | $341.279^{1+}$ |

TABLE 4

| | Y $657.394^{2+}$ | | | | | | |
|---|---|---|---|---|---|---|---|
| $MS^2$ Product $Ions^{1+}$ | 269.222 | 283.238 | 297.253* | 311.269 | 325.285* | 339.301* | |
| $MS^3$ | 251.212 | 265.227 | 279.243 | 293.258 | 307.274 | 321.290 | Water loss |
| Product $Ions^{1+}$ | 115.086 | 115.086 | 115.086 | 115.086 | 115.086 | 115.086 | Ornithine |
| Molecular Formula of the Fatty Acid | $C_{10}H_{19}O$ | $C_{11}H_{21}O$ | $C_{12}H_{23}O$ | $C_{13}H_{25}O$ | $C_{14}H_{27}O$ | $C_{15}H_{29}O$ | |

Example 5: Multiple Compounds with the Same Molecular Weight

Figure 14:
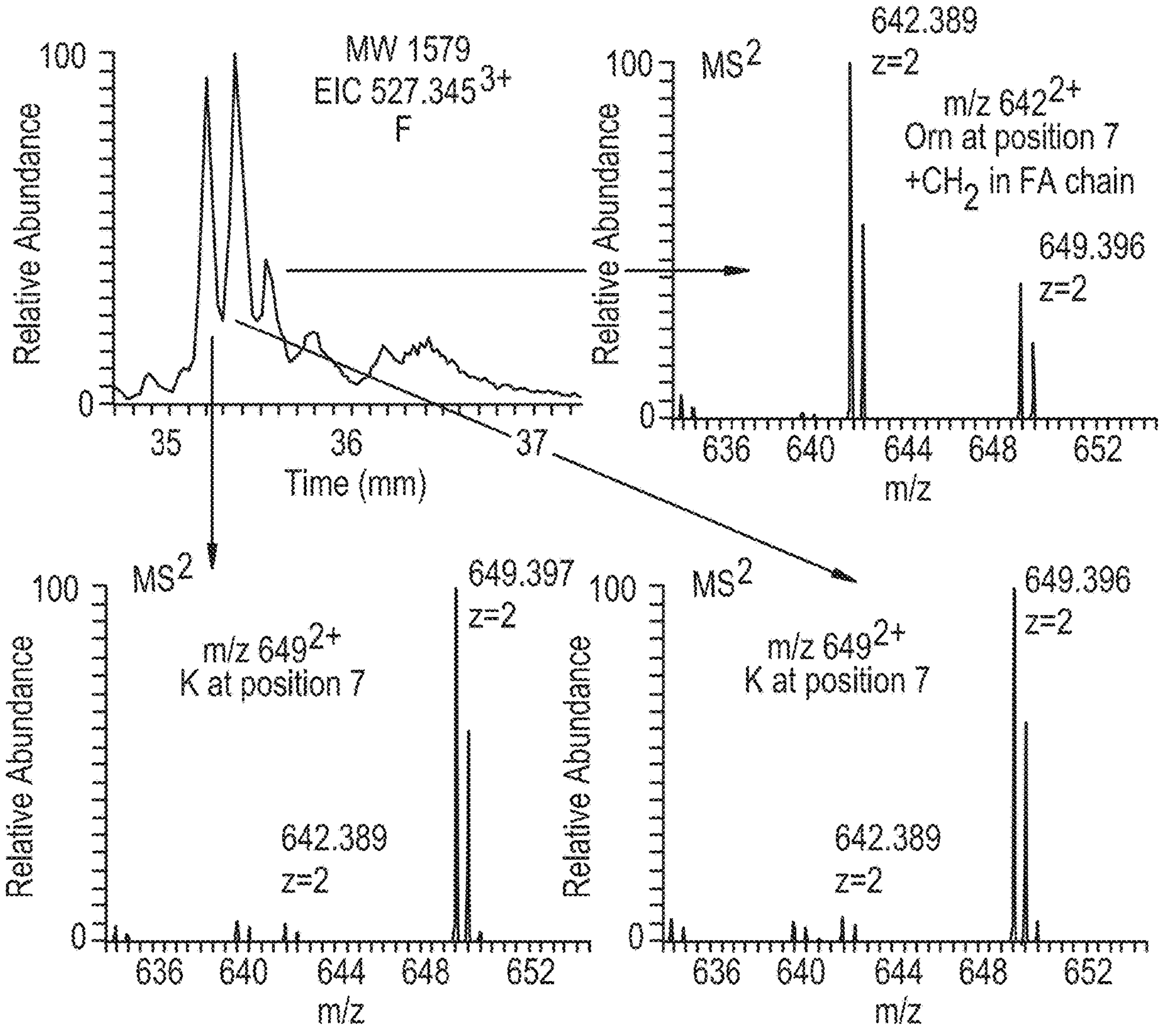
FIG. 14 shows different MS/MS spectra for three compounds of the same molecular weight indicate Lys or Orn at Position 7 in FIG. 8 and potential diversity in the structure of the attached fatty acid due to distinct chromatographic peaks shown in the extracted ion chromatogram (EIC).

It was also observed that more than one of the complementary ion pairs were occasionally present within the same $MS^2$ spectrum in the infusion experiment data. This corresponded to two compounds of the same precursor mass being fragmented within the same isolation window. There were multiple examples in the UPLC and NanoLC/MS data that showed several eluting peaks for entities with the same mass (example shown in FIG. 14). The $MS^2$ spectra of the ions in each of these chromatographic peaks showed small differences in the fragmentation pattern and thus, the primary sequences of these respective peptides. Nearly identical amino acid sequences were confirmed for compounds with an identical molecular weight (1579): a compound with Lys at position 7 and a compound with ornithine at position 7 with an additional $CH_2$ in the attached fatty acid (Lys and ornithine differ by a $CH_2$ in their side chains). Specifically, the product ion at m/z $649^{2+}$ corresponds to Lys at position 7 and m/z $642^{2+}$ corresponds to ornithine at position 7. The two chromatographic peaks with Lys at position 7 may indicate a structural difference in the attached fatty acid resulting in the observed difference in retention time (FIG.

14). A similar substitution was also found at position 1. Some of the subsequent $MS^3$ analyses of the fatty acid containing fragment ions (m/z $325^{1+}$ and $339^{1+}$ in FIG. 5B) indicated that Lys can also be present at position 1 rather than ornithine (m/z $129^{1+}$ in $MS^3$ spectra in FIG. 12). A Lys at position 1 and a decrease of $CH_2$ in the attached fatty acid resulted in identical molecular weights for each compound.

Example 6: Identification and Characterization of the Pbt Gene Cluster

The sequence shown in FIG. 8B was confirmed by genome mining for non-ribosomal peptide synthesis. Many pharmacologically important peptides in bacteria are synthesized by nonribosomal peptide synthetases (NRPS). NRPS machinery is composed of modular multi-domain enzymes which act as an assembly line to incorporate each amino acid monomer by one module. A typical module in an NRPS contains an adenylation (A) domain which possesses a conserved binding pocket for the recruitment of amino acid monomers that are to be incorporated into the final peptide product. A single contig of 6536324 bp (G+C content, 46.63%) and a single contig of 6784766 bp (G+C content, 46.69%) representing the complete chromosome for *P. alvei* strains A6-6i and TS-15 was generated, respectively. The draft genome sequences of strain A6-6i and TS-15 are available in DDBJ/EMBL/GENBANK® under GENBANK® accession # ATMS00000000 and ATMT00000000, respectively. The DNA sequences of A6-6i ptbA, ptbB, and ptbC are SEQ ID NOs: 5, 6, and 7, respectively. The DNA sequences of TS-15 ptbA, ptbB, and ptbC are SEQ ID NOs: 8, 9, and 10, respectively. The protein sequences for A6-6i ptbA, ptbB, and ptbC are SEQ ID NOs: 11, 12, and 13, respectively. The protein sequences for TS-15 ptbA, ptbB, and ptbC are SEQ ID NOs: 14, 15, and 16, respectively. A local BLASTX analysis against pbt gene cluster in *P. thiaminolyticus* strain OSY-SE (accession #ALKF00000000; U.S. Publication No. US2013/0164317) identified a 49-kb DNA region responsible for the compounds biosynthesis (Table 5). The protein sequences for OSY-SE ptbA, ptbB, and ptbC are SEQ ID NOs: 17, 18, and 19, respectively. Comparative genomic analysis showed 64% to 70% similarities in DNA sequences of the pbt gene cluster between the two *P. alvei* strains and *P. thiaminolyticus* strain OSY-SE; and only 60% to 67% similarities in amino acid sequences (FIGS. 16-18). This DNA region encodes three peptide synthetase units which consist of thirteen modules (Table 5) responsible for incorporating the thirteen amino acids in the compounds. The predicted peptide sequence agreed with the chemical structure of the compounds determined by MS/MS (Table 4). In addition, epimerization (E) domains were found in modules for $Orn_1$, $Orn_4$, $Orn_7$, and Serb, which indicated that those amino acids might be in the D-form.

The bacterially-produced cyclic peptides are synthesized by a class of enzymes known as the nonribosomal peptide synthetases (NRPSs). NRPSs are found in many organisms and synthesize a number of medically-important peptides such as antibiotics and immunosuppressants. By sequence analysis, 14 NRPS genes have been identified in the *P. alvei* A6-6i and TS-15 genomes. Three NRPS genes which covered 49 kb were found to control the production of the compounds in the current application. NRPSs are large enzymes that are organized into modules made up of functional domains. The entire length of the amino acid sequence showed homology to the Pbt encoded by the pbt gene cluster of *P. thiaminolyticus* strain OSY-SE in the prior art patent (66% similarity to pbtA gene, 66% similarity to pbtB gene, and 59% similarity to pbtC gene). Detailed analysis of the pbtABC gene cluster showed that each gene had domain and module organization as in Table 5B. To predict the substrate specificity-conferring amino acids in the adenylation (A) domain of each module, the structural regions, A3 and A6 motifs in the A domain, were blasted against the NCBI protein database and showed only 36% identity to the ptbB1 module, 38% identity to the ptbC1 module, and 35% identity to the ptbC2 module, indicating structurally unique antibiotics from paenibacterin in the prior art patent.

TABLE 5

A. Amino acid similarities between A6-6i, TS-15, and OSY-SE

| | A6-6i | TS-15 |
|---|---|---|
| pbtA | 66.95% | 66.73% |
| pbtB | 66.66% | 66.79% |
| pbtC | 59.72% | 59.31% |

B. Modules and domains predicted in the gene cluster

| | |
|---|---|
| pbtA | $CA_{Orn1}TECA_{Val2}TCA_{Thr3}TCA_{Orn4}TECA_{Ser5}T$ ("Orn Val Thr Orn Ser" disclosed as SEQ ID NO: 103) |
| pbtB | $CA_{Tyr6}TCA_{Orn7}TECA_{Ser8}TECA_{Ile9}TCA_{Pro10}T$ ("Tyr Orn Ser Ile Pro" disclosed as SEQ ID NO: 104) |
| pbtC | $CA_{Ile11}TCA_{Pro12}TCA_{Ile13}TTe$ |

Table 5 shows the predicted amino acids of the antimicrobial peptides generated by the PKS/NRPS web server. For example, the pbtA gene (encoding a non-ribosomal peptide synthetase) contains 5 modules, each comprised of a C (condensation) domain, an A (adenylation) domain, and a T (thiolation) domain. The A domain is responsible for amino acid activation and selectivity. Because the binding pocket of each A domain is a conserved sequence, the amino acid substrate can be predicted. Additionally, epimerization (E) domains were found in modules for $Orn_1$, $Orn_4$, $Orn_7$, and Serb, which indicate that those amino acids may be in the D-form. Likewise, pbtB gene contains 5 modules and pbtC gene contains 3 modules.

C. Predicted Amino Acid Substrates in the Adenylation (A) Domain in Each Module.

| A6-6i | | | |
|---|---|---|---|
| Module | Active site residue with 8 A of the amino acid substrate | Binding pocket | Predicted substrate |
| PbtA1 | LAWAFDVFTGDRESVVGSDLNSYGVTEACVDACY SEQ ID NO: 20 | DVGEVGSVDK SEQ ID NO: 21 | D-Orn |
| PbtA2 | LGASFDAATFEGWMLVGGDINGYGPTENTTFTCC SEQ ID NO: 22 | DAFWLGGTFK SEQ ID NO: 23 | Val |

-continued

| | | | |
|---|---|---|---|
| PbtA3 | LNSHFDFSVWEGNQIFGGEINMYGITETTVHVTY SEQ ID NO: 24 | DFWNIGMVHK SEQ ID NO: 25 | Thr |
| PbtA4 | MAWAFDVFSGDRESIIGSDINSYGVTEACVDSSY SEQ ID NO: 26 | DVGEIGSVDK SEQ ID NO: 27 | D-Orn |
| PbtA5 | RWMTFDVSVWEWHFFTSGEINLYGPTEATVDVTY SEQ ID NO: 28 | DVWHFSLVDK SEQ ID NO: 29 | Ser |
| PbtB1 | AWRFFDGFVMSCICTLAGEFNEYGPTENSVVATC SEQ ID NO: 30 | DGMITAEVVK SEQ ID NO: 31 | Tyr |
| PbtB2 | MAWAFDVFSGDRDCAVGSDINSYGVTETCIDASY SEQ ID NO: 32 | DVGDAGSIDK SEQ ID NO: 33 | D-Orn |
| PbtB3 | RWMTFDVSVWEWHFFTSGEINLYGPTEATVDVTY SEQ ID NO: 34 | DVWHFSLVDK SEQ ID NO: 35 | D-Ser |
| PbtB4 | VETSFDGSTFDGFILFGGEKHVYGPTESTVFATC SEQ ID NO: 36 | DGFFLGVVFK SEQ ID NO: 37 | Ile |
| PbtB5 | LYQAFDVCYQESFIITAGEHNHYGPSETHVVTTY SEQ ID NO: 38 | DVQFIAHVVK SEQ ID NO: 39 | Pro |
| PbtC1 | INTSFDGSAFDGLILFGGEKHAYGPSESTVYATW SEQ ID NO: 40 | DGFLLGAVYK SEQ ID NO: 41 | Ile |
| PbtC2 | LYQAFDVCYQESYIITAGEHNHYGPSETHVVTTY SEQ ID NO: 42 | DVQYIAHVVK SEQ ID NO: 43 | Pro |
| PbtC3 | VDASFDGSTFDGFILFGGEKHVYGPTESTVFATS SEQ ID NO: 44 | DGFFLGVVFK SEQ ID NO: 45 | Ile |

TS-15

| Module | Active site residue with 8 A of the amino acid substrate | Binding pocket | Predicted substrate |
|---|---|---|---|
| PbtA1 | LAWAFDVFTGDRESVVGSDLNSYGVTEACVDACY SEQ ID NO: 46 | DVGEVGSVDK SEQ ID NO: 47 | D-Orn |
| PbtA2 | LAASFDAATFEGWMLVGGDINGYGPTENTTFTCC SEQ ID NO: 48 | DAFWLGGTFK SEQ ID NO: 49 | Val |
| PbtA3 | LNSHFDFSVWEGNQIFGGEINMYGITETTVHVTY SEQ ID NO: 50 | DFWNIGMVHK SEQ ID NO: 51 | Thr |
| PbtA4 | MAWAFDVFSGDRESIIGSDINSYGVTEACVDSSY SEQ ID NO: 52 | DVGEIGSVDK SEQ ID NO: 53 | D-Orn |
| PbtA5 | RWMTFDVSVWEWHFFTSGEINLYGPTEATVDVTY SEQ ID NO: 54 | DVWHFSLVDK SEQ ID NO: 55 | Ser |
| PbtB1 | AWRFFDGFVMSCICTLAGEFNEYGPTENSVVATC SEQ ID NO: 56 | DGMITAEVVK SEQ ID NO: 57 | Tyr |
| PbtB2 | MAWAFDVFSGDRDCAVGSDINSYGVTETCIDASY SEQ ID NO: 58 | DVGDAGSIDK SEQ ID NO: 59 | D-Orn |
| PbtB3 | RWMTFDVSVWEWHFFTSGEINLYGPTEATVDVTY SEQ ID NO: 60 | DVWHFSLVDK SEQ ID NO: 61 | D-Ser |
| PbtB4 | VETSFDGSTFDGFILFGGEKHVYGPTESTVFATC SEQ ID NO: 62 | DGFFLGVVFK SEQ ID NO: 63 | Ile |
| PbtB5 | LYQAFDVCYQESFIITAGEHNHYGPSETHVVTTY SEQ ID NO: 64 | DVQFIAHVVK SEQ ID NO: 65 | Pro |
| PbtC1 | INTSFDGSAFDGLILFGGEKHAYGPSESTVYATW SEQ ID NO: 66 | DGFLLGAVYK SEQ ID NO: 67 | Ile |
| PbtC2 | LYQAFDVCYQESYIITAGEHNHYGPSETHVVTTY SEQ ID NO: 68 | DVQYIAHVVK SEQ ID NO: 69 | Pro |
| PbtC3 | VDASFDGSTFDGFILFGGEKHVYGPTESTVFATS SEQ ID NO: 70 | DGFFLGVVFK SEQ ID NO: 71 | Ile |

Table 5 shows the identification and characterization of the pbt gene cluster. A. DNA sequence similarities and amino acid sequence similarities of the pbt gene cluster between *P. alvei* strains A6-6i and TS-15 and *P. thiaminolyticus* strain OSY-SE. B. Modules and domains identified in the NRPS subunits: C, A, T, E, and Te representing condensation domain, adenylation domain, thiolation domain, epimerization domain, and thioesterase domain, respectively. C. Substrate prediction for each of the 13 modules in the peptide.

It is worth noting that genome mining did not predict the presence of abundant sequence variants. As Lys and ornithine differ by $CH_2$, their binding affinities are likely similar which may be contributing to the observed molecular diversity. Likewise, Tyr and Phe differ by a hydroxyl group. Furthermore, NRPS predictor 2 has lower single amino acid substrate prediction scores for Phe and Lys, which may indicate why these were not additionally predicted in the primary sequence. NRPSpredictor2 also predicted that the epimerization (E) domain was in modules 1, 4, 7, and 8, which indicated that these resulting amino acid substrates may be in the D-form. As expected, NRPS analysis does not offer information about the presence or length of the alkyl chain.

The NRPS analysis confirmed both the presence and order of the amino acids of the peptide assignments made through the combination of MALDI-MS, high-resolution mass spectrometry, and $MS^n$ analysis. NRPS can be used as a screening technique to identify potential nonribosomal peptides which may act as antibiotics; however, it does not yield information regarding any molecular variants that may be produced. Moving forward, NRPS analysis and mass spectrometry can be used to combine rapid prediction of candidate peptides with the molecular specificity of mass spectrometry to enable identification of cyclic antibiotics and their sequence and fatty acid variants despite the presence of molecular diversity and complicated spectra.

Example 7: Design and Characterization of a Synthetic Peptide

Figure 15:
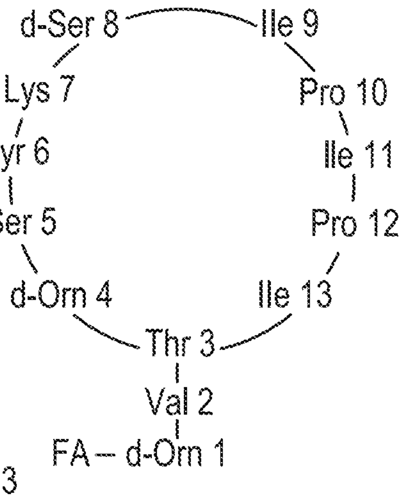
FIG. 15 shows a schematic of a chemically synthesized, fatty acid modified peptide.
Figure 15:
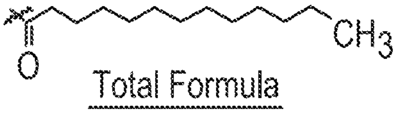
Figure 16A:
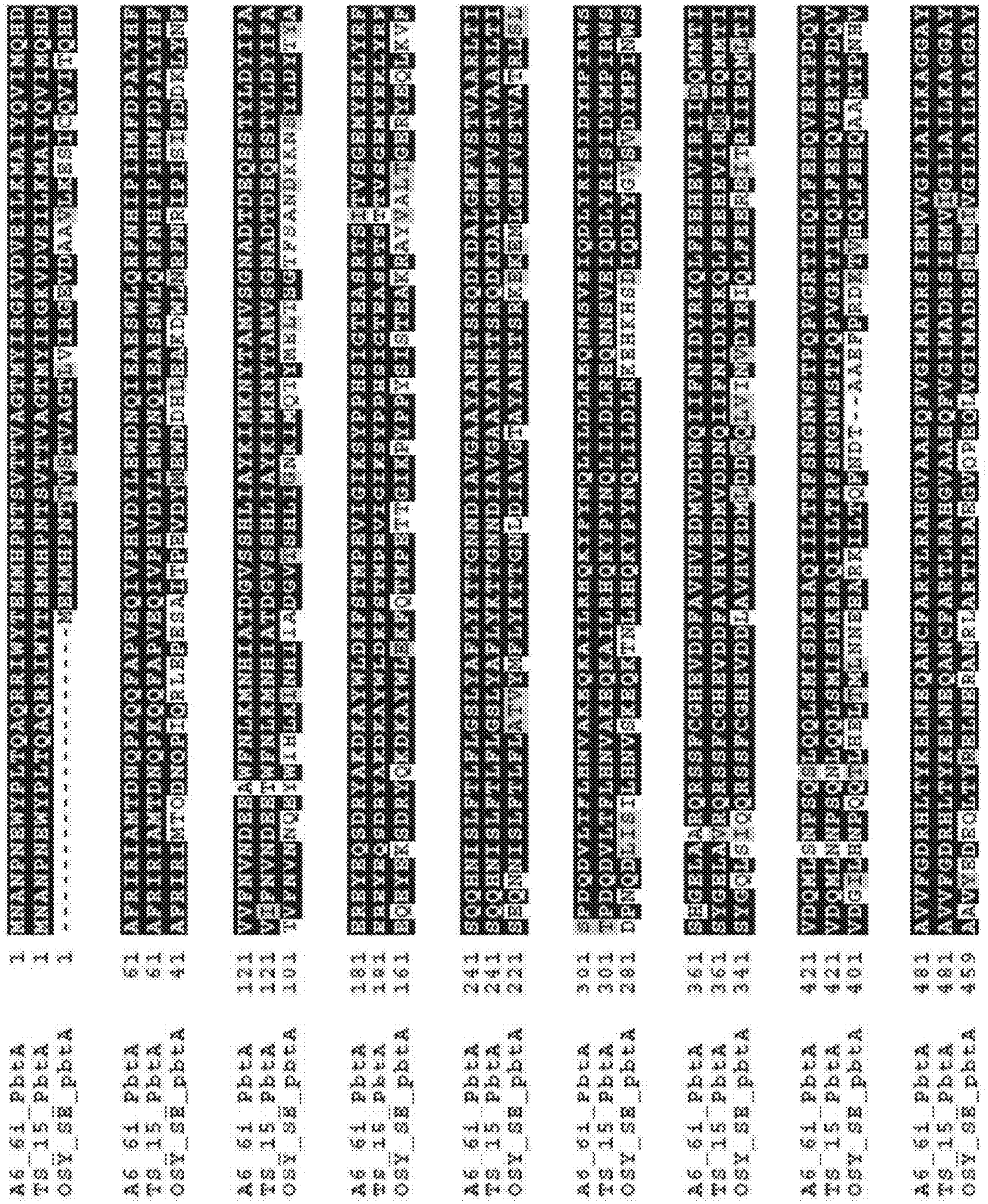
Figure 16B:
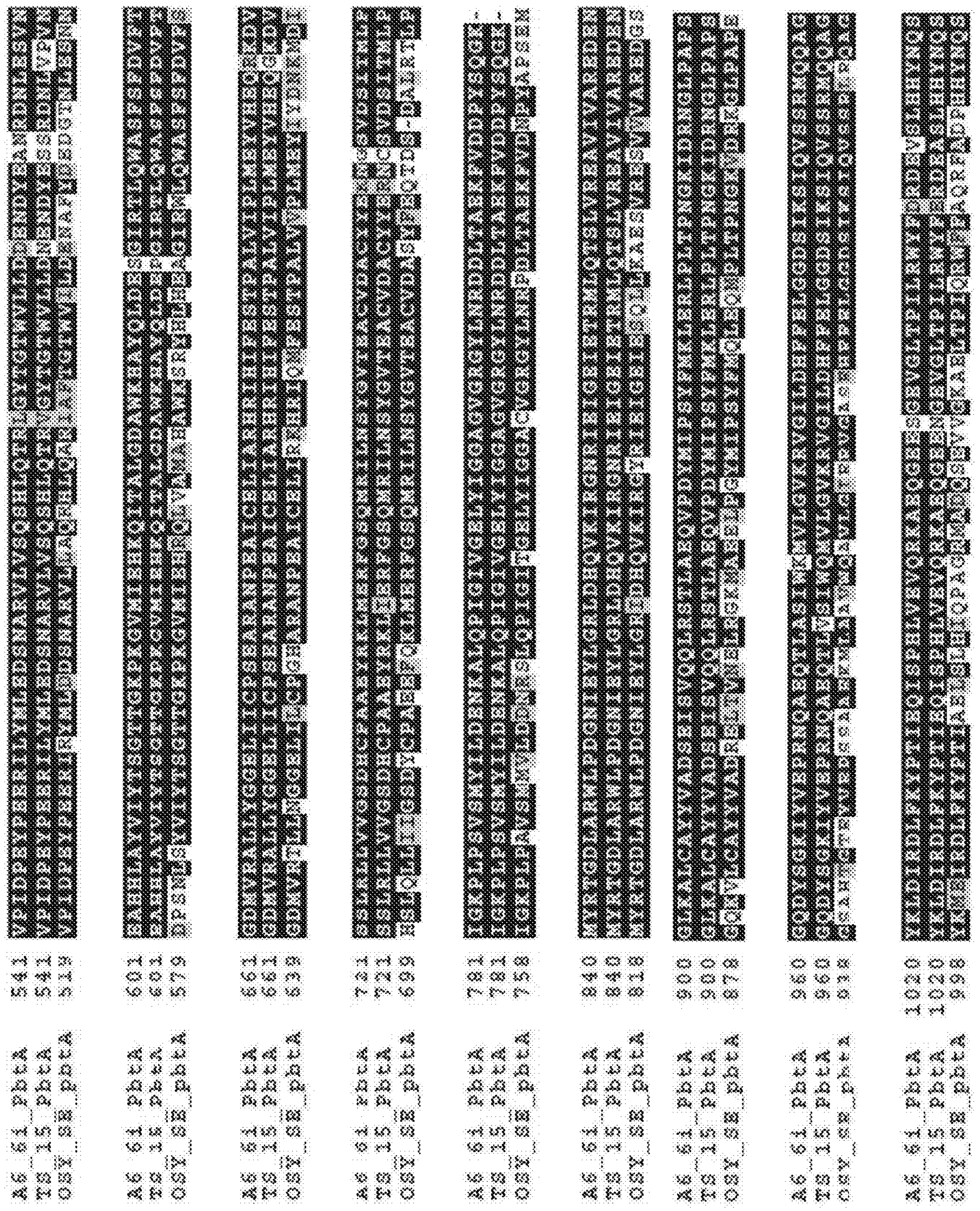
Figure 16C:
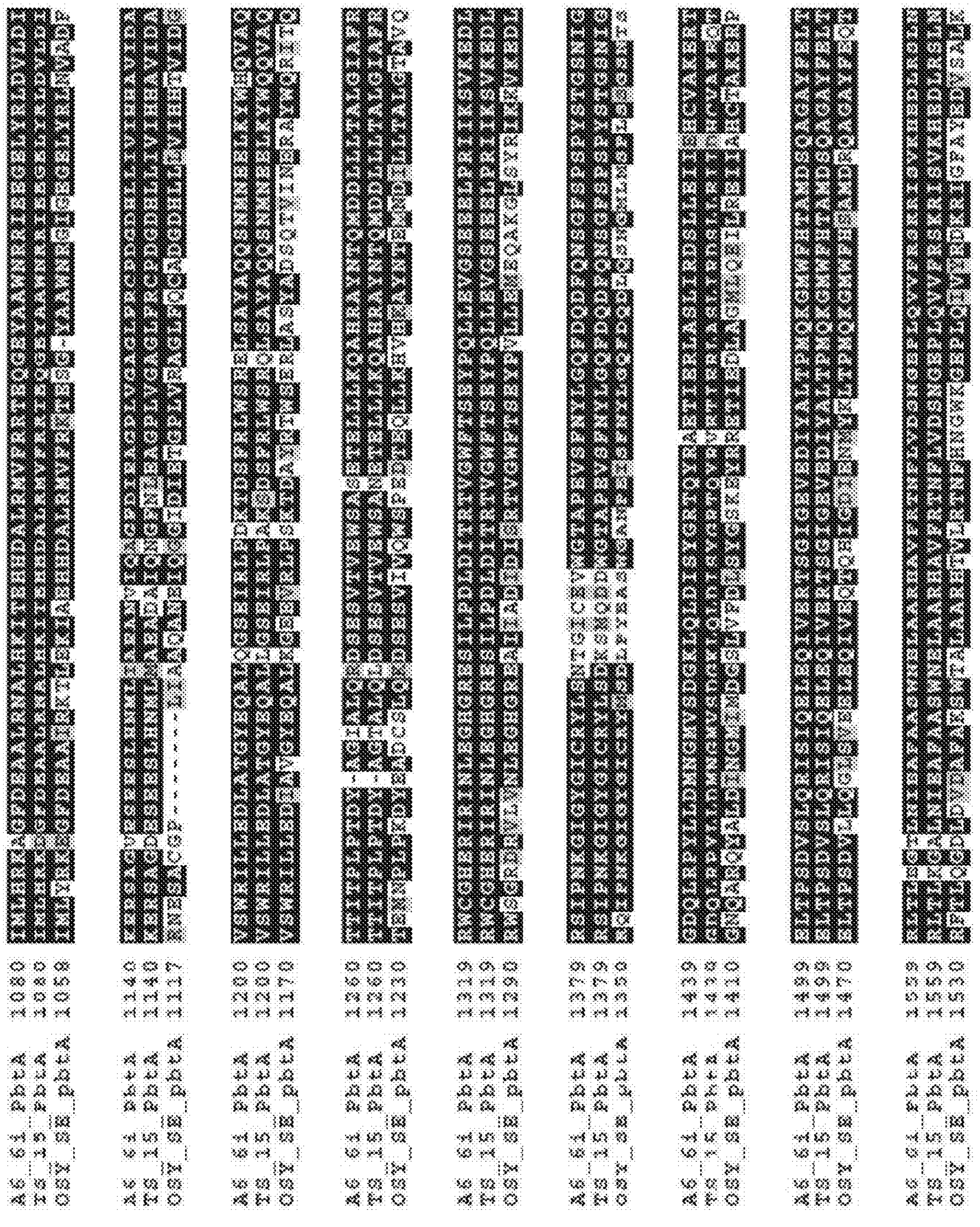
Figure 16D:
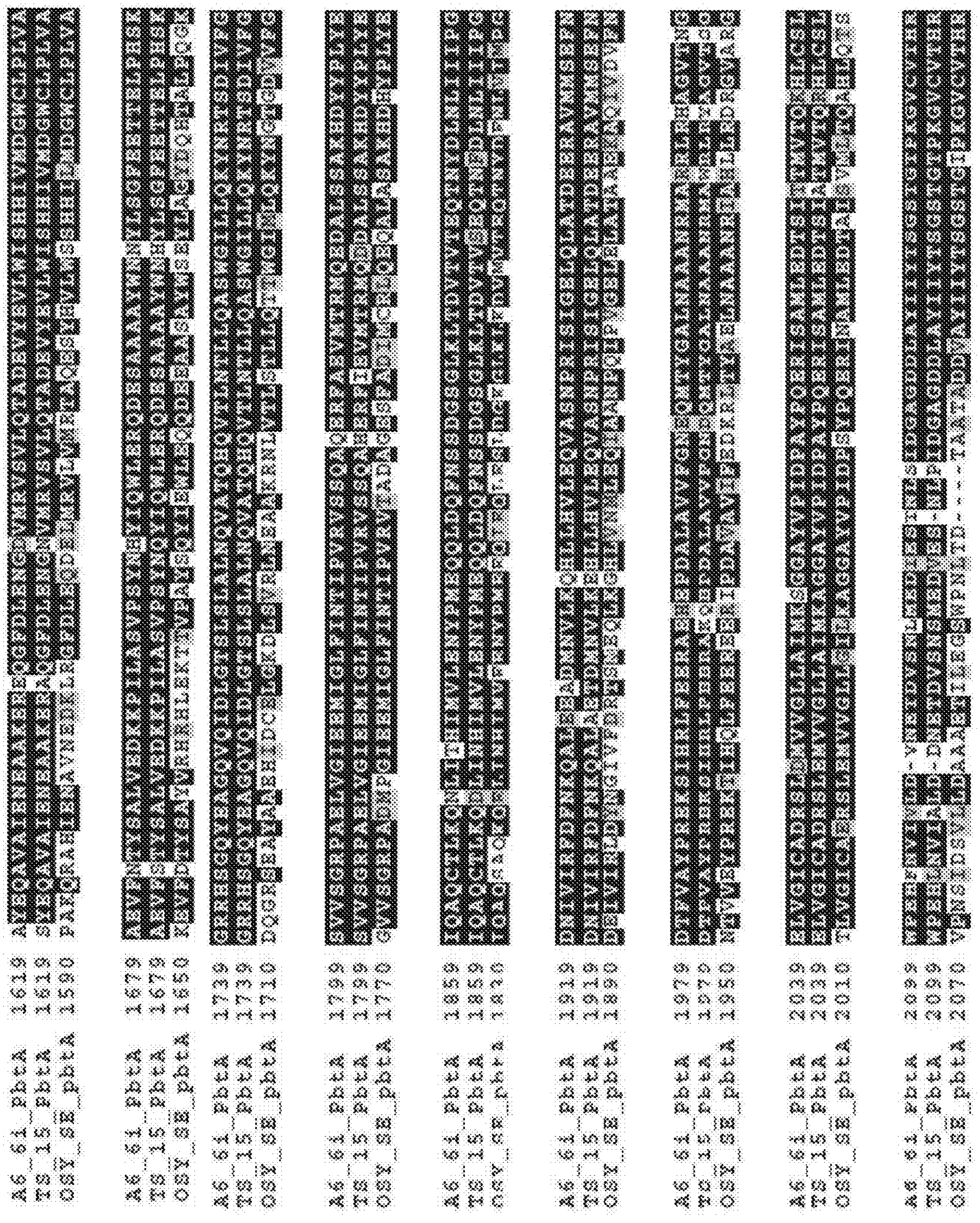
Figure 16E:
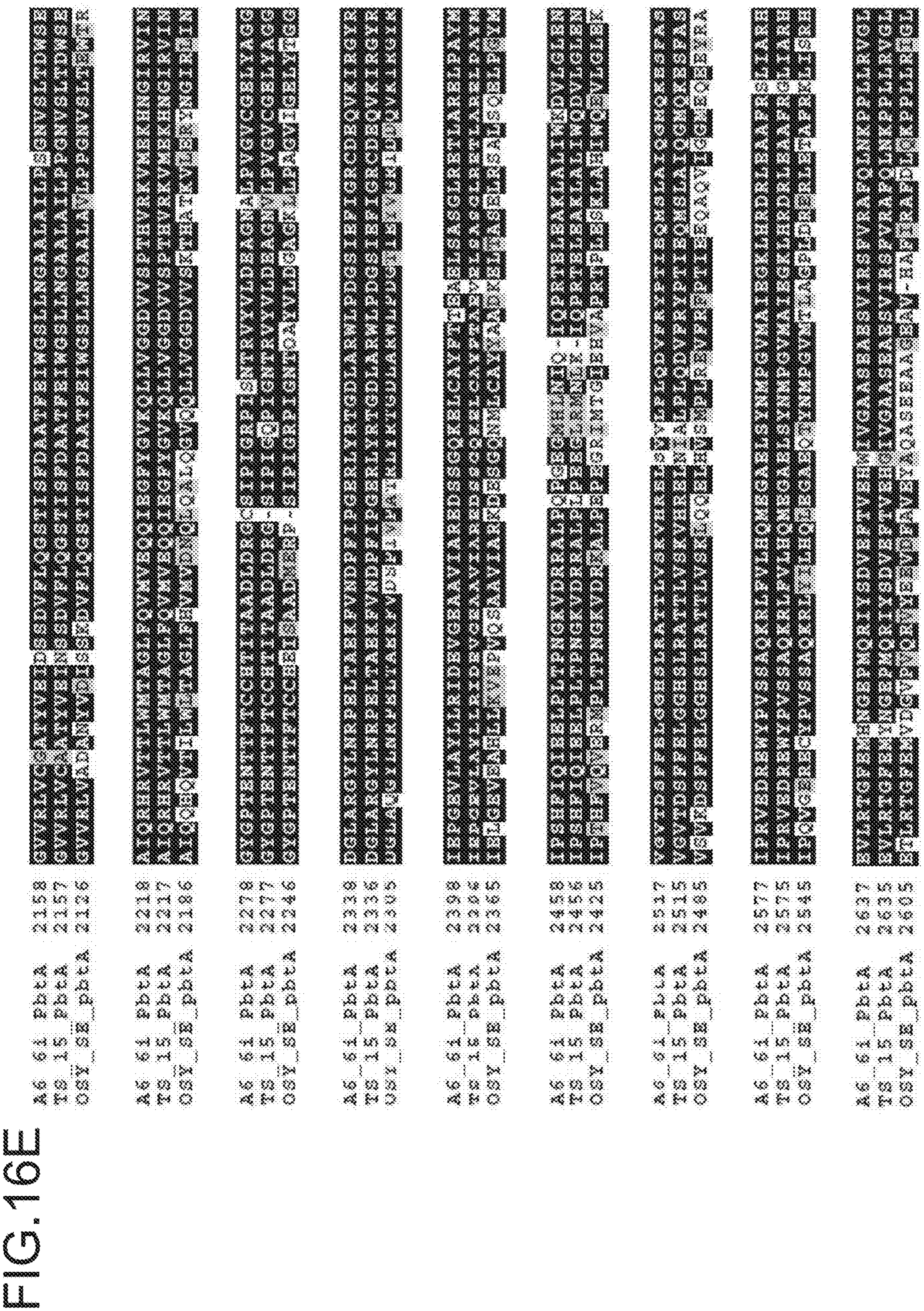
Figure 16F:
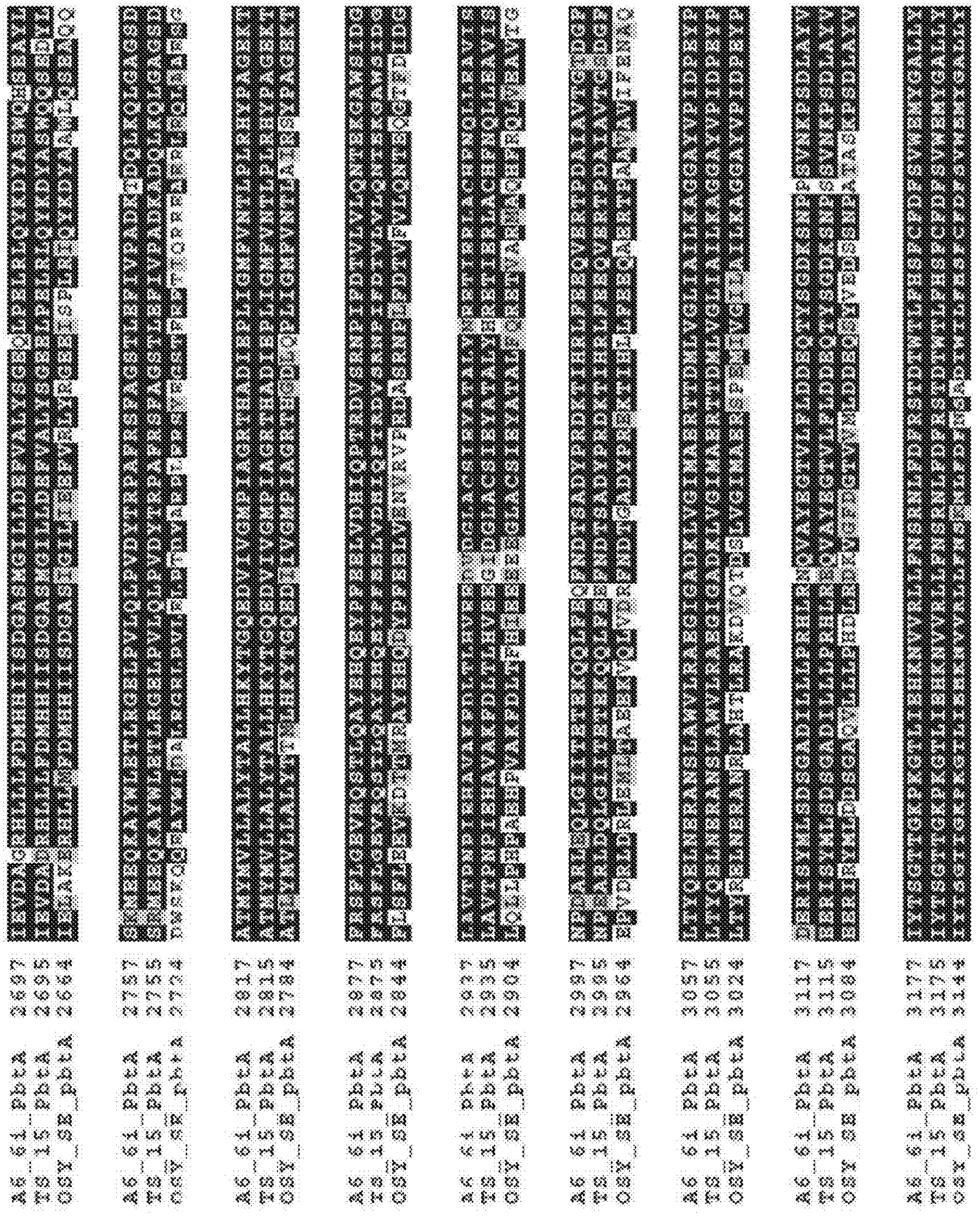
Figure 16G:
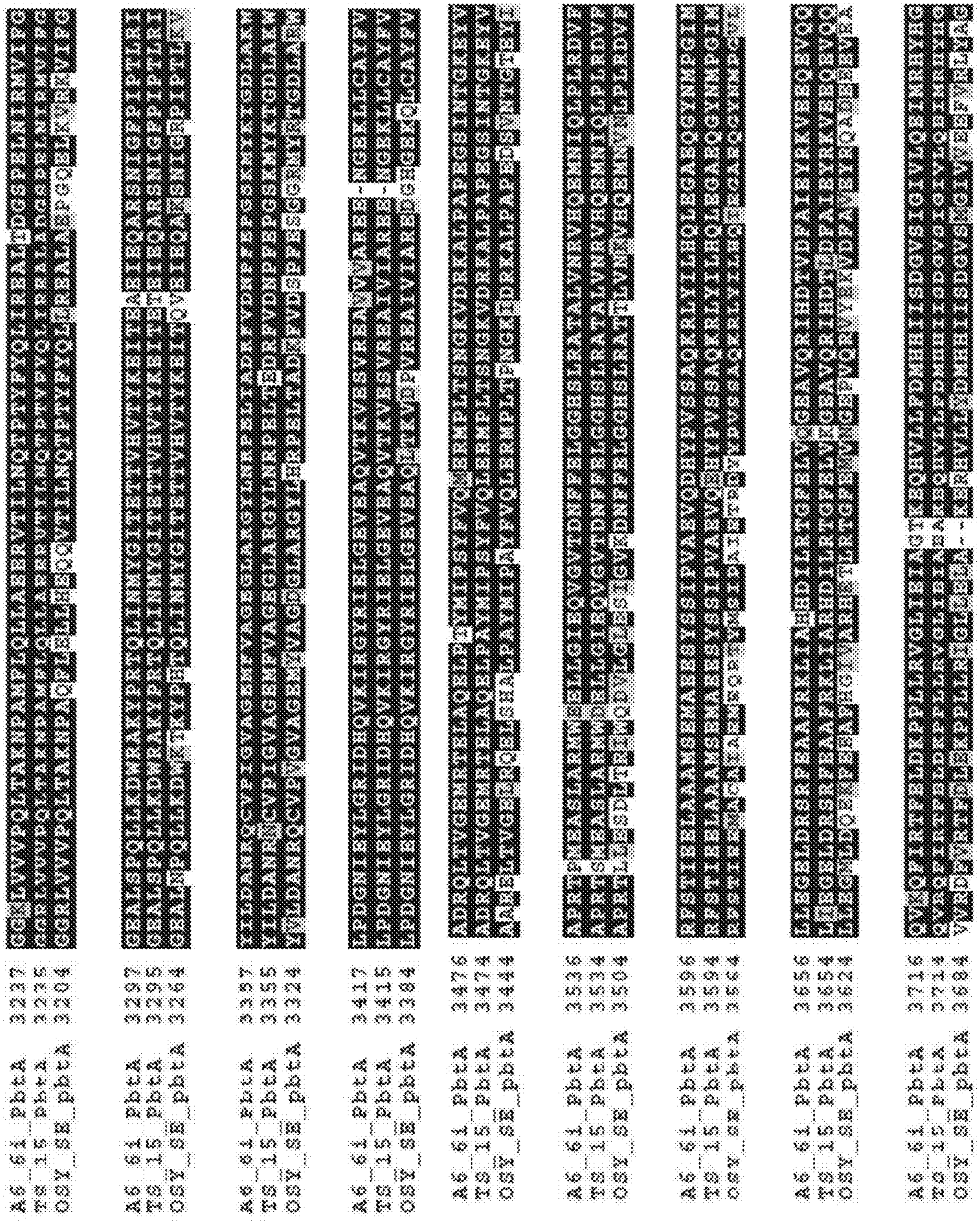
Figure 16H:
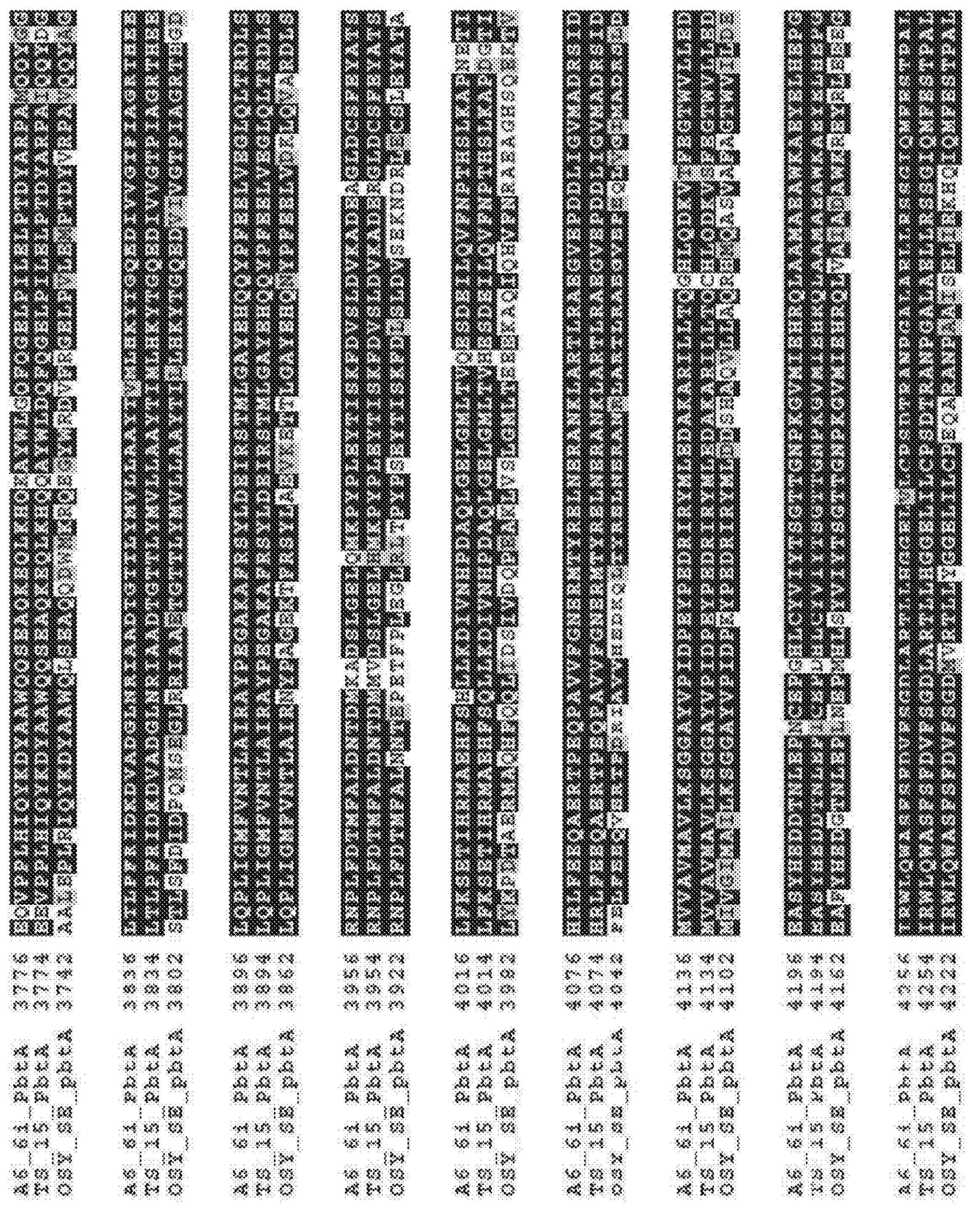
Figure 16I:
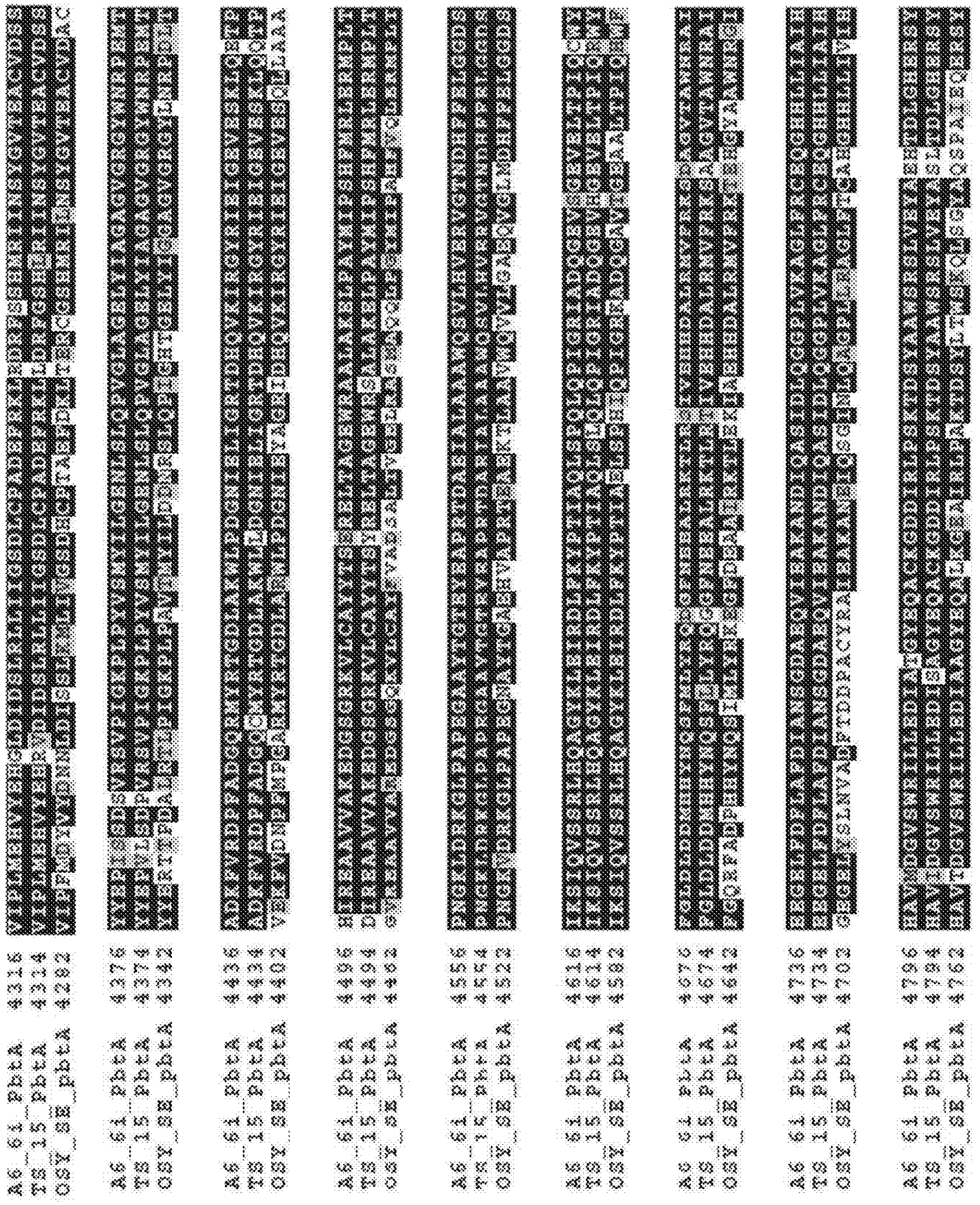
Figure 16J:
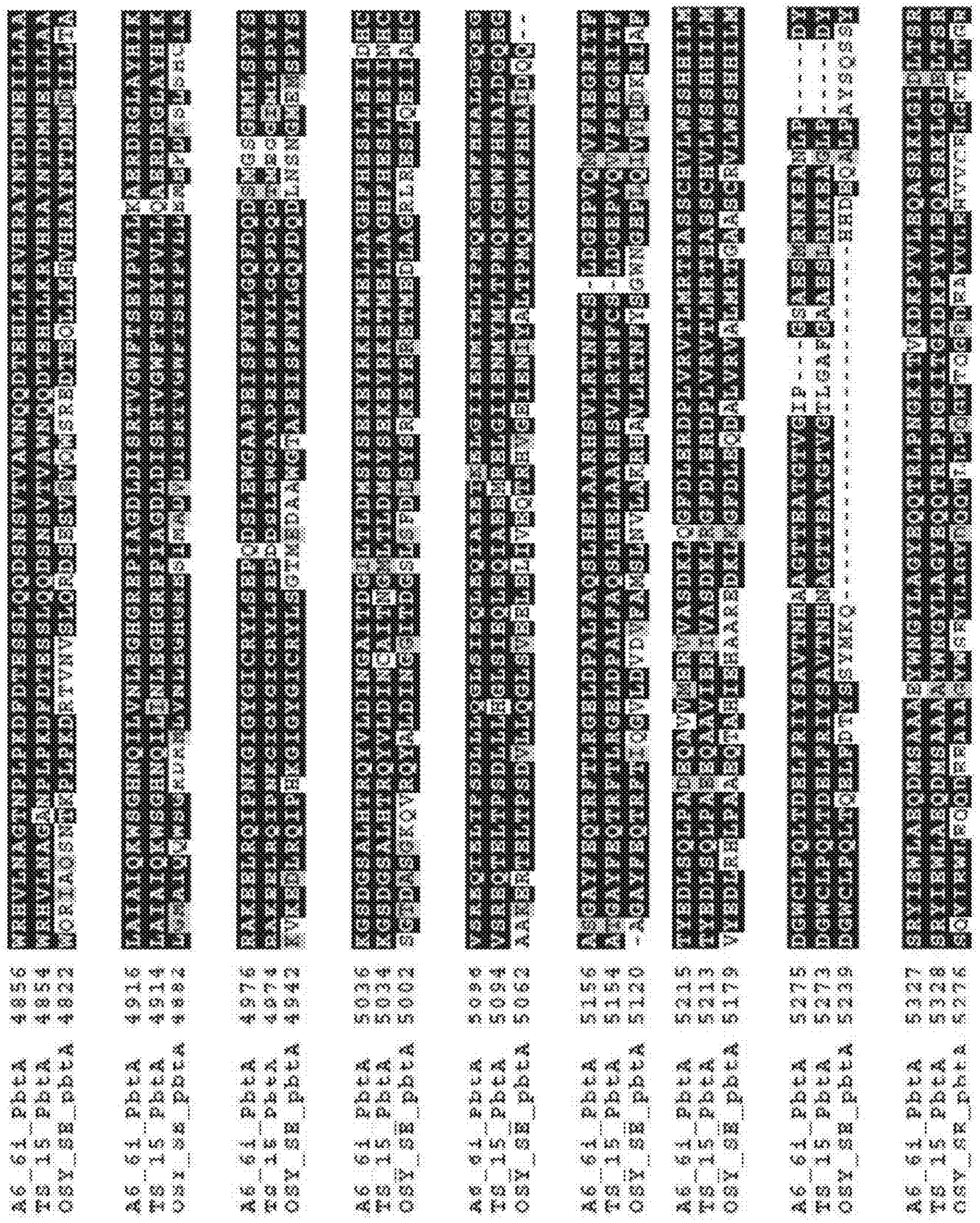
Figure 16K:
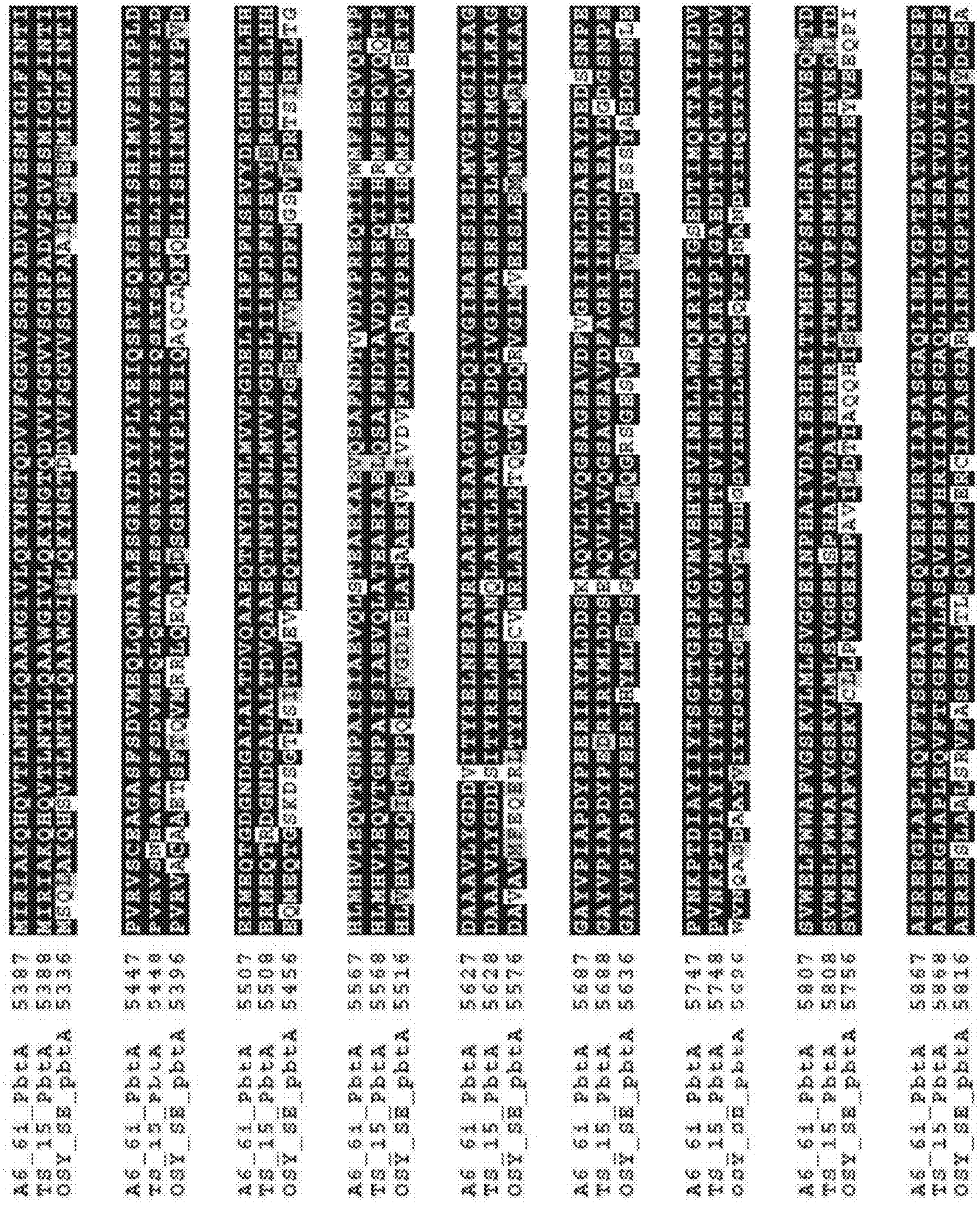
Figure 16L:
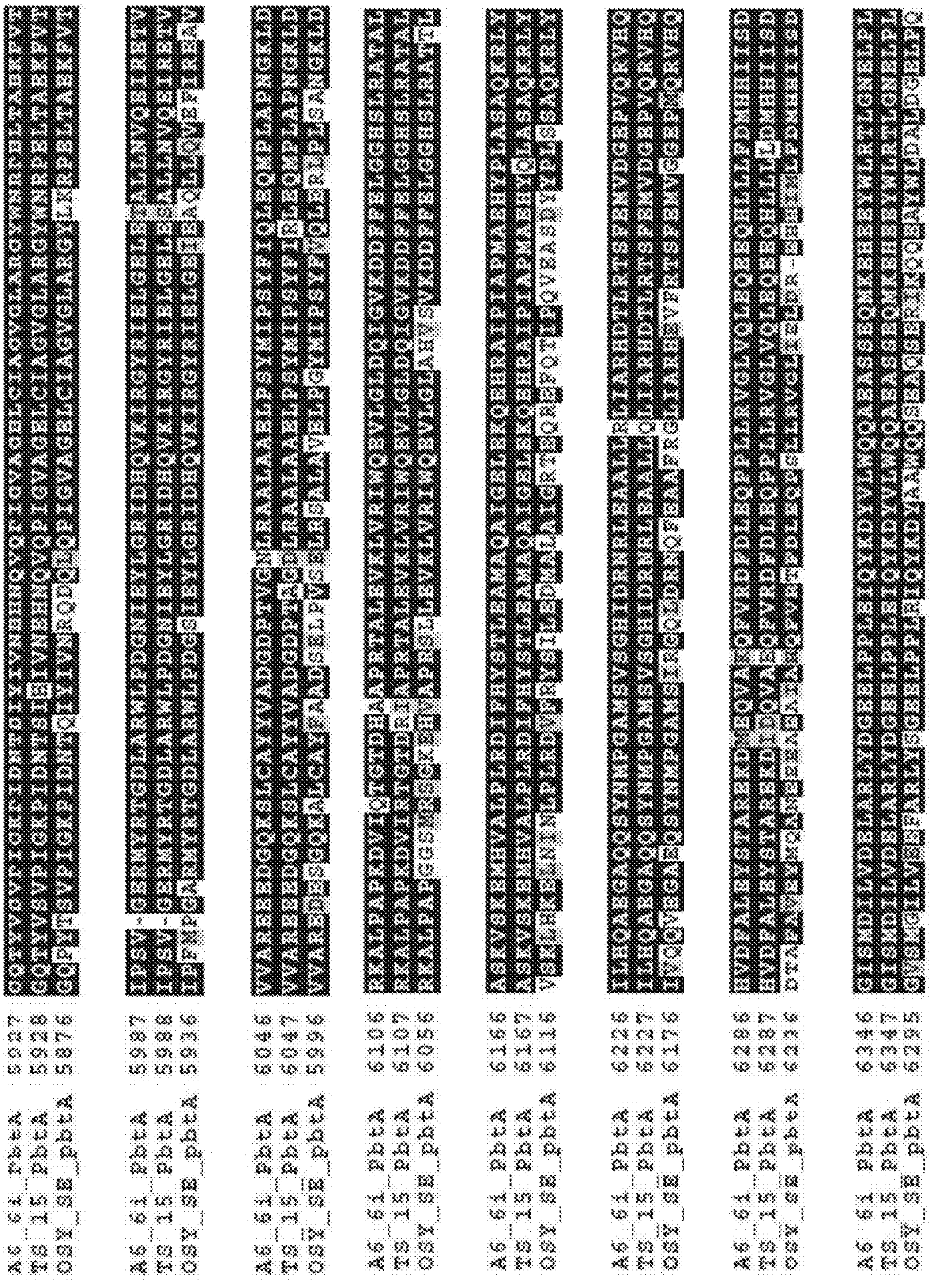
Figure 17A:
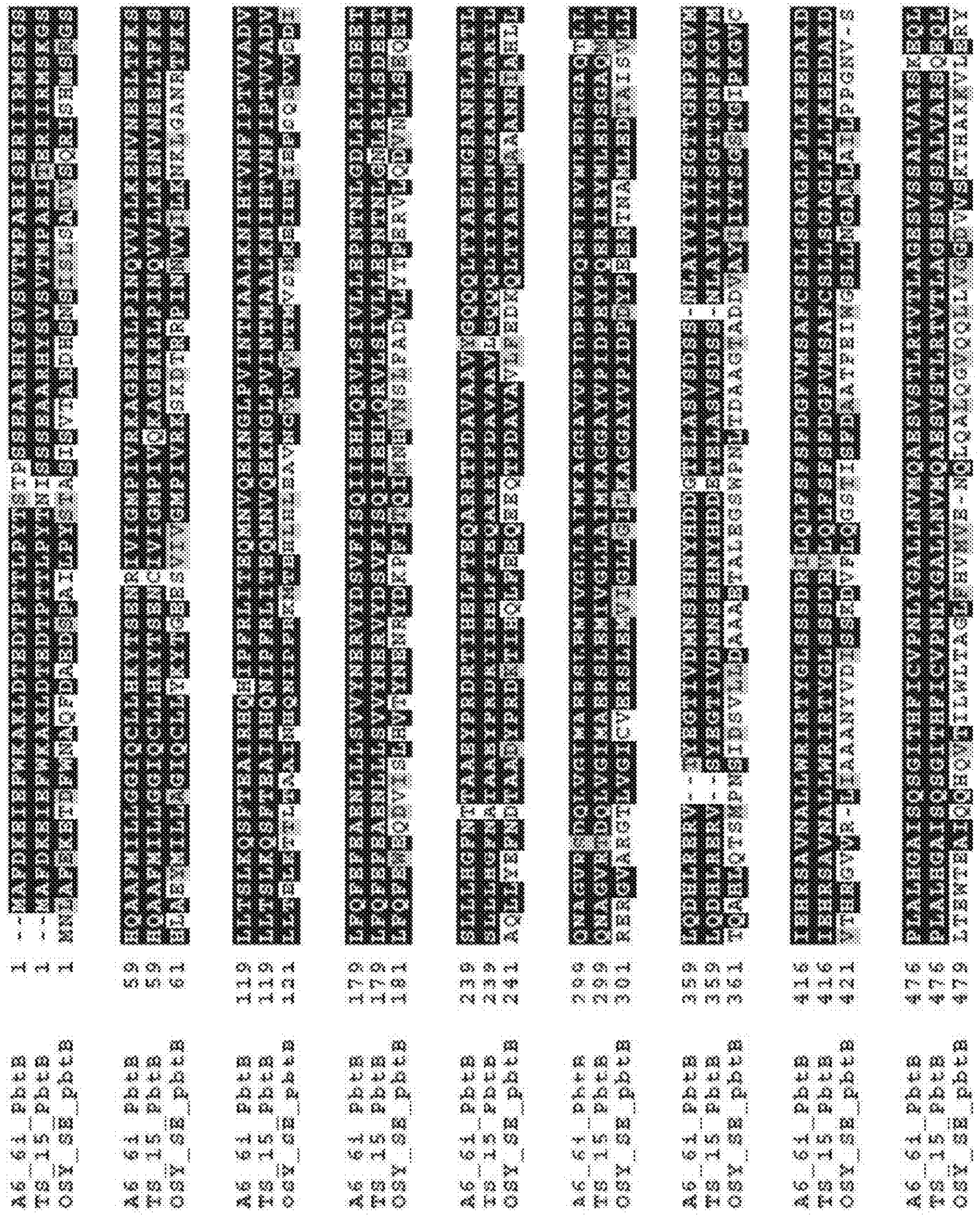
Figure 17B:
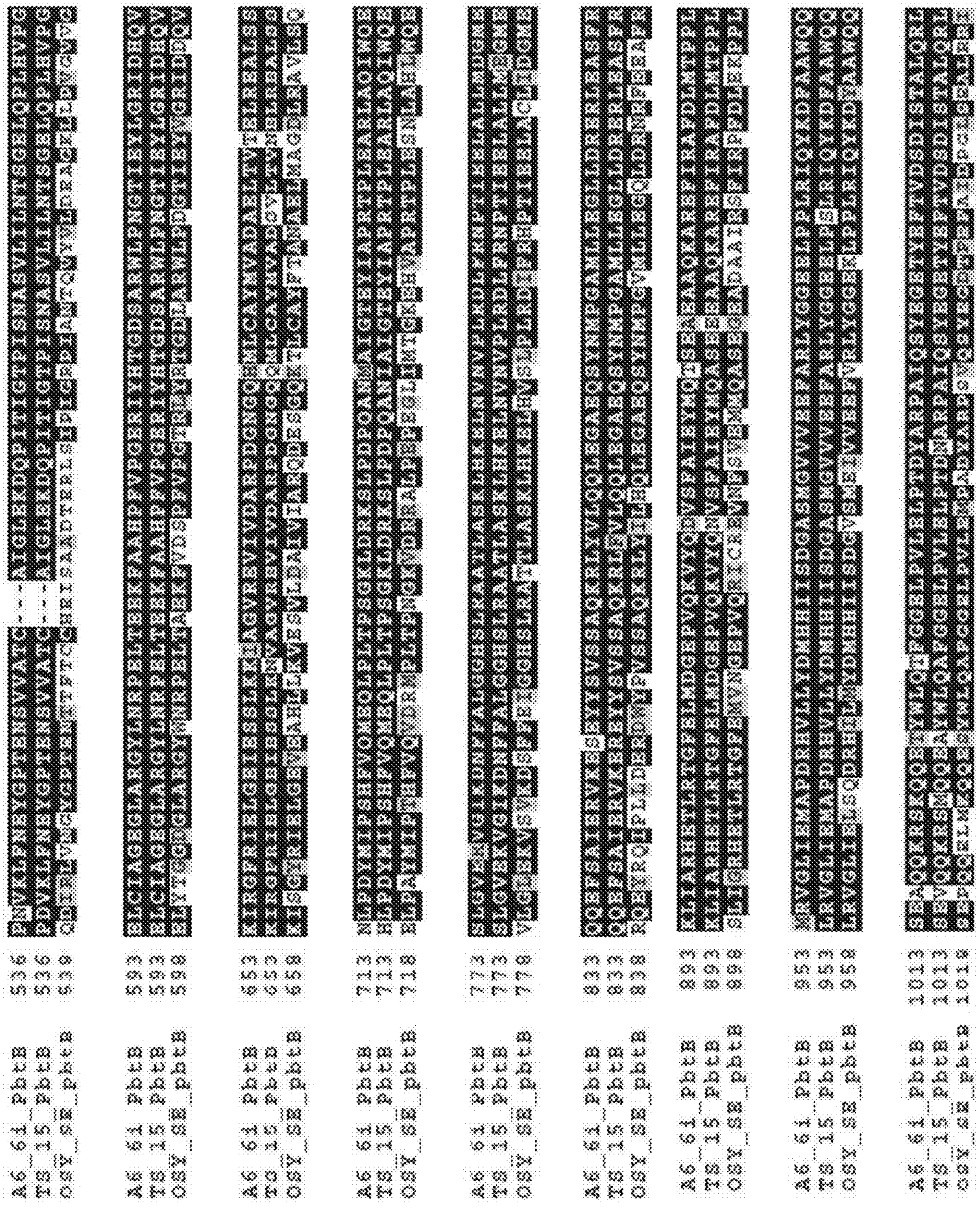
Figure 17C:
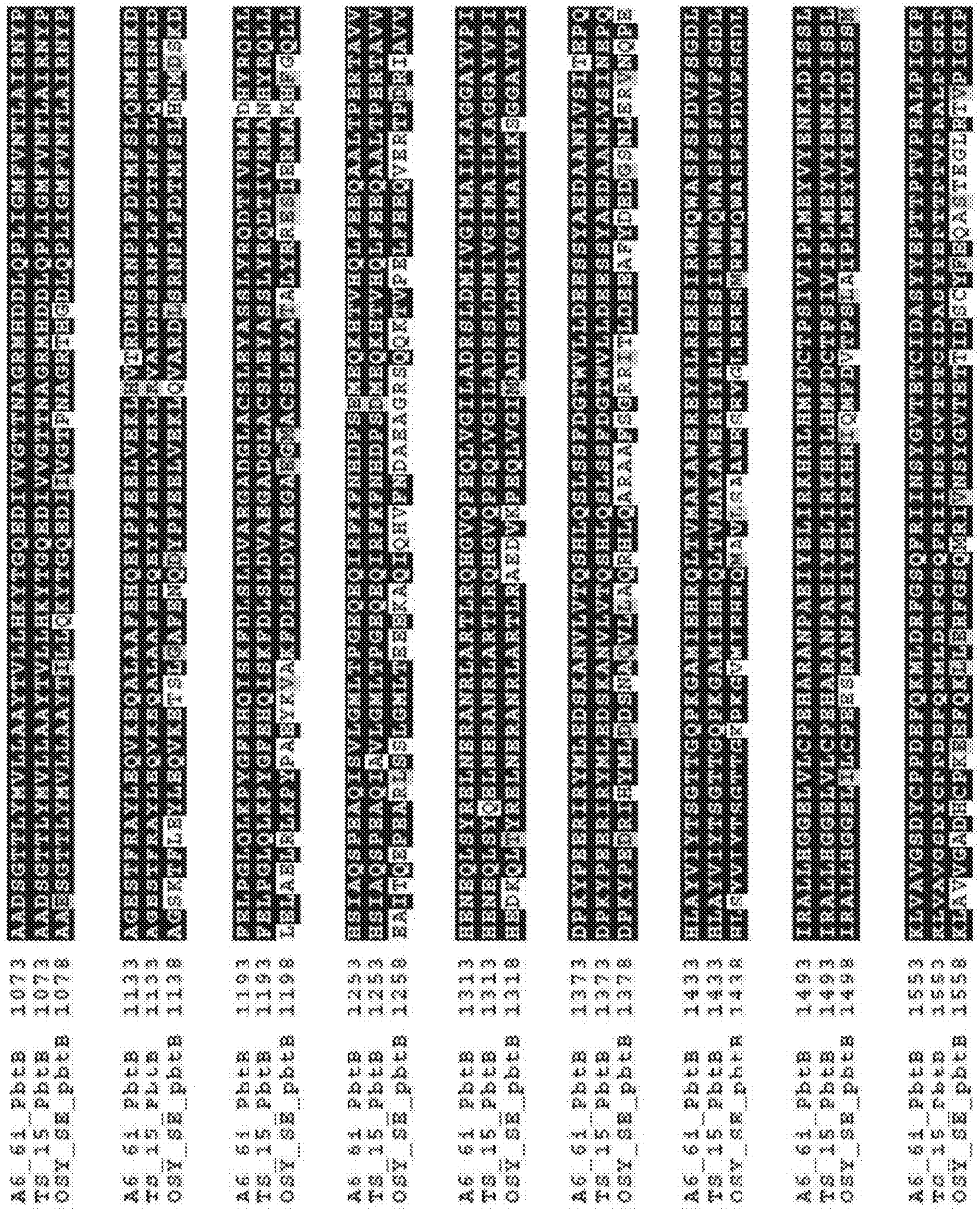
Figure 17D:
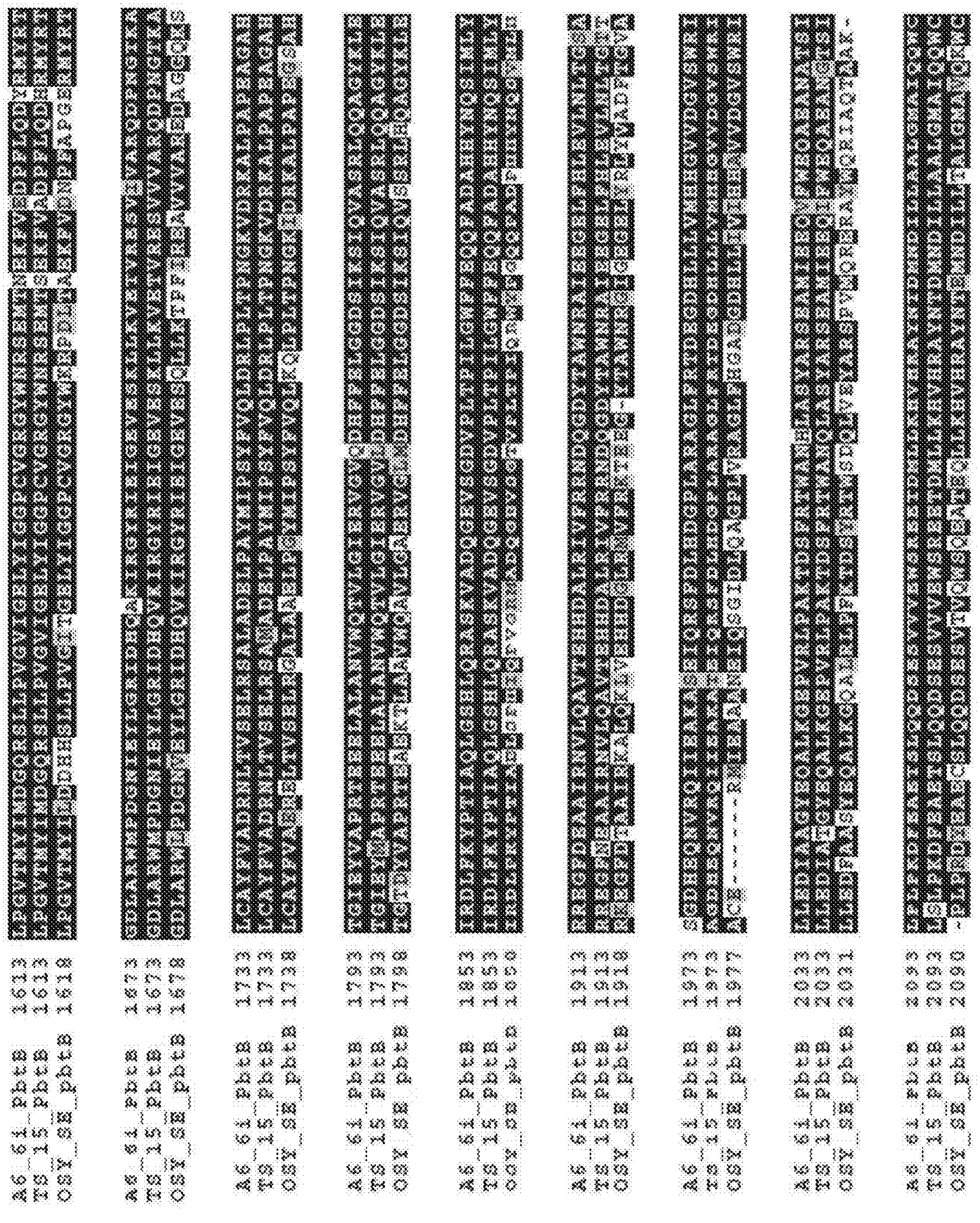
Figure 17E:
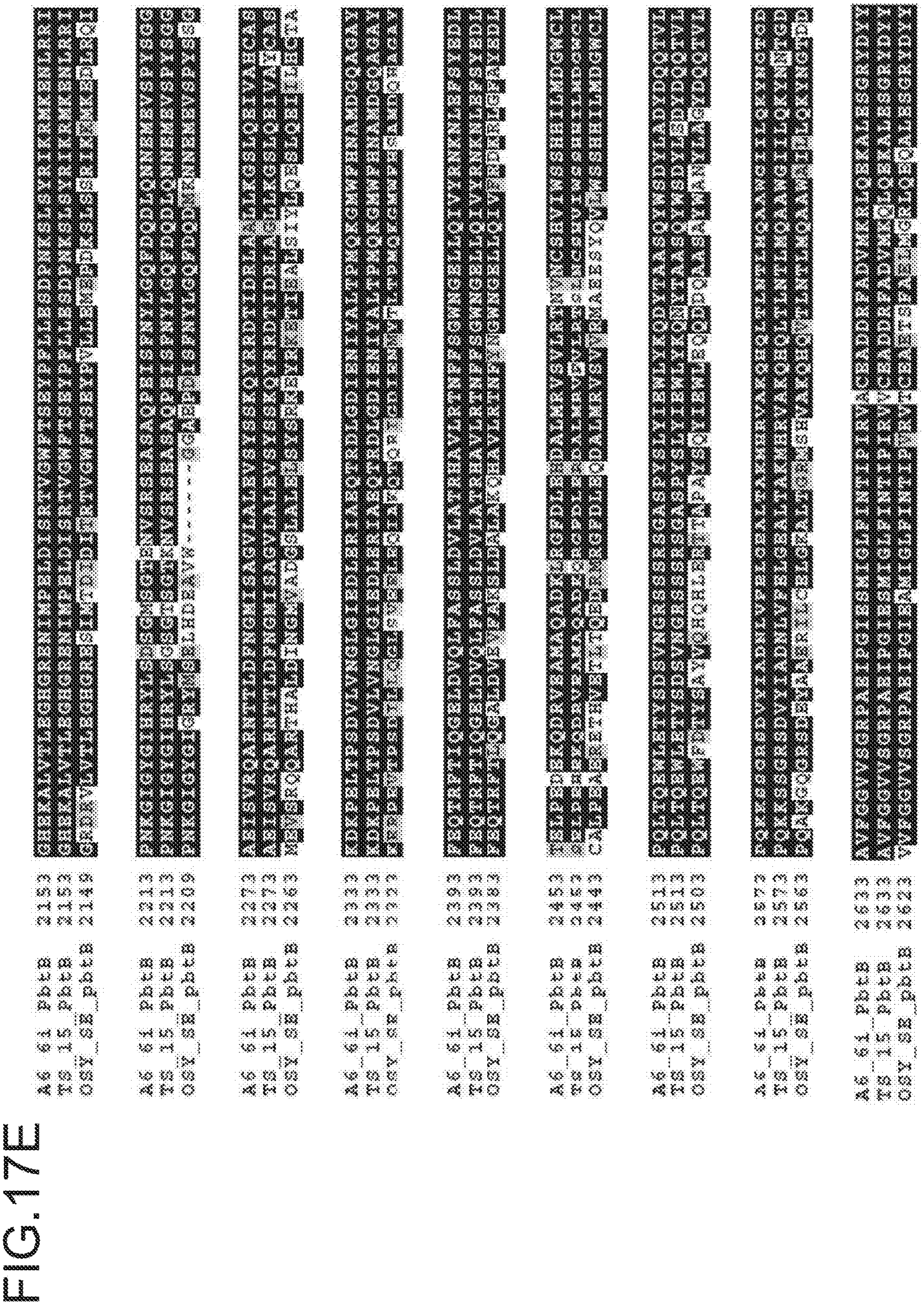
Figure 17F:
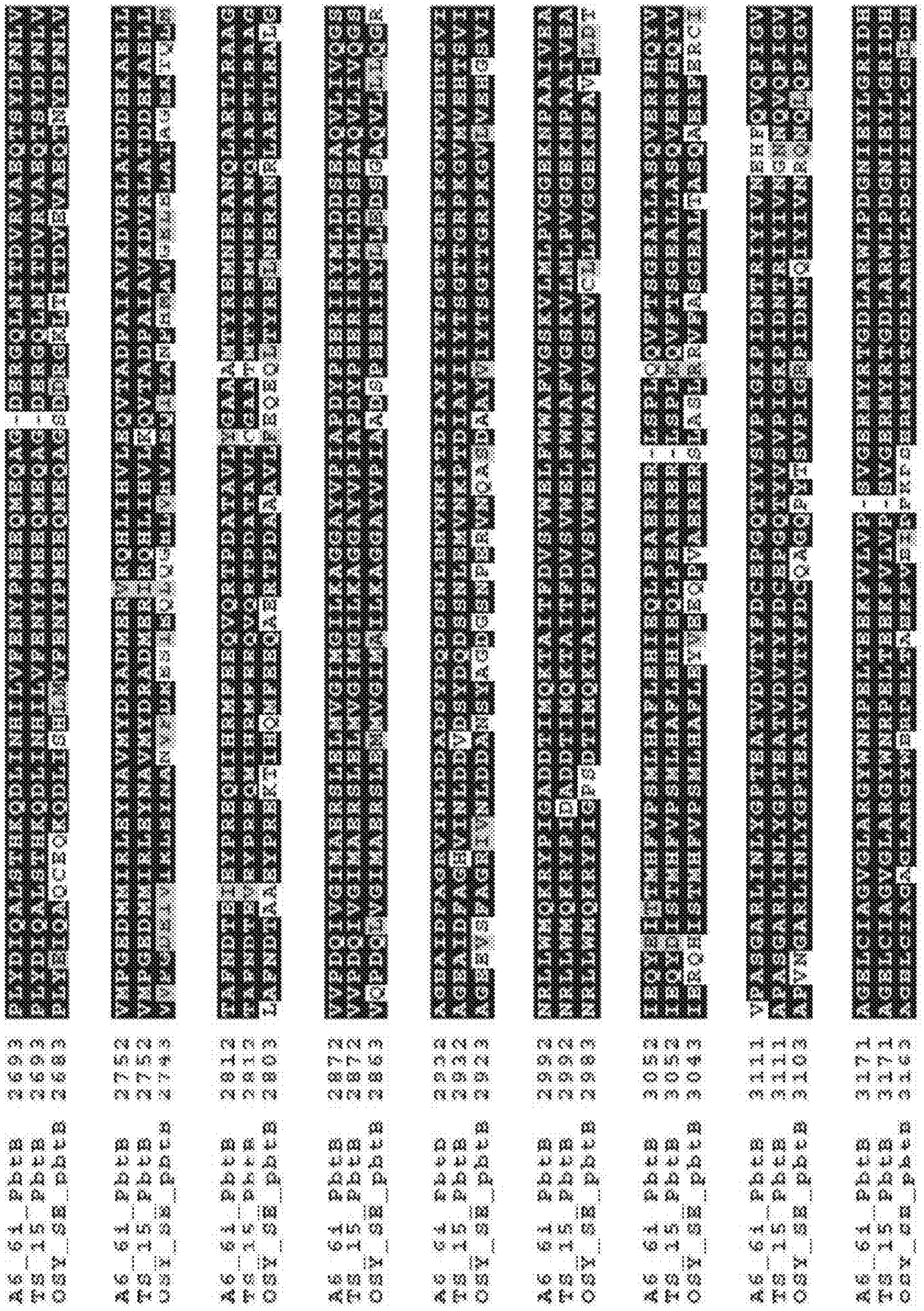
Figure 17G:
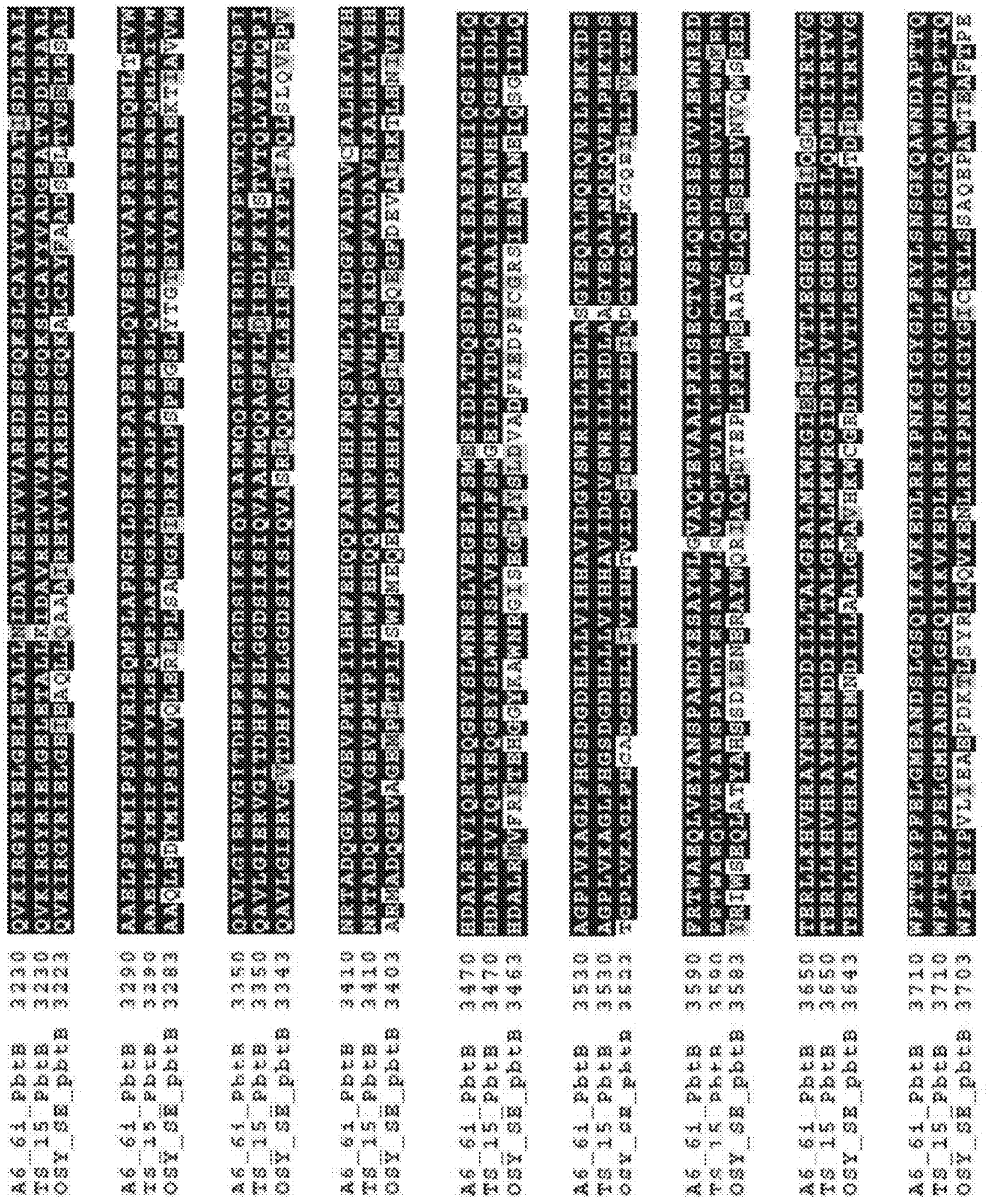
Figure 17H:
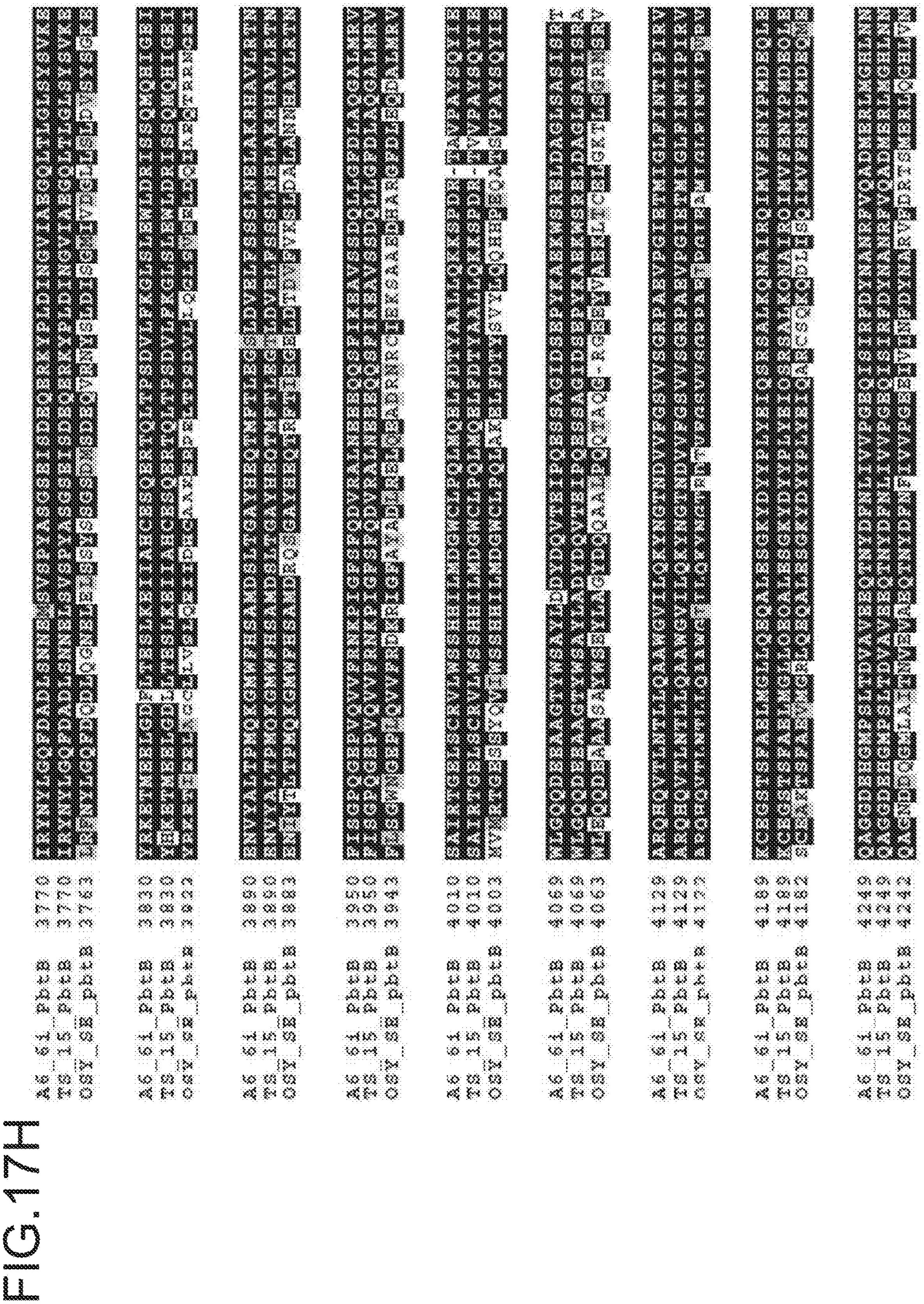
Figure 17I:
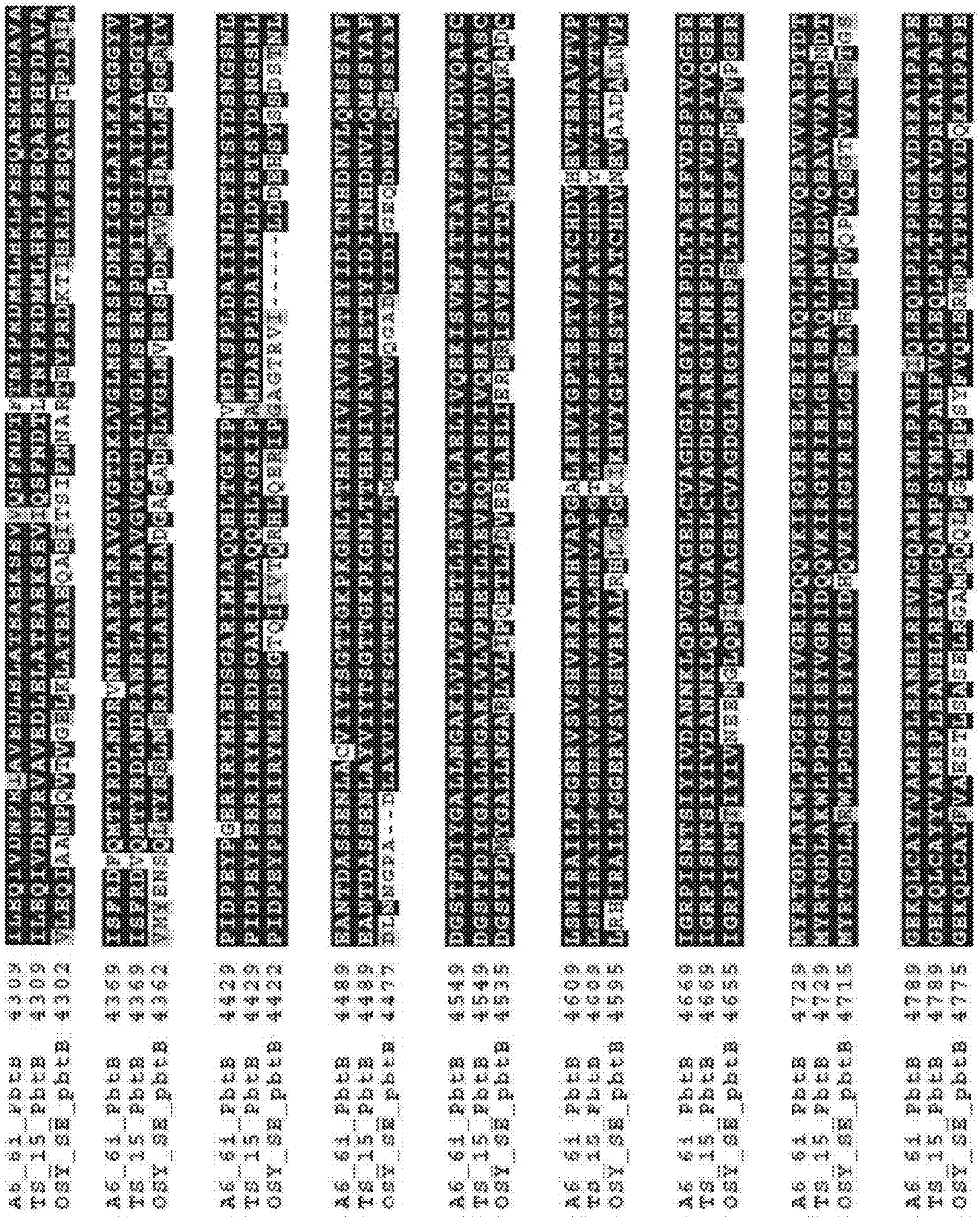
Figure 17J:
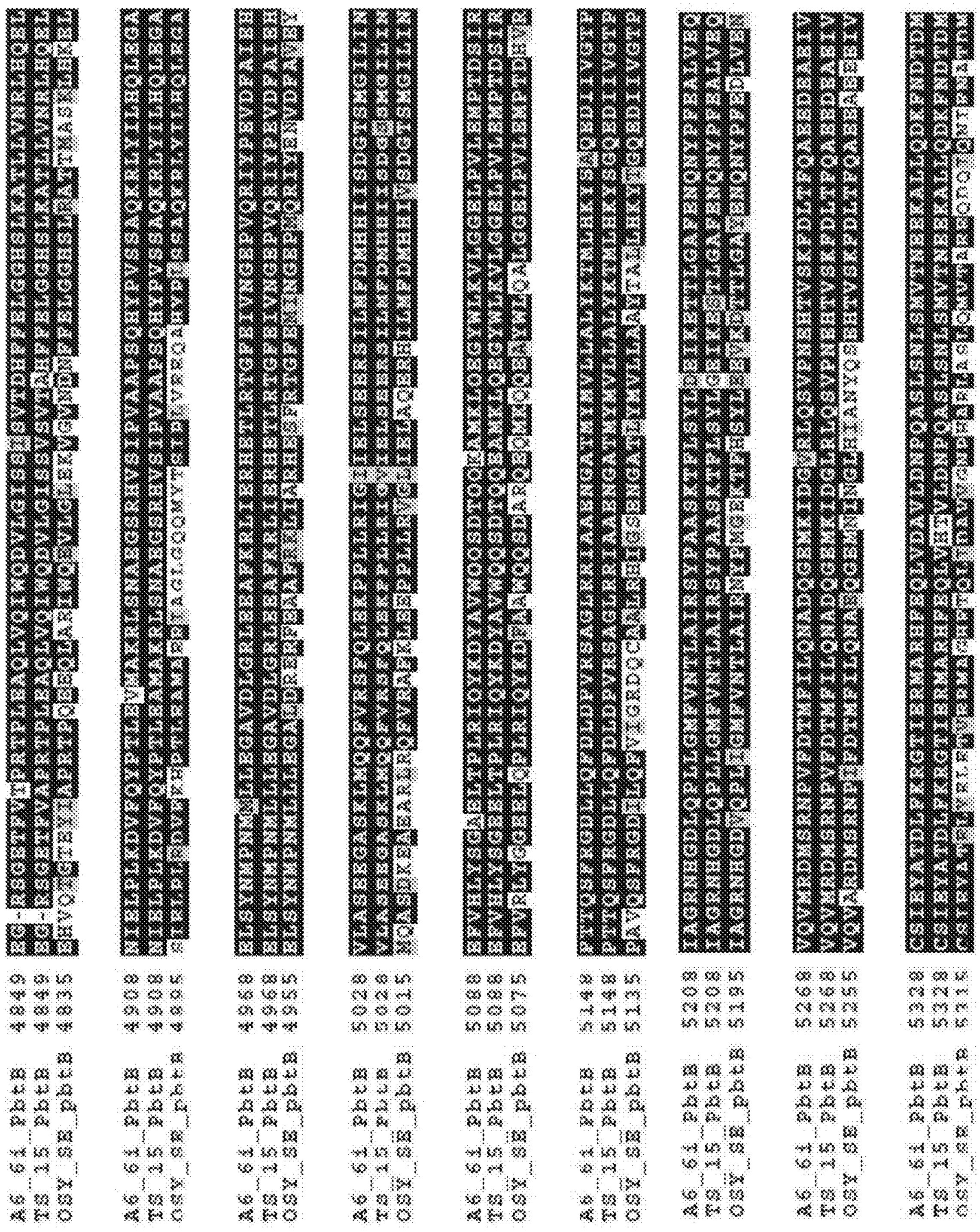
Figure 17K:
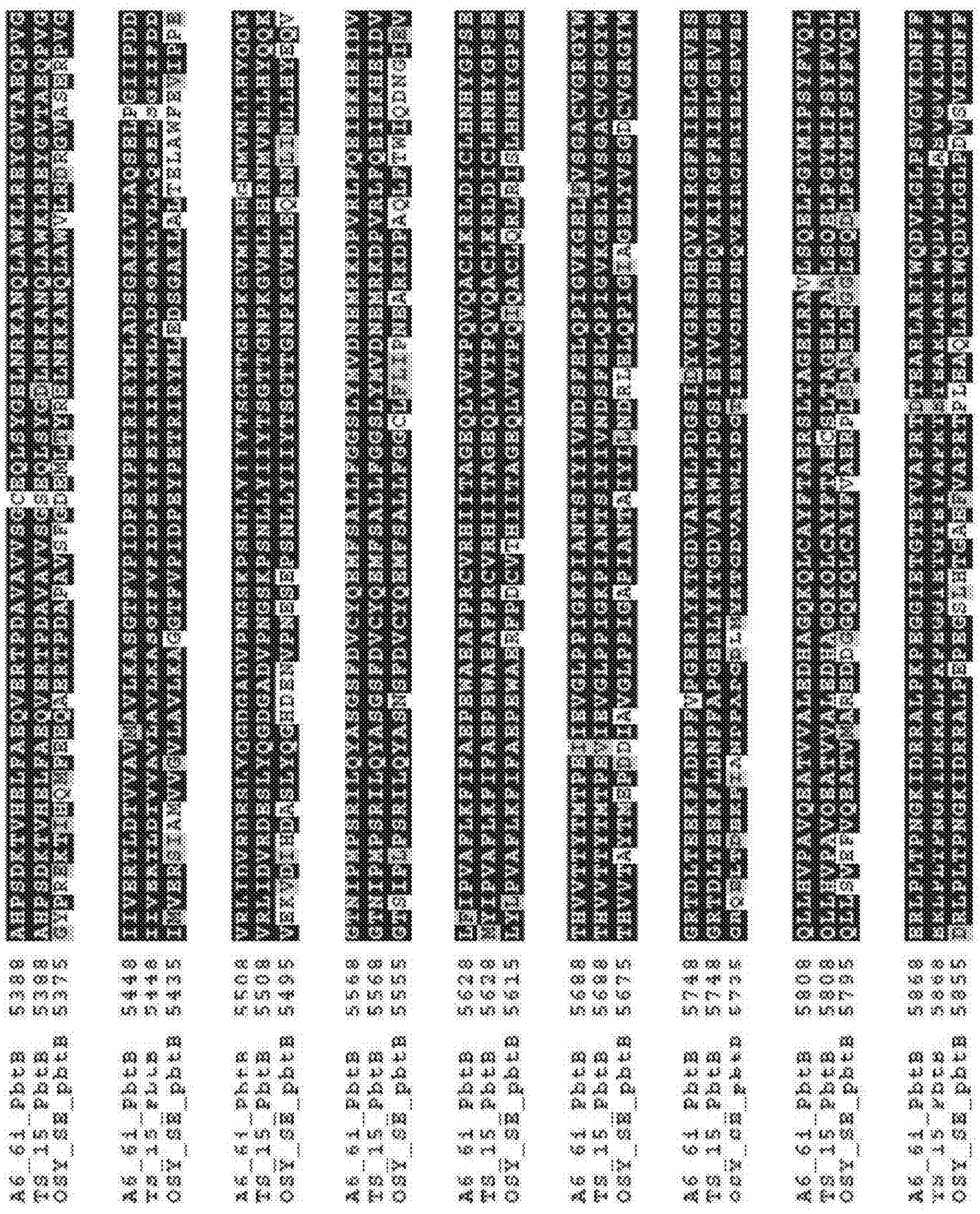
Figure 17L:
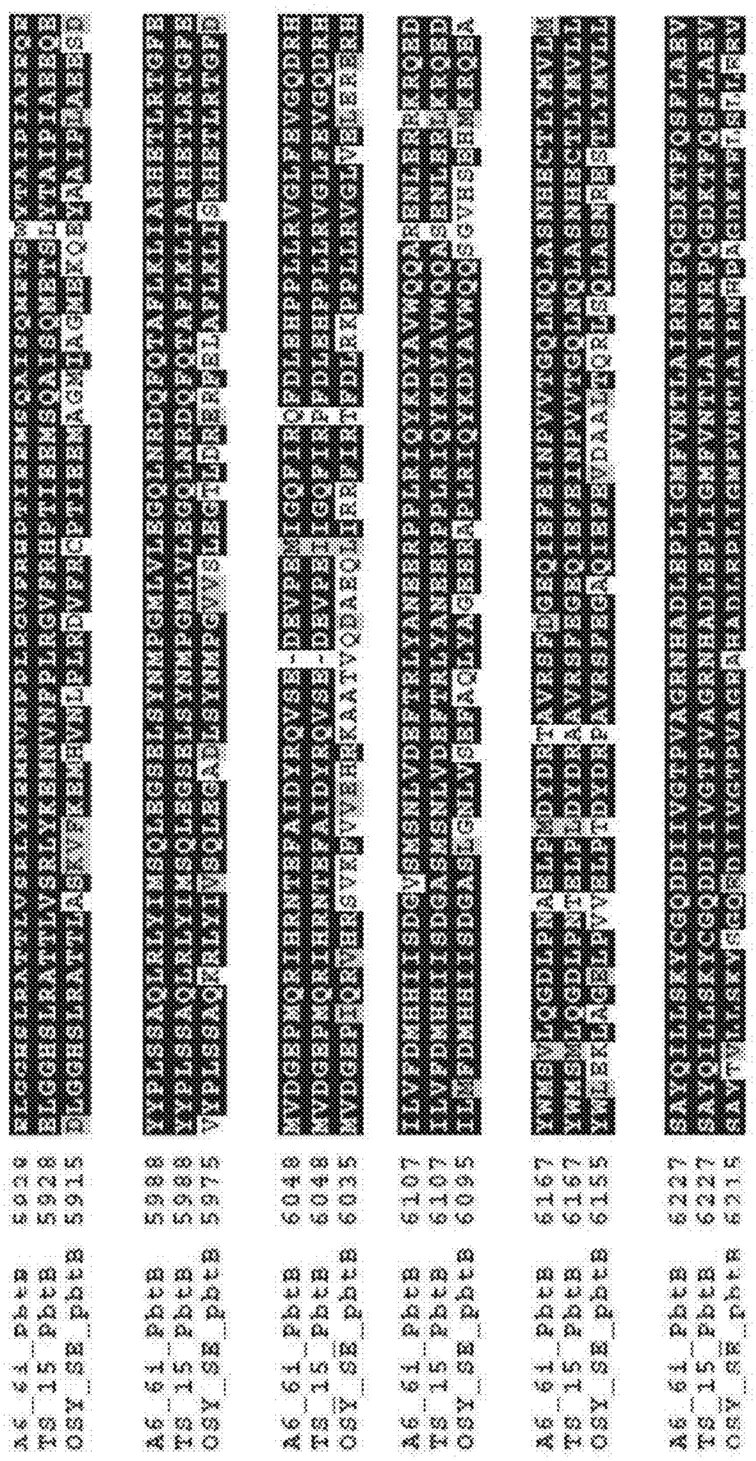
Figure 18A:
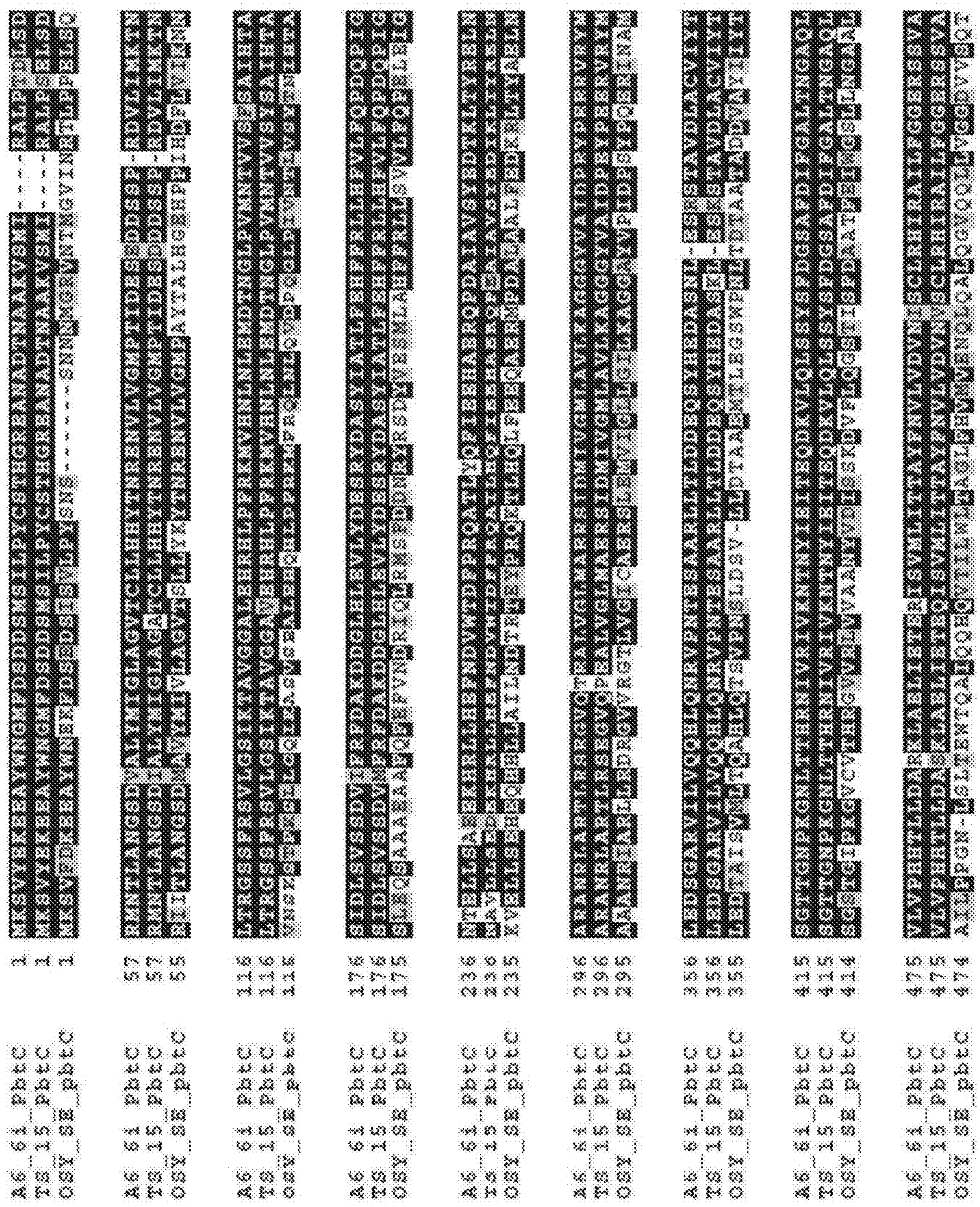
FIG. 18A-18G is a ptbC alignment for strains A6-6i, TS-15 and OSY SE. The protein sequences for A6-6i ptbC is SEQ ID NO: 13. The protein sequences for TS-15 ptbC is SEQ ID NO: 16. The protein sequences for OSY-SE ptbC is SEQ ID NO: 19.
Figure 18B:
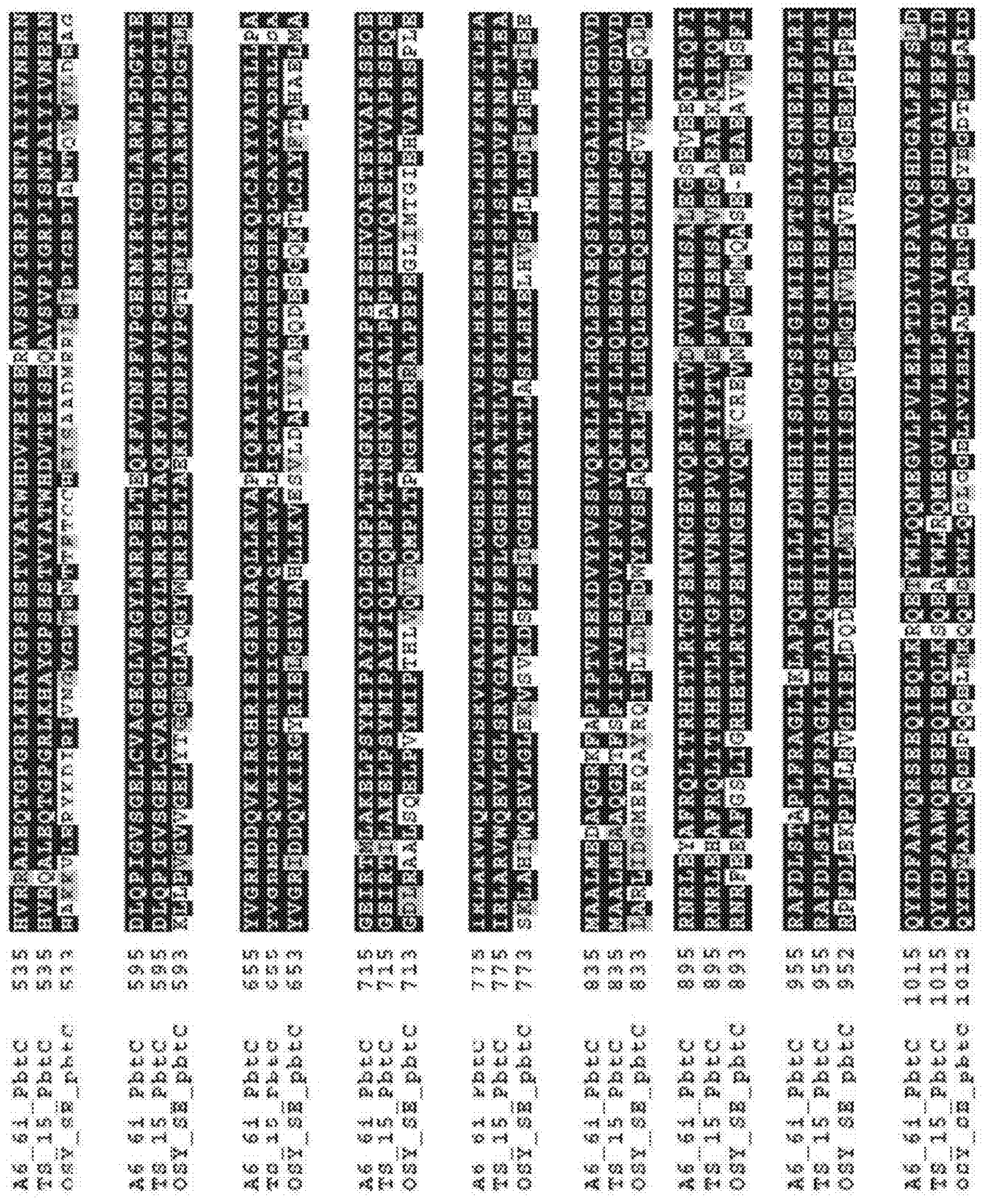
Figure 18C:
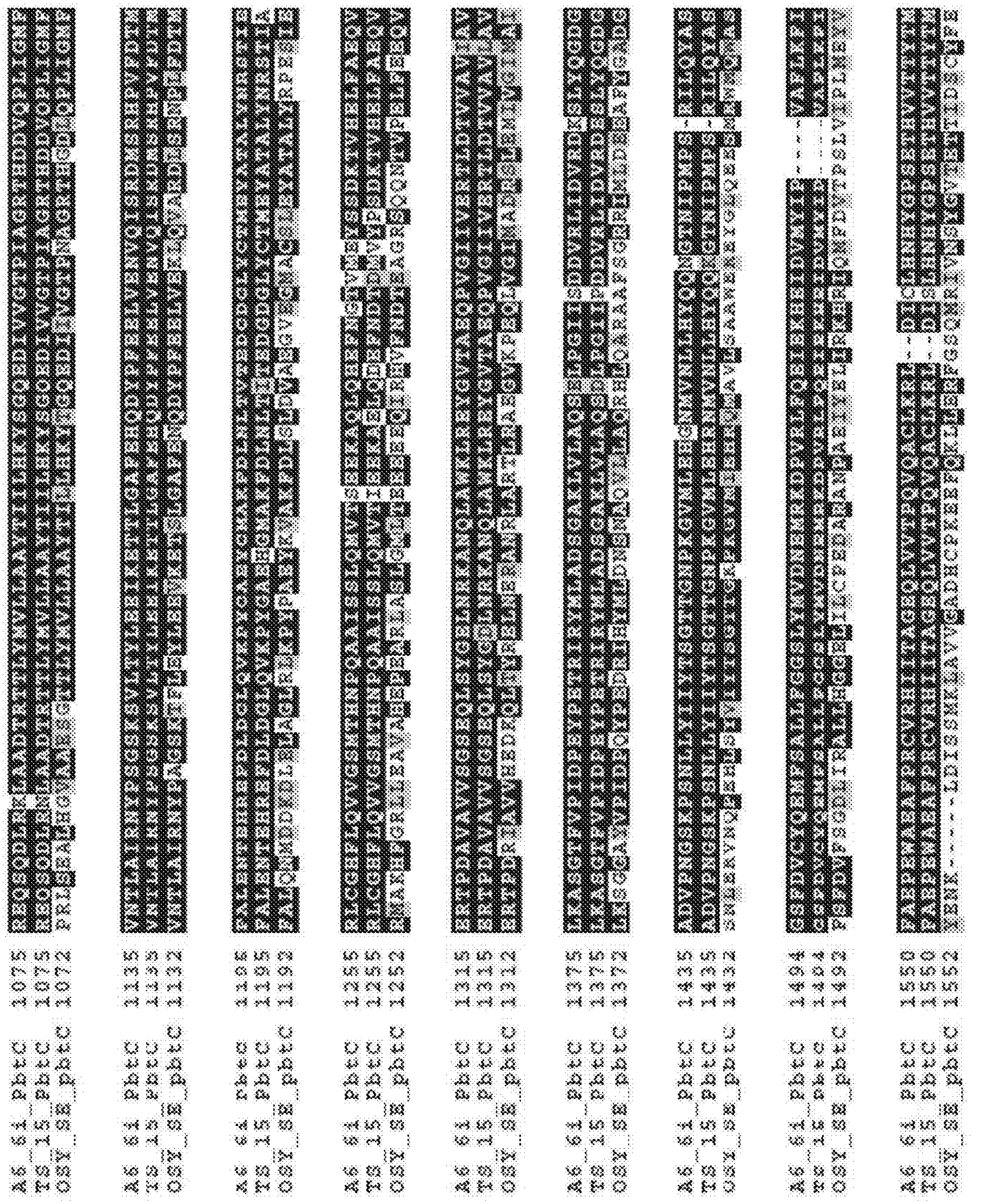
Figure 18D:
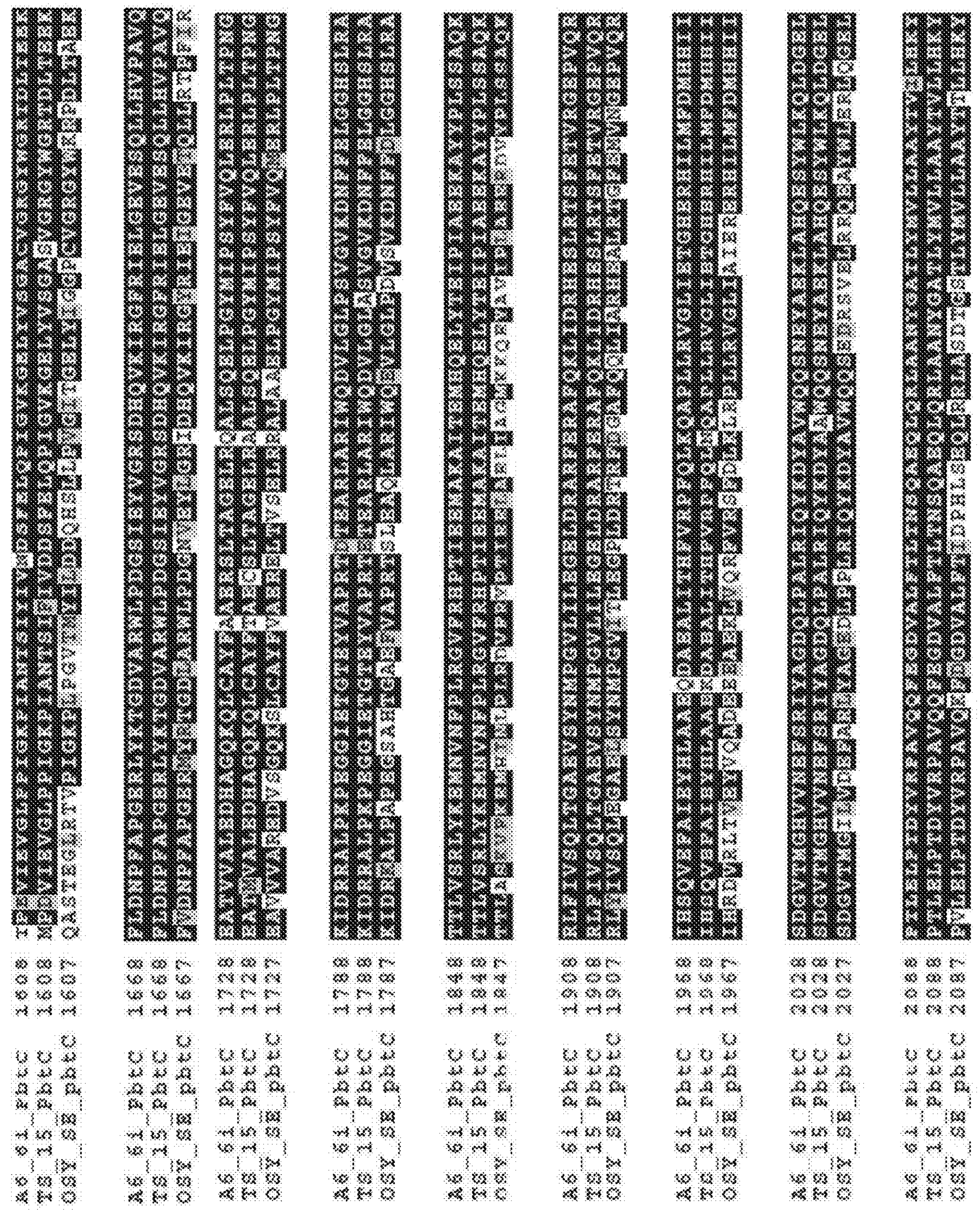
Figure 18E:
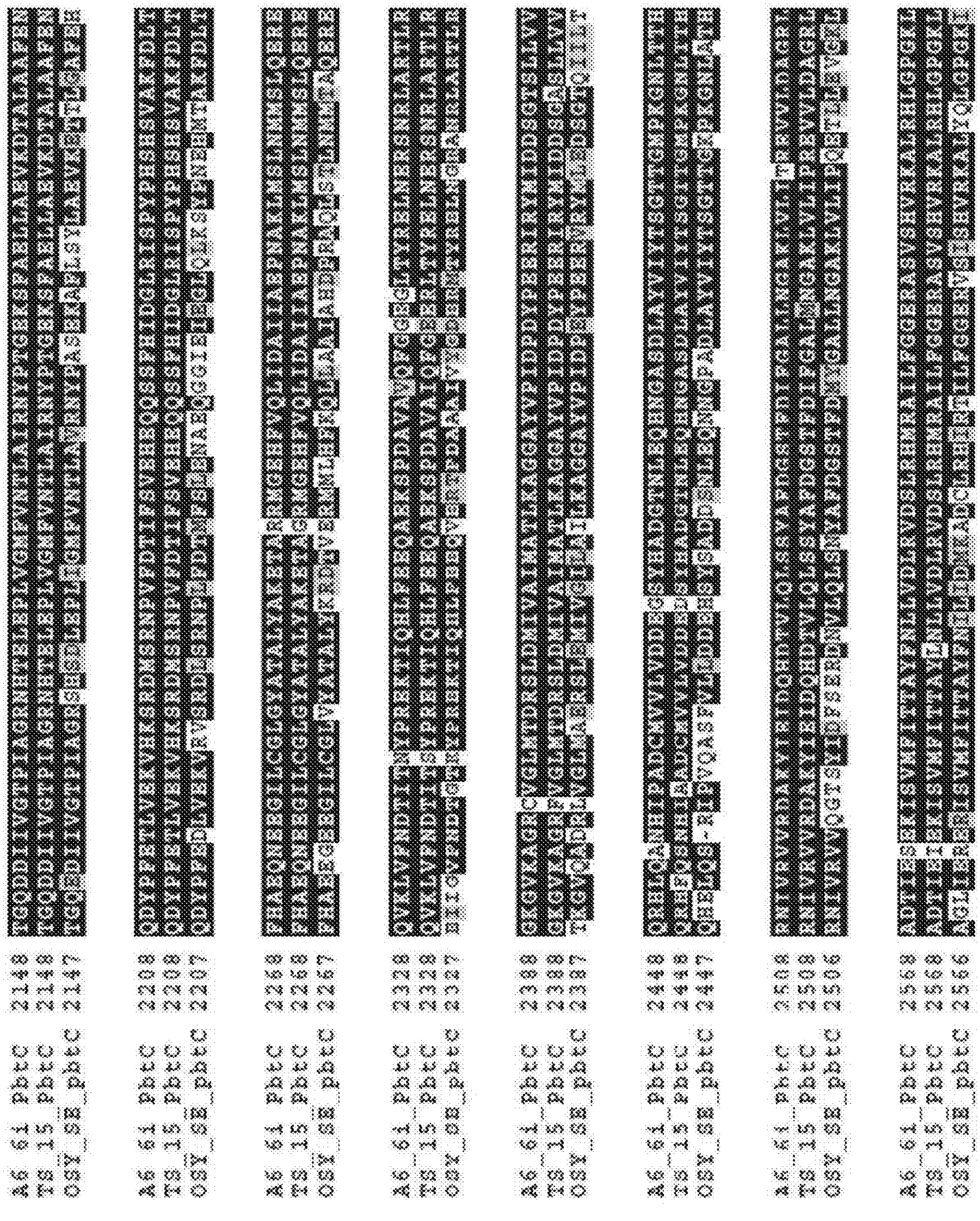
Figure 18F:
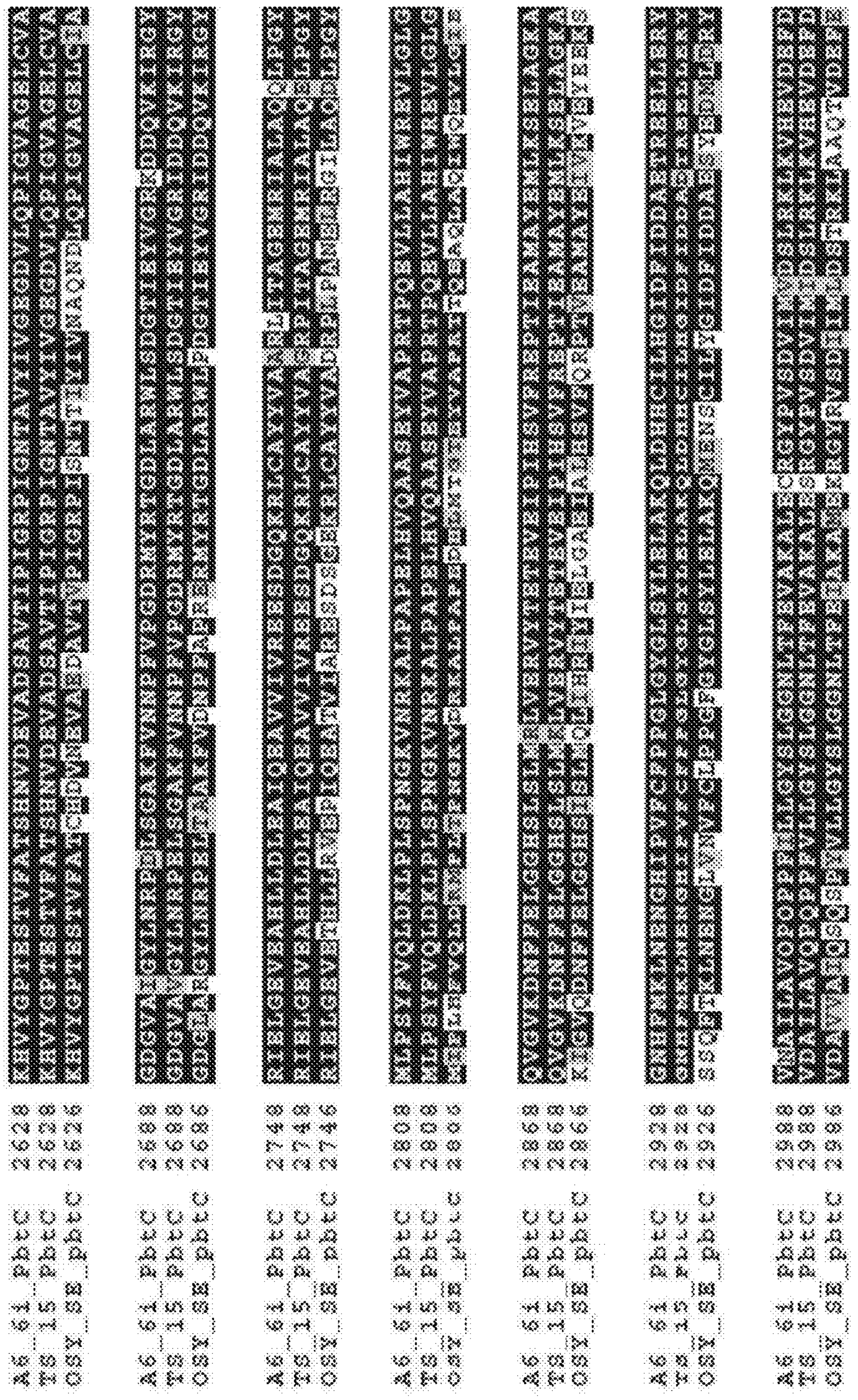
Figure 18G:
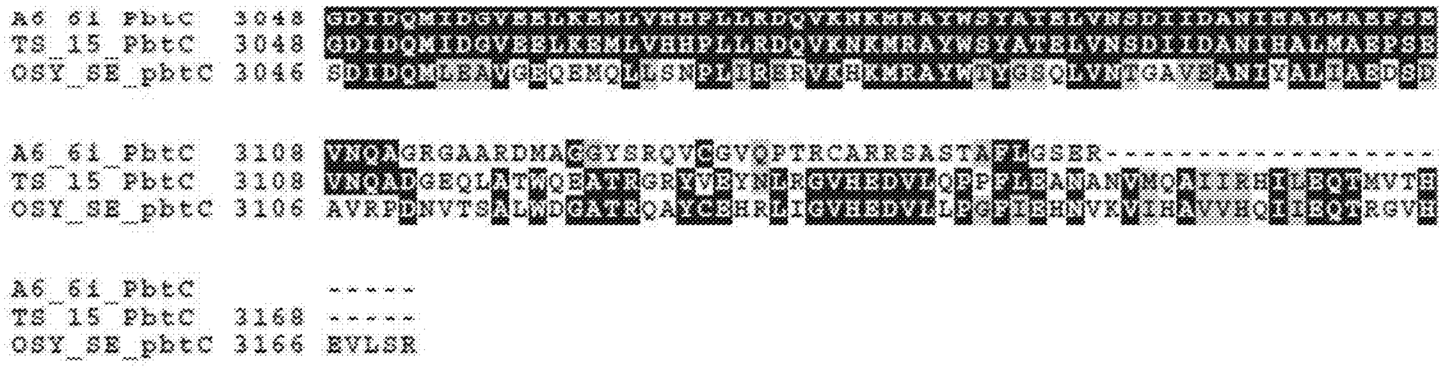

Based on the identified sequence in FIG. 8B, a peptide was chemically synthesized in accordance with FIG. 15, referred to herein as synthetic depsipeptide A or Compound A, L-form with L-Lys at position 7.

Minimum inhibitory concentrations (MICs) of synthetic depsipeptide A against selected bacteria, including antibiotic-resistant strains (Table 6), were determined by the broth microdilution method following the procedure of the Clinical and Laboratory Standards Institute (CLSI) as is known in the art. Briefly, synthesized depsipeptide was dissolved in Optima grade water to reach 25.6 mg/ml as the stock concentration. After 100 times dilution in cation-adjusted Mueller-Hinton II broth (CAMHBII) (Becton, Dickinson& Co., Sparks, Md.), the depsipeptide was then further two-fold serially diluted in CAMHBII in clear, sterile, non-treated round bottom 96-well plates (Nunc, Roskilde, Denmark). Bacterial cultures were suspended in demineralized water to achieve a turbidity equivalent to a 0.5 McFarland turbidity standard (Remel, Lenexa, Kans.). An equal volume of culture suspension was added to the diluted depsipeptide to give a final volume of 100 μl/well in the assay plates. Polymyxin B (Sigma, St Louis, Mo.) and vancomycin (Sigma) were used as positive controls in the AST assays. Strains *Escherichia coli* ATCC 25853, *Pseudomonas aeruginosa* ATCC 27853, *Enterococcus faecalis* ATCC 29212, and *Staphylococcus aureus* ATCC 29213 were used as quality control strains in the assays. The MIC end point refers to the lowest concentration of an antimicrobial agent that completely inhibits growth of bacterial cells after incubation at 35 C for 20-24 h.

TABLE 6

Table 6. Minimum inhibitory concentrations (MICs) of synthesized depsipeptide and other antibiotics

| | MIC(μg/ml) | | |
|---|---|---|---|
| Bacterial strain | Synthesized depsipeptide | PolymyxinB | Vancomycin |
| *E. coli* ATCC 25853 | 4 | 0.5 | — |
| *Salmonella* Newport #17 | 16 | 1 | — |
| *Enterobacter sakazakii* E784 | 8 | 0.5 | — |
| *E. coli* O157: H7 EDL933 | 4 | 0.5 | — |
| *Serratia marcescens* SBJ-9047 (CRE, clinical isolate) | 32 | >128 | — |
| *Klebsiella pneumoniae* SBJ-9149 (clinical isolate) | 4 | 0.5 | — |
| *Serratia marcescens* SBJ-8283 (CRE, clinical isolate) | 32 | >128 | — |
| *Enterobacter cloacae* SBJ-9395 (CRE, clinical isolate) | 4 | >128 | — |
| *Enterobacter cloacae* SBJ-7612 (clinical isolate) | 4 | 1 | — |
| *Klebsiella pneumoniae* SBJ-9483 (clinical isolate) | 4 | 0.5 | — |
| *Klebsiella pneumoniae* SBJ-9388 (clinical isolate) | 4 | 0.5 | — |
| *Enterobacter cloacae* SBJ-9222 (clinical isolate) | 8 | 1 | — |
| *P. aeruginosa* ATCC-27853 | 8 | 1 | — |
| *P. aeruginosa* SBJ-10884 (PMB-R, clinical isolate) | 4 | | |
| *P. aeruginosa* -03 (PMB-R, clinical isolate) | 8 | | |
| *P. aeruginosa* -02 (PMB-R, clinical isolate) | 8 | | |
| *P. aeruginosa* -01 (PMB-R, clinical isolate) | 8 | | |
| *P. aeruginosa* SBJ-10886 (PMB-R, clinical isolate) | 4 | | |
| *E. faecalis* ATCC 29212 | 4 | — | 2 |
| *Listeria monocytogenes* R2-583 | 2 | — | 1 |
| *S. aureus* ATCC25923 | 2 | — | 1 |
| *S. aureus* 19 (MRSA, MDR clinical isolate) | 4 | — | 1 |
| *S. aureus* 14 (MRSA, MDR clinical isolate) | 4 | — | 1 |
| *S. aureus* 12 (MRSA, MDR clinical isolate) | 4 | — | 1 |
| *S. aureus* ATCC 29213 | 4 | — | 1 |
| *S. aureus* 10 (MRSA, MDR clinical isolate) | 4 | — | 1 |

TABLE 6-continued

Table 6. Minimum inhibitory concentrations (MICs) of synthesized depsipeptide and other antibiotics

| Bacterial strain | MIC(μg/ml) Synthesized depsipeptide | PolymyxinB | Vancomycin |
|---|---|---|---|
| *S. aureus* 8 (MRSA, MDR clinical isolate) | 4 | — | 1 |
| *S. aureus* 6 (MRSA, MDR clinical isolate) | 4 | — | 1 |
| *S. aureus* 4 (MRSA, MDR clinical isolate) | 4 | — | 1 |
| *S. aureus* 2 (MRSA, MDR clinical isolate) | 4 | — | 1 |

PMB-R, polymyxin B-resistant; MDR, multidrug-resistant; MRSA, methicillin-resistant *S. aureus*; CRE, carbapenem-resistant.

The synthetic depsipeptide showed a broad antimicrobial spectrum against both Gram-negative and Gram-positive bacteria, including against significant antibiotic-resistant clinical isolates (Table 1). Specifically, the synthesized depsipeptide showed very potent activity against those carbapenem-resistant (CRE) strains and MRSA strains. Additionally, bacteria showed much greater sensitivity to this peptide than to paenibacterin in U.S. Publication No. US2013/0164317.

It is striking that the peptides found in this study are amphiphilic with distinct hydrophilic and hydrophobic regions: hydrophobicity on one side, the other side being predominantly polar and charged amino acids, and a hydrophobic fatty acid chain (FIG. 8B). Major differences between paenibacterin and the compounds discovered in this work are the length of the attached fatty acid, the different combinations of lysine and ornithine at positions 1 and 7, and the amino acids at position 6 and 12. This is particularly interesting because the amino acids at position 6 and 12 have different properties (e.g., hydrophobic, hydrophilic, or positively charged). Furthermore, the presence of D-amino acids influences the structure and properties of the peptide and will also make the compound more resistant to enzymatic degradation and thus inherently more stable.

Aspects of paenibacterin's mode of action have been previously studied. The results suggest that the compound has a high affinity to the negatively-charged outer membrane of gram-negative bacteria. This is likely due to the presence of positively charged amino acids in the molecule, which is similar to the mode of action of polymyxin. Three positively charged amino acids were found in the molecules discovered here compared to four in paenibacterin (FIG. 8), which may result in varying degrees of effectiveness. However, the Lys to Pro substitution at position 12 also increases the hydrophobicity of that portion of the molecule which may result in a better affinity to the hydrophobic core of cellular membranes, a characteristic that may aid in its disruption. Similarly, the presence of Tyr at position 6 contributes to a more polar region of the molecule. The mode of action may also be due to the amphiphilic nature of the compound, acting as a surfactant to disrupt cell membranes. It is notable that polymyxin also has distinct hydrophilic and hydrophobic domains.

It was also determined that paenibacterin resulted in the permeabilization of both gram-positive and -negative cell membranes, which was probably disrupted by the attached fatty acid. The chain length will likely affect observed antimicrobial activity, although it is uncertain if it will be less or more effective with a longer/shorter chain. For polymyxin, it is hypothesized that the fatty acyl chain disrupts the cellular membrane. Studies on the fatty acid chain of polymyxin indicate that antimicrobial activity correlates with the length and bulkiness of this moiety. However, reports are varied and subsequent experiments to design fatty acid analogues for the compounds in this study will yield insight into how this affects antimicrobial activity. It is also interesting that a single strain of bacteria can produce such a large number of molecular variants. This may enable the strain to exert a more concerted antimicrobial effect and may have resulted from extensive selection pressure in the community from which it was isolated.

The major significance of the antimicrobial peptides described herein relates to overcoming the worldwide public health crisis of drug resistance by several major classes of bacterial human pathogens. Several of the most dangerous bacterial pathogens such as MRSA, VRSA, and CRE are resistant to nearly every antibiotic currently in the arsenal of human antimicrobial prophylaxis. CRE, for instance, has no known antibiotic weakness. What is most important is that these antimicrobial peptides may represent entirely new classes of antibiotics, each with the ability to control these deadly bacteria and cure associated pathology. Safety studies in rat with the host organism that produces the antimicrobial peptides was most encouraging, with rats showing no overt pathology from this strain.

Example 8: Antimicrobial Susceptibility of Variant Compounds

The same MIC assay as in Example 6 was used to determine the antimicrobial susceptibility of Compound A, L-form (FIG. 15), and several variants. One variant was Compound A, D-form, with D-Lysine at position 7. Compound B is a variant in the fatty acid chain, with a fatty acid chain composition of $C_{15}H_{29}O$, and having D-Lys at position 7. Compound C is a variant in the fatty acid chain with a fatty acid chain composition of $C_{11}H_{21}O$, and having D-Lys at position 7. Variant D is a sequence variant with Phe at position 6 of the cyclic peptide, and having D-Lys at position 7. All variants were chemically synthesized. The results are given in Table 7.

TABLE 7

Antimicrobial Susceptibility of Variant Compounds

| Bacterial strain | MIC (ug/ml) A L-form | A D-form | B | C | D | Control 1 | Control 2 |
|---|---|---|---|---|---|---|---|
| *Serratia marcescens* SBJ-9047 | 32 | 32 | ≥128 | 64 | ≥128 | >128 | |
| *Serratia marcescens* SBJ-8283 | 32 | 16 | 32 | 32 | 32 | >128 | |
| *Enterobacter cloacae* SBJ-9395 | 4 | 8 | 16 | 8 | 32 | >128 | |
| *Serratia marcescens* SAMN 04276915 | ≥128 | 64 | ≥128 | ≥128 | ≥128 | ≥256 | |
| *Serratia marcescens* SAMN04022954 | ≥128 | 32 | ≥128 | 64 | ≥128 | ≥256 | |
| *Serratia marcescens* SAMN 04276914 | 64 | 32 | 64 | 64 | 64 | ≥256 | |
| *E. faecium* ATCC 700221 | 4 | 8 | 4 | 8 | 8 | | ≥256 |
| *E. faecium* BAA-2318 | 4 | 4 | 4 | 8 | 8 | | ≥256 |
| *E. faecium* ATCC 2320 | 4 | 8 | 4 | 8 | 8 | | ≥256 |
| *E. faecalis* ATCC 51575 | 8 | 8 | 8 | 32 | 8 | | ≥256 |
| *E. faecalis* BAA-2365 | 8 | 8 | 4 | 32 | 8 | | ≥256 |
| *S. aureus* 19 (MRSA, clinical isolate) | 4 | 8 | 4 | 8 | 8 | | 1 |
| *S. aureus* 14 (MRSA, clinical isolate) | 4 | 8 | 4 | 8 | 8 | | 1 |
| *S. aureus* 12 (MRSA, clinical isolate) | 4 | 4 | 4 | 8 | 8 | | 1 |
| *S. aureus* 10 (MRSA, clinical isolate) | 4 | 8 | 4 | 8 | 8 | | 1 |
| *S. aureus* 8 (MRSA, clinical isolate) | 4 | 4 | 4 | 8 | 8 | | 1 |
| *S. aureus* 6 (MRSA, clinical isolate) | 4 | 4 | 8 | 8 | 8 | | 1 |
| *S. aureus* 4 (MRSA, clinical isolate) | 4 | 4 | 4 | 8 | 8 | | 1 |
| *S. aureus* 2 (MRSA, clinical isolate) | 4 | 4 | 4 | 8 | 8 | | 1 |
| *Salmonella* CVM 1290 (cmy2) | 8 | 8 | 16 | 16 | 8 | | |
| *K. pneumoniae* CVM 9246 (shv18, oxa2) | 8 | 8 | 8 | 8 | 8 | | |
| *E. coli* CVM 15100 (mir1) | 8 | 8 | 16 | 8 | 8 | | |
| *E. cloacae* CVM 15101 (P99) | 8 | 8 | 8 | 8 | 8 | | |
| *K. pneumoniae* CVM 15102 (shv5) | 8 | 8 | 8 | 8 | 8 | | |
| *E. coli* CVM 15103 (tem2) | 8 | 8 | 8 | 8 | 8 | | |
| *E. coli* CVM 15104 (shv3) | 8 | 8 | 16 | 8 | 16 | | |
| *K. pneumonia* CVM 15105 (shv5) | 8 | 8 | 16 | 8 | 8 | | |
| *E. coli* CVM 35778 (ctx-m-2) | 8 | 8 | 32 | 16 | 16 | | |
| *S. Newport* CVM 40115 (cmy 2) | 8 | 8 | 16 | 16 | 8 | | |
| *S. Typhimurium* CVM 40117 (ctx-m-5) | 8 | 8 | 16 | 16 | 8 | | |
| *Salmonella* CVM 40118 (oxa-1) | 4 | 4 | 4 | 4 | 8 | | |
| *Salmonella* CVM 40119 (tem 12) | 8 | 16 | 8 | 8 | 8 | | |
| *E. coli* CVM 40126 (oxa-1) | 4 | 8 | 4 | 8 | 8 | | |
| *E. coli* CVM 40127 (oxa-2) | 8 | 8 | 16 | 8 | 8 | | |
| *E. coli* CVM 40128 (oxa-7) | 8 | 8 | 8 | 8 | 8 | | |
| *E. coli* CVM 40129 (oxa-5) | 4 | 8 | 8 | 8 | 8 | | |
| *E. coli* CVM 40130 (oxa-9) | 8 | 8 | 8 | 8 | 8 | | |
| *E. coli* CVM 40131 (ctx-m-2) | 4 | 8 | 8 | 8 | 8 | | |
| *E. coli* CVM 40132 (ctx-m-9) | 8 | 8 | 16 | 8 | 8 | | |
| *E. coli* CVM 40133 (ctx-m-14) | 8 | 16 | 16 | 8 | 8 | | |
| *E. coli* CVM 40134 (ctx-m-15) | 8 | 8 | 8 | 8 | 8 | | |
| *S. Keur massar* CVM 40135 (shv12) | 16 | 16 | 32 | 16 | 16 | | |

TABLE 7-continued

Antimicrobial Susceptibility of Variant Compounds

| Bacterial strain | MIC (ug/ml) A L-form | A D-form | B | C | D | Control 1 | Control 2 |
|---|---|---|---|---|---|---|---|
| *E. coli* CVM 40136 (tem 52b) | 8 | 16 | 8 | 8 | 16 | | |
| *E. coli* CVM 40137 (DHA-1) | 8 | 8 | 16 | 8 | 8 | | |
| *E. coli* CVM 40138 (LCR-1) | 8 | 8 | 8 | 8 | 8 | | |
| *E. coli* CVM 40139 (fox-1) | 8 | 8 | 16 | 8 | 8 | | |
| *S. Heidelberg* CVM 40140 (cmy-2) | 16 | 16 | 16 | 16 | 16 | | |
| *E. coli* CVM 40141 (imp-1) | 32 | 16 | 16 | 32 | 16 | | |
| *K. pneumonia* CVM 40142 (ges-1) | 8 | 8 | 16 | 8 | 8 | | |
| *E. coli* CVM 40143 (act-1) | 8 | 8 | 16 | 8 | 16 | | |
| *P. aeruginosa* CVM 40144 (PER-1) | 32 | 16 | 32 | 16 | 16 | | |
| *S. Bareilly* CVM40145 (ACC-1) | 16 | 8 | 32 | 16 | 32 | | |
| *E. coli* CVM40146 (vim-1) | 8 | 8 | 8 | 8 | 8 | | |
| *E. coli* CVM 40147 (vim-2) | 16 | 16 | 16 | 16 | 16 | | |
| *E. coli* CVM40148 (veb-1) | 8 | 8 | 8 | 8 | 8 | | |

Control 1 = Polymixin B
Control 2 = Vancomycin

As shown in Table 7, the minimum inhibitory concentrations (MICs) of both D-Lys and L-Lys Compound A were reduced by at least 16 to 64 folds in those polymyxin or vancomycin resistant strains and ESBL producing bacteria as well when comparing to the MICs of resistant antimicrobials that the strains originally developed, although changes in the fatty acid residues showed no comparative improvement. The use of the terms “a” and “an” and “the” and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms “comprising”, “having”, “including”, and “containing” are to be construed as open-ended terms (i.e., meaning “including, but not limited to”) unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., “such as”), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A composition comprising an effective amount of a peptide comprising the amino acid sequence $Xaa_1$-$Val_2$-$Thr_3$-D-$Orn_4$-$Ser_5$-$Xaa_6$-$Xaa_7$-D-$Ser_8$-$Ile_9$-$Pro_{10}$-$Ile_{11}$-$Pro_{12}$-$Ile_{13}$, wherein $Xaa_1$ is D-Orn, $Xaa_6$ is Tyr or Phe, and $Xaa_7$ is L-Lys, and wherein the peptide optionally comprises a saturated or unsaturated, substituted or unsubstituted, linear or branched $C_4$-$C_{20}$ fatty acid group, or a saturated or unsaturated, linear or branched $C_4$-$C_{20}$ ester covalently linked to $Xaa_1$; and a carrier, vehicle, excipient, or diluent.

2. The composition of claim 1, wherein the composition is a cleaning product, a disinfecting product, a personal care product, an animal feed product, or a food product.

3. The composition of claim 1, wherein the composition is a pharmaceutical composition comprising a pharmaceutically acceptable excipient.

4. The composition of claim 3, formulated for topical or oral administration.

5. The composition of claim 3, further comprising an effective amount of a penetrant.

6. The composition of claim 3, further comprising an effective amount of a preservative.

7. The composition of claim 1, wherein the composition is a cleaning product.

8. The composition of claim 1, wherein the peptide comprises the saturated or unsaturated, substituted or unsubstituted, linear or branched $C_4$-$C_{20}$ fatty acid group, or the saturated or unsaturated, linear or branched $C_4$-$C_{20}$ ester covalently linked to $Xaa_1$.

9. The composition of claim 1, wherein the peptide comprises D-$Orn_1$-$Va_{12}$-$Thr_3$-D-$Orn_4$-$Ser_5$-$Tyr_6$-[[L-]]$Lys_7$-D-$Ser_8$-$Ile_9$-$Pro_{10}$-$Ile_{11}$-$Pro_{12}$-$Ile_{13}$.

10. The composition of claim 9, wherein the peptide comprises the saturated or unsaturated, substituted or unsubstituted, linear or branched $C_4$-$C_{20}$ fatty acid group covalently linked to D-$Orn_1$.

11. The composition of claim 10, wherein the fatty acid group has the formula $C_{10}H_{19}O$, $C_{11}H_{21}O$, $C_{12}H_{23}O$, $C_{13}H_{25}O$, $C_{14}H_{27}O$, $C_{15}H_{29}O$.

12. The composition of claim 1, wherein $Xaa_6$ of the peptide is Phe.

13. The composition of claim 1, wherein $Xaa_6$ of the peptide is Tyr and the peptide comprises the saturated or unsaturated, linear or branched $C_4$-$C_{20}$ ester covalently linked to $Xaa_1$.

14. The composition of claim 13, wherein the ester has the formula $C_{10}H_{19}O_2$, $C_{11}H_{21}O_2$, $C_{12}H_{23}O_2$, $C_{13}H_{25}O_2$, $C_{14}H_{27}O_2$, $C_{15}H_{29}O_2$.

15. The composition of claim 1, wherein the peptide is cyclized through a bond between $Thr_3$ and $Ile_{13}$.

16. The composition of claim 1, wherein the peptide is covalently bound to $C_{13}H_{25}O$.

17. The composition of claim 1, wherein the composition further comprises a second peptide.

18. The composition of claim 1, further comprising an effective amount of a second peptide, wherein the second peptide comprises the amino acid sequence a) D-$Orn_1$-$Val_2$-$Thr_3$-D-$Orn_4$-$Ser_5$-$Tyr_6$-D-$Lys_7$-D-$Ser_8$-$Ile_9$-$Pro_{10}$-$Ile_{11}$-$Pro_{12}$-$Ile_{13}$; or b) D-$Orn_1$-$Val_2$-$Thr_3$-D-$Orn_4$-$Ser_5$-$Phe_6$-D-$Lys_7$-D-$Ser_8$-$Ile_9$-$Pro_{10}$-$Ile_{11}$-$Pro_{12}$-$Ile_{13}$, and wherein the second peptide optionally comprises a saturated or unsaturated, substituted or unsubstituted, linear or branched $C_4$-$C_{20}$ fatty acid group, or a saturated or unsaturated, linear or branched $C_4$-$C_{20}$ ester covalently linked to D-$Orn_1$.

19. A bandage or wound dressing comprising the composition of claim 3.

20. A method of inhibiting growth or proliferation of a bacterium, comprising contacting the bacterium with an effective amount of the composition of claim 1 thereby inhibiting the growth or proliferation of the bacterium, wherein the bacterium is *Escherichia coli, Salmonella, Klebsiella pneumoniae, Enterobacter sakazakii, Serratia marcescens, Enterobacter cloacae, Pseudomonas aeruginosa, Listeria monocytogenes, Staphylococcus aureus, Salmonella typhimurium, Salmonella Heidelberg, Salmonella Bareilly, Salmonella Keur massar* or *Enterococcus faecium.*

21. The method of claim 20, wherein the method comprises contacting the bacterium with the composition in vitro.

22. A method of inhibiting growth or proliferation of a bacterium in a subject in need thereof, the method comprising administering to the subject an effective amount of the composition of claim 1, wherein the bacterium is *Escherichia coli, Salmonella, Klebsiella pneumoniae, Enterobacter sakazakii, Serratia marcescens, Enterobacter cloacae, Pseudomonas aeruginosa, Listeria monocytogenes, Staphylococcus aureus, Salmonella typhimurium, Salmonella Heidelberg, Salmonella Bareilly, Salmonella Keur massar* or *Enterococcus faecium.*

23. The method of claim 22, wherein the subject is a mammal.

24. The method of claim 23, wherein the subject is a human subject.

25. The method of claim 23, wherein the subject is immunocompromised.

* * * * *